US008778967B2

(12) United States Patent
Bridger et al.

(10) Patent No.: US 8,778,967 B2
(45) Date of Patent: *Jul. 15, 2014

(54) CHEMOKINE RECEPTOR BINDING HETEROCYCLIC COMPOUNDS WITH ENHANCED EFFICACY

(75) Inventors: Gary Bridger, Bellingham, WA (US); Renato T Skelj, Newton, MA (US); Al Kaller, Vancouver (CA); Curtis Harwig, Vancouver (CA); David Bogucki, Surrey (CA); Trevor R Wilson, Langley (CA); Jason B Crawford, British Columbia (CA); Ernest J McEachern, White Rock (CA); Bem Atsma, Langley (CA); Siqiao Nan, Shenzhen (CN); Yuanxi Zhou, Richmond (CA); Dominique Schols, Herent (BE); Christopher Dennis Smith, Toronto (CA); Maria R Di Fluri, Burnaby (CA)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/358,041

(22) Filed: Jan. 25, 2012

(65) Prior Publication Data
US 2012/0301427 A1 Nov. 29, 2012

Related U.S. Application Data

(60) Continuation of application No. 12/036,187, filed on Feb. 22, 2008, now abandoned, which is a division of application No. 10/457,034, filed on Jun. 6, 2003, now Pat. No. 7,354,932, which is a continuation-in-part of application No. 10/446,170, filed on May 23, 2003, now abandoned, which is a continuation-in-part of application No. 10/329,329, filed on Dec. 23, 2002, now abandoned.

(60) Provisional application No. 60/342,716, filed on Dec. 21, 2001, provisional application No. 60/350,822, filed on Jan. 17, 2002.

(51) Int. Cl.
*A61K 31/4709* (2006.01)
*C07D 403/12* (2006.01)

(52) U.S. Cl.
USPC ........................................ 514/313; 546/171

(58) Field of Classification Search
USPC .......................................... 514/313; 546/171
See application file for complete search history.

(56) References Cited

U.S. PATENT DOCUMENTS

| | | | |
|---|---|---|---|
| 4,933,447 A | 6/1990 | Koono et al. | |
| 5,021,409 A | 6/1991 | Murrer et al. | |
| 5,583,131 A | 12/1996 | Bridger et al. | |
| 5,698,546 A | 12/1997 | Bridger et al. | |
| 5,817,807 A | 10/1998 | Bridger et al. | |
| 6,001,826 A | 12/1999 | Murrer et al. | |
| 6,365,583 B1 | 4/2002 | MacFarland et al. | |
| 6,506,770 B1 * | 1/2003 | Bridger et al. | 514/300 |
| 6,683,192 B2 * | 1/2004 | Baxter et al. | 549/32 |
| 6,734,191 B2 | 5/2004 | Bridger et al. | |
| 6,734,194 B2 | 5/2004 | End et al. | |
| 6,794,379 B2 | 9/2004 | Medina et al. | |
| 6,835,731 B2 | 12/2004 | Bridger et al. | |
| 6,864,265 B2 * | 3/2005 | Bridger et al. | 514/314 |
| 6,987,102 B2 | 1/2006 | Bridger et al. | |
| 7,053,215 B2 | 5/2006 | Medina et al. | |
| 7,091,217 B2 | 8/2006 | Bridger et al. | |
| 7,135,570 B2 | 11/2006 | McEachern et al. | |
| 7,332,605 B2 | 2/2008 | Crawford et al. | |
| 7,354,932 B2 | 4/2008 | Bridger et al. | |
| 7,354,934 B2 | 4/2008 | Bridger et al. | |
| 7,452,994 B2 | 11/2008 | McEachern et al. | |
| 7,723,525 B2 | 5/2010 | Crawford et al. | |
| 2003/0220341 A1 | 11/2003 | Bridger et al. | |
| 2003/0232808 A1 | 12/2003 | Kobayashi et al. | |
| 2008/0167341 A1 | 7/2008 | Bridger et al. | |

FOREIGN PATENT DOCUMENTS

| | | |
|---|---|---|
| EP | 0434385 B1 | 11/1995 |
| WO | WO 99/04794 | 2/1999 |
| WO | WO 00/56729 A1 | 9/2000 |
| WO | WO 02/22599 A2 | 3/2002 |
| WO | WO 02/22600 A2 | 3/2002 |
| WO | WO 02/34745 A1 | 5/2002 |
| WO | WO 03/011277 A2 | 2/2003 |
| WO | WO 03/055876 A1 | 7/2003 |
| WO | WO 2004/106493 | 12/2004 |

OTHER PUBLICATIONS

Aiuti et al. "The chemokine SDF-1 . . . " J. EXp. Med. v.185(1)p. 111-120 1997).*
Pike et al. "Nutrition an integrated . . . " p. 538-539 (1984).*
Abi-Younes et al., Circ. Res. (2000) 86:131-138.

(Continued)

*Primary Examiner* — Celia Chang
(74) *Attorney, Agent, or Firm* — Hamilton, Brook, Smith & Reynolds, P.C.

(57) ABSTRACT

The invention relates to heterocyclic compounds consisting of a core nitrogen atom surrounded by three pendant groups, wherein two of the three pendant groups are preferably benzimidazolyl methyl and tetrahydroquinolyl, and the third pendant group contains N and optionally contains additional rings. The compounds bind to chemokine receptors, including CXCR4 and CCR5, and demonstrate protective effects against infection of target cells by a human immunodeficiency virus (HIV).

20 Claims, No Drawings

(56) References Cited

OTHER PUBLICATIONS

Alkhatib et al., Science (1996) 272:1955-1958.
Arai et al., Eur. J. Haematol. (2000) 64:323-332.
Arenburg et al., J. Leukocyte Biol. (1997) 62:554-562.
Bennett, "Concise Chemical and Technical Dictionary" (1976) p. 234.
Blaak et al., Proc. Natl. Acad. Sci. USA (2000) 97:1269-1274.
Blanco et al., Antimircrobial. Agents and Chemother. (2000) 44:51-56.
Bleul et al., J. Exp. Med. (1998) 187:753-762.
Bleul et al., Nature (1996) 382:829-833.
Bradstock et al., Leukemia (2000) 14:882-888.
Bridger et al. in: Advances in Antiviral Drug Design vol. 3, E. De Clercq (Ed.), JAI press (1999) pp. 161-229.
Bridger et al., J. Med. Chem. (1999) 42:3971-3981.
Bundgaard (ed.), Design of prodrugs: Bioreversible derivatives for various functional groups and chemical entities, in: Design of prodrugs, Elsevier (1985) p. 1.
Burger et al., Blood (1999) 94:3658-3667.
Carroll et al., Science (1997) 276:273-276.
Cocchi et al., Science (1995) 270:1811-1815.
Connor and Ho, J. Virol. (1994) 68:4400-4408.
Database BIOSIS, accession No. PREV200200261505 (2001).
Database BIOSIS, accession No. PREV200200250113 (2001).
Deng et al., Nature (1996) 381:661-666.
Donzella et al., Nature Medicine (1998) 4:72-77.
Dragic et al., Nature (1996) 381:667-673.
Egberink et al., J. Virol. (1999) 73:6346-6352.
Eitner et al., Transplantation (1998) 66:1551-1557.
Fedyk et al., J. Leukocyte Biol. (1999) 66:667-673.
Feng et al., Science (1996) 272:872-877.
Gonzalo et al., J. Immunol. (2000) 165:499-508.
Gupta et al., J. Biolog. Chem. (1998) 7:4282-4287.
Hampson et al., "The Biology of Haemopoiesis" Google (1996).
Hendrix et al., CA (2000) 133:99145.
International Preliminary Examination Report for PCT/US02/41407, titled "Chemokine Receptor Binding Heterocyclic Compounds with Enhanced Efficacy," mailed Aug. 1, 2003, 4 pages.
International Preliminary Report on Patentability for PCT/US04/15977, titled "Chemokine Receptor Binding Heterocyclic Compounds with Enhanced Efficacy," mailed May 2, 2006, 4 pages.
International Search Report for PCT/US04/15977, titled "Chemokine Receptor Binding Heterocyclic Compounds with Enhanced Efficacy," mailed on Jul. 15, 2005, 3 pages.
Ishii et al., J. Immunol. (1999) 163:3612-3620.
Iwakura et al., Blood (2002) 100(11):293A-294A, Abstract #1127.
Kirkland et al., Blood (1996) 87(9):3963-69.
Labrosse et al., CA 129:197625 (1998).
Lapidot et al., Leukemia (2002) 16:1992-2003.
Lataillade et al., Blood (1999) 95:756-768.
Liu et al., Cell (1996) 86:367-377.
Maekawa et al., Internal Medicine (2000) 39:90-100.
Michael et al., J. Virol. (1998) 72:6040-6047.
Michael et al., Nature Med. (1997) 3:338-340.
Miedema et al., Immunol. Rev. (1994) 140:35.
Moore et al., Trends Cardiovasc. Med. (1998) 8:51-58.
Murdoch et al., Blood (2000) 95:3032-3043.
Nagasawa et al., Nature (1996) 382:635-638.
Nagase et al., J. Immunol. (2000) 164:5935-5943.
Nanki et al., J. Immunol. (2000) 164:5010-5014.
Oberlin et al., Nature (1996) 382:833-835.
Obrien et al., Lancet (1997) 349:1219.
Peled et al., Blood (2000) 95:3289-3296.
Peled et al., Science (1999) 283:845-848.
Ponath, Exp. Opin. Invest. Drugs (1998) 7:1-18.
Qing et al., Immunity (1999) 10:463-471.
Rana et al., J. Virol. (1997) 71:3219-3227.
Salcedo et al., Am. J. Pathol. (1999) 154:1125-1135.
Samson et al., Nature (1996) 382:722-725.
Schols et al., Anitviral Research (1997) 35:147-156.
Schols et al., J. Exp. Med. (1997) 186:1383-1388.
Schuitemaker et al., J. Virol. (1992) 66:1354-1360.
Seghal et al., J. Surg. Oncol. (1998) 69:99-104.
Silverman, "The Organic Chemistry of Drug Design and Drug Action" Academic Press (1993) pp. 72-75.
Simmonds et al., J. Virol. (1996) 70:8355-8360.
Simmonds et al., J. Virol. (1998) 72:8453-8457.
Supplementary European Search Report for EP 04752905.2, mailed Mar. 12, 2010, 6 pages.
Supplementary European Search Report for EP 02805977.2, mailed Apr. 16, 2008, 3 pages.
Tachibana et al., Nature (1998) 393:591-594.
Tersmette et al., J. Virol. (1988) 62:2026-2032.
Theodorou et al., Lancet (1997) 349:1219-1220.
Viardot et al., Ann Hematol. (1998) 77:195-197.
Written Opinion of the International Searching Authority for PCT/US04/15977, mailed Jul. 15, 2005, 4 pages.
Wyatt et al., Science (1998) 280:1884-1888.
Xia et al., J. Neurovirology (1999) 5:32-41.
Yssel et al., Clinical and Experimental Allergy (1998) 28:104-109.
Zhang et al., J. Virol. (1998) 72:9307-9312.
Zhang et al., J. Virol. (1999) 73:3443-3448.
Zhang et al., AIDS Res. Hum. Retroviruses (1997) 13:1357-1366.
Zou et al., Nature (1998) 393:591-594.
Comba et al., "Catalytic Aziridination of Styrene with Copper Complexes for Substituted 3,7-Diazabicyclo[3.3.1]nonanones" European Journal of Inorganic Chemistry, (2003) 9:1711-1718.
Kocher et al., "Neovascularization of ischemic myocardium by human bone-marrow-derived angioblasts prevents cardiomyocyte apoptosis, reduces remodeling and improves cardiac function" Nature Medicine (2001) 7:430-436.
Jackson et al., "Regeneration of ischemic cardiac muscle and vascular endothelium by adult stem cells" The Journal of Clinical Investigation (2001) 107:1395-1402.
Lukacs et al., "AMD3100, a CxCR4 Antagonist, Attenuates Allergic Lung Inflammation and Airway Hyperreactivity" American Journal of Pathology (2002) 160(4):1353-1360.
Matthys et al., J. Immunol. (2001) 107:4686-4692.

* cited by examiner

CHEMOKINE RECEPTOR BINDING HETEROCYCLIC COMPOUNDS WITH ENHANCED EFFICACY

CROSS-REFERENCE TO RELATED APPLICATIONS

This application is a continuation of U.S. Ser. No. 12/036,187 filed on 22 Feb. 2008, which is a divisional application of U.S. Ser. No. 10/457,034 filed on 6 Jun. 2003, now U.S. Pat. No. 7,354,932, which is a continuation-in-part of U.S. Ser. No. 10/446,170, filed 23 May 2003, now abandoned, which is a continuation-in-part of U.S. Ser. No. 10/329,329 filed 23 Dec. 2002, now abandoned, which claims benefit of U.S. provisional application Ser. No. 60/342,716 filed 21 Dec. 2001 and to U.S. provisional application Ser. No. 60/350,822 filed 17 Jan. 2002. The contents of these applications are incorporated herein by reference.

TECHNICAL FIELD

This invention generally relates to novel compounds, pharmaceutical compositions and their use. This invention more specifically relates to novel heterocyclic compounds that bind to chemokine receptors, including CXCR4 and CCR5, and demonstrate protective effects against infection of target cells by a human immunodeficiency virus (HIV).

BACKGROUND OF THE INVENTION

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1-18, 1998). These chemotactic cytokines, or chemokines, constitute a family of proteins, approximately 8-10 kDa in size. Chemokines appear to share a common structural motif, that consists of 4 conserved cysteines involved in maintaining tertiary structure. There are two major subfamilies of chemokines: the "CC" or β-chemokines and the "CXC" or α-chemokines. The receptors of these chemokines are classified based upon the chemokine that constitutes the receptor's natural ligand. Receptors of the β-chemokines are designated "CCR"; while those of the α-chemokines are designated "CXCR."

Chemokines are considered to be principal mediators in the initiation and maintenance of inflammation (see *Chemokines in Disease* published by Humana Press (1999), Edited by C. Herbert; Murdoch et al. *Blood* 95, 3032-3043 (2000)). More specifically, chemokines have been found to play an important role in the regulation of endothelial cell function, including proliferation, migration and differentiation during angiogenesis and re-endothelialization after injury (Gupta et al., *J. Biolog. Chem.*, 7:4282-4287, 1998). Two specific chemokines have been implicated in the etiology of infection by human immunodeficiency virus (HIV).

In most instances, HIV initially binds via its gp120 envelope protein to the CD4 receptor of the target cell. A conformational change appears to take place in the gp120 which results in its subsequent binding to a chemokine receptor, such as CCR-5 (Wyatt et al., *Science*, 280:1884-1888 (1998)). HIV-1 isolates arising subsequently in the infection bind to the CXCR-4 chemokine receptor. In view of the fact that the feline immunodeficiency virus, another related retrovirus, binds to a chemokine receptor without needing to bind first to the CD4 receptor, suggests that chemokine receptors may be the primordial obligate receptors for immunodeficiency retroviruses.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll et al., *Science*, 276: 273-276 1997; Feng et al. *Science* 272, 872-877 (1996); Bleul et al. *Nature* 382, 829-833 (1996); Oberlin et al. *Nature* 382, 833-835 (1996); Cocchi et al. *Science* 270, 1811-1815 (1995); Dragic et al. *Nature* 381, 667-673 (1996); Deng et al. *Nature* 381, 661-666 (1996); Alkhatib et al. *Science* 272, 1955-1958, 1996). During the course of infection within a patient, it appears that a majority of HIV particles shift from the M-tropic to the more aggressive pathogenic T-tropic viral phenotype (Miedema et al., *Immune. Rev.*, 140:35 (1994); Blaak et al. *Proc. Natl. Acad. Sci.* 97, 1269-1274 (2000); Simmonds et al. *J. Virol.* 70, 8355-8360 (1996); Tersmette et al. *J. Virol.* 62, 2026-2032, 1988); Connor, R. I., Ho, D. D. *J. Virol.* 68, 4400-4408 (1994); Schuitemaker et al. *J. Virol.* 66, 1354-1360 (1992)). The M-tropic viral phenotype correlates with the virus's ability to enter the cell following binding of the CCR-5 receptor, while the T-tropic viral phenotype correlates with viral entry into the cell following binding and membrane fusion with the CXCR-4 receptor. Clinically observations suggest that patients who possess genetic mutations in the CCR-5 or CXCR-4 appear resistant or less susceptible to HIV infection (Liu et al. *Cell* 86, 367-377 (1996); Samson et al. *Nature* 382, 722-725 (1996); Michael et al. *Nature Med.* 3, 338-340 (1997); Michael et al. *J. Virol.* 72, 6040-6047 (1998); Obrien et al. *Lancet* 349, 1219 (1997); Zhang et al. *AIDS Res. Hum. Retroviruses* 13, 1357-1366 (1997); Rana et al. *J. Virol.* 71, 3219-3227 (1997); Theodorou et al. *Lancet* 349, 1219-1220 (1997). Despite the number of chemokine receptors which have been reported to HIV mediate entry into cells, CCR5 and CXCR4 appear to be the only physiologically relevant coreceptors used by a wide variety of primary clinical HIV-1 strains (Zhang et al. *J. Virol.* 72, 9307-9312 (1998); Zhang et al. *J. Virol.* 73, 3443-3448 (1999); Simmonds et al. *J. Virol.* 72, 8453-8457 (1988)). Fusion and entry of T-tropic viruses that use CXCR4 are inhibited by the natural CXC-chemokine stromal cell-derived factor-1, whereas fusion and entry of M-tropic viruses that use CCR5 are inhibited by the natural CC-chemokines namely, Regulated on Activation Normal T-cell Expressed and Secreted (RANTES) and Macrophage Inflammatory proteins (MIP-1 alpha and beta).

However, the binding of chemokine receptors to their natural ligands appears to serve a more evolutionary and central role than only as mediators of HIV infection. The binding of the natural ligand, pre-B-cell growth-stimulating factor/stromal cell derived factor (PBSF/SDF-1) to the CXCR4 chemokine receptor provides an important signaling mechanism: CXCR4 or SDF-1 knock-out mice exhibit cerebellar, cardiac and gastrointestinal tract abnormalities and die in utero (Zou et al., *Nature*, 393:591-594 (1998); Tachibana et al., *Nature*, 393:591-594 (1998); Nagasawa et al. *Nature* 382, 635-638 (1996)). CXCR4-deficient mice also display hematopoietic defects (Nagasawa et al. *Nature* 382, 635-638 (1996)); the migration of CXCR4 expressing leukocytes and hematopoietic progenitors to SDF-1 appears to be important for maintaining B-cell lineage and localization of CD34+ progenitor cells in bone marrow (Bleul et al. *J. Exp. Med.* 187, 753-762 (1998); Viardot et al. *Ann. Hematol.* 77, 195-197 (1998); Auiti et al. *J. Exp. Med.* 185, 111-120 (1997); Peled et al. *Science* 283, 845-848 (1999); Qing et al. *Immunity* 10, 463-471 (1999); Lataillade et al. *Blood* 95, 756-768 (1999); Ishii et al. *J. Immunol.* 163, 3612-3620 (1999); Maekawa et al. *Internal Medicine* 39, 90-100 (2000); Fedyk et al. *J. Leukocyte Biol.* 66, 667-673 (1999); Peled et al. *Blood* 95, 3289-3296 (2000)).

The signal provided by SDF-1 on binding to CXCR4 may also play an important role in tumor cell proliferation and regulation of angiogenesis associated with tumor growth (See "*Chemokines and Cancer*" published by Humana Press (1999); Edited by B. J. Rollins; Arenburg et al. *J. Leukocyte Biol.* 62, 554-562 (1997); Moore et al. *J. Invest. Med.* 46, 113-120 (1998); Moore et al. *Trends cardiovasc. Med.* 8, 51-58 (1998); Seghal et al. *J. Surg. Oncol.* 69, 99-104 (1998)); the known angiogenic growth factors VEG-F and bFGF, up-regulate levels of CXCR4 in endothelial cells, and SDF-1 can induce neovascularization in vivo (Salcedo et al. *Am. J. Pathol.* 154, 1125-1135 (1999)); Leukemia cells that express CXCR4 migrate and adhere to lymph nodes and bone marrow stromal cells that express SDF-1 (Burger et al. *Blood* 94, 3658-3667 (1999); Arai et al. *Eur. J. Haematol.* 64, 323-332 (2000); Bradstock et al. *Leukemia* 14, 882-888 (2000)).

The binding of SDF-1 to CXCR4 has also been implicated in the pathogenesis of atherosclerosis (Abi-Younes et al. *Circ. Res.* 86, 131-138 (2000)), renal allograft rejection (Eitner et al. *Transplantation* 66, 1551-1557 (1998)), asthma and allergic airway inflammation (Yssel et al. *Clinical and Experimental Allergy* 28, 104-109 (1998); *J. Immunol.* 164, 5935-5943 (2000); Gonzalo et al. *J. Immunol.* 165, 499-508 (2000)), Alzheimer's disease (Xia et al. *J. Neurovirology* 5, 32-41 (1999)) and Arthritis (Nanki et al. *J. Immunol.* 164, 5010-5014 (2000)).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols et al., *J. Exp. Med.* 186:1383-1388 (1997); Schols et al., *Antiviral Research* 35:147-156 (1997); Bridger et al. *J. Med. Chem.* 42, 3971-3981 (1999); Bridger et al. "Bicyclam Derivatives as HIV Inhibitors" in *Advances in Antiviral Drug Design Volume* 3, p161-229; Published by JAI press (1999); Edited by E. De Clercq). Small molecules, such as bicyclams, appear to specifically bind to CXCR4 and not CCR5 (Donzella et al., *Nature Medicine*, 4:72-77 (1998)). These experiments demonstrated interference with HIV entry and membrane fusion into the target cell in vitro. More recently, bicyclams were also shown to inhibit fusion and replication of Feline Immunodeficiency Virus (FIV) that uses CXCR4 for entry (Egberink et al. *J. Virol.* 73, 6346-6352 (1999)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco et al. *Antimicrobial Agents and Chemother.* 44, 51-56 (2000)).

U.S. Pat. Nos. 5,583,131; 5,698,546; 5,817,807; 5,021,409; and 6,001,826 which are incorporated herein in their entirety by reference, disclose cyclic compounds that are active against HIV-1 and HIV-2 in in vitro tests. It was subsequently discovered and further disclosed in PCT WO 02/34745 that these compounds exhibit anti-HIV activity by binding to the chemokine receptor CXCR4 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). We further disclosed that these novel compounds demonstrate protective effects against HIV infection of target cells by binding in vitro to the CCR5 receptor.

Additionally we have disclosed in U.S. Pat. No. 6,365,583 that these cyclic polyamine antiviral agents described in the above-mentioned patents/patent applications have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

More recently, we disclosed in PCT WO 00/56729, PCT WO 02/22600, PCT WO 02/22599, and PCT WO 02/34745 a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

The chemokine receptor, CXCR-4 has been found to be essential for the vascularization of the gastrointestinal tract (Tachibana, et al., *Nature* (1998) 393:591-594) as well as haematopoiesis and cerebellar development (Zou, et al., *Nature* (1998) 393:591-594). Interference with any of these important functions served by the binding of pre-B-cell growth-stimulating factor/stromal derived factor (PBSF/SDF-1) to the CXCR-4 chemokine receptor results in lethal deficiencies in vascular development, haematopoiesis and cardiogenesis. Similarly, fetal cerebellar development appears to rely upon the effective functioning of CXCR-4 in neuronal cell migration and patterning in the central nervous system. This G-protein-coupled chemokine receptor appears to play a critical role in ensuring the necessary patterns of migration of granule cells in the cerebellar anlage.

Herein, we disclose compounds that have unique chemical attributes and that exhibit protective effects against HIV infection of target cells by binding to chemokine receptor CXCR4 or CCR5 in a similar manner to the previously disclosed macrocyclic compounds. In addition, these compounds antagonize the binding, signaling and chemotactic effects of the natural ligand for CXCR4, the chemokine stromal cell-derived factor 1α (SDF-1) and/or the natural ligand for CCR5 (the chemokine RANTES).

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

DISCLOSURE OF THE INVENTION

The present invention provides novel compounds that bind chemokine receptors and interfere with the binding of the natural ligand thereto. The compounds of the present invention are useful as agents demonstrating protective effects on target cells from HIV infection, and which are useful to treat rheumatoid arthritis. Embodiments of the present invention are compounds that act as antagonists or agonists of chemokine receptors, which are useful as agents capable of reconstituting the immune system by increasing the level of CD4+ cells; as antagonist agents of apoptosis in immune cells, such as CD8+ cells, and neuronal cells; as antagonist agents of migration of human bone marrow B lineage cells to stromal-derived factor 1, as well as other biological activities related to the ability of these compounds to inhibit the binding of chemokines to their receptors.

More particularly, the present invention relates to macrocyclic compounds that can be described generally as consisting of a "core" nitrogen atom surrounded by three pendant groups, wherein two of the three pendant groups are preferably benzimidazolyl methyl and tetrahydroquinolinyl, and the third is a pendant group which contains an additional nitrogen.

In one aspect, the invention is directed to a compound of the formula

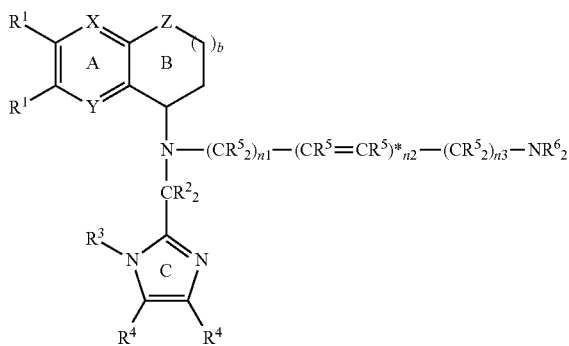

(I)

X and Y are independently N or $CR^1$;
Z is S, O, $NR^1$ or $CR^1{}_2$;
each $R^1$-$R^6$ is independently H or a noninterfering substituent;
n1 is 0-4;
n2 is 0-1, wherein the * signifies C≡C may be substituted for $CR^5$=$CR^5$;
n3 is 0-4;
wherein n1+n2+n3 is greater than or equal to 2;
b is 0-2;
wherein the following combinations of R groups may be coupled to generate a ring, which ring may be saturated or unsaturated:
$R^2$+$R^2$
one $R^2$+$R^3$
$R^3$+one $R^4$,
$R^4$+$R^4$,
one $R^5$+another $R^5$,
one $R^5$+one $R^6$, and
$R^6$+$R^6$;
wherein the ring may not be aromatic when the participants in ring formation are two $R^5$; and
wherein when n2 is 1, neither n1 nor n3 can be 0.
It should be noted that two $R^5$ on the same atom (and two $R^2$ or $R^6$ on the same atom) may form a bridge.

Six-membered rings are preferred for ring B, with the preferred combination of rings A and B being tetrahydroquinolinyl.

Suitable noninterfering substituents include alkyl ($C_{1-10}$), alkenyl ($C_{2-10}$), alkynyl ($C_{2-10}$), aryl ("C"$_{5-12}$), arylalkyl, arylalkenyl, or arylalkynyl, each of which may optionally contain one or more heteroatoms selected from O, S, and N and each of which may further be substituted; or optionally substituted forms of acyl, arylacyl, alkyl-alkenyl-, alkynyl- or arylsulfonyl and forms thereof which contain heteroatoms in the alkyl, alkenyl, alkynyl or aryl moieties. Other noninterfering substituents include OR, SR, $NR_2$, COOR, $CONR_2$, where R is H or alkyl, alkenyl, alkynyl or aryl as defined above. Where the substituted atom is C, the substituents may include, in addition to the substituents listed above, halo, OOCR, NROCR, where an R is H or a substituent set forth above, or may be =O.

In general, a "noninterfering substituent" is a substituent whose presence does not destroy the ability of the compound of formula I to behave as a chemokine. Specifically, the presence of the substituent does not destroy the effectiveness of the compound. Because the compounds of the present invention have been shown to inhibit HIV replication, and specifically to interact with the CXCR4 receptor, the compounds of the invention are shown to be effective in treating conditions which require modulation of CXCR4 and CCR5 mediated activity.

In other aspects, the invention is directed to pharmaceutical compositions containing at least one compound of Formula I, and to methods of ameliorating conditions that are modulated by the CXCR4 receptor or the CCR5 receptor. Such conditions include, HIV infection, diseases associated with inflammation, diseases that are associated with immunosuppression and certain tumors.

MODES OF CARRYING OUT THE INVENTION

The invention provides compounds described above of Formula I which are chemokines and thus modulators of chemokine receptors.

In more detail, the compounds bind chemokine receptors and interfere with the binding of the natural ligand thereto, and demonstrate protective effects on target cells from HIV infection. The compounds are also useful as antagonists or agonists of chemokine receptors, and are thus capable of reconstituting the immune system by increasing the level of CD4+ cells; as antagonist agents of apoptosis in immune cells, such as CD8+ cells, and neuronal cells; as antagonist agents of migration of human bone marrow B lineage cells to stromal-derived factor 1, as well as other biological activities related to the ability of these compounds to inhibit the binding of chemokines to their receptors.

Chemokine antagonists that interfere in the binding of a chemokine to its receptor are useful to reconstitute the immune system by increasing the level of CD4+ cells (Biard-Piechaczyk, et al., Immunol. Lett., 70:1-3 1999); as antagonist agents of apoptosis in immune cells, such as CD8+ cells (Herbin, et al., Nature 395: 189-193, 1998), and as antagonist agents of apoptosis in neuronal cells (Ohagen et al., J. of Virol., 73: 897-906, 1999; and Hesselgesser, et al., Curr. Biol. 8: 595-598, 1998). Chemokine receptor antagonist agents also inhibit the migration of human bone marrow B lineage cells to stromal-derived factor 1 (See, for example: E. Fedyk, et al., J of Leukocyte Biol., 66:667-783, 1999).

The invention includes pharmaceutical compositions comprising a therapeutically effective amount of a compound of Formula I along with at least one excipient, and methods of treating diseases of the human body or the bodies of other mammals with such compositions. The invention provides a method for blocking or interfering with the binding by a chemokine receptor with its natural ligand, comprising contacting of said chemokine receptor with an effective amount of the compound according to Formula I. Also included is a method of protecting target cells possessing chemokine receptors, the binding to which by a pathogenic agent results in disease or pathology, comprising administering to a mammalian subject a pharmaceutical composition comprising a therapeutically effective amount of the compound according to Formula I. The invention includes the use of a compound of Formula I in the manufacture of a medicament for the treatment of a disease in which blocking or interfering with binding of a chemokine receptor with its natural ligand is advantageous. The compound is formulated into a composition in amount corresponding to a therapeutically effective amount of a compound of Formula I.

The Invention Compounds

The invention compounds are described generally by Formula I which is reproduced below for purposes of the present discussion.

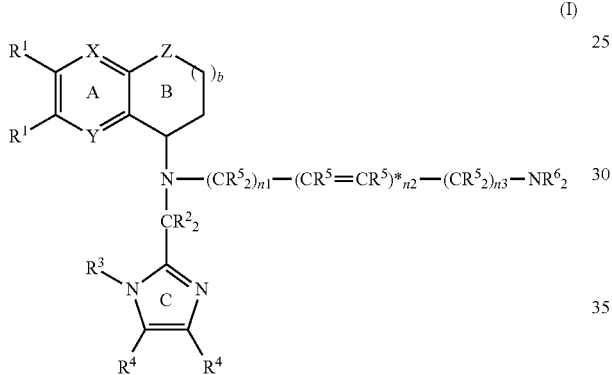

(I)

In one embodiment, the compounds of the present invention are of Formula II:

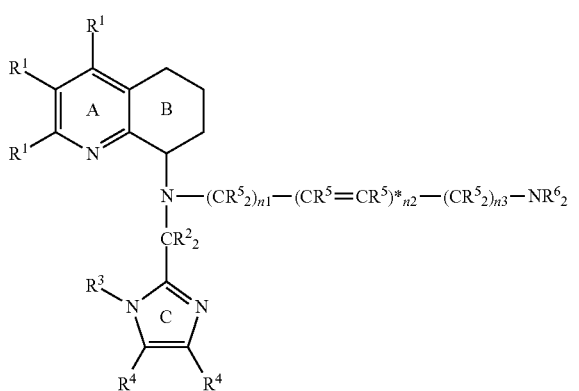

(II)

or the salts and pro-drug forms thereof, representing a subset of the compounds of Formula I wherein b is 1, X is $CR^1$, Y is N, and Z is $CR^1{}_2$ and $R^1$ to $R^6$ and n1-n3 are as defined for Formula I. In this subgenus, the preferred tetrahydroquinolyl and imidazole/benzimidazolyl methyl groups are attached to the core nitrogen.

In one embodiment, no rings are formed in the portion of the molecule containing the non-core nitrogen (that to which two $R^6$ are coupled). In another embodiment, any two $R^5$ (including two $R^5$ on the same C), two $R^6$ or one $R^5$ and one $R^6$ can be joined together via a 1-6 membered linker to form a ring. Also contemplated are rings formed by two $R^2$, by one $R^2$ and $R^3$, and by $R^3$ and one $R^4$. Exemplary rings include, inter alfa, cycloalkyl, cycloalkenyl, saturated or partially saturated heterocycles (piperidine, piperazine, pyrrolidine, pyrroline, pyrazolidine, imidazoline, morpholine, thiomorpholine, pyrazoline, tetrahydrofuran, dihydrofuran, tetrahydrothiophene, dihydrothiophene, dihydropyran, tetrahydropyran and the like). However, rings formed from two $R^5$ from other than the same C cannot be aromatic.

Thus, alternatively, the present invention provides compounds of Formulas IIIa-IIIe:

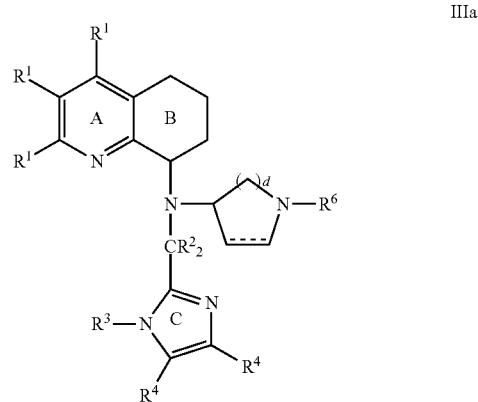

IIIa

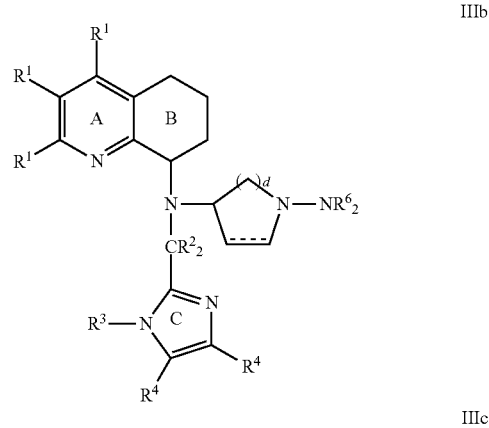

IIIb

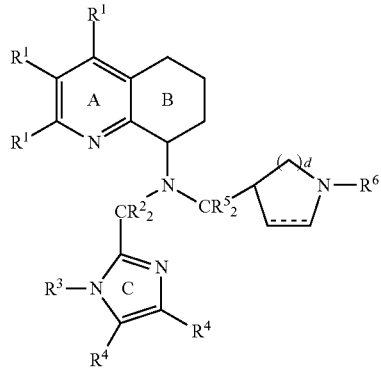

IIIc

-continued

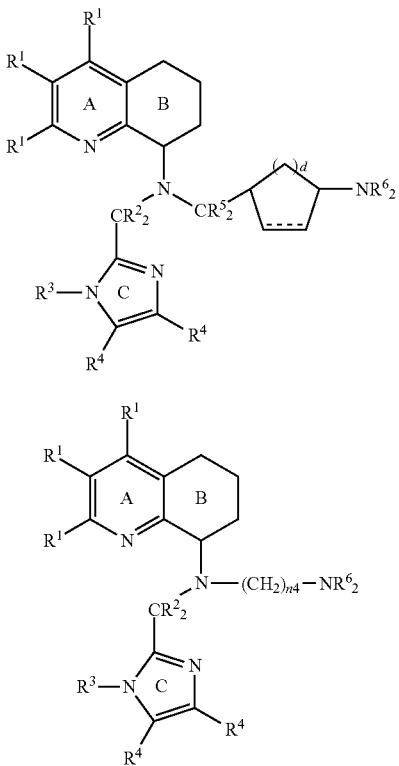

IIId

IIIe or salts or pro-drug forms thereof wherein:
d=0-3 and n4 is 2-6
especially wherein both $R^6$ are H or one $R^6$ is H and the other includes an aryl moiety, or wherein two $R^6$ form a ring.

The compounds may be supplied as "pro-drugs", that is, protected forms, which release the compound after administration to a subject. For example, the compound may carry a protective group which is split off by hydrolysis in body fluids, e.g., in the bloodstream, thus releasing active compound or is oxidized or reduced in body fluids to release the compound. A discussion of pro-drugs may be found in "Smith and Williams' Introduction to the Principles of Drug Design," H. J. Smith, Wright, Second Edition, London 1988.

The compounds may also be supplied as salts with organic or inorganic acids or bases that are nontoxic. Non-toxic in the present sense has to be considered with reference to the prognosis for the infected patient without treatment. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases include trimethylamine, triethylamine, pyridine, picoline, ethanolamine, diethanolamine, triethanolamine, dicyclohexylamine, N,N'-dibenzylethylenediamine, etc. Examples of inorganic acids include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

All of the compounds of the invention contain at least one chiral center. The invention includes mixtures of stereoisomers, individual stereoisomers, and enantiomeric mixtures, and mixtures of multiple stereoisomers. In short, the compound may be supplied in any desired degree of chiral purity.

As set forth above, the basic structure of the compounds of the invention is defined by Formula I, and particular illustrative embodiments are found in Formulas I-III. The further definition of the compounds of the invention rest on the identification of the noninterfering substituents.

Preferred embodiments of $R^1$ include H, halo, alkyl, alkoxy, $CF_3$, and the like. Preferably, all $R^1$ are H or one $R^1$ is other than H and the remaining two $R^1$ are H.

Preferred embodiments of $R^2$ include H alkyl, and alkenyl especially H and methyl.

Preferred embodiments of $R^3$ include H, alkyl, alkenyl, arylalkyl, and aryl.

Preferred embodiments of $R^4$ include H, alkyl, alkenyl and especially those wherein the two $R^4$ are bridged to form an aromatic ring so that the substituent on the core nitrogen is benzimidazolylmethyl, including a further heteroatom-containing form thereof.

Preferred embodiments of $R^5$ include H, alkyl and alkenyl, each optionally substituted, including those wherein alkyl or alkenyl substituents on a single carbon or on adjacent or nonadjacent carbons forth a saturated or unsaturated ring. This ring cannot be aromatic. Alternative embodiments for $R^5$, oximes, alkylated oximes hydroxylamine, including alkylated hydroxylamine, halo and the like.

Preferred embodiments of $R^6$ include H, arylalkyl, arylsulfonyl, including those wherein one or more nitrogen atoms is present in the ring, and including fused ring aryl groups such as indolyl. Also preferred for $R^6$ are heteroatom containing groups such as guanidyl groups carboxyl and carbamino groups, amides, arylsulfonic acids and aryl acyl substituents, again including aryl groups which comprise one or more nitrogens, alkenyl, cycloalkyl, carboxyl, and optionally substitutes, alkyl and alkenyl moieties, including those that are substituted by alcohols or amines are also preferred. Two $R^6$ may form a saturated, unsaturated or aromatic ring, optionally including one or more N, O and/or S. An $R^5$ and an $R^6$ or two $R^6$ may also constitute a shared alkylene or alkenylene bridge to obtain the saturated or unsaturated ring, which may, be aromatic. In all cases ($R^5$+$R^5$ or $R^5$+$R^6$ or $R^6$+$R^6$), the shared alkylene or alkenylene substituent may include one or more heteroatoms such as N, S or O.

It is preferred, that only 1-3, preferably 1-2 of the $R^5$ groups be other than hydrogen. In one embodiment, all $R^5$ are hydrogen, in another embodiment, one pair of $R^5$ is a shared alkylene, alkenylene, or such moieties which include a heteroatom.

Examples of optionally substituted alkyl groups include methyl, ethyl, propyl, etc. and including cycloalkyls such as cyclopropyl, cyclobutyl, cyclopentyl, cyclohexyl, cycloheptyl, etc.; examples of optionally substituted alkenyl groups include allyl, crotyl, 2-pentenyl, 3-hexenyl, 2-cyclopentenyl, 2-cyclohexenyl, 2-cyclopentenylmethyl, 2-cyclohexenylmethyl, etc.; $C_{1-6}$ alkyl and alkenyl are preferred.

Examples of halogen include fluorine, chlorine, bromine, iodine, etc., with fluorine and chlorine preferred.

Examples of optionally substituted hydroxyl and thiol groups include optionally substituted alkyloxy or alkylthio (e.g., $C_{1-10}$ alkyl) such as methyl, ethyl, propyl, isopropyl, butyl, isobutyl, sec-butyl, tert-butyl, pentyl, cyclopropyl, cyclobutyl, cyclopentyl, cyclohexyl, cycloheptyl, etc.); an optionally substituted arylalkyloxy or arylalkylthio (e.g., phenyl-$C_{1-4}$ alkyl, e.g., benzyl, phenethyl, etc.). Where there are two adjacent hydroxyl or thiol substituents, the heteroatoms may be connected via an alkylene group such as $O(CH_2)_nO$ and $S(CH_2)_nS$ (where n=1-5). Examples include methylenedioxy, ethylenedioxy, etc. Oxides of thio-ether groups such as sulfoxides and sulfones are also envisioned.

Examples of optionally substituted hydroxyl groups also include optionally substituted $C_{2-4}$alkanoyl (e.g., acetyl, propionyl, butyryl, isobutyryl, etc.), $C_{1-4}$ alkylsulfonyl (e.g., methanesulfonyl, ethanesulfonyl, etc.) and an optionally substituted aromatic and heterocyclic carbonyl group including benzoyl, pyridinecarbonyl etc.

Substituents on optionally substituted amino groups may bind to each other to form a cyclic amino group (e.g., 5- to 6-membered cyclic amino, etc. such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g., fluorine, chlorine, bromine, iodine, etc.), nitro, cyano, hydroxy group, thiol group, amino group, carboxyl group, an optionally halogenated $C_{1-4}$ alkyl (e.g., trifluoromethyl, methyl, ethyl, etc.), an optionally halogenated $C_{1-4}$ alkoxy (e.g., methoxy, ethoxy, trifluoromethoxy, trifluoroethoxy, etc.), $C_{2-4}$ alkanoyl (e.g., acetyl, propionyl, etc.), $C_{1-4}$ alkylsulfonyl (e.g., methanesulfonyl, ethancsulfonyl, etc.) the number of preferred substituents are 1 to 3.

An amino group may also be substituted once or twice (to form a secondary or tertiary amine) with a group such as an optionally substituted alkyl group including $C_{1-10}$alkyl (e.g., methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$ alkyl, alkenyl and cycloalkyl are preferred. The amine group may also be optionally substituted with an aromatic or heterocyclic group, aralkyl (e.g., phenyl$C_{1-4}$ alkyl) or heteroalkyl for example, phenyl, pyridine, phenylmethyl (benzyl), phenethyl, pyridinylmethyl, pyridinylethyl, etc. The heterocyclic group may be a 5 or 6 membered ring containing 1-4 heteroatoms.

An amino group may be substituted with an optionally substituted $C_{2-4}$ alkanoyl, e.g., acetyl, propionyl, butyryl, isobutyryl etc., or a $C_{1-4}$alkylsulfonyl (e.g., methanesulfonyl, ethanesulfonyl, etc.) or a carbonyl or sulfonyl substituted aromatic or heterocyclic ring, e.g., benzenesulfonyl, benzoyl, pyridinesulfonyl, pyridinecarbonyl etc. The heterocycles are as defined above.

Examples of optionally substituted carbonyl groups, or sulfonyl groups include optionally substituted forms of such groups formed from various hydrocarbyls such as alkyl, alkenyl and 5- to 6-membered monocyclic aromatic group (e.g., phenyl, pyridyl, etc.), as defined above.

Utility and Administration

The invention is directed to compounds of Formula I that modulate chemokine receptor activity. Chemokine receptors include but are not limited to CCR-1, CCR-2, CCR-3, CCR-4, CCR-5, CXCR-3, and CXCR-4.

In one embodiment, the invention provides compounds of Formula I that demonstrate protective effects on target cells from HIV infection by binding specifically to the chemokine receptor thus affecting the binding of a natural ligand to the CCR-5 and/or CXCR-4 of a target cell.

In another embodiment, the compounds of the present invention are useful as agents which affect chemokine receptors, such as CCR-1, CCR-2, CCR-3, CCR-4, CCR-5, CXCR-3, CXCR-4 where such chemokine receptors have been correlated as being important mediators of many inflammatory as well as immunoregulatory diseases.

Other diseases that are also implicated with chemokines as mediators include angiogenesis, and tumorigenesis such as brain, and breast tumors. Thus, a compound that modulates the activity of such chemokine receptors is useful for the treatment or prevention of such diseases.

The term "modulators" as used herein is intended to encompass antagonist, agonist, partial antagonist, and or partial agonist, i.e., inhibitors, and activators. In one embodiment of the present invention, compounds of Formula I demonstrate a protective effect against HIV infection by inhibiting the binding of HIV to a chemokine receptor such as CCR-5 and/or CXCR-4, of a target cell. Such modulation is obtained by a method which comprises contacting a target cell with an amount of the compound which is effective to inhibit the binding of the virus to the chemokine receptor.

Compounds that inhibit chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myastenia gravis, juvenile onset diabetes; glomerulonephritiS, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition compounds that activate or promote chemokine receptor function are used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva *migrans (Ancylostoma braziliense, Ancylostoma caninum)*; the malaria-causing protozoan *Plasmodium vivax*, Human cytomegalovirus, *Herpesvirus saimiri*, and Kaposi's sarcoma herpesvirus, also known as human herpesvirus 8, and poxvirus *Moluscum contagiosum*.

Compounds of the present invention may be used in combination with any other active agents or pharmaceutical compositions where such combined therapy is useful to modulate chemokine receptor activity and thereby prevent and treat inflammatory and immunoregulatory diseases.

The compounds may further be used in combination with one or more agents useful in the prevention or treatment of HIV. Examples of such agents include:

(1) nucleotide reverse transcriptase inhibitor such as tenofovir disoproxil fumarate; lamivudine/zidovudine; abacavir/lamivudine/zidovudine; emtricitabine; amdoxovir; alovudine; DPC-817; SPD-756; SPD-754; GS7340; ACH-126,443 (beta)-L-F d4C; didanosine, zalcitabine, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, TMC-125; DPC-083; capravarine; calanolide A; SJ-3366 series, etc.;

(3) protease inhibitors such as saquinavir, lopinavir/ritonavir, atazanavir, fosamprenavir, tipranavir, TMC-114, DPC-684, indinavir, nelfinavir, amprenavir, palinavir, lasinavir, etc.;

(4) entry inhibitors such as T-20; T-1249; PRO-542; PRO-140; TNX-355; BMS-806 series; and 5-Helix;

(5) CCR5-receptor inhibitors such as Sch-C (or SCH351125); Sch-D, and SCH350634; TAK779; UK 427,857 and TAK 449;

(6) Integrase inhibitors such as L-870,810; GW-810781 (S-1360); and (7) Budding inhibitors such as PA-344; and PA-457.

Combinations of compounds of the present invention with HIV agents is not limited to (1), (2), and or (3), but includes combination with any agent useful for the treatment of HIV. Combinations the compounds of the invention and other HIV agents may be administered separately or in conjunction. The administration of one agent may be prior to, concurrent to, or subsequent to the administration of other agent(s).

Like the compounds of the present invention, AMD3100 is an antagonist with the CXCR4 chemokine receptor (Gerlach, et al., *J. Biol. Chem.* (2001) 276:14153-14160). These compounds interfere with the binding of bone marrow stromal cell derived SDF-1 with CXCR4 on stem cells which leads to the release of hematopoietic stem cells from bone marrow into the circulation (Broxmeyer, et al., *Blood* (2001) 98:811 a (Abstract)). In a Phase 1 study at the University of Washington, Seattle, a single dose of 80 µg/kg of AMD-3100 resulted in a WBC count of 17,000/µl and a peak 6-fold increase in circulating CD34+ progenitor/stem cells at the 6 hour time point (Liles, et al., *Blood* (2001) 98:737a (Abstract)). In another recent study mice were injected with rhG-CSF and recombinant rat Stern Cell Factor (rrSCF) in order to mobilize large numbers of bone marrow stem cells into the circulation and then we induced a heart attack. The combination of rrSCF and rhG-CSF provides a peak number of circulating stem cells after 5 daily injections. At 27 days post surgery there was a 68% improvement in survival in the treated group versus the controls. At this time the dead tissue was replaced with regenerating myocardium and all functional parameters tested were improved compared with controls (Orlic, et al., *PNAS* (2001) 98:10344-10349).

Thus, the compounds of the invention are useful to stimulate the production and proliferation of stem cells and progenitor cells.

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in *Smith and Williams Introduction to the Principles of Drug Design*, Smith, H. J.; Wright, 2$^{nd}$ ed., London (1988).

The compounds of the invention, as they are polyamines, may be administered prepared in the forms of their acid addition salts or metal complexes thereof. Suitable acid addition salts include salts of inorganic acids that are biocompatible, including HCl, HBr, sulfuric, phosphoric and the like, as well as organic acids such as acetic, propionic, butyric and the like, as well as acids containing more than one carboxyl group, such as oxalic, glutaric, adipic and the like. Typically, at physiological pH, the compounds of the invention will be in the forms of the acid addition salts. Particularly preferred are the hydrochlorides. In addition, when prepared as purified forms, the compounds may also be crystallized as the hydrates.

The compounds of the invention may be administered as sole active ingredients, as mixtures of various compounds of formula (1), and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, growth related oncogene or chemotherapy and the like.

The compounds of the invention may be formulated for administration to animal subject using commonly understood formulation techniques well known in the art. Formulations which are suitable for particular modes of administration and for compounds of the type represented by those of formula (I) may be found in *Remington's Pharmaceutical Sciences*, latest edition, Mack Publishing Company, Easton, Pa.

Preferably, the compounds are administered by injection, most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Besides injection, other routes of administration may also be used. The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The formulation and route of administration chosen will be tailored to the individual subject, the nature of the condition to be treated in the subject, and generally, the judgment of the attending practitioner.

Suitable dosage ranges for the compounds of formula (1) vary according to these considerations, but in general, the compounds are administered in the range of about 0.1 µg/kg-5 mg/kg of body weight; preferably the range is about 1 µg/kg-300 µg/kg of body weight; more preferably about 10 µg/kg-100 µg/kg of body weight. For a typical 70-kg human subject, thus, the dosage range is from about 0.7 µg-350 mg; preferably about 700 µg-21 mg; most preferably about 700 µg-7 mg. Dosages may be higher when the compounds are administered orally or transdermally as compared to, for example, i.v. administration.

The compounds may be administered as a single bolus dose, a dose over time, as in i.v. or transdermal administration, or in multiple dosages.

In addition to direct administration to the subject, the compounds of formula (1) can be used in ex vivo treatment protocols to prepare cell cultures which are then used to replenish the blood cells of the subject. Ex vivo treatment can be conducted on autologous cells harvested from the peripheral blood or bone marrow or from allografts from matched donors. The concentration of the compound or compounds of formula (1) alone or in combination with other agents, such as macrophage inflammatory protein is a matter of routine optimization.

Subjects that will respond favorably to the method of the invention include medical and veterinary subjects generally, including human patients. Among other subjects for whom the methods of the invention is useful are cats, dogs, large animals, avians such as chickens; and the like. In general, any subject who would benefit from an elevation of progenitor cells and/or stem cells, or whose progenitor cells and/or stem cells are desirable for stem cell transplantation are appropriate for administration of the invention method.

Typical conditions which may be ameliorated or otherwise benefited by stimulation of hematopoiesis, include hematopoietic disorders, such as aplastic anemia, leukemias, drug-induced anemias, and hematopoietic deficits from chemotherapy or radiation therapy. The compounds of the invention are also useful in enhancing the success of transplantation during and following immunosuppressive treatments as well as in effecting more efficient wound healing and treatment of bacterial inflammation, and for treating subjects who are immuno-compromised or whose immune system is otherwise impaired. Typical conditions which are ameliorated or otherwise benefited by hematopoiesis stimulation include those subjects who are infected with a retrovirus and more specifically who are infected with human immunodeficiency virus (HIV). The compounds of the invention thus target a broad spectrum of conditions for which elevation of progenitor cells and/or stem cells in a subject would be beneficial or, where harvesting of progenitor cells and/or stem cell for subsequent stem cell transplantation or transfusion would be beneficial.

The invention compounds are also administered to regenerate myocardium by mobilizing bone marrow stem cells.

The compounds according to the present invention may be administered by oral, intramuscular, intraperitoneal, intravenous, intracisternal injection or infusion, subcutaneous injection, transdermal or transmucosal administration or by implant. They may also be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention are used to treat animals, including mice, rats, horses, cattle, sheep, dogs, cats, and monkeys. The compounds of the invention are also effective for use in humans.

EXAMPLES

The intermediates 8-hydroxy-5,6,7,8-tetrahydroquinoline and 8-amino-5,6,7,8-tetrahydroquinoline were prepared according to the procedures described in Bridger et al. PCT Patent Application WO 00/56729. The intermediate N'-(1H-benzimidazol-2-ylmethyl)-N'-(5,6,7,8-tetrahydro-8-quinolinyl)-1,4-benzenedimethanamine was prepared as described by Bridger et al, U.S. Patent Applications US Ser. No. 60/232,891, U.S. Ser. No. 60/234,510. The intermediate 1-N-tert-butoxycarbonyl-2-chloromethylbenzimidazole was prepared as described by An, H.; Wang, T.; Mohan, V.; Griffey, R. H.; Cook, P. D. Tetrahedron 1998, 54, 3999-4012.

GENERAL SYNTHESIS PROCEDURES

General Procedure for N-Alkylation of (1-tert-butoxycarbonyl-1H-Benzimidazol-2-ylmethyl)-(5,6,7,8-tetrahydro-quinolin-8-yl)-amine with Mesylates or Alkyl Chlorides To a solution of (1-tert-butoxycarbonyl-1H-Benzimidazol-2-ylmethyl)-(5,6,7,8-tetrahydro-quinolin-8-yl)-amine (or amine) (1-1.4 equivalents), N,N,-diisopropylethylamine (or $K_2CO_3$) (1.5-2 equivalents) and KT (0.05-0.16 equivalent) in $CH_3CN$ (concentration ~0.1-0.2 M) was added the mesylate or alkyl chloride (such as 1-N-tert-butoxycarbonyl-2-chloromethylbenzimidazole) (1-1.4 equivalents) and the mixture stirred at 50-70° C. for 3-25 hours, as monitored by analytical thin layer chromatography. The reaction mixture was cooled, diluted with $CH_2Cl_2$ (10 mL/mmol amine) and poured into either saturated aqueous $NaHCO_3$ or brine (10 mL/mmol alcohol). The phases were separated and the aqueous phase extracted with $CH_2Cl_2$ (3×10 mL/mmol amine). The combined organic phases were dried ($Na_2SO_4$ or $MgSO_4$) and concentrated under reduced pressure. The crude material was purified by chromatography to afford the desired N-alkylated product.

General Procedure A: Direct Reductive Amination with $NaBH_3CN$

To a stirred solution of the amine (1 equivalent) in anhydrous methanol (concentration ~0.1 M), at room temperature, was added the carbonyl compound (~1-2 equivalents) in one portion. Once the carbonyl had dissolved (~5 minutes), $NaBH_3CN$ (~2-4 equiv.) was added in one portion and the resultant solution was stirred at room temperature. The solvent was removed under reduced pressure and $CH_2Cl_2$ (20 mL/mmol of amine) and brine or 1.0 M aqueous NaOH (10 mL/mmol amine) were added to the residue. The phases were separated and the aqueous phase was extracted with $CH_2Cl_2$ (3×10 mL/mmol amine). The combined organic phases were dried ($Na_2SO_4$) and concentrated under reduced pressure. The crude material was purified by chromatography.

General Procedure B: Direct Reductive Amination with $NaBH(OAc)_3$ or $NaBH_4$

To a stirred solution of the amine (1 equivalent) in $CH_2Cl_2$ (concentration ~0.2 M), at room temperature, was added the carbonyl compound (~1-2 equivalents), glacial acetic acid (0-2 equivalents) and $NaBH(OAc)_3$ (~1.5-3 equivalents) and the resultant solution stirred at room temperature. The reaction mixture was poured into either saturated aqueous $NaHCO_3$ or 1.0 M aqueous NaOH (10 mL/mmol amine). The phases separated and the aqueous phase extracted with $CH_2Cl_2$ (3×10 mL/mmol amine). The combined organic phases were dried ($Na_2SO_4$) and concentrated under reduced pressure. The crude material was purified by chromatography.

Similarly, to a stirred solution of the amine (1 equivalent) in anhydrous MeOH (concentration ~0.1 M), at room temperature, was added the carbonyl compound (1 equivalent). The resultant solution was stirred at room temperature or heated to reflux for 4-24 hours. $NaBH_4$ (1-2 equivalents) was added and the resultant mixture stirred at room temperature for ~20 minutes. The reaction mixture was concentrated, dissolved in CH$_2$Cl$_2$, washed consecutively with saturated aqueous NaHCO$_3$ and saturated aqueous NaCl. The aqueous layers were extracted with CH$_2$Cl$_2$ (2×) and the combined organic extracts were dried (MgSO$_4$) and concentrated.

General Procedure C: Reaction of Alcohols with Methanesulfonyl Chloride

To a stirred solution of the alcohol (1 equivalent) and Et$_3$N (1.5-2 equivalents) in CH$_2$Cl$_2$ (or THF) (concentration ~0.1 M) at room temperature (or 0° C.) was added methanesulfonyl chloride (~1.5 equivalents) and the reaction stirred at room temperature for 0.5-1, h. The reaction mixture was poured into either saturated aqueous NaHCO$_3$ or saturated NH$_4$Cl (10 mL/mmol alcohol). The phases were separated and the aqueous phase extracted with CH$_2$Cl$_2$ (3×10 mL/mmol amine). The combined organic phases were dried (Na$_2$SO$_4$) and concentrated under reduced pressure. The crude material was either purified by chromatography or used without further purification in the N-alkylation step.

General Procedure D: Salt Formation Using Saturated HBr(G) in Acetic Acid

To a solution of the free base in glacial acetic acid (2 mL) was added, a saturated solution of HBr(g) in acetic acid (2 mL). A large volume of ether (25 mL) was then added to precipitate a solid, which was allowed to settle to the bottom of the flask and the supernatant solution was decanted. The solid was washed by decantation with ether (3×25 mL) and the remaining traces of solvent were removed under vacuum. For additional purification, the solid was dissolved in methanol and re-precipitated with a large volume of ether. Washing the solid with ether by decantation, followed by drying of the solid in vacuo (0.1 Torr) gave the desired compound.

INTERMEDIATES

Preparation of 4-hydroxymethylbenzaldehyde

Terephthaldicarboxaldehyde (30.02 g, 224 mmol), methanol (200 mL), palladium on activated carbon, (10%, 3.02 g) and 2-(aminomethyl)pyridine (2.3 mL, 22 mol, 0.01 mol equiv) were combined in a hydrogenation vessel and the reaction mixture was shaken on a Parr hydrogenator for 2.5 hours at 40 psi of hydrogen. The mixture was filtered through celite, the cake washed with methanol and the solvent from the eluent removed in vacuo. Purification of the crude product by column chromatography on silica gel (EtOAc/Hexanes, 1:1) afforded the title compound (23.8 g, 78%) as a white solid. $^1$H NMR (CDCl$_3$) δ 4.80 (s, 2H), 7.53 (d, 2H, J=9 Hz), 7.87 (d, 2H, J=9 Hz), 10.00 (s, 1H).

Preparation of 6,7-Dihydro-5H-quinolin-8-one

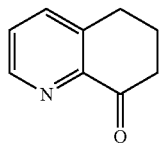 [SMILES: O=C1CCCc2cccnc21]

To a stirred solution of 8-hydroxy-5,6,7,8-tetrahydroquinoline (13.96 g, 93.6 mmol) in dry CH$_2$Cl$_2$ (400 mL) was added activated manganese dioxide (85% purity, 82.22 g, 804 mmol). The resulting heterogeneous mixture was stirred 18 h, at which point the black slurry was filtered through a cake of celite and washed with CH$_2$Cl$_2$ (3×50 mL). The combined washings were concentrated to afford 11.27 g (82%) of the title compound as a pale yellow solid, which was used in subsequent reactions without further purification. $^1$H NMR (CDCl$_3$) δ 2.17-2.25 (m, 2H), 2.82 (t, 2H, J=7 Hz), 3.04 (t, 2H, J=6 Hz), 7.37 (dd, 1H, J=9, 6 Hz), 7.66 (dd, 1H, J=9, 1 Hz), 8.71 (dd, 1H, J=6, 1 Hz); $^{13}$C NMR (CDCl$_3$) δ 22.2, 28.6, 39.2, 126.6, 137.3, 140.5, 147.6, 148.6, 196.5. ES-MS m/z 148 (M+H).

Preparation of (1-tert-butoxycarbonyl-1H-Benzimidazol-2-ylmethyl)-(5,6,7,8-tetrahydro-quinolin-8-yl)-amine

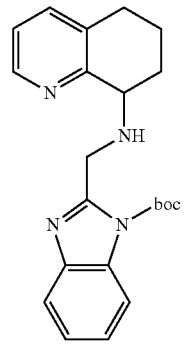

Using General Procedure for N-Alkylation: To a stirred solution of 8-amino-5,6,7,8-tetrahydroquinoline (7.34 g, 49.6 mmol) in dry CH$_3$CN (250 mL) was added 1-N-tert-butoxycarbonyl-2-chloromethylbenzimidazole (13.22 g, 49.6 mmol), N,N-diisopropylethylamine (15.5 mL, 89.2 mmol) and potassium iodide (0.41 g, 8.2 mmol) and the mixture was stirred at 60° C. for 3.5 h. Purification by column chromatography on silica gel (CH$_2$Cl$_2$/MeOH, 99:1 followed by 97:3 and 96:4) gave the intermediate amine (6.38 g, 34%) as an orange, sticky oil. $^1$H NMR (CDCl$_3$) δ 1.76 (s, 9H), 1.81-2.10 (m, 2H), 2.25-2.37 (m, 1H), 2.72-2.89 (m, 2H), 3.77-3.84 (m, 1H), 4.39 (d, 1H, J=15.0 Hz), 4.56 (d, 1H, J=15.0 Hz), 7.00-7.06 (m, 1H), 7.27-7.37 (m, 1H), 7.64-7.74 (m, 1H), 7.90-7.96 (d, 2H, J=8.1 Hz), 8.34 (d, 1H, J=3.0 Hz); $^{13}$C NMR (CDCl$_3$) δ 20.13, 28.48, 29.00, 29.20, 47.15, 56.89, 86.20, 115.32, 120.28, 122.06, 124.43, 124.85, 132.77, 133.74, 137.01, 142.44, 147.10, 149.22, 154.90, 157.72; ES-MS m/z 279 (M+H-boc).

Preparation of (1H-Benzimidazol-2-ylmethyl)-(5,6,7,8-tetrahydro-quinolin-8-yl)-amine

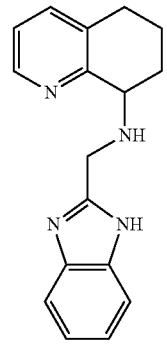 [SMILES: c1cnc2c(c1)CCCC2NCc1nc2ccccc2[nH]1]

To a stirred solution of (2-aminomethyl)benzimidazole dihydrochloride hydrate (5.96 g, 27.1 mmol) in dry MeOH (225 mL) was added 6,7-dihydro-5H-quinolin-8-one (3.99 g, 27.1 mmol) and the mixture stirred at room temperature for 69 h. To the resultant solution was added sodium borohydride (2.06 g, 54.2 mmol) in two portions and the mixture stirred for 1.5 h. The reaction mixture was concentrated in vacuo and diluted with CH$_2$Cl$_2$ (150 mL). The organic layer was washed with saturated aqueous sodium bicarbonate (200 mL), the aqueous layer extracted with CH$_2$Cl$_2$ (2×50 mL) and the combined organic layers dried (Na$_2$SO$_4$), filtered, and concentrated in vacuo. Purification by column chromatography on silica gel (CH$_2$Cl$_2$/MeOH, 99:1 followed by 98:2 and 96:4) gave the intermediate amine (3.59 g, 50%) as a yellow foam. $^1$H NMR (CDCl$_3$) δ 1.66-1.90 (m, 3H), 1.91-2.00 (m, 1H), 2.00-2.17 (m, 1H), 2.33-2.69 (br m, 1H), 3.88-3.96 (m, 1H), 4.37 (d, 1H, J=3.0 Hz), 7.18-7.26 (m, 4H), 7.48 (d, 1H, J=6.0 Hz), 7.58-7.78 (br m, 1H), 8.55-8.58 (m, 1H); $^{13}$C NMR (CDCl$_3$) δ 19.66, 29.12, 30.24, 46.62, 57.28, 122.21, 122.83, 133.55, 138.07, 146.98, 156.17, 157.73.

Preparation of 1-(2-trimethylsilylethoxymethyl)-2-formyl-benzimidazole

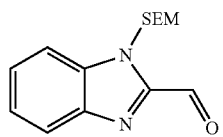 [SMILES: C[Si](C)(C)CCOCn1c(C=O)nc2ccccc21]

To a stirred solution of 2-hydroxymethylbenzimidazole (31.94, 0.216 mol) in dry DMF (450 mL) was added N,N-diisopropylethylamine (90 mL, 0.52 mol) followed by 2-(trimethylsily)ethoxymethyl chloride (75% in pentane, 55 g, 0.25 mol) and the mixture heated to 60° C. for 2 h. The mixture was cooled to room temperature, concentrated under reduced pressure and partitioned between EtOAc (400 mL) and distilled water (700 mL). The phases were separated and the aqueous layer extracted with EtOAc (2×200 mL). The combined organic extracts were washed with brine (1×400 mL), dried (Na$_2$SO$_4$), filtered and concentrated under reduced pressure. Purification of the crude oil by column chromatography on silica gel (4% MeOH/CH$_2$Cl$_2$) afforded the desired 1-(2-trimethylsilylethoxymethyl)-2-hydroxymethylbenzimidazole (26.28 g, 44%) as a yellow oil. $^1$H NMR (CDCl$_3$) δ −0.04 (s, 9H), 0.89 (t, 2H, J=9 Hz), 1.75 (br s, 1H), 3.55 (t, 2H, J=9 Hz), 4.94 (s, 2H), 5.58 (s, 2H), 7.26-7.30 (m, 2H), 7.43-7.45 (m, 1H), 7.70-7.72 (m, 1H).

To a stirred solution of the alcohol from above (26.58 g, 0.096 mol) in dry CH$_2$Cl$_2$ (450 mL) was added activated MnO$_2$ (<5 micron, ~85%, 93 g, 0.91 mol) and the suspension stirred at room temperature overnight. The mixture was filtered through Celite© (175 g) and the cake was washed with CH$_2$Cl$_2$. The solvent was removed from the eluent under reduced pressure and the resultant residue purified by column chromatography on silica gel (3% MeOH/CH$_2$Cl$_2$) to provide the title aldehyde (14.41 g, 55%) as a pale yellow oil. $^1$H NMR (CDCl$_3$) δ −0.07 (s, 9H), 0.90 (t, 2H, J=9 Hz), 3.56 (t, 2H, J=9 Hz), 6.04 (s, 2H), 7.43-7.51 (m, 2H), 7.66 (d, 1H, J=9 Hz), 7.95 (d, 1H, J=9 Hz), 10.13 (s, 1H); $^{13}$C NMR (CD$_3$OD) δ −1.19, 17.94, 66.62, 73.30, 112.22, 122.51, 124.64, 127.43, 136.62, 143.11, 146.39, 185.10; ES-MS m/z (M+H);

Preparation of [1-(2-trimethylsilylethoxymethyl)-1H-Benzimidazol-2-ylmethyl]-(5,6,7,8-tetrahydro-quinolin-8-yl)-amine

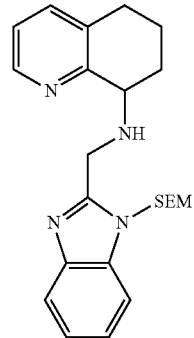 [SMILES: C[Si](C)(C)CCOCn1c(CNC2CCCc3cccnc32)nc2ccccc21]

To a stirred solution of 1-(2-trimethylsilylethoxymethyl)-2-formyl-benzimidazole (4.26 g, 15.4 mmol) in dry MeOH (50 mL) was added a solution of 8-amino-5,6,7,8-tetrahydroquinoline (2.20 g, 14.8 mmol) in dry MeOH (20 mL) and the mixture stirred for 2 h at room temperature under an argon atmosphere. The reaction mixture was concentrated under reduced pressure and the resultant residue analyzed by $^1$H NMR to confirm imine formation. The residue was re-dissolved in dry MeOH (80 mL) and to the resultant solution was added sodium borohydride (1.17 g, 30.8 mmol). The mixture was stirred for 5 h, concentrated in vacuo and diluted with CH$_2$Cl$_2$ (100 mL) and saturated aqueous NaHCO$_3$ (125 mL). The phases were separated and the aqueous layer was extracted with CH$_2$Cl$_2$ (2×75 mL). The combined organic extracts were dried (Na$_2$SO$_4$), filtered and concentrated in vacuo. Purification of the crude material through a plug of silica gel (CH$_2$Cl$_2$/MeOH 96:4) afforded the desired amine (5.91 g, 98%) as an orange oil. $^1$H NMR (CDCl$_3$) δ −0.07 (s, 9H), 0.90 (t, 2H, J=9 Hz), 1.72-1.83 (m, 2H), 1.95-2.01 (m, 1H), 2.76-2.85 (m, 2H), 3.54 (t, 2H, J=9 Hz), 4.33 (m, 2H), 5.68 (d, 1H, J=12 Hz), 5.75 (d, 1H, J=12 Hz), 7.05-7.09 (m, 1H), 7.25-7.30 (m, 2H), 7.38 (d, 1H, J=9 Hz), 7.44-7.46 (m, 1H), 7.71-7.73 (m, 1H), 8.36-8.38 (m, 1H).

Preparation of N$^1$-(5,6,7,8-tetrahydro-quinolin-8-yl)-N$^1$-[1-(2-trimethylsilanyl-ethoxymethyl)-1H-benzoimidazol-2-ylmethyl]-butane-1,4-diamine

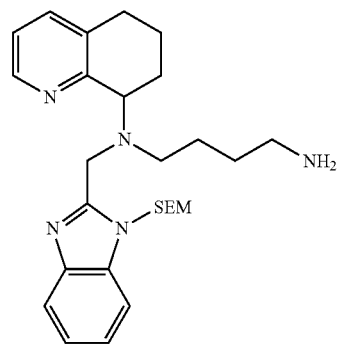 [SMILES: C[Si](C)(C)CCOCn1c(CN(CCCCN)C2CCCc3cccnc32)nc2ccccc21]

A solution of (5,6,7,8-tetrahydro-quinolin-8-yl)-[1-(2-trimethylsilanyl-ethoxymethyl)-1H-benzoimidazol-2-ylmethyl]-amine (2.86 g, 6.93 mmol), bromobutyronitrile (1.4 mL, 14.1 mmol) and DIPEA (3.0 mL, 17.2 mmol) in CH$_3$CN (75 mL) was stirred at 80° C. for 2 days. KI (54 mg, 0.33 mmol) was added and the resultant mixture stirred at 80° C. for 20 hours. The mixture was concentrated under reduced pressure, diluted with CH$_2$Cl$_2$ (100 mL) and washed with saturated aqueous NaCl. The aqueous layer was extracted with CH$_2$Cl$_2$ (3×50 mL) and the combined organic extracts were dried (MgSO$_4$), filtered and concentrated under reduced pressure. Purification by column chromatography on silica gel (CH$_2$Cl$_2$/MeOH, 80:1) afforded the desired nitrile (1.19 g, 36%) as an orange syrup. $^1$H NMR (CDCl$_3$) δ −0.09 (s, 9H), 0.81-0.87 (m, 2H), 1.56-1.75 (m, 2H), 1.87-2.07 (m, 2H), 2.01-2.26 (m, 1H), 2.29-2.53 (m, 2H), 2.62-2.86 (m, 4H), 3.35-3.48 (m, 2H), 3.95-4.01 (m, 1H), 4.16 (d, 1H, J=13.8 Hz), 4.26 (d, 1H, J=13.5 Hz), 5.76 (d, 1H, Jr=11.1 Hz), 6.17 (d, 1H, J=11.0 Hz), 7.04 (dd, 1H, J=7.5, 4.5 Hz), 7.22-7.28 (m, 2H), 7.32 (d, 1H, J=7.5 Hz), 7.43-7.46 (m, 1H), 7.69-7.73 (m, 1H), 8.46 (dd, 1H, J=4.8, 1.3 Hz).

4-{(5,6,7,8-Tetrahydro-quinolin-8-yl)-[1-(2-trimethylsilanyl-ethoxymethyl)-1H-benzoimidazol-2-ylmethyl]-amino}-butyronitrile (840 mg, 1.75 mmol) was dissolved in NH$_3$ saturated MeOH (15 mL), treated with Raney nickel (excess), and placed under 45 psi H$_2$ on a Parr shaker for 16 hours. The mixture was diluted with MeOH and filtered through Celite. The cake was washed with MeOH and the combined filtrate was concentrated under reduced pressure. Purification by column chromatography on silica gel (CH$_2$Cl$_2$/MeOH/NH$_4$OH, 50:2:1) afforded the desired amine (560 mg, 66%) as an orange syrup. $^1$H NMR (CDCl$_3$) δ −0.10 (s, 9H), 0.81 (t, 2H, J=9.0 Hz), 1.43-1.50 (m, 4H), 1.59-1.76 (m, 1H), 1.86-2.09 (m, 2H), 2.08-2.23 (m, 1H), 2.56-2.71 (m, 4H), 2.76-2.85 (m, 2H), 2.41 (t, 2H, J=8.1 Hz), 4.07-4.12 (m, 3H), 5.71 (d, 1H, J=11.1 Hz), 7.37 (d, 1H, J=11.1 Hz), 7.05 (dd, 1H, J=7.5, 4.5 Hz), 7.21-7.29 (m, 2H), 7.34 (d, 1H, J=6.6 Hz), 7.40-7.45 (m, 1H), 7.71-7.76 (m, 1H), 8.58 (d, 1H, J=3.6 Hz).

Preparation of N$^1$-(1H-Benzimidazol-2-ylmethyl)-N$^1$-(5,6,7,8-tetrahydro-quinolin-8-yl)-cyclohexane-trans-1,4-diamine

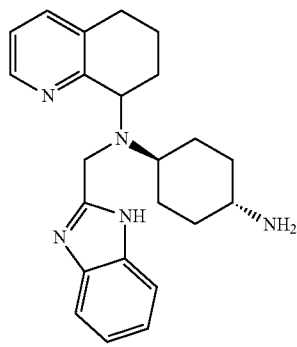 [SMILES: N[C@H]1CC[C@H](N(Cc2nc3ccccc3[nH]2)C2CCCc3cccnc32)CC1]

Preparation of N-tert-butoxycarbonyl-trans-1,4-cyclohexanediamine (Smith, J.; Liras, J. L.; Schneider, S. E.; Anslyn, E J. Org. Chem. 1996, 61, 8811-8818)

To a solution of trans-1,4-cyclohexanediamine (8.01 g, 70.1 mmol) in CHCl$_3$ (230 mL) was added a solution of di-tert-butyl dicarbonate (7.67 g, 35.1 mmol) in CHCl$_3$ (50 mL) via syringe pump over a period of 6 hours. The resultant white suspension was stirred at room temperature for an additional 10 hours then concentrated in vacuo and diluted with CH$_2$Cl$_2$ (100 mL) and saturated aqueous Na$_2$CO$_3$ (100 mL). The layers were separated and the organic layer was washed saturated aqueous Na$_2$CO$_3$ (2×30 mL). The combined organic phases were dried (Na$_2$SO$_4$), filtered and concentrated to give the title compound (5.30 g, 71% based on Boc$_2$O) as a white solid.

Following General Procedure for Reductive Amination Using NaBH(OAc)$_3$: To a stirred solution of 6,7-dihydro-5H-quinolin-8-one (3.04 g, 20.65 mmol) and N-tert-butoxycarbonyl-trans-1,4-cyclohexanediamine (4.42 g, 20.65 mmol) in dry THF (100 mL) was added AcOH (3 mL) and NaBH(OAc)$_3$ (5.69 g, 26.85 mmol) and the mixture stirred overnight at room temperature. Purification by column chromatography on silica gel (CH$_2$Cl$_2$/MeOH/NR$_4$OH, 96:4:0 then 94:5:1) afforded the desired amine (3.79 g, 53%) as a white solid.

Example 1

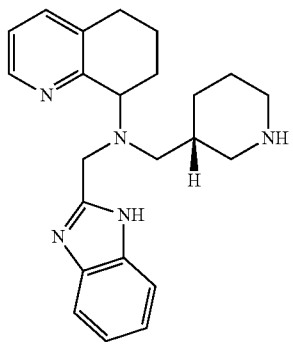 [SMILES: c1cnc2c(c1)CCCC2N(Cc1nc2ccccc2[nH]1)C[C@@H]1CCCNC1]

Compound 1: Preparation of (1H-Benzimidazol-2-ylmethyl)-piperidin-3-ylmethyl-(5,6,7,8-tetrahydro-quinolin-8-yl)-amine (hydrobromide salt)

Preparation of 3-formyl-N-tert-butoxycarbonyl-piperidine

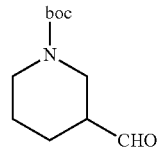

To a solution of 3-piperidinemethanol (0.544 g, 4.72 mmol) in THF (20 mL) was added di-tert-butyl dicarbonate (1.01 g, 4.63 mmol) and the mixture stirred at room temperature for 2 hours. The mixture was concentrated under reduced pressure and the resultant crude product was used without further purification in the next reaction.

To a suspension of the alcohol from above (~4.7 mmol) and powdered 3 Å molecular sieves (1.17 g) in CH$_2$Cl$_2$ (10 mL) was added 4-methylmorpholine N-oxide (0.672 g, 5.74 mmol) and tetrapropylammonium perruthenate (0.084 g, 0.24 mmol) and the mixture stirred overnight. The reaction was concentrated under reduced pressure and purified by column chromatography through a plug of silica gel (ethyl acetate/hexanes, 1:2) to afford the title compound (0.429 g, 43% over 2 steps) as a clear oil. $^{1}$H NMR (CDCl$_{3}$) δ 1.46 (br s, 9H), 1.48-1.55 (m, 1H), 1.65-1.73 (m, 2H), 1.91-1.99 (m, 1H), 2.40-2.44 (m, 1H), 3.04-3.13 (m, 1H), 3.32 (dd, 1H, J=15, 9 Hz), 3.60-3.65 (m, 1H), 3.89-3.94 (m, 1H), 9.70 (s, 1H).

Using General Procedure B: To a stirred solution of (1H-Benzimidazol-2-ylmethyl)-(5,6,7,8-tetrahydro-quinolin-8-yl)-amine (159 mg, 0.57 mmol) and 3-formyl-N-tert-butoxycarbonyl-piperidine (125 mg, 0.59 mmol) in CH$_{2}$Cl$_{2}$ (5 mL) was added NaBH(OAc)$_{3}$ (157 mg, 0.74 mmol) and the resultant mixture was stirred at room temperature for 2.5 hours. Purification of the crude material by column chromatography on silica gel (CH$_{2}$Cl$_{2}$/MeOH, 96:4) afforded the alkylated product (185 mg, 68%) as a mixture of diastereomers.

The yellow foam from above (185 mg, 0.39 mmol) oil was dissolved in CH$_{2}$Cl$_{2}$/TFA (1:1, 2 mL) and the mixture stirred overnight. The reaction was then concentrated and diluted with CH$_{2}$Cl$_{2}$ (30 mL) and 1 N NaOH (30 mL). The aqueous layer was washed with CH$_{2}$Cl$_{2}$ (2×10 mL) and the combined organic extracts were dried (Na$_{2}$SO$_{4}$), filtered and concentrated to afford the Boc-deprotected material as a mixture of diastereomers. Purification and separation of the diastereomers by radial chromatography on silica gel (1 mm plate, 50:1:1 CH$_{2}$Cl$_{2}$/MeOH/NH$_{4}$OH) afforded a top, less polar diastereomer (25 mg, 17%) and a bottom, more polar one (20 mg, 14%), both as clear foams.

Using General Procedure D: Conversion of the more polar, bottom diastereomer from above (20 mg, 0.05 mmol) to the hydrobromide salt followed by re-precipitation of the intermediate solid from methanol/ether gave COMPOUND 1 (34 mg, 97%) as a white solid. $^{1}$H NMR (D$_{2}$O) δ 0.97-1.09 (m, 1H), 1.44-1.57 (m, 1H), 1.72-1.88 (m, 2H), 1.90-2.07 (m, 2H), 2.13-2.36 (m, 4H), 2.53 (br t, 1H, J=12 Hz), 2.74-2.90 (m, 2H), 2.98-3.00 (m, 2H), 3.27-3.32 (m, 2H), 4.38 (d, 1H J=16.5 Hz), 4.48 (d, 1H J=16.5 Hz), 4.50-4.55 (m, 1H), 7.62 (dd, 2H, J=6.3, 3.3 Hz), 7.81 (dd, 2H, J=6.3, 3.3 Hz), 7.89 (dd, 1H, J=7.8, 6 Hz), 8.37 (d, 1H, J=8.1 Hz), 8.67 (d, 1H, J=5.6 Hz); $^{13}$C NMR (D$_{2}$O) δ 19.89, 20.27, 21.58, 26.64, 27.79, 31.91, 44.57, 47.09, 48.00, 54.69, 59.91, 114.34, 126.18, 127.09, 131.14, 139.59, 141.23, 148.32, 150.59, 150.76. ES-MS m/z 376 (M+H). Anal. Calcd. for C$_{23}$H$_{29}$N$_{5}$·3.0HBr·2.2H$_{2}$O: C, 41.99; H, 5.58; N, 10.65; Br, 36.44. Found: C, 42.05; H, 5.44; N, 10.50; Br, 36.40.

Example 2

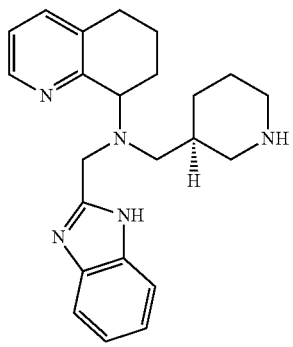 [SMILES: c1cnc2c(c1)CCCC2N(Cc1nc2ccccc2[nH]1)C[C@H]1CCCNC1]

Compound 2: Preparation of (1H-Benzimidazol-2-ylmethyl)-piperidin-3-ylmethyl-(5,6,7,8-tetrahydro-quinolin-8-yl)-amine (hydrobromide salt)

Using General Procedure D: Conversion of the top, less polar diastereomer from above (see COMPOUND 1) (25 mg, 0.07 mmol) to the hydrobromide salt followed by re-precipitation of the intermediate solid from methanol/ether gave COMPOUND 2 (39 mg, 88%) as a white solid. $^{1}$H NMR (D$_{2}$O) δ 1.07-1.19 (m, 1H), 1.54-1.68 (m, 1H), 1.74-1.90 (m, 3H), 1.97-2.07 (m, 2H), 2.13-2.22 (m, 1H), 2.30-2.43 (m, 2H), 2.52 (br t, 1H, J=12 Hz), 2.80 (td, 1H, J=13.2, 2.4 Hz), 2.92 (dd, 1H, J=13.8, 4.5 Hz), 2.98-3.00 (m, 2H), 3.32-3.36 (m, 1H), 3.61-3.65 (m, 1H), 4.38 (d, 1H J=16.5 Hz), 4.46 (d, 1H J=16.5 Hz), 4.52 (dd, 1H, J=10.5, 5.7 Hz), 7.63 (dd, 2H, J=6.3, 3.3 Hz), 7.82 (dd, 2H, 0.1=6.3, 3.3 Hz), 7.90 (dd, 1H, J=7.5, 6.3 Hz), 8.37 (d, 1H, J=7.8 Hz), 8.68 (d, 1H, J=6 Hz); $^{13}$C NMR (D$_{2}$O) δ 18.97, 19.39, 21.05, 26.03, 26.91, 31.14, 43.69, 46.67, 47.04, 54.41, 58.71, 113.46, 125.31, 126.27, 130.15, 138.77, 140.30, 147.54, 149.50, 149.74. ES-MS m/z 376 (M+H). Anal. Calcd. for C$_{23}$H$_{29}$N$_{5}$·3.0HBr·2.6H$_{2}$O: C, 41.54; H, 5.64; N, 10.53; Br, 36.04. Found: C, 41.47; H, 5.41; N, 10.22; Br, 36.19.

Example 3

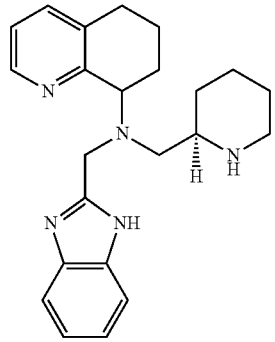 [SMILES: c1cnc2c(c1)CCCC2N(Cc1nc2ccccc2[nH]1)C[C@H]1CCCCN1]

Compound 3: Preparation of (1H-Benzimidazol-2-ylmethyl)-piperidin-2-ylmethyl-(5,6,7,8-tetrahydro-quinolin-8-yl)-amine (hydrobromide salt)

Preparation of 2-formyl-piperidine-1-carboxylic acid tert-butyl ester

To a solution of 2-piperidinemethanol (561 mg, 4.9 mmol) in dry THF (10 mL) was added di-tert-butyl dicarbonate (1.14 g, 5.2 mmol) and the mixture stirred overnight at room temperature. The reaction mixture was concentrated in vacuo to afford a colourless oil which was used in the next step without any further purification.

To a stirred solution of 2-hydroxymethyl-piperidine-1-carboxylic acid tert-butyl ester (0.737 g, 3.4 mmol) in dry CH$_{2}$Cl$_{2}$ (10 mL) was added 3 Å molecular sieves (1.03 g), N-methylmorpholine N-oxide (0.644 g, 5.5 mmol), and tetrapropylammonium perruthenate (72 mg, 0.21 mmol) and the mixture stirred at room temperature for 3 h. The reaction mixture was purified through a silica gel plug (Hexanes/EtOAc, 70:30 followed by 100:0) to afford the title aldehyde (0.500 g, 70%) as a pale yellow oil.

Using General Procedure B: To a stirred solution of 2-formyl-piperidine-1-carboxylic acid tert-butyl ester (0.163 g, 0.76 mmol) in dry CH$_2$Cl$_2$ (3.5 mL) was added (1H-benzimidazol-2-ylmethyl)-(5,6,7,8-tetrahydro-quinolin-8-yl)-amine (0.210 g, 0.76 mmol) and sodium triacetoxyborohydride (0.240 g, 1.1 mmol) and the mixture stirred overnight at room temperature. Purification by column chromatography on silica gel (CH$_2$Cl$_2$/MeOH, 98:2 followed by 96:4) gave a pale yellow foam containing a mixture of diastereomers (0.305 g).

To a stirred solution of the diastereomers (0.305 g) in dry CH$_2$Cl$_2$ (2 mL) was added trifluoroacetic acid (1 mL) dropwise and the mixture stirred at room temperature for 3.5 h. The reaction mixture was diluted with CH$_2$Cl$_2$ (10 mL) and then concentrated in vacuo. The concentrate was diluted with CH$_2$Cl$_2$ (20 mL) and extracted with 1N NaOH (30 mL). The aqueous layer was washed with CH$_2$Cl$_2$ (2×15 mL) and then the combined organic layers were dried (Na$_2$SO$_4$), filtered, and concentrated in vacuo. Purification and separation of the two diastereomers by radial chromatography on a 1 mm TLC grade silica gel plate (CH$_2$Cl$_2$/MeOH/NH$_4$OH, 100:1:1 followed by 50:1:1) afforded a less polar diastereomer (63 mg, 22%) and a more polar one (22 mg, 8%) (stereochemistry unknown), both as colourless oils.

Using General Procedure D: Conversion of the less polar distereomer from above (63 mg, 0.17 mmol) to the hydrobromide salt gave COMPOUND 3 (83 mg) as a white solid. $^1$H NMR (D$_2$O) δ 1.34-1.68 (m, 3H), 1.73-1.93 (m, 3H), 1.93-2.08 (m, 2H), 2.08-2.23 (m, 1H), 2.24-2.38 (m, 1H), 2.79 (dd, 1H, J=14.7, 9.9 Hz), 2.94-3.07 (m, 3H), 3.27 (dd, 1H, J=14.7, 9.9 Hz), 3.38-3.56 (m, 2H), 4.33 (s, 2H), 4.57 (dd, 1H, J=9.9, 5.7 Hz), 7.56-7.62 (m, 2H), 7.70-7.83 (m, 3H), 8.28 (d, 1H, J=7.8 Hz), 8.57 (d, 1H, J=4.8 Hz); $^{13}$C NMR (D$_2$O) δ 19.84, 20.28, 21.76, 22.16, 26.99, 27.83, 45.34, 47.01, 54.30, 54.82, 58.86, 114.55, 125.99, 127.08, 131.59, 140.23, 141.046, 147.96, 149.03, 149.84; ES-MS m/z 376 (M+H); Anal. Calcd. for C$_{23}$H$_{29}$N$_5$·3.0HBr·1.2H$_2$O·0.3C$_4$H$_{10}$O: C, 43.90; H, 5.69; N, 10.58; Br, 36.20. Found: C, 43.78; H, 5.47; N, 10.54; Br, 36.41.

Example 4

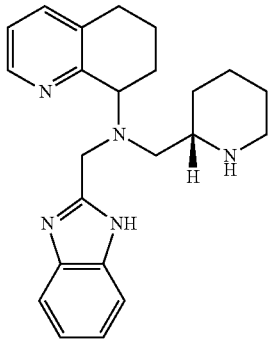 [SMILES: c1cnc2c(c1)CCCC2N(Cc1nc2ccccc2[nH]1)C[C@@H]1CCCCN1]

Compound 4: Preparation of (1H-Benzimidazol-2-ylmethyl)-piperidin-2-ylmethyl-(5,6,7,8-tetrahydro-quinolin-8-yl)-amine (hydrobromide salt)

Using General Procedure D: Conversion of the more polar distereomer from above (see COMPOUND 3) (22 mg, 0.059 mmol) to the hydrobromide salt gave COMPOUND 4 (35 mg) as a white solid. $^1$H NMR (D$_2$O) δ 1.22-1.39 (m, 1H), 1.39-1.68 (m, 2H), 1.71-1.93 (m, 3H), 2.03-2.24 (m, 3H), 2.31-2.42 (m, 1H), 2.79-2.89 (m, 1H), 2.91-3.07 (m, 3H), 3.16 (dd, 1H, J=13.8, 6.0 Hz), 3.32-3.49 (m, 2H), 4.34 (d, 1H, J=15.9 Hz), 4.43 (d, 1H, J=16.2 Hz), 4.53 (dd, 1H, J=10.2, 6.0 Hz), 7.54-7.61 (m, 2H), 7.65-7.77 (m, 3H), 8.25 (d, 1H, J=7.8 Hz), 8.49 (d, 1H, J=5.4 Hz); $^{13}$C NMR (D$_2$O) δ 20.04, 20.25, 21.54, 22.23, 27.04, 27.75, 45.22, 46.43, 54.61, 55.98, 60.69, 114.46, 125.90, 127.01, 131.66, 139.70, 140.96, 148.03, 149.70; ES-MS m/z 376 (M+H); Anal. Calcd. for C$_{23}$H$_{29}$N$_5$·3.0HBr·2.2H$_2$O: C, 41.99; H, 5.58; N, 10.65; Br, 36.44. Found: C, 42.22; H, 5.46; N, 10.47; Br, 36.23.

Example 5

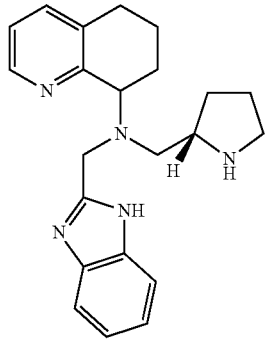 [SMILES: c1cnc2c(c1)CCCC2N(Cc1nc2ccccc2[nH]1)C[C@@H]1CCCN1]

Compound 5: Preparation of (1H-Benzimidazol-2-ylmethyl)-(S)-1-pyrrolidin-2-ylmethyl-(5,6,7,8-tetrahydro-quinolin-8-yl)-amine (hydrobromide salt)

Using General Procedure B: To a stirred solution of (1H-Benzimidazol-2-ylmethyl)-(5,6,7,8-tetrahydro-quinolin-8-yl)-amine (148 mg, 0.53 mmol) and N-tert-butoxycarbonyl-L-prolinal (110 mg, 0.55 mmol) in CH$_2$Cl$_2$ (5 mL) was added NaBH(OAc)$_3$ (146 mg, 0.69 mmol) and the resultant mixture was stirred at room temperature overnight. Purification of the crude material by radial chromatography on silica gel gel (2 mm plate, 50:1:1 CH$_2$Cl$_2$/MeOH/NH$_4$OH then 10:1:1 CH$_2$Cl$_2$/MeOH/NH$_4$OH) afforded the desired amine (73 mg, 30%) as a yellow oil.

Using General Procedure D: Conversion of the oil from above (40 mg, 0.11 mmol) to the hydrobromide salt followed by re-precipitation of the intermediate solid from methanol/ether gave COMPOUND 5 (53 mg, 73%) as a beige solid. $^1$H NMR (D$_2$O) δ 1.22-1.28 (m, 1H), 1.61-1.74 (m, 1H), 1.75-1.89 (m, 1H), 1.99-2.09 (m, 3H), 2.16-2.31 (m, 1H), 2.33-2.39 (m, 1H), 2.92 (dd, 1H, J=14.4, 9.3 Hz), 2.97-3.03 (m, 1H), 3.25 (q, 1H, J=7.2 Hz), 3.33-3.41 (m, 1H), 3.35 (td, 2H, J=7.5, 2.4 Hz), 3.86-3.96 (m, 1H), 4.34 (d, 1H, J=16.2 Hz), 4.42 (d, 1H, J=16.2 Hz), 4.59 (dd, 1H, J=10.2, 6 Hz), 7.59 (dd, 2H, J=6.3, 3.3 Hz), 7.78 (dd, 2H, J=6.3, 3.3 Hz), 7.79-7.83 (m, 1H), 8.31 (d, 1H, J=8.7 Hz), 8.60 (d, 1H, J=5.1 Hz); $^{13}$C NMR (D$_2$O) δ 19.91, 20.29, 22.88, 27.80, 28.46, 45.88, 47.28, 52.97, 58.23, 58.77, 114.47, 126.02, 127.00, 131.50, 140.22, 141.00, 147.99, 149.62, 149.98. ES-MS m/z 362 (M+H). Anal. Calcd. for C$_{22}$H$_{27}$N$_5$·3HBr·2H$_2$O·0.2C$_4$H$_{10}$O: C, 41.80; H, 5.54; N, 10.69; Br, 36.59. Found: C, 41.66; H, 5.45; N, 10.65; Br, 36.93.

Example 6

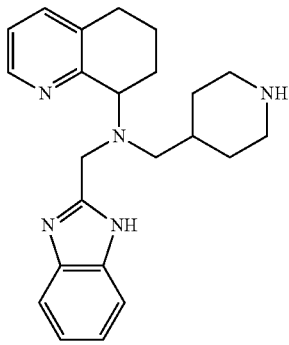 [SMILES: c1cnc2c(c1)CCCC2N(Cc1nc2ccccc2[nH]1)CC1CCNCC1]

Compound 6: Preparation of (1H-Benzimidazol-2-ylmethyl)-piperidin-4-ylmethyl-(5,6,7,8-tetrahydro-quinolin-8-yl)-amine (hydrobromide salt)

Preparation of 1-(tert-butoxycarbonyl)-piperidine-4-carboxaldehyde

To a solution of ethyl isonipecotate (0.750 g, 4.77 mmol) in THF (24 mL) was added water (1 mL) followed by di-tert-butyl dicarbonate (1.09 g, 5.00 mmol) and the resultant mixture was stirred at room temperature for one hour. The mixture was diluted with ethyl acetate (50 mL) and the organic phase was washed with brine (3×20 mL), dried (MgSO$_4$), and concentrated to provide 1.20 g (98%) of 1-(tert-butoxycarbonyl)-4-(carboethoxy)-piperidine as a colorless oil.

To a cold (−78° C.), stirred solution of the oil from above (1.20 g, 4.67 mmol) in dry THF (46 mL) was added diisobutylaluminum hydride (1.0 M in THF, 15 mL; 15 mmol). After 30 minutes, the reaction mixture was warmed to room temperature and stirred for an additional 20 minutes. Saturated aqueous NR$_4$Cl (5 mL) was added and the resultant white slurry was stirred at room temperature for 45 minutes. Solid MgSO$_4$ (5 g) was added and the mixture was filtered through Florisil.© The column was washed with ethyl acetate (200 mL). The combined eluant was concentrated under reduced pressure to provide 1.01 g (97%) of 1-(tert-butoxycarbonyl)-4-(hydroxymethyl)-piperidine as a white solid.

To a solution of the above alcohol (0.437 g, 2.03 mmol) in CH$_2$Cl$_2$ (10 mL), at room temperature, was added sequentially 3 Å molecular sieves (1.07 g), N-methylmorpholine N-oxide (0.365 g, 3.11 mmol), and tetrapropylammonium perruthenate (70 mg, 0.20 mmol). After 1 hour, the mixture was filtered through a short column of silica gel and the cake was washed with ethyl acetate. The solvent was removed from the filtrate under reduced pressure. Purification of the crude material by column chromatography on silica gel (4:1 hexanes-ethyl acetate) provided 90 mg (20%) of 1-(tert-butoxycarbonyl)-piperidine-4-carboxaldehyde as a colorless oil. $^1$H NMR (CDCl$_3$) δ 1.46 (s, 9H), 1.51-1.62 (m, 2H), 1.85-1.93 (m, 2H), 2.37-2.46 (m, 1H), 2.88-2.97 (m, 2H), 3.94-4.00 (m, 2H), 9.66 (s, 1H).

Using General Procedure B: Reaction of 1-(tert-butoxycarbonyl)-piperidine-4-carboxaldehyde (0.090 g, 0.42 mmol) and (1H-benzimidazol-2-ylmethyl)-(5,6,7,8-tetrahydro-quinolin-8-yl)-amine (0.110 g, 0.40 mmol) with NaBH(OAc)$_3$ (0.223 g, 1.05 mmol) in CH$_2$Cl$_2$ (5 mL) for 20 h followed by purification of the crude material by column chromatography on silica gel (50:1:1 CH$_2$Cl$_2$—CH$_3$OH—NH$_4$OH) provided 0.120 g (63%) of an off-white solid.

Using General Procedure D: Conversion of the off-white solid (120 mg) to the hydrobromide salt with simultaneous removal of the BOC-protecting group, followed by re-precipitation of the intermediate solid from methanol/ether, gave COMPOUND 6 (98 mg) as a white solid. $^1$H NMR (D$_2$O) δ 1.13-1.28 (m, 2H), 1.80-2.36 (m, 8H), 2.81-3.00 (m, 5H), 3.35-3.43 (m, 2H), 4.38 (d, 1H, J=16.5 Hz), 4.46 (d, 1H, J=16.5 Hz), 4.52 (dd, 1H, J=10.5, 6.0 Hz), 7.59-7.65 (m, 2H), 7.78-7.85 (m, 2H), 7.89 (dd, 1H, J=7.8, 6.0 Hz), 8.37 (d, 1H, J=8.1 Hz), 8.67 (d, 1H, J=5.7 Hz); $^{13}$C NMR (D$_2$O) δ 17.72, 18.24, 24.98 (2 carbons), 25.71, 29.64, 41.94, 42.05, 45.79, 54.96, 57.53, 112.25, 124.08, 125.04, 128.97, 137.47, 139.09, 146.24, 148.75 (2 carbons); ES-MS m/z 376 (M+H). Anal. Calcd. for C$_{23}$H$_{29}$N$_5$.3.1HBr.1.8H$_2$O: C, 41.93; H, 5.46; N, 10.63; Br, 37.60. Found: C, 42.07; H, 5.55; N, 10.28; Br, 37.43.

Example 7

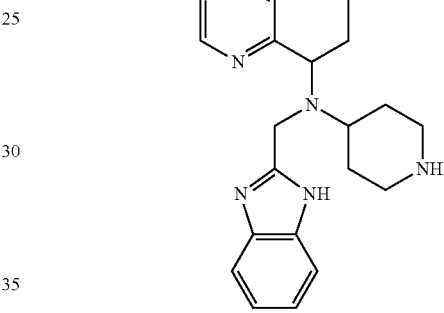

Compound 7: (1H-Benzimidazol-2-ylmethyl)-piperidin-4-yl-(5,6,7,8-tetrahydro-quinolin-8-yl)-amine (hydrobromide salt)

Preparation of 4-(5,6,7,8-Tetrahydro-quinolin-8-ylamino)-piperidine-1-carboxylic acid tert-butyl ester

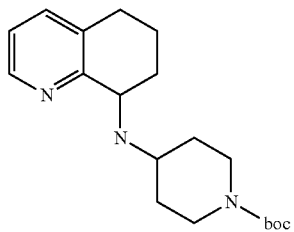

Using general procedure B: Reaction of Boc-4-piperidone (641 mg, 3.22 mmol 5,6,7,8-Tetrahydro-quinolin-8-ylamine (476 mg, 3.22 mmol), sodium triacetoxyborohydride (1.36 g, 6.44 mmol) and acetic acid (0.25 mL) in THF (25 mL) at room temperature under N$_2$ for 20 min afforded the title compound (1.05 g, 98%) as a yellow oil.

The 4-(5,6,7,8-Tetrahydro-quinolin-8-ylamino)-piperidine-1-carboxylic acid tert-butyl ester (240 mg, 0.72 mmol), 2-Chloromethyl-benzimidazole-1-carboxylic acid tert-butyl ester (212 mg, 0.79 mmol), DIPEA (0.20 mL, 1.58 mmol), and KI (6 mg, 0.036 mmol) were heated to 60° C. in CH$_3$CN (7 mL) overnight under N$_2$. The reaction mixture was concentrated in vacuo, diluted with ethyl acetate, washed with NH$_4$Cl (aq), NaCl (aq), and dried (MgSO$_4$). Evaporation of the solvent and purification of the residue by flash chromatography on silica gel (CH$_2$Cl$_2$—MeOH—NH$_4$OH 98:1:1) afforded the title compound (331 mg, 82%) as a white foam.

Using General Procedure D: Conversion of the foam from above (100 mg, 0.18 mmol) to the hydrobromide salt using an acetic acid/HBr solution, followed by re-precipitation of the salt from diethyl ether gave COMPOUND 7 as a white solid. $^1$H NMR (CD$_3$OD) mixture of isomers δ 1.94-2.15 (m, 3H), 2.19-2.26 (m, 2H), 2.41-2.51 (m, 2H), 2.60-2.65 (m, 1H), 3.03-3.14 (m, 4H), 3.18-3.28 (m, 1H), 3.41-3.52 (m, 2H), 4.61 (d, 2H, J=3.9 Hz), 4.67-4.72 (m, 1H), 7.58-7.63 (m, 2H), 7.86-7.94 (m, 3H), 8.37 (d, 1H, J=8.1 Hz), 8.91 (d, 1H, J=5.7 Hz); $^{13}$C NMR (CD$_3$OD) mixture of isomers δ 25.71, 29.19, 31.67, 32.47, 33.30, 48.62, 48.76, 48.93, 60.93, 63.27, 118.96, 130.51, 131.51, 136.12, 144.91, 145.36, 152.51, 156.45, 156.63; ES-MS m/z 362.3 (M+H); Anal. Calcd. For (C$_{22}$H$_{27}$N$_5$).3.0(HBr).1.8 (H$_2$O).0.4(C$_4$H$_{10}$O): C, 42.54; H, 5.69; N, 10.51; Br, 35.98. Found C, C, 42.61; H, 5.47; N, 10.46; Br, 35.93

Example 8

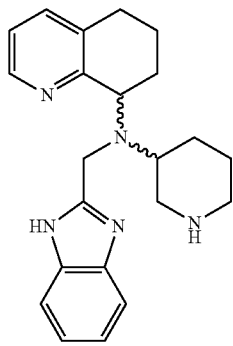

Compound 8: Preparation of (1H-benzimidazol-2-ylmethyl)-piperidin-3-yl-(5,6,7,8-tetrahydroquinolin-8-yl)amine (hydrobromide salt)

Preparation of tert-butyl 3-hydroxy-1-piperidinecarboxylate

To a 0° C. solution of 3-hydroxypiperidine (2.12 g, 21.0 mmol) in EtOH (20 mL) was added NEt$_3$ (5.6 mL, 40.2 mmol), followed by a solution of (Boc)$_2$O (5.03 g, 23.0 mmol) in EtOH (20 mL). The reaction stirred at room temperature for one hour, and then the solvent was evaporated under reduced pressure. The residue was dissolved in EtOAc (50 mL) and washed with 10% citric acid (50 mL), water (50 mL) and brine (50 mL). The organic solution was dried (MgSO$_4$), filtered and evaporated under reduced pressure to afford the crude product as a white solid (3.55 g, 17.6 mmol, 84%). $^1$H NMR (CDCl$_3$) δ 1.45 (s, 9H), 1.48-1.52 (m, 2H), 1.72-1.78 (m, 1H), 1.84-1.94 (m, 1H), 2.12 (br. s, 1H), 3.01-3.12 (m, 2H), 3.46-3.59 (m, 1H), 3.65-3.78 (m, 2H).

Preparation of tert-butyl 3-oxo-1-piperidinecarboxylate

To a 0° C. solution of the alcohol (2.01 g, 10.0 mmol) in CH$_2$Cl$_2$ (50 mL) was added crushed 3 Å molecular sieves (5.26 g), 4-methylmorpholine-N-oxide (1.76 g, 15.0 mmol) and tetrapropylammonium perruthenate (357 mg, 1.02 mmol). The resulting black solution was stirred at 0° C. for 20 minutes, then at room temperature for a further one hour. The mixture was filtered through a plug of silica, rinsed with EtOAc and the concentrated filtrate was purified by flash chromatography on silica gel (EtOAc/hexane, 1:1) to afford the ketone as a yellow liquid (1.49 g, 7.48 mmol, 75%). $^1$H NMR (CDCl$_3$) δ 1.46 (s, 9H), 1.98 (ddd, 2H, J=12.3, 6.5, 6.0 Hz), 2.47 (t, 2H, J=6.5 Hz), 3.58 (t, 2H, J=6.0 Hz), 4.00 (s, 2H).

Preparation of tert-butyl 3-(5,6,7,8-tetrahydroquinolin-8-ylamino)-piperidine-1-carboxylate To a solution of 8-amino-5,6,7,8-tetrahydroquinoline (1.00 g, 6.75 mmol) in MeOH (30 mL) was added a solution of the ketone (1.40 g, 7.03 mmol) in MeOH (20 mL). The reaction stirred at room temperature for 16 hours. NaBH$_4$ (848 mg, 22.4 mmol) was added and the mixture stirred for a further 45 minutes. The solvent was evaporated under reduced pressure, and the residue was taken up into CH$_2$Cl$_2$ (50 mL) and washed with saturated aqueous NaHCO$_3$ (10 mL) and brine (10 mL). The organic solution was dried (MgSO$_4$), filtered and evaporated under reduced pressure. Purification by flash column chromatography on silica gel (CH$_2$Cl$_2$/MeOH/NH$_4$OH, 9:1:0.5) gave a brown oil which, following a second purification (CH$_2$Cl$_2$/MeOH, 97:3) afforded the amine as a yellow oil (638 mg, 1.92 mmol, 28%). $^1$H NMR (CDCl$_3$) δ 1.22-1.40 (m, 2H), 1.47 (s, 9H), 1.65-1.81 (m, 314), 1.91-2.04 (m, 2H), 2.11-2.25 (m, 2H), 2.44-2.65 (m, 1H), 2.65-2.90 (m, 4H), 3.88-4.05 (m, 2H), 4.05-4.31 (m, 1H), 7.06 (dd, 1H, J=7.7, 4.7 Hz), 7.36 (d, 1H, J=7.8 Hz), 8.37 (d, 1H, J=4.3 Hz).

Preparation of Compound 8

A mixture of this amine (247 mg, 0.75 mmol), tert-butyl 2-chloromethyl-benzimidazole-1-carboxylate (238 mg, 0.89 mmol), DIPEA (0.20 mL, 1.2 mmol) and KI (14 mg, 0.08 mmol) in CH$_3$CN (4 mL) was heated at 60° C. for 20 hours. After cooling, the reaction was diluted with saturated aqueous NaHCO$_3$ (10 mL) and extracted with CH$_2$Cl$_2$ (25 mL×3). The organic solution was dried (MgSO$_4$), filtered and evaporated under reduced pressure. The resulting dark red oil was purified by flash column chromatography on silica gel (CH$_2$Cl$_2$/MeOH, 9:1) giving an orange foam. A second purification (CH$_2$Cl$_2$/MeOH, 19:1) gave the tertiary amine as an orange solid (83 mg, 20%).

This material was stirred in TFA (1.5 mL) at room temperature for 2 hours, and then the excess solvent was evaporated under reduced pressure. The residue was taken up into CH$_2$Cl$_2$ (20 mL) and washed with saturated aqueous NaHCO$_3$ (10 mL). The aqueous solution was extracted with CH$_2$Cl$_2$ (20 mL×2) and the combined organic extracts were dried (MgSO$_4$), filtered and concentrated under reduced pressure. Purification by flash column chromatography on silica gel (CH$_2$Cl$_2$/MeOH/NH$_4$OH, 89:10:1) gave an approximately 2:1 mixture of diastereomers of the free amine as a yellow foam (21 mg, 0.06 mmol, 41%).

To a solution of this material (20 mg, 0.055 mmol) in glacial HOAc (1 mL) was added a saturated HBr in HOAc solution (0.5 mL). The reaction stirred at room temperature for 40 minutes. Et$_2$O (2 mL) was added, the suspension was stirred and the solvent was decanted. The precipitate was washed with Et$_2$O (1 mL×5), then dried under reduced pressure giving COMPOUND 8 as a yellow solid (26 mg, 0.038 mmol, 70%). $^1$H NMR (D$_2$O) δ 1.61-1.94 (m, 3H), 1.98-2.11 (m, 1H), 2.11-2.17 (m, 2H), 2.17-2.49 (m, 1H), 2.80-2.92 (m, 1H), 2.93-3.01 (m, 2H), 3.09-3.25 (m, 2H), 3.31-3.40 (m, 1H), 3.82-3.90 (m, 1H), 4.43 (d, 1H, J=16.5 Hz), 4.55 (d, 1H, J=16.5 Hz), 4.55-4.65 (m, 1H), 7.53-7.60 (m, 2H), 7.67-7.77 (m, 3H), 8.20 (d, 0.67H, J=7.8 Hz), 8.23 (d, 0.33H, J=7.8 Hz), 8.51 (d, 0.67H, J=5.7 Hz), 8.55 (d, 0.33H, J=5.7 Hz). $^{13}$C NMR (D$_2$O) δ 20.5 and 20.6, 21.9 and 22.1, 24.2 and 24.5, 26.8 and 27.5, 28.0, 43.2, 44.0, 46.2 and 47.0, 58.5 and 59.2, 114.4, 125.8, 126.8, 131.7, 139.5, 140.5 and 141.6, 147.7 and 147.8, 150.6 and 151.2. ES-MS m/z 362 (M+H). Anal. Calcd. for C$_{22}$H$_{27}$N$_5$.3.1HBr.1.8H$_2$O.0.3C$_4$H$_{10}$O: C, 41.78; H, 5.55; N, 10.50; Br, 37.14. Found: C, 41.48; H, 5.44; N, 10.44; Br, 37.50.

Example 9

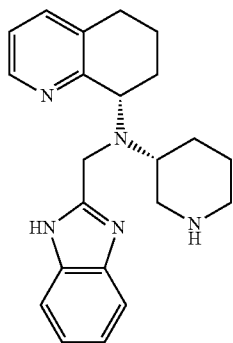 [SMILES: c1cnc2c(c1)CCC[C@@H]2N(Cc1nc2ccccc2[nH]1)[C@@H]1CCCNC1]

Compound 9: Preparation of (1H-benzimidazol-2-ylmethyl)-piperidin-3-yl-(5,6,7,8-tetrahydroquinolin-8-yl)amine (hydrobromide salt)

The free base was prepared by N-alkylation and TFA deprotection, as described previously (see COMPOUND 8). The crude material was purified by flash column chromatography on silica gel (CH$_2$Cl$_2$/MeOH/NH$_4$OH, 9:1:0.1) giving 18 mg of a single diastereomer (0.05 mmol, 5%) as a brown foam, along with 51 mg of the mixture of diastereomers (0.14 mmol, 14%) as a yellow foam.

The single diastereomer (18 mg, 0.05 mmol) was dissolved into HOAc (1 mL) and saturated HBr in HOAc (0.5 mL) was added. The solution stirred at room temperature for 40 minutes. Et$_2$O (2 mL) was added, the mixture was stirred and the solvent was decanted. The precipitate was washed with Et$_2$O (1 mL×5) and dried under reduced pressure at 90° C., giving the diastereomer COMPOUND 9 as a yellow powder (22 mg, 0.03 mmol, 67%). $^1$H NMR (D$_2$O) δ 1.57-1.74 (m, 1H), 1.75-1.90 (m, 2H), 2.03-2.12 (m, 1H), 2.12-2.24 (m, 2H), 2.31-2.47 (m, 2H), 2.80-2.92 (m, 1H), 2.92-3.00 (m, 2H), 3.06-3.20 (m, 2H), 3.29-3.38 (m, 1H), 3.47-3.57 (m, 1H), 4.43-4.53 (m, 1H), 4.48 (d, 1H, J=16.4 Hz), 4.57 (d, 1H, J=16.4 Hz), 7.51-7.58 (m, 2H), 7.68-7.76 (m, 3H), 8.20 (d, 1H, J=7.5 Hz), 8.53 (d, 1H, J=5.7 Hz). $^{13}$C NMR (D$_2$O) δ 20.5, 21.9, 24.2, 26.8, 27.5, 43.4, 43.9, 47.0, 55.5, 59.2, 114.4, 125.8, 126.6, 132.0, 139.7, 140.5, 147.6, 150.9, 151.1. ES-MS m/z 362 (M+H). Anal. Calcd. for C$_{22}$H$_{27}$N$_5$.3.0HBr.1.8 H$_2$O.0.3C$_4$H$_{10}$O: C, 42.29; H, 5.60; N, 10.63; Br, 36.38. Found: C, 42.27; H, 5.60; N, 10.62; Br, 36.42.

Example 10

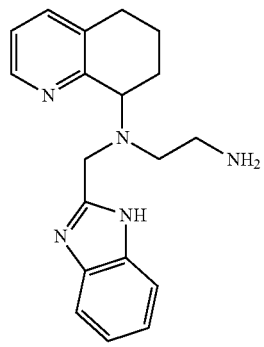 [SMILES: NCCN(Cc1nc2ccccc2[nH]1)C1CCCc2cccnc21]

Compound 10: Preparation of N$^1$-(1H-Benzimidazol-2-ylmethyl)-N$^1$-(5,6,7,8-tetrahydro-quinolin-8-yl)-ethane-1,2-diamine (hydrobromide salt)

Using General Procedure B: Reaction of N-(tert-butoxycarbonyl)-2-amino-acetaldehyde (0.112 g, 0.71 mmol) and (1-tert-butoxycarbonyl-1H-Benzimidazol-2-ylmethyl)-(5,6,7,8-tetrahydro-quinolin-8-yl)-amine (0.189 g, 0.50 mmol) with NaBH(OAc)$_3$ (0.215 g, 1.01 mmol) in CH$_2$Cl$_2$ (5 mL) for 18 h followed by purification of the crude material by radial chromatography on silica gel (2 mm plate, 100:1:1 CH$_2$Cl$_2$—CH$_3$OH—NH$_4$OH) provided a white solid (0.167 g, 64%).

Using General Procedure D: Conversion of the white solid (167 mg) to the hydrobromide salt with simultaneous removal of the BOC-protecting groups, followed by re-precipitation of the intermediate solid from methanol/ether, gave COMPOUND 10 (173 mg) as a white solid. $^1$H NMR (D$_2$O) δ 1.75-1.89 (m, 1H), 1.98-2.11 (m, 1H), 2.15-2.22 (m, 1H), 2.38-2.43 (m, 1H), 2.91-3.02 (m, 3H), 3.16-3.31 (m, 3H), 4.40 (d, 1H, J=16.5 Hz), 4.52-4.67 (m, 2H), 7.58-7.63 (m, 2H), 7.76-7.84 (m, 3H), 8.32 (d, 1H, J=7.8 Hz), 8.59 (d, 1H, J=5.4 Hz); $^{13}$C NMR (D$_2$O) δ 20.30, 20.44, 27.68, 37.75, 47.12, 49.11, 60.07, 114.40, 126.08, 127.11, 131.17, 139.78, 140.92, 148.23, 150.09, 150.17; ES-MS m/z 322 (M+H). Anal. Calcd. for C$_{19}$H$_{23}$N$_5$.3.0 HBr.1.1H$_2$O: C, 39.08; H, 4.87; N, 11.99; Br, 41.05. Found: C, 39.19; H, 4.98; N, 11.76; Br, 40.89.

Example 11

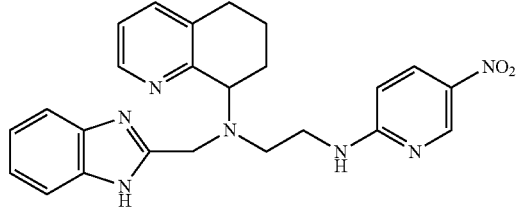 [SMILES: O=[N+]([O-])c1ccc(NCCN(Cc2nc3ccccc3[nH]2)C2CCCc3cccnc32)nc1]

Compound 11: Preparation of N¹-(1H-Benzimidazol-2-ylmethyl)-N²-(5-nitro-pyridin-2-yl)-N¹-(5,6,7,8-tetrahydro-quinolin-8-yl)-ethane-1,2-diamine (hydrobromide salt)

Using General Procedure B: To a solution of 6,7-dihydro-5H-quinolin-8-one (294 mg, 2 mmol) in MeOH (6 mL) was added 2-(2-aminoethylamino)-5-nitropyridine (368 mg, 2.02 mmol) and the resultant solution was stirred at room temperature for 3 hours. Solid NaBH₄ (168 mg, 4.44 mmol) was added to the solution and the mixture was stirred at room temperature for an additional 45 minutes. The resultant crude yellow foam (639 mg) was used without further purification in the next step.

Using the General procedure for N-alkylation: To a solution of the material from above (639 mg), potassium iodide (5 mg, 0.030 mmol) and N,N-diisopropylethylamine (0.70 mL, 4.0 mmol) in CH₃CN (10 mL) was added N-(tert-butoxycarbonyl)-2-chloromethylbenzimidazole (prepared as described by An, H.; Wang, T.; Mohan, V.; Griffey, R. H.; Cook, P.D *Tetrahedron* 1998, 54, 3999-4012) (527 mg, 1.98 mmol) and the reaction stirred at 60° C. for 6.5 h. Purification of the crude brown foam by flash chromatography on silica gel (99:1 CH₂Cl₂/MeOH then 98:2) gave the alkylated product, 2-{[[2-(5-Nitro-pyridin-2-ylamino)-ethyl]-(5,6,7,8-tetrahydro-quinolin-8-yl)-amino]-methyl}-benzimidazole-1-carboxylic acid tert-butyl ester, (645 mg, 60%) as a yellow foam.

Using General Procedure D: Conversion of the free base from above (84 mg, 0.16 mmol) to the hydrobromide salt, followed by re-precipitation of the intermediate solid from methanol/ether, gave COMPOUND 11 (87 mg, 78%) as a yellow solid. ¹H NMR (D₂O) δ 1.81-1.88 (m, 1H), 2.06-2.17 (m, 2H), 2.38-2.43 (m, 1H), 2.88-2.96 (m, 1H), 3.01-3.03 (m, 2H), 3.14-3.21 (m, 1H), 3.39-3.57 (m, 2H), 4.37 (d, 1H, J=16.8 Hz), 4.57 (d, 1H, J=16.8 Hz), 4.61-4.66 (m, 1H), 6.49 (d, 1H, J=9.6 Hz), 7.42 (dd, 2H, J=6, 3 Hz), 7.57 (dd, 2H, J=6, 3 Hz), 7.86-7.93 (m, 2H), 8.33 (br s, 1H), 8.37 (d, 1H, J=7.8 Hz), 8.70 (d, 1H, J=6.6 Hz); ¹³C NMR (D₂O) δ 20.41, 20.79, 27.80, 41.02, 49.30, 50.55, 62.07, 110.03, 110.77, 114.22, 126.02, 126.66, 130.60, 133.75, 135.36, 139.77, 140.95, 143.67, 148.28, 150.42, 151.28, 179.57; ES-MS m/z 444 (M+H). Anal. Calcd. for C₂₄H₂₅N₇O₂.2.9HBr.2.4 H₂O: C, 39.96; H, 4.57; N, 13.59; Br, 32.12. Found: C, 40.17; H, 4.47; N, 13.20; Br, 32.03.

Example 12

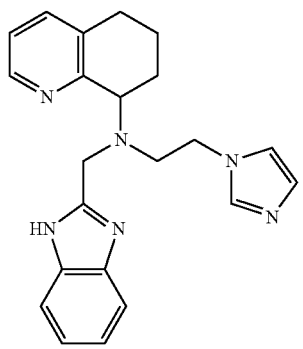 [SMILES: c1cnc2c(c1)CCCC2N(CCn1ccnc1)Cc1nc2ccccc2[nH]1]

Compound 12: Preparation of (1H-benzimidazol-2-ylmethyl)-(2-imidazol-1-yl-ethyl)-(5,6,7,8-tetrahydro-quinolin-8-yl)-amine Preparation of toluene-4-sulfonic acid 2-tert-butoxycarbonylamino-ethyl ester

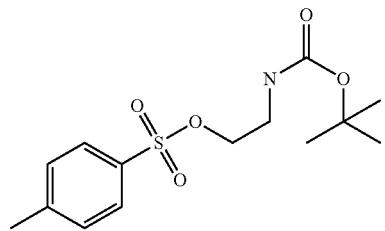 [SMILES: Cc1ccc(S(=O)(=O)OCCNC(=O)OC(C)(C)C)cc1]

Tosyl chloride (1.50 g, 7.87 mmol) was added to a solution of (2-hydroxy-ethyl)-carbamic acid tert-butyl ester (0.84 g, 5.2 mmol) and Et₃N (1.23 mL, 8.82 mmol) in CH₂Cl₂ (26 mL), and the solution was stirred at room temperature for 17 h. The solution was washed with H₂O (15 mL), and the aqueous phase was extracted with CH₂Cl₂ (10 mL). The combined organic phases were dried (MgSO₄) and concentrated in vacuo. Purification of the crude material by column chromatography on silica gel (20% EtOAc/hexanes) gave yellow crystals (1.29 g, 79%). ¹H NMR (CDCl₃) δ 1.41 (s, 9H), 2.45 (s, 3H), 3.38 (m, 2H), 4.07 (m, 2H), 4.82 (br s, 1H), 7.35 (d, 2H, J=8.1 Hz), 7.79 (d, 2H, J=8.1 Hz).

(2-Imidazol-1-yl-ethyl)-carbamic acid tert-butyl ester

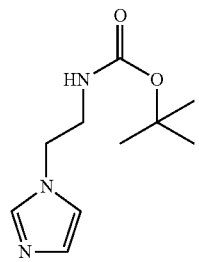

A solution of imidazole (253 mg, 3.72 mmol) in DMF (2 mL) was added to a suspension of NaH (60% in mineral oil, 164 mg, 4.10 mmol) in DMF (8 mL), and the mixture was stirred at room temperature for 45 minutes. A solution of toluene-4-sulfonic acid 2-tert-butoxycarbonylamino-ethyl ester (1.29 g, 4.09 mmol) in DMF (6 mL) was added, and the mixture was stirred at room temperature for 16 h then concentrated in vacuo. The residue was partitioned between H₂O (25 mL) and EtOAc (25 mL), and the aqueous phase was extracted with EtOAc (25 mL). The combined organic phases were dried (MgSO₄) and concentrated in vacuo. Purification of the crude material by column chromatography on silica gel (200:5:1-100:5:1 CH₂Cl₂/MeOH/NH₄OH) gave a colourless oil (224 mg, 29%). ¹H NMR (CDCl₃) δ 1.44 (s, 9H), 3.43 (m, 2H), 4.08 (m, 2H), 4.64 (br s, 1H), 6.92 (s, 1H), 7.09 (s, 1H), 7.46 (s, 1H).

(2-Imidazol-1-yl-ethyl)-(5,6,7,8-tetrahydro-quinolin-8-yl)-amine

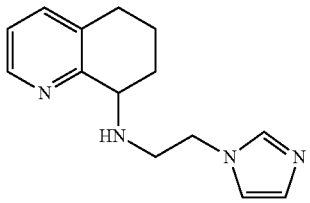 [SMILES: c1cnc2c(c1)CCCC2NCCn1ccnc1]

A solution of (2-imidazol-1-yl-ethyl)-carbamic acid tert-butyl ester (224 mg, 1.06 mmol) in 1:1 TFA/CH$_2$Cl$_2$ (4 mL) was stirred at room temperature for 1 h then concentrated in vacuo. The residue was dissolved in 1 N NaOH(aq) (10 mL) then saturated with sodium chloride and extracted with CHCl$_3$ (5×15 mL). The combined organic extracts were dried (MgSO$_4$) and concentrated in vacuo to give a yellow oil (55 mg).

Using General Procedure B: To a stirred solution of the amine from above (55 mg), 6,7-dihydro-5H-quinolin-8-one (73 mg, 0.50 mmol), and AcOH (0.030 mL, 0.52 mmol) in THF (5 mL) was added NaBH(OAc)$_3$ (315 mg, 1.49 mmol) and the mixture was stirred at room temperature for 2 h. The crude material was dissolved in saturated HBr/AcOH (2 mL) and stirred at room temperature for 15 minutes. The solution was made basic with 10 N NaOH(aq) and extracted with CH$_2$Cl$_2$ (3×15 mL). The combined organic extracts were dried (MgSO$_4$) and concentrated in vacuo. Purification of the crude material by column chromatography on silica gel (200:5:1 CH$_2$Cl$_2$/MeOH/NH$_4$OH) gave a yellow oil (92 mg, 77%). $^1$H NMR (CDCl$_3$) δ 1.73 (m, 2H), 1.91-2.13 (m, 2H), 2.76 (m, 2H), 3.12 (m, 2H), 3.78 (m, 1H), 4.11 (m, 2H), 7.01 (s, 1H), 7.08 (m, 2H), 7.38 (d, 1H, Jr=7.5 Hz), 7.56 (s, 1H), 8.37 (d, 1H, J=3.9 Hz).

2-{[(2-Imidazol-1-yl-ethyl)-(5,6,7,8-tetrahydro-quinolin-8-yl)-amino]-methyl}-benzimidazole-1-carboxylic acid tert-butyl ester

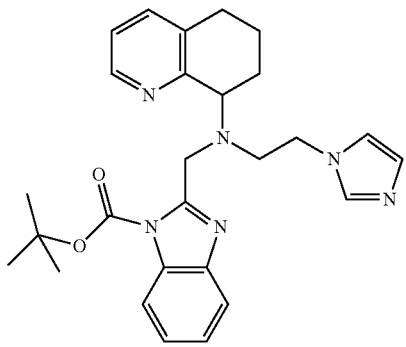 [SMILES: CC(C)(C)OC(=O)n1c(CN(CCn2ccnc2)C2CCCc3cccnc32)nc2ccccc21]

A mixture of (2-imidazol-1-yl-ethyl)-(5,6,7,8-tetrahydro-quinolin-8-yl)-amine (92 mg, 0.37 mmol), 2-chloromethyl-benzimidazole-1-carboxylic acid tert-butyl ester (101 mg, 0.379 mmol), potassium iodide (3 mg, 0.02 mmol), and N,N-diisopropylethylamine (0.10 mL, 0.57 mmol) in acetonitrile (4 mL) was heated at 60° C. for 15 h. Saturated NaHCO$_3$(aq) (15 mL) was added, and the mixture was extracted with CH$_2$Cl$_2$ (3×15 mL). The combined organic extracts were dried (MgSO$_4$) and concentrated in vacuo. Purification of the crude material by column chromatography on silica gel (250:5:1 CH$_2$Cl$_2$/MeOH/NH$_4$OH) gave a yellow oil (21 mg, 12%).

$^1$H NMR (CDCl$_3$) δ 1.45 (m, 1H), 1.66 (m, 10H), 1.91 (m, 2H), 2.69 (m, 2H), 2.92 (m, 1H), 3.18 (m, 1H), 3.67 (m, 2H), 4.20 (dd, 1H, J=10, 5.6 Hz), 4.67 (d, 1H, J=15 Hz), 4.80 (d, 1H, J=15 Hz), 6.74 (s, 1H), 6.90 (s, 1H), 7.01 (dd, 1H, J=7.7, 4.7 Hz), 7.33 (m, 4H), 7.73 (m, 1H), 7.86 (m, 1H), 8.38 (d, 1H, J=3.3 Hz).

(1H-Benzimidazol-2-ylmethyl)-(2-imidazol-1-yl-ethyl)-(5,6,7,8-tetrahydro-quinolin-8-yl)-amine (Compound 12)

A solution of 2-{[(2-imidazol-1-yl-ethyl)-(5,6,7,8-tetrahydro-quinolin-8-yl)-amino]-methyl}-benzimidazole-1-carboxylic acid tert-butyl ester (21 mg, 0.044 mmol) in 3:1 TFA/CH$_2$Cl$_2$ (4 mL) was stirred at room temperature for 30 minutes then concentrated in vacuo. The residue was partitioned between CH$_2$Cl$_2$ (20 mL) and 1 N NaOH(aq) (10 mL), and the aqueous phase was extracted with CH$_2$Cl$_2$ (10 mL). The combined organic extracts were dried (MgSO$_4$) and concentrated in vacuo to afford COMPOUND 12 as a yellow foam (15 mg, 83%). $^1$H NMR (CDCl$_3$) δ 1.73 (m, 2H), 1.99 (m, 1H), 2.20 (m, 1H), 2.69-2.88 (m, 2H), 2.92-3.08 (m, 2H), 3.82-3.98 (m, 2H), 4.04 (d, 1H, J=17 Hz), 4.09 (m, 1H), 4.19 (d, 1H, J=17 Hz), 6.70 (s, 1H), 6.93 (s, 1H), 7.18 (m, 3H), 7.42 (m, 2H), 7.57 (br s, 2H), 8.51 (d, 1H, J=3.9 Hz); $^{13}$C NMR (CDCl$_3$) δ 21.55, 25.06, 29.36, 46.03, 50.34, 52.23, 62.59, 119.32, 122.26, 122.82, 129.55, 134.97, 137.93, 147.26, 155.42, 156.77. ES-MS m/z 373 (M+H). Anal. Calcd. for C$_{22}$H$_{24}$N$_6$.0.2CH$_2$Cl$_2$.0.8CH$_4$O: C, 66.55; H, 6.70; N, 20.25. Found: C, 66.64; H, 6.40; N, 20.06.

Example 13

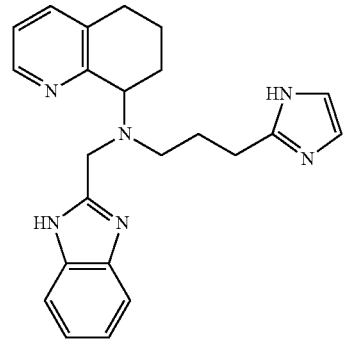 [SMILES: c1cnc2c(c1)CCCC2N(CCCc1ncc[nH]1)Cc1nc2ccccc2[nH]1]

Compound 13: Preparation of (1H-benzimidazol-2-ylmethyl)-[3-(1H-imidazol-2-yl)-propyl]-(5,6,7,8-tetrahydro-quinolin-8-yl)-amine Preparation of 1-trityl-1H-imidazole-2-carbaldehyde

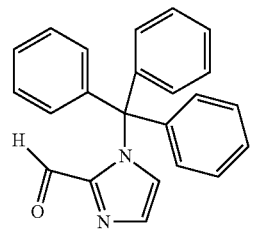 [SMILES: O=Cc1nccn1C(c1ccccc1)(c1ccccc1)c1ccccc1]

To a suspension of imidazole-2-carboxaldehyde (1.00 g, 10.4 mmol) in DMF (16 mL) was added N,N-diisopropylethylamine (4.0 mL, 23.0 mmol) followed by a solution of trityl chloride (3.19 g, 11.4 mmol) in DMF (10 mL), and the mixture was stirred at 30° C. for 21 h. The mixture was concentrated in vacuo then dissolved in EtOAc (60 mL). The solution was washed with saturated NaHCO$_3$(aq) (2×30 mL) and brine (15 mL) then dried (MgSO$_4$) and concentrated in vacuo. Purification of the crude material by column chromatography on silica gel (20% EtOAc/hexanes) gave a yellow solid (1.63 g, 46%). $^1$H NMR (CDCl$_3$) δ 7.03 (s, 1H), 7.12 (m, 6H), 7.32 (m, 10H), 9.23 (s, 1H).

(E)-3-(1-Trityl-1H-imidazol-2-yl)-acrylic acid ethyl ester

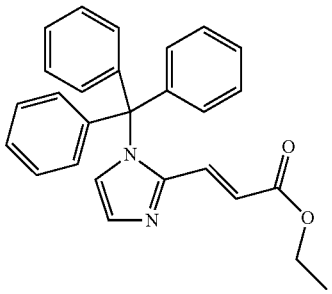 [SMILES: CCOC(=O)/C=C/c1nccn1C(c1ccccc1)(c1ccccc1)c1ccccc1]

Triethyl phosphonoacetate (1.24 mL, 6.25 mmol) was added dropwise to a suspension of sodium hydride (60% in mineral oil, 212 mg, 5.30 mmol) in DME (5 mL) and stirred at room temperature for 30 minutes. The solution was added to a suspension of 1-trityl-1H-imidazole-2-carbaldehyde (1.63 g, 4.82 mmol) in DME (7 mL), and the mixture was heated at reflux for 15 minutes then stirred at 60° C. for 1 hr. The reaction mixture was quenched with H$_2$O (30 mL) and extracted with CH$_2$Cl$_2$ (3×15 mL). The combined organic extracts were dried (MgSO$_4$) and concentrated in vacuo. Purification of the crude material by column chromatography on silica gel (25% EtOAc/hexanes) gave a yellow solid (1.32 g, 67%). $^1$H NMR (CDCl$_3$) δ 1.13 (t, 3H, J=7.1 Hz), 4.00 (q, 2H, J=7.1 Hz), 6.52 (d, 1H, J=15 Hz), 6.70 (d, 1H, J=15 Hz), 6.87 (d, 1H, J=1.2 Hz), 7.13 (m, 7H), 7.33 (m, 9H).

3-(1-Trityl-1H-imidazol-2-yl)-propan-1-ol

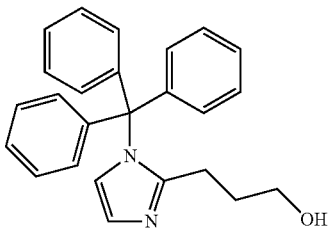 [SMILES: OCCCc1nccn1C(c1ccccc1)(c1ccccc1)c1ccccc1]

A solution of (E)-3-(1-trityl-1H-imidazol-2-yl)-acrylic acid ethyl ester (1.32 g, 3.23 mmol) in 4:1 MeOH/EtOAc (20 mL) was stirred at room temperature with a suspension of 10% Pd/C (132 mg, 0.124 mmol) under hydrogen atmosphere (1 atm) for 20 h. The catalyst was removed by filtration, and the filtrate was concentrated in vacuo to give yellow crystals (1.49 g).

To a solution of the crude ester from above (1.49 g) in THF (7 mL) was added LiAlH$_4$ (1.0 M/THF, 7.0 mL, 7.0 mmol) at 0° C., and the mixture was stirred at room temperature for 1 h. Methanol (5 mL) was added followed by 1 N NaOH(aq) (40 mL), and the mixture was extracted with CH$_2$Cl$_2$ (2×25 mL). The combined organic extracts were dried (MgSO$_4$) and concentrated in vacuo. $^1$H NMR (CDCl$_3$) δ 1.37 (m, 2H), 2.09 (m, 2H), 3.51 (m, 2H), 6.68 (d, 1H, J=1.5 Hz), 6.92 (d, 1H, J=1.5 Hz), 7.13 (m, 6H), 7.33 (m, 9H).

3-(1-Trityl-1H-imidazol-2-yl)-propionaldehyde

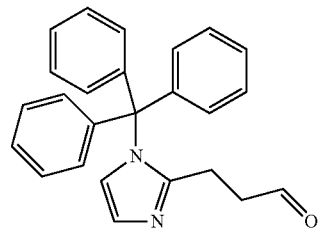 [SMILES: O=CCCc1nccn1C(c1ccccc1)(c1ccccc1)c1ccccc1]

To a solution of 3-(1-trityl-1H-imidazol-2-yl)-propan-1-ol (201 mg, 0.545 mmol) in CH$_2$Cl$_2$ (6 mL) was added Dess-Martin periodinane (278 mg, 0.655 mmol) at room temperature. After stirring at room temperature for 1 h, the mixture was diluted with EtOAc (30 mL), washed with 1 N NaOH(aq) (2×10 mL) and brine (10 mL), then dried (MgSO$_4$) and concentrated in vacuo to give a tan foam (178 mg, 89%). $^1$H NMR (CDCl$_3$) δ 2.19 (m, 2H), 2.37 (m, 2H), 6.75 (d, 1H, J=1.5 Hz), 6.93 (d, 1H, J=1.5 Hz), 7.13 (m, 6H), 7.34 (m, 9H), 9.54 (s, 1H).

(1H-Benzimidazol-2-ylmethyl)-[3-(1H-imidazol-2-yl)-propyl]-(5,6,7,8-tetrahydro-quinolin-8-yl)-amine (Compound 13)

Using General Procedure B: To a stirred solution of 2-[(5,6,7,8-tetrahydro-quinolin-8-ylamino)-methyl]-benzoimidazole-1-carboxylic acid tert-butyl ester (184 mg, 0.486 mmol) and 3-(1-trityl-1H-imidazol-2-yl)-propionaldehyde (178 mg, 0.486 mmol) in THF (5 mL) was added NaBH(OAc)$_3$ (206 mg, 0.972 mmol), and the mixture was stirred at room temperature for 3.5 h. Purification of the crude material by column chromatography on silica gel (200:5:1 CH$_2$Cl$_2$/MeOH/NH$_4$OH) afforded a yellow oil (168 mg) that was determined by $^1$H NMR to be a mixture of 2-({(5,6,7,8-tetrahydro-quinolin-8-yl)-[3-(1-trityl-1H-imidazol-2-yl)-propyl]-amino}-methyl)-benzimidazole-1-carboxylic acid tert-butyl ester and 3-(1-trityl-1H-imidazol-2-yl)-propan-1-ol and was used in the next step without further purification.

A solution of the crude amine from above (168 mg) in saturated HBr/AcOH (3 mL) was stirred at room temperature for 1 h then basified with 10 N NaOH(aq) and extracted with CH$_2$Cl$_2$ (3×10 mL). The combined organic extracts were dried (MgSO$_4$) and concentrated in vacuo. Purification of the crude material by column chromatography on silica gel (300:5:1 CH$_2$Cl$_2$/MeOH/NH$_4$OH) afforded (1H-benzimidazol-2-ylmethyl)-(5,6,7,8-tetrahydro-quinolin-8-yl)-[3-(1-trityl-1H-imidazol-2-yl)-propyl]-amine as a yellow oil (101 mg, 33% over 2 steps).

To a solution of (1H-benzimidazol-2-ylmethyl)-(5,6,7,8-tetrahydro-quinolin-8-yl)-[3-(1-trityl-1H-imidazol-2-yl)-propyl]-amine (101 mg, 0.161 mmol) in CH$_2$Cl$_2$ (1.6 mL) was added triethylsilane (0.38 mL, 2.4 mmol) followed by TFA (1.9 mL, 25 mmol), and the solution was stirred at room temperature for 21 h then concentrated in vacuo. The residue was dissolved in CH₂Cl₂ (15 mL) and washed with 1 N NaOH(aq) (10 mL). The aqueous phase was extracted with CH₂Cl₂ (2×10 mL), and the combined organic phases were dried (MgSO₄) and concentrated in vacuo. Purification of the crude material by column chromatography on silica gel (150:5:1 CH₂Cl₂/MeOH/NH₄OH) afforded COMPOUND 13 as a colourless foam (47 mg, 69%). $^1$H NMR (CDCl₃) δ 1.62-1.93 (m, 4H), 2.02 (m, 1H), 2.16 (m, 1H), 2.58-2.88 (m, 6H), 3.91 (d, 1H, J=16 Hz), 3.98 (d, 1H, J=16 Hz), 4.02 (m, 1H), 6.86 (s, 2H), 7.18 (m, 3H), 7.43 (d, 1H, J=7.2 Hz), 7.55 (m, 2H), 8.55 (d, 1H, J=3.6 Hz); $^{13}$C NMR (CDCl₃) δ 21.52, 23.71, 25.96, 26.67, 29.43, 49.21, 51.07, 62.23, 115.28, 120.75, 122.41, 122.81, 135.47, 138.23, 138.86, 146.68, 148.71, 155.28, 157.49. ES-MS m/z 387 (M+H). Anal. Calcd. for C₂₃H₂₆N₆.0.21H₂O.0.36CH₂Cl₂: C, 66.67; H, 6.50; N, 19.97. Found: C, 66.77; H, 6.65; N, 19.69.

Example 14

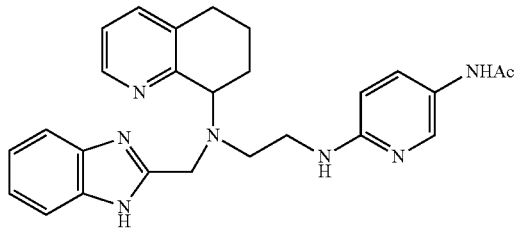 [SMILES: CC(=O)Nc1ccc(NCCN(Cc2nc3ccccc3[nH]2)C2CCCc3cccnc32)nc1]

Compound 14: Preparation of N-(6-2-[(1H-Benzimidazol-2-ymethyl)-(5,6,7,8-tetrahydro-quinolin-8-yl)-amino]-ethylamino}-pyridin-3-yl)-acetamide To a solution of 2-{[[2-(5-Nitro-pyridin-2-ylamino)-ethyl]-(5,6,7,8-tetrahydro-quinolin-8-yl)-amino]-methyl}-benzimidazole-1-carboxylic acid tert-butyl ester (see COMPOUND 11) (316 mg, 0.58 mmol) in AcOH (4 mL) was added iron powder (172 mg, 3.08 mmol) and the reaction heated to reflux for 2 h. The mixture was cooled to room temperature, diluted with water (5 mL) and extracted with CH₂Cl₂ (3×25 mL). The combined organic extracts were dried (Na₂SO₄), concentrated in vacuo and purified by radial chromatography on silica gel (1 mm plate, 100:1:1 CH₂Cl₂/MeOH/NR₄OH then 50:1:1) to give the desired product (96 mg, 30%) as a clear oil.

Using General Procedure D: Conversion of the free base (25 mg, 0.055 mmol) to the hydrobromide salt, followed by re-precipitation of the intermediate solid from methanol/ether, gave COMPOUND 14 (36 mg) as a white solid. $^1$H NMR (D₂O) δ 1.83-1.90 (m, 1H), 2.05-2.20 (m, 2H), 2.14 (s, 3H), 2.39-2.43 (m, 1H), 2.86-2.94 (m, 1H), 3.01-3.03 (m, 2H), 3.18-3.25 (m, 1H), 3.39-3.49 (m, 2H), 4.38 (d, 1H, J=16.5 Hz), 4.58 (d, 1H, J=16.5 Hz), 4.62-4.68 (m, 1H), 6.75 (d, 1H, J=9.6 Hz), 7.47 (dd, 2H, J=6, 3 Hz), 7.49 (s, 1H), 7.60 (dd, 2H, J=6, 3 Hz), 7.83 (s, 1H), 7.89 (t, 1H, J=6.6 Hz), 8.38 (d, 1H, J=7.8 Hz), 8.71 (d, 1H, J=6.6 Hz); $^{13}$C NMR (D₂O) δ 20.39, 20.84, 23.07, 27.83, 41.24, 49.13, 50.29, 62.01, 113.37, 114.24, 125.70, 125.82, 126.11, 126.96, 130.58, 138.24, 139.94, 141.08, 148.39, 149.47, 150.18, 151.32, 172.99; ES-MS m/z 456 (M+H). Anal. Calcd. for C₂₆H₂₉N₇O.3.2HBr.2.4H₂O: C, 41.21; H, 4.92; N, 12.94; Br, 33.75. Found: C, 41.12; H, 4.98; N, 12.77; Br, 34.06.

Example 15

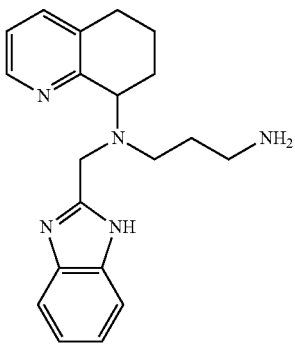 [SMILES: NCCCN(Cc1nc2ccccc2[nH]1)C1CCCc2cccnc21]

Compound 15: Preparation of N¹-(1H-Benzimidazol-2-ylmethyl)-N¹-(5,6,7,8-tetrahydro-quinolin-8-yl)-propane-1,3-diamine (hydrobromide salt)

Preparation of N-(tert-butoxycarbonyl)-3-amino-propionaldehyde

To a solution of tert-butyl N-(3-hydroxypropyl)carbamate (0.177 g, 1.01 mmol) in CH₂Cl₂ (5 mL) was added Dess-Martin periodinane (0.545 g, 1.28 mmol) and the resultant mixture was stirred at room temperature for 2.5 hours. The mixture was diluted with ether (20 mL) and treated with 20% aqueous Na₂S₂O₃ (5 mL) and saturated aqueous NaHCO₃ (5 mL). After 10 minutes the mixture became clear and colorless and the phases were separated. The aqueous phase was extracted with ether (3×10 mL). The combined organic extracts were washed sequentially with 20% aqueous Na₂S₂O₃ (10 mL), saturated aqueous NaHCO₃ (10 mL), and brine (10 mL), dried (MgSO₄), and concentrated to provide 0.127 g (96%) of N-(tert-butoxycarbonyl)-3-amino-propionaldehyde as a colorless oil. $^1$H NMR (CDCl₃) δ 1.43 (s, 9H), 2.71 (t, 2H, J=6.0 Hz), 3.42 (m, 2H), 4.89 (br s, 1H), 9.81 (s, 1H).

Using General Procedure B: Reaction of N-(tert-butoxycarbonyl)-2-amino-propionaldehyde (0.127 g, 0.73 mmol) and (1H-benzimidazol-2-ylmethyl)-(5,6,7,8-tetrahydro-quinolin-8-yl)-amine (0.152 g, 0.55 mmol) with NaBH(OAc)₃ (0.262 g, 1.24 mmol) in CH₂Cl₂ (5 mL) for 18 hours followed by purification of the crude material by radial chromatography on silica gel (2 mm plate, 50:1:1 CH₂Cl₂—CH₃OH—NH₄OH) provided 0.169 g of a yellow foam. The foam was dissolved in CH₂Cl₂ (2 mL) and treated with trifluoroacetic acid (1 mL). The resultant solution was stirred at room temperature for 2 hours then concentrated under reduced pressure. The residue was dissolved in CH₂Cl₂ (10 mL) and treated with NaOH (10 M, ~2 mL) until the aqueous phase was basic (pH 14). The phases were separated and the aqueous phase was extracted with CH₂Cl₂ (3×5 mL). The combined organic extracts were dried (Na₂SO₄) and concentrated. Purification of the crude material by radial chromatography on silica gel (1 mm plate, 10:1:1 CH₂Cl₂—CH₃OH—NH₄OH) provided 57 mg of a white foam.

Using General Procedure D: Conversion of the free base (57 mg) to the hydrobromide salt, followed by re-precipitation of the intermediate solid from methanol/ether, gave COMPOUND 15 (75 mg) as a white solid. $^1$H NMR (D₂O) δ 1.77-2.09 (m, 4H), 2.18-2.22 (m, 1H), 2.38-2.42 (m, 1H), 2.60-2.70 (m, 1H), 2.87-2.97 (m, 3H), 3.01-3.04 (m, 2H), 4.42 (d, 1H, J=16.8 Hz), 4.51-4.49 (m, 2H), 7.60-7.63 (m, 2H), 7.79-7.90 (m, 3H), 8.36 (d, 1H, J=7.8 Hz), 8.65 (d, 1H, J=5.7 Hz); $^{13}$C NMR (D$_2$O) δ 20.41 (2 carbons), 26.38, 27.66, 37.69, 47.94, 49.13, 60.39, 114.32, 126.02, 126.98, 131.10, 139.50, 140.73, 148.18, 150.96, 151.36; ES-MS m/z 336 (M+H). Anal. Calcd. for $C_{20}H_{25}N_5 \cdot 3.0HBr \cdot 1.6H_2O$: C, 39.57; H, 5.18; N, 11.54; Br, 39.49. Found: C, 39.85; H, 5.10; N, 11.45; Br, 39.15.

Example 16

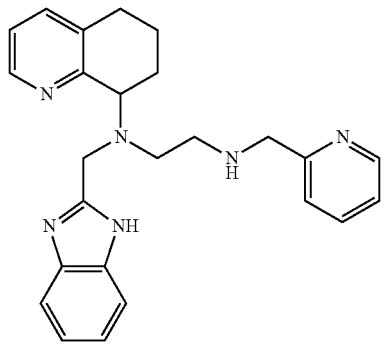 [SMILES: c1ccc(CNCCN(Cc2nc3ccccc3[nH]2)C2CCCc3cccnc32)nc1]

Compound 16: Preparation of N$^1$-(1H-Benzimidazol-2-ylmethyl)-N$^2$-pyridin-2-ylmethyl-N$^1$-(5,6,7,8-tetrahydro-quinolin-8-yl)-ethane-1,2-diamine (hydrobromide salt)

To a solution of N$^1$-(1H-Benzimidazol-2-ylmethyl)-N$^1$-(5,6,7,8-tetrahydro-quinolin-8-yl)-ethane-1,2-diamine hydrobromide salt [COMPOUND 10] (98 mg, 0.168 mmol) in H$_2$O (2 mL) was added NaOH (10 M, 2 mL). The resultant solution was extracted with CH$_2$Cl$_2$ (4×5 mL). The combined organic extracts were dried (Na$_2$SO$_4$) and concentrated and provided 53 mg of the free base. To a solution of the free base from above (53 mg, 0.165 mmol) in methanol (2 mL) was added pyridine-2-carboxaldehyde (20 μL, 0.210 mmol) and the resultant solution was stirred at room temperature for 2 hours. NaBH$_4$ (36 mg, 0.95 mmol) was added and the mixture was stirred for 15 minutes. The mixture was concentrated and the residue was partitioned between CH$_2$Cl$_2$ (10 mL) and brine (5 mL). The phases were separated and the aqueous phase was extracted with CH$_2$Cl$_2$ (3×5 mL). The combined organic extracts were dried (Na$_2$SO$_4$) and concentrated. Purification of the crude material by radial chromatography on silica gel (1 mm plate, 25:1:1 CH$_2$Cl$_2$—CH$_3$OH—NH$_4$OH) provided 34 mg (45%) of the free base of the title compound.

Using General Procedure D: Conversion of the free base (34 mg) to the hydrobromide salt, followed by re-precipitation of the intermediate solid from methanol/ether, gave COMPOUND 16 (57 mg) as a white solid. $^1$H NMR (D$_2$O) δ 1.78-1.90 (m, 1H), 1.98-2.11 (m, 1H), 2.17-2.22 (m, 1H), 2.39-2.43 (m, 1H), 2.97-3.09 (m, 3H), 3.25-3.37 (m, 3H), 4.39 (d, 1H, J=16.5 Hz), 4.47 (d, 2H, J=2.4 Hz), 4.54-4.59 (m, 2H), 7.57-7.65 (m, 4H), 7.77-7.88 (m, 3H), 8.04 (dt, 1H, J=1.5, 7.5 Hz), 8.35 (d, 1H, J=7.8 Hz), 8.50 (d, 1H, J=4.8 Hz), 8.61 (d, 1H, J=5.4 Hz); $^{13}$C NMR (D$_2$O) δ 20.27, 20.54, 27.67, 45.45, 47.48, 48.12, 50.32, 60.32, 114.42, 125.85, 126.11, 126.19, 127.27, 130.98, 139.83, 141.03, 141.70, 147.87, 148.39 (2 carbons), 149.85, 150.06; ES-MS m/z 413 (M+H). Anal. Calcd. for $C_{25}H_{28}N_6 \cdot 4.1HBr \cdot 2.0H_2O$: C, 38.48; H, 4.66; N, 10.77; Br, 41.98. Found: C, 38.69; H, 4.78; N, 10.60; Br, 41.70.

Example 17

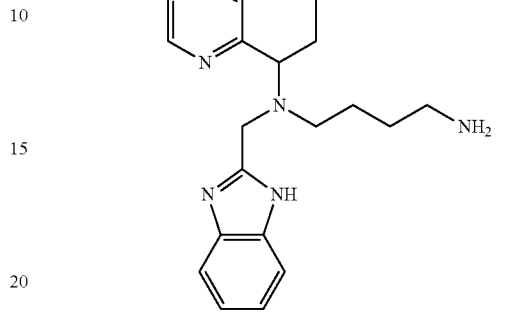

Compound 17: Preparation of N$^1$-(1H-Benzimidazol-2-ylmethyl)-N$^1$-(5,6,7,8-tetrahydro-quinolin-8-yl)-butane-1,4-diamine (hydrobromide salt)

To a solution of (1-tert-butoxycarbonyl-1H-Benzimidazol-2-ylmethyl)-(5,6,7,8-tetrahydro-quinolin-8-yl)-amine (0.169 g, 0.451 mmol) in CH$_3$CN (5 mL) was added N,N-diisopropylethylamine (0.25 mL, 1.44 mmol) followed by 4-bromobutyronitrile (0.10 mL, 1.01 mmol). The resultant mixture was heated to 80° C. for 5 d then cooled to room temperature. The mixture was concentrated and the residue was partitioned between CH$_2$Cl$_2$ (20 mL) and brine (10 mL). The phases were separated and the aqueous phase was extracted with CH$_2$Cl$_2$ (3×10 mL). The combined organic extracts were dried (Na$_2$SO$_4$) and concentrated. Purification of the crude material by column chromatography on silica gel (30:1:1 CH$_2$Cl$_2$—CH$_3$OH—NH$_4$OH) provided 0.108 mg (54%) of a yellow foam.

The intermediate from above (108 mg, 0.24 mmol) was dissolved in NH$_3$ saturated methanol (4 mL), treated with Raney nickel (100 mg), and placed under 50 psi H$_2$ on a Parr shaker, for 24 h. The mixture was filtered through Celite© and the cake was washed with methanol. The eluant was concentrated under reduced pressure. Purification of the crude material by radial chromatography on silica gel (1 mm plate, 20:1:1 CH$_2$Cl$_2$—CH$_3$OH—NH$_4$OH) provided 33 mg (39%) of the free base of the title compound as a white foam.

Using General Procedure D: Conversion of the white foam (33 mg) to the hydrobromide salt, followed by re-precipitation of the intermediate solid from methanol/ether, gave COMPOUND 17 (40 mg) as a white solid. $^1$H NMR (D$_2$O) δ 1.52 (br s, 4H), 1.74-1.88 (m, 1H), 1.95-2.08 (m, 1H), 2.15-2.21 (m, 1H), 2.34-2.39 (m, 1H), 2.50-2.61 (m, 1H), 2.79-2.86 (m, 3H), 2.99-3.02 (m, 2H), 4.38 (d, 1H, J=16.8 Hz), 4.47-4.56 (m, 2H), 7.58-7.63 (m, 2H), 7.76-7.88 (m, 3H), 8.34 (d, 1H, J=7.8 Hz), 8.62 (d, 1H, J=5.7 Hz); $^{13}$C NMR (D$_2$O) δ 20.42(2 carbons), 25.03, 25.42, 27.64, 39.50, 48.20, 51.71, 60.64, 114.26, 125.93, 126.93, 131.05, 139.32, 140.62, 148.09, 150.31, 151.82; ES-MS m/z 350 (M+H). Anal. Calcd. for $C_{21}H_{27}N_5 \cdot 2.9HBr \cdot 2.2H_2O$: C, 40.44; H, 5.54; N, 11.23; Br, 37.15. Found: C, 40.38; H, 5.42; N, 10.85; Br, 37.42.

Example 18

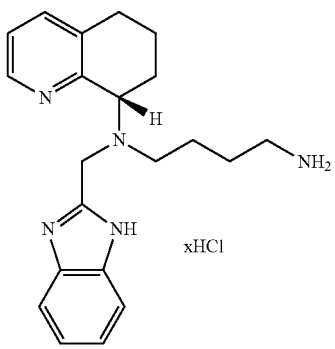 [SMILES: NCCCCN(Cc1nc2ccccc2[nH]1)[C@H]1CCCc2cccnc21]

Compound 18: Preparation of N'-(1H-benzimidazol-2-ylmethyl)-N'-(S)-5,6,7,8-tetrahydro-quinolin-8-yl-butane-1,4-diamine (hydrochloride salt)

Preparation of 4-phthalamido-butyraldehyde

A solution of 4-amino-1-butanol (5.0 g, 56 mmol) and phthalic anhydride (8.3 g, 56 mmol) in 20% MeOH/CHCl$_3$ (140 mL) was stirred at reflux for 66 h. The mixture was cooled to room temperature and washed sequentially with water (3×75 mL) and 1N NaOH (3×50 mL). The separated organic layer was dried (MgSO$_4$), concentrated, and purified by flash chromatography (5 cm id., 120 g silica gel, eluted with 2% MeOH/CH$_2$Cl$_2$) to give the desired alcohol as a white solid (4.21 g, 34%).

To a stirred slurry of TPAP (340 mg, 0.96 mmol), NMO (3.4 g, 29 mmol) and 3 Å molecular seives (10 g) in CH$_2$Cl$_2$ (100 mL) was added dropwise a solution of the alcohol from above (4.2 g, 19 mmol) in CH$_2$Cl$_2$ (50 mL) over 30 min. The black slurry was stirred under N$_2$ for 30 min after the addition, concentrated in vacuo, and purified by flash chromatography (5 cm id., 80 g silica gel, eluted with EtOAc) to afford the pure title compound as a grey solid (3.30 g, 80%). $^1$H NMR (CDCl$_3$) δ 1.97-2.07 (m, 2H), 2.54 (t, 2H, J=7.2 Hz), 3.74 (t, 2H, J=6.8 Hz), 7.71-7.75 (m, 2H), 7.82-7.88 (m, 2H), 9.77 (s, 1H).

Using General Procedure B: 4-phthalamido-butyraldehyde from above (3.21 g, 14.8 mmol) was reacted with S-(5,6,7,8-tetrahydro-quinolin-8-yl)-amine (2.40 g, 16.3 mmol) and NaBH(OAc)$_3$ (9.54 g, 45.0 mmol) in dichloromethane (150 mL). Flash chromatography (5 cm id, 200 g silica gel, eluted with 5% MeOH/CH$_2$Cl$_2$) provided the pure 2° amine as a white foamy solid (2.48 g, 48%).

To a solution of the amine from above (2.5 g, 7.1 mmol) in acetonitrile (70 mL) was added diisopropylethylamine (1.9 mL, 10.7 mmol), 1-boc-2-chloromethylbenzimidazole (2.3 g, 8.6 mmol), and potassium iodide (115 mg, 0.70 mmol). The mixture was stirred under an N$_2$ atmosphere at 60° C. for 15 h, cooled to room temperature and concentrated in vacuo. The residue was partitioned between chloroform (150 mL) and water (100 mL). The separated organic layer was dried (MgSO$_4$), concentrated, and purified by flash chromatography (5 cm id, 120 g silica gel, eluted with CH$_2$Cl$_2$ to remove unreacted chloride then 2% MeOH/CH$_2$Cl$_2$ to remove desired product) to give the desired amine as a pale yellow foamy solid (3.50 g, 85%).

A solution of the amine from above (3.33 g, 5.7 mmol) in ethanol (30 mL) was treated with hydrazine monohydrate (1.80 g, 36 mmol), stirred for three hours. The mixture was then concentrated in vacuo and purified by flash chromnatography (5 cm id., 80 g silica gel, eluted with 5% MeOH/CH$_2$Cl$_2$) to give the unprotected amine as a pale yellow foamy solid (1.70 g, 86%).

The amine from above (1.70 g, 4.86 mmol) was dissolved in glacial acetic acid (5 mL) and treated with HCl saturated acetic acid (5 mL). The solution was allowed to stir at room temperature 5 min, then it was slowly dropped into diethyl ether (400 mL) with vigorous stirring. The resultant slurry was suction filtered through a glass fritted funnel and the filter cake was washed with diethyl ether (3×100 mL) and dried in a vacuum oven at 40° C. for 16 h to give COMPOUND 18 as a white solid (2.34 g, 94%). $^1$H NMR (D$_2$O) δ 1.46-1.63 (m, 4H), 1.70-1.87 (m, 1H), 1.97-2.07 (m, 1H), 2.10-2.21 (m, 1H), 2.28-2.38 (m, 1H), 2.55-2.65 (m, 1H), 2.81-2.90 (m, 3H), 2.91-3.00 (m, 2H), 4.30 (d, 1H, J=16.3 Hz), 4.41 (d, 1H, J=16.3 Hz), 4.42-4.48 (m, 1H), 7.48-7.51 (m, 2H), 7.70-7.75 (m, 3H), 8.20 (d, 1H, J=8.2 Hz), 8.53 (d, 1H, J=4.5 Hz); $^{13}$C NMR (D$_2$O) δ 20.36, 20.43, 21.67, 24.99, 25.24, 27.60, 39.51, 48.29, 51.78, 60.54, 114.46 (2 carbons), 125.63, 126.10 (2 carbons), 132.53, 139.58, 140.16, 147.34, 151.41, 151.81. ES-MS m/z 350 (M+H). Anal. Calcd. for C$_{21}$H$_{27}$N$_5$.2.5HCl.2.0H$_2$O.0.6CH$_3$COOH: C, 52.01; H, 7.06; N, 13.66; Cl, 17.29. Found: C, 52.15; H, 7.09; N, 13.40; Cl, 17.56.

The enantiomeric purity of COMPOUND 18 was determined to be 96.7% by chiral HPLC using the following conditions: Instrument: Hewlett Packard 1100 HPLC (VWD1); Column: Chiralpak OD, 0.46 cm×25 cm; Mobile Phases: A: 90:10 hexanes/isopropanol with 0.1% DEA, 13: isopropanol; Isocratic: 90%A, 10% B; Total Run Time: 20 min; Flow Rate: 0.5 mL/min; Temperature: 10° C.; Detector: UV @ 270 nm; Injection volume: 20 μL.

Retention time of the S enantiomer=16.3 min.
Retention time of the R enantiomer=21.9 min.

Example 19

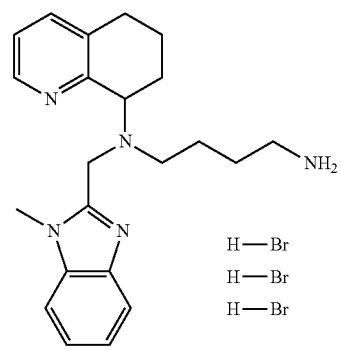

Compound 19: Preparation of N$^1$-(1-Methyl-1H-benzoimidazol-2-ylmethyl)-N$^1$-(5,6,7,8-tetrahydro-quinolin-8-yl)-butane-1,4-diamine (hydrobromide salt)

2-[4-(5,6,7,8-Tetrahydro-quinolin-8-ylamino)-butyl]-isoindole-1,3-dione was prepared following the procedure for COMPOUND 18. 2-{4-[(1-Methyl-1H-benzoimidazol-2-ylmethyl)-(5,6,7,8-tetrahydro-quinolin-8-yl)-amino]-butyl}-isoindole-1,3-dione was prepared following the general procedure for reductive aminations.

To a solution of 2-[4-(5,6,7,8-Tetrahydro-quinolin-8-ylamino)-butyl]-isoindole-1,3-dione (0.2011 g, 0.58 mmol) in dichloromethane (5.8 mL) was added 1-Methyl-1H-benoimidazole-2-carbaldehyde (0.1844 g, 1.15 mmol) and NaBH(OAc)$_3$ (0.2462 g, 1.16 mmol), and was stirred at room temperature for four days. The organic phase was washed with NaHCO$_3$ (2×10 mL), dried over Na$_2$SO$_4$, filtered, and concentrated. Purification of the crude material by column chromatography on silica gel (47:2:1 CH$_2$Cl$_2$—MeOH—NH$_4$OH) provided 103 mg (36%) of 2-{4-[(1-Methyl-1H-benzoimidazol-2-ylmethyl)-(5,6,7,8-tetrahydro-quinolin-8-yl)-amino]-butyl}-isoindole-1,3-dione. $^1$H NMR (CDCl$_3$) δ 1.30-1.44 (m, 2H), 1.48-1.63 (m, 3H), 1.84-1.96 (m, 2H), 2.03-2.07 (m, 1H), 2.54-2.81 (m, 4H), 3.51 (t, 2H, J=7.2 Hz), 3.95 (s, 3H), 3.99-4.06 (m, 2H), 4.19 (d, 1H, J=13.5 Hz), 6.94-6.98 (m, 1H), 7.13-7.21 (m, 2H), 7.24-7.29 (m, 2H), 7.63-7.68 (m, 3H), 7.74-7.78 (m, 2H), 8.40 (d, 1H, J=3.6 Hz).

To a solution of 2-{4-[(1-Methyl-1H-benzoimidazol-2-ylmethyl)-(5,6,7,8-tetrahydro-quinolin-8-yl)-amino]-butyl}-isoindole-1,3-dione (0.1030 g, 0.21 mmol) in ethanol (1 mL) was added hydrazine monohydrate (0.51 mL, 10.5 mmol), and the reaction mixture was stirred at room temperature for 18 hours. The mixture was concentrated and purified first via column chromatography on silica gel (91:12:1 CH$_2$Cl$_2$—MeOH—NH$_4$OH) and then by radial chromatography on silica (18:1:1 CH$_2$Cl$_2$—MeOH—NH$_4$OH) to yield 0.0246 g (32%) of N$^1$-(1-Methyl-1H-benzoimidazol-2-ylmethyl)-N$^1$-(5,6,7,8-tetrahydro-quinolin-8-yl)-butane-1,4-diamine. $^1$H NMR (CDCl$_3$) δ 1.32-1.42 (m, 5H), 1.91-2.02 (m, 2H), 2.05-2.11 (m, 1H), 2.55 (t, 2H, J=6.9 Hz), 2.60-2.64 (m, 3H), 2.76-2.86 (m, 1H), 3.98 (s, 3H), 4.04-4.17 (m, 3H), 7.00-7.04 (m, 1H), 7.21-7.27 (m, 2H), 7.30-7.33 (m, 2H), 7.68-7.72 (m, 1H), 8.47 (d, 1H, J=3.3 Hz).

Following a general procedure D, N$^1$-(1-Methyl-1H-benzoimidazol-2-ylmethyl)-N$^1$-(5,6,7,8-tetrahydro-quinolin-8-yl)-butane-1,4-diamine was salted out. To a solution of N$^1$-(1-Methyl-1H-benzoimidazol-2-ylmethyl)-N$^1$-(5,6,7,8-tetrahydro-quinolin-8-yl)-butane-1,4-diamine (0.0246 g, 0.068 mmol) in acetic acid (0.8 mL) was added HBr/AcOH (1 mL), followed by the addition of diethyl ether (50 mL), which resulted in the precipitation of the salt. The ether was decanted off and the remaining solid was washed with diethyl ether (2×50 mL). Any residual diethyl ether was removed by vacuum and methanol (1 mL) was added to the solid. Again, diethyl ether (50 mL) was added and the salt was washed with diethyl ether (3×50 mL) to give COMPOUND 19 (23 mg, 76%) as a white solid. $^1$H NMR (D$_2$O) δ 1.52-1.53 (m, 4H), 1.73-1.87 (m, 1H), 1.99-2.11 (m, 1H), 2.15-2.19 (m, 1H), 2.40-2.43 (m, 1H), 2.51-2.58 (m, 1H), 2.78-2.84 (m, 3H), 2.97-2.99 (m, 2H), 3.96 (s, 3H), 4.38 (d, 1H, J=17.7 Hz), 4.48-4.54 (m, 1H), 4.59 (d, 1H, J=17.7 Hz), 7.58-7.61 (m, 2H), 7.75-7.84 (m, 3H), 8.30 (d, 1H, J=7.8 Hz), 8.58 (d, 1H, J=5.4 Hz); $^{13}$C NMR (D$_2$O) 20.44 (2H), 25.03, 25.44, 27.69, 31.52, 39.47, 47.70, 52.18, 60.88, 112.80, 114.22, 125.88, 126.73, 127.12, 130.08, 133.45, 139.32, 140.64, 148.09, 151.13, 151.68. ES-MS m/z 364 (M−1-H). Anal. Calcd. for C$_{22}$H$_{29}$N$_5$.3.2HBr.2.2H$_2$O: C, 39.91; H, 5.57; N, 10.58; Br, 38.62. Found: C, 39.97; H, 5.44; N, 10.37; Br, 38.49.

Example 20

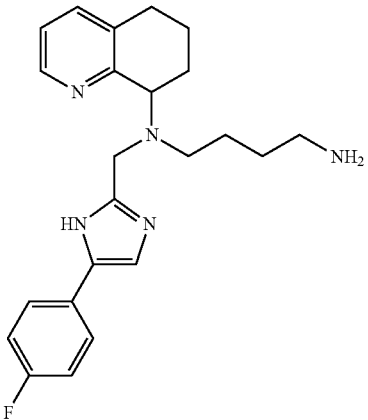 [SMILES: NCCCCN(Cc1ncc(-c2ccc(F)cc2)[nH]1)C1CCCc2cccnc21]

Compound 20: Preparation of N$^1$-[5-(4-Fluoro-phenyl)-1H-imidazol-2-ylmethyl]-N$^1$-(5,6,7,8-tetrahydro-quinolin-8-yl)-butane-1,4-diamine 2-[4-(5,6,7,8-Tetrahydro-quinolin-8-ylamino)-butyl]-isoindole-1,3-dione was prepared following the general procedure B for reductive amination. To a solution of 5,6,7,8-Tetrahydro-quinolin-8-ylamine (1.0609 g, 7.1 mmol) and 4-(1,3-Dioxo-1,3-dihydro-isoindol-2-yl)-butyraldehyde (1.4079 g, 6.8 mmol) (prepared according to the procedure for COMPOUND 18) in methylene chloride (64 mL) was added NaBH(OAc)$_3$ (4.07 g, 19.2 mmol) and the reaction stirred at room temperature for two hours. The reaction was quenched with 1N NaOH (45 mL), extracted with methylene chloride (2×55 mL), dried (Na$_2$SO$_4$), filtered, and concentrated. Purification of the crude material by column chromatography on silica gel (40:1:1 CH$_2$Cl$_2$—MeOH—NH$_4$OH) provided 1.16 g (52%) of 2-[4-(5,6,7,8-Tetrahydro-quinolin-8-ylamino)-butyl]-isoindole-1,3-dione. $^1$H NMR (CDCl$_3$) δ 1.57-1.66 (m, 3H), 1.69-1.84 (m, 4H), 1.93-2.03 (m, 1H), 2.07-2.13 (m, 1H), 2.69-2.86 (m, 4H), 3.70-3.77 (m, 3H), 7.03-7.07 (m, 1H), 7.35 (d, 1H, J=7.2 Hz), 7.67-7.73 (m, 2H), 7.80-7.85 (m, 2H), 8.37 (d, 1H, J=3 Hz).

To a solution of 4-(4-Fluoro-phenyl)-1-(2-trimethylsilanyl-ethoxymethyl)-1H-imidazole-2-carbaldehyde (0.2301 g, 0.72 mmol) in methylene chloride (7.2 mL) was added 2-[4-(5,6,7,8-Tetrahydro-quinolin-8-ylamino)-butyl]-isoindole-1,3-dione (0.3030 g, 0.87 mmol) and then NaBH(OAc)$_3$ (0.3060 g, 1.44 mmol), and the reaction mixture was stirred at room temperature for four days. The reaction was quenched with saturated NaHCO$_3$ (6 mL), extracted with CH$_2$Cl$_2$ (2×25 mL), dried (Na$_2$SO$_4$), filtered, and concentrated. Purification of the crude material by column chromatography on silica gel (50:1:1 CH$_2$Cl$_2$—MeOH—NH$_4$OH) provided 0.3125 g (66%) of 2-{4-[[5-(4-Fluoro-phenyl)-1-(2-trimethylsilanyl-ethoxymethyl)-1H-imidazol-2-ylmethyl]-(5,6,7,8-tetrahydro-quinolin-8-yl)-amino]-butyl}-isoindole-1,3-dione. $^1$H NMR (CDCl$_3$) δ 0.82-0.87 (m, 2H), 1.25-1.37 (m, 2H), 1.48-1.69 (m, 10H), 1.88-2.08 (m, 3H), 2.56-2.82 (m, 4H), 3.38-3.44 (m, 2H), 3.53 (t, 2H, J=7.2 Hz), 3.96 (s, 2H), 4.01-4.04 (m, 1H), 5.56 (d, 1H, 10.8 Hz), 5.79 (d, 1H, J=10.5 Hz), 6.97-7.03 (m, 3H), 7.12 (s, 1H), 7.30 (d, 1H, J=7.5 Hz), 7.61-7.70 (m, 4H), 7.75-7.79 (m, 2H), 8.44 (d, 1H, J=4.5 Hz).

To a solution of 2-{4-[[5-(4-Fluoro-phenyl)-1-(2-trimethylsilanyl-ethoxymethyl)-1H-1-imidazol-2-ylmethyl]-(5,6,7, 8-tetrahydro-quinolin-8-yl)-amino]-butyl}-isoindole-1,3-dione (0.3125 g, 0.48 mmol) in ethanol (5 mL) was added hydrazine monohydrate (0.12 mL), and the reaction mixture was stirred at room temperature for 17 hours. The reaction mixture was concentrated, and purified via column chromatography on silica gel (20:1:1 $CH_2Cl_2$—MeOH—$NH_4OH$) to yield 0.1838 g (73%) of $N^1$-[5-(4-Fluoro-phenyl)-1-(2-trimethylsilanyl-ethoxymethyl)-1H-imidazol-2-ylmethyl]-$N^1$-(5,6,7,8-tetrahydro-quinolin-8-yl)-butane-1,4-diamine. $^1$H NMR ($CDCl_3$) δ 0.85 (t, 2H, J=8.1 Hz), 1.25-1.34 (m, 7H), 1.61-1.72 (m, 1H), 1.89-2.05 (m, 4H), 2.54-2.82 (m, 8H), 3.35-3.47 (m, 3H), 3.93 (s, 2H), 4.06 (t, 1H, J=8.1 Hz), 5.53 (d, 2H, J=10.5 Hz), 5.78 (d, 2H, J=10.8 Hz), 6.99-7.04 (m, 3H), 7.15 (s, 1H), 7.31 (d, 1H, J=7.5 Hz), 7.66-7.70 (m, 2H), 8.47 (d, 1H, J=3.6 Hz).

To a solution of $N^1$-[5-(4-fluoro-phenyl)-1-(2-trimethylsilanyl-ethoxymethyl)-1H-imidazol-2-ylmethyl]-N1-(5,6,7,8-tetrahydro-quinolin-8-1)-butane-1,4-diamine (0.1838 g, 0.35 mmol) in nethylene chloride (5 mL) was added TFA (5 mL), and was stirred in a room temperature for 3 days. The mixture was concentrated, dissolved in $CH_2Cl_2$, and neutralized with 10N NaOH. The aqueous phase was extracted with $CH_2Cl_2$ (4 times), and the combined organic extracts were then washed with brine, dried ($Na_2SO_4$), filtered and concentrated. The crude material was purified by column chromatography on silica gel (15:1:1 $CH_2Cl_2$MeOH—$NH_4OH$) and then by radial chromatography on silica (15:1:1 $CH_2Cl_2$MeOH—$NH_4OH$) to give COMPOUND 20 (0.0421 G, 31%) as an orange oil. $^1$H NMR ($CDCl_3$) δ 1, 25-1.43 (m, 4H), 1.62-1.75 (m, 1H), 1.84-1.92 (m, 1H), 1.96-2.05 (m, 1H), 2.13-2.15 (m, 1H), 2.44-2.50 (m, 3H), 2.63-2.73 (m, 2H), 2.79-2.89 (m, 1H), 3.87 (s, 1H), 3.99-4.04 (m, 2H), 7.04 (t, 2H, J=9 Hz), 7.10-7.14 (m, 1H), 7.23 (s, 1H), 740 (d, 1H, J=7.5 Hz), 7.65-7.70 (m, 2H), 8.50 (d, 1H, J=4.2 Hz); $^{13}$C NMR ($CDCl_3$) δ 21.70, 23.02, 26.37, 29.57, 30.17, 41.44, 49.02, 50.72, 61.70, 115.83 (d, 2C, J=14.34 Hz), 122.49, 126.43 (d, 2C, J=5.18 Hz), 130.26, 135.01, 137.74, 147.14 (2C), 149.64, 157.77, 160.34, 163.58. ES-MS m/z 394 (M+H). Anal. Calcd. For C23H28N5F.1.3$CH_2Cl_2$: C, 70.20; H, 7.17; N, 17.80. Found: C, 58.09; H, 6.23; N, 13.59.

Example 21

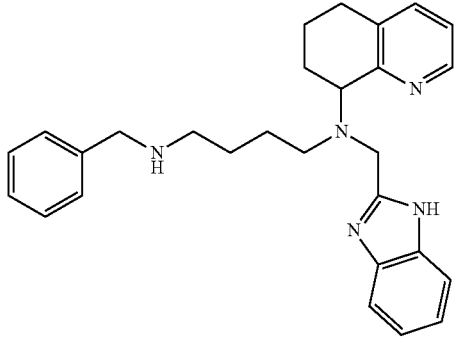 [SMILES: c1ccc(CNCCCCN(Cc2nc3ccccc3[nH]2)C2CCCc3cccnc32)cc1]

Compound 21: Preparation of $N^1$-(1H-Benzimidazol-2-ylmethyl)-(5,6,7,8-tetrahydroquinolin-8-yl)-N-benzyl-1,4-butanediamine (hydrobromide salt)

To a solution of N'-(1-(2-trimethylsilyl)-ethan-lyloxymethyl)-benzimidazol-2-ylmethyl)-(5,6,7,8-tetrahydroquinolin-8-yl)-1,4-butanediamine (70 mg, 0.15 mmol) in methanol (4 mL) was added benzaldehyde (0.015 mL, 0.15 mmol). The mixture was stirred overnight at room temperature, then cooled to 0° C. Sodium borohydride (38 mg, 1.0 mmol) was then added, and the reaction was stirred for one hour, gradually warming to room temperature. The solution was then concentrated. The residue was taken up in dichloromethane and washed with 1N sodium hydroxide (3 mL), then dried over anhydrous sodium sulfate, concentrated and purified by chromatography on silica gel (10:1 dichloromethane:methanol) to afford N'-(1-(2-trimethylsilyl)-ethan-lyloxymethyl)-benzimidazol-2-ylmethyl)-(5,6,7,8-tetrahydroquinolin-8-yl)-N-benzyl-1,4-butanediamine (39 mg, 49%). $^1$H NMR ($CDCl_3$) δ 0.10(s, 9H), 0.80 (t, 2H, J=7.0 Hz), 1.41 (m, 3H), 1.76-2.21 (m, 5H), 2.44 (m, 2H), 2.46-2.26 (m, 2H), 3.35 (t, 2H, J=7.0 Hz), 3.67 (s, 2H), 4.06 (m, 1H), 4.08 (d, 1H, J=15.8 Hz), 4.22 (d, 1H, J=15.8 Hz), 5.80 (d, 1H, J=14.6 Hz), 6.02 (d, 1H, J=14.6 Hz), 7.00 (m, 1H), 7.27 (m, 8H), 7.42 (m, 1H), 7.80 (m, 1H), 8.44 (d, 1H, J=4.8 Hz).

as taken up in acetic acid (1 mL), to which a saturated solution of HBr in acetic acid (1 mL) was added. The mixture was then stirred, precipitated and isolated as per procedure D to yield COMPOUND 21 as a white crystalline solid (26 mg). $^1$H NMR ($D_2O$). δ 1.52 (m, 4H), 1.88 (m, 1H), 2.01 (m, 1H), 2.08 (m, 1H), 2.31 (m, 1H), 2.44 (m, 1H), 2.88 (m, 1H), 3.00 (t, 2H, J=6.9 Hz), 3.03 (m, 2H), 4.13 (s, 1H), 4.31 (d, 1H, J=16.1 Hz), 4.47 (m, 1H), 4.49 (d, 1H, J=16.1 Hz), 7.36 (m, 5H), 7.60 (m, 2H), 7.77 (m, 2H), 7.83 (m, 1H), 8.26 (d, 1H, J=7.8 Hz), 8.68 (d, 1H, J=4.9 Hz). $^{13}$C NMR ($D_2O$) δ 20.41, 23.68, 25.45, 27.63, 46.86, 48.24, 51.34, 51.57, 60.63, 114.25, 125.93, 126.95, 129.66, 130.08, 130.17, 130.98, 139.30, 140.60, 148.10, 151.24, 151.77. ES-MS m/z 440 (M+H); Anal. Calcd. for ($C_{28}H_{33}N_5$×3.1 HBr×1.4$H_2O$): C, 46.99; H, 5.48; N, 9.79; Br 34.61. Found: C, 47.00; H, 5.44; N, 9.54; Br, 34.57.

Example 22

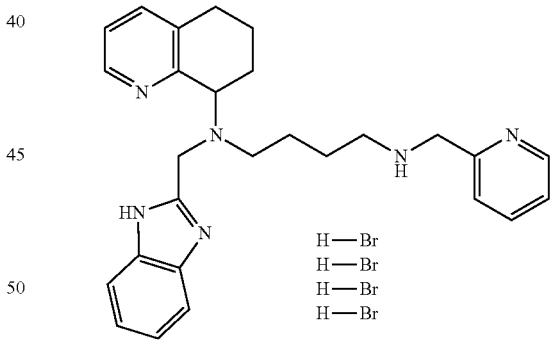

Compound 22: Preparation of $N^1$-(1H-Benzimidazol-2-ylmethyl)-$N^4$-pyridin-2-ylmethyl-$N^1$-(5,6,7,8-tetrahydro-quinolin-8-yl)-butane-1,4-diamine (hydrobromide salt)

Using General Procedure B (Two step reductive amination): Reaction of $N^1$-(1-(2-(trimethylsilypethoxymethyl)-1H-Benzimidazol-2-ylmethyl)-$N^1$-(5,6,7,8-tetrahydroquinolin-8-yl)-butane-1,4-diamine (101 mg, 0.21 mmol) with pyridine-2-carboxaldehyde (30 μL, 0.32 mmol) in $CH_3OH$ (4 mL) for 6 hours and with $NaBH_4$ (35 mg, 0.92 mmol) for 40 minutes followed by purification of the crude material by radial chromatography on silica gel (1 mm plate, 20:1:1 CH$_2$Cl$_2$—CH$_3$OH—NH$_4$OH) provided 84 mg (70%) of a colorless oil. The oil from above (84 mg, 0.15 mmol) was dissolved in 6 N HCl (2 mL), heated at 50° C. for 4.5 hours then cooled to room temperature. The solution was treated with 10 N NaOH (2 mL) and extracted with CH$_2$Cl$_2$ (3×10 mL). The combined organic extracts were dried (Na$_2$SO$_4$) and concentrated. Purification of the crude material by radial chromatography on silica gel (1 mm plate, 10:1:1 CH$_2$Cl$_2$—CH$_3$OH—NH$_4$OH) provided 41 mg (63%) of the free base of the title compound as a colorless oil.

Using General Procedure D: Conversion of the oil from above (41 mg, 0.092 mmol) to the hydrobromide salt followed by re-precipitation of the intermediate solid from methanol/ether gave COMPOUND 22 (72 mg, 93%) as a white solid. $^1$H NMR (D$_2$O) δ 1.50-1.66 (m, 4H), 1.79-1.89 (m, 1H), 1.96-2.08 (m, 1H), 2.15-2.20 (m, 1H), 2.35-2.39 (m, 1H), 2.50-2.60 (m, 1H), 2.80-2.88 (m, 1H), 3.00-3.10 (m, 4H), 4.36-4.56 (m, 5H), 7.58-7.63 (m, 2H), 7.72-7.88 (m, 5H), 8.22 (dt, 1H, J=1.5, 7.8 Hz), 8.35 (d, 1H, J=8.1 Hz), 8.62 (d, 1H, J=5.7 Hz), 8.66 (d, 1H, J=5.4 Hz); $^{13}$C NMR (D$_2$O) δ 20.43(2 carbons), 23.77, 25.43, 27.65, 47.86, 48.23, 49.66, 51.64, 60.64, 114.26, 125.94, 126.42, 126.54, 126.95, 130.97, 139.33, 140.62, 143.16, 146.99, 148.09, 148.11, 151.23, 151.76. ES-MS m/z 441 (M+H). Anal. Calcd. for C$_{27}$H$_{32}$N$_6$.4.0HBr.3.7H$_2$O: C, 39.03; H, 5.26; N, 10.11; Br, 38.47. Found: C, 39.04; H, 5.22; N, 10.04; Br, 38.52.

Example 23

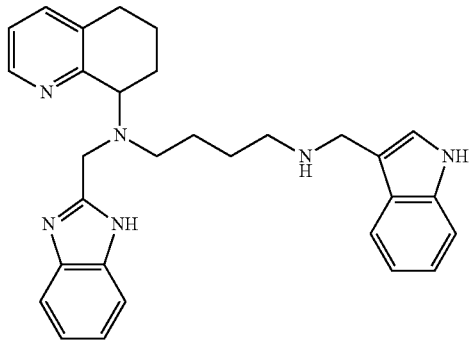 [SMILES: c1cnc2c(c1)CCCC2N(CCCCNCc1c[nH]c2ccccc12)Cc1nc2ccccc2[nH]1]

Compound 23: Preparation of N$^1$-(1H-Benzimidazol-2-ylmethyl)-N$^4$-(1H-indol-3-ylmethyl)-N$^1$-(5,6,7,8-tetrahydro-quinolin-8-yl)-butane-1,4-diamine (free base)

To a solution of N$^1$-(1-(2-(trimethylsilyl)ethoxymethyl)-1H-Benzimidazol-2-ylmethyl)-N$^1$-(5,6,7,8-tetrahydro-quinolin-8-yl)-butane-1,4-diamine (73 mg, 0.16 mmol) in CH$_2$Cl$_2$ (2 mL) was added trifluoroacetic acid (4 mL) and the resultant solution was stirred at room temperature overnight then concentrated under reduced pressure. The residue was dissolved in CH$_2$Cl$_2$ (10 mL) and water (5 mL) and treated with NaOH (10 M, ~2 mL) until the aqueous phase was basic (pH 14). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (1 mm plate, 15:1:1 CH$_2$Cl$_2$—CH$_3$OH—NH$_4$OH) provided 37 mg of N$^1$-(1H-Benzimidazol-2-ylmethyl)-N$^1$-(5,6,7,8-tetrahydro-quinolin-8-yl)-butane-1,4-diamine as a white foam.

Using General Procedure B (Two step reductive amination): Reaction of N$^1$-(1H-Benzimidazol-2-ylmethyl)-N$^1$-(5,6,7,8-tetrahydro-quinolin-8-yl)-butane-1,4-diamine (86 mg, 0.25 mmol) with indole-3-carboxaldehyde (55 mg, 0.38 mmol) in CH$_3$OH (2.5 mL) overnight and with NaBH$_4$ (27 mg, 0.71 mmol) for 30 minutes followed by purification of the crude material by radial chromatography on silica gel (1 mm plate, 50:1:1 CH$_2$Cl$_2$—CH$_3$OH—NH$_4$OH) provided 74 mg (60%) of COMPOUND 23 as a white solid. $^1$H NMR (CDCl$_3$) δ 1.38-1.52 (m, 4H), 1.64-1.73 (m, 1H), 1.83-1.95 (m, 1H), 2.00-2.05 (m, 1H), 2.15-2.21 (m, 1H), 2.49-2.56 (m, 3H), 2.67-2.89 (m, 3H), 3.88 (s, 2H), 3.96-4.10 (m, 3H), 7.03 (br s, 1H), 7.07-7.13 (m, 2H), 7.16-7.22 (m, 3H), 7.35 (dd, 1H, J=7.8, 1.0 Hz), 7.40 (d, 1H, J=7.8 Hz), 7.58-7.60 (m, 3H), 8.17 (br s, 1H), 8.55 (d, 1H, J=4.5 Hz); $^{13}$C NMR (CDCl$_3$) δ 21.79, 23.58, 26.53, 27.64, 29.64, 44.94, 49.34, 49.88, 50.59, 61.83, 111.66, 114.88, 118.99, 119.72, 121.96, 122.29, 122.51, 123.13, 127.42, 135.05, 136.74, 137.72, 147.10, 156.87, 157.83. ES-MS m/z 479 (M+H). Anal. Calcd. for C$_{30}$H$_{34}$N$_6$.1.3H$_2$O: C, 71.77; H, 7.35; N, 16.74. Found: C, 71.69; H, 7.14; N, 16.59.

Example 24

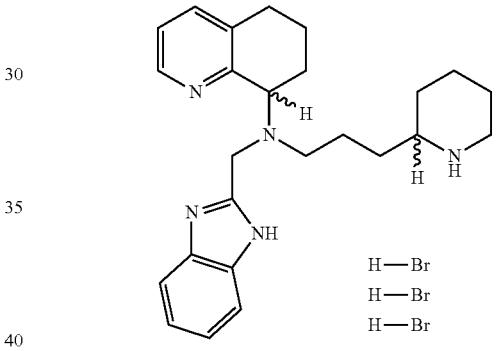

Compound 24: Preparation of (1H-Benzimidazol-2-ylmethyl)-(3-piperidin-2-yl-propyl)-(5,6,7,8-tetrahydro-quinolin-8-yl)-amine (hydrobromide salt)

A mixture of 3-(2-pyridyl)-1-propanol (0.75 mL, 5.83 mmol), PtO$_2$ (60 mg, 0.26 mmol) and concentrated HCl (0.48 mL, 5.86 mmol) in ethanol (3.1 mL) was hydrogenated (50 psi) on a Parr shaker at room temperature for 20 hours. The mixture was filtered through celite and the cake was washed with methanol. The solvent was removed from the filtrate under reduced pressure and provided 1.34 g of a white slushy solid. The solid (1.34 g) was dissolved in THF (30 mL) and water (1 mL), treated with N,N-diisopropylethylamine (2.0 mL, 11.42 mmol) and di-tert-butyl dicarbonate (2.16 g, 9.89 mmol) and the resultant mixture was stirred at room temperature overnight. The reaction mixture was diluted with water (30 mL) and extracted with EtOAc (3×60 mL). The combined organic extracts were washed with brine (2×20 mL), dried (Na$_2$SO$_4$) and concentrated. Purification of the crude material by column chromatography on silica gel (2:1 hexanes-ethyl acetate) provided 1.38 g (97% from 3-(2-pyridyl)-1-propanol) of N-tert-butoxycarbonyl-3-piperidin-2-yl-propan-1-ol as a colorless oil. $^1$H NMR (CDCl$_3$) δ 1.40-2.04 (m, 20H), 2.75 (t, 1H, J=12 Hz), 3.66-3.69 (m, 1H), 3.94-3.96 (m, 1H), 4.25 (br s, 1H).

To a solution of N-tert-butoxycarbonyl-3-piperidin-2-yl-propan-1-ol (0.372 g, 1.53 mmol) in $CH_2Cl_2$ (7.5 mL), at room temperature, was added sequentially 3 Å molecular sieves (0.814 g), N-methylmorpholine N-oxide (0.278 g, 2.37 mmol) and tetrapropylammonium perruthenate (56 mg, 0.16 mmol). After 90 minutes, the mixture was filtered through a short column of silica gel and the cake was washed with ethyl acetate. The solvent was removed from the filtrate under reduced pressure to provide 0.32 g (86%) of N-tert-butoxy-carbonyl-3-piperidin-2-yl-propionaldehyde as a green oil which was used without further purification.

Using general procedure B: Reaction of N-tert-butoxycarbonyl-3-piperidin-2-yl-propionaldehyde (0.32 g, 1.33 mmol) and (1H-Benzimidazol-2-ylmethyl)-(5,6,7,8-tetrahydro-quinolin-8-yl)-amine (0.307 g, 1.10 mmol) with $NaBH(OAc)_3$ (0.448 g, 2.11 mmol) in $CH_2Cl_2$ (10 mL) for 16 hours followed by purification of the crude material by column chromatography on silica gel (30:1:1 $CH_2Cl_2$—$CH_3OH$—$NH_4OH$) provided 0.285 g of a yellow foam. The foam (0.285 g) was dissolved in THF (10 mL), treated with 3 N HCl (10 mL), and the resultant solution was stirred at room temperature for 75 minutes. The pH of the solution was adjusted to ~14 using 10 N NaOH (~4 mL). The solution was extracted with $CH_2Cl_2$ (4×30 mL) and the combined organic extracts were dried ($Na_2SO_4$) and concentrated. Purification of the crude material by column chromatography on silica gel (25:1:1 $CH_2Cl_2$—$CH_3OH$—$NH_4OH$) provided 0.176 g (40%) of the free base of the title compound as white foam.

Using General Procedure D: Conversion of the foam from above (69 mg, 0.17 mmol) to the hydrobromide salt followed by re-precipitation of the intermediate solid from methanol/ether gave COMPOUND 24 (79 mg, 67%) as a white solid. $^1H$ NMR and HPLC analysis indicated a ~1:1 mixture of diastereomers. $^1H$ NMR ($D_2O$) δ 1.18-1.53 (m, 7H), 1.78-1.84 (m, 4H), 1.96-2.08 (m, 1H), 2.15-2.20 (m, 1H), 2.35-2.40 (m, 1H), 2.49-2.56 (m, 1H), 2.81-3.00 (m, 5H), 3.28-3.32 (m, 1H), 4.35-4.56 (m, 3H), 7.59-7.62 (m, 2H), 7.79-7.89 (m, 3H), 8.34 (br d, 1H, J=7.8 Hz), 8.63 (br d, 1H, J=5.4 Hz); $^{13}C$ NMR ($D_2O$) δ 20.42(2 carbons), 21.82, 22.22, 24.03, 27.64, 28.23, 31.02 & 31.11, 45.11, 48.13 & 48.24, 51.76 & 51.88, 56.76 & 56.83, 60.59 & 60.71, 114.25, 125.94, 126.97, 130.99, 139.31, 140.65, 148.11, 151.26, 151.75. ES-MS m/z 404 (M+H). Anal. Calcd. for $C_{25}H_{33}N_5 \cdot 3.0HBr \cdot 3.2H_2O$: C, 42.66; H, 6.07; N, 9.95; Br, 34.05. Found: C, 42.47; H, 5.82; N, 9.78; Br, 34.43.

Example 25

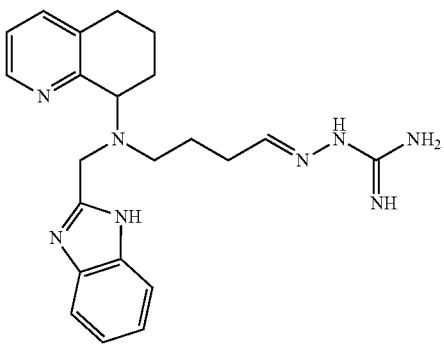 [SMILES: N=C(N)N/N=C/CCCN(Cc1nc2ccccc2[nH]1)C1CCCc2cccnc21]

Compound 25: Preparation of 4-[(1H-Benzoimidazole-2-ylmethyl)-(5,6,7,8-tetrahydro-quinolin-8-yl)-amino]-butyraldehyde aminoguanidine hydrazone (hydrobromide salt)

Using General Procedure B: To a stirred solution of 4-[(1H-Benzoimidazole-2-ylmethyl)-(5,6,7,8-tetrahydro-quinolin-8-yl)-amino]-butyraldehyde (see COMPOUND 32 for preparation) (0.2182 g, 0.63 mmol) and aminoguanadine hydrochloride (69 mg, 0.63 mmol) in dry MeOH (4 mL) was added AcOH (75 μL, 1.26 mmol) and the mixture was stirred at room temperature for 3 h. The reaction was concentrated and the residue was partitioned between $CH_2Cl_2$ (20 mL) and saturated aqueous $NaHCO_3$ (30 mL), the phases separated and the aqueous layer extracted with $CH_2Cl_2$ (2×15 mL). The combined organic extracts were dried ($Na_2SO_4$), filtered, and concentrated under reduced pressure. Purification of the crude material by radial chromatography on silica gel (1 mm plate, $CH_2Cl_2$/MeOH/$NH_4OH$, 20:1:1 then 10:1:1) afforded the desired aminoguanidine hydrazone (69 mg, 30%) as a pale yellow foam.

Using General Procedure D: Conversion of the foam from above (69 mg, 0.17 mmol) to the hydrobromide salt followed by re-precipitation of the intermediate solid from methanol/ether gave COMPOUND 25 (93 mg, 76%) as a beige solid. $^1H$ NMR ($D_2O$) δ 1.54-1.77 (m, 2H), 1.78-1.94 (m, 1H), 1.95-2.11 (m, 1H), 2.12-2.31 (m, 3H), 2.32-2.44 (m, 1H), 2.45-2.62 (m, 1H), 2.79-2.91 (m, 1H), 2.96-3.08 (m, 2H), 4.35 (d, 1H, J=16.5 Hz), 4.50 (d, 1H, J=16.5 Hz), 4.51-4.59 (m, 1H), 7.32 (t, 1H, J=5.1 Hz), 7.58-7.64 (m, 2H), 7.77-7.81 (m, 2H), 7.88 (dd, 1H, J=7.8, 5.7 Hz), 8.36 (d, 1H, J=7.8 Hz), 8.65 (d, 1H, J=9.6 Hz); $^{13}C$ NMR ($D_2O$) δ 20.40, 23.75, 27.69, 29.09, 48.45, 50.79, 60.42, 114.20, 125.88, 126.99, 130.98, 139.35, 140.72, 148.06, 151.35, 151.79, 152.94. ES-MS m/z 405 (M+H). Anal. Calcd. for $C_{22}H_{28}N_8 \cdot 3.1HBr \cdot 1.4H_2O \cdot 0.4C_4H_{10}O$: C, 39.91; H, 5.38; N, 15.78; Br, 34.88. Found: C, 39.89; H, 5.29; N, 15.84; Br, 34.94.

Example 26

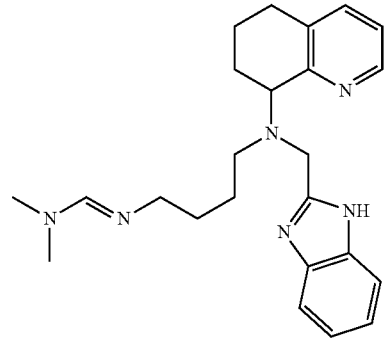 [SMILES: CN(C)/C=N/CCCCN(Cc1nc2ccccc2[nH]1)C1CCCc2cccnc21]

Compound 26: Preparation of 1-N'-[4-(1H-Benzimidazol-2-ylmethyl)-(5,6,7,8-tetrahydroquinolin-8-yl)-amino]-aminobutane-N,N-dimethylformamidine (hydrobromide salt)

Using the procedure of L. Cai (Y. Han and L. Cai *Tetrahedron Lett.* 1997, 38(31), 5423-5426) a solution of 2-pyridinesulfonyl chloride (56 mg, 0.32 mmol) in DMF (1 mL) was stirred for 10 minutes at room temperature. N-(1H-Benzimidazol-2-ylmethyl)-N-(5,6,7,8-tetrahydro-quinolin-8-yl)-butane-1,4-diamine (73 mg, 0.21 mmol) was then added, and the mixture was stirred at room temperature for 2 hours. The DMF was then removed in vacuo, and the residue was taken up in dichloromethane and washed sequentially with a saturated aqueous sodium carbonate solution, followed by distilled water. The organic fraction was then dried over anhydrous sodium sulfate and concentrated. The residue was then purified by silica gel flash chromatography to afford two products: 1-N'-[4-(1H-Benzimidazol-2-ylmethyl)-(5,6,7,8-tetrahydroquinolin-8-yl)-amino]-aminobutane-N,N-dimethylformamidine (51 mg, 59%), and N-(1H-benzimidazol-2-ylmethyl)-N-(5,6,7,8-tetrahydro-quinolin-8-yl)-butane-1,4-diamine-N-(2-pyridinyl)-sulfonamide (31 mg, 29%). The spectral data for the formamidine is as follows: $^1$H NMR (CDCl$_3$) δ 1.38-1.44 (m, 4H), 1.68 (m, 1H), 2.00 (m, 1H), 2.15 (m, 1H), 2.35 (m, 1H), 2.66-3.01 (m, 4H), 3.01 (s, 6H), 3.16 (t, 2H, J=6.9 Hz), 4.05 (s, 2H), 4.12 (m, 1H), 7.18 (m, 2H), 7.46 (m, 1H), 7.58 (m, 2H), 8.53 (m, 1H). The sulfonamide showed an excessive broadening of resonances in the $^1$H NMR spectrum (in CDCl$_3$), so it was not characterized fully at this stage, and was instead taken directly to the salting reaction.

1-N'-[4-(1H-Benzimidazol-2-ylmethyl)-(5,6,7,8-tetrahydroquinolin-8-yl)-amino]-aminobutane-N,N-dimethylformamidine (49 mg, 0.120 mmol) was taken up in acetic acid (1 mL), to which a saturated solution of HBr in acetic acid (1 mL) was added. The mixture was then stirred, precipitated and isolated as per procedure D to yield COMPOUND 26 as a white crystalline solid (52 mg). $^1$H NMR (D$_2$O). δ 1.39 (m, 4H), 1.85 (m, 1H), 2.01 (m, 1H), 2.15 (m, 1H), 2.36 (m, 1H), 2.53 (m, 1H), 2.78 (m, 1H), 2.85 (s, 3H), 3.00 (m, 2H), 3.07 (s, 3H), 3.25 (t, 2H, J=6.9 Hz), 4.46 (d, 1H, J=16.8 Hz), 4.51 (m, 1H), 4.52 (d, 1H, J=16.8 Hz), 7.60 (m, 2H), 7.65 (s, 1H), 7.80 (m, 2H), 7.87 (dd, 1H, J=7.8, 5.8 Hz), 8.35 (d, 1H, J=7.8 Hz), 8.63 (d, 1H, J=5.8 Hz). $^{13}$C NMR (D$_2$O) δ 22.89, 23.27, 27.81, 30.10, 38.38, 45.57, 49.52, 51.21, 54.51, 63.61, 116.70, 128.35, 129.43, 133.35, 141.73, 143.03, 150.53, 153.75, 154.54, 158.63. ES-MS m/z 405 (M+H); Anal. Calcd. for (C$_{24}$H$_{32}$N$_6$×3.3HBr×1.8H$_2$O): C, 40.95; H, 5.57; N, 11.94; Br 37.46. Found: C, 40.77; H, 5.59; N, 11.78; Br, 37.72.

Example 27

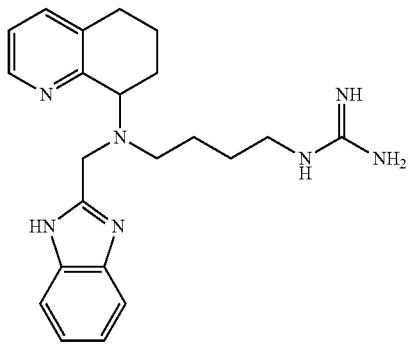 [SMILES: N=C(N)NCCCCN(Cc1nc2ccccc2[nH]1)C1CCCc2cccnc21]

Compound 27: Preparation of N-{4-[(1H-benzoimidazol-2-ylmethyl)-(5,6,7,8-tetrahydro-quinolin-8-yl)-amino]-butyl}-guanidine (hydrobromide salt)

A solution of N$^1$-(5,6,7,8-tetrahydro-quinolin-8-yl)-N$^1$-[1-(2-trimethylsilanyl-ethoxymethyl)-1H-benzoimidazol-2-ylmethyl]-butane-1,4-diamine (170 mg, 0.35 mmol), 1-H-pyrazole-1-carboxamidine hydrochloride (51 mg, 0.35 mmol) and DIPEA (61 μL, 0.35 mmol) in THF (0.2 mL) was stirred at room temperature for 3 hours. Ether (1×10 mL and 3×5 mL) was added and decanted. The resulting syrup was dried in vacuo to afford a white foam (150 mg) that was used in the next reaction without further purification.

A solution of the guanidine from above (150 mg) in 6N HCl (5 mL) was heated to 50° C. for 4 hours. The reaction mixture was cooled to room temperature, H$_2$O (5 mL) was added and the mixture was neutralized with NaHCO$_3$ (s) and saturated with NaCl (s). The aqueous layer was extracted with CHCl$_3$ (3×50 mL). The combined organic extracts were dried (MgSO$_4$), filtered and concentrated under reduced pressure. Purification by column chromatography on silica gel (CH$_2$Cl$_2$/MeOH/NH$_4$OH, 20:2:1) afforded the desired guanidine as a light yellow foam (63 mg, 46% over 2 steps).

Using General Procedure D: Conversion of the foam from above to the hydrobromide salt afforded COMPOUND 27 as a light beige solid. $^1$H NMR (D$_2$O) δ 1.40 (br s, 4H), 1.81-1.90 (m, 1H), 1.98-2.10 (m, 2H), 2.34-2.38 (m, 1H), 2.48-2.54 (m, 1H), 2.74-2.83 (m, 1H), 2.99-3.03 (m, 4H), 4.44 (d, 1H, J=10.8 Hz), 4.51-4.63 (m, 2H), 7.57-7.63 (m, 2H), 7.77-7.82 (m, 2H), 7.87 (dd, 1H, J=7.8, 6.0 Hz), 8.35 (d, 1H, J=8.1 Hz), 8.64 (d, 1H, J=5.5 Hz); $^{13}$C NMR (D$_2$O) δ 20.45, 25.52, 26.10, 27.66, 41.01, 48.97, 51.89, 61.17, 114.27, 125.92, 126.92, 131.04, 139.29, 140.50, 148.04, 151.41, 152.03, 156.91. ES-MS m/z 392.3 (M+H). Anal. Calcd. for C$_{22}$H$_{29}$N$_7$.3.1HBr.1.2H$_2$O.0.3C$_4$H$_{10}$O: C, 40.61; H, 5.51; N, 14.29; Br, 36.10. Found: C, 40.92; H, 5.31; N, 14.28; Br, 35.70.

Example 28

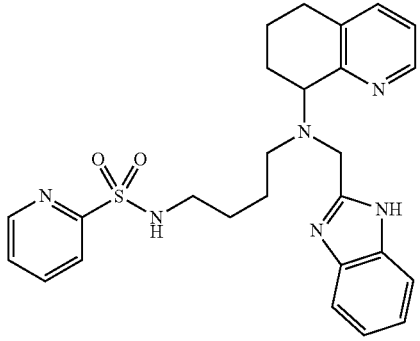 [SMILES: O=S(=O)(NCCCCN(Cc1nc2ccccc2[nH]1)C1CCCc2cccnc21)c1ccccn1]

Compound 28: Preparation of N'-(1H-benzimidazol-2-ylmethyl)-N'-(5,6,7,8-tetrahydro-quinolin-8-yl)-butane-1,4-diamine-N-(2-pyridinyl)-sulfonamide (hydrobromide salt)

N'-(1H-benzimidazol-2-ylmethyl)-N'-(5,6,7,8-tetrahydro-quinolin-8-yl)-butane-1,4-diamine-N-(2-pyridinyl)-sulfonamide (from the above reaction, 31 mg, 0.063 mmol) was taken up in acetic acid (1 mL), to which a saturated solution of HBr in acetic acid (1 mL) was added. The mixture was then stirred, precipitated and isolated as per procedure D to yield COMPOUND 28 as a white crystalline solid (52 mg). $^1$H NMR (D$_2$O) δ 1.30 (m, 4H), 1.81 (m, 1H), 1.91 (m, 1H), 2.05 (m, 1H), 2.31 (m, 1H), 2.43 (m, 1H), 2.79 (m, 1H), 2.83 (t, 2H, J=6.9 Hz), 3.00 (m, 2H), 4.31 (d, 1H, J=16.3 Hz), 4.49 (m, 1H), 4.51 (d, 1H, J=16.3 Hz), 7.57 (m, 2H), 7.86 (m, 2H), 7.83

(m, 2H), 8.00 (t, 2H, J=7.8 Hz), 8.32 (d, 1H, J=7.8 Hz), 8.56 (d, 1H, J=4.9 Hz), 8.68 (d, 1H, J=5.4 Hz). $^{13}$C NMR (D$_2$O) δ 20.43, 20.81, 24.95, 26.54, 27.64, 42.44, 48.80, 51.47, 60.94, 114.26, 122.86, 125.92, 126.91, 128.36, 130.97, 139.30, 140.08, 140.48, 140.06, 150.22, 151.40, 152.00. ES-MS m/z 491 (M+H); Anal. Calcd. for (C$_{26}$H$_{30}$N$_6$O$_2$S×3.1 HBr×1.7 H$_2$O×0.9 HOAc): C, 40.42; H, 4.89; N, 10.17; Br 29.98. Found: C, 40.31; H, 4.98; N, 10.13; Br, 30.22.

Example 29

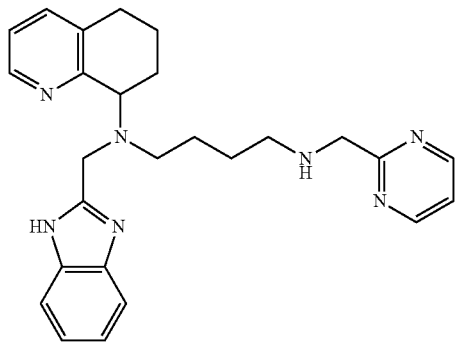 [SMILES: c1cnc(CNCCCCN(Cc2nc3ccccc3[nH]2)C2CCCc3cccnc32)nc1]

Compound 29: Preparation of N-(1H-benzoimidazol-2-ylmethyl)-N'-pyrimidin-2-ylmethyl-N-(5,6,7,8-tetrahydro-quinolin-8-yl)-butane-1,4-diamine(hydrobromide salt)

Pyrimidine-2-carbaldehyde was prepared as described for COMPOUND 68 using pyrimidine-2-carboxylic acid methyl ester (255 mg, 1.85 mmol), THF (18 mL), and LiAlH$_4$ (1.0 M/THF, 0.55 mL, 0.55 mmol). The crude material (332 mg) was determined by $^1$H NMR to be a mixture of pyrimidine-2-carbaldehyde, pyrimidine-2-carboxylic acid methyl ester, and THF (1.0:12.6:6.0 respectively) and was used in the next step without further purification.

Using General Procedure B: To a solution of the crude aldehyde from above (332 mg) and N'-(1H-benzoimidazol-2-ylmethyl)-N'-(5,6,7,8-tetrahydro-quinolin-8-yl)-butane-1,4-diamine (49 mg, 0.14 mmol) in THF (2 mL) was added NaBH(OAc)$_3$ (89 mg, 0.42 mmol) and the mixture was stirred at room temperature for 1.5 h. The crude material was dissolved in saturated HBr/AcOH (2 mL) and stirred at room temperature for 5 minutes. The solution was made basic with 10 N NaOH(aq) and extracted with CH$_2$Cl$_2$ (3×15 mL). The combined organic extracts were dried (MgSO$_4$) and concentrated in vacuo. Purification of the crude material by column chromatography on silica gel (200:5:1 CH$_2$Cl$_2$/MeOH/ NH$_4$OH) afforded a yellow oil (44 mg).

Using General Procedure D: Conversion of the oil from above (44 mg, 0.10 mmol) to the hydrobromide salt followed by re-precipitation of the intermediate solid from methanol/ ether gave COMPOUND 29 (68 mg, 84%) as a colourless solid. $^1$H NMR (D$_2$O) δ 1.64-1.93 (m, 5H), 2.07 (m, 1H), 2.22 (m, 1H), 2.42 (m, 1H), 2.61 (m, 1H), 2.89 (m, 1H), 3.04 (m, 2H), 3.15 (m, 2H), 4.41-4.61 (m, 5H), 7.53 (t, 1H, J=5.1 Hz), 7.63 (m, 2H), 7.87 (m, 3H), 8.38 (d, 1H, J=8.1 Hz), 8.67 (d, 1H, J=5.7 Hz), 8.80 (d, 2H, J=5.1 Hz); $^{13}$C NMR (D$_2$O) δ 20.44, 23.80, 25.46, 27.66, 47.61, 48.30, 51.00, 51.68, 60.67, 114.27, 121.65, 125.94, 126.94, 130.95, 139.35, 140.62, 148.12, 151.24, 151.78, 158.37, 160.71. ES-MS m/z 442 (M+H). Anal. Calcd. for C$_{26}$H$_{31}$N$_7$.4.0HBr.3.2H$_2$O: C, 37.95; H, 5.07; N, 11.92; Br, 38.84. Found: C, 38.20; H, 5.04; N, 11.77; Br, 38.61.

Example 30

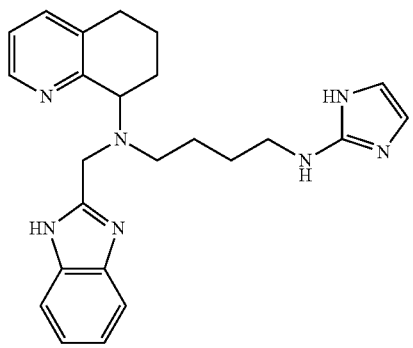 [SMILES: c1cnc2c(c1)CCCC2N(CCCCNc1ncc[nH]1)Cc1nc2ccccc2[nH]1]

Compound 30: Preparation of N-(1H-benzoimidazol-2-ylmethyl)-N'-(1H-imidazol-2-yl)-N-(5,6,7,8-tetrahydro-quinolin-8-yl)-butane-1,4-diamine To a partially dissolved solution of 2-aminoimidazole sulfate (200 mg, 1.51 mmol) in MeOH (2 mL) was added NaOH (s) (65 mg, 1.59 mmol) and the mixture was stirred at room temperature overnight. The mixture was diluted with CH$_2$Cl$_2$ (20 mL), dried (MgSO$_4$) and filtered through Celite. The cake was washed with CH$_2$Cl$_2$/MeOH (10:1) and the filtrate was concentrated under reduced pressure to afford a brown syrup (115 mg) that was used in the next reaction without further purification.

A solution of the amine from above (39 mg, 0.47 mmol) and 4-{[1-(tert-butyloxycarbonyl)-(1H-benzimidazol-2-ylmethyl)]-(5,6,7,8-tetrahydro-quinolin-8-yl)-amino}butyraldehyde (see COMPOUND 32 for preparation) (100 mg, 0.22 mmol) in MeOH (1.5 mL) was stirred at 40° C. for 3 days. NaBH$_4$ (17 mg, 0.44 mmol) was added and the resultant mixture stirred for an additional 15 minutes. The reaction mixture was diluted with CH$_2$Cl$_2$, filtered through Celite and the cake was washed with CH$_2$Cl$_2$. The combined filtrate was concentrated under reduced pressure. Purification of the crude orange foam by column chromatography on silica gel (CH$_2$Cl$_2$/MeOH/NH$_4$OH, 50:2:1) followed by radial chromatography on silica gel (1 mm plate, EtOAc/ MeOH/NH$_4$OH, 100:3:1) afforded COMPOUND 30 (32 mg, 35%) as a light purple foam. $^1$H NMR (CDCl$_3$) δ 1.32-1.75 (m, 5H), 1.83-1.95 (m, 1H), 2.02-2.10 (m, 1H), 2.17-2.21 (m, 1H), 2.51-2.91 (m, 4H), 3.05-3.09 (m, 2H), 3.98-4.11 (m, 3H), 4.31 (br s, 1H), 6.61 (s, 2H), 7.12-7.16 (m, 1H), 7.18-7.23 (m, 2H), 7.43 (d, 1H, J=7.2 Hz), 7.56 (br s, 2H), 8.52 (d, 1H, J=3.3 Hz); $^{13}$C NMR (CDCl$_3$) δ 21.12, 23.92, 25.24, 27.29, 29.14, 43.55, 4917, 50.22, 62.13, 114.93, 117.27, 121.89, 122.34, 134.91, 137.65, 146.48, 150.88, 156.09, 157.26. ES-MS m/z 416.3 (M+H). Anal. Calcd. for C$_{24}$H$_{29}$N$_7$.0.9H$_2$O.0.3C$_4$H$_8$O$_2$: C, 66.06; H, 7.30; N, 21.40. Found: C, 66.12; H, 7.32; N, 21.34.

Example 31

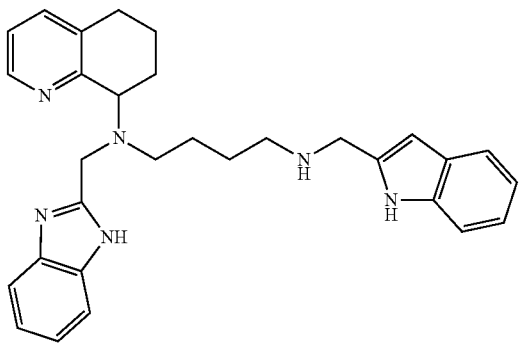 [SMILES: c1cnc2c(c1)CCCC2N(CCCCNCc1cc2ccccc2[nH]1)Cc1nc2ccccc2[nH]1]

Compound 31: Preparation of N¹-(1H-benzimidazol-2-ylmethyl)-N⁴-(1H-indol-2-ylmethyl)-N¹-(5,6,7,8-tetrahydroquinolin-8-yl)-butane-1,4-diamine A solution of indole-2-carboxaldehyde (prepared as described for COMPOUND 65) (31 mg, 0.21 mmol) and N¹-(1H-benzimidazol-2-ylmethyl)-N¹-(5,6,7,8-tetrahydroquinolin-8-yl)-butane-1,4-diamine (see COMPOUND 17) (51 mg, 0.15 mmol) in MeOH (1.8 mL) was stirred at room temperature under nitrogen for 23 hours. NaBH₄ (14 mg, 0.37 mmol) was added, and the reaction stirred for a further 15 minutes before the solvent was evaporated under reduced pressure. The residue was dissolved into CH₂Cl₂ (25 mL) and was washed with saturated aqueous NaHCO₃ (5 mL) and brine (5 mL). The organic solution was dried (MgSO₄), filtered and evaporated under reduced pressure. The yellow residue was purified by flash column chromatography on silica gel (CH₂Cl₂/MeOH/NH₄OH, 19:1:0.1) giving COMPOUND 31 as a white solid (37 mg, 0.077 mmol, 53%). ¹H NMR (CDCl₃) δ 1.35-1.49 (m, 4H), 1.60-1.76 (m, 1H), 1.81-1.96 (m, 1H), 1.96-2.08 (m, 1H), 2.11-2.22 (m, 1H), 2.45 (t, 2H, J=6.5 Hz), 2.50-2.60 (m, 1H), 2.66-2.76 (m, 2H), 2.76-2.90 (m, 1H), 3.83 (s, 2H), 3.93-4.10 (m, 3H), 6.27 (s, 1H), 7.02-7.16 (m, 3H), 7.16-7.24 (m, 2H), 7.32 (d, 1H, J=7.8 Hz), 7.41 (d, 1H, J=7.8 Hz), 7.53 (d, 1H, J=7.8 Hz), 7.55-7.62 (m, 2H), 8.56 (d, 1H, J=3.6 Hz), 9.01 (br. s, 1H). ¹³C NMR (CDCl₃) δ 21.6, 23.8, 26.2, 27.5, 29.6, 47.2, 48.9, 49.8, 50.8, 62.3, 100.6, 111.2, 119.8, 120.4, 121.7, 122.0, 122.6, 128.8, 135.1, 136.5, 137.8, 147.1, 156.9, 157.8. ES-MS m/z 479 (M+H). Anal. Calcd. for C₃₀H₃₄N₆.0.5CH₂Cl₂.0.2C₄H₁₀O: C, 70.15; H, 6.96; N, 15.68. Found: C, 70.16; H, 6.97; N, 15.73.

Example 32

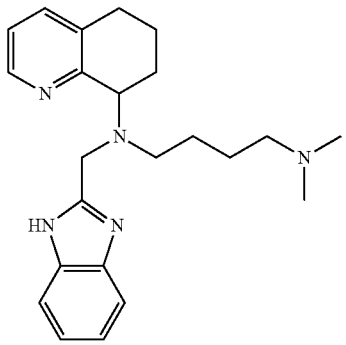 [SMILES: CN(C)CCCCN(Cc1nc2ccccc2[nH]1)C1CCCc2cccnc21]

Compound 32: (1H-Benzimidazol-2-ylmethyl)-(5,6,7,8-tetrahydroquinolin-8-yl)-(N,N-dimethyl-4-amino-but-1-yl)-amine (Hydrobromide salt)

Preparation of [1-(tert-butyloxycarbonyl)-(1H-benzimidazol-2-ylmethyl)]-(5,6,7,8-tetrahydroquinolin-8-yl)-(4-hydroxy-but-1-yl)-amine

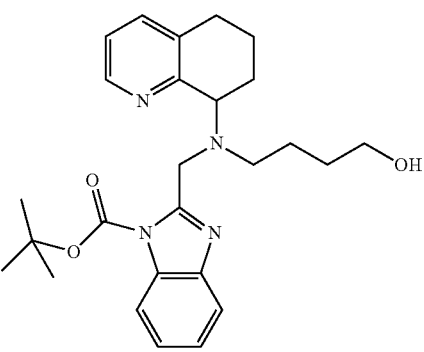 [SMILES: CC(C)(C)OC(=O)n1c(CN(CCCCO)C2CCCc3cccnc32)nc2ccccc21]

To a stirred suspension of NaH (95%, 0.81 g, 33.8 mmol) in THF (68 mL) at room temperature was added 1,4-butanediol (3.0 mL, 33.9 mmol). After 1.5 hours, tert-butyldimethylsilyl chloride (5.14 g, 34.1 mmol) was added. After stirring for a further 2.5 hours, the reaction was diluted with diethyl ether (250 mL). The organic phase was washed with saturated aqueous NaHCO₃ (2×75 mL) and brine (1×75 mL). The combined aqueous phases were extracted with ether (1×75 mL). The combined organic extracts were dried (Na₂SO₄), filtered and concentrated under reduced pressure to give a colourless liquid (6.40 g, 92%).

To a stirred solution of oxalyl chloride (6.0 mL, 68.8 mmol) in CH₂Cl₂ (450 mL) at −78° C. was added DMSO (6.5 mL, 91.6 mmol). After 2 hours, the alcohol from above (6.40 g, 31.3 mmol) was added as a solution in CH₂Cl₂ (90 mL). Triethylamine (32 mL, 230 mmol) was added after 20 minutes, followed by removal of the ice bath. After 1 hour the reaction was washed with water (1×200 mL). The aqueous phase was extracted with CH₂Cl₂ (3×100 mL). The combined organic phase was washed with 1N HCl (1×200 mL), saturated aqueous NaHCO₃ (1×200 mL) and brine (1×200 mL). The organic phase was dried (Na₂SO₄), filtered and concentrated under reduced pressure to give 6.36 g of a yellow liquid (quantitative).

Using the General Procedure B: To a stirred solution of the aldehdye from above (3.085 g, 15.2 mmol) and (1H-benzimidazol-2-ylmethyl)-(5,6,7,8-tetrahydroquinolin-8-yl)-amine (3.67 g, 13.2 mmol) in CH₂Cl₂ (90 mL) was added NaBH(OAc)₃ (6.33 g, 29.9 mmol) and the mixture stirred for 16 hours. The yellow foam obtained (8.06 g) was dissolved in THF (20 mL) and treated with 3N HCl (80 mL). After 2 hours, the reaction was basified with saturated aqueous NaHCO₃. The phases were separated, and the aqueous phase was extracted with diethyl ether (4×150 mL) and CH₂Cl₂ (2×150 mL). The organic phase was dried (Na₂SO₄), filtered and concentrated under reduced pressure to give an orange oil (4.44 g, 72%).

To a stirred solution of the protected alcohol from above (5.01 g, 10.8 mmol) in THF (50 mL) at 0° C. was added hydrogen fluoride-pyridine (~5 mL, ~175 mmol). After 75 minutes, a further 1 mL of HF-pyridine was added. After a further 20 minutes, the pH of the solution was raised to pH 13 with 1N NaOH followed by 10N NaOH. The mixture was extracted with $CH_2Cl_2$ (5×40 mL). The organic phase was dried ($Na_2SO_4$), filtered and concentrated under reduced pressure to give a crude oil (4.22 g). Purification of this oil by column chromatography (4 cm OD, 100 g silica, 30:1 $CH_2Cl_2$: $CH_3OH$) afforded the deprotected alcohol as a yellow foam (2.92 g, 77%).

To a stirred solution of the deprotected alcohol from above (2.92 g, 8.33 mmol) and diisopropylethyl amine (15 drops) in THF (40 mL) at 0° C. was added di-tert-butyl di-carbonate (1.96 g, 8.98 mmol). After stirring for 17 hours (over which time the reaction warmed to room temperature), the reaction was concentrated under reduced pressure. The residue was dissolved in $CH_2Cl_2$ (100 mL) and washed with brine (3×50 mL). The organic phase was dried ($Na_2SO_4$), filtered and concentrated under reduced pressure to afford the N-protected material as a crude yellow foam (3.79 g, quantitative). $^1$H NMR ($CDCl_3$) δ 1.48-1.71 (m, 14H), 1.93-2.05 (m, 2H), 2.15-2.25 (m, 1H), 2.57-2.67 (m, 1H), 2.71-2.94 (m, 3H), 2.53-2.59 (m, 2H), 4.32 (dd, 1H, J=9.7, 6.5 Hz), 4.49 (d, 1H, J=15.8 Hz), 4.61 (d, 1H, J=15.8 Hz), 6.93 (dd, 1H, J=7.7, 4.6 Hz), 7.20-7.30 (m, 3H), 7.68-7.72 (m, 1H), 7.78-7.83 (m, 1H), 8.33 (d, 1H, J=3.7 Hz).

Preparation of 4-{[1-(tert-butyloxycarbonyl)-(1H-benzimidazol-2-ylmethyl)]-(5,6,7,8-tetrahydro-quinolin-8-yl)-amino}butyraldehyde

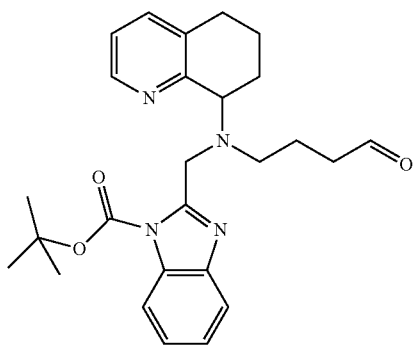 [SMILES: CC(C)(C)OC(=O)n1c(CN(CCCC=O)C2CCCc3cccnc32)nc2ccccc21]

To a stirred solution of oxalyl chloride (4.5 mL, 9.0 mmol) in $CH_2Cl_2$ (40 mL) at −78° C. was added DMSO (0.86 mL, 12.1 mmol). After 30 minutes [1-(tert-butyloxycarbonyl)-(1H-benzimidazol-2-ylmethyl)]-(5,6,7,8-tetrahydroquinolin-8-yl)-(4-hydroxy-but-1-yl)-amine (3.66 g, 8.13 mmol) was added as a solution in $CH_2Cl_2$ (7.5 mL). After a further 20 minutes, triethylamine (70 mL, 71.7 mmol) was added and the ice bath was removed. The reaction was stirred for a further 75 minutes then concentrated under reduced pressure. The residue was taken up in ethyl acetate and filtered through celite to give a crude yellow oil (3.88 g). Purification of this oil by column chromatography on silica gel (solvent=35:1:1 $CH_2Cl_2$: $CH_3OH$: $NH_4OH$) afforded the desired pure aldehyde (1.25 g, 39%). $^1$H NMR ($CDCl_3$) δ 1.52-1.72 (m, 13H), 1.74-1.88 (m, 1H), 1.90-2.00 (m, 1H), 2.06-2.17 (m, 1H), 2.36 (t, 2H, J=6.6 Hz), 2.53-2.74 (m, 2H), 2.79-2.88 (m, 1H), 4.22 (dd, 1H, J=9.7, 6.3 Hz), 4.48 (d, 1H, J=15.4 Hz), 4.66 (d, 1H, J=15.2 Hz), 6.93 (dd, 1H, J=7.6, 4.7 Hz), 7.19-7.28 (m, 4H), 7.65-7.70 (m, 1H), 7.73-7.82 (m, 1H), 8.33 (d, 1H, J=3.6 Hz), 9.56 (s, 1H).

Using the General Procedure B: To a stirred solution of 4-{[1-(tert-butyloxycarbonyl)-(1H-benzimidazol-2-ylm- ethyl)]-(5,6,7,8-tetrahydro-quinolin-8-yl)-amino}butyraldehyde (119 mg, 0.265 mmol) and dimethyl amine (2.0M in THF, 0.145 mL, 0.290 mmol) in THF (5 mL) was added $NaBH(OAc)_3$ (84 mg, 0.396 mmol) and the mixture stirred for 17 hours. Purification of the crude orange oil (116 mg) by radial chromatography on silica gel (75:1:1 $CH_2Cl_2$: $CH_3OH$: $NH_4OH$) afforded the desired N-protected intermediate (69 mg, 55%).

Using the General Procedure D for simultaneous Deprotection and HBr salting: Conversion of the N-protected material from above (69 mg) to the hydrobromide salt was afforded a white solid (80 mg). This solid was diluted with 10N NaOH (3 mL) and extracted with $CH_2Cl_2$ (5×3 mL). The organic phase was dried ($Na_2SO_4$), filtered and concentrated under reduced pressure. Purification of the yellow oil (40 mg) obtained by radial chromatography on silica gel (60:1:1 $CH_2Cl_2$: $CH_3OH$: $NH_4OH$) afforded the pure freebase as a colourless oil (19 mg, 35%)

Using the General Procedure D: Conversion of the freebase from above (19 mg) to the hydrobromide salt gave COMPOUND 32 as a white solid (24 mg, 71%). $^1$H NMR ($D_2O$) δ 1.46-1.64 (m, 4H), 1.77-1.90 (m, 1H), 1.95-2.09 (m, 1H), 2.13-2.23 (m, 1H), 2.33-2.42 (m, 1H), 2.51-2.62 (m, 1H), 2.74-2.89 (m, 7H) containing 2.81 (s, 6H), 2.96-3.03 (m, 4H), 4.39 (d, 1H, J=16.6 Hz), 4.48-4.58 (m, 2H) containing 4.53 (d, 1H, J=17.1 Hz), 7.61 (dd, 2H, J=6.2, 3.1 Hz), 7.81 (dd, 2H, J=6.2, 3.2 Hz), 7.87 (dd, 1H, J=6.7, 6.9 Hz), 8.35 (d, 1H, J=7.9 Hz), 8.63 (d, 1H, J=5.4 Hz). $^{13}$C NMR ($D_2O$) δ 20.43 (2 carbons), 22.27, 25.33, 27.63, 43.02 (2 carbons), 48.23, 51.66, 57.62, 60.70, 114.25 (2 carbons), 125.93, 126.93 (2 carbons), 131.01, 139.31, 140.60, 148.10, 151.24, 151.76. ES-MS m/z 378 (M+H) Anal Calc. for $C_{23}H_{31}N_5$.3.0HBr 3.1$H_2O$: C, 40.86; H, 5.99; N, 10.36; Br, 35.45. Found: C, 40.74; H, 5.91; N, 10.22; Br, 35.71.

Example 33

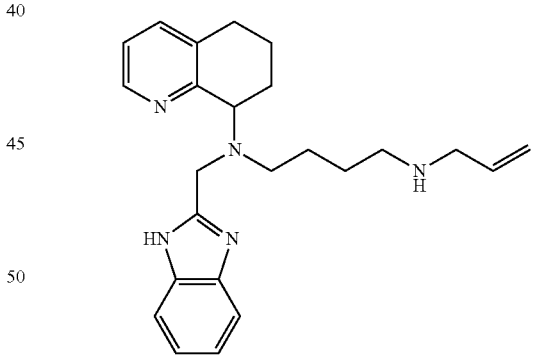

Compound 33: (1H-Benzimidazol-2-ylmethyl)-(5,6,7,8-tetrahydroquinolin-8-yl)-(N-allyl-4-amino-but-1-yl)-amine 4-Bromo-butan-1-ol (1.30 mL, 11.8 mmol) was added dropwise to refluxing allylamine (2.05 g, 35.9 mmol) and the mixture was stirred at 65° C. for 23 hours. The orange solution was diluted with 10N NaOH (15 mL) and diethyl ether (30 mL). The aqueous phase was subsequently extracted with ether (2×30 mL). The organic phase was dried ($MgSO_4$), filtered and concentrated under reduced pressure to give a yellow oil (841 mg, 55%).

To a stirred solution of the secondary amine from above (841 mg, 6.51 mmol) in THF at 0° C. was added di-tert-butyl di-carbonate (1.449 g, 6.64 mmol) and the reaction was stirred at 0° C. for 2 hours. The reaction was concentrated under reduced pressure. The yellow oil (1.645 g) was purified by column chromatography (4 cm OD, 35 g silica, EtOAc) to afford the N-protected alcohol (1.246 g, 84%).

To a suspension of the N-protected alcohol from above (236 mg, 1.03 mmol), NMO (187 mg, 1.59 mmol) and 3 Å molecular sieves (537 mg) in $CH_2Cl_2$ (5 mL) was added TPAP (37 mg, 0.106 mmol) and the mixture was stirred at room temperature for 2 hours. The mixture was filtered through a silica gel plug with ethyl acetate. The filtrate was concentrated under reduced pressure. The yellow oil (197 mg) was purified by column chromatography (12 g silica, 10:1 hexanes:ethyl acetate) to give the N-protected aldehyde (112 mg, 48%).

Using the General Procedure B: To a stirred solution of the N-protected aldehyde from above (112 mg, 0.49 mmol) and [1-(tert-butyloxycarbonyl)-(1H-benzimidazol-2-ylmethyl)]-(5,6,7,8-tetrahydroquinolin-8-yl)-amine (187 mg, 0.49 mmol) in $CH_2Cl_2$ (5 mL) was added $NaBH(OAc)_3$ (208 mg, 0.98 mmol) and the mixture was stirred for 17 hours. Purification of the crude yellow oil (286 mg) by flash chromatography (12 g silica, 50:1:1 $CH_2Cl_2$: $CH_3OH$: $NH_4OH$) afforded the N-protected tertiary amine (172 mg, 59%).

Using the General Procedure D: the N-protected tertiary amine from above (172 mg, 0.308 mmol) was converted to COMPOUND 33 as a white solid (145 mg, 70%). $^1H$ NMR ($D_2O$) δ 1.53 (br s, 4H), 1.77-1.90 (m, 1H), 1.95-2.03 (m, 1H), 2.13-2.23 (m, 1H), 2.32-2.42 (m, 1H), 2.50-2.60 (m, 1H), 2.77-2.86 (m, 1H), 2.88-2.95 (m, 2H), 2.97-3.03 (m, 2H), 3.56 (d, 2H, J=6.5 Hz), 4.38 (d, 1H, J=16.7 Hz), 4.47-4.56 (m, 2H) containing 4.53 (d, 1H, J=17.0 Hz), 5.39 (s, 1H), 5.44 (d, 1H, J=4.8 Hz), 5.74-5.89 (m, 1H), 7.60 (dd, 2H, J=6.1, 3.0 Hz), 7.80 (dd, 2H, J=6.4, 3.4 Hz), 7.86 (dd, 1H, J=7.9, 5.8 Hz), 8.34 (d, 1H, J=7.9°Hz), 8.62 (d, 1H, J=5.3 Hz). $^{13}C$ NMR ($D_2O$) δ 19.81 (2 carbons), 20.42, 23.79, 25.47, 27.28, 27.63, 46.75, 48.23, 49.80, 51.65, 50.65, 114.25 (2 carbons), 124.01, 125.93, 126.94 (2 carbons), 127.70, 130.98, 139.31, 140.61, 148.10, 151.26, 151.78. ES-MS m/z 390 (M+H) Anal Calc. for $C_{21}H_{25}N_5O.3.2HBr.1.9H_2O$: C, 38.41; H, 4.91; N, 10.67; Br, 38.94. Found: C, 38.53; H, 5.02; N, 10.42; Br, 38.79.

Example 34

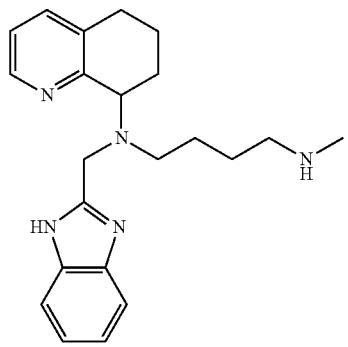 [SMILES: CNCCCCN(Cc1nc2ccccc2[nH]1)C1CCCc2cccnc21]

Compound 34: (1H-Benzimidazol-2-ylmethyl)-(5,6,7,8-tetrahydroquinolin-8-yl)-(N-methyl-4-aminobut-1-yl)-amine To a stirred solution of 4-(methylamino)-butyric acid hydrochloride (303 mg, 1.97 mmol) and dioxane (2 mL) in saturated aqueous $NaHCO_3$ (2 mL) was added added di-tert-butyl di-carbonate (523 mg, 2.40 mmol) and the mixture was stirred at 0° C. for 20 minutes followed by stirring at room temperature for 22 hours. The reaction was concentrated under reduced pressure and the residue was diluted with water (20 mL). The aqueous phase was extracted with ethyl acetate (2×15 mL). The aqueous phase was treated with 5% w/v aqueous citric acid until a pH of 4 was obtained. The aqueous phase was then again extracted with ethyl acetate (4×15 mL). The combined organic phase was dried ($MgSO_4$), filtered and concentrated under reduced pressure to give a colourless oil (300 mg, 70%).

To a stirred solution of the N-protected acid from above (143 mg, 0.659 mmol) in THF (5 mL) was added $BH_3$.THF (1.0M in THF, 2.5 mmol) and the mixture was stirred at 50° C. for 64 hours. Dry $CH_3OH$ (5 mL) was added, and the mixture stirred at 70° C. for 1 hour. The reaction was concentrated under reduced pressure. The crude yellow oil (148 mg) was purified by column chromatography (2 cm OD, 20 g silica, 1:1 EtOAc:hexanes) to afford the N-protected alcohol (71 mg, 53%).

To a suspension of the N-protected alcohol from above (71 mg, 0.35 mmol), NMO (65 mg, 0.56 mmol) and 3 Å molecular sieves (186 mg) in $CH_2Cl_2$ (2.55 mL) was added TPAP (13 mg, 0.04 mmol) and the mixture was stirred at room temperature for 1 hour. The mixture was filtered through a silica gel plug with ethyl acetate. The filtrate was concentrated under reduced pressure to give a yellow oil (46 mg, 65%).

Using the General Procedure B: To a stirred solution of the N-protected aldehyde from above (46 mg, 0.229 mmol) and [1-(tert-butyloxycarbonyl)-(1H-benzimidazol-2-ylmethyl)]-(5,6,7,8-tetrahydroquinolin-8-yl)-amine (89 mg, 0.229 mmol) in $CH_2Cl_2$ (2.55 mL) was added $NaBH(OAc)_3$ (100 mg, 0.47 mmol) and the mixture was stirred for 19 hours. Purification of the crude yellow oil (126 mg) by flash chromatography (12 g silica, 50:1:1 $CH_2Cl_2$: $CH_3OH$: $NH_4OH$) afforded the N-protected tertiary amine (80 mg, 62%).

Using the General Procedure D: The N-protected tertiary amine from above (76 mg, 0.135 mmol) was converted to COMPOUND 34 as a white solid (71 mg, 75%). $^1H$ NMR ($D_2O$) δ 1.54 (br s, 4H), 1.74-1.90 (m, 1H), 1.95-2.09 (m, 1H), 2.13-2.23 (m, 1H), 2.32-2.42 (m, 1H), 2.50-2.64 (m, 4H) containing 2.61 (s, 3H), 2.77-2.94 (m, 3H), 2.97-3.04 (m, 2H), 4.39 (d, 1H, J=17.1 Hz), 4.47-4.60 (m, 2H) containing 4.53 (d, 1H, J=17.2 Hz), 7.60 (dd, 2H, J=6.1, 3.0 Hz), 7.80 (dd, 2H, J=6.1, 3.0 Hz), 7.86 (dd, 1H, J=7.9, 6.2 Hz), 8.34 (d, 1H, f=7.9 Hz), 8.62 (d, 1H, J=5.0 Hz). $^{13}C$ NMR ($D_2O$) δ 20.42 (2 carbons), 23.69, 25.40, 27.64, 33.05, 48.23, 49.00, 51.68, 60.66, 114.25 (2 carbons), 125.93, 126.93 (2 carbons), 130.97, 139.31, 140.61, 148.10, 151.25, 151.77. ES-MS m/z 364 (M+H). Anal Calc. for $C_{21}H_{25}N_5O.3.2HBr.1.9H_2O$: C, 38.41; H, 4.91; N, 10.67; Br, 38.94. Found: C, 38.53; H, 5.02; N, 10.42; Br, 38.79.

Example 35

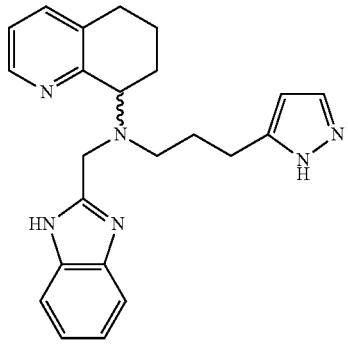 [SMILES: c1cnc2c(c1)CCCC2N(CCCc1ccn[nH]1)Cc1nc2ccccc2[nH]1]

Compound 35: Preparation of (1H-benzimidazol-2-ylmethyl)-[3-(2H-pyrazol-3-yl)-propyl]-(5,6,7,8-tetrahydro-quinolin-8-yl)-amine (hydrobromide salt)

Preparation of (cyanomethyl)triphenylphosphonium bromide

To a solution of PPh$_3$ (1.57 g, 5.99 mmol) in Et$_2$O (30 mL) was added BrCH$_2$CN (0.42 mL, 6.0 mmol). The reaction was stirred at reflux for 17 hours. The solvent was removed under reduced pressure, the residue was suction filtered from a small portion of ice-cold Et$_2$O, and washed with a small amount of cold Et$_2$O, giving the phosphonium salt as a white powder (1.05 g, 2.74 mmol, 46%). $^1$H NMR (CDCl$_3$) δ 6.39 (d, 2H, J=15.3 Hz), 7.69-7.76 (m, 6H), 7.82-7.87 (m, 3H), 7.96-8.03 (m, 6H).

Preparation of 3-(2H-pyrazol-3-yl)-acrylonitrile

To a suspension of the phosphonium salt (900 mg, 2.35 mmol) in THF (10 mL) under nitrogen was added NaH (60% in mineral oil, 99 mg, 2.5 mmol) in one portion. The suspension stirred at room temperature for 10 minutes, then pyrazole-3-carboxaldehyde (211 mg, 2.20 mmol) was added as a solid in one portion. The reaction was heated to reflux for 30 minutes, then cooled to room temperature and saturated aqueous NH$_4$Cl (10 mL) was added. The mixture was extracted with CH$_2$Cl$_2$ (25 mL×3) and the combined organic solution was dried (MgSO$_4$), filtered and concentrated under reduced pressure. Purification by flash column chromatography on silica (EtOAc/hexane, 1:1) gave the alkene (white solid) as an approximately 1.5:1 mixture of the E:Z isomers (232 mg, 1.95 mmol, 89%).

Data for E-isomer: $^1$H NMR (CDCl$_3$) δ 5.92 (d, 1H, J=16.5 Hz), 6.54 (d, 1H, J=2.4 Hz), 7.43 (d, 1H, J=16.8 Hz), 7.60 (d, 1H, J=2.4 Hz).

Data for Z-isomer: $^1$H NMR (CDCl$_3$) δ 5.46 (d, 1H, J=12.0 Hz), 6.98 (d, 1H, J=2.4 Hz), 7.24 (d, 1H, J=12.3 Hz), 7.66 (d, 1H, J=2.4 Hz).

Preparation of 3-(2H-pyrazol-3-yl)-propylamine

The α,β-unsaturated nitrile (mixture of isomers, 250 mg, 2.10 mmol) was hydrogenated (45 psi) over Raney-nickel in MeOH saturated with NH$_3$ (15 mL) for 15.5 hours. The mixture was suction filtered through Celite and washed with MeOH. The filtrate was concentrated under reduced pressure giving a brown oil. Purification by flash column chromatography on silica (CH$_2$Cl$_2$/MeOH/NR$_4$OH, 5.6:1:0.07) gave the saturated primary amine as a yellow oil (197 mg, 1.57 mmol, 75%). $^1$H NMR (CDCl$_3$) δ 1.82 (quint, 2H, J=7.1 Hz), 2.76 (apparent q, 4H, J=6.8 Hz), 4.46 (br. s, 3H), 6.07 (d, 1H, J=2.1 Hz), 7.47 (d, 1H, J=1.8 Hz).

Preparation of [3-(2H-pyrazol-3-yl)-propyl]-(5,6,7,8-tetrahydro-quinolin-8-yl)-amine A solution of the primary amine (190 mg, 1.52 mmol) and 8-oxo-5,6,7,8-tetrahydroquinoline (270 mg, 1.83 mmol) in MeOH (4 mL) was stirred at room temperature for 6 hours. NaBH$_4$ (75 mg, 2.0 mmol) was added and the reaction was stirred for an additional 15 minutes, then the solvent was evaporated under reduced pressure. The residue was taken up into CH$_2$Cl$_2$ (20 mL) and was washed with saturated aqueous NaHCO$_3$ (5 mL) and brine (5 mL). The organic solution was dried (MgSO$_4$), filtered and concentrated under reduced pressure. Purification by flash column chromatography on silica (CH$_2$Cl$_2$/MeOH/NH$_4$OH, 19:1:0.1, then MeOH) gave the secondary amine as a yellow oil (100 mg, 0.39 mmol, 26%). $^1$H NMR (CDCl$_3$) δ 1.67-1.87 (m, 2H), 1.90-2.03 (m, 3H), 2.11-2.23 (m, 1H), 2.67-2.89 (m, 6H), 3.84 (dd, 1H, J=7.7, 5.3 Hz), 6.03 (d, 1H, J=1.8 Hz), 7.09 (dd, 1H, J=7.7, 4.7 Hz), 7.39 (d, 1H, J=7.6 Hz), 7.41 (d, 1H, J=1.8 Hz), 8.42 (d, 1H, J=3.9 Hz).

Preparation of 2-{[[3-(2H-pyrazol-3-yl)-propyl]-(5,6,7,8-tetrahydro-quinolin-8-yl)-amino]-methyl}-benzimidazole-1-carboxylic acid tert-butyl ester A solution of the amine (100 mg, 0.39 mmol), tert-butyl 2-chloromethyl-benzimidazole-1-carboxylate (107 mg, 0.40 mmol), DIPEA (0.10 mL, 0.57 mmol) and KI (approx. 10 mg) in CH$_3$CN (2.5 mL) was heated to 60° C. under nitrogen for 18.5 hours. Once cooled to room temperature, saturated aqueous NaHCO$_3$ (10 mL) was added and the mixture was extracted with CH$_2$Cl$_2$ (15 mL×3). The combined organic solution was dried (MgSO$_4$), filtered and concentrated under reduced pressure. Three attempts at purification by flash column chromatography on silica, the first eluted with CH$_2$Cl$_2$/MeOH/NH$_4$OH, 19:1:0.1, the second eluted with CH$_2$Cl$_2$/MeOH/NH$_4$OH, 49:1:0.25, gradually increased to 19:1:0.1, and the third eluted with CH$_2$Cl$_2$/MeOH/NH$_4$OH, 49:1:0.25, gave the tertiary amine as a white foam (70.6 mg, 0.15 mmol, 37%[1]). $^1$H NMR (CDCl$_3$) δ 1.64 (s, 9H), 1.64-1.80 (m, 2H), 1.90-2.12 (m, 3H), 2.19-2.33 (m, 1H), 2.41-2.51 (m, 1H), 2.60-2.86 (m, 4H), 3.06-3.15 (m, 1H), 3.23-337 (m, 1H), 4.04 (dd, 1H, J=10.4, 6.8 Hz), 4.19 (d, 1H, J=15.0 Hz), 4.53 (d, 1H, J=15.0 Hz), 6.00 (d, 1H, J=1.5 Hz), 6.72 (dd, 1H, J=7.5, 4.8 Hz), 6.89 (d, 1H, J=7.5 Hz), 7.14-7.29 (m, 2H), 7.45 (d, 1H, J=1.5 Hz), 7.63 (dd, 1H, J=7.9, 1.5 Hz), 7.73 (dd, 1H, J=7.9, 1.5 Hz), 8.35 (d, 1H, J=3.6 Hz).

Preparation of Compound 35

To a solution of the tertiary amine (30.8 mg, 0.063 mmol) in glacial HOAc (1.0 mL) was added a saturated solution of HBr in HOAc (0.5 mL). The mixture was stirred at room temperature for 1 hour, then was diluted with Et$_2$O (5 mL). The solvent was decanted and the precipitate was washed with Et$_2$O (1 mL×5) and dried at 90° C. under reduced pressure giving COMPOUND 35 as a yellow solid (35.5 mg, 0.049 mmol, 78%). $^1$H NMR (D$_2$O) δ 1.68-2.00 (m, 4H), 2.07-2.19 (m, 1H), 2.27-2.49 (m, 2H), 2.66 (t, 1H, J=7.4 Hz), 2.73-2.85 (m, 1H), 2.92-3.01 (m, 2H), 4.32 (d, 1H, J=16.8 Hz), 4.47 (d, 1H, J=16.8 Hz), 4.49 (dd, 1H, J=10.7, 5.9 Hz), 6.32 (d, 1H, J=2.7 Hz), 7.54-7.61 (m, 2H), 7.71-7.79 (m, 3H), 7.83 (dd, 1H, J=8.1, 5.4 Hz), 8.32 (d, 1H, J=7.8 Hz), 8.59 (d, 1H, J=5.7 Hz). $^{13}$C NMR (D$_2$O) δ 20.4, 20.5, 22.8, 27.1, 27.6, 48.1, 50.9, 60.5, 106.2, 114.2, 125.9, 127.0, 130.9, 134.4, 139.3, 140.7, 148.1, 149.0, 151.1, 151.5. ES-MS m/z 387 (M+H). Anal. Calcd. for C$_{23}$H$_{26}$N$_6$.3.3HBr.1.9H$_2$O.0.9C$_4$H$_{10}$O: C, 40.85; H, 5.10; N, 11.53; Br, 36.16. Found: C, 41.02; H, 5.05; N, 11.56; Br, 35.98.

Example 36

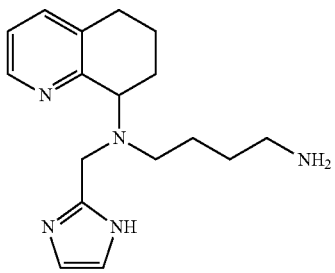 [SMILES: NCCCCN(Cc1ncc[nH]1)C1CCCc2cccnc21]

Compound 36: N'-(1H-imidazol-2-ylmethyl)-N'-(5,6,7,8-tetrahydro-quinolin-8-yl)-butane-1,4-diamine (hydrobromide salt)

Preparation of 2-[4-(5,6,7,8-tetrahydro-quinolin-8-ylamino)-butyl]-isoindole-1,3-dione 4-(1,3-Dioxo-1,3-dihydro-isoindol-2-yl)-butyraldehyde (617 mg, 2.84 mmol), 6,7-dihydro-5H-quinolin-8-one (463 mg, 3.13 mmol), and sodium triacetoxyborohydride (1.81 g, 8.53 mmol) in CH$_2$Cl$_2$ (25 mL) were stirred at room temperature for 2 hours. Then it was quenched with 1N NaOH (20 mL) and the mixture was washed with CH$_2$Cl$_2$ (2×25 mL). The organic layer was dried (MgSO$_4$), filtered, concentrated, and dried in vacuo to afford a brown oil. Purification by flash column chromatography on silica gel using CH$_3$OH/CH$_2$Cl$_2$ (5:95) afforded the product pure as a yellow oil (506 mg, 51%). $^1$H NMR (CDCl$_3$) δ 1.59-1.83 (m, 6H), 1.98-2.00 (m, 1H), 2.14-2.16 (m, 1H), 2.73-2.81 (m, 4H), 3.70-3.76 (m, 3H), 7.06 (dd, 1H, J=6.0, 3.0 Hz), 7.36 (d, 1H, J=6.0 Hz), 7.68-7.71 (m, 2H), 7.82-7.84 (m, 2H), 8.36 (d, 1H, J=6.0 Hz).

Preparation of N'-(1H-imidazol-2-ylmethyl)-N-(5,6,7,8-tetrahydro-quinolin-8-yl)-butane-1,4-diamine The above amine (215 mg, 0.62 mmol), 2-imidazolecarboxaldehyde (118 mg, 1.23 mmol), and sodium cyanoborohydride (114 mg, 1.85 mmol) were stirred in methanol (5 mL) overnight. Then the reaction mixture was dissolved in CH$_2$Cl$_2$ (15 mL) and extracted with saturated NaHCO$_3$ (3×10 mL). The aqueous layer was washed with CH$_2$Cl$_2$ (2×20 mL). Then the combined organic extracts were dried (MgSO$_4$), filtered, concentrated, and dried in vacuo to afford a yellow foam. Purification by radial chromatography on silica gel (2 mm plate, using NH$_4$OH/CH$_3$OH/CH$_2$Cl$_2$; 1:1:100→1:3:100) afforded the product partially clean as a yellow foam (179 mg, 67%). $^1$H NMR (CDCl$_3$) δ 1.36-1.41 (m, 3H), 1.55-1.63 (m, 3H), 2.00-2.04 (m, 2H), 2.52-2.76 (m, 4H), 3.46-3.79 (m, 2H), 3.83 (q, 2H, J=18 Hz), 4.18 (m, 1H), 3.96 (s, 1H), 7.03-7.10 (m, 1H), 7.05 (s, 1H), 7.45-7.49 (m, 1H), 7.67-7.71 (m, 2H), 7.79-7.81 (m, 2H), 8.48 (d, 3.0 Hz).

To a solution of the above amine (179 mg, 0.42 mmol) in ethanol (4 mL) was added hydrazine hydrate (0.12 mL, 2.49 mmol). The reaction mixture was stirred at room temperature for 3 days. Then the solvent was removed under reduced pressure and the residue was dissolved in CH$_2$Cl$_2$ and filtered. The filtrate was concentrated to dryness to afford a yellow oil. Purification by radial chromatography on silica gel (2 mm plate, using NH$_4$OH/CH$_3$OH/CH$_2$Cl$_2$; 1:5:100→1:10:100) afforded the product as a yellow oil (66.1 mg, 53%). $^1$H NMR (CDCl$_3$) δ 1.31-1.38 (m, 4H), 1.61-1.65 (m, 1H), 1.79-1.83 (m, 1H), 1.96-2.02 (m, 1H), 2.11-2.15 (m, 1H), 2.32-2.39 (m, 1H), 2.46-2.55 (m, 2H), 2.61-2.70 (m, 2H), 2.74-2.80 (m, 1H), 3.78 (q, 2H, J=15.3 Hz), 3.95 (dd, 1H, J=9.3, 6.3 Hz), 6.93 (s, 2H), 7.09 (dd, 1H, J=7.7, 4.5 Hz), 7.39 (d, 1H, J=7.5 Hz), 8.42 (d, 1H, J=3.9 Hz).

Preparation of N'-(1H-imidazol-2-ylmethyl)-N'-(5,6,7,8-tetrahydro-quinolin-8-yl)-butane-1,4-diamine (hydrobromide salt)

To a solution of the above amine (66 mg, 0.22 mmol) in acetic acid (1 mL) was added a hydrobromic acid saturated acetic acid (0.5 mL). The reaction mixture was stirred for 30 minutes and then diethyl ether was added until the precipitation of COMPOUND 36 was afforded as an orange oil (22 mg, 33%). $^1$H NMR (D$_2$O) δ 1.47-1.50 (m, 4H), 1.81-1.94 (m, 2H), 2.12-2.16 (m, 1H), 2.25-2.29 (m, 1H), 2.46-2.50 (m, 1H), 2.71-2.75 (m, 1H), 2.84-2.86 (m, 2H), 2.97-3.00 (m, 2H), 4.19 (q, 2H, J=19.8 Hz), 4.33-4.38 (m, 1H), 7.40 (s, 2H), 7.83 (t, 1H, J=6.3 Hz), 8.31 (d, 1H, J=8.1 Hz), 8.55 (d, 1H, J=6.0 Hz). $^{13}$C NMR (D$_2$O) δ 20.19, 20.41, 25.02, 25.29, 27.57, 39.53, 47.09, 49.29, 51.20, 60.10, 119.54, 125.82, 139.22, 140.45, 145.32, 147.96, 151.46. ES-MS m/z 300 [M+H]$^+$. Anal. Calcd. for C$_{17}$H$_{25}$N$_5$.3.6HBr.1.4H$_2$O.0.4C$_2$H$_4$—O$_2$: C, 33.41; H, 5.12; N, 10.84; Br, 44.76. Found: C, 33.41; H, 5.12; N, 10.84; Br, 44.76.

Example 37

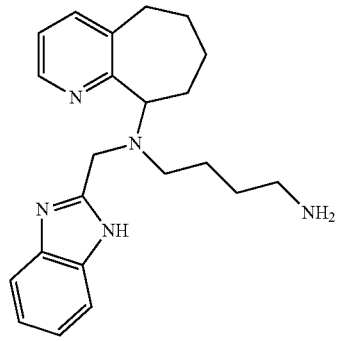 [SMILES: NCCCCN(Cc1nc2ccccc2[nH]1)C1CCCCc2cccnc21]

Compound 37: Preparation of N$^1$-(1H-Benzimidazol-2-ylmethyl)-N$^1$-(6,7,8,9-tetrahydro-5H-cyclohepta[b]pyridin-9-yl)-butane-1,4-diamine

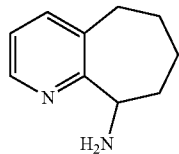 [SMILES: NC1CCCCc2cccnc21]

Preparation of 6,7,8,9-Tetrahydro-5H-cyclohepta[b]pyridin-9-ylamine

To a stirred solution of 2,3-cycloheptenopyridine (42.94 g, 0.292 mol) in glacial acetic acid (160 mL) at room temperature was added 30% H$_2$O$_2$ (30 mL) and the resultant solution was heated to 70° C. After 6 hours, the reaction mixture was cooled to room temperature, additional H$_2$O$_2$ (30 mL) was added, and the solution was heated at 70° C. overnight. The reaction mixture was cooled to room temperature and concentrated under reduced pressure. The residue was dissolved in CHCl$_3$ (200 mL) and treated with solid Na$_2$CO$_3$ (100 g). After 1 hour, the supernatant was decanted and the residue was washed with warm CHCl$_3$ (3×200 mL). The combined supernatants were filtered and concentrated to provide 60 g of 6,7,8,9-tetrahydro-5H-cyclohepta[b]pyridine 1-oxide as a yellow oil. $^1$H NMR (CDCl$_3$) δ 1.63-1.73 (m, 4H), 1.82-1.91 (m, 2H), 2.77-2.83 (m, 2H), 3.36-3.42 (m, 2H), 6.94-7.05 (m, 2H), 8.17 (d, 1H, J=6.1 Hz).

The N-oxide was dissolved in acetic anhydride (222 mL) and heated at 90° C. overnight. The mixture was cooled to room temperature and concentrated. Distillation (Kugelrohr, bp 110-140° C. @ 1 Torr) of the resultant oil provided 53.26 g of acetic acid 6,7,8,9-tetrahydro-5H-cyclohepta[b]pyridin-9-yl ester.

To a solution of acetic acid 6,7,8,9-tetrahydro-5H-cyclohepta[b]pyridin-9-yl ester (53.26 g, 0.259 mol) in methanol (350 mL) was added K$_2$CO$_3$ (72.98 g, mol) and the resultant mixture was stirred at room temperature overnight. The mixture was poured into water (350 mL) and extracted with CHCl$_3$ (3×300 mL). The combined organic extracts were dried (Na$_2$SO$_4$), and concentrated to provide 41.70 g of 6,7,8,9-tetrahydro-5H-cyclohepta[b]pyridin-9-ol.

To a stirred solution of 6,7,8,9-tetrahydro-5H-cyclohepta[b]pyridin-9-ol (41.70 g, 0.255 mol) in CH$_2$Cl$_2$ (300 mL) at 0° C. was added triethylamine (72 mL, 0.517 mol) followed by methanesulfonyl chloride (30 mL, 0.388 mol). The resultant mixture was stirred at room temperature over night. The mixture was poured into water (200 mL) and the phases were separated. The organic phase was washed with brine (2×150 mL), dried (Na$_2$SO$_4$), and concentrated to give 50.87 g of crude methanesulfonic acid 6,7,8,9-tetrahydro-5H-cyclohepta[b]pyridin-9-yl ester.

This ester was dissolved in DMF (420 mL), treated with sodium azide (33.40 g, 0.514 mol), and heated at 60° C. overnight. The mixture was cooled to room temperature and concentrated. The resultant slurry was poured into brine (500 mL) and extracted with ether (4×500 mL). The combined organic extracts were washed with brine (2×100 mL), dried (Na$_2$SO$_4$), and concentrated. The crude material was filtered (eluant CH$_2$Cl$_2$) through a short plug of silica gel to provide 23.18 g (42% from 2,3-cycloheptenopyridine) of 9-azido-6,7,8,9-tetrahydro-5H-cyclohepta[b]pyridine as a red oil. $^1$H NMR (CDCl$_3$) δ 1.53-1.66 (m, 1H), 1.73-2.14 (m, 5H), 2.63-2.72 (m, 1H), 2.99-3.09 (m, 1H), 4.93 (dd, 1H, J=7.8, 1.7 Hz), 7.13 (dd, 1H, J=7.9, 4.8 Hz), 7.44 (d, 1H, J=5.7 Hz), 8.39 (dd, 1H, J=4.8, 1.9 Hz).

To a solution of the azide (23.18 g, 0.123 mol) in methanol (150 mL) was added Palladium, 10 wt. % on activated carbon (1.95 g) and the resultant mixture was hydrogenated at 40 psi on a Parr shaker. The mixture was vacuum filtered through celite and the cake was washed with methanol. The solvent was removed from the filtrate under reduced pressure and the oil obtained was distilled (Kugelrohr, by 105-140° C. @ 0.2 Ton) to provide 17.56 g (88%) of 6,7,8,9-Tetrahydro-5H-cyclohepta[b]pyridin-9-ylamine as a pale yellow oil. $^1$H NMR (CDCl$_3$) δ 1.23-1.37 (m, 1H), 1.43-1.57 (m, 1H), 1.78-2.10 (m, 6H) including 2.04 (s, 2H), 2.71-2.85 (m, 2H), 4.19 (dd, 1H, J=10.0, 1.5), 7.05 (dd, 1H, J=7.4, 4.9 Hz), 7.36 (d, 1H, J=5.9 Hz), 8.38 (d, 1H, J=4.9 Hz).

To a stirred solution of 6,7,8,9-Tetrahydro-5H-cyclohepta[b]pyridin-9-ylamine (0.235 g, 1.45 mmol) from above and NaBH(OAc)$_3$ (0.461 g, 2.18 mmol) in anhydrous CH$_2$Cl$_2$ (8 mL) was added dropwise 4-(1,3-Dioxo-1,3-dihydro-isoindol-2-yl)-butyraldehyde (0.263 g, 1.21 mmol) in anhydrous CH$_2$Cl$_2$ (4 mL). The resultant mixture was stirred at room temperature for 3 hours, diluted with CH$_2$Cl$_2$ (25 mL), and quenched with saturated aqueous NaHCO$_3$ (15 mL). The two phases were stirred together for 1 hour and then separated. The organic phase was dried (Na$_2$SO$_4$), filtered, and concentrated under reduced pressure. Purification of the crude material by flash column chromatography on silica gel (30:1 CH$_2$Cl$_2$/MeOH followed by 20:1 CH$_2$Cl$_2$/MeOH) provided 0.34 g (65%) of the amine as a colourless oil.

To a stirred solution of 2-[4-(6,7,8,9-Tetrahydro-5H-cyclohepta[b]pyridin-9-ylamino)-butyl]-isoindole-1,3-dione from above (0.34 g, 0.94 mmol) in CH$_3$CN (5 mL) was added N,N-diisopropylethylamine (0.30 mL, 1.7 mmol), KI (7.8 mg, 0.047 mmol) and 1-(tert-butoxycarbonyl)-2-(chloromethyl)benzimidazole (0.302 g, 1.13 mmol). The resultant mixture was stirred at 60° C. overnight, cooled, and concentrated under reduced pressure. The residue was partitioned between CH$_2$Cl$_2$ (25 mL) and saturated aqueous NaHCO$_3$ (15 mL). The aqueous phase was extracted with CH$_2$Cl$_2$ (2×10 mL), dried (Na$_2$SO$_4$), filtered, and concentrated under reduced pressure. Purification of the crude material by flash column chromatography on silica gel (50:1 CH$_2$Cl$_2$/MeOH) afforded the desired alkylated amine (0.33 g, 60%) as a white foam.

To a stirred solution of 2-{[[4-(1,3-Dioxo-1,3-dihydro-isoindol-2-yl)-butyl]-(6,7,8,9-tetrahydro-5H-cyclohepta[b]pyridin-9-yl)-amino]-methyl}-benzimidazole-1-carboxylic acid tert-butyl ester (0.33 g, 0.56 mmol) from above in EtOH (4 mL) was added anhydrous hydrazine (0.090 mL, 2.8 mmol) and the resultant mixture stirred at room temperature for 16 hours. The mixture was filtered and concentrated under reduced pressure. Purification of the crude material by radial chromatography on silica gel (TLC grade 2 mm plate, 50:1:1 CH$_2$Cl$_2$/MeOH/NH$_4$OH followed by 40:1:1 CH$_2$Cl$_2$/MeOH/NH$_4$OH) afforded 0.13 g (62%) of the free base of the title compound as a white foam. $^1$H NMR (CDCl$_3$) δ 1.30-1.85 (m, 7H), 1.90-2.00 (m, 2H), 2.10-2.24 (m, 1H), 2.40-2.52 (m, 1H), 2.57-2.78 (m, 4H), 3.15-3.27 (m, 1H), 3.77-3.86 (m, 1H), 4.00 (d, 1H, J=18 Hz), 4.15 (t, 1H, J=6 Hz), 7.16 (dd, 1H, J=2.7, 7.5 Hz), 7.20-7.26 (m, 4H), 7.48 (dd, 1H, J=1.5, 7.5 Hz), 7.56-7.69 (m, 2H), 8.48 (dd, 1H, J=1.5, 4.8 Hz); $^{13}$C NMR (CDCl$_3$) δ 25.04, 27.46, 27.85, 28.85, 31.63, 34.58, 42.25, 48.21, 51.26, 67.12, 122.18, 122.76, 138.74, 145.95, 163.11. ES-MS m/z 364 (M+H). Anal. Calcd. for C$_{22}$H$_{29}$N$_5$.0.3CH$_2$Cl$_2$: C, 68.86; H, 7.67; N, 18.00. Found: C, 68.99; H, 7.84; N, 17.63.

Example 38

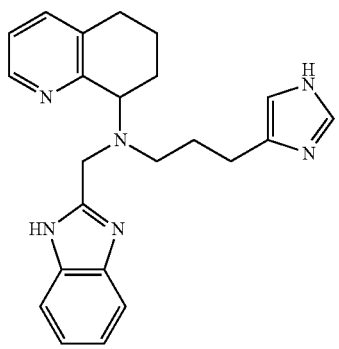 [SMILES: c1cnc2c(c1)CCCC2N(CCCc1c[nH]cn1)Cc1nc2ccccc2[nH]1]

Compound 38: Preparation of (1H-benzoimidazol-2-ylmethyl)-[3-(1H-imidazol-4-yl)-propyl]-(5,6,7,8-tetrahydro-quinolin-8-yl)-amine Preparation of 3-(1H-imidazol-4-yl)-propionic acid

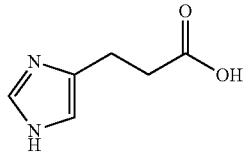

A suspension of urocanic acid (2.00 g, 14.5 mmol) in H$_2$O (40 mL) was shaken at room temperature with a suspension of 10% Pd/C (200 mg, 0.19 mmol) under hydrogen atmosphere (30 psi) for 2 h. The catalyst was removed by filtration, and the filtrate was concentrated in vacuo to give a colourless solid (1.95 g, 96%). $^1$H NMR (D$_2$O) δ 2.52 (t, 2H, J=7.2 Hz), 2.92 (t, 2H, J=7.2 Hz), 7.16 (s, 1H), 8.49 (s, 1H).

Preparation of 3-(1H-Imidazol-4-yl)-propionic acid methyl ester

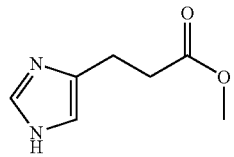

A solution of 3-(1H-imidazol-4-yl)-propionic acid (1.95 g, 13.9 mmol) and H$_2$SO$_4$ (catalytic) in MeOH (30 mL) was heated at reflux for 15 h, then concentrated in vacuo. The residue was dissolved in CH$_2$Cl$_2$ (40 mL) and washed with saturated NaHCO$_3$(aq) (30 mL). The aqueous phase was saturated with sodium chloride and extracted with EtOAc (4×25 mL). The combined organic phases were dried (MgSO$_4$) and concentrated in vacuo to give a yellow oil (1.93 g, 90%). $^1$H NMR (CDCl$_3$) δ 2.68 (t, 2H, J=7.2 Hz), 2.93 (t, 2H, J=7.2 Hz), 3.69 (s, 3H), 6.81 (s, 1H), 7.55 (s, 1H).

Preparation of 4-(3-Hydroxy-propyl)-imidazole-1-carboxylic acid tert-butyl ester

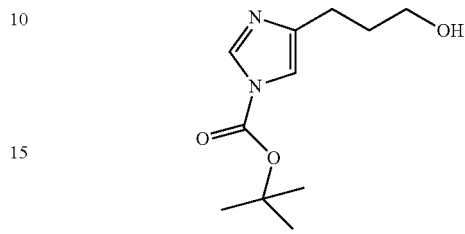

To a solution of 3-(1H-imidazol-4-yl)-propionic acid methyl ester (1.92 g, 12.5 mmol) in THF (25 mL) was added LiAlH$_4$ (1.0 M/THF, 12.5 mL, 12.5 mmol) at 0° C., and the mixture was stirred at 0° C. for 15 minutes. To the mixture was added H$_2$O (0.50 mL) followed by 15% NaOH(aq) (0.50 mL) and H$_2$O (1.5 mL). The mixture was allowed to warm to room temperature then filtered and concentrated in vacuo to give a colourless oil (930 mg).

To a solution of the crude alcohol from above (930 mg) in THF (25 mL) was added di-t-butyl dicarbonate (2.40 g, 11.0 mmol), and the solution was stirred at room temperature for 3 days. The solution was concentrated in vacuo, and crude material was purified by column chromatography on silica gel (200:5:1 CH$_2$Cl$_2$/V1e0H/NH$_4$OH) to give colourless crystals (1.04 g, 37%). $^1$H NMR (CDCl$_3$) δ 1.61 (s, 9H), 1.89 (m, 2H), 2.69 (t, 2H, J=6.9 Hz), 2.98 (t, 1H, J=5.7 Hz), 3.73 (dd, 2H, J=12, 5.7 Hz), 7.10 (s, 1H), 7.99 (s, 1H).

Preparation of 4-(3-Oxo propyl)-imidazole-1-carboxylic acid tert-butyl ester

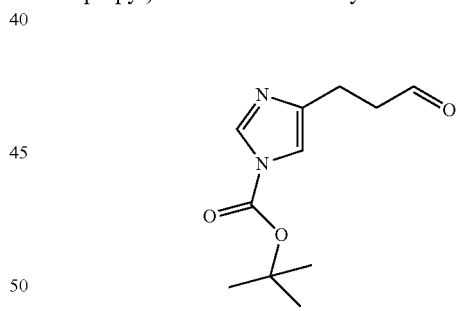

To a solution of 4-(3-hydroxy-propyl)-imidazole-1-carboxylic acid tert-butyl ester (95 mg, 0.42 mmol) in CH$_2$Cl$_2$ (4 mL) was added Dess-Martin periodinane (214 mg, 0.505 mmol) at room temperature. After stirring at room temperature for 1 h, the mixture was diluted with EtOAc (20 mL), washed with 1 N NaOH(aq) (2×10 mL) and brine (10 mL), then dried (MgSO$_4$) and concentrated in vacuo to give a colourless oil (86 mg, 91%). $^1$H NMR (CDCl$_3$) δ 1.61 (s, 9H), 2.86 (m, 4H), 7.11 (s, 1H), 7.99 (s, 1H), 9.84 (s, 1H).

Using General Procedure B: To a stirred solution of 2-[(5,6,7,8-tetrahydro-quinolin-8-ylamino)-methyl]-benzoimidazole-1-carboxylic acid tert-butyl ester (145 mg, 0.383 mmol) and 4-(3-oxo-propyl)-imidazole-1-carboxylic acid tert-butyl ester (86 mg, 0.38 mmol) in THF (4 mL) was added NaBH(OAc)$_3$ (244 mg, 1.15 mmol) and the mixture was stirred at room temperature for 16 h. Purification of the crude material by column chromatography on silica gel (200:5:1 CH$_2$Cl$_2$/MeOH/NH$_4$OH) afforded a colourless oil (39 mg, 17%). $^1$H NMR (CDCl$_3$) δ 1.64 (m, 20H), 1.92 (m, 2H), 2.14 (m, 1H), 2.44 (m, 2H), 2.60-2.92 (m, 5H), 4.26 (dd, 1H, J=9.5, 5.9 Hz), 4.52 (d, 1H, J=16 Hz), 4.66 (d, 1H, J=16 Hz), 6.85 (d, 1H, J=0.9 Hz), 6.95 (dd, 1H, J=7.5, 4.8 Hz), 7.27 (m, 3H), 7.69 (m, 1H), 7.80 (m, 1H), 7.88 (d, 1H, J=1.2 Hz), 8.37 (dd, 1H, J=4.5, 1.2 Hz).

A solution of 2-{[[3-(1-tert-butoxycarbonyl-1H-imidazol-4-yl)-propyl]-(5,6,7,8-tetrahydro-quinolin-8-yl)-amino]-methyl}-benzoimidazole-1-carboxylic acid tert-butyl ester (39 mg, 0.066 mmol) in 3:1 TFA/CH$_2$Cl$_2$ (4 mL) was stirred at room temperature for 30 minutes then concentrated in vacuo. The residue was partitioned between CH$_2$Cl$_2$ (15 mL) and 1 N NaOH(aq) (10 mL), and the aqueous phase was extracted with CH$_2$Cl$_2$ (15 mL). The combined organic extracts were dried (MgSO$_4$) and concentrated in vacuo to afford COMPOUND 38 as a yellow foam (24 mg, 80%). $^1$H NMR (CDCl$_3$) δ 1.67 (m, 3H), 1.86 (m, 1H), 2.00 (m, 1H), 2.16 (m, 1H), 2.42-2.87 (m, 6H), 4.01 (m, 3H), 6.51 (s, 1H), 7.15 (m, 3H), 7.42 (m, 2H), 7.53 (m, 2H), 8.54 (d, 1H, J=3.6 Hz); $^{13}$C NMR (CDCl$_3$) δ 21.66, 23.85, 24.01, 28.39, 29.50, 49.64, 50.78, 62.36, 115.22, 118.74, 122.23, 122.74, 134.47, 135.25, 135.58, 138.03, 139.02, 146.88, 156.37, 157.69. ES-MS m/z 387 (M+H). Anal. Calcd. for C$_{23}$H$_{26}$N$_6$.0.4CH$_2$Cl$_2$.0.9CH$_4$O: C, 64.96; H, 6.82; N, 18.70. Found: C, 65.13; H, 6.93; N, 18.91.

Example 39

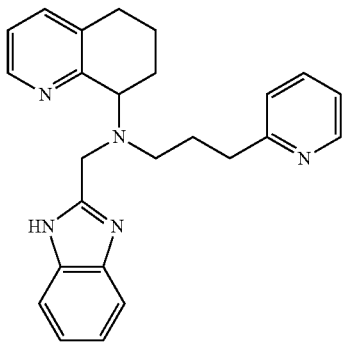 [SMILES: c1ccc(CCCN(Cc2nc3ccccc3[nH]2)C2CCCc3cccnc32)nc1]

Compound 39: Preparation of (1H-benzoimidazol-2-ylmethyl)-(3-pyridin-2-yl-propyl)-(5,6,7,8-tetrahydro-quinolin-8-yl)-amine (hydrobromide salt)

Preparation of 3-pyridin-2-yl-propionaldehyde

To a stirred suspension of 2-pyridinepropanol (1.00 g, 7.29 mmol), NMO (1.281 g, 10.94 mmol) and 3 Å molecular sieves (3.645 g) in CH$_2$Cl$_2$ (37 mL) was added TPAP (256 mg, 0.73 mmol). The resulting black mixture was stirred at room temperature overnight. The mixture was concentrated and filtered through a silica gel plug. Purification by column chromatography on silica gel (EtOAc, 100%) afforded the desired aldehyde (111 mg, 11%) as a yellow syrup. $^1$H NMR (CDCl$_3$) δ 2.90-2.95 (m, 2H), 3.11 (t, 2H, J=7.0 Hz), 7.09 (dd, 1H, J=7.0, 4.8 Hz), 7.17 (d, 1H, J=7.8 Hz), 7.54-7.63 (m, 1H), 8.48 (d, 1H, J=4.2 Hz), 9.86 (s, 1H).

To a stirred solution of the aldehyde from above (67.6 mg, 0.50 mmol) and 2-[(5,6,7,8-tetrahydro-quinolin-8-ylamino)-methyl]-benzoimidazole-1-carboxylic acid tert-butyl ester (200 mg, 0.50 mmol) in THF (5 mL) was added NaBH(OAc)$_3$ and the resultant mixture was stirred at room temperature for 3 days. The reaction mixture was concentrated under reduced pressure, diluted with CH$_2$Cl$_2$ (75 mL) and washed consecutively with H$_2$O (5 mL), saturated aqueous NaHCO$_3$ (7 mL), and saturated aqueous NaCl (7 mL). The aqueous layers were extracted with CH$_2$Cl$_2$ (20 mL) and the combined organic extracts were dried (MgSO$_4$), filtered and concentrated under reduced pressure. Purification by column chromatography on silica gel (CH$_2$Cl$_2$/MeOH/NH$_4$OH, 100:1:1) afforded the desired compound (172 mg) as an orange syrup which was used in the next reaction without further purification.

To a solution of the amine from above (172 mg, 0.35 mmol) in CH$_2$Cl$_2$ (2 mL) was added TFA (2 mL) and the resultant mixture was stirred overnight at room temperature. The reaction mixture was concentrated under reduced pressure, the syrup was dissolved in a minimum amount of H$_2$O and basified with 1N NaOH (pH 10). CHCl$_3$ (75 mL) was added, the phases were separated and the aqueous layer was extracted with CHCl$_3$ (2×75 mL). The combined organic extracts were dried (MgSO$_4$), filtered and concentrated under reduced pressure. Purification of the crude yellow syrup by column chromatography on silica gel (CH$_2$Cl$_2$/MeOH/NH$_4$OH, 100:1:1) followed by radial chromatography on silica gel (CH$_2$Cl$_2$/MeOH/NH$_4$OH, 100:1:1) afforded the desired compound (97 mg, 70%) as a yellow syrup.

Using General Procedure D: Conversion of the yellow syrup from above to the hydrobromide salt afforded COMPOUND 39 as a white solid. $^1$H NMR (D$_2$O) δ 1.82-2.06 (m, 4H), 2.14-2.19 (m, 1H), 2.35-2.38 (m, 1H), 2.51-2.61 (m, 1H), 2.85-3.01 (m, 5H), 4.36 (d, 1H, J=16.8 Hz), 4.47-4.56 (m, 2H), 7.56-7.61 (m, 2H), 7.72-7.79 (m, 4H), 7.85 (dd, 1H, J=7.8, 6.0 Hz), 8.30-8.35 (m, 2H), 8.48-8.51 (m, 1H), 8.62 (d, 1H, J=4.8 Hz); $^{13}$C NMR (D$_2$O) δ 20.41, 20.58, 27.61, 27.65, 30.85, 47.99, 51.00, 60.39, 114.31, 125.32, 126.00, 127.00, 127.36, 130.96, 139.44, 140.71, 141.08, 147.26, 148.16, 151.05, 151.41, 156.22. ES-MS m/z 398.3 (M+H). Anal. Calcd. for C$_{25}$H$_{27}$N$_5$.3.2HBr.1.2H$_2$O: C, 44.28; H, 4.85; N, 10.33; Br, 37.71. Found: C, 44.31; H, 5.06; N, 10.19; Br, 37.71.

Example 40

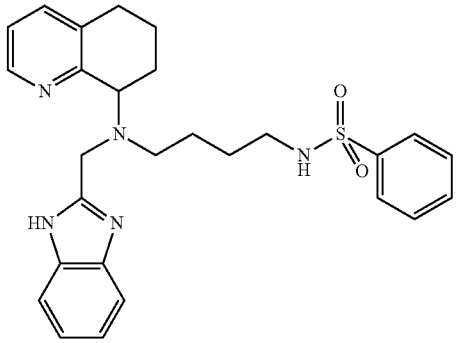 [SMILES: O=S(=O)(NCCCCN(Cc1nc2ccccc2[nH]1)C1CCCc2cccnc21)c1ccccc1]

Compound 40: Preparation of N-{4-[(1H-benzoimidazol-2-ylmethyl)-(5,6,7,8-tetrahydro-quinolin-8-yl)-amino]-butyl}-benzenesulfonamide To a solution of N$^1$-(1H-benzoimidazol-2-ylmethyl)-N$^1$-(5,6,7,8-tetrahydro-quinolin-8-yl)-butane-1,4-diamine (56 mg, 0.16 mmol) and DIPEA (33 μL, 0.19 mmol) in CH₂Cl₂ (1.0 mL) cooled to 0° C. was added PhSO₂Cl (45 μL, 0.35 mmol). The resultant mixture was stirred overnight at room temperature. The mixture was concentrated under reduced pressure, diluted with CH₂Cl₂ (75 mL) and washed consecutively with H₂O (5 mL), saturated aqueous NaHCO₃ (7 mL) and saturated aqueous NaCl (7 mL). The aqueous layers were extracted with CH₂Cl₂ (20 mL) and the combined organic extracts were dried (MgSO₄), filtered and concentrated under reduced pressure. The resultant disulfonamide (98 mg) was used without further purification in the next reaction.

The disulfonamide from above (98 mg, 0.16 mmol) was stirred in a saturated HBr (g) in AcOH solution (1.5 mL) for 3 hours. The mixture was concentrated in vacuo and a suspension of the resultant yellow syrup and powdered K₂CO₃ (excess) in MeOH was stirred at room temperature for 1 hour. The mixture was concentrated under reduced pressure, diluted with CH₂Cl₂ and filtered through Celite. The cake was washed with CH₂Cl₂ and the combined filtrate was concentrated under reduced pressure. Purification of the crude yellow foam by column chromatography on silica gel (CH₂Cl₂/MeOH/NH₄OH, 100:1:1) followed by radial chromatography on silica gel (CH₂Cl₂/MeOH/NH₄OH, 100:1:1) afforded COMPOUND 40 (50 mg, 64% over 2 steps). $^1$H NMR (CDCl₃) δ 1.42-1.46 (m, 3H), 1.61-1.75 (m, 1H), 1.81-1.99 (m, 1H), 2.00-2.09 (m, 1H), 2.14-2.21 (m, 1H), 2.46-2.55 (m, 1H), 2.67-2.90 (m, 6H), 3.91 (d, 1H, J=16.2 Hz), 3.98-4.05 (m, 2H), 5.80 (br s, 1H), 7.12-7.21 (m, 3H), 7.39-7.44 (m, 3H), 7.48-7.57 (m, 3H), 7.75-7.79 (m, 2H), 8.53-8.55 (m, 1H); $^{13}$C NMR (CDCl₃) δ 21.21, 23.06, 25.25, 27.47, 29.10, 42.81, 49.38, 50.21, 61.41, 121.73, 122.29, 126.92, 128.97, 132.37, 134.72, 137.51, 140.22, 146.71, 155.65, 157.25. ES-MS m/z 490.3 (M+H). Anal. Calcd. for C₂₇H₃₁N₅O₂S.1.0H₂O: C, 63.88; H, 6.55; N, 13.80; S, 6.32. Found: C, 63.91; H, 6.32; N, 13.46; S, 6.33.

Example 41

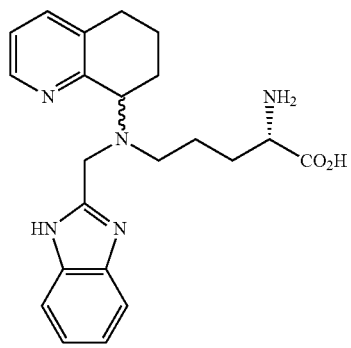 [SMILES: N[C@@H](CCCN(Cc1nc2ccccc2[nH]1)C1CCCc2cccnc21)C(=O)O]

Compound 41: Preparation of (2S)-2-Amino-5-[(1H-benzimidazol-2-ylmethyl)-(5,6,7,8-tetrahydroquinolin-8-yl)-amino]-pentanoic acid (hydrobromide salt)

To a solution of (2S)-5-amino-2-(tert-butoxycarbonylamino)-pentanoic acid tert-butyl ester (free base) (0.905 g, 3.11 mmol) in CH₃OH (15 mL) was added 6,7-dihydro-5H-quinolin-8-one (0.504 g, 3.43 mmol) and the resultant solution was stirred at room temperature for 5 hours. Powdered NaBH₄ (0.379 g, 9.98 mmol) was added, and the mixture was stirred at room temperature for 25 minutes then concentrated under reduced pressure. The residue was dissolved in CH₂Cl₂ (100 mL) and brine (20 mL). The phases were separated and the aqueous phase was extracted with CH₂Cl₂ (3×20 mL). The combined organic extracts were dried (Na₂SO₄) and concentrated. Purification of the crude material by column chromatography on silica gel (20:1 CH₂Cl₂—CH₃OH) provided 0.700 g (54%) of (2S)-2-tert-butoxycarbonylamino-5-(5,6,7,8-tetrahydroquinolin-8-ylamino)-pentanoic acid tert-butyl ester as a yellow oil.

Using the General Procedure for N-alkylation: A solution of (2S)-2-(tert-butoxycarbonylamino)-5-(5,6,7,8-tetrahydroquinolin-8-ylamino)-pentanoic acid tert-butyl ester (0.700 g, 1.67 mmol), 1-(tert-butoxycarbonyl)-2-(chloromethyl)-benzimidazole (0.690 g, 2.59 mmol) and N,N-diisopropylethylamine (0.60 mL, 3.44 mmol) in CH₃CN (16 mL) was heated at 60° C. for 24 hours. Purification of the crude material by column chromatography on silica gel (50:1 CH₂Cl₂—MeOH) provided 0.830 g (77%) of 2-{[(4-tert-butoxycarbonyl-4-tert-butoxycarbonylamino-butyl)-(5,6,7,8-tetrahydroquinolin-8-yl)-amino]-methyl}-benzoimidazole-1-carboxylic acid tert-butyl ester as a tan foam.

General Procedure D: Conversion of 2-{[(4-tert-butoxycarbonyl-4-tert-butoxycarbonylamino-butyl)-(5,6,7,8-tetrahydroquinolin-8-yl)-amino]-methyl}-benzoimidazole-1-carboxylic acid tert-butyl ester (139 mg) to the hydrobromide salt with simultaneous removal of the BOC-protecting groups and hydrolysis of the tert-butyl ester, followed by re-precipitation of the intermediate solid from methanol/ether, gave COMPOUND 41 (116 mg, 81%) as a tan solid (mixture of 2 diastereomers). $^1$H NMR (D₂O) δ 1.54-1.84 (m, 5H), 1.96-2.06 (m, 1H), 2.15-2.19 (m, 1H), 2.34-2.38 (m, 1H), 2.53-2.60 (m, 1H), 2.80-2.87 (m, 1H), 2.99-3.01 (m, 2H), 3.82 (t, 1H, J=6.3 Hz), 4.38 (d, 1H, J=16.8 Hz), 4.50-4.55 (m, 2H), 7.57-7.62 (m, 2H), 7.76-7.88 (m, 3H), 8.33 (br d, 1H, J=5.1 Hz), 8.62 (br d, 1H, J=6.0 Hz); $^{13}$C NMR (D₂O) δ 20.32, 20.40, 23.87, 24.12, 27.63, 27.93, 28.04, 48.16, 51.34, 51.51, 53.41, 53.54, 60.48, 60.58, 114.24, 125.92, 126.92, 130.98, 139.36, 140.60, 148.08, 151.18, 151.61, 173.06; ES-MS m/z 394 (M+H). Anal. Calcd. for C₂₂H₂₇N₅O₂.2.9HBr.2.1H₂O: C, 39.68; H, 5.16; N, 10.52; Br, 34.79. Found: C, 39.81; H, 5.19; N, 10.14; Br, 34.70.

Example 42

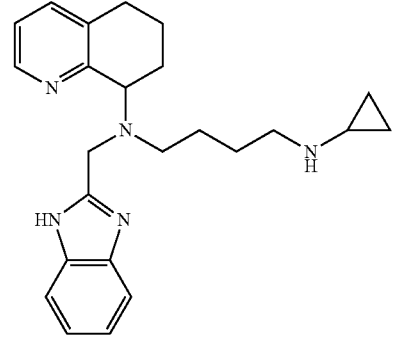 [SMILES: c1cnc2c(c1)CCCC2N(CCCCNC1CC1)Cc1nc2ccccc2[nH]1]

Compound 42: Preparation of N¹-(1H-Benzimidazol-2-ylmethyl)-N⁴-cyclopropyl-N¹-(5,6,7,8-tetrahydro-quinolin-8-yl)-butane-1,4-diamine (HBr salt)

1,4-Butanediol (0.90 ml, 10.16 mmol) was added to a stirred suspension of NaH (246 mg, 10.25 mmol) in THF (20 ml) at room temperature and stirred for 30 minutes. Acetyl chloride (0.70 mL, 9.84 mmol) was then added to the thick white slurry. Following 45 minutes of stirring, the solution was diluted with diethyl ether (30 mL) and 10 w/v % $K_2CO_{3(aq)}$. The phases were separated and the organic phase washed with 10% $K_2CO_3$ (1×15 mL) and brine (1×15 mL). The combined aqueous phase was extracted with diethyl ether (1×30 mL). The organic phase was dried ($MgSO_4$) and concentrated to afford 933 mg crude product as a colourless liquid. Purification by column chromatography (25 g silica, 2:1 hexanes:ethyl acetate) afforded 686 mg of acetic acid 4-hydroxy-butyl ester (51%). $^1$H NMR ($CDCl_3$) δ 1.58-1.77 (m, 4H), 2.05 (s, 3H), 3.68 (t, 2H, J=6.1 Hz), 4.10 (t, 2H, J=6.4 Hz).

Tetrapropylammonium perruthenate (195 mg, 0.555 mmol) was added to a solution of the mono-protected diol from above (715 mg, 5.41 mmol), as well as crushed and dried 3 Å molecular sieves (2.71 g, 5.42 mmol) and NMO (953 mg, 8.13 mmol), in $CH_2Cl_2$ (27 mL) and the mixture stirred for 75 minutes. The suspension was filtered through a plug of silica with ethyl acetate to give 0.48 g of acetic acid 4-oxo-butyl ester as a colourless oil (68%). $^1$H NMR ($CDCl_3$) δ 1.98 (pent, 4H, J=6.6 Hz), 2.05 (s, 3H), 2.55 (t, 2H, J=7.4 Hz), 4.10 (t, 2H, J=6.4 Hz), 9.80 (s, 1H).

Using general procedure B: Reaction of cyclopropylamine (0.51 mL, 7.36 mmol) and the mono-protected aldehyde from above (480 mg, 3.69 mmol) with $NaBH(OAc)_3$ (1.573 g, 7.42 mmol) in $CH_2Cl_2$ (18 mL) for 19 hours provided a crude product. Purification of the crude material by column chromatography on silica gel (20 g silica, 50:1→25:1 $CH_2Cl_2$: $CH_3OH$) provided 293 mg (46%) of acetic acid 4-cyclopropylamino-butyl ester. $^1$H NMR ($CDCl_3$) δ 0.29-0.45 (m, 4H), 1.49-1.71 (m, 4H), 2.04 (s, 3H), 2.07-2.14 (m, 1H), 2.70 (t, 2H, J=6.9 Hz), 4.07 (t, 2H, J=6.7 Hz).

Di-tert-butyl-dicarbonate (399 mg, 1.83 mmol) was added to a solution of the amine from above (293 mg, 1.71 mmol) in THF (8.5 mL) at room temperature and the solution was stirred for 75 minutes, after which time the solution was concentrated under reduced pressure. The residue was diluted with $CH_2Cl_2$ (30 mL) and brine (20 mL). The phases were separated and the organic phase was washed with brine (2×20 mL). The combined aqueous phases were extracted with $CH_2Cl_2$ (2×20 mL). The combined organic phase was dried ($Na_2SO_4$) and concentrated under reduced pressure to give 622 mg colourless liquid containing acetic acid 4-(tert-butoxycarbonyl-cyclopropyl-amino)-butyl ester and excess di-tert-butyl-dicarbonate.

Potassium carbonate (2.53 g, 18.3 mmol) was added to a solution of the ester from above (622 mg, 1.71 mmol) in methanol (10 ml) at room temperature and the suspension was stirred for 80 minutes. The solution was then diluted with distilled water (20 mL). The mixture was extracted with $CHCl_3$ (4×20 mL). The organic phase was dried ($Na_2SO_4$) and concentrated to afford 399 mg (100% over two steps) crude cyclopropyl-(4-hydroxy-butyl)-carbamic acid tert-butyl ester as a colourless oil.

Tetrapropylammonium perruthenate (65 mg, 0.185 mmol) was added to a suspension of the alcohol from above (399 mg, 1.74 mmol), NMO (305 mg, 2.60 mmol) and 3 Å molecular seives (861 mg, 1.72 mmol) in dry $CH_2Cl_2$ (8.5 mL) at room temperature and the mixture was stirred for 1 hour. The suspension was then filtered through silica gel with ethyl acetate. The filtrate was concentrated under reduced pressure to give 545 mg crude product. This crude material was purified by column chromatography (28 g silica, 10:1→5:1 hexanes: ethyl acetate) to give 63 mg (16%) of pure cyclopropyl-(4-oxo-butyl)-carbamic acid tert-butyl ester and 434 mg impure material. $^1$H NMR ($CDCl_3$) δ 0.56-0.62 (m, 2H), 0.71-0.78 (m, 2H), 1.45 (s, 9H), 1.62 (s, 1H), 1.87 (pent, 2H, J=7.3 Hz), 2.45 (t, 2H, J=6.6 Hz), 3.24 (t, 2H, J=7.2 Hz), 9.79 (s, 1H).

Using general procedure B: To a stirred solution of the N-protected aldehyde from above (63 mg, 0.277 mmol) and [1-(tert-butyloxycarbonyl)-(1H-benzimidazol-2-ylmethyl)]-(5,6,7,8-tetrahydroquinolin-8-yl)-amine (103 mg, 0.273 mmol) in $CH_2Cl_2$ (2.5 mL) was added $NaBH(OAc)_3$ (86 mg, 0.406 mmol) and the mixture was stirred for 19 hours. Purification of the crude yellow oil (165 mg) by radial chromatography (2 mm plate, 150:1:1 $CH_2Cl_2$: $CH_3OH$: $NH_4OH$) afforded 116 mg (72%) 2-{[[4-(tert-butoxycarbonyl-cyclopropyl-amino)-butyl]-(5,6,7,8-tetrahydro-quinolin-8-yl)-amino]-methyl}-benzimidazole-1-carboxylic acid tert-butyl ester.

Using the General Procedure D: The double-protected tertiary amine from above (116 mg, 0.197 mmol) was converted to COMPOUND 42 as a white solid (99 mg, 70%). $^1$H NMR ($D_2O$) δ 0.76-0.79 (m, 4H), 1.54 (br s, 4H), 1.81-1.85 (m, 1H), 1.95-2.07 (m, 1H), 2.15-2.19 (m, 1H), 2.34-2.38 (m, 1H), 2.55-2.61 (m, 2H), 2.79-2.84 (m, 1H), 3.01 (br s, 4H), 4.38 (d, 1H, J=17.4 Hz), 4.50-4.56 (m, 2H), 7.57-7.59 (m, 2H), 7.77-7.79 (m, 2H), 7.83 (t, 1H, J=6.6 Hz), 8.33 (d, 1H, J=7.8 Hz), 8.62 (d, 1H, J=5.4 Hz). $^{13}$C NMR ($D_2O$) δ 3.35, 20.45, 23.69, 25.57, 27.67, 30.32, 48.12, 48.32, 51.71, 60.70, 114.28, 125.95, 126.94, 130.97, 139.34, 140.62, 148.12, 151.26, 151.79. ES-MS m/z 390 (M+H). Anal Calc. for $C_{24}H_{31}N_5 \cdot 3.4HBr \cdot 3.0H_2O$: C, 40.11; H, 5.67; N, 9.74; Br, 37.80. Found: C, 40.33; H, 5.57; N, 9.60; Br, 37.63.

Example 43

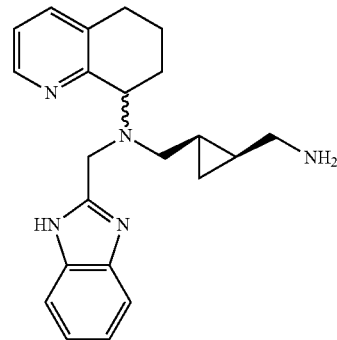 [SMILES: NC[C@H]1C[C@H]1CN(Cc1nc2ccccc2[nH]1)C1CCCc2cccnc21]

Compound 43: Preparation of (cis-2-aminomethyl-cyclopropylmethyl)-(1H-benzimidazol-2-ylmethyl)-(5,6,7,8-tetrahydro-quinolin-8-yl)-amine (hydrobromide salt)

Preparation of (cis-2-hydroxymethyl-cyclopropyl)-methanol

To a 0° C. solution of dimethyl cis-1,2-cyclopropanedicarboxylate (3.03 g, 19.1 mmol) in THF (25 mL) under nitrogen was slowly added $LiAlH_4$ (1.0 M in hexane, 25 mL). The resulting mixture was stirred at room temperature for 1.5 hours, then was quenched by the careful addition of $H_2O$ (1 mL), 15% NaOH (1 mL) and $H_2O$ (3 mL). The precipitate was removed by suction filtration, washing with EtOAc and the filtrate was concentrated under reduced pressure. Purification by flash column chromatography on silica ($CH_2Cl_2$/MeOH, 19:1) gave the diol as a colourless liquid (1.79 g, 17.5 mmol, 92%). $^1$H NMR (CDCl$_3$) δ 0.21 (dd, 1H, J=10.5, 5.4 Hz), 0.80 (td, 1H, J=8.3, 5.1 Hz), 1.24-1.38 (m, 2H), 3.16-3.29 (m, 4H), 4.02-4.14 (m, 2H).

Preparation of [cis-2-(tert-butyl-dimethyl-silanyloxymethyl)-cyclopropyl]-methanol To a 0° C. suspension of NaH (60% in mineral oil, 733 mg, 18.3 mmol) in THF (25 mL) under nitrogen was added a solution of the diol (1.78 g, 17.4 mmol) in THF (10 mL). The mixture was stirred for 10 minutes, then t-BDMSCl (2.73 g, 18.1 mmol) was added at once as a solid. The reaction was stirred at room temperature for 25 minutes, then saturated aqueous NaHCO$_3$ (35 mL) was added, the layers were separated and the aqueous solution was extracted with CH$_2$Cl$_2$ (25 mL×2). The combined organic solution was dried (Na$_2$SO$_4$), filtered and concentrated under reduced pressure. Purification by flash column chromatography on silica (hexane/EtOAc, 4:1) gave the silane as a pale yellow liquid (3.12 g, 14.4 mmol, 83%). $^1$H NMR (CDCl$_3$) δ 0.09 (s, 3H), 0.11 (s, 3H), 0.19 (dd, 1H, J=10.5, 4.5 Hz), 0.76 (td, 1H, J=7.5, 6.0 Hz), 0.91 (s, 9H), 1.17-1.29 (m, 1H), 1.30-1.43 (m, 1H), 3.19-3.32 (m, 3H), 3.96 (td, 1H, J=11.5, 5.3 Hz), 4.14 (dd, 1H, J=11.7, 5.4 Hz).

Preparation of tert-butyl-(cis-2-chloromethyl-cyclopropylmethoxy)-dimethyl-silane To a solution of the alcohol (3.11 g, 14.4 mmol) and NEt$_3$ (3.0 mL, 21.5 mmol) in CH$_2$Cl$_2$ (45 mL) under nitrogen was added MsCl (1.65 mL, 21.3 mmol). The reaction was heated at reflux for 17 hours. Once cooled to room temperature, saturated aqueous NaHCO$_3$ (45 mL) was added, the layers were separated and the aqueous solution was extracted with CH$_2$Cl$_2$ (25 mL). The combined organic solution was dried (MgSO$_4$), filtered and concentrated under reduced pressure. Purification by flash column chromatography on silica (hexane/EtOAc, 9:1) gave the chloride as a light yellow liquid (1.52 g, 6.46 mmol, 45%). $^1$H NMR (CDCl$_3$) δ 0.06 (s, 3H), 0.07 (s, 3H), 0.40 (dd, 1H, J=10.5, 4.6 Hz), 0.84-0.93 (m, 10H), 1.23-1.42 (m, 2H), 3.57-3.72 (m, 3H), 3.81 (dd, 1H, J=11.6, 5.7 Hz).

Preparation of N-(cis-2-hydroxymethyl-cyclopropylmethyl)-phthalimide

A mixture of the chloride (1.51 g, 6.43 mmol) and potassium phthalimide (1.31 g, 7.07 mmol) in DMF (25 mL) was heated to 80° C. for 3.5 hours. Once cooled to room temperature, H$_2$O (25 mL) was added and the mixture was extracted with CH$_2$Cl$_2$ (25 mL×3). The combined organic solution was dried (MgSO$_4$), filtered and concentrated under reduced pressure giving the crude phthalimide as a yellow oil.

To a solution of this material in THF (15 mL) was added a 1M HCl solution (15 mL) and the reaction was stirred at room temperature for 30 minutes. The THF was evaporated under reduced pressure and the aqueous solution was extracted with CH$_2$Cl$_2$ (25 mL×3). The organic solution was dried (Na$_2$SO$_4$), filtered and concentrated under reduced pressure. Purification by flash column chromatography on silica (EtOAc/hexane, 1.5:1) gave the alcohol as a white solid (880 mg, 3.80 mmol, 59%). $^1$H NMR (CDCl$_3$) δ 0.18 (dd, 1H, J=12.5, 5.0 Hz), 0.79 (td, 1H, J=8.8, 5.2 Hz), 1.18-1.34 (m, 2H), 2.93 (br. s, 1H), 3.50-3.60 (m, 2H), 3.92-4.01 (m, 2H), 7.71-7.75 (m, 2H), 7.83-7.87 (m, 2H).

Preparation of cis-[2-(phthalimidomethyl)-1-cyclopropyl]methyl methanesulfonate To a 0° C. solution of the alcohol (443 mg, 1.92 mmol) and NEt$_3$ (0.40 mL, 2.9 mmol) in CH$_2$Cl$_2$ (7 mL) under nitrogen was added a solution of MsCl (0.22 mL, 2.8 mmol) in CH$_2$Cl$_2$ (0.8 mL). The reaction was stirred at 0° C. for 15 minutes, then saturated aqueous NaHCO$_3$ (10 mL) was added. The layers were separated and the aqueous solution was extracted with CH$_2$Cl$_2$ (15 mL×2). The combined organic solution was dried (MgSO$_4$), filtered and concentrated under reduced pressure. Purification by flash column chromatography on silica (EtOAc/hexane, 1:1) gave the mesylate as a white solid (513 mg, 1.66 mmol, 86%). $^1$H NMR (CDCl$_3$) δ 0.52 (dd, 1H, J=11.4, 5.7 Hz), 1.89 (td, 1H, J=8.4, 5.4 Hz), 1.32-1.45 (m, 1H), 1.53-1.66 (m, 1H), 3.01 (s, 3H), 3.71 (dd, 1H, J=14.4, 7.8 Hz), 3.79 (dd, 1H, J=14.4, 7.8 Hz), 4.23 (dd, 1H, J=11.0, 8.9 Hz), 4.57 (dd, 1H, J=11.1, 6.9 Hz), 7.70-7.75 (m, 2H), 7.83-7.88 (m, 2H).

Preparation of (cis-2-aminomethyl-cyclopropylmethyl)-(1H-benzimidazol-2-ylmethyl)-(5,6,7,8-tetrahydro-quinolin-8-yl)-amine A solution of the mesylate (371 mg, 1.20 mmol), (1-tert-butoxycarbonyl-1H-benzimidazol-2-ylmethyl)-(5,6,7,8-tetrahydro-quinolin-8-yl)-amine (379 mg, 1.00 mmol), DIPEA (0.26 mL, 1.5 mmol) and KI (19 mg, 0.11 mmol) in CH$_3$CN (7 mL) was heated to 60° C. under nitrogen for 19 hours. Once cooled, saturated aqueous NaHCO$_3$ (10 mL) was added and the mixture was extracted with CH$_2$Cl$_2$ (25 mL×3). The combined organic solution was dried (MgSO$_4$), filtered and concentrated under reduced pressure. Purification by flash column chromatography on silica (CH$_2$Cl$_2$/MeOH/NH$_4$OH, 19:1:0.1) gave the tertiary amine (yellow foam) as an approximately 3:1 mixture of diastereomers (432 mg, 73%).

This material (420 mg, 0.71 mmol) and hydrazine monohydrate (0.35 mL, 7.2 mmol) in EtOH (9 mL) was heated at reflux under nitrogen for 1 hour. Once cooled, the solvent was evaporated under reduced pressure. The residue was taken up into saturated aqueous NaHCO$_3$ (10 mL) and extracted with CH$_2$Cl$_2$ (25 mL×3). The combined organic solution was dried (MgSO$_4$), filtered and concentrated under reduced pressure. Purification by flash column chromatography on silica (CH$_2$Cl$_2$/MeOH/NH$_4$OH, 19:1:0.1, followed by 9:1:0.05) gave the fully deprotected amine as a white foam (147 mg, 0.41 mmol, 58%). $^1$H NMR (CDCl$_3$) δ −0.15-0.02 (m, 1H), 0.49-0.59 (m, 1H), 0.72-0.92 (m, 2H), 1.64-1.81 (m, 1H), 1.86-1.98 (m, 1H), 1.99-2.11 (m, 2H), 2.15-2.32 (m, 2H), 2.47-2.61 (m, 1H), 2.66-2.90 (m, 3H), 2.96-3.13 (m, 1H), 3.89 (2×d, 0.3H, J=15.1 Hz), 4.06 (s, 0.7H), 4.13 (dd, 0.7H, J=10.1, 5.9 Hz), 4.40 (2×d, 0.3H, J=6.2 Hz), 7.02-7.09 (m, 1H), 7.15-7.20 (m, 2H), 7.37 (d, 1H, J=7.5 Hz), 7.52-7.62 (m, 2H), 8.51 (d, 1H, J=3.3 Hz).

Preparation of Compound 43

To a solution of the amine (75 mg, 0.21 mmol) in glacial HOAc (1.0 mL) was added a saturated solution of HBr in HOAc (0.5 mL). The solution was stirred at room temperature for 25 minutes, then Et$_2$O (5 mL) was added. The precipitate was washed with Et$_2$O (1 mL×5) and dried at 90° C. under reduced pressure giving COMPOUND 43 as a yellow solid (131 mg, 0.19 mmol, 91%). $^1$H NMR (MeOH-d$_4$) δ 0.23-0.32 (m, 0.7H), 0.36-0.45 (m, 0.3H), 0.51-0.69 (m, 1H), 1.01-1.20 (m, 1H), 1.33-1.57 (m, 1H), 1.87-2.04 (m, 1H), 2.06-2.31 (m, 2H), 2.37-2.60 (m, 1H), 2.63-2.88 (m, 2H), 2.99-3.27 (m, 4H), 4.52-4.83 (m, 3H), 7.57-7.67 (m, 2H), 7.86-8.02 (m, 3H), 8.38-8.46 (m, 1H), 8.87-8.95 (m, 1H). $^{13}$C NMR (D$_2$O) δ 10.0 and 10.9, 12.4 and 13.6, 15.5, 20.4 and 20.6, 20.7, 27.7, 39.8, 48.6, 51.7 and 52.6, 61.3 and 62.0, 114.2, 125.9, 126.9, 130.9, 139.3 and 139.4, 140.5 and 140.6, 148.1, 151.0 and 151.2, 151.9 and 152.6. ES-MS m/z 362 (M+H). Anal. Calcd. for C$_{22}$H$_{27}$N$_5$.3.2HBr.2.4H$_2$O.0.3C$_4$H$_{10}$O: C, 40.63; H, 5.58; N, 10.21; Br, 37.28. Found: C, 40.61; H, 5.45; N, 10.10; Br, 37.19.

Example 44

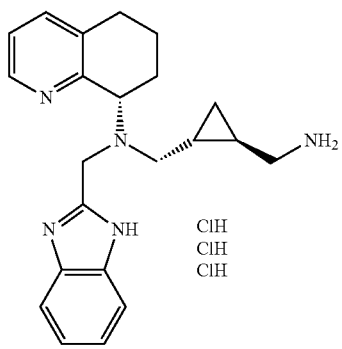

Compound 44: Preparation of (trans-2-aminomethyl-cyclopropylmethyl)-(1H-benz-imidazol-2-ylmethyl)-(S)-5,6,7,8-tetrahydroquinlin-8-yl-amine (hydrochloride salt)

Preparation of trans-1,2-cyclopropanedimethanol

To a solution of diethyl trans-1,2-cyclopropanedicarboxylate (14.9 g, 80 mmol) in THF (50 mL), cooled to 0° C. under nitrogen, was added dropwise a 1.0 M solution of LAH in THF (107 mL, 107 mmol). The resultant mixture was heated at reflux for 2 hours, then cooled to room temperature and stirred for 16 h. The crude mixture was cooled to 0° C. and carefully quenched by the slow addition of deionized water (4 mL), followed by 15% NaOH solution (4 mL), and more deionized water (12 mL). The mixture was stirred at room temperature for 20 min. The thick slurry was diluted with diethyl ether (100 mL), dried over MgSO$_4$, filtered through a glass sintered funnel, and concentrated in vacuo to afford the title compound as a colorless oil (6.30 g, 78%). $^1$H NMR (CDCl$_3$) δ 0.43 (t, 2 H, J=6.8 Hz), 0.96-1.07 (m, 2H), 3.05 (dd, 2H, J=11.4, 8.7 Hz), 3.13 (br. s, 2H), 3.83 (dd, 2H, J=11.4, 4.7 Hz).

Preparation of trans-1-hydroxymethyl-2-(tert-butyl-dimethyl-silanyloxymethyl)-cyclopropane (McDougal, P. G.; Rico, J. G.; Oh, Y.; Condon, B. D. *J. Org. Chem.* 1986, 51, 3388-3390)

To a cooled (0° C.) stirred solution of trans-1,2-cyclopropanedimethanol (2.0 g, 20 mmol) in THF (40 mL) was slowly added NaH (60% dispersion in oil, 0.80 g, 20 mmol). Stirring was continued at 0° C. for 10 min. tert-Butyldimethylchlorosilane (3.0 g, 20 mmol) was added. The thick white slurry was allowed to warm to room temperature and stirring was continued for 10 min. The resultant mixture was poured into diethyl ether (400 mL) and washed with 10% K$_2$CO$_3$ (100 mL) then washed again with brine (100 mL). The separated organic layer was dried over Na$_2$SO$_4$ and concentrated. The crude material was purified by flash column chromatography (5 cm id., 100 g silica gel, eluted with 5:1 hexanes/ethyl acetate) to give the mono-protected desired product as a clear oil (2.8 g, 65%). $^1$H NMR (CDCl$_3$) δ 0.05 (s, 6H), 0.41-0.53 (m, 2H), 0.89 (s, 9H), 0.89-1.04 (m, 2H), 1.41 (t, 1H, J=5.8 Hz), 3.41-3.50 (m, 3H), 3.60 (dd, 1H, J=11.2, 5.8 Hz).

Preparation of trans-N-{[2-(hydroxymethyl)cyclopropyl]methyl}phthalimide

To a stirred solution of trans-1-hydroxymethyl-2-(tert-butyl-dimethyl-silanyloxymethyl)-cyclopropane (4.7 g, 22 mmol) and triethylamine (9.2 mL, 65 mmol) in CH$_2$Cl$_2$ (75 mL) was added dropwise methanesulfonyl chloride (3.7 mL, 48 mmol). The mixture was heated at reflux for 16 h, then allowed to cool to room temperature. Deionized water (50 mL) was added to the red solution and the layers were separated. The organic layer was washed with brine (50 mL), dried over MgSO$_4$, and concentrated to a red oil. The crude material was purified by flash column chromatography (5 cm id., 140 g silica gel, eluted with 5% EtOAc/hexanes) to give the chloride as a yellow oil (4.0 g, 78%).

The chloride from above (4.0 g, 17 mmol) and potassium phthalimide (4.8 g, 26 mmol) were stirred in anhydrous DMF (115 mL) at 100° C., under a nitrogen atmosphere, for 3 h. The mixture was concentrated to remove DMF. The resultant residue was diluted with CH$_2$Cl$_2$ (200 mL), washed with brine (50 mL), dried over MgSO$_4$, and concentrated in vacuo. The crude material was purified by flash chromatography (5 cm id., 160 g silica gel, eluted with 10:1 hexanes/ethyl acetate) to provide the phthalimide as a pale yellow oil (5.4 g, 92%).

The phthalimide from above (5.3 g, 15 mmol) was stirred in a mixture of THF (40 mL) and 1N HCl (40 mL) for 1.5 h. The THF was removed in vacuo and the solution was extracted with CH$_2$Cl$_2$ (3×50 mL). The separated organic layers were combined, dried over MgSO$_4$, and concentrated. The crude material was purified by flash column chromatography (5 cm id., 120 g silica gel, 1:1 hexanes/ethyl acetate) to afford the pure title compound as a white solid (3.5 g, 97%). $^1$H NMR (CDCl$_3$) δ 0.50 (ddd, 1H, J=8.4, 5.1, 5.1 Hz), 0.66 (ddd, 1H, J=8.4, 5.1, 5.1 Hz), 1.13-1.25 (m, 2H), 1.50 (br. s, 1H), 3.33-3.43 (m, 1H), 3.45-3.53 (m, 1H), 3.60 (dd, 2H, J=6.9, 5.1 Hz), 7.69-7.74 (m, 2H), 7.82-7.86 (m, 2H).

Preparation of 2-[(trans-2-phthalimidomethyl-cyclopropylmethyl)-(S)-(5,6,7,8-tetrahydro-quinolin-8-yl)-aminomethyl]-benzimidazole-1-carboxylic acid tert-butyl ester To a 0° C. solution of trans-N-{[2-(hydroxymethyl)cyclopropyl]methyl}phthalimide (3.4 g, 15 mmol) and triethylamine (8.4 mL, 60 mmol) in CH$_2$Cl$_2$ (50 mL) was added dropwise methanesulfonyl chloride (2.9 mL, 37 mmol). The mixture was heated at reflux for 18 h, cooled to room temperature and washed with deionized water (100 mL), followed by saturated NaHCO$_3$ (100 mL), and finally washed with brine (100 mL). The separated organic layer was dried over MgSO$_4$ and concentrated to a tan solid. The crude solid was purified by flash column chromatography (5 cm id., 100 g silica gel, eluted with 9:1 hexanes/ethyl acetate) to give the chloride as an off-white solid (3.2 g, 85%).

Sodium iodide (12 g, 80 mmol) was added to a solution of the chloride from above (2.0 g, 8.0 mmol) in acetone (40 mL). The mixture was stirred vigorously at reflux for 68 h, then cooled to room temperature and concentrated. The residue was partitioned between deionized water (100 mL) and CH₂Cl₂ (100 mL). The separated organic layer was dried over MgSO₄ and concentrated to an orange solid (3.2 g). This material was used without further purification.

A solution of the iodide from above (2.7 g, 8.0 mmol), (1-tert-butoxycarbonyl-1H-benzimidazol-2-ylmethyl)-(5,6,7,8-tetrahydro-quinolin-8-yl)-amine (2.9 g, 7.6 mmol) and DIPEA (2.1 mL, 12 mmol) in CH₃CN (40 mL) was heated at 60° C., under nitrogen, for 15.5 hours. Once cooled to room temperature, the mixture was concentrated, saturated aqueous NaHCO₃ (100 mL) was added and the aqueous layer was extracted with CHCl₃ (3×100 mL). The combined organic portions were dried (MgSO₄), filtered and concentrated under reduced pressure giving a brown foam. Purification by flash column chromatography on silica (5 cm id., 170 g silica gel, eluted with 2% MeOH/CH₂Cl₂) followed by a second column chromatography purification of the product containing material (5 cm id., 150 g silica gel, eluted with 5% NH₄OH/EtOAc) gave a 1:1 mixture of two diastereomers of the title compound as a pale yellow foam (2.7 g, 59%). $^1$H NMR (CDCl₃) δ 0.17-0.27 (m, 1H), 0.42-0.51 (m, 1H), 0.89-1.11 (m, 2H), 1.69 and 1.70 (2×s, 9H), 1.79-2.02 (m, 3H), 2.08-2.20 (m, 1H), 2.52-2.83 (m, 4H), 3.16 (dd, 0.5H, J=14.2, 7.7 Hz), 3.34 (dd, 0.5H, J=14.2, 7.7 Hz), 3.50-3.58 (m, 1H), 4.24-4.34 (m, 1H), 4.40-4.52 (m, 1H), 4.62 (d, 1H, J=16.5 Hz), 6.88-6.94 (m, 1H), 7.18-7.29 (m, 4H), 7.57-7.64 (m, 2H), 7.67-7.76 (m, 2H), 7.78-7.83 (m, 1H), 8.28-8.33 (m, 1H).

Preparation of (trans-2-aminomethyl-cyclopropylmethyl)-(1H-benz-imidazol-2-ylmethyl)-(S)-5,6,7,8-tetrahydroquinlin-8-yl-amine A solution of 2-[(trans-2-phthalimidomethyl-cyclopropylmethyl)-(S)-(5,6,7,8-tetrahydro-quinolin-8-yl)-aminomethyl]-benzimidazole-1-carboxylic acid tert-butyl ester (3.5 g, 5.9 mmol) and hydrazine hydrate (1.76 mL, 35 mmol) in EtOH (27 mL) was stirred at room temperature under nitrogen for 2 h. The white slurry was diluted with diethyl ether, filtered, and the filtrate was concentrated. The crude material was purified by flash column chromatography (5 cm id.; 80 g silica gel, eluted with 2% NH₄OH/2% McOH/CH₂Cl₂) to afford the pure title compound as a pale yellow foamy solid (1.8 g, 83%). $^1$H NMR (CDCl₃) δ 0.15-0.31 (m, 2H), 0.58-0.74 (m, 2H), 1.59-1.76 (m, 1H), 1.79-1.92 (m, 1H), 1.96-2.07 (m, 1H), 2.15-2.91 (m, 7H), 4.06-4.16 (m, 2H), 4.21 (2×d, 1H, J=14.6 Hz), 7.10-7.22 (m, 3H), 7.41 (d, 1H, J=7.5 Hz), 7.54-7.62 (m, 2H), 8.57 (d, 1H, J=4.5 Hz).

Preparation of (trans-2-aminomethyl-cyclopropylmethyl)-(1H-benz-imidazol-2-ylmethyl)-(S)-5,6,7,8-tetrahydroquinlin-8-yl-amine (hydrochloride salt) (Compound 44)

A stirred solution of (trans-2-aminomethyl-cyclopropylmethyl)-(1H-benz-imidazol-2-ylmethyl)-(S)-5,6,7,8-tetrahydroquinlin-8-yl-amine (1.7 g, 4.8 mmol) in glacial acetic acid (10 mL) was treated with a saturated solution of HCl$_{(g)}$ in glacial acetic acid (10 mL). The resultant solution was added dropwise to diethyl ether (300 mL) with vigorous stirring. Once the addition was complete, the white precipitate was allowed to settle and the clear liquid was decanted. The solid was washed repeatedly with ether (4×300 mL), decanting each time. The solid was then collected on a sintered glass funnel, rinsed with diethyl ether (3×50 mL), and dried in a vacuum oven at 40° C. for 60 h to afford COMPOUND 44 as a white solid (2.1 g, 88%, 1:1 mixture of diastereomers). $^1$H NMR (D₂O) δ 0.11-0.18 (m, 0.5H), 0.30-0.41 (m, 1H), 0.44-0.50 (m, 0.5H), 0.69-0.87 (m, 2H), 1.71-1.86 (m, 1H), 1.91-2.52 (m, 5H), 2.70 (ddd, 1H, J=27.0, 13.2, 6.0 Hz), 2.90-2.99 (m, 3H), 4.33-4.61 (m, 3H), 7.51-7.55 (m, 2H), 7.72-7.83 (m, 3H), 8.26 (t, 1H, J=7.6 Hz), 8.59 (t, 1H, J=7.6 Hz); $^{13}$C NMR (D₂O) δ 10.12, 11.19, 13.71, 15.45, 16.88, 17.04, 20.42, 20.56, 20.63, 27.62, 43.20, 43.31, 48.93, 49.64, 55.43, 55.73, 61.58, 61.89, 114.38, 125.71, 126.38, 126.43, 131.75, 132.04, 139.54, 140.30, 147.54, 147.64, 151.27, 152.28. ES-MS m/z 362 (M+H). Anal. Calcd. for C₂₂H₂₇N₅.2.9HCl.1.7H₂O: C, 53.08; H, 6.74; N, 14.07; Cl, 20.65. Found: C, 52.91; H, 6.90; N, 14.20; Cl, 20.90.

The enantiomeric purity of COMPOUND 44 was determined to be 100% by chiral HPLC using the following conditions: Instrument: Hewlett Packard 1100 HPLC (VWD1); Column: ChiralCel OD, 0.46 cm×25 cm; Mobile Phases: A=90:10 hexanes/reagent alcohol with 0.1% DEA, B=hexanes; Isocratic: 50% A, 50% B; Total Run Time: 30 min; Flow Rate: 1.0 mL/min; Temperature: 40° C.; Detector: UV @ 270 nm; Injection volume: 20 μL.

Retention time of the S enantiomer=13.0 min.
Retention time of the R enantiomer=16.7 min.

Example 45

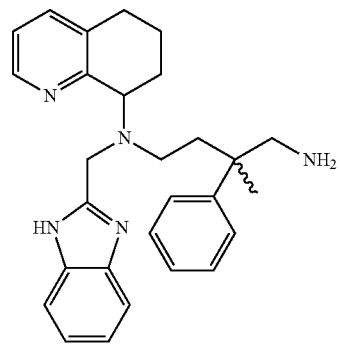 [SMILES: CC(CN)(CCN(Cc1nc2ccccc2[nH]1)C1CCCc2cccnc21)c1ccccc1]

Compound 45: Preparation of N'-(1H-benzimidazol-2-ylmethyl)-3-methyl-3-phenyl-N'-(5,6,7,8-tetrahydro-quinolin-8-yl)-butane-1,4-diamine

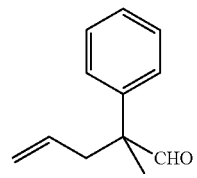

Preparation of 2-methyl-2-phenyl-pent-4-enal (prepared as described by Ciganek, E.; Read, J. M.; Calabrese, J. C. *J. Org. Chem.* 1995, 60, 5795-5802)

A solution of 2-phenylpropionaldehyde (9.90 mL, 74.5 mmol), allyl alcohol (20.4 mL, 300 mmol) and p-toluene sulfonic acid (0.8560 g, 4.5 mmol) in benzene (37 mL) was heated to reflux for 19 hours and a Dean-Stark trap was used to collect the water formed. The mixture was cooled to room temperature and saturated aqueous NaHCO$_3$ (5 mL) and H$_2$O (5 mL) were added. The phases were separated and the organic layer was washed a second time with saturated aqueous NaHCO$_3$ (5 mL) and H$_2$O (5 mL). The organic layer was dried (MgSO$_4$) and concentrated under reduced pressure. A solution of the resultant yellow residue in p-xylene (150 mL) was heated to reflux for 24 hours. The solution was cooled to room temperature and concentrated under reduced pressure. The resultant aldehyde (13.0 g) was used in the next reaction without further purification.

Preparation of acetic acid 2-methyl-2-phenyl-pent-4-enyl ester

To a solution of 2-methyl-2-phenyl-pent-4-enal (1.23 g, 7.02 mmol) in ethanol (20 mL) was added sodium borohydride (0.80 g, 21.15 mmol) and the resultant suspension was stirred at room temperature for 3 days. The mixture was concentrated under reduced pressure, diluted in saturated NaHCO$_3$ (10 mL), and extracted with chloroform (5×25 mL). The combined organic extracts were dried (Na$_2$SO$_4$), filtered, concentrated, and dried in vacuo to afford a yellow oil (1.04 g), which was used without further purification in the next step.

To a solution of the crude alcohol from above (360 mg, 2.03 mmol), 4-dimethylaminopyridine (24.4 mg, 0.20 mmol) and triethylamine (340 µL, 2.44 mmol) in CH$_2$Cl$_2$ (10 mL) was added acetic anhydride (230 µL) and the resultant mixture was stirred at room temperature overnight. Then the mixture was quenched with saturated NaHCO$_3$ (30 mL) and the phases were separated. The aqueous layer was washed with CH$_2$Cl$_2$ (2×20 mL). Then the combined organic extracts were washed with saturated NaHCO$_3$ (2×30 mL), dried (MgSO$_4$), filtered, concentrated, and dried in vacuo to afford a yellow oil. Purification by column chromatography on silica gel (CH$_3$OH/CH$_2$Cl$_2$, 1:9) afforded the title compound (400 mg, 70% over 2 steps). $^1$H NMR (CDCl$_3$) δ 1.36 (s, 3H), 2.01 (s, 3H), 2.45 (qd, 2H, J=29.1, 16.2, 7.1 Hz), 4.19 (q, 2H, J=11.1, 7.8 Hz), 4.97-5.05 (m, 2H), 5.48-5.54 (m, 1H), 7.21-7.44 (m, 5H).

Preparation of acetic acid 2-methyl-5-oxo-2-phenyl-pentyl ester

To a solution of the acetate from above (400 mg, 1.82 mmol) and 4-methylmorpholine N-oxide (427 mg, 3.65 mmol) in CH$_2$Cl$_2$ (10 mL) was added osmium tetraoxide (2.5% in t-butanol) (680 µL, 0.06 mmol) and the mixture was stirred at room temperature overnight. Then the mixture was diluted with ethyl acetate and filtered through a layer of celite. The filtrate was concentrated under reduced pressure and was dried in vacuo to afford an orange oil. Partial purification by column chromatography on silica gel (CH$_3$OH/NH$_4$—OH/CH$_2$Cl$_2$, 4:1:95) followed by radial chromatography on silica gel (2 mm plate, CH$_3$OH/CH$_2$—Cl$_2$, 0:100 then 2:98) afforded the diol (198 mg) as a yellow oil, which was used without further purification in the next step.

To a solution of the crude diol from above (198 mg, 0.82 mmol) in THF (5 mL) and H$_2$O (1 mL) was added sodium periodate (351 mg, 1.64 mmol) and the mixture was stirred for 2 hours at room temperature. The mixture was diluted with CH$_2$Cl$_2$ (15 mL) and washed with saturated NaCl (15 mL). The aqueous layer was washed with CH$_2$Cl$_2$ (15 mL). Then the combined organic extracts were dried (MgSO$_4$), filtered, concentrated, and dried in vacuo to cleanly afford the product as a pale yellow oil (146 mg, 36% over 2 steps). $^1$H NMR (CDCl$_3$) 1.53 (s, 3H), 2.03 (s, 3H), 2.81 (ABqd, 2H, J=49.2, 15.9, 2.7 Hz), 3.75 (t, 1H, J=6.3 Hz), 4.23 (ABq, 2H, J=20.4, 11.1 Hz), 7.24-7.34 (m, 4H), 7.38 (d, 1H, J=3.0 Hz), 9.54 (t, 1H, J=3.0 Hz).

Preparation of 4-[1H-benzoimidazol-2-ylmethyl)-(5.6.7.8-tetrahydro-quinolin-8-yl)-amino]-2-methyl-2-phenyl-butan-1-ol To a solution of the 2-[(5,6,7,8-tetrahydro-quinolin-8-ylamino)-methyl]-benzimidazole-1-carboxylic acid tert-butyl ester (299 mg, 0.79 mmol) and the above aldehyde (146 mg, 0.66 mmol) in CH$_2$Cl$_2$ (4 mL) was added sodium triacetoxyborohydride (251 mg, 1.18 mmol) and the mixture was stirred at room temperature for 3 days. The mixture was diluted with CH$_2$Cl$_2$ (10 mL) and was extracted with NaOH (1N, 2×10 mL) and brine (2×10 mL). The organic layer was dried (Na$_2$SO$_4$), filtered, concentrated, and dried in vacuo to afford a dark yellow oil. Partial purification by two attempts of radial chromatography on silica gel (2 mm plate, CH$_3$OH/NH$_4$OH/CH$_2$Cl$_2$, 0:1:99 then 3:1:96), and (2 mm plate, NH$_4$OH/CH$_2$—Cl$_2$, 0:100 then 1:99) afforded the compound as a yellow oil (198 mg), which was used without further purification To a solution of the crude amine from above (198 mg, 0.34 mmol) in methanol (3.5 mL) was added potassium carbonate (84 mg, 0.61 mmol) and the mixture was stirred at room temperature for 1 hour. Then the solvent was removed under reduced pressure and dissolved in CH$_2$Cl$_2$. The mixture was filtered to remove the inorganic salt and the filtrate was concentrated and dried in vacuo to afford a yellow oil. Purification by radial chromatography on silica gel (1 mm plate, CH$_3$OH/NH$_4$OH/CH$_2$Cl$_2$, 1:1:98 then 3:1:96) to afford the product as a pale yellow foam (85 mg, 24% over 2 steps). $^1$H NMR (CDCl$_3$) δ 1.20 and 1.26 (s, total 3H), 1.65-1.68 (m, 2H), 1.93-2.01 (m, 3H), 2.13-2.16 (m, 1H), 2.53-2.74 (m, 3H), 3.53-3.76 (m, 2H), 3.91-4.01 (m, 3H), 7.00-7.09 (m, 3H), 7.17-7.19 (m, 3H), 7.26-7.29 (m, 2H), 7.41 (t, 2H, J=7.8 Hz), 7.64-7.67 (br m, 1H), 8.43 and 8.47 (d, total 1H, J=3.5 Hz).

To a solution of the above alcohol (80 mg, 0.15 mmol) in CH$_2$Cl$_2$ (1.5 mL) was added Dess-Martin reagent (75 mg, 0.18 mmol) and the mixture was stirred at room temperature for 20 minutes. Saturated NaHCO$_3$ (1 mL) and aqueous sodium dithionite (20%, 1 mL) was added to the mixture and stirred until the layers clarified. The mixture was diluted with CH$_2$Cl$_2$ (5 mL) and the phases were separated. The aqueous layer was washed with CH$_2$Cl$_2$ (3×10 mL). Then the combined organic extracts were dried (Na$_2$SO$_4$), filtered, concentrated, and dried in vacuo to afford a yellow foam (91 mg), which was used without further purification.

Preparation of N'-(1H-benzimidazol-2-ylmethyl-3-methyl-3-phenyl-N'-(5,6,7,8-tetrahydro-quinolin-8-yl)-butane-1,4-diamine To a solution of the crude aldehyde from above (90 mg, 0.17 mmol) in methanol (1.5 mL) was added hydroxyamine hydrochloride salt (23 mg, 0.33 mmol) and the mixture was stirred at room temperature for 40 minutes. The mixture was concentrated under reduced pressure and the residue was dissolved in CH$_2$Cl$_2$ (5 mL). The mixture was basified to pH9 with saturated NaHCO$_3$ and the phases were separated. The aqueous layer was extracted with CH$_2$Cl$_{-2}$ (2×10 mL). Then the combined organic extracts were dried (Na$_2$SO$_4$), filtered, concentrated, and dried in vacuo to afford a pale yellow foam (72 mg), which was used without further purification.

To a solution of the crude oxime from above (285 mg, 0.63 mmol) in methanol (20 mL) was added a slurry of Raney-nickel in water (approximately 30 mg). The mixture was purged with ammonium gas and then hydrogenated overnight at 35 psi. Then the mixture was filtered through a layer of celite and the filtrate was concentrated and dried in vacuo to afford a yellow oil. Purification by three attempts at radial chromatography on silica gel (2 mm plate, $CH_3OH/NH_4OH/CH_2Cl_2$, 0:1:99 then 1:1:98), (2 mm plate, $CH_3OH/NH_4OH/CH_2Cl_2$, 1:1:98 then 3:1:96), (1 mm plate, $CH_3OH/NH_4OH/CH_2Cl_2$, 1:1:98 then 2:1:97) to afford the minor spot, COMPOUND 45 as a yellow foam (16 mg, 4% over 3 steps). $^1H$ NMR ($CDCl_3$) δ 1.21 and 1.25 (s, total 3H), 1.62-2.05 (m, 6H), 2.25-2.80 (m, 7H), 3.48 (q, 1H, J=6.9 Hz), 3.89-4.15 (m, 3H), 7.00-7.26 (m, 8H), 7.36-7.38 (m, 1H), 7.58 (br s, 2H), 8.58 (br m, 1H). $^{13}C$ NMR ($CDCl_3$) δ 21.70, 23.07, 23.71, 29.36, 30.09, 38.19, 38.57, 46.76, 49.87, 49.96, 62.02, 62.20, 122.10, 122.44, 126.34, 126.49, 126.56, 128.68, 128.97, 134.87, 137.63, 147.11, 147.20. ES-MS m/z 440 [M+H]$^+$. Anal. Calcd. for $C_{28}H_{33}N_5 \cdot 0.2CH_2Cl_2 \cdot 0.6C_4H_{10}O$: C, 73.35; H, 7.93; N, 13.98. Found: C, 72.97; H, 7.87; N, 13.78.

Example 46

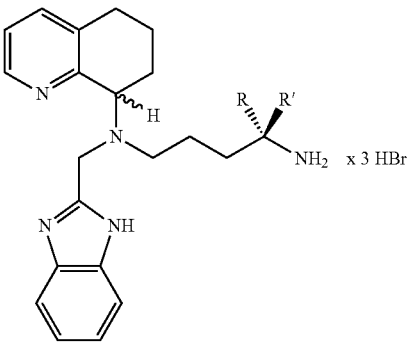

R = H, R' = Ph or
R = Ph, R' = H

Compound 46(R), Compound 46(S): Preparation of (1H-benzimidazol-2-ylmethyl)-(5,6,7,8-tetrahydro-quinolin-8-yl)-(1-phenyl-1-aminobut-4-yl)-amine (hydrobromide salt)

NOTE: Synthesis of COMPOUND 46(R) is listed below, proceeding from (R)-(N-t-butoxycarbonyl)-2-phenylglycinol. The synthesis of COMPOUND 46(S) proceeds identically from the (S)-isomer.

A solution of DMSO (2.13 mL, 30 mmol) in dichloromethane (100 mL) was chilled under nitrogen to −60° C. To this stirred solution, oxalyl chloride (15 mL of a 2.0 M solution in dichloromethane, 30 mmol) was added over five minutes. The mixture was stirred at −60° C. for ten minutes, then a solution of (R)-(N-t-butoxycarbonyl)-2-phenylglycinol (5.3 g, 20 mmol) in dichloromethane (40 mL) was added over ten minutes. The mixture was stirred at −60° C. for 20 minutes, then triethylamine (8.35 mL, 60 mmol) was added. The mixture was stirred gradually warming to room temperature, over 60 minutes. A saturated aqueous solution of ammonium chloride (75 mL) was then added. The aqueous and organic layers were separated, and the aqueous layer was washed twice with dichloromethane. The combined organic fractions were then dried over anhydrous sodium sulfate, filtered and concentrated in vacuo to afford (R)-(N-t-butoxycarbonyl)-2-phenylglyeinal as an unstable yellow oil, which was used immediately without further purification in the next reaction (assuming 100% conversion). $^1H$ NMR ($CDCl_3$) δ 1.43 (s, 9H), 5.31 (m, 1H), 5.75 (br s, 1H(NH)), 7.30-7.41 (m, 5H), 9.55 (s, 1H).

The aldehyde was dissolved in benzene (150 mL), and methyl (triphenylphoshporanylidene) acetate (6.96 g, 20 mmol) was added. The mixture was then stirred at room temperature overnight. The suspension was then concentrated in vacuo and loaded directly onto a silica gel column (1:1 hexanes:ethyl acetate). The product (E)-methyl 4-[(t-butoxycarbonyl)-amino]-4-phenylbut-2-enoate was collected as a colourless oil in a yield of 3.17 g (52%). s, 9H), 3.71 (s, 3H), 4.95 (m, 1H), 5.56 (br s, 1H(NH)), 5.96 (dd, 1H, J=15.2, 2.9 Hz), 7.05 (dd, 1H, J=15.2, 4.1 Hz), 7.27-7.49 (m, 5H).

To a solution of methyl 4-[(t-butoxycarbonyl)-amino]-4-phenylbut-2-enoate (3.17 g) in methanol (100 mL) was added palladium on carbon (250 mg (10% by wt. Pd)). The mixture was then placed under 50 psig hydrogen gas, and was shaken on a Parr hydrogenator for 2 hours. The mixture was then filtered through celite, concentrated in vacuo and purified by silica gel flash chromatography (3:1 hexanes:ethyl acetate) to afford methyl 4-[(t-butoxycarbonyl)-amino]-4-phenylbutanoate as a pale yellow oil in a yield of 2.61 g (82%). $^1H$ NMR ($CDCl_3$) δ 1.45 (s, 9H), 2.07 (m, 2H), 2.36 (m, 2H), 3.69 (s, 3H), 4.59 (m, 1H), 5.15 (br s, 1H(NH)), 7.21-7.34 (m, 5H).

To a 0° C. solution of methyl 4-[(t-butoxycarbonyl)-amino]-4-phenylbutanoate (293 mg, 1.0 mmol) in dichloromethane (25 mL) was added Dibal-H (3 mL of a 1.0 M solution in dichloromethane, 3.0 mmol). The mixture was then stirred at 0° C. for 2 hours before being quenched with a saturated aqueous sodium potassium tartrate solution (10 mL). The biphasic mixture was then rapidly stirred for approximately 45 minutes, until the aqueous and organic layers clarified. The aqueous and organic layers were then separated and the aqueous layer was extracted twice with dichloromethane. The combined organic fractions were dried over anhydrous sodium sulfate, filtered and concentrated in vacuo to afford a pale yellow residue, which was purified by silica gel flash chromatography (1:1 hexanes:ethyl acetate) to afford 4-[(t-butoxycarbonyl)-amino]-4-phenylbutanol as a colourless oil in a yield of 138 mg (52%). $^1H$ NMR ($CDCl_3$) δ 1.43 (s, 9H), 1.45 (m, 2H), 1.56 (m 2H), 2.71 (br s, 1H (OH)), 3.54 (t, 2H, J=6.9 Hz), 4.56 (m, 1H), 5.22 (br s, 1H(NH)), 7.16-7.26 (m, 5H).

To a 0° C. solution of 4-[(t-butoxycarbonyl)-amino]-4-phenylbutanol (133 mg, 0.5 mmol) in dichloromethane (8 mL) was added triethylamine (0.140 mL, 1.0 mmol), followed by methanesulfonylchloride (0.057 mL, 0.75 mmol). The solution was then stirred at 0° C. for 15 minutes before being quenched with an aqueous ammonium chloride solution (2 mL). The aqueous and organic layers were then separated, the aqueous layer extracted twice with dichloromethane, and the combined organic fractions were dried over anhydrous sodium sulfate, filtered and concentrated in vacuo to afford 4-[(t-butoxycarbonyl)-amino]-4-phenylbutanol mesylate as a yellow oil, which was used immediately in the next reaction without further purification. $^1H$ NMR ($CDCl_3$) δ 1.43 (s, 9H), 1.67-2.00 (m, 4H), 2.95 (s, 3H), 4.18 (t, 2H, J=7.1 Hz), 4.20 (m, 1H), 4.92 (br s, 1H(NH)), 7.21-7.33 (m, 5H).

To a solution of the mesylate (0.5 mmol, assumed 100% conversion from the previous step) in dimethylformamide (5 mL) was added sodium azide (130 mg, 2 mmol). The mixture was then heated to 70° C. for 2 hours under nitrogen. After cooling, the reaction was diluted with 40 mL ethyl acetate, and extracted repeatedly with distilled water. The organic fraction was then dried over anhydrous sodium sulfate, filtered and concentrated in vacuo. The residue was purified by silica gel flash chromatography (1:1 hexanes:ethyl acetate) to afford 4-[(t-butoxycarbonyl)-amino]-4-phenylbutyl azide in a yield of 100 mg (69% from alcohol). $^1$H NMR (CDCl$_3$) δ 1.38 (s, 9H), 1.47-1.61 (m, 2H), 1.78 (m, 2H), 3.25 (t, 2H, J=6.8 Hz), 4.58 (m, 1H), 4.97 (m, 1H(NH)), 7.20-7.33 (m, 5H).

To a solution of the azide (100 mg, 0.34 mmol) in methanol (20 mL) was added Lindlar's catalyst (5% Pd on CaCO$_3$, poisoned with lead (15 mg)). The mixture was then placed under 1 atmosphere H$_2$ and was stirred overnight. The mixture was then filtered through celite, concentrated in vacuo and purified by silica gel flash chromatography (15% Methanol, 1% NH$_4$OH in dichloromethane) to afford 4-amino-1-phenyl-1-(t-butoxycarbonyl)-amine in a yield of 65 mg (72%). $^1$H NMR (CDCl$_3$) δ 1.40 (s, 9H), 1.77 (m, 2H), 2.29 (m, 2H), 2.70 (t, 2H, J=7.8 Hz), 4.58 (m, 1H), 5.11 (m, 1H(NH)), 7.20-7.33 (m, 5H).

To a solution of 5,6,7,8-tetrahydroquinolin-8-one (40 mg, 0.271 mmol) and 4-amino-1-phenyl-1-(t-butoxycarbonyl)-amine (65 mg, 0.246 mmol) in dichloromethane (8 mL) was added sodium triacetoxyborohydride (115 mg, 0.542 mmol). The reaction was then stirred overnight at room temperature. A saturated sodium carbonate solution (5 mL) was added, and the aqueous and organic layers were then separated. The aqueous layer was extracted twice with dichloromethane and the combined organic fractions were dried over anhydrous sodium sulfate, filtered and concentrated in vacuo. The residue was purified by silica gel flash chromatography to yield and 4-[(5,6,7,8-tetrahydroquinolin-8-yl)-amino]-1-phenyl-1-(t-butoxycarbonyl)-amine in a yield of 65 mg (61%). $^1$H NMR (CDCl$_3$) δ 1.40 (s, 9H), 1.61-1.85 (m, 6H), 1.94 (m, 1H), 2.04 (m, 1H), 2.74 (m, 4H), 3.78 (m, 1H), 4.91 (m, 1H), 5.35 (m, 1H(NH)), 7.07 (dd, 1H, J=8.1, 4.9 Hz), 7.24-7.28 (m, 5H), 7.36 (d, 1H, J=8.1 Hz), 8.36 (d, 1H, J=4.9 Hz).-fix 1H To a solution of (N-t-butoxycarbonyl)-2-chloromethylbenzimidazole (53 mg, 0.20 mmol), 4-[(5,6,7,8-tetrahydroquinolin-8-yl)-amino]-1-phenyl-1-(t-butoxycarbonyl)-amine (65 mg, 0.165 mmol) and diisopropylethylamine (0.043 mL, 0.25 mmol) in acetonitrile (5 mL) were stirred at 70° C. for 16 hours. After cooling, the mixture was diluted with dichloromethane (20 mL) and washed with a saturated sodium bicarbonate solution (5 mL). The aqueous and organic layers were then separated, and the aqueous layer was extracted twice with dichloromethane. The combined organic fractions were then dried over anhydrous sodium sulfate, filtered and concentrated. The residue was purified by silica gel flash chromatography to afford N-[(t-butoxycarbonyl)-benzimidazol-2-ylmethyl)]-(5,6,7,8-tetrahydro-quinolin-8-yl)-(1-phenyl-1-aminobut-4-yl)-(t-butoxycarbonyl)-amine as a pale foam in a yield of 73 mg (71%). $^1$H NMR (CDCl$_3$) δ 1.40 (s, 9H), 1.63 (s, 9H), 1.71-2.11 (m, 8H), 2.58-2.79 (m, 4H), 4.16 (dd, 1H, J=10.9, 8.1 Hz), 4.43 (m, 3H), 5.05 (m, 1H(NH)), 6.96 (m, 1H), 7.15-7.31 (m, 8H), 7.75 (m, 1H), 7.83 (m, 1H), 8.30 (m, 1H).

Using General Procedure D: Conversion of the foam from above (72 mg, 0.117 mmol) to the hydrobromide salt followed by re-precipitation of the intermediate solid from methanol/ether gave COMPOUND 46(R) (58 mg, 70%) as a beige solid. $^1$H NMR (D$_2$O) δ 0.83 (m, 1H), 1.84 (m, 5H), 2.06-2.20 (m, 2H), 2.30-2.55 (m, 2H), 2.90 (m, 2H), 4.05 (m, 1H), 4.22 (d, 1H, J=15.8 Hz), 4.45 (m, 1H), 4.48 (d, 1H, J=15.8 Hz), 7.07-7.18 (m, 5H), 7.62 (m, 2H), 7.73 (m, 2H), 7.87 (dd, 1H, J=13.2, 5.7 Hz), 8.28 and 8.31 (d, 1H total, J=5.7 Hz (each doublet from a diastereomer)), 8.54 (d, 1H, J=5.4 Hz); $^{13}$C NMR (D$_2$O) δ 20.59, 25.10, 25.23, 27.59, 30.46, 30.56, 49.59, 55.04, 55.50, 61.15, 61.98, 114.29, 125.92, 126.94, 127.28, 127.39, 129.47, 129.61, 129.84, 129.92, 130.82, 139.07, 139.23, 140.41, 148.13, 151.72. ES-MS m/z 426 (M+H). Anal. Calcd. for C$_{27}$H$_{31}$N$_5$.3.0HBr.2.6H$_2$O: C, 45.35; H, 5.52; N, 9.79; Br, 33.52. Found: C, 45.72; H, 5.34; N, 9.43; Br, 33.34.

COMPOUND 46(S) was prepared using the same procedure described above from 73 mg (0.117 mmol) of N-[(t-butoxycarbonyl)-benzimidazol-2-ylmethyl)]-(5,6,7,8-tetrahydro-quinolin-8-yl)-(1-phenyl-1-aminobut-4-yl)-(t-butoxycarbonyl)-amine to afford 49 mg (58%) of the hydrobromide salt as a white solid. $^1$H, $^{13}$C and MS data identical to that for COMPOUND 46(R). Anal. Calcd. for C$_{27}$H$_{31}$N$_5$.3.0HBr.2.7H$_2$O: C, 45.23; H, 5.54; N, 9.77; Br, 33.43. Found: C, 45.52; H, 5.49; N, 9.39; Br, 33.45.

Example 47

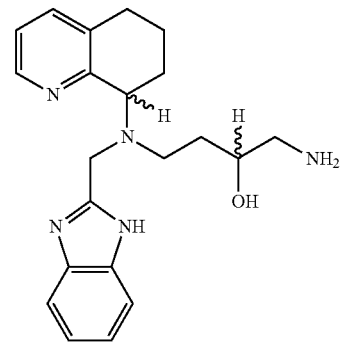 [SMILES: NCC(O)CCN(Cc1nc2ccccc2[nH]1)C1CCCc2cccnc21]

Compound 47: Preparation of (1H-benzimidazol-2-ylmethyl)-(5,6,7,8-tetrahydro-quinolin-8-yl)-(1-aminobutan-3-ol-4-yl)-amine To a solution of 3-buten-1-ol (10 g, 138 mmol) in dichloromethane (150 mL) was added acetic anhydride (13 mL, 138 mmol) and 4-dimethylaminopyridine (244 mg, 2 mmol). The mixture was then stirred at room temperature for 8 hours. The reaction mixture was then poured into a saturated aqueous sodium bicarbonate solution (100 mL). After separation of the aqueous and organic layers, the aqueous layer was extracted twice with 100 mL portions of dichloromethane. The combined organic fractions were then dried over anhydrous sodium sulfate, filtered, and concentrated in vacuo to afford 3-buten-1-yl acetate as a colourless oil in a yield of 12.9 g (82%). $^1$H NMR (CDCl$_3$) δ 2.04 (s, 3H), 2.38 (m, 2H), 4.11 (t, 3H, J=7.1 Hz), 5.04 (d, 1H, J=9.1 Hz), 5.08 (d, 1H, J=15.3 Hz), 5.77 (m, 1H).

To a solution of 3-buten-1-yl acetate (5.7 g, 50 mmol) in dichloromethane (200 mL) was added m-chloroperoxybenzoic acid (12.9 g, 75 mmol). The reaction was then stirred at room temperature for 3 hours. The reaction mixture was then filtered through celite and concentrated in vacuo. The residue was purified by silica gel flash chromatography (4:1 hexanes: ethyl acetate) to yield 3,4-epoxybutan-1-yl acetate as a colourless oil in a yield of 3.8 g (58%). $^1$H NMR (CDCl$_3$) δ 1.78-1.88 (m, 2H), 2.03 (s, 3H), 2.47 (m, 1H), 2.75 (m, 1H), 2.99 (m, 1H), 4.18 (t, 1H, J=6.6 Hz).

To a solution of 3,4-epoxybytan-1-yl acetate (3.9 g, 29 mmol) in DMF (50 mL) was added potassium phthalimide (6.47 g, 35 mmol). The stirred mixture was then heated to 90° C. for 16 hours. After cooling, the mixture was diluted with ethyl acetate (200 mL) and extracted repeatedly with water. The organic fraction was then dried over anhydrous sodium sulfate, filtered and concentrated in vacuo. The residue was purified by silica gel flash chromatography (1:1 hexanes: ethyl acetate) to afford N-(3-hydroxybutan-4-yl-1-acetate)-phthalimide as a pale yellow oil in a yield of 1.65 g (20%). $^1$H NMR (CDCl$_3$) δ 1.69-1.88 (m, 2H), 2.04 (s, 3H), 2.90 (m, 1H(OH)), 3.79 (d, 2H, J=5.7 Hz), 4.03 (m, 1H), 4.21-4.31 (m, 2H), 7.70 (m, 2H), 7.83 (m, 2H). MS m/z 300 (M+Na).

To a solution of afford N-(3-hydroxybutan-4-yl-1-acetate)-phthalimide (554 mg, 2.0 mmol) in acetonitrile (15 mL) was added imidazole (150 mg, 2.2 mmol) and t-butyldimethylsilyl chloride (310 mg, 2.05 mmol). The mixture was then stirred overnight at room temperature. Dichloromethane (50 mL) was then added to the reaction, and the mixture was extracted with a saturated ammonium chloride solution. The organic layer was then dried over anhydrous sodium sulfate, filtered and concentrated to leave a yellow oily residue which was purified by silica gel flash chromatography (3:1 hexanes: ethyl acetate) to afford N-(3-t-butyldimethylsiloxybutan-4-yl-1-acetate)-phthalimide in a yield of 570 mg (73%). $^1$H NMR (CDCl$_3$) δ −0.04 (s, 3H), −0.01 (s, 3H), 0.84 (s, 9H), 1.78 (m, 2H), 3.68 (dd, 1H, J=8.1, 6.5 Hz), 3.73 (dd, 1H, J=8.1, 6.2 Hz), 4.15 (m, 3H), 7.71 (m, 2H), 7.85 (m, 2H).

To a stirred −78° C. solution of afford N-(3-t-butyldimethylsiloxybutan-4-yl-1-acetate)-phthalimide (670 mg, 1.71 mmol) in THF (20 mL) was added DIBAL-H (5.1 mL of a 1.0M solution in hexanes, 5.1 mmol). The reaction was stirred at −78° C. for 45 minutes, then a saturated solution of ammonium chloride (5 mL) was added. The mixture was allowed to warm to room temperature, then ethyl acetate (20 mL) and 1N HCl (2 mL) were added. The mixture was then shaken in a separatory funnel to speed the clarification of the layers, then the organic and aqueous layers were separated. The aqueous layer was extracted twice with ethyl acetate, then the combined organic fractions were separated and the aqueous layer was extracted twice with ethyl acetate. The combined organic fractions were then dried over anhydrous sodium sulfate, filtered and concentrated in vacuo. The residue was purified by silica gel flash chromatography (1:1 hexanes:ethyl acetate) to afford N-(3-t-butyldimethylsiloxybutan-1-ol-4-yl)-phthalimide as a colourless oil in a yield of 465 mg (78%). $^1$H NMR (CDCl$_3$) δ −0.02 (s, 3H), 0.09 (s, 3H), 0.86 (s, 9H), 1.71-1.82 (m, 2H), 2.11 (m, 1H(OH)), 3.76 (m, 4H), 4.28 (m, 1H), 7.73 (m, 2H), 7.85 (m, 2H).

To a solution of N-(3-t-butyldimethylsiloxybutan-1-ol-4-yl)-phthalimide (160 mg, 0.4 mmol) in dichloromethane (10 mL) was added Dess-Martin Periodinane (212 mg, 0.5, mmol). The mixture was then stirred at room temperature for 30 minutes. A 5% solution of sodium thiosulfate (10 mL) and a saturated sodium bicarbonate solution (10 mL) was added along with another 20 mL of dichloromethane. The mixture was then stirred rapidly for 20 minutes, and the aqueous and organic layers were separated. The aqueous layer was extracted twice with dichloromethane, and the combined organic fractions were dried over anhydrous sodium sulfate, filtered and concentrated in vacuo to afford N-(3-t-butyldimethylsiloxybutan-1-al-4-yl)-phthalimide as a yellow oil, which was used immediately in the next reaction without further purification. $^1$H NMR (CDCl$_3$) δ −0.02 (s, 3H), 0.05 (s, 3H), 0.81 (s, 9H), 2.61 (m, 2H), 3.74 (m, 2H), 4.51 (m, 1H), 7.71 (m, 2H), 7.85 (m, 2H), 9.81 (m, 1H).

To a solution of N-(3-t-butyldimethylsiloxybutan-1-al-4-yl)-phthalimide (0.4 mmol) in dichloromethane (15 mL) was added (5,6,7,8-tetrahydroquinolin-8-yl)-[(N-t-butoxycarbonyl)-benzimidazol-2-yl)methyl]-amine (151 mg, 0.4 mmol). The mixture was stirred at room temperature for 30 minutes, then sodium triacetoxyborohydride (170 mg, 0.8 mmol) was added, and the reaction was allowed to stir for 16 hours. A saturated sodium bicarbonate solution (10 mL) was added, and the aqueous and organic layers were separated. The aqueous layer was then extracted twice with dichloromethane, and the combined organic fractions were dried over anhydrous sodium sulfate, filtered and concentrated in vacuo. The residue was then purified by silica gel flash chromatography (3% methanol in dichloromethane) to afford [(N-t-butoxycarbonyl)-benzimidazol-2-ylmethyl]-(5,6,7,8-tetrahydro-quinolin-8-yl)-(1-(N-phthalimidyl)-butan-3-(t-butyldimethylsiloxy)-4-yl)-amine as a pale yellow foam in a yield of 224 mg (79%). $^1$H NMR (CDCl$_3$) δ −0.25 (s, 3H), −0.23 (s, 3H), 0.69 (s, 9H), 1.44-1.63 (m, 4H), 1.68 (s, 9H), 2.00 (m, 2H), 2.16 (m, 1H), 2.65-2.74 (m, 3H), 3.48-3.62 (m, 2H), 3.94 (m, 1H), 4.23 (m, 1H), 4.44 (d, 1H, J=15.3 Hz), 4.72 (m, 1H, J=15.3 Hz), 6.95 (m, 1H), 7.20 (m, 3H), 7.67 (m, 3H), 7.77 (m, 3H), 8.44 (m, 1H).

To a solution of [(N-t-butoxycarbortyl)-benzimidazol-2-ylmethyl]-(5,6,7,8-tetrahydro-quinolin-8-yl)-(1-(N-phthalimidyl)-butan-3-(t-butyldimethylsiloxy)-4-yl)-amine (170 mg, 0.24 mmol) in THF (8 mL) was added 1N HCl (2 mL). The mixture was then heated to 50° C. for 2 hours. After cooling, dichloromethane (50 mL) was added, and the mixture was shaken with a saturated sodium bicarbonate solution (20 mL). After separation of the aqueous and organic layers, the aqueous layer was extracted twice with dichloromethane. The combined organic fractions were then dried over anhydrous sodium sulfate, filtered and concentrated in vacuo to afford a foamy residue, which was purified by silica gel flash chromatography (5% methanol in dichloromethane) to afford (1-H-benzimidazol-2-ylmethyl)-(5,6,7,8-tetrahydro-quinolin-8-yl)-(1-(N-phthalimidyl)-butan-3-ol-4-yl)-amine as a white foam in a yield of 73 mg (49%). $^1$H NMR (CDCl$_3$) δ 1.50-1.59 (m, 2H), 1.70-2.07 (m, 5H), 2.21 (m, 1H), 2.75-3.00 (m, 4H), 3.78-3.94 (m, 2H), 4.00-4.22 (m, 2H), 7.04 (m, 1H), 7.16 (m, 2H), 7.24 (d, 1H, J=5.8 Hz), 7.68 (br s, 1H(NH)), 7.71 (m, 3H), 7.81 (m, 3H), 8.21 and 8.42 (d, total of 1H, f=4.9, 5.1 Hz respectively).

To a solution of (1-H-benzimidazol-2-ylmethyl)-(5,6,7,8-tetrahydro-quinolin-8-yl)-(1-(N-phthalimidyl)-butan-3-ol-4-yl)-amine (73 mg, 0.147 mmol) in denatured ethanol (5 mL) was added hydrazine hydrate (0.07 mL, 1.5 mmol). The mixture was then heated to reflux for 60 minutes. After cooling, the reaction was concentrated in vacuo, taken up in dichloromethane (20 mL) and washed with an aqueous sodium carbonate solution (5 mL). The aqueous layer was then extracted twice with dichloromethane, and the combined organic fractions were dried over anhydrous sodium sulfate, filtered and concentrated to afford a foamy residue which was purified by silica gel flash chromatography (10% methanol, 0.5% ammonium hydroxide in dichloromethane) to afford (1H-benzimidazol-2-ylmethyl)-(5,6,7,8-tetrahydro-quinolin-8-yl)-(1-aminobutan-3-ol-4-yl)-amine (COMPOUND 47-diastereomeric mixture) as a white foam in a yield of 22 mg (41%). $^1$H NMR (CDCl$_3$) δ 1.35 (m, 1H), 1.70-1.82 (m, 2H), 2.06 (m, 1H), 2.26 (m, 1H), 2.54-2.99 (m, 5H), 3.57 and 3.84 (m, total of 1H), 3.94 (d, 1H, J=15.3 Hz), 4.01 (m, 1H), 4.13 (s, 1H), 4.13 (d, 1H, J=15.3 Hz), 7.14-7.21 (m, 3H), 7.42 (d, 1H, J=7.5 Hz), 7.57 (m, 2H), 8.46 and 8.56 (d, total of 1H, J=3.6, 3.6 Hz respectively); $^{13}$C NMR (CDCl$_3$) δ 21.57, 22.25, 29.33, 31.52, 32.30, 46.46, 47.69, 48.69, 49.91, 62.15, 62.67, 70.11, 74.23, 122.33, 122.67, 122.99, 135.61, 138.21, 146.93, 147.29, 141.15, 154.89. ES-MS m/z 366 (M+H). Anal. Calcd. for $C_{21}H_{27}N_5O.0.4.CH_2Cl_2$: C, 64.35; H, 7.01; N, 17.53. Found: C, 64.16; H, 7.20; N, 17.22.

Example 48

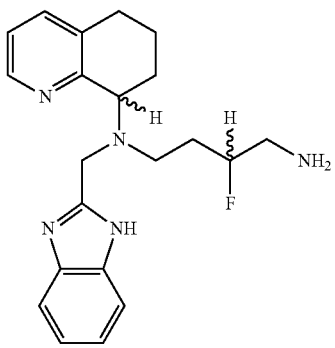 [SMILES: NCC(F)CCN(Cc1nc2ccccc2[nH]1)C1CCCc2cccnc21]

Compound 48: Preparation of (1H-benzimidazol-2-ylmethyl)-(5,6,7,8-tetrahydro-quinolin-8-yl)-(1-amino-3-fluoro-butan-4-yl)-amine To a 0° C. solution of (1-H-benzimidazol-2-ylmethyl)-(5,6,7,8-tetrahydro-quinolin-8-yl)-(1-(N-phthalimidyl)-butan-3-ol-4-yl)-amine (81 mg, 0.163 mmol (preparation described above)) in dichloromethane (5 mL) in a polyethylene test tube under a nitrogen atmosphere was added diethylaminosulfur trifluoride (0.065 mL, 0.5 mmol). The mixture was stirred, gradually warming to room temperature for 2 hours. The mixture was then poured into a saturated sodium bicarbonate solution (10 mL). The aqueous and organic layers were then separated, and the aqueous layer was extracted twice with dichloromethane. The combined organic fractions were then dried over anhydrous sodium sulfate, filtered and concentrated in vacuo. The residue was purified by silica gel flash chromatography (5% methanol in dichloromethane) to afford (1-H-benzimidazol-2-ylmethyl)-(5,6,7,8-tetrahydro-quinolin-8-yl)-(1-(N-phthalimidyl)-3-fluoro-butan-4-yl)-amine as a white foam in a yield of 55 mg (67%). $^1$H NMR (CDCl$_3$) δ 1.69 (m, 2H), 1.86-2.04 (m, 4H), 2.75-2.88 (m, 4H), 3.99 (m, 1H), 4.02-4.20 (m, 4H), 5.01 and 5.08 (m, total of 1H), 7.13 (m, 4H), 7.26 (m, 1H), 7.59-7.73 (m, 4H), 7.89 (m, 1H), 8.78 (m, 1H).

To a solution of (1-H-benzimidazol-2-ylmethyl)-(5,6,7,8-tetrahydro-quinolin-8-yl)-(1-(N-phthalimidyl)-3-fluoro-butan-4-yl)-amine (55 mg, 0.110 mmol) in denatured ethanol (5 mL) was added hydrazine hydrate (0.07 mL, 1.5 mmol). The mixture was then heated to reflux for 60 minutes. After cooling, the reaction was concentrated in vacuo, taken up in dichloromethane (20 mL) and washed with an aqueous sodium carbonate solution (5 mL). The aqueous layer was then extracted twice with dichloromethane, and the combined organic fractions were dried over anhydrous sodium sulfate, filtered and concentrated to afford a foamy residue which was purified by silica gel flash chromatography (10% methanol, 0.5% ammonium hydroxide in dichloromethane) to afford (1H-benzimidazol-2-ylmethyl)-(5,6,7,8-tetrahydro-quinolin-8-yl)-(1-amino-3-fluorobutan-4-yl)-amine (COMPOUND 48-diastereomeric mixture) as a white foam in a yield of 16 mg (40%). $^1$H NMR (CDCl$_3$) δ 1.73 (m, 2H), 1.91-2.04 (m, 2H), 2.23 (m, 1H), 2.61-2.86 (m, 6H), 4.00 (d, 1H, J=16.5 Hz), 4.05 (s, 1H), 4.07 (m, 1H), 4.15 (m, 1H), 4.17 (d, 1H, J=16.5 Hz), 4.47 and 4.53 (m, total of 1H), 7.14-7.22 (m, 4H), 7.42 (d, 1H, J=8.1 Hz), 7.57 (m, 1H), 7.58 (br s, 1H(NH)), 8.58 (d, 1H, J=4.5 Hz); $^{13}$C NMR (CDCl$_3$) δ 21.73 and 23.83 (d, total of 1C, $J_{C-F}$=23 Hz), 29.30, 29.54, 30.73, 39.09, 45.92 and 46.60 (total of 1C), 47.35, 50.10 and 62.23 (d, total of 1C, $J_{C-F}$=27 Hz), 92.65 and 95.11 (d, total of 1H, $J_{C-F}$=167 Hz), 115.38, 122.08, 122.73, 129.19, 131.29, 135.07, 137.82, 137.98, 146.99, 147.11, 156.49, 157.65. ES-MS m/z 368 (M+H). Anal. Calcd. for $C_{21}H_{26}N_5F.0.1CH_2Cl_2.0.2C_6H_{12}$: C, 68.19; H, 7.34; N, 17.83. Found: C, 67.82; H, 7.14; N, 17.66.

Example 49

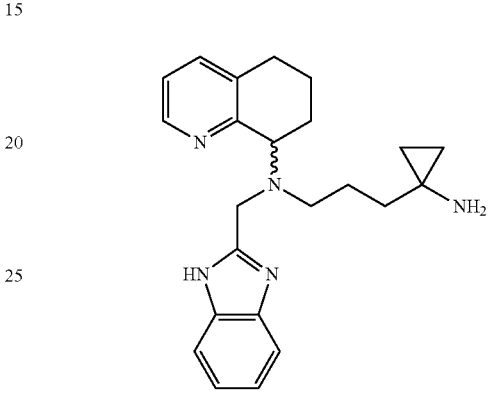

Compound 49: Preparation of [3-(1-amino-cyclopropyl)-propyl]-(1H-benzimidazol-2-ylmethyl)-(5,6,7,8-tetrahydro-quinolin-8-yl)-amine (hydrobromide salt)

Preparation of
1-tert-butoxycarbonylamino-cyclopropanecarboxylic acid ethyl ester (Wentland, M. P.; Perni, R. B.; Dorff, P. H.; Rake, J. B. *J. Med. Chem.* 1988, 31, 1694-1697.)

To a suspension of 1-aminocyclopropanecarboxylic acid (998 mg, 9.87 mmol) in EtOH (25 mL), cooled to 0° C., was added SOCl$_2$ (2.0 mL, 27 mmol) dropwise over 10 minutes. The resulting solution was heated at reflux under nitrogen for 2 hours, then was evaporated under reduced pressure, giving the ester as a light brown oil.

This material was dissolved into EtOAc (25 mL) and a solution of KHCO$_3$ (1.51 g, 15.1 mmol) in H$_2$O (9 mL) was added dropwise. The resulting solution was cooled to 0° C. and a solution of Boc$_2$O (2.97 g, 13.6 mmol) in EtOAc (10 mL) was added. The reaction was stirred at room temperature for 16 hours, the layers were separated and the aqueous solution was extracted with EtOAc (25 mL). The combined organic solution was dried (MgSO$_4$), filtered and concentrated under reduced pressure. Purification by flash column chromatography on silica (EtOAc/hexane, 1:3) gave the protected amine as light brown solid (1.27 g, 5.54 mmol, 56%). $^1$H NMR (CDCl$_3$) δ 1.08-1.18 (m, 2H), 1.23 (t, 3H, J=7.2 Hz), 1.44 (s, 9H), 1.46-1.53 (m, 2H), 4.14 (q, 2H, J=7.2 Hz), 5.13 (br. s, 1H).

Preparation of
(1-hydroxymethyl-cyclopropyl)-carbamic acid tert-butyl ester

To a solution of the ester (1.18 g, 5.15 mL) in THF (10 mL) under nitrogen was added a solution of LiBH$_4$ (200 mg, 9.2 mmol) in THF (10 mL) dropwise over 10 minutes. The reaction was stirred at room temperature for 17.5 hours, then was cooled to 0° C. A solution of 50% HOAc was added dropwise until the evolution of gas had ceased (approx. 8 mL). The resulting white suspension was diluted with $H_2O$ (15 mL) and was extracted with $Et_2O$ (30 mL). The organic solution was washed with 15% aqueous $NaHCO_3$ (15 mL) and brine (15 mL), then dried ($Na_2SO_4$), filtered and concentrated under reduced pressure. Purification by flash column chromatography on silica (EtOAc/hexane, 1:1) gave the alcohol as a white solid (592 mg, 3.16 mmol, 61%).[2] $^1H$ NMR ($CDCl_3$) δ 0.81 (s, 4H), 1.43 (s, 9H), 3.52 (br. s, 1H), 3.58 (s, 2H), 5.12 (br. s, 1H).

Preparation of (1-formyl-cyclopropyl)-carbamic acid tert-butyl ester

To a solution of the alcohol (389 mg, 2.08 mmol) in $CH_2Cl_2$ (11 mL), cooled to 0° C., was added crushed, dried 3 Å molecular sieves (1.05 g), NMO (382 mg, 3.26 mmol) and TPAP (76 mg, 0.22 mmol). The black mixture was stirred at 0° C. for 30 minutes and at room temperature for a further 30 minutes. The mixture was diluted with EtOAc (20 mL) and flushed through a short silica column, rinsing with EtOAc. The product containing material was concentrated under reduced pressure giving the aldehyde as a white solid (345 mg, 1.86 mmol, 90%). $^1H$ NMR ($CDCl_3$) δ 1.27-1.37 (m, 2H), 1.40-1.52 (m, 2H), 1.46 (s, 9H), 5.22 (br. s, 1H), 9.16 (s, 1H).

Preparation of (E)-3-(1-tert-butoxycarbonylamino-cyclopropyl)-acrylic acid ethyl ester Triethyl phosphonoacetate (0.62 mL, 3.13 mmol) was added dropwise to a suspension of 60% NaH in mineral oil (120 mg, 3.00 mmol) in THF (5 mL). The resulting solution was stirred at room temperature for 10 minutes, then cooled to 0° C. for the dropwise addition of a solution of the aldehyde (463 mg, 2.50 mmol) in THF (5 mL). The reaction was stirred at 0° C. for 15 minutes, then heated to reflux for 1 hour. Once cooled to room temperature, saturated aqueous $NH_4Cl$ (10 mL) was added, the layers were separated and the aqueous solution was extracted with $CH_2Cl_2$ (10 mL×2). The organic solution was dried ($MgSO_4$), filtered and concentrated under reduced pressure. Purification by flash column chromatography on silica (EtOAc/hexane, 1:1) gave the unsaturated ester as a pale yellow solid (539 mg, 2.11 mmol, 84%). $^1H$ NMR ($CDCl_3$) δ 1.11-1.18 (m, 2H), 1.24-1.29 (m, 5H), 1.44 (s, 9H), 4.17 (q, 2H, J=7.1 Hz), 5.02 (br. s, 1H), 5.84 (d, 1H, J=15.3 Hz), 6.47 (d, 1H, J=15.6 Hz).

Preparation of 3-(1-tert-butoxycarbonylamino-cyclopropyl)-propionic acid ethyl ester A solution of the unsaturated ester (495 mg, 1.94 mmol) in EtOAc (10 mL) was hydrogenated ($H_2$ balloon) over 10% Pd/C (25 mg, 0.023 mmol) at room temperature for 3 hours. The mixture was suction filtered through Celite, washing with EtOAc and evaporation of the filtrate under reduced pressure gave the saturated ester as a colourless oil (500 mg, 1.94 mmol, 100%). $^1H$ NMR ($CDCl_3$) δ 0.61-0.65 (m, 1H), 0.73-0.78 (m, 1H), 0.91 (t, 2H, J=7.4 Hz), 1.25 (td, 3H, J=7.1, 1.4 Hz), 1.43 (s, 9H), 1.78-1.90 (m, 2H), 2.36 (t, 1H, J=7.7 Hz), 2.44 (t, 1H, J=7.5 Hz), 4.12 (q, 2H, J=7.1 Hz).

Preparation of [1-(3-hydroxy-propyl)-cyclopropyl]-carbamic acid tert-butyl ester $LiBH_4$ (70 mg, 3.2 mmol) was added to a solution of the ester (500 mg, 1.94 mmol) in THF (8 mL). The reaction was stirred at room temperature under nitrogen for 18 hours, then was quenched by the dropwise addition of 50% aqueous HOAc until the evolution of gas had ceased (approx. 2 mL). The suspension was diluted with $H_2O$ (10 mL) and extracted with $Et_2O$ (15 mL). The organic solution was washed with saturated aqueous $NaHCO_3$ (10 mL) and brine (10 mL), dried ($Na_2SO_4$), filtered and concentrated under reduced pressure. Purification by flash column chromatography on silica (hexane/EtOAc, 2:1; increased to 1:1) gave the alcohol as a colourless oil (164 mg, 0.77 mmol, 40%). $^1H$ NMR ($CDCl_3$) δ 0.55-0.62 (m, 2H), 0.69-0.75 (m, 2H), 1.40 (s, 9H), 1.52-1.72 (m, 4H), 2.10 (br. s, 1H), 3.64 (t, 2H, J=6.3 Hz), 4.96 (br. s, 1H).

Preparation of {1-[3-(5,6,7,8-tetrahydro-quinolin-8-ylamino)-propyl]-cyclopropyl}-carbamic acid tert-butyl ester To a solution of the alcohol (160 mg, 0.74 mmol) in $CH_2Cl_2$ (4 mL), cooled to 0° C., was added crushed, dried 3 Å molecular sieves (374 mg), NMO (125 mg, 1.07 mmol) and TPAP (26 mg, 0.07 mmol). The reaction was stirred at 0° C. for 25 minutes, then at room temperature for a further 15 minutes. The reaction was diluted with EtOAc (8 mL) and the mixture was flushed through a short silica column, eluting with EtOAc. Removal of the solvent under reduced pressure gave the aldehyde as a pale yellow oil (123 mg, 78%).

A solution of this material (120 mg, 0.56 mmol) and 8-amino-5,6,7,8-tetrahydroquinoline (90 mg, 0.61 mmol) in MeOH (1.5 mL) was stirred at room temperature under nitrogen for 17 hours. $NaBH_4$ (35 mg, 0.93 mmol) was added and the reaction was stirred for a further 15 minutes. The solvent was evaporated under reduced pressure, the residue was taken up into $CH_2Cl_2$ (20 mL) and was washed with saturated aqueous $NaHCO_3$ (5 mL) and brine (5 mL). The organic solution was dried ($MgSO_4$), filtered and concentrated under reduced pressure. Purification by flash column chromatography on silica ($CH_2Cl_2$/MeOH/$NH_4OH$, 19:1:0.1) gave the secondary amine as an orange oil (51 mg, 0.15 mmol, 26%). $^1H$ NMR ($CDCl_3$) δ 0.57-0.63 (m, 2H), 0.69-0.76 (m, 2H), 1.42 (s, 9H), 1.56-1.80 (m, 5H), 1.80-2.06 (m, 3H), 2.09-2.20 (m, 1H), 2.68-2.87 (m, 4H), 3.77 (t, 1H, J=6.3 Hz), 5.16 (br. s, 1H), 7.06 (dd, 1H, J=7.7, 4.7 Hz), 7.37 (d, 1H, J=7.5 Hz), 8.38 (d, 1H, J=4.2 Hz).

Preparation of 2-{[[3-(1-tert-butoxycarbonylamino-cyclopropyl)-propyl]-(5,6,7,8-tetrahydro-quinolin-8-yl)-amino]-methyl}-benzimidazole-1-carboxylic acid tert-butyl ester A solution of the secondary amine (51 mg, 0.147 mmol), tert-butyl 2-chloro-methylbenzimidazole-1-carboxylate (47 mg, 0.18 mmol), DIPEA (0.04 mL, 0.2 mmol) and KI (5 mg, 0.03 mmol) in $CH_3CN$ (0.8 mL) was stirred at 60° C. under nitrogen for 18 hours. Once cooled to room temperature, saturated aqueous $NaHCO_3$ (5 mL) was added and the mixture was extracted with $CH_2Cl_2$ (10 mL×3). The combined organic solution was dried ($MgSO_4$), filtered and concentrated under reduced pressure. Purification by flash column chromatography on silica ($CH_2Cl_2$/MeOH/$NH_4OH$, 19:1:0.1) gave the tertiary amine as a pale orange foam (60 mg, 0.104 mmol, 71%). $^1$H NMR (CDCl$_3$) δ 0.30-0.46 (m, 2H), 0.48-0.63 (m, 2H), 1.29-1.50 (m, 11H), 1.60-1.76 (m, 12H), 1.79-1.90 (m, 1H), 1.95-2.05 (m, 1H), 2.08-2.19 (m, 1H), 2.59-2.70 (m, 2H), 2.72-2.87 (m, 2H), 4.26 (dd, 1H, J=9.5, 6.5 Hz), 4.50 (d, 1H, J=15.6 Hz), 4.63 (d, 1H, J=15.0 Hz), 5.10 (br. s, 1H), 6.98 (dd, 1H, J=7.7, 4.7 Hz), 7.26-7.32 (m, 3H), 7.72 (dd, 1H, J=6.2, 3.2 Hz), 7.83 (dd, 1H, J=6.0, 3.0 Hz), 8.37 (d, 1H, J=3.0 Hz).

Preparation of Compound 49

To a solution of the tertiary amine (57.6 mg, 0.100 mmol) in glacial HOAc (1.0 mL) was added a saturated solution of HBr in HOAc (0.5 mL). The reaction was stirred at room temperature for one hour and Et$_2$O (5 mL) was added. The resulting sticky solid was washed with Et$_2$O (1 mL×2), then crushed with a spatula while under Et$_2$O (~2 mL). The resulting precipitate was washed with Et$_2$O (1 mL×2), then dried under reduced pressure affording COMPOUND 49 as an orange powder (65.7 mg, 0.091 mmol, 91%). $^1$H NMR (D$_2$O) δ 0.63-0.68 (m, 2H), 0.81-0.86 (m, 2H), 1.46-1.67 (m, 4H), 1.76-1.90 (m, 1H), 1.93-2.06 (m, 1H), 2.12-2.22 (m, 1H), 2.31-2.41 (m, 1H), 2.48-2.58 (m, 1H), 2.77-2.87 (m, 1H), 2.96-3.02 (m, 2H), 4.39 (d, 1H, J=16.8 Hz), 4.47-4.56 (m, 2H), 7.59 (dd, 2H, J=6.2, 3.2 Hz), 7.79 (dd, 2H, J=6.2, 3.2 Hz), 7.85 (dd, 1H, J=7.8, 6.0 Hz), 8.33 (d, 1H, J=7.8 Hz), 8.62 (d, 1H, J=5.4 Hz). $^{13}$C NMR (D$_2$O) δ 9.6, 20.4, 24.3, 27.6, 31.8, 34.3, 48.0, 51.8, 60.5, 114.3, 125.9, 126.9, 131.0, 139.3, 140.6, 148.1, 151.2, 151.7. ES-MS m/z 376 (M+H). Anal. Calcd. for C$_{23}$H$_{29}$N$_5$.3.1HBr.1.5C$_2$H$_4$O$_2$.0.2H$_2$O: C, 43.37; H, 5.39; N, 9.73; Br, 34.40. Found: C, 43.26; H, 5.67; N, 9.64; Br, 34.68.

Example 50

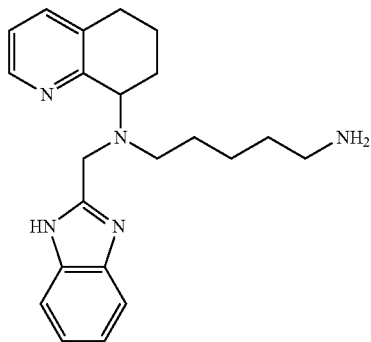 [SMILES: NCCCCCN(Cc1nc2ccccc2[nH]1)C1CCCc2cccnc21]

Compound 50: (1H-Benzimidazol-2-ylmethyl)-(5,6,7,8-tetrahydroquinolin-8-yl)-(5-amino-pent-1-yl)-amine (Hydrobromide salt)

To a stirred solution of [1-(2-(trimethylsilyl)ethoxymethyl)-(1H-benzimidazol-2-ylmethyl)]-(5,6,7,8-tetrahydroquinolin-8-yl)-amine (188 mg, 0.455 mmol) and diisopropylethyl amine (0.26 ml<1.49 mmol) in CH$_3$CN was added 5-bromovaleronitrile (0.12 mL, 1.03 mmol). The mixture was heated at 80° C. for 47 hours, after which time the reaction was cooled to room temperature. After removal of volatiles under reduced pressure, the residue was dissolved in CH$_2$Cl$_2$ (20 mL). The solution was washed with brine (3×15 mL). The aqueous phase was extracted with CH$_2$Cl$_2$ (1×15 mL). The combined organic phases were dried (Na$_2$SO$_4$), filtered and concentrated under reduced pressure to give a crude orange oil (306 mg). Purification of this oil by column chromatography (1.75 cm OD, 14 g silica, 40:1 CH$_2$Cl$_2$: CH$_3$OH) afforded the purified tertiary amine (110 mg, 50%).

The amine from above (110 mg) was dissolved in ammonia saturated CH$_3$OH (12 mL) and treated with Raney-Nickel (410 mg). The mixture was shaken on a Parr hydrogenator at 50 psi H$_2$ for 20 hours, after which time the mixture was filtered through celite and concentrated to give a crude yellow-orange oil (124 mg).

The amine from above (124 mg) was dissolved in 4N HCl (2 mL) and heated to 50° C. for 6 hours. The mixture was then cooled to room temperature and basified with 10N NaOH (final pH>13). This aqueous phase was extracted with CH$_2$Cl$_2$ (4×10 mL). The organic phase was then dried (Na$_2$SO$_4$), filtered and concentrated to give a crude brown foam (83 mg). Purification of this foam by radial chromatography on silica gel (40:1:1 CH$_2$Cl$_2$: CH$_3$OH: OH) afforded the pure freebase (38 mg, 46% over two steps).

Using the General Procedure D: Conversion of the freebase from above (38 mg) to the hydrobromide salt gave COMPOUND 50 as a white solid (53 mg, 76%). $^1$H NMR (D$_2$O) δ 1.14-1.28 (m, 2H), 1.39-1.57 (m, 4H), 1.77-1.90 (m, 1H), 1.96-2.10 (m, 1H), 2.13-2.23 (m, 1H), 2.31-241 (m, 1H), 2.46-2.57 (m, 1H), 2.73-2.90 (m, 3H), 2.96-3.03 (m, 2H), 4.38 (d, 1H, J=16.7 Hz), 4.47-4.57 (m, 2H), 7.60 (dd, 2H, J=6.3, 3.3 Hz), 7.80 (dd, 2H, J=6.2, 3.1 Hz), 7.86 (dd, 1H, J=7.9, 6.0 Hz), 8.31 (d, 1H, J=7.0 Hz), 8.62 (d, 1H, J=4.7 Hz). $^{13}$C NMR (D$_2$O) δ 20.40, 23.88, 26.92, 27.63, 27.87, 39.68, 48.51, 52.09, 60.86, 114.26 (2 carbons), 125.85, 126.83 (2 carbons), 131.17, 139.29, 140.47, 147.92 (2 carbons), 151.48, 152.00. ES-MS m/z 364 (M+H) Anal Calc. for C$_{22}$H$_{29}$N$_5$.3.1HBr.2.6H$_2$O: C, 39.97; H, 5.69; N, 10.59; Br, 37.46. Found: C, 39.96; H, 5.64; N, 10.62; Br, 37.36.

Example 51

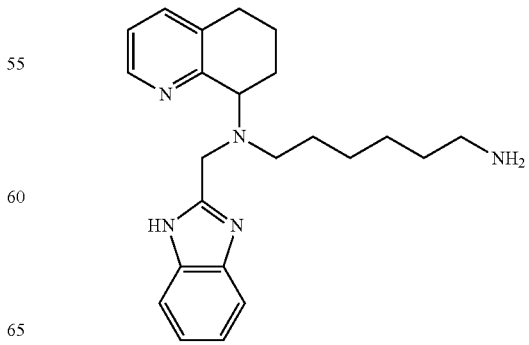

Compound 51: (1H-Benzimidazol-2-ylmethyl)-(5,6,7,8-tetrahydroquinolin-8-yl)-(6-amino-hex-1-yl)-amine (Hydrobromide salt)

Preparation of N-(tert-butoxycarbonyl)-6-amino-1-hexanal

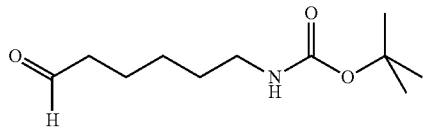

Di-tert-butyl-dicarbonate (1.155 g, 5.29 mmol) was added to a solution of 6-amino-1-hexanol (541 mg, 4.62 mmol) and diisopropylethyl amine (0.25 mL) in THF (10 mL). The mixture was stirred at ambient temperature for 18 hours, after which time the volatile components were removed under reduced pressure. The residue was dissolved in $CH_2Cl_2$ (30 mL) and washed with brine (3×20 mL). The organic phase was dried ($Na_2SO_4$), filtered and removed on a rotovap to leave a crude yellow oil (1.090 g).

Some of the above-obtained oil (220 mg, 1.01 mmol) was dissolved in $CH_2Cl_2$ (5 mL) and treated with Dess-Martin periodinane (455 mg, 1.07 mmol). After 2 hours, the reaction was diluted with diethyl ether (20 mL) and treated with 20% w/v $Na_2S_2O_{3\ (aq)}$. The phases were separated after 10 minutes, and the aqueous phase was extraced with ether (3×10 mL). The combined organic phase was washed with 20% w/v $Na_2S_2O_3$ (1×12 mL), saturated aqueous $NaHCO_3$ (1×12 mL) and brine (1×12 mL). The organic phase was dried ($MgSO_4$), filtered and removed under reduced pressure to give a crude colourless oil (172 mg). This oil was purified by column chromatography (1.75 cm OD, 14 g silica, 4:1 hexanes:ethyl acetate) to give 31 mg of desired intermediate (14%). $^1H$ NMR ($CDCl_3$) d 1.29-1.50 (m, 13H), 1.63 (pentet, 2H, J=7.4 Hz), 2.42 (td, 2H, J=7.2, 1.6 Hz), 3.06-3.12 (m, 2H), 4.57 (br s, 1H), 9.74 (s, 1H).

Using the General Procedure B: To a stirred solution of [1-(2-(trimethylsilyl)ethoxymethyl)-(1H-benzimidazol-2-ylmethyl)]-(5,6,7,8-tetrahydro-quinolin-8-yl)-amine (62 mg, 0.150 mmol) and N-(tert-butoxycarbonyl)-6-amino-1-hexanal (31 mg, 0.144 mmol) in $CH_2Cl_2$ (2.5 mL) was added $NaBH(OAc)_3$ (66 mg, 0.311 mmol) and the mixture stirred for 24 hours to afford a crude yellow oil (91 mg).

This oil (91 mg) was dissolved in 4N HCl (2 mL) and heated to 50° C. After 4 hours the reaction was allowed to cool. The reaction was basified with 10N NaOH (final pH>13) and the aqueous phase was extracted with $CH_2Cl_2$ (8×7 mL). The organic phase was dried ($Na_2SO_4$), filtered and removed on a rotovap to give 52 mg crude yellow oil freebase. This oil was purified by radial chromatography on silica gel (40:1:1 $CH_2Cl_2$: $CH_3OH$: $NH_4OH$) to give 36 mg yellow film (66% yield over two steps).

Using the General Procedure D: conversion of the freebase from above (36 mg) to the hydrobromide salt gave COMPOUND 51 as a white solid (53 mg, 84%).

$^1H$ NMR ($D_2O$) δ 1.13-1.23 (m, 4H), 1.31-1.56 (m, 4H), 1.75-1.90 (m, 1H), 1.96-2.10 (m, 1H), 2.13-2.23 (m, 1H), 2.31-241 (m, 1H), 2.44-2.55 (m, 1H), 2.71-2.81 (m, 1H), 2.85 (t, 2H, J=7.8 Hz), 2.97-3.04 (m, 2H), 4.38 (d, 1H, J=17.0 Hz), 4.48-4.59 (m, 2H), 7.61 (dd, 2H, J=6.1, 3.1 Hz), 7.80 (dd, 2H, J=6.1, 3.0 Hz), 7.86 (dd, 1H, J=7.7, 5.9 Hz), 8.34 (d, 1H, J=8.3 Hz), 8.62 (d, 1H, J=5.7 Hz). $^{13}C$ NMR ($D_2O$) δ 20.39, 20.45, 25.81, 26.41, 27.07, 27.64, 28.14, 39.74, 48.67, 52.22, 60.95, 114.24 (2 carbons), 125.86, 126.88 (2 carbons), 131.01, 139.21, 140.49, 147.99, 151.55, 152.12. ES-MS m/z 378 (M+H) Anal Calc. for $C_{23}H_{31}N_5·3.1HBr·1.9H_2O$: C, 41.69; H, 5.77; N, 10.57; Br, 37.38. Found: C, 41.77; H, 5.60; N, 10.60; Br, 37.36.

Example 52

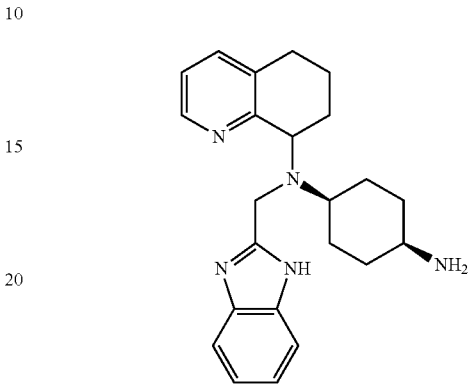

Compound 52: Preparation of $N^1$-(1H-Benzimidazol-2-ylmethyl)-$N^1$-(5,6,7,8-tetrahydro-quinolin-8-yl)-cyclohexane-cis-1,4-diamine (hydrobromide salt)

Preparation of 4-[N-(tert-butyloxycarbonyl)]amino-cyclohexanone

A solution of trans-4-aminocyclohexanol hydrochloride (2.67 g, 1.14 mol) in 1 N NaOH (40 mL) was washed with $CHCl_3$ (40 mL), $CH_2Cl_2$ (2×30 mL) and EtOAc (4×30 mL). The combined organic extracts were dried ($Na_2SO_4$), filtered and concentrated in vacuo to afford the desired free base (0.43 g) as a white solid. To a suspension of trans-4-aminocyclohexanol (0.43 g, 4.09 mmol) in THF (20 mL) was added di-tert-butyl dicarbonate (0.89 g, 4.09 mmol) and the mixture stirred at room temperature for 2 hours. The mixture was concentrated under reduced pressure and the resultant crude product was used without further purification in the next reaction.

To a suspension of the alcohol from above (~3.7 mmol) and powdered 3 Å molecular sieves (0.90 g) in $CH_2Cl_2$ (10 mL) was added 4-methylmorpholine N-oxide (0.696 g, 5.95 mmol) and tetrapropylammonium perruthenate (0.089 g, 0.25 mmol) and the mixture stirred overnight. The reaction was concentrated under reduced pressure and purified by column chromatography through a plug of silica gel (ethyl acetate/hexanes, 1:1) to afford the title compound (0.670 g, 84% over 2 steps) as a white solid. $^1H$ NMR ($CDCl_3$) δ 1.45 (br s, 9H), 1.64-1.73 (m, 2H), 2.21-2.27 (m, 2H), 2.37-2.44 (m, 4H), 3.89-3.95 (m, 1H), 4.50 (br s, 1H, N$\underline{H}$).

Following General Procedure B: To a stirred solution of 8-amino-5,6,7,8-tetrahydroquinoline (195 mg, 1.32 mmol) and 4-[N-(tert-butyloxycarbonyl)]amino-cyclohexanone (293 mg, 1.38 mmol) in dry THF (5 mL) was added $NaBH(OAc)_3$ (392 mg, 1.85 mmol) and the mixture stirred for 2 h at room temperature. The reaction was diluted with $CH_2Cl_2$ (20 mL) and saturated aqueous sodium bicarbonate (40 mL) and the aqueous phase was washed with $CH_2Cl_2$ (2×10 mL). The combined organic extracts were dried ($Na_2SO_4$), filtered and concentrated to afford the desired secondary amine as a mixture of diastereomers (520 mg). The diastereomers were separated and purified by column chromatography with silica gel ($CH_2Cl_2$/MeOH, 96:4) to give a top, less polar diastereomer (179 mg, 39%) and a lower, more polar one (107 mg, 23%), each as an orange oil.

Following the General Procedure for N-alkylation: To a stirred solution of the top, less polar diastereomer from above (179 mg, 0.52 mmol) in $CH_3CN$ (5 mL) was added N,N-diisopropylethylamine (0.18 mL, 1.04 mmol), KI (24 mg, 0.14 mmol) and 1-(tert-butoxycarbonyl)-2-(chloromethyl)benzimidazole (149 mg, 0.56 mmol). The mixture was stirred at 60° C. for 4 h then cooled, diluted with $CH_2Cl_2$ (40 mL) and saturated aqueous sodium bicarbonate (30 mL). The aqueous phase was washed with $CH_2Cl_2$ (2×10 mL), dried ($Na_2SO_4$), filtered and concentrated. Purification of the resultant brown oil by column chromatography with silica gel ($CH_2Cl_2$/MeOH, 96:4) afforded the desired alkylated cis-1,4-diamine, $N^1$-(1-tert-butoxycarbonyl-benzimidazol-2-ylmethyl)-$N^1$-(5,6,7,8-tetrahydro-quinolin-8-yl)-cyclohexane-cis-1,4-diamine-4-carboxylic acid tert-butyl ester, (142 mg, 47%) as a yellow oil.

Using General Procedure D: Conversion of the oil from above (72 mg, 0.13 mmol) to the hydrobromide salt with simultaneous removal of the N-tert-butoxycarbonyl protecting group followed by re-precipitation of the intermediate solid from methanol/ether gave COMPOUND 52 (67 mg, 82%) as an orange solid. $^1H$ NMR ($D_2O$) δ 1.66-1.81 (m, 4H), 1.85-2.08 (m, 4H), 2.11-2.18 (m, 3H), 2.42-2.47 (m, 1H), 2.81-2.85 (m, 1H), 3.00-3.02 (m, 2H), 3.53-3.55 (m, 1H), 4.45 (d, 1H, J=16.8 Hz), 4.57-4.63 (m, 1H), 4.60 (d, 1H, J=16.8 Hz), 7.59 (dd, 2H, J=6.3, 3.3 Hz), 7.76 (dd, 2H, J=6.3, 3.3 Hz), 7.80 (dd, 1H, J=7.8, 6.3 Hz), 8.28 (d, 1H, J=7.8 Hz), 8.58 (d, 1H, J=5.5 Hz); $^{13}C$ NMR ($D_2O$) δ 20.79, 23.38, 24.33, 25.64, 27.55, 27.70, 27.90, 43.83, 46.55, 58.06, 59.77, 114.25, 125.82, 127.02, 130.95, 139.12, 140.53, 147.99, 151.38, 152.14. ES-MS m/z 376 (M+H). Anal. Calcd. for $C_{23}H_{29}N_5$.2.9HBr.2.5$H_2O$: C, 42.16; H, 5.68; N, 10.69; Br, 35.37. Found: C, 42.55; H, 5.43; N, 10.31; Br, 35.28.

Example 53

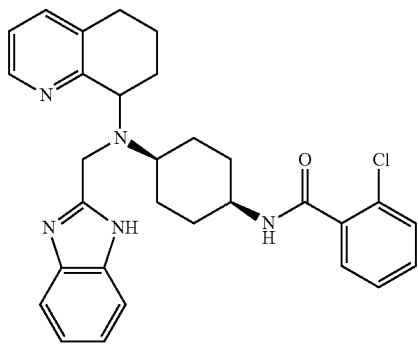 [SMILES: O=C(N[C@H]1CC[C@@H](N(Cc2nc3ccccc3[nH]2)C2CCCc3cccnc32)CC1)c1ccccc1Cl]

Compound 53: Preparation N-{4-cis-[(1H-Benzimidazol-2-ylmethyl)-(5,6,7,8-tetrahydro-quinolin-8-yl)-amino]-cyclohexyl}-2-chloro-benzamide (hydrobromide salt)

A solution of the diprotected amine from above, $N^1$-(1-tert-butoxycarbonyl-benzimidazol-2-ylmethyl)-$N^1$-(5,6,7,8-tetrahydro-quinolin-8-yl)-cyclohexane-cis-1,4-diamine-4-carboxylic acid tert-butyl ester, (sec COMPOUND 52) (70 mg, 0.12 mmol) in $CH_2Cl_2$/TFA (1:1, 2 mL) was stirred at room temperature for 1.5 h. The reaction was then concentrated and diluted with $CH_2Cl_2$ (15 mL) and 1 N NaOH (15 mL). The aqueous layer was washed with $CH_2Cl_2$ (2×10 mL) and the combined organic extracts were dried ($Na_2SO_4$), filtered and concentrated. To a solution of the resultant crude amine (32 mg) $CH_2Cl_2$ (3 mL) was added $Et_3N$ (0.045 mL, 0.32 mmol) and 2-chlorobenzoylchloride (0.030 mL, 0.24 mmol) and the mixture stirred overnight. The reaction was diluted with $CH_2Cl_2$ (10 mL) saturated aqueous sodium bicarbonate (10 mL). The aqueous layer was washed with $CH_2Cl_2$ (2×5 mL) and the combined organic extracts were dried ($Na_2SO_4$), filtered and concentrated. Purification of the crude foam by radial chromatography on silica gel gel (1 mm plate, 100:1:1 $CH_2Cl_2$/MeOH/$NH_4OH$) afforded the title amide (23 mg, 37% over 2 steps) as a yellow foam.

Using General Procedure D: Conversion of the foam from above (23 mg, 0.045 mmol) to the hydrobromide salt followed by re-precipitation of the intermediate solid from methanol/ether gave COMPOUND 53 (27 mg, 83%) as a yellow solid. $^1H$ NMR ($D_2O$) δ 1.44-1.62 (m, 4H), 1.74-1.97 (m, 4H), 2.04-2.21 (m, 3H), 2.41-2.46 (m, 1H), 2.80-2.84 (m, 1H), 3.00-3.02 (m, 2H), 3.98-3.99 (m, 1H), 4.41 (d, 1H, J=16.8 Hz), 4.55-4.60 (m, 1H), 4.58 (d, 1H, J=16.8 Hz), 7.30-7.37 (m, 2H), 7.43-7.45 (m, 2H), 7.60 (dd, 2H, J=6, 3 Hz), 7.75 (dd, 2H, J=6, 3 Hz), 7.82 (dd, 1H, J=7.8, 6 Hz), 8.31 (d, 1H, J=8.1 Hz), 8.58 (d, 1H, J=5.7 Hz); $^{13}C$ NMR ($D_2O$) δ 20.78, 23.87, 25.39, 27.11, 27.59, 28.54, 28.92, 44.11, 45.77, 59.89, 60.00, 114.24, 125.83, 127.07, 127.73, 128.61, 130.18, 130.88, 131.89, 135.36, 139.08, 140.55, 148.01, 151.94, 152.11, 170.46. ES-MS m/z 514 (M+H). Anal. Calcd. for $C_{30}H_{32}N_5OCl$.2.2HBr.1.9$H_2O$: C, 49.61; H, 5.27; N, 9.64; Br, 24.20. Found: C, 49.65; H, 5.22; N, 9.50; Br, 24.17.

Example 54

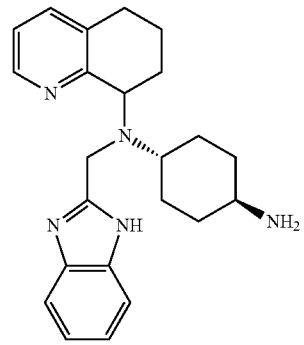 [SMILES: N[C@H]1CC[C@H](N(Cc2nc3ccccc3[nH]2)C2CCCc3cccnc32)CC1]

Compound 54: Preparation of $N^1$-(1H-Benzimidazol-2-ylmethyl)-$N^1$-(5,6,7,8-tetrahydro-quinolin-8-yl)-cyclohexane-trans-1,4-diamine (hydrobromide salt)

Following the General Procedure for N-alkylation: To a stirred solution of the bottom, more polar diastereomer from above (see COMPOUND 52) (107 mg, 0.31 mmol) in $CH_3CN$ (5 mL) was added N,N-diisopropylethylamine (0.11 mL, 0.63 mmol), KI (14 mg, 0.08 mmol) and 1-(tert-butoxycarbonyl)-2-(chloromethyl)benzimidazole (106 mg, 0.40 mmol) and the mixture was stirred at 60° C. for 7 h. Purification of the resultant brown oil by column chromatography with silica gel ($CH_2Cl_2$/MeOH/$NH_4OH$, 96:4:0 then 95:4:1) followed by radial chromatography on silica gel (1 mm plate, (CH₂Cl₂/MeOH/NH₄OH, 50:1:1) afforded the desired alkylated trans-1,4-diamine (44 mg, 25%) as a clear oil.

Using General Procedure D: Conversion of the foam from above (31 mg, 0.054 mmol) to the hydrobromide salt with simultaneous removal of the N-tert-butoxycarnoyl protecting group followed by re-precipitation of the intermediate solid from methanol/ether gave COMPOUND 54 (32 mg, 90%) as a white solid. $^1$H NMR (D₂O) δ 1.40-1.61 (m, 4H), 1.86-2.30 (m, 7H), 2.42-2.46 (m, 1H), 2.76-2.84 (m, 1H), 3.00-3.02 (m, 2H), 3.11-3.18 (m, 1H), 4.44 (d, 1H, J=16.8 Hz), 4.52-4.57 (m, 1H), 4.57 (d, 1H, J=16.8 Hz), 7.60 (dd, 2H, J=6, 3 Hz), 7.77 (dd, 2H, J=6, 3 Hz), 7.81 (dd, 1H, J=7.8, 6 Hz), 8.29 (d, 1H, J=7.8 Hz), 8.58 (d, 1H, J=5.7 Hz); $^{13}$C NMR (D₂O) δ 20.73, 24.05, 27.54, 27.62, 29.60, 29.74, 29.85, 44.06, 49.58, 58.80, 59.30, 114.25, 125.80, 126.97, 131.03, 139.10, 140.46, 147.96, 151.62, 152.09. ES-MS m/z 376 (M+H). Anal. Calcd. for C₂₃H₂₉N₅.3.0HBr.2.1H₂O: C, 42.11; H, 5.56; N, 10.67; Br, 36.54. Found: C, 42.24; H, 5.60; N, 10.51; Br, 36.50.

Example 55

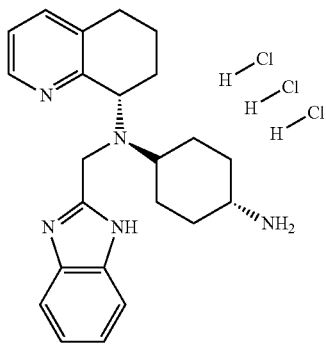

Compound 55: Preparation of N$^1$-(1H-Benzimidazol-2-ylmethyl)-N$^1$-((S)-5,6,7,8-tetrahydro-quinolin-8-yl)-trans-cyclohexane-1,4-diamine (hydrochloride salt)

To a solution of trans-4-aminocyclohexanol hydrochloride (10.0 g, 65.9 mmol) and triethylamine (18.4 mL, 132.0 mmol) in tetrahydrofuran (132 mL) was added di-tert-butyl dicarbonate (15.31 g, 70.1 mmol). The mixture was stirred at 25° C. under nitrogen for 17 h at which time ethyl acetate (250 mL) was added. The solution was washed with water (2×100 mL), dried (Na₂SO₄) and concentrated to afford (4-Hydroxycyclohexyl)-carbamic acid tert-butyl ester as a white solid (13.82 g, 97%). $^1$H NMR (CDCl₃) δ 1.09-1.25 (m, 2H), 1.31-1.39 (m, 2H), 1.44 (s, 9H), 1.94-2.03 (m, 4H), 3.42 (bs, 1H), 3.56-3.64 (m, 1H), 4.34 (bs, 1H).

To a solution of (4-hydroxy-cyclohexyl)-carbamic acid tert-butyl ester (5.80 g, 26.9 mmol) in dry methylene chloride (67 mL) was added in order activated 3 Å molecular sieves (6.54 g), 4-methylmorpholine N-oxide (5.04 g, 43.0 mmol) and tetrapropylammonium perruthenate (380 mg, 1.08 mmol). The mixture was stirred at 25° C. for 18 h under nitrogen then the mixture was concentrated. Purification by column chromatography on silica gel with hexane/ethyl acetate (1:1) afforded (4-oxo-cyclohexyl)-carbamic acid tert-butyl ester as a white solid (5.52 g, 96%). $^1$H NMR (CDCl₃) δ 1.46 (s, 9H), 1.64-1.74 (m, 2H), 2.21-2.27 (m, 2H), 2.39-2.45 (m, 4H), 3.97 (bs, 1H), 4.40 (bs, 1H).

Acetic acid (2.9 mL, 50.7 mmol), (4-oxo-cyclohexyl)-carbamic acid tert-butyl ester (4.32 g, 20.2 mmol) and sodium triacetoxyborohydride (7.56 g, 35.7 mmol) were added to a solution of (S)-5,6,7,8-tetrahydro-quinolin-8-ylamine (2.86 g, 19.3 mmol) in tetrahydrofuran (78 mL) and the mixture was stirred at 25° C. for 3.5 h. The mixture was diluted with methylene chloride (500 mL) and washed with saturated sodium bicarbonate (600 mL). The aqueous layer was extracted with methylene chloride (2×150 mL). The combine organic layers were dried (Na₂SO₄) and concentrated. The crude mixture of isomers was purified by column chromatography on silica gel with methanol/methylene chloride (4:96) to afford the trans-isomer [4-((S)-5,6,7,8-tetrahydro-quinolin-8-ylamino)-trans-cyclohexyl]-carbamic acid tert-butyl ester as a white solid (2.01 g, 30%). $^1$H NMR (CDCl₃) δ 1.06-1.39 (m, 4H), 1.69 (s, 9H), 1.65-1.80 (m, 2H), 1.90-2.14 (m, 5H), 2.16-2.25 (m, 1H), 2.29 (bs, 1H), 2.56-2.71 (m, 1H), 2.72-2.88 (m, 2H), 3.43 (bs, 1H), 3.92 (t, 1H, J=6.3 Hz), 4.39 (bs, 1H), 7.04 (dd, 1H, J=7.9, 4.5 Hz), 7.35 (d, 1H, J=7.5 Hz), 8.38 (d, 1H, J=4.5 Hz).

The enantiomeric purity of [4-((S)-5,6,7,8-tetrahydro-quinolin-8-ylamino)-trans-cyclohexyl]-carbamic acid tert-butyl ester was determined to be 95% by chiral HPLC using the following conditions: Instrument: Hewlett Packard 1100 HPLC (VWD2); Column: ChiralPak AD, 2.1 cm×100 cm; Mobile Phases: A=90:10 hexanes/isopropanol with 0.1% TFA, B=isopropanol; Isocratic: 90% A, 10% B; Total Run Time: 25 min; Flow Rate: 1.0 mL/min; Temperature: 10° C.; Detector: UV @ 254 nm; Injection volume: 30 μL.

Retention time of the S enantiomer=5.3 min.

Retention time of the R enantiomer=8.1 min.

To a suspension of [4-((S)-5,6,7,8-tetrahydro-quinolin-8-ylamino)-trans-cyclohexyl]-carbamic acid tert-butyl ester (1.95 g, 5.64 mmol) in dry acetonitrile (60 mL) was added 2-chloromethyl-benzoimidazole-1-carboxylic acid tert-butyl ester (1.65 g, 6.20 mmol), diisopropylethylamine (2.0 mL, 11.4 mmol) and potassium iodide (100 mg, 0.60 mmol). The mixture was warmed to 60° C. and stirred for 2 days under nitrogen. The mixture was concentrated, dissolved in methylene chloride (80 mL) and washed with brine (50 mL). The aqueous layer was extracted with methylene chloride (3×50 mL). The combined organic layers were dried (Na₂SO₄) and concentrated. The crude mixture was purified by column chromatography on silica gel (80 g) with methanol/methylene chloride (4:96) to afford 2-{[(4-tert-butoxycarbonylamino-trans-cyclohexyl)-(5,6,7,8-tetrahydro-quinolin-8-yl)-amino]-methyl}-benzimidazole-1-carboxylic acid tert-butyl ester as a white solid (1.82 g, 56%). $^1$H NMR (CDCl₃) δ 1.09 (bs, 2H), 1.43 (s, 9H), 1.68 (s, 9H), 1.83-2.14 (m, 6H), 2.47-2.63 (m, 1H), 2.65-2.79 (m, 1H), 2.79-2.95 (m, 1H), 3.32 (bs, 1H), 4.30 (bs, 2H), 4.46 (s, 2H), 6.75-6.89 (m, 1H), 7.00-7.13 (m, 1H), 7.61-7.70 (m, 1H), 7.70-7.79 (m, 1H), 8.32 (bs, 1H).

2-{[(4-tert-Butoxycarbonylamino-trans-cyclohexyl)-(5,6,7,8-tetrahydro-quinolin-8-yl)-amino]-methyl}-benzimidazole-1-carboxylic acid tert-butyl ester was dissolved in acetic acid (15 mL) and hydrogen chloride gas was bubbled through the solution for 10 min. The mixture was stirred for an additional 1.75 h then diluted with acetic acid (15 mL). The acetic acid solution was added dropwise, over 40 min., to a rapidly stirred flask of diethyl ether (300 mL) where a white fluffy precipitate formed. The ether mixture was allowed to settle and decanted. The slurry was washed with ether (4×300 mL) and then the precipitate was collected on a glass frit and rinsed thoroughly with ether. The frit was placed into a vacuum oven (40° C.) for 18 h to afford COMPOUND 55 as a beige solid (1.36 g, 79%). $^1$H NMR (D₂O) δ 1.34-1.1.52 (m, 2H), 1.57

(dq, 2H, J=12.3, 2.4 Hz), 1.77-1.92 (m, 1H), 1.97-2.21 (m, 6H), 2.24-2.42 (m, 1H), 2.82 (tt, 1H, J=11.6, 3.1 Hz), 3.09 (d, 2H, J=3.9 Hz), 3.13 (tt, 1H, J=11.7, 3.6 Hz), 4.38 (d, 1H, J=16.5 Hz), 4.51 (m, 2H), 7.52-7.58 (m, 2H), 7.71-7.77 (m, 3H), 8.23 (d, 1H, J=7.5 Hz), 8.54 (d, 1H, J=4.8 Hz); $^{13}$C NMR (D$_2$O) δ 20.70, 24.04, 27.51, 27.62, 29.62, 29.67, 29.85, 44.05, 49.60, 58.74, 59.42, 114.30 (2C), 125.64, 126.63 (2C), 131.62, 139.11, 140.28, 147.65, 151.75, 152.19. ES-MS m/z 376 (M+H). Anal. Calcd. for C$_{23}$H$_{29}$N$_5$.3.0HCl.2.5H$_2$O.0.2Et$_2$O: C, 52.47; H, 7.22; N, 12.86, Cl 19.52. Found: C 52.46, H 6.97, N 12.85, Cl 19.56.

The enantiomeric purity of COMPOUND 55 was determined to be 97% by chiral HPLC using the following conditions: Instrument: Hewlett Packard 1100 HPLC (VWD2); Column: ChiralPak AD, 2.1 cm×100 cm; Mobile Phases: A=90:10 hexanes/isopropanol with 0.1% DEA, B=isopropanol; Isocratic: 70% A, 30% B; Total Run Time: 20 min; Flow Rate: 0.6 mL/min; Temperature: 5° C.; Detector: UV @ 270 nm; Injection volume: 20 μL.

Retention time of the S enantiomer=11.1 min.
Retention time of the R enantiomer=8.8 min.

Example 56

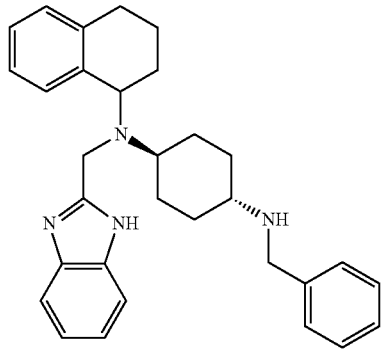 [SMILES: c1ccc(CN[C@H]2CC[C@H](N(Cc3nc4ccccc4[nH]3)C3CCCc4ccccc43)CC2)cc1]

Compound 56: Preparation of N$^1$-(1H-Benzimidazol-2-ylmethyl)-N$^1$-(5,6,7,8-tetrahydro-quinolin-8-yl)-N$^2$-benzyl-cyclohexane-trans-1,4-diamine (hydrobromide salt)

Preparation of N$^1$-(1H-Benzimidazol-2-ylmethyl)-N$^1$-(5,6,7,8-tetrahydro-quinolin-8-yl)-cyclohexane-trans-1,4-diamine

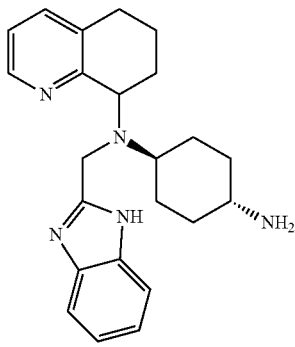 [SMILES: N[C@H]1CC[C@H](N(Cc2nc3ccccc3[nH]2)C2CCCc3cccnc32)CC1]

Preparation of N-tert-butoxycarbonyl-trans-1,4-cyclohexanediamine (Smith, J.; Liras, J. L.; Schneider, S. E.; Anslyn, E. *J. Org. Chem.* 1996, 61, 8811-8818)

To a solution of trans-1,4-cyclohexanediamine (8.01 g, 70.1 mmol) in CHCl$_3$ (230 mL) was added a solution of di-tert-butyl dicarbonate (7.67 g, 35.1 mmol) in CHCl$_3$ (50 mL) via syringe pump over a period of 6 hours. The resultant white suspension was stirred at room temperature for an additional 10 hours then concentrated in vacuo and diluted with CH$_2$Cl$_2$ (100 mL) and saturated aqueous Na$_2$CO$_3$ (100 mL). The layers were separated and the organic layer was washed saturated aqueous Na$_2$CO$_3$ (2×30 mL). The combined organic phases were dried (Na$_2$SO$_4$), filtered and concentrated to give the title compound (5.30 g, 71% based on Boc$_2$O) as a white solid.

Following General Procedure for Reductive Amination B: To a stirred solution of 6,7-dihydro-5H-quinolin-8-one (3.04 g, 20.65 mmol) and N-tert-butoxycarbonyl-trans-1,4-cyclohexanediamine (4.42 g, 20.65 mmol) in dry THF (100 mL) was added AcOH (3 mL) and NaBH(OAc)$_3$ (5.69 g, 26.85 mmol) and the mixture stirred overnight at room temperature. Purification by column chromatography on silica gel (CH$_2$Cl$_2$/MeOH/NH$_4$OH, 96:4:0 then 94:5:1) afforded the desired amine (3.79 g, 53%) as a white solid.

Following the general procedure for N-alkylation: To, a stirred solution of the trans-1,4-diamine from above (3.79 g, 11.0 mmol) in CH$_3$CN (55 mL) was added N,N-diisopropylethyl amine (3.5 mL, 19.7 mmol), KI (91 mg, 0.55 mmol) and 1-(tert-butoxycarbonyl)-2-(chloromethyl)benzimidazole (2.93 g, 11.0 mmol) and the mixture was stirred at 60° C. overnight. Purification of the resultant orange foam by column chromatography on silica gel (CH$_2$Cl$_2$/MeOH/NH$_4$OH, 96:4:0 then 94:5:1) afforded the desired alkylated amine (3.28 g, 52%) as a yellow foam.

The yellow foam from above (3.28 g, 5.70 mmol) oil was dissolved in CH$_2$Cl$_2$/TFA (1:1, 10 mL) and the mixture stirred at room temperature for 2.5 hours. The reaction was then concentrated and diluted with CH$_2$Cl$_2$ (80 mL) and 1 N NaOH (75 mL). The aqueous layer was washed with CH$_2$Cl$_2$ (2×50 mL) and the combined organic extracts were dried (Na$_2$SO$_4$), filtered and concentrated to afford the title compound (1.97 g, 92%) as a yellow foam. $^1$H NMR (CDCl$_3$) δ 0.92-1.10 (m, 2H), 1.21-1.28 (m, 2H), 1.45-1.58 (m, 4H), 1.66-1.77 (m, 2H), 1.82-1.90 (m, 2H), 1.95-2.09 (m, 1H), 2.17-2.35 (m, 1H), 2.39-2.59 (m, 2H), 2.67-2.80 (m, 1H), 2.83-2.96 (m, 1H), 4.10 (dd, 1H, J=9, 6 Hz), 4.19 (s, 2H), 7.14-7.21 (m, 4H), 7.43 (d, 1H, J=6 Hz), 7.55-7.62 (br m, 2H), 8.60 (d, 1H, J=6 Hz); $^{13}$C NMR (CDCl$_3$) δ 21.85, 27.32, 29.31, 29.84, 30.97, 45.61, 50.03, 56.58, 62.37, 110.77, 118.96, 121.36, 122.23, 134.74, 137.52, 146.34, 158.32, 158.60.

To a stirred solution of N$^1$-(1H-Benzimidazol-2-ylmethyl)-N$^1$-(5,6,7,8-tetrahydro-quinolin-8-yl)-cyclohexane-trans-1,4-diamine (140 mg, 0.37 mmol) in dry MeOH (3 mL) was added benzaldehyde (0.038 mL, 0.37 mmol) and the solution stirred at room temperature for 3 h. The mixture was concentrated in vacuo, analyzed by $^1$H NMR and redissolved in MeOH (3 mL) and CH$_2$Cl$_2$ (0.8 mL). To this solution was added sodium borohydride (28 mg, 0.74 mmol) and the mixture stirred for 2 h at room temperature. (see General Procedure B). Purification of the crude material by radial chromatography on silica gel gel (1 mm plate, CH$_2$Cl$_2$/MeOH/NH$_4$OH, gradient elution from 100:1:1 to 20:1:1) afforded the free amine (119 mg, 69%) as a clear oil.

Using General Procedure D: Conversion of the oil from above (119 mg, 0.26 mmol) to the hydrobromide salt followed by re-precipitation of the intermediate solid from methanol/ether gave COMPOUND 56 (149 mg, 79%) as a white solid. $^1$H NMR (D$_2$O) δ 1.44-1.60 (m, 4H), 1.79-1.93 (m, 1H), 2.00-2.11 (m, 1H), 2.14-2.32 (m, 5H), 2.40-2.44 (m, 1H), 2.77-2.85 (m, 1H), 2.98-3.01 (m, 2H), 3.12-3.20 (m, 1H), 4.21 (s, 2H), 4.42 (d, 1H, J=16.8 Hz), 4.52-4.56 (m, 1H), 4.55 (d, 1H, J=16.8 Hz), 7.41-7.47 (m, 5H), 7.59 (dd, 2H, J=6, 3 Hz), 7.76 (dd, 2H, J=6, 3 Hz), 7.79 (dd, 1H, J=8.1, 6.3 Hz), 8.28 (d, 1H, J=7.5 Hz), 8.57 (d, 1H, J=5.5 Hz); $^{13}$C NMR (D$_2$O) δ 20.72, 24.03, 27.54, 27.61, 28.08, 28.35, 29.71, 44.01, 48.93, 56.04, 58.79, 59.32, 114.24, 125.80, 126.95, 129.72, 130.04, 131.06, 131.31, 139.10, 140.46, 147.95, 151.56, 152.03. ES-MS m/z 466 (M+H). Anal. Calcd. for C$_{30}$H$_{35}$N$_5$.3.0HBr.2.0H$_2$O: C, 48.41; H, 5.69; N, 9.41; Br, 32.20. Found: C, 48.65; H, 5.92; N, 9.32; Br, 31.97.

Example 57

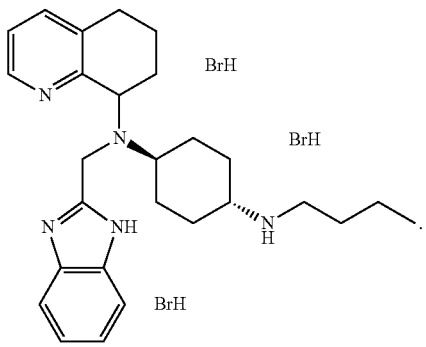 [SMILES: CCCCN[C@H]1CC[C@H](N(Cc2nc3ccccc3[nH]2)C2CCCc3cccnc32)CC1 ; Br ; Br ; Br]

Compound 57: Preparation of N$^1$-(1H-Benzimidazol-2-ylmethyl)-N$^4$-butyl-N$^1$-(5,6,7,8-tetrahydroquinolin-8-yl)-cyclohexane-trans-1,4-diamine (hydrobromide salt)

Preparation of N-tert-butoxycarbonyl-trans-1,4-cyclohexanediamine$^{ref}$ $^{ref}$ Smith, J.; Liras, J. L.; Schneider, S. E.; Anslyn, E. Solid and Solution Phase Organic Syntheses of Oligomeric Thioureas *J. Org. Chem.* 1996, 61, 8811-8818.

To a solution of trans-1,4-cyclohexanediamine (8.01 g, 70.1 mmol) in CHCl$_3$ (230 mL) was added a solution of di-tert-butyl dicarbonate (7.67 g, 35.1 mmol) in CHCl$_3$ (50 mL) via syringe pump over a period of 6 hours. The resultant white suspension was stirred at room temperature for an additional 10 hours then concentrated under reduced pressure and diluted with CH$_2$Cl$_2$ (100 mL) and saturated aqueous Na$_2$CO$_3$ (100 mL). The layers were separated and the organic layer was washed with saturated aqueous Na$_2$CO$_3$ (2×30 mL). The combined organic phases were dried (Na$_2$SO$_4$), filtered, and concentrated to give the desired compound (5.30 g, 71% based on Boc$_2$O) as a white solid.

Preparation of N$^1$-(1H-Benzimidazol-2-ylmethyl)-N$^1$-(5,6,7,8-tetrahydro-quinolin-8-yl)-cyclohexanetrans-1,4-diamine Following General Procedure B: To a stirred solution of 6,7-dihydro-5H-quinolin-8-one (3.04 g, 20.65 mmol) and N-tert-butoxycarbonyl-trans-1,4-cyclohexanediamine (4.42 g, 20.65 mmol) in dry THF (100 mL) was added AcOH (3 mL) and NaBH(OAc)$_3$ (5.69 g, 26.85 mmol) and the mixture stirred overnight at room temperature. The reaction mixture was concentrated under reduced pressure, diluted with CH$_2$Cl$_2$ (100 mL) and saturated aqueous sodium bicarbonate (100 mL), and the aqueous phase was extracted with CH$_2$Cl$_2$ (3×75 mL). The combined organic extracts were dried (Na$_2$SO$_4$), filtered, and concentrated. Purification by column chromatography on silica gel (CH$_2$Cl$_2$/MeOH/NH$_4$OH, 96:4:0 then 94:5:1) afforded the desired amine (3.79 g, 53%) as a white solid.

Following the general procedure for N-alkylation: To a stirred solution of [4-(5,6,7,8-Tetrahydro-quinolin-8-ylamino)-trans-cyclohexyl]-carbamic acid tert-butyl ester from above (3.79 g, 11.0 mmol) in CH$_3$CN (55 mL) was added N,N-diisopropylethylamine (3.5 mL, 19.7 mmol), KI (91 mg, 0.55 mmol) and 1-(tert-butoxycarbonyl)-2-(chloromethyl)benzimidazole (2.93 g, 11.0 mmol). The mixture was stirred at 60° C. Overnight, cooled, concentrated, diluted with CH$_2$Cl$_2$ (100 mL) and saturated aqueous sodium bicarbonate (75 mL). The aqueous phase was washed with CH$_2$Cl$_2$ (2×50 mL), dried (Na$_2$SO$_4$), filtered, and concentrated under reduced pressure. Purification of the resultant orange foam by column chromatography on silica gel (CH$_2$Cl$_{21}$MeOH/NH$_4$OH, 96:4:0 then 94:5:1) afforded the desired alkylated amine (3.28 g, 52%) as a yellow foam.

The yellow foam from above (3.28 g, 5.70 mmol) was dissolved in CH$_2$Cl$_2$/TFA (1:1, 10 mL) and the mixture stirred at room temperature for 2.5 hours. The reaction was then concentrated and diluted with CH$_2$Cl$_2$ (80 mL) and 1 N NaOH (75 mL). The aqueous layer was washed with CH$_2$Cl$_2$ (2×50 mL) and the combined organic extracts were dried (Na$_2$SO$_4$), filtered, and concentrated to afford N$^1$-(1H-Benzimidazol-2-ylmethyl)-N$^1$-(5,6,7,8-tetrahydro-quinolin-8-yl)-cyclohexane-trans-1,4-diamine (1.97 g, 92%) as a yellow foam. $^1$H NMR (CDCl$_3$) δ 0.92-1.10 (m, 2H), 1.21-1.28 (m, 2H), 1.45-1.58 (m, 4H), 1.66-1.77 (m, 2H), 1.82-1.90 (m, 2H), 1.95-2.09 (m, 1H), 2.17-2.35 (m, 1H), 2.39-2.59 (m, 2H), 2.67-2.80 (m, 1H), 2.83-2.96 (m, 1H), 4.10 (dd, 1H, J=9, 6 Hz), 4.19 (s, 2H), 7.14-7.21 (m, 4H), 7.43 (d, 1H, J=6 Hz), 7.55-7.62 (br m, 2H), 8.60 (d, 1H, J=6 Hz); $^{13}$C NMR (CDCl$_3$) δ 21.85, 27.32, 29.31, 29.84, 30.97, 45.61, 50.03, 56.58, 62.37, 110.77, 118.96, 121.36, 122.23, 134.74, 137.52, 146.34, 158.32, 158.60.

To a stirred solution of N$^1$-(1H-Benzimidazol-2-ylmethyl)-N$^1$-(5,6,7,8-tetrahydro-quinolin-8-yl)-cyclohexane-trans-1,4-diamine (0.0753 g, 0.20 mmol) in anhydrous MeOH (2 mL) was added freshly distilled butyraldehyde (22 μL, 0.24 mmol). The resultant mixture was stirred at room temperature for 0.5 h and concentrated under reduced pressure. The residue was redissolved in anhydrous MeOH (2 mL) and NaBH$_4$ (15 mg, 0.40 mmol) was added. The resultant mixture was stirred at room temperature for 22 hours. The mixture was concentrated and the residue was partitioned between CH$_2$Cl$_2$ (20 mL) and saturated sodium bicarbonate (30 mL). The phases were separated and the aqueous phase was extracted with CH$_2$Cl$_2$ (2×15 mL). The combined organic extracts were dried (Na$_2$SO$_4$), filtered, and concentrated under reduced pressure. Purification of the crude material by radial chromatography on silica gel (TLC grade 1 mm plate, 100:1:1 CH$_2$Cl$_2$/CH$_3$OH/NH$_4$OH followed by 50:1:1 CH$_2$Cl$_2$/CH$_3$OH/NH$_4$OH) provided 23 mg (30%) of the free base of the title compound as a pale yellow oil. Using General Procedure D: Conversion of the foam from above (23 mg, 0.05 mmol) to the hydrobromide salt followed by re-precipitation of the intermediate solid from methanol/ ether gave COMPOUND 57 (73 mg, quantitative) as a white solid. $^1$H NMR (D$_2$O) δ 0.88 (t, 3H, J=7.5 Hz), 1.26-1.47 (m, 4H), 1.48-1.65 (m, 4H), 1.79-1.92 (m, 1H), 1.93-2.34 (br m, 7H), 2.35-2.47 (m, 1H), 2.75-2.88 (m, 1H), 2.95-3.14 (m, 5H), 4.42 (d, 1H, J=16.8 Hz), 4.49-4.55 (m, 1H), 4.56 (d, 1H, J=16.5 Hz), 7.54-7.63 (m, 2H), 7.72-7.84 (m, 3H), 8.28 (d, 1H, J=7.5 Hz), 8.56 (d, 1H, J=5.4 Hz); $^{13}$C NMR (D$_2$O) δ 13.17, 19.61, 20.71, 24.03, 27.53, 27.59, 28.09, 28.20, 28.34, 29.69, 44.00, 45.15, 56.08, 58.78, 59.39, 114.24, 125.79, 126.96, 131.06, 139.10, 140.46, 147.942, 151.58, 152.05. ES-MS m/z 432 (M+H). Anal. Calcd. for C$_{27}$H$_{37}$N$_5$.3.0HBr.2.1H$_2$O: C, 45.54; H, 6.26; N, 9.83; Br, 33.66. Found: C, 45.62; H, 6.07; N, 9.66; Br, 33.51.

Example 58

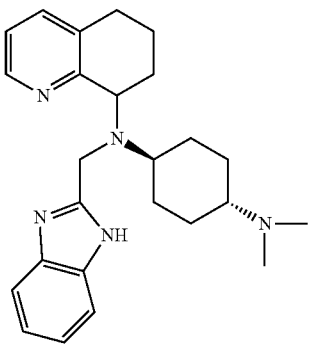 [SMILES: CN(C)[C@H]1CC[C@H](N(Cc2nc3ccccc3[nH]2)C2CCCc3cccnc32)CC1]

Compound 58: Preparation of N$^1$-(1H-Benzimida-zol-2-ylmethyl)-N$^1$-(5,6,7,8-tetrahydro-quinolin-8-yl)-N$^2$,N$^2$-dimethyl-cyclohexane-trans-1,4-diamine (hydrobromide salt)

To a stirred solution of N$^1$-(1H-Benzimidazol-2-ylmethyl)-N$^1$-(5,6,7,8-tetrahydro-quinolin-8-yl)-cyclohexane-trans-1,4-diamine (157 mg, 0.42 mmol) in dry MeOH (3 mL) was added paraformaldehyde (powder) (17 mg, 0.57 mmol) and the solution stirred at room temperature for 3 h. The mixture was concentrated in vacuo, analyzed by $^1$H NMR and redissolved in MeOH (2.5 mL) and CH$_2$Cl$_2$ (1 mL). To this solution was added sodium borohydride (32 mg, 0.83 mmol) and the mixture stirred for 1.5 h at room temperature (see General Procedure A and B). Purification of the crude material by radial chromatography on silica gel gel (1 mm plate, CH$_2$Cl$_2$/MeOH/NH$_4$OH, gradient elution from 50:1:1 to 10:1:1) afforded the dimethylated and monomethylated free amines (138 mg) as an inseparable yellow foam mixture. Repurification and separation of the two amines by column chromatography on basic alumina (CH$_2$Cl$_2$/MeOH, 98:2 then 95:5) afforded the dimethylated product (44 mg, 26%) and the monomethylated free amine (21 mg, 13%), both as clear oils.

Using General Procedure D: Conversion of the dimethylated amine from above (44 mg, 0.11 mmol) to the hydrobromide salt followed by re-precipitation of the intermediate solid from methanol/ether gave COMPOUND 58 (72 mg, 97%) as a white solid. $^1$H NMR (D$_2$O) δ 1.46-1.65 (m, 4H), 1.79-1.93 (m, 1H), 2.05-2.21 (m, 5H), 2.31-2.53 (m, 2H), 2.75-2.82 (m, 1H), 2.77 (s, 6H), 2.99-3.01 (m, 2H), 3.15-3.22 (m, 1H), 4.43 (d, 1H, J=16.8 Hz), 4.50-4.55 (m, 1H), 4.56 (d, 1H, J=16.8 Hz), 7.58 (dd, 2H, J=6, 3 Hz), 7.76 (dd, 2H, J=6, 3 Hz), 7.80 (dd, 1H, J=7.8, 6 Hz), 8.28 (d, 1H, J=7.8 Hz), 8.57 (d, 1H, J=5.1 Hz); $^{13}$C NMR (D$_2$O) δ 20.71, 23.97, 25.62, 25.82, 27.55, 27.76, 29.81, 40.05, 44.03, 58.87, 59.26, 64.33, 114.24, 125.82, 127.01, 130.98, 139.12, 140.48, 148.00, 151.53, 151.97. ES-MS m/z 404 (M+H). Anal. Calcd. for C$_{25}$H$_{33}$N$_5$.3.0HBr.2.0H$_2$O: C, 44.01; H, 5.91; N, 10.26; Br, 35.13. Found: C, 44.14; H, 6.02; N, 10.01; Br, 34.98.

Example 59

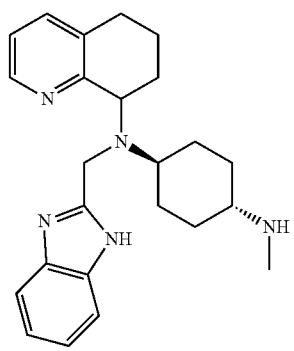 [SMILES: CN[C@H]1CC[C@H](N(Cc2nc3ccccc3[nH]2)C2CCCc3cccnc32)CC1]

Compound 59: Preparation of N$^1$-(1H-Benzimidazol-2-ylmethyl)-N$^1$-(5,6,7,8-tetrahydro-quinolin-8-yl)-N$^2$-methyl-cyclohexane-trans-1,4-diamine (hydrobromide salt)

Using General Procedure D: Conversion of the monomethylated amine from above (see COMPOUND 58) (21 mg, 0.054 mmol) to the hydrobromide salt followed by re-precipitation of the intermediate solid from methanol/ether gave COMPOUND 59 (25 mg, 71%) as a white solid. $^1$H NMR (D$_2$O) δ 1.31-1.43 (m, 2H), 1.51-1.63 (m, 2H), 1.78-1.93 (m, 1H), 1.99-2.31 (m, 6H), 2.40-2.44 (m, 1H), 2.63 (s, 3H), 2.75-2.87 (m, 1H), 2.98-3.01 (m, 3H), 4.42 (d, 1H, J=16.8 Hz), 4.51-4.55 (m, 1H), 4.55 (d, 1H, J=16.8 Hz), 7.59 (dd, 2H, J=6, 3 Hz), 7.75 (dd, 2H, J=6, 3 Hz), 7.79 (dd, 1H, J=7.8, 6 Hz), 8.28 (d, 1H, J=8.1 Hz), 8.56 (d, 1H, J=5.4 Hz); $^{13}$C NMR (D$_2$O) δ 20.71, 24.01, 27.54, 27.85, 28.09, 29.63, 30.36, 44.00, 57.11, 58.81, 59.40, 114.24, 125.78, 126.94, 131.09, 139.10, 140.45, 147.93, 151.59, 152.05. ES-MS m/z 390 (M+H). Anal. Calcd. for C$_{24}$H$_{31}$N$_5$.2.9HBr.3.0H$_2$O: C, 42.50; H, 5.93; N, 10.33; Br, 34.17. Found: C, 42.48; H, 5.65; N, 10.12; Br, 34.31.

Example 60

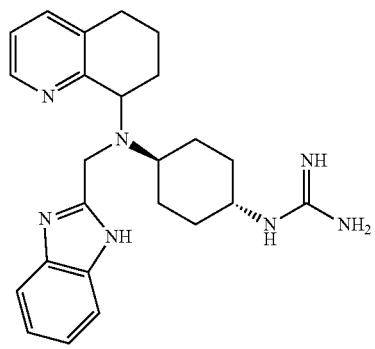 [SMILES: N=C(N)N[C@H]1CC[C@H](N(Cc2nc3ccccc3[nH]2)C2CCCc3cccnc32)CC1]

Compound 60: Preparation of N-{4-trans-[(1H-Benzimidazol-2-ylmethyl)-(5,6,7,8-tetrahydro-uinolin-8-yl)-amino]-cyclohexyl}-guanidine (hydrobromide salt)

To a solution of $N^1$-(1H-benzimidazol-2-ylmethyl)-$N^1$-(5,6,7,8-tetrahydro-quinolin-8-yl)-$N^2$-benzyl-cyclohexane-trans-1,4-diamine (174 mg, 0.46 mmol) in dry THF (1.5 mL) was added N. N'-bis-(tert-butoxycarbonyl)-1H-pyrazole-1-carboxamidine (*Tetrahedron Lett.* 1993, 34, 3389) and the resultant mixture was stirred at room temperature for 26 hours. The reaction was concentrated and purified by radial chromatography on silica gel (2 mm plate, $CH_2Cl_2$/MeOH/$NH_4OH$, gradient elution from 50:1:1 to 5:1:1) to afford the desired guanidine (51 mg, 18%) as a clear oil.

Using General Procedure D: Conversion of the oil from above (51 mg, 0.083 mmol) to the hydrobromide salt followed by re-precipitation of the intermediate solid from methanol/ether gave COMPOUND 60 (50 mg, 85%) as a white solid. $^1$H NMR ($D_2O$) δ 1.22-1.34 (m, 2H), 1.49-1.60 (m, 2H), 1.79-2.21 (m, 8H), 2.40-2.44 (m, 1H), 2.70-2.78 (m, 1H), 2.98-3.01 (m, 2H), 3.24-3.32 (m, 1H), 4.42 (d, 1H, J=16.8 Hz), 4.50-4.55 (m, 1H), 4.56 (d, 1H, J=16.8 Hz), 7.59 (dd, 2H, J=6, 3 Hz), 7.76 (dd, 2H, J=6, 3 Hz), 7.80 (dd, 1H, J=7.8, 6 Hz), 8.28 (d, 1H, J=7.8 Hz), 8.57 (d, 1H, J=5.4 Hz); $^{13}$C NMR ($D_2O$) δ 20.75, 24.04, 27.55, 28.14, 30.36, 31.23, 31.51, 44.11, 50.20, 58.86, 59.67, 114.23, 125.78, 126.98, 130.97, 139.05, 140.45, 147.94, 151.73, 152.23, 156.22. ES-MS m/z 418 (M+H). Anal. Calcd. for $C_{24}H_{31}N_7 \cdot 3.0HBr \cdot 2.0H_2O \cdot 0.2C_4H_{10}O$: C, 41.78; H, 5.68; N, 13.75; Br, 33.62. Found: C, 41.74; H, 5.63; N, 13.62; Br, 33.65.

Example 61

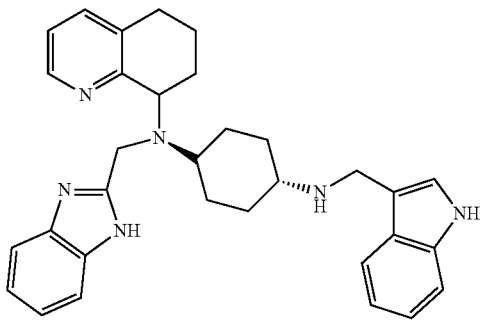

Compound 61: Preparation of $N^1$-(1H-Benzimidazol-2-ylmethyl)-$N^4$-(TH-indol-3-ylmethyl)-$N^1$-(5,6,7,8-tetrahydro-quinolin-8-yl)-cyclohexane-trans-1,4-diamine (free base)

General procedure B (Two step reductive amination): To a solution of $N^1$-(1H-Benzimidazol-2-ylmethyl)-$N^1$-(5,6,7,8-tetrahydro-quinolin-8-yl)-cyclohexane-trans-1,4-diamine (104 mg, 0.28 mmol) in $CH_3OH$ (5 mL) was added indole-3-carboxaldehyde (52 mg, 0.36 mmol) and the resultant solution was stirred at room temperature overnight. $NaBH_4$ (26 mg, 0.68 mg) was added and the mixture was stirred for an additional 15 minutes. The mixture was concentrated under reduced pressure and the residue was partitioned between $CH_2Cl_2$ (20 mL) and saturated aqueous $NaHCO_3$ (5 mL). The phases were separated and the aqueous phase was extracted with $CH_2Cl_2$ (3×5 mL). The combined organic extracts were dried ($Na_2SO_4$) and concentrated. Purification of the crude material by radial chromatography on silica gel (1 mm plate, 50:1:1 $CH_2Cl_2$—$CH_3OH$—$NH_4OH$) provided 105 mg of COMPOUND 61 as a white foam. $^1$H NMR (CDCl$_3$) δ 0.93-1.30 (m, 3H), 1.47-2.02 (m, 9H), 2.20-2.25 (m, 1H), 2.50-2.51 (m, 2H), 2.65-2.76 (m, 1H), 2.83-2.94 (m, 1H), 3.93 (s, 2H), 4.10 (dd, 1H, J=5.7, 10.2 Hz), 4.20 (s, 2H), 7.07-7.12 (m, 2H), 7.15-7.21 (m, 4H), 7.34 (d, 1H, J=7.8 Hz), 7.42-7.49 (m, 2H), 7.59 (d, 1H, J=7.8 Hz), 7.66-7.69 (m, 1H), 8.23 (br s, 1H), 8.34 (br s, 1H), 8.60 (d, 1H, J=3.6 Hz); $^{13}$C NMR (CDCl$_3$) δ 22.22, 27.63, 29.71, 30.34, 31.43, 33.00, 33.14, 42.46, 46.01, 56.15, 57.61, 62.78, 111.30, 111.65, 115.35, 119.00 (2 carbons), 119.78, 121.59, 121.88, 122.40, 122.60, 122.78, 127.31, 134.03, 135.12, 136.78, 137.87, 145.03, 146.74, 158.77, 159.11. ES-MS m/z 505 (M+H). Anal. Calcd. for $C_{32}H_{36}N_6 \cdot 0.5H_2O \cdot 0.5CH_2Cl_2$: C, 70.19; H, 6.89; N, 15.11. Found: C, 69.94; H, 6.81; N, 15.15.

Example 62

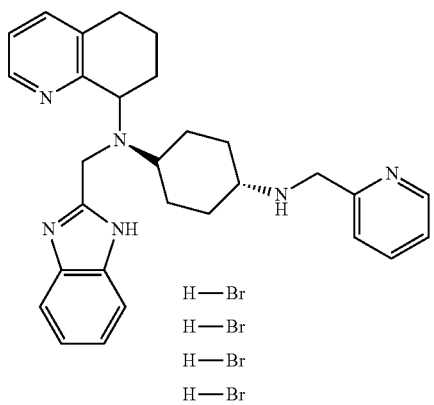

Compound 62: Preparation of $N^1$-(1H-Benzimidazol-2-ylmethyl)-$N^4$-(pyridin-2-ylmethyl)-$N^1$-(5,6,7,8-tetrahydro-quinolin-8-yl)-cyclohexane-trans-1,4-diamine (hydrobromide salt)

Using General Procedure B (Two step reductive amination): Reaction of $N^1$-(1H-Benzimidazol-2-ylmethyl)-$N^1$-(5,6,7,8-tetrahydro-quinolin-8-yl)-cyclohexane-trans-1,4-diamine (98 mg, 0.26 mmol) with pyridine-2-carboxaldehyde (30 µL, 0.32 mmol) in $CH_3OH$ (5 mL) for 2.5 hours and with $NaBH_4$ (27 mg, 0.71 mmol) for 15 minutes followed by purification of the crude material by radial chromatography on silica gel (1 mm plate, 50:1:1 $CH_2Cl_2$—$CH_3OH$—$NH_4OH$) provided 79 mg (65%) of the free base of the title compound as a colorless oil.

Using General Procedure D: Conversion of the oil from above (79 mg, 0.17 mmol) to the hydrobromide salt followed by re-precipitation of the intermediate solid from methanol/ether gave COMPOUND 62 (126 mg, 85%) as a white solid. $^1$H NMR ($D_2O$) δ 1.45-1.63 (m, 4H), 1.79-1.93 (m, 1H), 2.02-2.45 (m, 7H), 2.79-2.86 (m, 1H), 2.99-3.01 (m, 2H), 3.25-3.33 (m, 1H), 4.41-4.60 (m, 5H), 7.56-7.61 (m, 2H), 7.75-7.82 (m, 5H), 8.22-8.30 (m, 2H), 8.57 (d, 1H, J=5.1 Hz), 8.69 (d, 1H, J=4.5 Hz); $^{13}$C NMR ($D_2O$) δ 20.71, 24.03, 27.55 (2 carbons), 28.06, 28.31, 29.67, 43.99, 47.18, 57.04, 58.78, 59.21, 114.22, 125.83, 126.41, 126.60, 127.03, 130.91, 139.10, 140.51, 143.47, 146.81, 148.02, 148.03, 151.48, 151.97. ES-MS m/z 467 (M+H). Anal. Calcd. for $C_{29}H_{34}N_6\cdot 4.2HBr\cdot 3.7H_2O$: C, 39.89; H, 5.26; N, 9.63; Br, 38.44. Found: C, 39.95; H, 5.19; N, 9.61; Br, 38.45.

Example 63

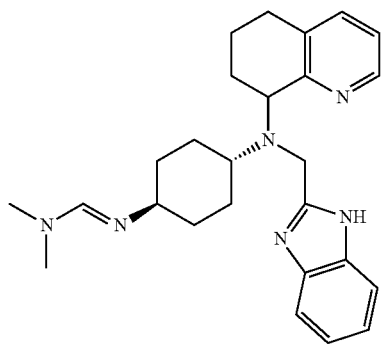 [SMILES: CN(C)/C=N/[C@H]1CC[C@H](N(Cc2nc3ccccc3[nH]2)C2CCCc3cccnc32)CC1]

Compound 63: Preparation of 1-N'-[trans-4-(1H-Benzimidazol-2-ylmethyl)-(5,6,7,8-tetrahydroquinolin-8-yl)-amino]-cyclohexanyl-N,N-dimethylformamidine (hydrobromide salt)

Using the procedure of L. Cai (Y. Han and L. Cai *Tetrahedron Lett.* 1997, 38(31), 5423-5426) a solution of 2-pyridinesulfonyl chloride (71 mg, 0.40 mmol) in DMF (1 mL) was stirred for 10 minutes at room temperature. N'-(1H-Benzimidazol-2-ylmethyl)-N'-(5,6,7,8-tetrahydro-quinolin-8-yl)-cyclohexane-trans-1,4-diamine (100 mg, 0.267 mmol) was then added, and the mixture was stirred at room temperature for 2 hours. The DMF was then removed in vacuo, and the residue was taken up in dichloromethane and washed sequentially with a saturated aqueous sodium carbonate solution, followed by distilled water. The organic fraction was then dried over anhydrous sodium sulfate and concentrated. The residue was purified by silica gel flash chromatography to afford two products: 1-N'-[trans-4-(1H-Benzimidazol-2-ylmethyl)-(5,6,7,8-tetrahydroquinolin-8-yl)-amino]-cyclohexanyl-N,N-dimethylformamidine (52 mg (45%)), and N'-(1H-benzimidazol-2-ylmethyl)-N'-(5,6,7,8-tetrahydro-quinolin-8-yl)-cyclohexane-trans-1,4-diamine-N-(2-pyridinyl)-sulfonamide (41 mg, 29%). The spectral data for the formamidine is as follows: $^1$H NMR (CDCl$_3$) δ 1.41 (m, 2H), 1.56 (m, 2H), 1.67 (m, 2H), 1.79-1.91 (m, 3H), 2.21 (m, 1H), 2.51 (m, 1H), 2.74-2.81 (m, 3H), 2.83 (s, 6H), 4.06 (dd, 1H, J=8.1, 5.4 Hz), 4.17 (s, 2H), 7.16 (m, 5H), 7.41 (d, 1H, J=8.1 Hz), 7.44 (br s, 1H(NH)), 7.68 (br s, 1H), 8.58 (d, 1H, J=4.8 Hz). The sulfonamide showed an excessive broadening of resonances in the $^1$H NMR spectrum (in CDCl$_3$), so it was not characterized fully at this stage, and was instead taken directly to the salting reaction.

1-N'-[trans-4-(1H-Benzimidazol-2-ylmethyl)-(5,6,7,8-tetrahydroquinolin-8-yl)-amino]-cyclohexanyl-N,N-dimethylformamidine (52 mg, 0.120 mmol) was taken up in acetic acid (1 mL), to which a saturated solution of HBr in acetic acid (1 mL) was added. The mixture was then stirred, precipitated and isolated as per procedure D to yield COMPOUND 63 as a white crystalline (36 mg). $^1$H NMR (D$_2$O). δ 1.45 (m, 4H), 1.82-2.20 (m, 7H), 2.42 (m, 1H), 3.74 (dd, 1H, J=10.5, 11.1 Hz), 2.94 (s, 3H), 2.99 (m, 2H), 3.16 (s, 3H), 3.33 (m, 1H), 4.41 (d, 1H, J=15.3 Hz), 4.52 (d, 1H, J=15.3 Hz), 4.54 (m, 1H), 7.58 (m, 2H), 7.75 (m, 2H), 7.77 (s, 1H), 7.80 (dd, 1H, J=8.1, 5.7 Hz), 8.28 (d, 1H, J=8.1 Hz), 8.56 (d, 1H, J=5.7 Hz). $^{13}$C NMR (D$_2$O) δ 20.73, 24.04, 27.54, 28.10, 30.34, 32.07, 32.32, 36.05, 43.21, 44.11, 56.62, 58.79, 59.36, 114.21, 125.78, 126.99, 130.92, 139.03, 140.45, 147.99, 151.68, 152.19, 155.22. ES-MS m/z 431 (M+H); Anal. Calcd. for $(C_{26}H_{34}N_6\times 2.9HBr\times 2.7\ H_2O)$: C, 43.74; H, 5.97; N, 11.77; Br 32.46. Found: C, 43.81; H, 5.70; N, 11.44; Br, 32.39.

Example 64

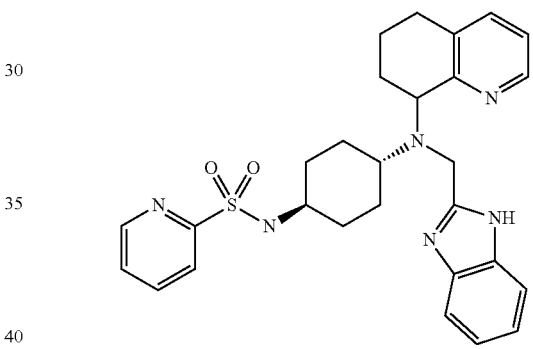

Compound 64: Preparation of N'-(1H-benzimidazol-2-ylmethyl)-N'-4,5,6,7,8-tetrahydro-quinolin-8-yl)-cyclohexane-trans-1,4-diamine-N-(2-pyridinyl)-sulfonamide N'-(1H-benzimidazol-2-ylmethyl)-N'-(5,6,7,8-tetrahydroquinolin-8-yl)-cyclohexane-trans-1,4-diamine-N-(2-pyridinyl)-sulfonamide (from the above reaction, 41 mg, 0.079 mmol) was taken up in acetic acid (1 mL), to which a saturated solution of HBr in acetic acid (1 mL) was added. The mixture was then stirred, precipitated and isolated as per procedure D to yield COMPOUND 64 as a white crystalline solid (52 mg). $^1$H NMR (D$_2$O) δ 1.20-2.16 (series of m, 9H), 2.38 (m, 1H), 2.60 (m, 1H), 2.82 (m, 1H), 2.98 (m, 2H), 3.10 (m, 1H), 3.62 (m, 1H), 4.46 (d, 1H, J=15.3 Hz), 4.49 (m, 1H), 4.51 (d, 1H, J=15.3 Hz), 7.56 (m, 2H), 7.73 (m, 3H), 7.94 (m, 1H), 8.06 (m, 1H), 8.26 (m, 1H), 8.56 (m, 2H). $^{13}$C NMR (D$_2$O) δ 20.70, 27.51, 28.25, 30.44, 32.47, 44.04, 49.31, 52.58, 58.81, 59.48, 114.18, 122.92, 125.74, 126.97, 128.47, 130.87, 138.98, 140.25, 140.38, 147.90, 150.28, 151.72, 152.19. ES-MS m/z 517 (M+H); Anal. Calcd. for $(C_{28}H_{32}N_6O_2S\times 2.6\ HBr\times 3.3H_2O)$: C, 42.76; H, 5.28; N, 10.69; Br 26.42. Found: C, 42.86; H, 5.07; N, 10.32; Br, 26.77.

Example 65

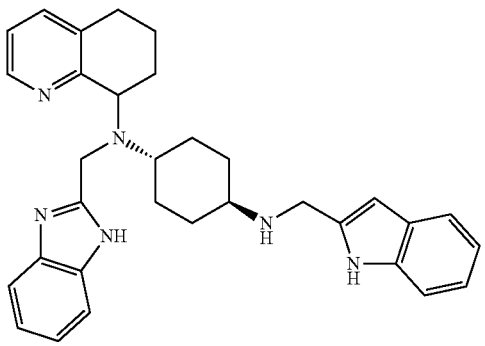 [SMILES: c1cnc2c(c1)CCCC2N(Cc1nc2ccccc2[nH]1)[C@H]1CC[C@H](NCc2cc3ccccc3[nH]2)CC1]

Compound 65: Preparation of $N^1$-(1H-benzimidazol-2-ylmethyl)-$N^4$-(1H-indol-2-ylmethyl)-$N^1$-(5,6,7,8-tetrahydroquinolin-8-yl)-cylcohexane-1,4-diamine Preparation of 2-hydroxymethylindole To a solution of indole-2-carboxylic acid (485 mg, 3.01 mmol) in THF (20 mL), cooled to 0° C. under nitrogen, was added a suspension of LiAlH4 (248 mg, 6.2 mmol) in THF (6 mL). The resultant green suspension was stirred at room temperature for 4 hours. The reaction was quenched by slow addition of an 80% aqueous MeOH solution (1.0 mL) and the solvent was evaporated under reduced pressure. The residue was suspended in MeOH and filtered through Celite, rinsing with MeOH. Concentration of the filtrate under reduced pressure gave a yellow oil. Purification by flash column chromatography on silica (MeOH/$CH_2Cl_2$, 19:1 then 9:1) gave the alcohol as a beige solid (357 mg, 2.43 mmol, 81%). $^1$H NMR ($CDCl_3$) δ 1.85 (t, 1H, J=6.0 Hz), 4.83 (d, 2H, J=6.0 Hz), 6.42 (d, 1H, J=1.5 Hz), 7.11 (td, 1H, J=6.9, 1.5 Hz), 7.20 (td, 1H, J=6.9, 1.5 Hz), 7.35 (dd, 1H, J=6.9, 1.5 Hz), 7.59 (d, 1H, J=6.9 Hz), 8.33 (br s., 1H).

Preparation of indole-2-carboxaldehyde

To a solution of the alcohol (341 mg, 2.32 mmol) in $CH_2Cl_2$ (12 mL) was added activated $MnO_2$ (2.40 g, 22.1 mmol). The suspension was stirred at room temperature for 2.5 hours, then was diluted with $CH_2Cl_2$ and suction filtered through Celite. The filtrate was concentrated under reduced pressure affording the crude aldehyde as an orange solid (288 mg, 1.98 mmol, 86%). $^1$H NMR ($CDCl_3$) δ 7.18 (td, 1H, J=6.9, 1.5 Hz), 7.29 (d, 1H, J=1.5 Hz), 7.37-7.50 (m, 2H), 7.76 (d, 1H, J=6.9 Hz), 9.18 (br s., 1H), 9.86 (s, 1H).

Preparation of Compound 65

A solution of the aldehyde (74 mg, 0.51 mmol) and $N^1$-(1H-benzimidazol-2-ylmethyl)-$N^1$-(5,6,7,8-tetrahydroquinolin-8-yl)-cyclohexane-1,4-diamine (189 mg, 0.50 mmol) in MeOH (5 mL) was stirred at room temperature under nitrogen for 20 hours. $NaBH_4$ (39 mg, 1.0 mmol) was added and the reaction was stirred for another 20 minutes. The solvent was evaporated under reduced pressure, and the residue was dissolved into $CH_2Cl_2$ (50 mL) washing with saturated aqueous $NaHCO_3$ (5 mL) and brine (5 mL). The organic solution was dried ($MgSO_4$), filtered and concentrated under reduced pressure. Purification by flash column chromatography on silica ($CH_2Cl_2$/MeOH/$NH_4OH$, 19:1:0.1) gave COMPOUND 65 as a light yellow solid (118 mg, 0.23 mmol, 47%). $^1$H NMR ($CDCl_3$) δ 0.88-1.13 (m, 2H), 1.16-1.29 (m, 1H), 1.39-1.52 (m, 1H), 1.63-1.73 (m, 1H), 1.80-2.04 (m, 6H), 2.19-2.23 (m, 1H), 2.33-2.41 (m, 1H), 2.44-2.52 (m, 1H), 2.67-2.74 (m, 1H), 2.81-2.94 (m, 1H), 3.91 (s, 2H), 4.09 (dd, 1H, J=9.9, 5.9 Hz), 4.18 (s, 2H), 6.27 (s, 1H), 7.02-7.21 (m, 5H), 7.28 (d, 1H, J=10.2 Hz), 7.43 (d, 1H, J=7.8 Hz), 7.45-7.48 (m, 1H), 7.52 (d, 1H, J=7.8 Hz), 7.66-7.69 (m, 1H), 8.60 (d, 1H, J=4.2 Hz), 8.69 (br s., 1H). $^{13}$C NMR ($CDCl_3$) δ 21.8, 27.3, 29.3, 29.9, 31.0, 32.7, 32.9, 44.4, 45.7, 56.1, 57.2, 62.1, 99.6, 110.6, 110.9, 118.6, 119.5, 120.0, 121.2, 121.3, 121.5, 122.2, 128.5, 133.6, 134.7, 135.8, 137.4, 138.3, 144.6, 146.4, 158.4, 158.5. ES-MS m/z 505 (M+H). Anal. Calcd. for $C_{32}H_{36}N_6 \cdot CH_2Cl_2 \cdot 0.1H_2O$: C, 67.07; H, 6.51; N, 14.22. Found: C, 67.34; H, 6.55; N, 14.23.

Example 66

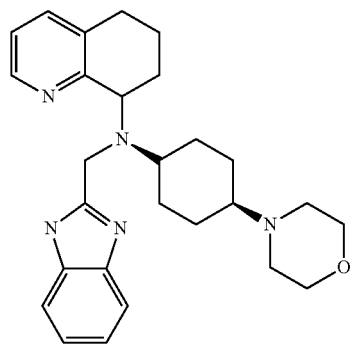

Compound 66: Preparation of cis-(1H-benzimidazol-2-ylmethyl)-(4-morpholin-4-yl-cyclohexyl)-(5,6,7,8-tetrahydro-quinolin-8-yl)-amine Cis-(4-morpholin-4-yl-cyclohexyl)-(5,6,7,8-tetrahydroquinolin-8-yl)-amine was prepared as described for COMPOUND 67. $^1$H NMR ($CDCl_3$) δ 1.61-1.75 (m, 12H), 1.85-1.92 (m, 1H), 2.01-2.18 (m, 1H), 2.54 (t, 4H, J=4.5 Hz), 2.76-2.81 (m, 2H), 2.92 (br m, 1H), 3.74 (t, 4H, J=4.5 Hz), 3.87-3.93 (m, 1H), 7.03-7.07 (m, 1H), 7.36 (d, 1H, J=9.0 Hz), 8.39 (d, 1H, J=6.0 Hz).

The above amine (69.0 mg, 0.22 mmol), 2-chloromethyl-benzimidazole-1-carboxylic acid tert-butyl ester (70.0 mg, 0.26 mmol), N,N-diisopropylethylamine (50 μL, 0.28 mmol), and potassium iodide (3.7 mg, 0.02 mmol) in $CH_3CN$ (1.5 mL) were stirred at 60° C. overnight. The reaction mixture was cooled to room temperature and the solvent was removed under reduced pressure. Purification of the crude material by radial chromatography on silica gel (1 mm plate, $NH_4OH$/MeOH/$CH_2Cl_2$, 1:1:98 then 1:2:97) afforded the desired compound (56.8 mg, 47%) as a pale yellow solid. $^1$H NMR ($CDCl_3$) δ 1.30-1.34 (m, 2H), 1.45-1.66 (m, 11H), 1.88-2.01 (m, 4H), 2.05-2.16 (m, 4H), 2.40 (br m, 4H), 2.54 (t, 1H, J=4.4 Hz), 2.59 (t, 1H, J=3.9 Hz), 2.68-2.73 (m, 1H), 3.04-3.11 (m, 1H), 3.61-3.71 (m, 4H), 4.29 (dd, 1H, J=8.7, 5.7 Hz), 4.43 (s, 2H), 6.829 (dd, 1H, J=7.5, 4.8 Hz), 7.07 (d, 1H, J=6.9 Hz), 7.22-7.28 (m, 2H), 7.61-7.70 (m, 1H), 7.73-7.79 (m, 1H), 8.32 (dd, 1H, J=4.8, 1.5 Hz).

To a solution of the above solid (56.8 mg, 0.10 mmol) in acetic acid (1 mL) was added a solution of hydrobromic acid in acetic acid (0.5 mL) and the reaction mixture was stirred for 1 hour. The diethyl ether was added until a precipitation of COMPOUND 67 was afforded as a pale yellow solid (49.1 mg, 62%). $^1$H NMR (D$_2$O) δ 1.75-1.89 (m, 6H), 2.12-2.36 (m, 8H), 2.98-3.99 (m, 4H), 3.11 (br m, 2H), 3.31 (br t, 2H), 3.64 (br m, 2H), 3.91 (m, 2H), 4.07 (br m, 2H), 7.565 (dd, 2H, J=6.0, 3.2 Hz), 7.72-7.77 (m, 3H), 8.24 (d, 1H, J=7.8 Hz), 8.52 (d, 1H, J=6.0 Hz). $^{13}$C NMR (D$_2$O) δ 20.73, 23.37, 24.35, 24.46, 25.70, 27.50, 43.76, 50.48, 57.69, 59.40, 63.50, 63.78, 114.25, 125.73, 126.91, 131.23, 139.12, 140.44, 147.84, 151.29, 152.19. ES-MS m/z 446 [M+H]$^+$. Anal. Calcd. for C$_{27}$H$_{35}$N$_5$O.3.0HBr.2.0H$_2$O: C, 44.83; H, 5.71; N, 9.68; Br, 33.14. Found: C, 44.88; H, 5.72; N, 9.49; Br, 33.13.

Example 67

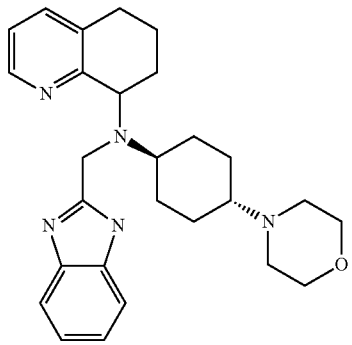 [SMILES: c1cnc2c(c1)CCCC2N(Cc1nc2ccccc2[nH]1)[C@H]1CC[C@H](N2CCOCC2)CC1]

Compound 67: Preparation of trans-(1H-Benzimidazol-2-ylmethyl)-(4-morpholin-4-yl-cyclohexyl)-(5,6,7,8-tetrahydro-quinolin-8-yl)-amine (hydrobromide salt)

Preparation of (4-morpholin-4-yl-cyclohexylamine)-carbamic acid tert-butyl ester To a solution of (4-oxo-cyclohexyl)-carbamic acid tert-butyl ester (426 mg, 2.00 mmol) and morpholine (175 μL, 2.00 mmol) in CH$_2$Cl$_2$ (25 mL) and acetic acid (120 μL) was added sodium triacetoxyborohydride (636 mg, 3.00 mmol) and the mixture was stirred at room temperature overnight. The mixture was concentrated under reduced pressure and diluted with saturated aqueous sodium carbonate (30 mL). The aqueous layer was washed with CH$_2$Cl$_2$ (4×20 mL), and the combined organic extracts were dried (MgSO$_4$), filtered, and concentrated under reduced pressure. Purification by flash column chromatography on silica gel (MeOH/CH$_2$Cl$_2$, 1:9) afforded the title compound as a white solid (76.2 mg, 13%). $^1$H NMR (CDCl$_3$) δ 1.04-1.17 (m, 6H), 1.25-1.38 (m, 4H), 1.44 (s, 9H), 1.93 (d, 2H, J=12.0 Hz), 2.07 (d, 2H, J=12.0 Hz), 2.12-2.17 (m, 2H), 3.25-3.36 (br m, 1H), 4.35 (br m, 1H), 4.81 (br d, 1H).

Preparation of 4-morpholin-4-yl-cyclohexylamine

To a solution of the acetamine from above (60.7 mg, 0.21 mmol) in CH$_2$Cl$_2$ (2 mL) was added trifluoroacetic acid (1 mL) and the mixture was stirred at room temperature for 1 hour. The solvent was removed under reduced pressure and the residue was taken up in NaOH (10 N) plus an equal volume of water. The aqueous layer was washed with CH$_2$Cl$_2$ (5×10 mL), and the combined organic extracts were dried (MgSO$_4$), filtered, and concentrated under reduced pressure to afford the product as an off-white solid (33.5 mg, 85%). $^1$H NMR (CDCl$_3$) δ 1.08-1.27 (m, 4H), 1.39 (s, 2H), 1.88 (dd, 1H, J=10.5, 2.4 Hz), 2.16 (tt, 1H, J=11.3, 3.2 Hz), 2.53 (t, 4H, J=4.7 Hz), 2.61 (tt, 4H, J=10.8, 3.6 Hz), 3.69 (t, 414, J=4.5 Hz).

Preparation of trans-(4-morpholin-4-yl-cyclohexyl)-(5,6,7,8-tetrahydro-quinolin-8-yl)-amine The above amine (50.2 mg, 0.27 mmol) and 6,7-dihydro-5H-quinolin-8-one (40.1 mg, 0.27 mmol) in MeOH (2 mL) were stirred at room temperature overnight to form the imine. To the above solution was added sodium borohydride (20.6 mg, 0.544 mmol) and the mixture was stirred for an additional 2 hour. The solvent was removed under reduced pressure and to the residue was added CH$_2$Cl$_2$ and NaOH (0.5 N) until basic. The mixture was extracted with CH$_2$—Cl$_2$ (3×15 mL), and the combined organic extracts were dried (MgSO$_4$), filtered, and concentrated under reduced pressure. Purification by radial chromatography on silica gel (1 mm plate, CH$_2$Cl$_2$ then NH$_4$OH/CH$_2$Cl$_2$, 1:99) afforded the desired amine (35.9 mg, 42%) as a yellow oil. $^1$H NMR (CDCl$_3$) δ 1.24-1.29 (m, 2H), 1.71-1.74 (m, 2H), 1.95-2.16 (m, 8H), 2.56 (t, 3H, J=4.5 Hz), 2.75-2.79 (m, 2H), 3.41 (s, 2H), 3.71 (t, 4H, J=4.5 Hz), 3.92 (t, 1H, J=6.0 Hz), 7.02-7.06 (m, 1H), 7.35 (d, 1H, J=9.0 Hz), 8.37 (d, 1H, J=3.0 Hz).

Preparation of trans-2-{[(4-morpholin-4-yl-cyclohexyl)-(5,6,7,8-tetrahydro-quinolin-8-yl)-amino]-methyl}-benzimidazole-1-carboxylic acid tert-butyl ester The above amine (35.9 mg, 0.11 mol), 2-chloromethyl-benzimidazole-1-carboxylic acid tert-butyl ester (36.7 mg, 0.14 mmol), N,N-diisopropylethylamine (25 μL, 0.14 mmol), and potassium iodide (1.8 mg, 0.01 mmol) were stirred in CH$_3$CN (1 mL) at 60° C. overnight. The reaction mixture was cooled to room temperature and the solvent was removed under reduced pressure. Purification of the crude material by radial chromatography on silica gel (1 mm plate, CH$_2$Cl$_2$ then NH$_4$OH/CH$_2$Cl$_2$, 1:99) afforded the desired compound (33.7 mg, 54%) as a yellow oil. $^1$H NMR (CDCl$_3$) δ 1.13-1.36 (m, 3H), 1.49-1.68 (m, 11H), 1.89-1.97 (m, 4H), 2.02-2.14 (m, 4H), 2.49-2.52 (m, 4H), 2.59 (br t, 1H), 2.67-2.84 (m, 2H), 3.68 (t, 4H, J=4.5 Hz), 4.24 (t, 1H, J=6.0 Hz), 4.44 (d, 2H, J=6.0 Hz), 6.834 (dd, 1H, J=7.5, 4.7 Hz), 7.08 (d, 1H, J=6.3 Hz), 7.22-7.25 (m, 2H), 7.34-7.69 (m, 1H), 7.71-7.78 (m, 1H), 8.32 (dd, 1H, J=4.5, 1.2 Hz).

Preparation of (S)-(1H-Benzimidazol-2-ylmethyl)-(4-morpholin-4-yl-cyclohexyl)-(5,6,7,8-tetrahydro-quinolin-8-yl)-amine (hydrobromide salt)

To a solution of the above oil (33.7 mg, 0.062 mmol) in acetic acid (1.5 mL) was added a solution of hydrobromic acid in acetic acid (1 mL) and the reaction mixture was stirred for 1 hour. The diethyl ether was added until a precipitation of COMPOUND 67 was afforded as a pale yellow solid (28.9 mg, 63%). $^1$H NMR (D$_2$O) δ 1.48-1.61 (m, 4H), 1.82-1.88 (m, 2H), 2.07-2.39 (m, 6H), 2.75-2.81 (br t, 2H), 2.99 (br d, 2H, J=4.5 Hz), 3.19 (t, 2H, J=10.7 Hz), 3.44 (br d, 2H, J=12.3 Hz), 3.76 (br td, 2H, J=12.3 Hz), 4.09 (br d, 2H, J=11.7 Hz), 4.39-4.57 (m, 3H), 7.59 (dd, 2H, J=6.3, 3.2 Hz), 7.74-7.77 (m, 3H), 8.27 (d, 1H, J=7.8 Hz), 8.55 (d, 1H, J=5.7 Hz). $^{13}$C NMR (D$_2$O) δ 20.68, 23.95, 25.72, 25.93, 27.52, 27.80, 29.81, 43.97, 49.29, 58.82. 59.19, 64.38, 64.77, 114.23, 125.79, 126.96, 131.07, 139.11, 140.45, 147.95, 151.53, 151.95. ES-MS m/z 446 [M+H]⁺, 468 [M+Na]⁺. Anal. Calcd. For $C_{27}H_{35}N_5O \cdot 3.0HBr \cdot 3.0H_2O$: C, 43.68; H, 5.97; N, 9.43; Br, 32.29. Found: C, 43.72; H, 5.76; N, 9.25; Br, 32.06.

Example 68

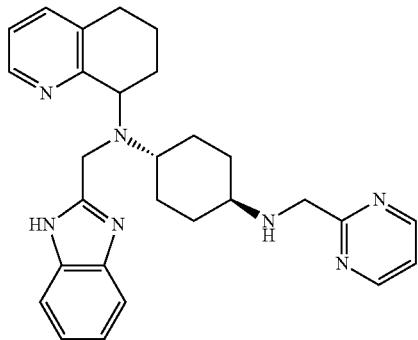 [SMILES: c1cnc(CN[C@H]2CC[C@H](N(Cc3nc4ccccc4[nH]3)C3CCCc4cccnc43)CC2)nc1]

Compound 68: Preparation of N-(1H-benzoimidazol-2-ylmethyl)-N'-pyrimidin-2-ylmethyl-N-(5,6,7,8-tetrahydro-quinolin-8-yl)-transcyclohexane-1,4-diamine(hydrobromide salt)

Preparation of pyrimidine-2-carboxylic acid methyl ester

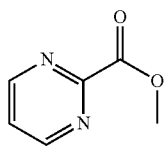

To a saturated HCl(g)/MeOH solution (40 mL) was added a solution of 2-cyanopyrimidine (1.97 g, 18.7 mmol) in MeOH (6 mL) at 0° C. The solution was stiffed at room temperature for 30 minutes then poured into diethyl ether (200 mL) to give a colourless precipitate that was collected by filtration. The crude material was dissolved in H₂O (50 mL), adjusted to pH 4 using saturated NaHCO₃(aq) and 10% HCl (aq) then extracted with CHCl₃ (5×25 mL). The combined organic extracts were washed with saturated NaHCO₃(aq) (25 mL) then dried (MgSO₄) and concentrated in vacuo to give a colourless solid (1.49 g, 58%). ¹H NMR (CDCl₃) δ 4.08 (s, 3H), 7.51 (t, 1H, J=5.1 Hz), 8.96 (d, 2H, J=5.1 Hz).

To a solution of pyrimidine-2-carboxylic acid methyl ester (243 mg, 1.76 mmol) in THF (17 mL) at −78° C. was added LiAlH₄ (1.0 M/THF, 0.47 mL, 0.47 mmol) over 30 minutes, and the solution was stirred at −78° C. for 15 minutes. Acetic acid (0.25 mL, 4.4 mmol) was added dropwise, and the solution was allowed to warm to room temperature then concentrated in vacuo. The residue was dissolved in H₂O (15 mL), adjusted to pH 4 using 10% HCl(aq) then extracted with CHCl₃ (4×10 mL). The combined organic extracts were washed with saturated NaHCO₃(aq) (20 mL) then dried (MgSO₄) and concentrated in vacuo to give a yellow liquid (156 mg). The crude material was determined by ¹H NMR to be a mixture of pyrimidine-2-carbaldehyde, pyrimidine-2-carboxylic acid methyl ester, and THF (1.0:1.7:7.7 respectively) and was used in the next step without further purification.

Using General Procedure B: To a solution of the crude aldehyde from above (156 mg) and N-(1H-benzoimidazol-2-ylmethyl)-N-(5,6,7,8-tetrahydro-quinolin-8-yl)-cyclohexane-trans-1,4-diamine (68 mg, 0.18 mmol) in THF (2 mL) was added NaBH(OAc)₃ (114 mg, 0.538 mmol) and the mixture was stirred at room temperature for 1.5 h. The crude material was dissolved in saturated HBr/AcOH (2 mL) and stirred at room temperature for 5 minutes. The solution was made basic with 10 N NaOH(aq) and extracted with CH₂Cl₂ (3×15 mL). The combined organic extracts were dried (MgSO₄) and concentrated in vacuo. Purification of the crude material by column chromatography on silica gel (200:5:1 CH₂Cl₂/MeOH/NH₄OH) afforded a colourless oil (50 mg).

Using General Procedure D: Conversion of the oil from above (50 mg, 0.11 mmol) to the hydrobromide salt followed by re-precipitation of the intermediate solid from methanol/ether gave COMPOUND 68 (78 mg, 85%) as a colourless solid. ¹H NMR (D₂O) δ 1.58 (m, 4H), 1.89 (m, 1H), 2.03-2.45 (m, 7H), 2.84 (m, 1H), 3.00 (m, 2H), 3.30 (m, 1H), 4.42-4.60 (m, 5H), 7.50 (t, 1H, J=5.1 Hz), 7.58 (m, 2H), 7.78 (m, 3H), 8.29 (d, 1H, J=8.1 Hz), 8.58 (d, 1H, J=5.7 Hz), 8.79 (d, 2H, J=5.1 Hz); ¹³C NMR (D₂O) δ 20.73, 24.04, 27.56, 28.08, 28.33, 29.73, 44.05, 48.59, 56.44, 58.80, 59.26, 114.24, 121.65, 125.84, 127.02, 130.91, 139.12, 140.51, 148.03, 151.51, 152.00, 158.38, 160.98. ES-MS m/z 468 (M+H). Anal. Calcd. for $C_{28}H_{33}N_7 \cdot 3.9HBr \cdot 3.2H_2O \cdot 0.2C_4H_{10}O$: C, 40.43; 1-1, 5.34; N, 11.46; Br, 36.42. Found: C, 40.37; H, 5.05; N, 11.35; Br, 36.58.

Example 69

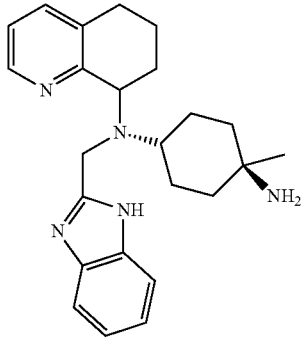

Compound 69: Preparation of N-(1H-Benzoimidazol-2-ylmethyl)-1-methyl-N-(5,6,7,8-tetrahydro-quinolin-8-yl)-trans-cyclohexane-1,4-diamine (hydrobromide salt)

Preparation of trans-(4-Cyano-4-diallylamino-cyclohexyl)-carbamic acid tert-butyl ester To a stirred solution of (4-Oxo-cyclohexyl)-carbamic acid tert-butyl ester (3.07 g, 14.4 mmol) and diallylamine (1.78 mL, 14.4 mmol) in anhydrous ClCH₂CH₂Cl (25 mL) was added titanium(IV) isopropoxide (4.28 mL, 14.4 mmol) at 0° C. The reaction mixture was allowed to warm to room temperature and was stirred overnight. The mixture was then cooled to 0° C. and diethylaluminum cyanide (1M in toluene, 17 ml, 17 mmol) was added with vigorous stirring. The reaction was allowed to warm to room temperature and stirred an additional 3.5 hours, after which are added CH$_2$Cl$_2$ (30 mL), EtOAc (40 mL), and celite (3 g). The reaction mixture was cooled to 0° C., water (8 mL) was added slowly with vigorous stirring and, after an additional 5 minutes of stirring at room temperature, the excess water was quenched with Na$_2$SO$_4$. The final mixture was then filtered over celite, concentrated under reduced pressure, and subjected to flash chromatography over silica gel (Hexanes/EtOAc, 4:1) to afford the desired nitrile (3.11 g, 68% over 2 steps) as a pale yellow oil. $^1$H NMR (CDCl$_3$) δ 1.44 (s, 9H), 1.53-1.59 (m, 3H), 1.78-1.99 (m, 2H), 2.07 (d, 2H, J=9 Hz), 2.28 (d, 2H, J=12 Hz), 3.33 (t, 4H, J=4.5 Hz), 3.37-3.55 (br m, 1H), 4.33-4.53 (br m, 1H), 5.12-5.24 (m, 4H), 5.82-5.94 (m, 2H).

Preparation of trans-(4-Diallylamino-4-methyl-cyclohexyl)-carbamic acid tert-butyl ester To a solution of the nitrile from above (3.11 g, 9.7 mmol) in anhydrous THF (30 mL) at 0° C. was added dropwise methylmagnesium bromide (3.0 M in Et$_2$O, 10.0 mL, 29.2 mmol). After the addition, the reaction was allowed to warm to RT and stirred overnight. The reaction was then quenched with saturated aqueous NaHCO$_3$ (50 mL), diluted with EtOAc (30 mL), and the layers separated. The aqueous layer was extracted with EtOAc (1×20 mL) and CH$_2$Cl$_2$ (1×20 mL). The combined organic extracts were dried (Na$_2$SO$_4$), filtered, and concentrated under reduced pressure to afford a crude mixture of the desired product (19%) and N-(4-Diallylamino-4-methyl-cyclohexyl)-acetamide (72%). The resultant crude, yellow oil (1.21 g) was used without further purification in the next step.

Preparation of trans-N,N-Diallyl-1-methyl-cyclohexane-1,4-diamine

To a stirred solution of the crude mixture from above in dry CH$_2$Cl$_2$ (4 mL) was added TFA (4 mL) and the reaction stirred at RT for 2.5 h. The reaction mixture was diluted with CH$_2$Cl$_2$ (30 mL) and concentrated under reduced pressure. The residue was diluted with CH$_2$Cl$_2$ (50 mL) and washed with 1N NaOH (1×40 mL) and the aqueous phase extracted with CH$_2$Cl$_2$ (2×25 mL). The combined organic extracts were dried (Na$_2$SO$_4$), filtered, and concentrated under reduced pressure to afford a yellow oil (0.840 g, 12% desired amine).

The byproduct from above, N-(4-Diallylamino-4-methyl-cyclohexyl)-acetamide (0.1979 g, 0.79 mmol), was dissolved in 6N HCl (6 mL) and refluxed for 6 h. The reaction was cooled to RT and made basic with 10N NaOH and extracted with CH$_2$Cl$_2$ (3×20 mL). The combined organic extracts were dried (Na$_2$SO$_4$), filtered, and concentrated under reduced pressure to give the desired primary amine (0.1063 g, 65%) as a yellow/green oil, which was used without further purification in the next reaction.

Preparation of 2-{[trans-(4-Amino-4-methyl-cyclohexyl)-(5,6,7,8-tetrahydro-quinolin-8-yl)-amino]-methyl}-benzoimidazole-1-carboxylic acid tert-butyl ester Following General Procedure B: To a stirred solution of 6,7-dihydro-5H-quinolin-8-one (0.0895 g, 0.61 mmol) and the crude N,N-Diallyl-1-methyl-cyclohexane-1,4-diamine from above (0.1063 g, 0.51 mmol) in dry THF (5 mL) was added AcOH (5 drops) and NaBH(OAc)$_3$ (0.1805 g, 0.85 mmol) and the mixture stirred overnight at room temperature. Purification by column chromatography on silica gel (CH$_2$Cl$_2$/MeOH/NH$_4$OH, 96:4:0 then 95:4:1) afforded the desired amine (75.2 mg, 36%) as a colourless oil.

Following the general procedure for N-alkylation: To a stirred solution of the combined amines from above (0.1842 g, 0.54 mmol) in CH$_3$CN (4 mL) was added N,N-diisopropylethylamine (0.17 mL, 0.98 mmol), KI (4.5 mg, 0.027 mmol) and 1-(tert-butoxycarbonyl)-2-(chloromethyl)benzimidazole (0.1449 g, 0.54 mmol). The mixture was stirred at 60° C. overnight. Purification of the resultant orange oil by column chromatography on silica gel (CH$_2$Cl$_2$/MeOH/NH$_4$OH, 96:4:0 then 89:10:1) afforded the desired alkylated amine (0.1364 g, 44%) as a orange foam.

To a stirred solution of the alkylated amine from above (0.1364 g, 0.24 mmol) in dry CH$_2$Cl$_2$ (4 mL) was added N,N-dimethylbarbituric acid (0.1869 g, 1.2 mmol) and tetrakis(triphenylphosphine)-palladium(0) (0.028 g, 0.024 mmol) and the mixture stirred at room temperature for 64 h. The reaction was diluted with CH$_2$Cl$_2$ (20 mL) and saturated aqueous NaHCO$_3$ (30 mL). The phases were separated and the aqueous layer extracted with CH$_2$Cl$_2$ (2×20 mL). The combined organic extracts were dried (Na$_2$SO$_4$), filtered and concentrated under reduced pressure. Purification of the crude material by radial chromatography on silica gel (2 mm plate, CH$_2$Cl$_2$/MeOH/NH$_4$OH, 50:1:1 then 25:1:1) afforded the desired amine (28.9 mg, 25%) and the monoallyl-protected amine (51.0 mg, 40%).

Preparation of 2-{[trans-(4-tert-Butoxycarbonylamino-4-methyl-cyclohexyl)-(5,6,7,8-tetrahydroquinolin-8-yl)-amino]-methyl}-benzoimidazole-1-carboxylic acid tert-butyl ester To a stirred solution of the desired primary amine (28.9 mg, 0.059 mmol) from above in dry THF (1.5 mL) was added Di-tert-butyl dicarbonate (47 mg, 0.22 mmol) and the mixture stirred at room temperature overnight. The reaction was concentrated under reduced pressure and the residue was purified by radial chromatography on silica gel (1 mm plate, CH$_2$Cl$_2$/MeOH/NH$_4$OH, 100:1:1) to afford the protected amine (25 mg, 71%) as a colourless oil.

Using General Procedure D: Conversion of the oil from above (25 mg, 0.042 mmol) to the hydrobromide salt followed by re-precipitation of the intermediate solid from methanol/ether gave COMPOUND 69 (23 mg, 82%) as a white solid. $^1$H NMR (D$_2$O) δ 1.29 (s, 3H), 1.56-1.78 (m, 4H), 1.79-2.04 (m, 4H), 2.07-2.27 (m, 3H), 2.38-2.48 (m, 1H), 2.77-2.83 (m, 1H), 2.99 (d, 2H, J=5.4 Hz), 4.42 (d, 1H, J=16.5 Hz), 4.58 (d, 1H, J=16.8 Hz), 4.54-4.61 (m, 1H), 7.56-7.61 (m, 2H), 7.72-7.81 (m, 3H), 8.27 (d, 1H, J=7.8 Hz), 8.55 (d, 1H, J=5.1 Hz); $^{13}$C NMR (D$_2$O) δ 20.71, 24.24, 26.56, 26.86, 27.50, 34.87, 35.05, 43.78, 53.48, 58.03, 59.84, 114.21, 125.76, 126.97, 131.05, 139.08, 140.46, 147.91, 151.38, 152.11. ES-MS m/z 390 (M+H). Anal. Calcd. for C$_{24}$H$_{31}$N$_5$.2.9HBr.3.1H$_2$O: C, 42.39; H, 5.94; N, 10.30; Br, 34.08. Found: C, 42.30; H, 5.69; N, 10.11; Br, 34.18.

Example 70

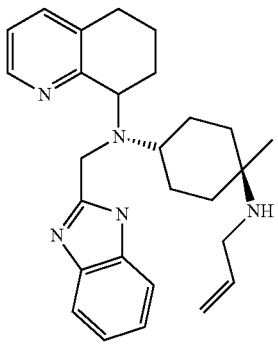

Compound 70: Preparation of N¹-Allyl-N-(1H-Benzoimidazol-2-ylmethyl)-1-methyl-N-(5,6,7,8-tetrahydro-quinolin-8-yl)-trans-cyclohexane-1,4-diamine (hydrobromide salt)

Repurification of the monoallyl-protected amine (51 mg, 0.10 mmol) from above by radial chromatography on silica gel (1 mm plate, $CH_2Cl_2$/MeOH/$NH_4OH$, 100:1:1 then 50:1:1 then 25:1:1) afforded the monoallyl-protected amine (24.6 mg, 20%) as an orange oil.

Using General Procedure D: Conversion of the oil from above (25 mg, 0.047 mmol) to the hydrobromide salt followed by re-precipitation of the intermediate solid from methanol/ether gave COMPOUND 70 (32 mg, 94%) as an off-white solid. $^1$H NMR ($D_2O$) δ 1.29 (s, 3H), 1.55-1.95 (br m, 7H), 2.01-2.22 (m, 6H), 2.38-2.45 (m, 1H), 2.77-2.86 (m, 1H), 2.97-3.02 (m, 2H), 3.65 (d, 2H, J=6.9 Hz), 4.43 (d, 1H, J=16.8 Hz), 4.57 (d, 1H, J=16.8 Hz), 4.59-4.65 (m, 1H), 5.44 (d, 1H, J=16.2 Hz), 5.48 (d, 1H, J=23.1 Hz), 5.86-6.00 (m, 1H), 7.56-7.62 (m, 2H), 7.72-7.81 (m, 3H), 8.27 (d, 1H, J=7.8 Hz), 8.55 (d, 1H, J=5.4 Hz); $^{13}$C NMR ($D_2O$) δ 14.52 ($Et_2O$), 20.70, 23.66, 24.11, 24.33, 26.08, 27.49, 33.48, 33.85, 43.72, 44.50, 66.47 ($Et_2O$), 114.20, 123.96, 125.78, 127.03, 128.43, 130.95, 139.08, 140.51, 147.95, 151.28, 152.12. ES-MS m/z 430 (M+H). Anal. Calcd. for $C_{27}H_{35}N_5 \cdot 3.0HBr \cdot 2.9H_2O$: C, 44.76; H, 6.09; N, 9.67; Br, 33.08. Found: C, 45.00; H, 5.96; N, 9.61; Br, 32.72.

Example 71

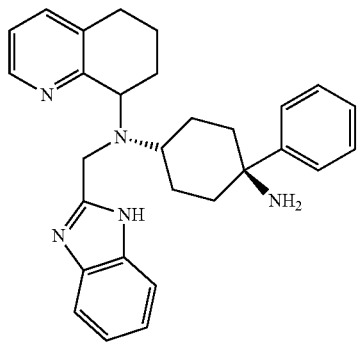

Compound 71: Preparation of N-(1H-Benzoimidazol-2-ylmethyl)-1-phenyl-N-(5,6,7,8-tetrahydro-quinolin-8-yl)-trans-cyclohexane-1,4-diamine (hydrobromide salt)

Preparation of trans-(4-Cyano-4-diallylamino-cyclohexyl)-carbamic acid tert-butyl ester To a stirred solution of (4-Oxo-cyclohexyl)-carbamic acid tert-butyl ester (3.55 g, 16.6 mmol) and diallylamine (2.05 mL, 16.6 mmol) in anhydrous $ClCH_2CH_2Cl$ (30 mL) was added titanium(IV) isopropoxide (4.95 mL, 16.6 mmol) at 0° C. The reaction mixture was allowed to warm to room temperature and was stirred overnight. The mixture was then cooled to 0° C. and diethylaluminum cyanide (1M in toluene, 19.6 ml, 19.6 mmol) was added with vigorous stirring. The reaction was allowed to warm to room temperature and stirred an additional 5 h, after which were added $CH_2Cl_2$ (40 mL), EtOAc (40 mL), and celite (4 g). The reaction mixture was cooled to 0° C., water (10 mL) was added slowly with vigorous stirring and, after an additional 5 minutes of stirring at room temperature, the excess water was quenched with $Na_2SO_4$. The final mixture was then filtered over celite, concentrated under reduced pressure, and subjected to flash chromatography over silica gel (Hexanes/EtOAc, 4:1) to afford the desired nitrile (2.62 g, 66% over 2 steps) as a pale yellow oil. $^1$H NMR ($CDCl_3$) δ 1.44 (s, 9H), 1.50-1.70 (m, 4H), 1.77-1.99 (m, 2H), 2.07 (d, 2H, J=9 Hz), 2.28 (d, 2H, J=12 Hz), 3.33 (t, 4H, J=6.0 Hz), 4.33-4.53 (br m, 1H), 5.11-5.24 (m, 4H), 5.82-5.95 (m, 2H).

Preparation of trans-(4-Diallylamino-4-phenyl-cyclohexyl)-carbamic acid tert-butyl ester To a solution of the nitrile from above (1.00 g, 3.1 mmol) in anhydrous THF (16 mL) at 0° C. was added dropwise phenylmagnesium bromide (3.0 M in $Et_2O$, 3.1 mL, 9.4 mmol). After the addition, the reaction was allowed to warm to RT and stirred for 3 h. The reaction was then quenched with saturated aqueous $NH_4Cl$ (40 mL), diluted with EtOAc (30 mL), and the layers separated. The aqueous layer was extracted with EtOAc (1×20 mL) and $CH_2Cl_2$ (1×20 mL). The combined organic extracts were dried ($Na_2SO_4$), filtered, and concentrated under reduced pressure. Purification by column chromatography on silica gel (Hexanes/EtOAc, 4:1) afforded both the desired product (0.2057 g, 32%) and N-(4-Diallylamino-4-phenyl-cyclohexyl)-benzamide (0.11 g, 17%) as white solids.

Preparation of trans-N,N-Diallyl-1-phenyl-cyclohexane-1,4-diamine

To a stirred solution of the desired product (0.2057 g, 0.56 mmol) from above in dry $CH_2Cl_2$ (2 mL) was added TFA (2 mL) and the reaction stirred at RT for 4 h. The reaction mixture was diluted with $CH_2Cl_2$ (15 mL) and concentrated under reduced pressure. The residue was diluted with $CH_2Cl_2$ (20 mL) and washed with 1N NaOH (1×30 mL) and the aqueous phase extracted with $CH_2Cl_2$ (2×20 mL). The combined organic extracts were dried ($Na_2SO_4$), filtered, and concentrated under reduced pressure to afford a yellow oil (0.1055 g, 70%). The resultant amine was used without further purification in the next reaction.

The byproduct from above, trans-N-(4-Diallylamino-4-phenyl-cyclohexyl)-benzamide (0.4558 g, 1.22 mmol), was dissolved in a solution of $H_2O$ (2.5 mL), 6N HCl (3.5 mL) and THF (2 mL) and refluxed overnight. The reaction was cooled to RT, diluted with H₂O (15 mL) and made basic with 10N NaOH after which the aqueous solution was extracted with CH₂Cl₂ (3×20 mL). The combined organic extracts were dried (Na₂SO₄), filtered, and concentrated under reduced pressure. Purification by column chromatography on silica gel (CH₂Cl₂/MeOH/NH₄OH, 96:4:0 then 89:10:1) afforded the desired primary amine (80 mg, 24%) as a yellow oil.

Preparation of 2-{[trans-(4-Amino-4-phenyl-cyclo-hexyl)-(5,6,7,8-tetrahydro-quinolin-8-yl)-amino]-methyl}-benzoimidazole-1-carboxylic acid tert-butyl ester Following General Procedure B (Stepwise Reductive Amination Using NaBH₄): To a stirred solution of 6,7-dihydro-5H-quinolin-8-one (0.099 g, 0.67 mmol) and N,N-Diallyl-1-phenyl-cyclohexane-1,4-diamine (0.181 g, 0.48 mmol) in dry MeOH (3 mL) was added NaBH₄ (0.051 g, 1.3 mmol) after 2 h and the mixture stirred for an additional 2 h at room temperature. Purification by radial chromatography on silica gel (2 mm plate, CH₂Cl₂/MeOH/NH₄OH, 100:1:1 then 75:1:1) afforded the desired amine (150 mg, 56%) as a pale yellow oil.

Following the general procedure for N-alkylation: To a stirred solution of the amine from above (0.150 g, 0.37 mmol) in CH₃CN (2 mL) was added N,N-diisopropylethylamine (0.12 mL, 0.67 mmol), KI (3 mg, 0.019 mmol) and 1-(tert-butoxycarbonyl)-2-(chloromethyl)benzimidazole (0.099 g, 0.37 mmol). The mixture was stirred at 60° C. overnight. Purification of the resultant beige foam by radial chromatography on silica gel (2 mm plate, CH₂Cl₂/MeOH/NH₄OH, 100:1:1 then 50:1:1) afforded the desired alkylated amine (0.149 g, 64%) as a yellow oil.

To a stirred solution of the alkylated amine (0.149 g, 0.24 mmol) from above in dry CH₂Cl₂ (2.5 mL) was added N,N-dimethylbarbituric acid (0.1841 g, 1.2 mmol) and Tetrakis(triphenylphosphine)-palladium(0) (0.068 g, 0.06 mmol) and the mixture stirred at room temperature for 64 h. The reaction was diluted with CH₂Cl₂ (20 mL) and saturated aqueous NaHCO₃ (30 mL). The phases were separated and the aqueous layer extracted with CH₂Cl₂ (2×20 mL). The combined organic extracts were dried (Na₂SO₄), filtered and concentrated under reduced pressure. Purification of the crude material by radial chromatography on silica gel (2 mm plate, CH₂Cl₂/MeOH/NH₄OH, 50:1:1 then 25:1:1 then 20:1:1) afforded the deprotected amine (28.9 mg, 25%) and the monoallyl-protected amine (70.1.0 mg, 54%, 90% purity).

Preparation of 2-{[trans-(4-tert-Butoxycarbonylamino-4-phenyl-cyclohexyl)-(5,6,7,8-tetrahydro-quinolin-8-yl)-amino]-methyl}-benzoimidazole-1-carboxylic acid tert-butyl ester To a stirred solution of the desired primary amine (28.9 mg, 0.13 mmol) from above in dry THF (2 mL) was added Di-tert-butyl dicarbonate (42 mg, 0.19 mmol) and the mixture stirred at room temperature overnight. The reaction was concentrated under reduced pressure and the residue was purified by radial chromatography on silica gel (1 mm plate, CH₂Cl₂/MeOH/NH₄OH, 100:1:1 the 50:1:1) to afford the boc-protected amine (34 mg, 44%) as a colourless oil.

Using General Procedure D: Conversion of the oil from above (24 mg, 0.037 mmol) to the hydrobromide salt followed by re-precipitation of the intermediate solid from methanol/ether gave COMPOUND 71 (24 mg, 85%) as a beige solid. ¹H NMR (D₂O) δ 1.80-1.99 (m, 3H), 2.00-2.27 (m, 5H), 2.28-2.53 (m, 4H), 2.89-3.04 (m, 3H), 4.47 (d, 1H, J=16.8 Hz), 4.61 (d, 1H, J=16.5 Hz), 4.60-4.68 (m, 1H), 7.40-7.53 (m, 5H), 7.55-7.61 (m, 2H), 7.71-7.81 (m, 3H), 8.26 (d, 1H, J=7.2 Hz), 8.55 (d, 1H, J=5.1 Hz); ¹³C NMR (D₂O) δ 20.74, 24.26, 24.54, 26.75, 27.53, 34.29, 34.46, 43.85, 57.40, 58.08, 59.61, 114.24, 125.12, 125.79, 126.97, 129.40, 129.64, 131.08, 139.14, 140.51, 140.91, 147.94, 151.34, 152.04. ES-MS m/z 452 (M+H). Anal. Calcd. for C₂₉H₃₃N₅.2.7HBr.5.3H₂O: C, 45.50; H, 6.10; N, 9.15; Br, 28.18. Found: C, 45.43; H, 5.43; N, 8.93; Br, 28.23.

Example 73

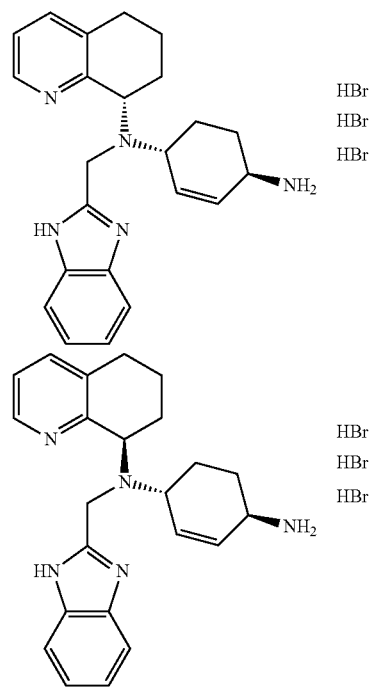

Compound 73(R) and (S): Preparation of the two diastereomers of N¹-(1H-Benzimidazol-2-ylmethyl)-N¹-(5,6,7,8-tetrahydro-quinolin-8-yl)-cyclohex-2-ene-trans-1,4-diamine Cis-1-acetoxy-4-chloro-2-cyclohexene was prepared from 1,3-cyclohexadiene following the procedure reported by Bäckvall et al (J. Am. Chem. Soc. 1985, 107, 3676-3686).

To a stirred solution of cis-1-acetoxy-4-chloro-2-cyclohexene (6.87 g, 39.4 mmol) in DMF (160 mL) was added sodium azide (5.29 g, 81.1 mmol) and the resultant mixture was stirred at room temperature for 2 hours. The reaction mixture was poured into brine (160 mL) and diluted with diethyl ether (300 mL) and water (80 mL). The phases were separated and the organic phase was washed with brine (5×50 mL). The organic phase was dried (MgSO₄), and concentrated to provide 6.13 g (85%) of trans-1-acetoxy-4-azido-2-cyclohexene as a pale red oil which was used without further purification.

A mixture of trans-1-acetoxy-4-azido-2-cyclohexene (6.13 g, 33.9 mmol), Lindlar's catalyst (1.18 g), and di-tert-butyl dicarbonate (11.35 g, 52.1 mmol) in methanol (170 mL) was hydrogenated under atmospheric pressure for 19 hours. The mixture was filtered through Celite® and the cake was washed with methanol. The filtrate was concentrated and the resultant oil was purified by column chromatography on silica gel (6:1 hexanes-ethyl acetate) and provided 6.70 g (77%) of trans-1-acetoxy-4-(tert-butoxycarbonylamino)-2-cyclohexene as a white solid.

To a solution of trans-1-acetoxy-4-(tert-butoxycarbonylamino)-2-cyclohexene (6.70 g, 26.3 mmol) in methanol (130 mL) was added solid $K_2CO_3$ (7.50 g, 54.4 mmol) and the mixture was stirred at room temperature for 1 hour. The reaction mixture was concentrated and the residue was dissolved in $CH_2Cl_2$ (250 mL) and saturated aqueous $NaHCO_3$ (100 mL). The phases were separated and the aqueous phase was extracted with $CH_2Cl_2$ (3×50 mL). The combined organic extracts were dried ($Na_2SO_4$) and concentrated. Purification of the crude material by column chromatography on silica gel (20:1 $CH_2Cl_2$—$CH_3OH$) provided 3.38 g (60%) of trans-1-hydroxy-4-(tert-butoxycarbonylamino)-2-cyclohexene as a white solid. $^1H$ NMR ($CDCl_3$) δ 1.44 (s, 9H), 1.52-1.57 (m, 1H), 2.05-2.14 (m, 3H), 4.20-4.26 (br s, 2H), 4.45 (br s, 1H), 4.47-4.60 (m, 1H), 5.70 (d, 1H, J=10.2 Hz), 5.81 (d, 1H, J=10.2 Hz);

To a mixture of trans-1-hydroxy-4-(tert-butoxycarbonylamino)-2-cyclohexene (2.93 g, 13.8 mmol) in hexachloroacetone (70 mL) was added triphenylphosphine (7.51 g, 28.6 mmol) and the mixture was stirred at room temperature for 1 hour. The mixture was concentrated and the thus obtained oil was purified by column chromatography on silica gel (10:1 hexanes-ethyl acetate) and provided 1.98 g (62%) of cis-1-(tert-butoxycarbonylamino)-4-chloro-2-cyclohexene as a yellow solid.

To a stirred solution of cis-1-(tert-butoxycarbonylamino)-4-chloro-2-cyclohexene (1.85 g, 8.00 mmol) in DMF (40 mL) was added sodium azide (1.17 g, 18.0 mmol) and the resultant mixture was stirred at room temperature for 16 hours. The reaction mixture was poured into brine (40 mL) and diluted with ethyl acetate (120 mL) and water (20 mL). The phases were separated and the organic phase was washed with brine (4×25 mL). The organic phase was dried ($MgSO_4$), and concentrated. Purification of the crude material by column chromatography on silica gel (10:1 hexanes-ethyl acetate) provided 1.14 g (60%) of trans-1-azido-4-(tert-butoxycarbonylamino)-2-cyclohexene as a colorless oil.

To a solution of trans-1-azido-4-(tert-butoxycarbonylamino)-2-cyclohexene (1.14 g, 4.79 mmol) in THF (50 mL) and water (5 mL) was added triphenylphosphine (2.60 g, 10 mmol) and the mixture was stirred at room temperature for 20 hours. The mixture was concentrated and the thus obtained material was purified by column chromatography on silica gel (10:1:1 $CH_2Cl_2$—$CH_3OH$—$NH_4OH$) followed by radial chromatography on silica gel (2 mm plate, 100:1:1 $CH_2Cl_2$—$CH_3OH$—$NH_4OH$) and provided 0.32 g (31%) of trans-1-amino-4-(tert-butoxycarbonylamino)-2-cyclohexene as a colorless oil. $^1H$ NMR ($CDCl_3$) δ 1.44 (s, 9H), 1.50-1.92 (m, 2H), 1.99-2.10 (m, 2H), 3.32 (br s, 1H), 4.10-4.19 (m, 1H), 4.47-4.60 (m, 1H), 5.57-5.77 (m, 2H);

Using General Procedure B: Reaction of trans-1-amino-4-(tert-butoxycarbonylamino)-2-cyclohexene (0.222 g, 1.05 mmol) and 6,7-dihydro-5H-quinolin-8-one (0.304 g, 2.06 mmol) in THF (10 mL) with $NaBH(OAc)_3$ (0.423 g, 2.00 mmol) for 4 hours followed by purification of the crude material by column chromatography on silica gel (25:1 $CH_2Cl_2$—$CH_3OH$) provided 0.277 g (77%) of $N^1$-(5,6,7,8-tetrahydro-quinolin-8-yl)-$N^4$-(tert-butoxycarbonyl)-cyclohex-2-ene-trans-1,4-diamine as a yellow foam.

Using the General Procedure for N-alkylation: A solution of $N^1$-(5,6,7,8-tetrahydro-quinolin-8-yl)-$N^4$-(tert-butoxycarbonyl)-cyclohex-2-ene-trans-1,4-diamine (0.277 g, 0.81 mmol), 1-tort-(butoxycarbonyl)-2-(chloromethyl)benzimidazole (0.327 g, 1.22 mmol), catalytic potassium iodide (14 mg), and N,N-diisopropylethylamine (0.28 mL, 1.61 mmol) in $CH_3CN$ (8 mL) was heated at 60° C. for 20 hours. Purification of the crude material by column chromatography on silica gel (20:1:1 $CH_2Cl_2$—MeOH—$NH_4OH$) followed by radial chromatography on silica gel (1 mm plate, 100:1:1 $CH_2Cl_2$—MeOH—$NH_4OH$) provided two diasteriomers of $N^1$-(5,6,7,8-tetrahydro-quinolin-8-yl)-$N^1$-(1-tert-butoxycarbonyl-1H-Benzimidazol-2-ylmethyl)-$N^4$-(tert-butoxycarbonyl)-cyclohex-2-ene-trans-1,4-diamine, 129 mg (28%) of a white foam and 18 mg (4%) of a white solid.

General Procedure D: Conversion of the major diastereomer (100 mg) to the hydrobromide salt with simultaneous removal of the BOC-protecting groups, followed by re-precipitation of the intermediate solid from methanol/ether, gave COMPOUND 73(R) (103 mg, 88%) as a white solid. $^1H$ NMR ($D_2O$) δ 1.45-1.57 (m, 1H), 1.70-1.82 (m, 2H), 2.00-2.17 (m, 4H), 2.48-2.52 (m, 1H), 2.93 (br d, 2H, J=5.1 Hz), 3.61-3.63 (m, 1H), 3.88-3.91 (m, 1H), 4.38-4.46 (m, 2H), 4.55 (d, 1H, J=16.8 Hz), 5.88 (br d, 1H, J=10.5 Hz), 6.25 (d, 1H, J=10.5 Hz), 7.52-7.57 (m, 2H), 7.69-7.77 (m, 3H), 8.22 (d, 1H, J=8.1 Hz), 8.55 (d, 1H, J=5.1 Hz; $^{13}C$ NMR ($D_2O$) δ 20.63, 23.56, 27.14, 27.30, 27.52, 42.75, 47.46, 56.83, 60.11, 114.17, 125.84, 127.00, 128.66, 130.94, 133.97, 139.22, 140.59, 147.98, 151.38, 151.46; ES-MS m/z 374 (M+H). Anal. Calcd. for $C_{23}H_{27}N_5$.3.0HBr.2.9$H_2O$: C, 41.33; H, 5.40; N, 10.48; Br, 35.86. Found: C, 41.14; H, 5.15; N, 10.28; Br, 36.10.

General Procedure D: Conversion of the minor diastereomer (18 mg) to the hydrobromide salt with simultaneous removal of the BOC-protecting groups, followed by re-precipitation of the intermediate solid from methanol/ether, gave COMPOUND 73(S) (15 mg, 68%) as a white solid. $^1H$ NMR ($D_2O$) δ 1.45-1.56 (m, 1H), 1.73-1.90 (m, 2H), 2.03-2.37 (m, 5H), 2.96 (d, 2H, J=4.8 Hz), 3.66-3.70 (m, 1H), 3.89-3.91 (m, 1H), 4.34-4.46 (m, 2H), 4.52 (d, 1H, J=16.2 Hz), 5.75 (d, 1H, J=10.25 Hz), 6.05 (d, 1H, J=10.2 Hz), 7.53-7.56 (m, 2H), 7.70-7.76 (m, 3H), 8.22 (d, 1H, J=7.8 Hz), 8.52 (d, 1H, J=5.7 Hz); $^{13}C$ NMR ($D_2O$) δ 20.56, 24.42, 25.14, 27.03, 27.40, 43.22, 47.65, 57.18, 58.39, 114.24, 125.76, 126.90, 128.40, 131.22, 135.51, 139.13, 140.42, 147.75, 150.87, 152.02; ES-MS m/z 374 (M+H). Anal. Calcd. for $C_{23}H_{27}N_5$.3.0HBr.3.1$H_2O$: C, 41.10; H, 5.43; N, 10.42; Br, 35.67. Found: C, 41.38; H, 5.09; N, 10.35; Br, 35.36.

Example 74

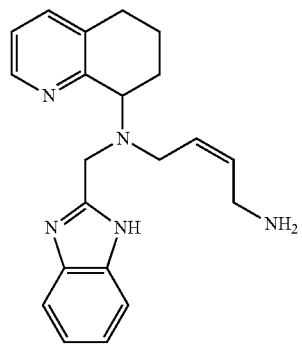 [SMILES: NC/C=C\CN(Cc1nc2ccccc2[nH]1)C1CCCc2cccnc21]

Compound 74: Preparation of (Z)-N40-(1H-Benz-imidazol-2-ylmethyl)-N'-(5,6,7,8-tetrahydro-quinolin-8-yl)-but-2-ene-1,4-diamine Preparation of ((Z)-4-Chloro-but-2-enyl)-carbamic acid tert-butyl ester

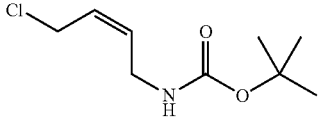

To a stirred suspension of (2)-4-chloro-2-butenylamine hydrochloride (1.0 g, 7.0 mmol) in THF (35 mL) and water (0.2 mL) was added N,N-diisopropylethylamine (2.7 mL, 15.4 mmol) followed by di-tert-butyl dicarbonate (1.8 g, 8.4 mmol). The resultant solution was stirred for 3 h, at which time saturated aqueous sodium bicarbonate (20 mL) and diethyl ether (40 mL) were added. The phases were separated and the aqueous layer was extracted with $Et_2O$ (3×30 mL). The combined organic extracts were washed once with brine (20 mL), dried ($MgSO_4$), and concentrated in vacuo. Purification of the crude material by flash chromatography (silica gel, 4:1 hexane-EtOAc) afforded 1.3 g (90%) of the title compound as a white solid. $^1$H NMR ($CDCl_3$) δ 1.44 (s, 9H), 3.82 (t, 2H, J=6 Hz), 4.12 (d, 2H, J=9 Hz), 4.62 (br s, 1H), 5.60-5.70 (m, 1H), 5.72-5.77 (m, 1H).

Following the General Procedure for N-alkylation: To a solution of (1H-N-tert-butoxycarbonyl-benzimidazol-2-ylmethyl)-(5,6,7,8-tetrahydroquinolin-8-yl)-amine (200 mg, 0.53 mmol) and ((Z)-4-chloro-but-2-enyl)-carbamic acid Cert-butyl ester (130 mg, 0.64 mmol) in $CH_3CN$ (3 mL) were added N,N-diisopropylethylamine (138 µL, 0.80 mmol) and KI (4.4 mg, 0.027 mmol) and the reaction stirred at 60° C. for 18 h. The crude material was taken up in neat TFA (1 mL) and stirred 3 h. Saturated aqueous sodium bicarbonate (5 mL) was cautiously added, and the resulting mixture was extracted with $CH_2Cl_2$ (3×10 mL) then the combined organic extracts were dried ($MgSO_4$), filtered and concentrated in vacuo. Purification of the crude material by radial chromatography (1 mm plate, 50:1:1 $CH_2Cl_2$—MeOH—$NH_4OH$) afforded the title compound (57 mg, 31%) as a white solid. $^1$H NMR ($CDCl_3$) δ 1.68-1.72 (m, 1H), 1.84-2.05 (m, 2H), 2.15-2.22 (m, 1H), 2.71 (dt, 1H, J=17, 5 Hz), 2.84 (ddd, 1H, J=16, 10, 5 Hz), 3.15-3.26 (m, 3H), 3.38 (dd, 1H, J=14, 7 Hz), 3.97-4.12 (m, 3H), 5.46-5.54 (m, 2H), 7.13 (dd, 1H, J=8, 5 Hz), 7.16-7.21 (m, 2H), 7.40 (dd, 1H, J=7, 1 Hz), 7.57 (br s, 2H), 8.57 (dd, 1H, J=5, 1 Hz); $^{13}$C NMR ($CDCl_3$) δ 21.0, 22.9, 28.9, 37.4, 46.4, 48.6, 60.5, 115.0, 121.8, 122.2, 130.7, 131.6, 134.6, 137.4, 146.6, 154.2, 156.8. ES-MS m/z 348 (M+H). Anal. Calcd. for $C_{21}H_{25}N_5 \cdot 0.1CHCl_3 \cdot 0.8CH_4O$: C, 68.32; H, 7.41; N, 18.19. Found: C, 68.60; 14, 7.05; N, 17.82.

Example 75

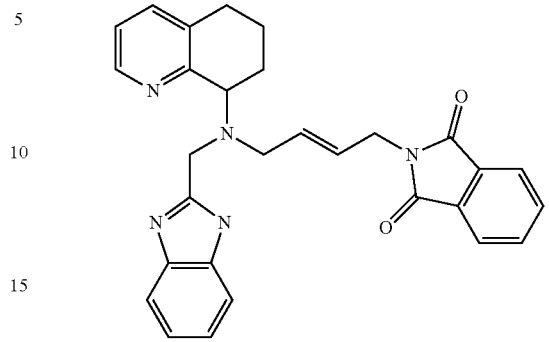

Compound 75: Preparation of 2-{4-[(1H-benzoimidazol-2-ylmethyl)-(5,6,7,8-tetrahydro-quinolin-8-yl)-amino]-(E)-but-2-enyl}-isoindole-1,3-dione

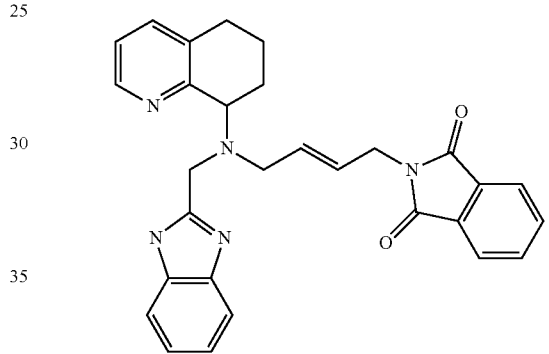

Preparation of 2-{[[(z)-4-(1,3-dioxo-1,3-dihydro-isoindol-2-yl)-but-2-enyl]-(5,6,7,8-tetrahydro-quinolin-8-yl)-amino]-methyl}-benzoimidazole-1-carboxylic acid tert-butyl ester Following the General Procedure for N-alkylation, (1H-N-tert-butoxycarbonyl-benzimidazol-2-ylmethyl)-(5,6,7,8-tetrahydroquinolin-8-yl)-amine (293 mg, 0.77 mmol) and (E)-N-(4-bromo-2-butenyl)phthalimide (prepared as described by Norman, M. H.; Minick, D. J.; Rigdon, G. C. *J. Med. Chem.* 1996, 39, 149-157) (260 mg, 0.93 mmol) were converted into the corresponding alkylation product using the following quantities of reagents and solvents: diisopropylethylamine (202 µL, 1.16 mmol), $CH_3CN$ (4 mL). The reaction time in this case was 18 h, while the reaction temperature was 40° C. The resulting crude material was purified by flash chromatography (silica gel, 20:2:1 $CH_2Cl_2$—MeOH—$NH_4OH$) to provide 360 mg (81%) of 2-{[[(Z)-4-(1,3-dioxo-1,3-dihydro-isoindol-2-yl)-but-2-enyl]-(5,6,7,8-tetrahydro-quinolin-8-yl)-amino]-methyl}-benzoimidazole-1-carboxylic acid tert-butyl ester. $^1$H NMR ($CDCl_3$) δ 1.67 (s, 9H), 1.68-1.70 (m, 1H), 1.79-1.91 (m, 1H), 1.93-2.04 (m, 1H), 2.14-2.19 (m, 1H), 2.59-2.79 (m, 2H), 3.33-3.48 (m, 2H), 4.00 (d, 2H, J=6 Hz), 4.25 (dd, 1H, J=10, 6 Hz), 4.42 (d, 1H, J=16 Hz), 4.60 (d, 1H, J=16 Hz), 5.29-5.57 (m, 1H), 5.65-5.74 (m, 1H), 6.95 (dd, 1H, J=7, 5 Hz), 7.17-7.25 (m, 3H), 7.63-7.72 (m, 3H), 7.74-7.80 (m, 3H), 8.37 (d, 1H, J=4 Hz).

2-{[[(Z)-4-(1,3-Dioxo-1,3-dihydro-isoindol-2-yl)-but-2-enyl]-(5,6,7,8-tetrahydro-quinolin-8-yl)-amino]-methyl}-benzoimidazole-1-carboxylic acid tert-butyl ester (150 mg, 0.26 mmol) was taken up in neat TFA (2 mL) and stirred 3 h. Saturated aqueous sodium bicarbonate (10 mL) was cautiously added, and the resulting mixture was extracted with $CH_2Cl_2$ (3×10 mL) then the combined organic extracts were dried ($MgSO_4$), and concentrated in vacuo. Purification of the crude material thus obtained by radial chromatography (silica gel, 1 mm plate, 50:1:1 $CH_2Cl_2$—MeOH—$NH_4OH$) afforded 102 mg (81%) of COMPOUND 75 as a white solid. $^1H$ NMR ($CDCl_3$) δ 1.66-1.71 (m, 1H), 1.84-1.97 (m, 2H), 2.13-2.15 (m, 1H), 2.66-2.79 (m, 2H), 3.22-3.26 (m, 2H), 3.99-4.07 (m, 3H), 4.13-4.16 (m, 2H), 5.67-5.71 (m, 2H), 7.10 (dd, 1H, J=8, 5 Hz), 7.14-7.20 (m, 2H), 7.36 (dd, 1H, J=8, 1 Hz), 7.43-7.62 (m, 2H), 7.64-7.69 (m, 2H), 7.74-7.79 (m, 2H), 8.56 (dd, 1H, J=5, 1 Hz); $^{13}C$ NMR ($CDCl_3$) δ 21.3, 24.0, 29.1, 39.1, 49.2, 52.0, 61.0, 110.9, 118.7, 121.6, 122.1, 123.2, 126.1, 132.0, 132.8, 133.9, 134.5, 137.2, 146.7, 156.3, 157.5, 167.8. ES-MS m/z 478 (M+H). Anal. Calcd. for $C_{29}H_{27}N_5O_2$·$0.2CH_2Cl_2$·$0.3H_2O$: C, 70.15; H, 5.64; N, 14.01. Found: C, 70.40; H, 5.73; N, 13.90.

Example 76

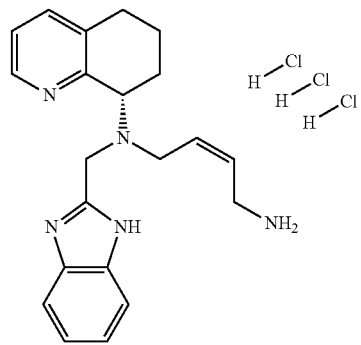

Compound 76: Preparation of (Z)-$N^1$-(1H-Benzimidazol-2-ylmethyl)-$N^1$-5,6,7,8-tetrahydro-quinolin-8-yl-but-2-ene-1,4-diamine (hydrochloride salt)

(Z)-4-chloro-2-butenylamine hydrochloride (3.88 g, 27.3 mmol), water (1 mL) and diisopropylethylamine (9.6 mL, 55.1 mmol) were dissolved in tetrahydrofuran (140 mL) and stirred for 5 min. under nitrogen. Di-tert-butyl dicarbonate (15.31 g, 70.1 mmol) was added and the mixture was stirred for an additional 4 h at 25° C. The mixture was concentrated and the residue dissolved in methylene chloride (100 mL) and washed with saturated sodium bicarbonate (80 mL). The aqueous layer was extracted with methylene chloride (2×50 mL). The combined organic layers were dried ($MgSO_4$) and concentrated to afford a brown oil which solidified on standing. Purification by column chromatography on silica gel afforded 6.4 g of a mixture of the desired product and di-tert-butyl dicarbonate. Recrystallization from hot hexanes afforded (4-chloro-but-2-enyl)-carbamic acid tert-butyl ester (3.27 g, 50%) as white crystals. $^1H$ NMR ($CDCl_3$) δ 1.45 (s, 9H), 3.83 (t, 2H, J=6.2 Hz), 4.12 (d, 2H, J=7.4 Hz), 4.58 (bs, 1H), 5.58-5.68 (m, 1H), 5.71-5.81 (m, 1H).

(4-Chloro-but-2-enyl)-carbamic acid tert-butyl ester (1.81 g, 7.47 mmol), potassium iodide (59 mg, 0.36 mmol) and diisopropylethylamine (1.80 mL, 10.3 mmol) were added to a solution of 2-[(5,6,7,8-tetrahydroquinolin-8-ylamino)-methyl]-benzimidazole-1-carboxylic acid tert-butyl ester (2.57 g, 6.79 mmol)) in acetonitrile (70 mL) and warmed to 60° C. and stirred for 17 h under nitrogen. The solvent was removed in vacuo. The residue was dissolved in methylene chloride (100 mL) and washed with brine (100 mL). The aqueous layer was extracted with methylene chloride (2×150 mL). The combined organic layers were dried ($Na_2SO_4$) and concentrated. The crude mixture was purified by column chromatography on silica gel (150 g) to afford 2-{[(S)-((Z)-4-tert-butoxycarbonylamino-but-2-enyl)-5,6,7,8-tetrahydro-quinolin-8-yl-amino]-methyl}-benzimidazole-1-carboxylic acid tert-butyl ester (5.99 g, 88%) as a white foamy solid. $^1H$ NMR ($CDCl_3$) δ 1.43 (s, 9H), 1.72 (s, 9H), 1.95-2.08 (m, 4H), 2.09-2.20 (m, 1H), 2.61 (d, 1H, J=16.2 Hz), 3.28 (dd, 1H, J=14.1, 5.4 Hz), 3.62 (dd, 1H, J=13.7, 7.2 Hz), 3.69-3.85 (m, 2H), 4.29 (dd, 1H, J=9.2, 6.6 Hz), 4.42 (d, 1H, J=14.9 Hz), 4.48 (d, 1H, J=14.9 Hz), 5.43-5.63 (m, 2H), 6.19 (s, 1H), 6.87 (dd, 1H, J=7.5, 4.8 Hz), 7.17 (d, 1H, J=7.7 Hz), 7.23-7.28 (m, 1H), 7.65-7.71 (m, 1H), 7.75-7.80 (m, 1H), 8.34 (d, 1H, J=4.4 Hz).

2-{[(S)-((Z)-4-tert-Butoxycarbonylamino-but-2-enyl)-5,6,7,8-tetrahydro-quinolin-8-yl-amino]-methyl}-benzimidazole-1-carboxylic acid tert-butyl ester was dissolved in acetic acid (15 mL) and hydrogen chloride gas was bubbled through the solution for 10 min. The mixture was stirred for an additional 60 min. then diluted with acetic acid (15 mL). The acetic acid solution was added dropwise, over to a flask containing of diethyl ether (600 mL), stirred rapidly, where a white fluffy precipitate formed. The ether mixture was allowed to settle and decanted. The slurry was washed with ether (3×500 mL) and then the precipitate was collected on a glass frit and rinsed thoroughly with ether. The frit was placed into a vacuum oven (40° C.) for 18 h to afford COMPOUND 76 as a light pink solid (2.20 g, 72%). $^1H$ NMR ($D_2O$) δ 1.75-1.88 (m, 1H), 1.98-2.11 (m, 1H), 2.17-2.22 (m, 1H), 2.37-2.42 (m, 1H), 3.00 (dd, 2H, J=7.8, 3.9 Hz), 3.25 (dd, 1H, J=14.7, 4.4 Hz), 3.58-3.65 (m, 3H), 4.4.32 (d, 1H, J=16.5 Hz), 4.46-4.55 (m, 2H), 5.43-5.53 (m, 1H), 5.77-5.86 (m, 1H), 7.55-7.62 (m, 2H), 7.74-7.81 (m, 2H), 7.84 (dd, 1H, J=7.9, 5.9 Hz), 8.33 (d, 1H, J=7.8 Hz), 8.62 (d, 1H, J=5.4 Hz); $^{13}C$ NMR ($D_2O$) 20.35, 20.47, 27.61, 36.45, 48.00, 48.67, 60.52, 114.31 (2C), 124.75, 125.91, 126.81 (2C), 131.27, 132.58, 139.49, 140.64, 147.98, 150.92, 151.47. ES-MS m/z 348 (M+H). Anal. Calcd. for $C_{21}H_{25}N_5$·$3.1HCl$·$2.5H_2O$·$0.3Et_2O$: C, 50.70; H, 6.88; N, 13.32, Cl 20.90. Found: C 50.81, H 6.89, N 13.45, Cl 20.80.

The enantiomeric purity of COMPOUND 76 was determined to be 98% by chiral HPLC using the following conditions: Instrument: Hewlett Packard 1100 HPLC (VWD2); Column: ChiralPak AD, 4.6 cm×25 cm; Mobile Phases: A=90:10 hexanes/reagent alcohol with 0.1% DEA, B=reagent alcohol; Isocratic: 90% A, 10% B; Total Run Time: 40 min; Flow Rate: 0.5 mL/min; Temperature: 40° C.; Detector: UV @ 270 nm; Injection volume: 10 µL.

Retention time of the S enantiomer=21.4 min.
Retention time of the R enantiomer=14.3 min.

Example 77

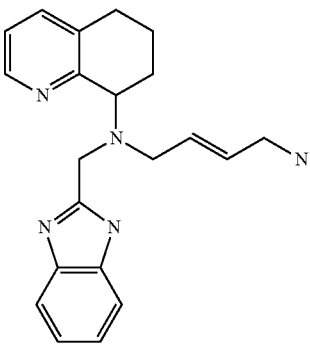 [SMILES: NC/C=C/CN(Cc1nc2ccccc2[nH]1)C1CCCc2cccnc21]

Compound 77: Preparation of N¹-(1H-benzoimidazol-2-ylmethyl)-N¹-(5,6,7,8-tetrahydro-quinolin-8-yl)-(E)-but-2-ene-1,4-diamine 2-{[[(Z)-4-(1,3-Dioxo-1,3-dihydro-isoindol-2-yl)-but-2-enyl]-(5,6,7,8-tetrahydro-quinolin-8-yl)-amino]-methyl}-benzoimidazole-1-carboxylic acid tert-butyl ester (prepared as described for COMPOUND 75) (200 mg, 0.35 mmol) was taken up in EtOH (3 mL) and hydrazine monohydrate (0.5 mL, 10 mmol) was added. The resulting mixture was heated to reflux for 18 h, at which point saturated aqueous sodium bicarbonate (15 mL) was added, and the resulting mixture was extracted with CH$_2$Cl$_2$ (3×20 mL) then the combined organic extracts were dried (MgSO$_4$), and concentrated in vacuo. Purification of the crude material thus obtained by radial chromatography (silica gel, 1 mm plate, 50:1:1 CH$_2$Cl$_2$—MeOH—NH$_4$OH) afforded 53 mg (44%) of COMPOUND 77 as a white solid. $^1$H NMR (CDCl$_3$) δ 1.47-1.71 (m, 3H), 1.89-2.08 (m, 2H), 2.18-2.20 (m, 1H), 2.74-2.83 (m, 2H), 3.13 (d, 2H, J=6 Hz), 3.25-3.27 (m, 2H), 4.06-4.10 (m, 3H), 5.46 (dt, 1H, J=15, 6 Hz), 5.71 (dt, 1H, J=15, 6 Hz), 7.12-7.21 (m, 3H), 7.41 (d, 1H, J=8 Hz), 7.50-7.58 (m, 2H), 8.60 (dd, 1H, J=5, 1 Hz); $^{13}$C NMR (CDCl$_3$) δ 21.3, 23.6, 29.2, 43.1, 48.8, 52.5, 61.3, 114.3, 121.5, 122.1, 128.5, 133.4, 134.6, 137.3, 146.7, 156.4, 157.5. ES-MS m/z 348 (M+H). Anal. Calcd. for C$_{21}$H$_{25}$N$_5$.0.2CH$_2$Cl$_2$.0.9CH$_4$O: C, 67.49; H, 7.43; N, 17.81. Found: C, 67.59; H, 7.31; N, 17.46.

Example 78

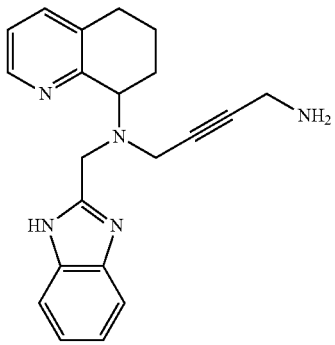 [SMILES: NCC#CCN(Cc1nc2ccccc2[nH]1)C1CCCc2cccnc21]

Compound 78: Preparation of N¹-(1H-benzimidazol-2-ylmethyl)-N¹-(5,6,7,8-tetrahydro-quinolin-8-yl)-but-2-yne-1,4-diamine Preparation of (4-chlorobut-2-ynyl)carbamic acid tert-butyl ester To a stirred mixture of 1-amino-4-chloro-2-butyne hydrochloride (1.12 g, 8.01 mmol) and Boc$_2$O (2.12 g, 9.71 mmol) in a solution of THF (40 mL) and H$_2$O (15 drops) was added DIPEA (3.1 mL, 17.8 mmol). The resultant solution was stirred at room temperature for 4.5 hours. Saturated aqueous NaHCO$_3$ (20 mL) was added, the layers were separated and the aqueous solution was extracted with Et$_2$O (25 mL×2). The combined organic extracts were dried (Na$_2$SO$_4$), filtered and concentrated under reduced pressure. Purification by flash column chromatography on silica gel (hexane/EtOAc, 7:3) gave the Boc-protected amine as an off-white solid (1.38 g, 6.79 mmol, 85%). $^1$H NMR (CDCl$_3$) δ 1.44 (s, 9H), 3.97 (d, 2H, J=4.5 Hz), 4.13 (t, 2H, J=2.1 Hz), 4.74 (br. s, 1H).

Preparation of 2-{[(4-tert-butoxycarbonylamino-2-butynyl)-(5,6,7,8-tetrahydroquinolin-8-yl)-amino]-methyl}-benzimidazole-1-carboxylic acid tert-butyl ester A solution of the chloride from above (182 mg, 0.89 mmol), (1-tert-butoxycarbonyl-1H-benzimidazol-2-ylmethyl)-(5,6,7,8-tetrahydro-quinolin-8-yl)-amine (285 mg, 0.75 mmol), DIPEA (0.20 mL, 1.2 mmol) and catalytic KI (8 mg, 0.05 mmol) in CH$_3$CN was heated at 60° C. for 17 hours. Saturated aqueous NaHCO$_3$ (10 mL) was added and the mixture was extracted with CH$_2$Cl$_2$ (25 mL×3). The organic solution was dried (MgSO$_4$), filtered and evaporated under reduced pressure. Purification by flash column chromatography on silica (CH$_2$Cl$_2$/MeOH/NH$_4$OH, 9:1:0.1) gave the tertiary amine as a pale brown foam (374 mg, 0.69 mmol, 91%). $^1$H NMR (CDCl$_3$) δ 1.43 (s, 9H), 1.67 (s, 9H), 1.97-2.14 (m, 4H), 2.61-2.73 (m, 1H), 2.75-2.88 (m, 1H), 3.61-3.80 (m, 4H), 4.31 (dd, 1H, J=7.8, 5.6 Hz), 4.45 (d, 1H, J=15.9 Hz), 4.54 (d, 1H, J=15.9 Hz), 4.63 (br. s, 1H), 7.01 (dd, 1H, J=7.5, 4.8 Hz), 7.27-7.34 (m, 3H), 7.72 (dd, 1H, J=6.0, 3.0 Hz), 7.83 (dd, 1H, J=6.0, 3.3 Hz), 8.39 (d, 1H, J=3.3 Hz).

Preparation of Compound 78

The di-Boc protected amine (365 mg, 0.67 mmol) was stirred in TFA (6 mL) at room temperature for 1.5 hours. Saturated aqueous NaHCO$_3$ (approx. 100 mL) was added until the mixture was neutral and the aqueous solution was extracted with CH$_2$Cl$_2$ (50 mL×3). The organic solution was dried (Na$_2$SO$_4$), filtered and concentrated under reduced pressure. Purification by flash column chromatography on silica gel (CH$_2$Cl$_2$/MeOH/NH$_4$OH, 19:1:0.1) gave COMPOUND 78 as a beige foam (90.4 mg, 0.26 mmol, 39%). $^1$H NMR (CDCl$_3$) δ 1.65-1.79 (m, 1H), 1.94-2.14 (m, 2H), 2.16-2.28 (m, 1H), 2.69-2.81 (m, 1H), 2.81-2.95 (m, 1H), 3.21 (s, 2H), 3.54 (d, 2H, J=2.1 Hz), 4.04 (d, 1H, J=16.2 Hz), 4.15 (d, 1H, J=16.2 Hz), 7.14-7.23 (m, 3H), 7.45 (d, 1H, J=7.5 Hz), 7.54-7.64 (m, 2H), 8.58 (d, 1H, J=4.3 Hz). $^{13}$C NMR (CDCl$_3$) δ 21.1, 24.6, 29.3, 31.9, 41.0, 49.9, 61.6, 79.2, 85.8, 122.1, 122.8, 135.0, 137.9, 147.0, 155.5, 157.4. ES-MS m/z 346 (M+H). Anal. Calcd. for C$_{21}$H$_{23}$N$_5$.0.2CH$_2$Cl$_2$.0.1C$_4$H$_{10}$O: C, 70.15; H, 6.65; N, 18.94. Found: C, 69.97; H, 6.85; N, 18.96.

Example 79

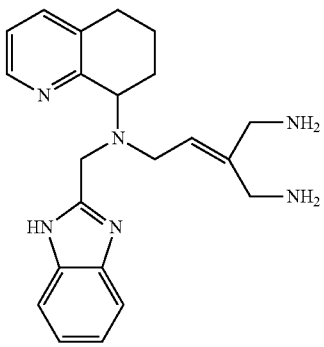 [SMILES: NCC(=CCN(Cc1nc2ccccc2[nH]1)C1CCCc2cccnc21)CN]

Compound 79: 3-Aminomethyl-N'-(1H-benzimidazol-2-ylmethyl)-N'-(5,6,7,8-tetrahydro-quinolin-8-yl)-but-2-ene-1,4-diamine (hydrobromide salt)

Preparation of (3-tert-Butoxycarbonylamino-2-oxo-propyl)-carbamic acid tert-butyl ester To a suspension of 1,3-diamino-2-hydroxypropane (2.43 g, 0.027 mol) in THF/H$_2$O (15:1, 80 mL) was added di-tert-butyl dicarbonate (11.77 g, 0.054 mol) and the reaction stirred for 2.5 h then concentrated in vacuo.

To a solution of oxalyl chloride in CH$_2$Cl$_2$ (2.0 M, 7.7 mL, 15.4 mmol) at −78° C. was added a solution of DMSO (1.7 ml, 24.0 mmol) in CH$_2$Cl$_2$ (12 mL) and the mixture allowed to stir for 30 min. at −78° C., after which the crude alcohol from above (2.86 g) in CH$_2$Cl$_2$ (10 ml) was added dropwise. Stirring was continued for 15 min. and then Et$_3$N (5.0 ml, 35.9 mmol) was added dropwise. The cooling bath was removed, stirring was continued for 1.5 h, and the mixture was diluted with CH$_2$Cl$_2$ (20 ml) and water (30 mL). The aqueous layer was extracted with CH$_2$Cl$_2$ (20 ml) and the combined organic extracts were washed with brine (30 mL), dried over Na$_2$SO$_4$ and concentrated. Evaporation of the solvent and purification of the residue by flash chromatography on silica gel, using 40% ethyl acetate in CH$_2$Cl$_2$, gave the title compound (350 mg, 16% over 2 steps) as a beige solid. $^1$H NMR (CDCl$_3$) δ 1.42 (s, 18H), 4.03 (br d, 4H, J=6 Hz), 5.26 (br s, 2H).

Preparation of (4-tert-butoxycarbonylamino-3-(tert-butoxycarbonylamino-methyl)-but-2-enoic acid ethyl ester To a solution of (3-tert-butoxycarbonylamino-2-oxo-propyl)-carbamic acid tert-butyl ester (310 mg, 1.08 mmol) in benzene (20 mL) was added (carbethoxymethylene)-triphenyl phosphorane (825 mg, 2.37 mmol) and the reaction mixture was stirred at 45° C. overnight. Then the mixture was cooled to room temperature and the solvent concentrated down. Purification by radical chromatography on silica gel (2 mm plate, using CH$_2$Cl$_2$) afforded the desired compound as a yellow oil (290 mg, 75%). $^1$H NMR (CDCl$_3$) δ 1.26 (t, 3H, J=9.0 Hz), 1.42 (s, 18H), 3.87 (d, 2H, J=6.0 Hz), 4.09 (d, 2H, J=6.0 Hz), 4.15 (q, 2H, J=9.0 Hz), 5.34 (br s, 1H), 5.85 (s, 1H), 7.34 (s, 1H).

Preparation of [2-(tert-butoxycarbonylaminomethyl)-4-hydroxy-but-2-enyl]-carbamic acid tert-butyl ester To a solution of the above ester (290 mg, 0.81 mmol) in THF (10 mL) was added DIBAL (1.0 M in CH$_2$Cl$_2$) (2.4 mL, 2.42 mmol) at −78° C. The temperature was increased to room temperature after 40 minutes. After 1 hour, the reaction was quenched with Rochelle's salt (10 mL) and was stirred overnight. Then it was extracted with CH$_2$Cl$_2$ (3×10 mL). The combined organic extracts were dried (Na$_2$SO$_4$), filtered, concentrated, and dried in vacuo to afford a yellow oil. Purification by flash column chromatography on silica gel using 50% hexanes/ethyl acetate afforded the desired product as a pale yellow oil (210 mg, 83%). $^1$H NMR (CDCl$_3$) δ 1.42 (s, 10H), 1.85 (br t, 1H), 3.89 (d, 4H, J=9.0 Hz), 4.15 (t, 2H, J=7.5 Hz), 4.75 (br t, 1H), 5.55 (br s, 1H), 5.78 (t, 1H, J=7.5 Hz).

Preparation of 2-{[[4-tert-butoxycarbonylamino-3-(tert-butoxycarbonylamino-methyl)-but-2-enyl]-(5,6,7,8-tetrahydro-quinolin-8-yl)-amino]-methyl}-benzimidazole-1-carboxylic acid tert-butyl ester To a solution of the above alcohol (107 mg, 0.34 mmol) and triethylamine (70 µL, 0.41 mmol) in CH$_2$Cl$_2$ was added methanesulfonyl chloride (30 µL, 0.41 mmol) at 0° C. After 20 minutes at that temperature, the reaction mixture was quenched with saturated NH$_4$Cl (10 mL). The organic layer was washed with saturated NH$_4$Cl (2×10 mL), dried (Na$_2$SO$_4$), filtered, concentrated, and dried in vacuo to afford a yellow oil (150 mg). This was used without further purification. $^1$H NMR (CDCl$_3$) δ 1.43 (s, 18H), 3.02 (s, 3H), 3.76 (t, 4H, J=6.0 Hz), 4.89 (d, 2H, J=6.0 Hz), 4.90 (br s, 1H), 4.99 (br s, 1H), 5.64 (t, 1H, J=6.0 Hz).

The above mesylate (150 mg, 0.43 mmol), 2-[(5,6,7,8-tetrahydro-quinolin-8-ylamino)-methyl]-benzimidazole-1-carboxylic acid tert-butyl ester (195 mg, 0.52 mmol), N,N-diisopropylethylamine (90 mL, 0.52 mmol), and potassium iodide (7 mg, 0.04 mmol) in CH$_3$CN (10 mL) was stirred at 40° C. for three days. Then the solvent was concentrated down and the residue was dissolved in CH$_2$Cl$_2$ (15 mL). The organic layer was extracted with saturated NaHCO$_3$ (3×15 mL), dried (MgSO$_4$), filtered, concentrated, and dried in vacuo to afford a yellow oil. Purification by four attempts at radial chromatography on silica gel (2 mm plate, using CH$_3$OH/NH$_4$OH/CH$_2$Cl$_2$ (0:1:99→4:1:95); 1 mm plate, using CH$_3$OH/NH$_4$OH/CH$_2$Cl$_2$ (0:1:99→2:1:97); 1 mm plate, using ethyl acetate; 1 mm plate, using CH$_3$OH/NH$_4$OH/CH$_2$Cl$_2$ (1:1:100)) afforded the desired compound as a while foam (39 mg, 13%). 111NMR (CDCl$_3$) δ 1.38 (s, 9H), 1.43 (s, 9H), 1.70 (s, 9H), 2.04-2.11 (m, 3H), 2.56 (d, 1H, J=16.2 Hz), 2.77 (br t, 1H), 3.22 (dd, 1H, J=13.7, 6.2 Hz), 3.39 (dd, 1H, J=15.6, 5.4 Hz), 3.49-3.58 (m, 2H), 3.76 (dd, 1H, J=14.1, 8.1 Hz), 3.96 (dd, 1H, J=14.1, 4.2 Hz), 4.22 (t, 1H, J=8.1 Hz), 4.39 (ABq, 2H, J=38.4, 14.4 Hz), 5.20 (br m, 1H), 5.47 (br m, 1H), 6.72 (dd, 1H, J=7.5, 4.8 Hz), 7.04 (d, 1H, J=7.2 Hz), 7.20-7.25 (m, 3H), 7.54-7.62 (m, 2H), 7.69-7.72 (m, 1H), 8.25 (d, 1H, J=3.9 Hz).

Preparation of 3-aminomethyl-N'-(1H-benzimidazol-2-ylmethyl)-N'-(5,6,7,8-tetrahydro-quinolin-8-yl)-but-2-ene-1,4-diamine (hydrobromide salt)

To a solution of the above diamine (39 mg, 0.06 mmol) in acetic acid (1 mL) was added a hydrobromic acid saturated acetic acid (0.5 mL) and the reaction mixture was stirred for 20 minutes. Then diethyl ether was added until the precipitation of COMPOUND 79 was afforded as a pink solid (20 mg, 30%). $^1$H NMR (D$_2$O) δ 1.76-1.84 (m, 1H), 2.16-2.21 (m, 1H), 2.37-2.41 (m, 1H), 2.98 (br d, 2H, J=5.1 Hz), 3.41 (dm, 1H, J=15.0 Hz), 3.68-3.70 (m, 3H), 3.76-3.85 (m, 2H), 4.26-4.46 (m, 3H), 6.23 (dd, 1H, J=10.8, 4.2 Hz), 7.56-7.60 (m, 2H), 7.73-7.84 (m, 3H), 8.30 (d, 1H, J=7.5 Hz), 8.59 (d, 1H), J=6.0 Hz). $^{13}$C NMR (D$_2$O) δ 20.22, 20.30, 27.59, 37.12, 42.32, 46.68, 48.91, 59.19, 114.28, 126.03, 127.04, 128.73, 131.00, 136.26, 139.60, 140.88, 148.14, 150.51. ES-MS m/z 399 [M+H]$^+$, 399 [M+Na]$^+$. Anal. Calcd. for C$_{22}$H$_{28}$N$_6$.4.2HBr.2.2H$_2$O.0.6C$_4$H$_{10}$O: C, 36.61; H, 5.36; N, 10.50; Br, 41.93. Found: C, 36.68; H, 5.08; N, 10.48; Br, 41.87.

Example 80

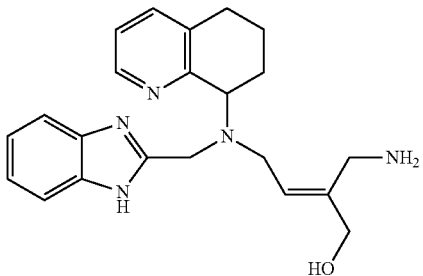 [SMILES: NC/C(=C\CN(Cc1nc2ccccc2[nH]1)C1CCCc2cccnc21)CO]

Compound 80: Preparation of (E)-2-aminomethyl-4-[(1H-benzimidazol-2-yl-methyl)-(5,6,7,8-tetrahydro-quinolin-8-yl)-amino]-but-2-en-1-ol To a solution of 3-amino-1,2 propanediol (7.75 g, 0.085 mmol) in THF (430 mL) was added water (20 mL) followed by tert-butyl dicarbonate (19.60 g, 0.0898 mmol) in one portion. The solution was stirred at room temperature for 23 hours. The solvent was removed under reduced pressure and the residue was dissolved in EtOAc (100 mL) and saturated sodium carbonate (100 mL). The phases were separated and the aqueous phase was extracted with ethyl acetate (3×75 mL). The combined organic extracts were dried over sodium sulfate, filtered, concentrated to give (1,2-dihydroxy-ethyl)-carbamic acid tert-butyl ester as a crude white solid (15 g, 92%).

To a solution of crude from above (494 mg, 2.6 mmol) in CH$_2$Cl$_2$ (13 mL) was added imidazole (236 mg, 3.5 mmol) followed by TBDMS-Cl (410 mg, 2.7 mmol) and the reaction was stirred at room temperature overnight. The reaction mixture was diluted with CH$_2$Cl$_2$ (40 mL) and saturated aqueous sodium bicarbonate (40 mL). The phases were separated and the aqueous layer was extracted with CH$_2$Cl$_2$ (3×30 mL). The combined organic extracts were dried over sodium sulfate, filtered and concentrated. Purification of the crude material by column chromatography (15 g silica, 8:1 hexanes/EtOAc) gave [2-(tert-butyl-dimethyl-silanyloxy)-1-hydroxy-ethyl]-carbamic acid tert-butyl ester as a colorless oil (555 mg, 70%). $^1$H NMR (CDCl$_3$) δ: 4.96 (broad s, 1H), 3.74-3.71 (m, 1H), 3.67-3.62 (m, 1H), 3.56-3.50 (m, 1H), 1.44 (s, 9H), 0.90 (s, 9H), 0.07 (s, 6H).

To a solution of the above material (555 mg, 1.81 mmol) in CH$_2$Cl$_2$ (9 mL) was added NMO (324 mg, 2.77 mmol), followed by 3 Å molecular sieves (960 mg) and TPAP (62 mg, 0.18 mmol). The green-black solution was stirred at room temperature for 2 hours. TLC (2:1 hexane/EtOAc-stained in ninhydrin) monitored the reaction. The reaction mixture was filtered through a cake of silica gel and the cake was washed with ethyl acetate. The filtrate was concentrated to provide crude [2-(tert-butyl-dimethyl-silanyloxy)-acetyl]carbamic acid tert-butyl ester as a yellow oil (458 mg, 83%).

Preparation of 3-tert-butoxycarbonylamino-4-(tert-butyl-dimethyl-silanyloxy)-but-2-enoic acid ethyl ester To the ketone from above (458 mg, 1.51 mmol) in benzene (8 mL) was added (carbethoxymethylene)triphenyl phosphorane (815 mg, 2.35 mmol). The reaction mixture was heated to ~40-45° C. and stirred at this temperature overnight. The reaction mixture was then concentrated and the residue purified by column chromatography (25 g silica, 25:1 hexane/EtOAc) to give two yellow oils (cis/trans isomers) as major products (430 mg total, 76%). $^1$H NMR of trans-isomer (CDCl$_3$) δ: 6.06 (s, 1H), 5.41 (broad s, 1H), 4.31 (s, 2H), 4.18 (q, 2H, J=7.5 Hz), 3.94 (d, 2H, J=7.0 Hz), 1.42 (s, 9H), 1.30 (t, 3H, J=7.5 Hz), 0.92 (s, 9H), 0.07 (s, 6H). $^1$H NMR of cis-isomer (CDCl$_3$) δ: 5.78 (s, 1H), 4.87 (s, 2H), 4.14 (q, 2H, J=7.5 Hz), 4.00 (d, 2H, J=7.0 Hz), 1.45 (s, 9H), 1.27 (t, 3H, J=7.5 Hz), 0.91 (s, 9H), 0.09 (s, 6H).

To a solution of Trans-3-tert-butoxycarbonylamino-4-(tert-butyl-dimethyl-silanyloxy)-but-2-enoic acid ethyl ester (0.66 g, 1.8 mmol) in dichloromethane (18 mL) added a solution of DIBAL-H (8.8 mL, 1.0 M in CH$_2$Cl$_2$, 8.8 mmol) at 0° C. The solution was allowed to stir for 1 h while warming to room temperature. Saturated potassium sodium tartrate solution (20 mL) was then added and the solution stirred for another hour. The phases were separated and the organic phase dried (MgSO$_4$), filtered and concentrated under reduced pressure to give, after column chromatography (1:3 ethyl acetate/hexane), trans-[2-(tert-butyl-dimethyl-silanyloxymethyl)-4-hydroxy-but-2-enyl]-carbamic acid tert-butyl ester (0.255 g, 39%).

Methanesulfonyl chloride (65 µL, 0.8 mmol) and triethylamine (0.15 mL, 1.0 mmol) was added to a solution of the above alcohol (0.23 g, 0.7 mmol) in dichloromethane (7.0 mL) at room temperature and stirred 0.5 hours. This gave, after aqueous work up, the crude allylic methanesulfonate (0.25 g, 80%) as a pale yellow crystalline solid.

Using general procedure D from above, the above methanesulfonate (0.25 g, 0.7 mmol), (N-tert-butoxycarbonylbenzimidazol-2-ylmethyl)-(5,6,7,8-tetrahydroquinolin-8-yl)-amine (0.26 g, 0.70 mmol) and potassium iodide (6 mg, 35 µmol) were stirred at 60° C. in acetonitrile (7.0 mL) and diisopropylethylamine (0.18 mL, 1.0 mmol)) for 16 hours to yield, after work-up and column chromatography (2.5:97.5 MeOH/CH$_2$Cl$_2$), the desired alkylated E-regioisomer (0.200 g, 42%).

A solution of the above compound (0.20 g, 0.30 mmol) in THF (1.0 mL) was treated with TBAF (0.6 mL, 1.0 M in THF, 0.6 mmol) for 0.5 hours. This gave, after column chromatography (1:99 MeOH/CH$_2$Cl$_2$), the di-boc-protected E-2-{[[3-(tert-butoxycarbonylaminomethyl)-4-hydroxy-but-2-enyl]-(5,6,7,8-tetrahydroquinolin-8-yl)-amino]-methyl}-benzimidazole-1-carboxylic acid tert-butyl ester (60 mg, 38%). $^1$H NMR (CDCl$_3$) δ 1.41 (s, 9H), 1.65 (br, 1H), 1.69 (s, 9H), 2.11 (m, 3H), 2.60 (m, 1H), 2.77 (m, 1H), 3.27 (m, 1H), 3.60 (m, 1H), 3.88 (m, 3H), 4.07 (m, 1H), 4.23 (m, 1H), 4.29 (d, 1H, J=15.0 Hz), 4.46 (d, 1H, J=15.0 Hz), 5.50 (m, 1H), 6.74 (m, 1H), 7.05 (d, 1H, J=6.0 Hz), 7.24 (m, 2H), 7.59 (m, 1H), 7.70 (m, 2H), 8.26 (d, 1H, J=3.0 Hz).

The above material (60 mg, 0.11 mmol) was then dissolved in neat TFA (1 mL) and stirred for 1 hour. CH$_2$Cl$_2$ (10 mL)

and 15% aqueous NaOH was added until pH=13. The organic phase was separated and the aqueous phase was extracted with CH$_2$Cl$_2$ (2×5 mL). The combined organic phases were then dried (MgSO$_4$), filtered, and concentrated under reduced pressure to provide COMPOUND 80 free base as a pale yellow free flowing powder (14 mg, 10%). $^1$H NMR (CDCl$_3$) δ 1.66 (br, 1H), 1.85 (m, 1H), 2.00 (br, 1H), 2.17 (br, 1H), 2.80 (m, 3H), 3.19 (m, 1H), 3.30 (m, 1H), 3.36 (s, 2H), 3.90 (d, 1H, J=15.0 Hz), 4.01 (d, 1H, J=18.0 Hz), 4.10 (br, 3H), 5.64 (m, 1H), 7.09 (m, 1H), 7.15 (m, 2H), 7.40 (d, 1H, J=9.0 Hz), 7.54 (br, 2H), 8.49 (d, 1H, J=3.0 Hz); $^{13}$C NMR (CDCl$_3$) δ 21.46, 23.21, 29.47, 39.86, 47.47, 49.46, 61.34, 67.08, 115.11 (3C), 122.165 (2C), 122.62, 126.31 (2C), 135.25, 137.97, 142.19, 147.02, 155.11, 157.26. ES-MS m/z 378 (M+H). Anal. Calcd. for C$_{22}$H$_{27}$N$_5$O.0.7CH$_2$Cl$_2$: C, 62.40; H, 6.55; N, 16.03. Found: C, 62.70; H, 6.70; N, 15.97.

Example 81

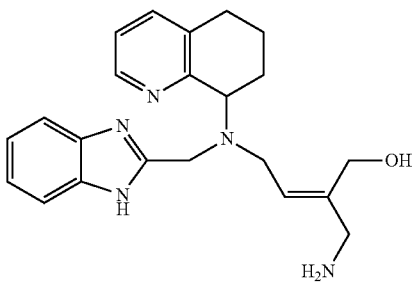 [SMILES: NC/C(=C/CN(Cc1nc2ccccc2[nH]1)C1CCCc2cccnc21)CO]

Compound 81: Preparation of (Z)-2-aminomethyl-4-[(1H-benzimidazol-2-yl-methyl)-(5,6,7,8-tetrahydroquinolin-8-yl)-amino]-but-2-en-1-ol To a solution of cis-3-tert-butoxycarbonylamino-4-(tert-butyl-dimethyl-silanyloxy)-but-2-enoic acid ethyl ester (0.49 g, 1.3 mmol) in dichloromethane (13 mL) was added a solution of DIBAL-H (6.5 mL, 1.0 M in CH$_2$Cl$_2$, 6.5 mmol) at 0° C. The solution was allowed to stir for 1 h while warming to room temperature. Saturated potassium sodium tartrate solution (15 mL) was then added and the solution stirred for another hour. The phases were separated and the organic phase dried (MgSO$_4$), filtered and concentrated to give the crude cis-[2-(tert-butyl-dimethyl-silanyloxymethyl)-4-hydroxy-but-2-enyl]-carbamic acid tert-butyl ester (0.33 g, 77%).

Methanesulfonyl chloride (39 μL, 0.42 mmol) and triethylamine (0.090 mL, 0.63 mmol) was added to a solution of the above alcohol (0.14 g, 0.42 mmol) in dichloromethane (4.2 mL) at room temperature and stirred 0.5 hours. This gave, after aqueous work up, the crude allylic methanesulfonate (0.14 g) which was used immediately in the next reaction.

Using the general procedure for N-alkylation, the methanesulfonate (0.14 g, 0.42 mmol), (N-tert-butoxycarbonyl-benzimidazol-2-ylmethyl)-(5,6,7,8-tetrahydroquinolin-8-yl)-amine (0.16 g, 0.42 mmol) and potassium iodide (3 mg, 21 μmol) were stirred at 60° C. in acetonitrile (4.2 mL) and diisopropylethylamine (0.11 mL, 0.63 mmol)) for 16 hours to yield, after work-up and column chromatography (1:99 MeOH/CH$_2$Cl$_2$), the desired alkylated Z-regioisomer (0.100 g, 34%).

A solution of the above compound (0.10 g, 0.16 mmol) in THF (2 mL) and 3N HCl (2 mL) was stirred for 1.5 hours. The solution was then cooled to 0° C. and 15% aqueous sodium hydroxide was added until the pH=12. The aqueous phase was then extracted with CH$_2$Cl$_2$ (3×15 mL) and the combined organic phases were dried (MgSO$_4$), filtered and concentrated under reduced pressure. This gave, after radial chromatography (8:2.5:89.5 MeOH/NH$_4$OH/CH$_2$Cl$_2$), Z-{4-[(1H-benzimidazol-2-yl-methyl)-(5,6,7,8-tetrahydroquinolin-8-yl)-amino]-2-hydroxymethyl-but-2-enyl}-carbamic acid tert-butyl ester (35 mg, 58%). $^1$H NMR (CDCl$_3$) δ 1.40 (s, 9H), 1.77 (br, 1H), 1.97 (m, 1H), 2.10 (m, 3H), 2.80 (m, 2H), 3.27 (m, 2H), 3.64 (br, 2H), 3.72 (d, 1H, J=15.0 Hz), 3.92 (d, 1H, J=15.0 Hz), 4.02 (s, 2H), 4.12 (m, 1H), 4.58 (m, NH), 7.18 (m, 3H), 7.50 (m, 2H), 7.68 (br, 1H), 8.52 (d, 1H, J=3.0 Hz).

The above compound (35 mg, 0.07 mmol) was then dissolved in neat TFA (1 mL) and stirred for 1 hour. CH$_2$Cl$_2$ (10 mL) and 15% aqueous NaOH was added until pH=12. The organic phase was separated and the aqueous phase was extracted with CH$_2$Cl$_2$ (2×5 mL). The combined organic phases were dried (MgSO$_4$), filtered, and concentrated under reduced pressure. This afforded, after radial chromatography (8:2.5:89.5 MeOH/NH$_4$OH/CH$_2$Cl$_2$), COMPOUND 81 free base as a pale yellow free flowing powder (18 mg, 68%). $^1$H NMR (CDCl$_3$) δ 1.75 (br, 1H), 1.94 (m, 1H), 2.08 (br, 2H), 2.85 (m, 3H), 3.30 (m, 4H), 3.78 (d, 1H, J=14.4 Hz), 3.95 (d, 1H, J=15.6 Hz), 4.11 (d 2H), 4.15 (m, 1H), 5.48 (m, 1H), 7.19 (m, 3H), 7.46 (d, 1H, J=7.2 Hz), 7.58 (br, 2H), 8.53 (d, 1H, J=3.3 Hz); $^{13}$C NMR (CDCl$_3$) δ 20.88, 23.54, 29.20, 47.22, 47.74, 49.28, 59.50, 61.77, 115.24 (3C), 122.42 (2C), 122.82, 125.40 (2C), 135.27, 138.23, 143.73, 146.88, 155.01, 157.26. ES-MS m/z 378 (M+H). Anal. Calcd. for C$_{22}$H$_{27}$N$_5$O.0.7CH$_2$Cl$_2$.0.2C$_6$H$_{12}$: C, 63.26; H, 6.84; N, 15.43. Found: C, 63.36; H, 6.79; N, 15.59.

Example 82

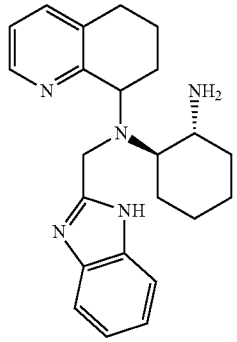 [SMILES: N[C@@H]1CCCC[C@H]1N(Cc1nc2ccccc2[nH]1)C1CCCc2cccnc21]

Compound 82: Preparation of N$^1$-(1H-Benzimidazol-2-ylmethyl)-N$^1$-(5,6,7,8-tetrahydro-quinolin-8-yl)-cyclohexane-trans-1,2-diamine (hydrobromide salt)

Preparation of N-(2-nitrobenzenesulfonyl)-7-azabicyclo[4.1.0]heptane (N-(2-nitrobenzenesulfonyl)-1,2-cyclohexeneaziridine)

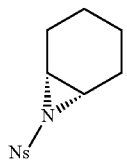

A solution of trans-2-aminocyclohexanol hydrochloride (1.185 g, 7.81 mmol) and 2-nitrobenzenesulfonyl chloride (1.73 g, 7.81 mmol) in CH$_2$Cl$_2$ (20 mL) was cooled in an ice bath under a nitrogen atmosphere while Et$_3$N (2.40 mL, 17.2 mmol) was added. The mixture was heated at reflux for 35 minutes, then concentrated in vacuo. Water (100 mL) was added to the residue, and the mixture was extracted with EtOAc (100 mL). The organic extract was washed with brine (2×30 mL), then dried (MgSO$_4$), filtered and concentrated in vacuo to give a green foam (2.32 g).

A solution of the foam from above and Et$_3$N (1.3 mL, 9.3 mmol) in CH$_2$Cl$_2$ (15 mL) was stirred at −78° C. under argon while methanesulfonyl chloride (0.66 mL, 8.5 mmol) was added. The mixture was stirred at −78° C. for 10 minutes, then the cold bath was removed and stirring was continued at room temperature for 30 minutes and the solution was then concentrated in vacuo. Water (30 mL) and saturated NaHCO$_3$(aq) (30 mL) were added to the residue, and the mixture was extracted with EtOAc (1×50 mL, 3×20 mL). The combined organic extracts were dried (MgSO$_4$) and concentrated in vacuo to give the crude mesylate as a light yellow solid (2.65 g).

The crude mesylate (2.65 g, 7.0 mmol) was stirred as a suspension in toluene (30 mL) at room temperature while a solution of 85% KOH (2.01 g, 35.9 mmol) in H$_2$O (12 mL) was added. The mixture was stirred for 40 minutes then diluted with EtOAc (50 mL) and brine (40 mL). The aqueous phase was separated and washed with EtOAc (1×40 mL) then dried (Na$_2$SO$_4$), filtered and concentrated in vacuo. The residue was purified by column chromatography on silica gel (25% EtOAc/hexanes) to give the desired aziridine as colorless crystals (1.54 g, 71% over 3 steps). $^1$H NMR (CDCl$_3$) δ 1.23-1.30 (m, 2H), 1.35-1.42 (m, 2H), 1.84-1.93 (m, 4H), 3.22 (dd, 2H, J=6, 1 Hz), 7.72-7.76 (m, 3H), 8.18-8.20 (m, 1H).

A solution of N-(2-nitrobenzenesulfonyl)-1,2-cyclohexeneaziridine from above (341 mg, 1.21 mmol), (1-tert-butoxycarbonyl-1H-benzimidazol-2-ylmethyl)-(5,6,7,8-tetrahydro-quinolin-8-yl)-amine (434 mg, 1.15 mmol) and Et$_3$N (0.16 mL, 1.15 mmol) in THF (5 mL) was heated at 60° C. under nitrogen atmosphere for 2.5 days. The solution was then cooled, concentrated and diluted with CH$_2$Cl$_2$ (40 mL) and saturated aqueous NaHCO$_3$ (40 mL). The aqueous phase was extracted with CH$_2$Cl$_2$ (2×20 mL). The combined organic extracts were dried (Na$_2$SO$_4$), filtered and concentrated in vacuo. The residue was purified by column chromatography on silica gel (CH$_2$Cl$_2$/MeOH, 98:2 then 96:4) to give the desired alkylated product as a yellow foam (411 mg, 54%).

The foam from above (271 mg, 0.41 mmol) oil was dissolved in CH$_2$Cl$_2$/TFA (1:1, 2 mL) and the mixture stirred overnight. The reaction was then concentrated and diluted with CH$_2$Cl$_2$ (30 mL) and 1 N NaOH (30 mL). The aqueous layer was washed with CH$_2$Cl$_2$ (2×10 mL) and the combined organic extracts were dried (Na$_2$SO$_4$), filtered and concentrated to afford the Boc-deprotected material as a yellow foam (159 mg, 69%).

Deprotection of the 2-nitrobenzenesulfonamide (nosyl) group: To a stirred solution of the nosyl-protected adduct from above (159 mg, 0.28 mmol) in dry CH$_3$CN (5 mL) was added benzenethiol (0.175 mL, 1.71 mmol) and powdered potassium carbonate (240 mg, 1.74 mmol) and the mixture was stirred at room temperature overnight. The reaction mixture was concentrated in vacuo and partitioned between CH$_2$Cl$_2$ (15 mL) and water (15 mL). The aqueous layer was separated and extracted with CH$_2$Cl$_2$ (2×10 mL) and the combined organic phases were dried (Na$_2$SO$_4$), filtered and evaporated in vacuo to give the crude product as a yellow oil. Purification by column chromatography on basic alumina (CH$_2$Cl$_2$/MeOH, 100:0 followed by 95:5) afforded the desired amine (85 mg, 80%) as a yellow foam.

Using General Procedure D: Conversion of the foam from above (34 mg, 0.091 mmol) to the hydrobromide salt followed by re-precipitation of the intermediate solid from methanol/ether gave COMPOUND 82 (38 mg, 65%) as a white solid. $^1$H NMR (D$_2$O) δ 1.36-1.46 (m, 2H), 1.59-1.91 (m, 5H), 2.22-2.32 (m, 3H), 2.35-2.45 (m, 2H), 2.81-2.84 (m, 2H), 3.21-3.28 (m, 1H), 3.44-3.56 (m, 1H), 4.33 (d, 1H, J=15.9 Hz), 4.42 (d, 1H, J=15.9 Hz), 4.65 (t, 1H, J=8.4 Hz), 7.23 (dd, 1H, J=7.5, 6 Hz), 7.51 (dd, 2H, J=6.3, 3.3 Hz), 7.59 (dd, 2H, J=6.3, 3.3 Hz), 7.86 (d, 1H, J=8.1 Hz), 8.11 (d, 1H, J=5.5 Hz); $^{13}$C NMR (D$_2$O) δ 19.35, 22.02, 22.46, 23.56, 26.46, 27.94, 29.94, 37.81, 50.82, 61.34, 66.88, 112.92, 123.83, 126.14, 129.54, 138.38, 139.34, 146.03, 148.26, 148.34. ES-MS m/z 376 (M+H). Anal. Calcd. for C$_{23}$H$_{29}$N$_5$.2.9HBr.1.8H$_2$O: C, 42.99; H, 5.57; N, 10.90; Br, 36.06. Found: C, 43.29; H, 5.55; N, 10.60; Br, 35.67.

Example 83

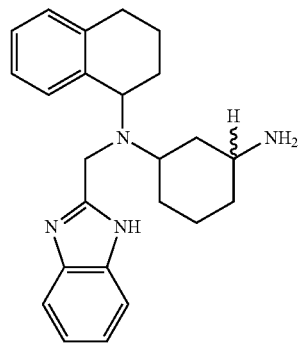 [SMILES: NC1CCCC(N(Cc2nc3ccccc3[nH]2)C2CCCc3ccccc32)C1]

Compound 83: Preparation of N-(1H-benzimidazol-2-ylmethyl)-N-(5,6,7,8-tetrahydro-quinolin-8-yl)-cyclohexane-1,3-diamine (hydrobromide salt)

Preparation of N-tert-butoxycarbonyl-1,3-cyclohexanediamine (Smith, J.; Liras, J. L.; Schneider, S. E.; Anslyn, E J. Org. Chem. 1996, 61, 8811-8818)

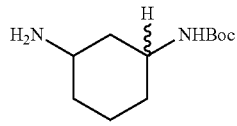

To a solution of 1,3-cyclohexanediamine (cis and trans) (1.00 g, 8.76 mmol) in CHCl$_3$ (20 mL) was added a solution of di-tert-butyl dicarbonate (0.95 g, 4.35 mmol) in CHCl$_3$ (15 mL) via syringe pump over a period of 3 hours. The resultant white suspension was stirred at room temperature overnight then concentrated in vacuo and purified by column chromatography on silica gel (CH$_2$Cl$_2$/MeOH/NH$_4$OH, 90:8:2) to afford the title compound (0.66 g, 35% based on starting diamine) as a clear oil.

Following General Procedure B: To a stirred solution of 6,7-dihydro-5H-quinolin-8-one (444 mg, 3.00 mmol) and N-tert-butoxycarbonyl-1,3-cyclohexanediamine (660 mg, 3.08 mmol) in dry THF (5 mL) was added AcOH (0.4 mL) and NaBH(OAc)$_3$ (822 mg, 3.88 mmol) and the mixture stirred overnight at room temperature. Purification by column chromatography on silica gel (CH$_2$Cl$_2$/MeOH, 96:4) afforded the desired amine (370 mg, 60%) as a mixture of inseparable diastereomers.

Following the general procedure for N-alkylation: To a stirred solution of the yellow foam from above (370 mg, 1.07 mmol) in CH$_3$CN (5 mL) was added N,N-diisopropylethylamine (0.35 mL, 2.01 mmol), KI (30 mg, 0.18 mmol) and 1-(tert-butoxycarbonyl)-2-(chloromethyl)benzimidazole (343 mg, 1.29 mmol). The mixture was stirred at 60° C. overnight. Purification of the resultant orange foam by column chromatography on silica gel (CH$_2$Cl$_2$/MeOH, 96:4 then 92:8) afforded the desired alkylated amine (430 mg, 70%) as a mixture of diastereomers.

Using General Procedure D: Conversion of the foam from above (96 mg, 0.17 mmol) to the hydrobromide salt with simultaneous removal of the N-tert-butoxycarbonyl protecting group followed by re-precipitation of the intermediate solid from methanol/ether gave COMPOUND 83 (96 mg, 88%) as an orange solid (mixture of diastereomers). $^1$H NMR (D$_2$O) δ 1.27-1.64 (m, 4H), 1.74-2.00 (m, 4H), 2.07-2.38 (m, 3H), 2.40-2.44 (m, 1H), 2.84-2.90 (m, 1H), 2.98-3.01 (m, 2H), 3.15-3.20 (m, 1H), 4.43-4.62 (m, 3H), 7.60 (dd, 2H, J=6, 3 Hz), 7.76 (dd, 2H, J=6, 3 Hz), 7.78-7.83 (m, 1H), 8.28 (br d, 1H, J=7.8 Hz), 8.57-8.60 (m, 1H); $^{13}$C NMR (D$_2$O) δ 19.58, 20.71, 22.37, 22.45, 24.23, 27.21, 27.51, 28.60, 29.16, 29.70, 30.54, 31.08, 31.75, 34.35, 36.21, 43.65, 48.61, 49.79, 54.46, 58.57, 58.70, 58.93, 114.23, 125.86, 127.05, 130.91, 139.16, 140.55, 148.03, 151.18, 151.26, 151.83. ES-MS m/z 376 (M+H). Anal. Calcd. for C$_{23}$H$_{29}$N$_5$.3.0HBr.1.96H$_2$O: C, 42.34; H, 5.53; N, 10.73; Br, 36.74. Found: C, 42.27; H, 5.59; N, 10.37; Br, 37.04.

Example 85

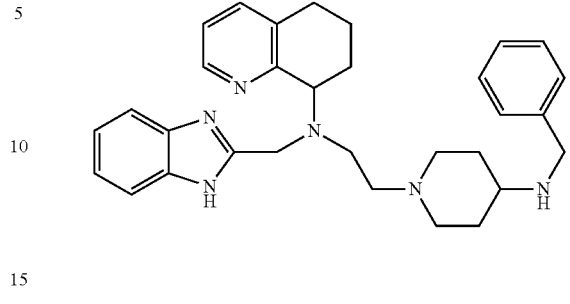

Compound 85: Preparation of (1H-benzimidazol-2-ylmethyl)-[2-(4-benzylamino-piperidin-1-yl)-ethyl]-(5,6,7,8-tetrahydroquinolin-8-yl)-amine (hydrobromide salt)

To a solution of N-Boc-piperidone (3.0 g, 15.1 mmol) in THF (76 mL) was added benzylamine (1.65 mL, 15.1 mmol), acetic acid (0.86 mL, 15.1 mmol) and sodium triacetoxyborohydride (4.8 g, 22.6 mmol). After stirring 2.5 hours the reaction mixture was concentrated under reduced pressure and CH$_2$Cl$_2$ (50 mL) and saturated aqueous NaHCO$_3$ solution (50 mL) was added. The organic phase was separated, and the aqueous was extracted with CH$_2$Cl$_2$ (2×50 mL). The combined organic phases were then dried (MgSO$_4$), filtered, and concentrated under reduced pressure to afford 4-benzylamino-piperidine-1-carboxylic acid tert-butyl ester (4.30 g, 98%).

The crude material from above (4.30 g, 14.8 mmol) and 2-nitrobenzenesulfonyl chloride (3.60 g, 16.3 mmol) were dissolved in CH$_2$Cl$_2$ (75 mL) and triethylamine (2.68 mL, 19.2 mmol) was added. The solution was stirred for 16 h and saturated aqueous NaHCO$_3$ solution (70 mL) was added. The organic phase was separated, and the aqueous extracted with CH$_2$Cl$_2$ (50 mL). The combined organic phases were then dried (MgSO$_4$), filtered, and concentrated under reduced pressure. This gave, after column chromatography (CH$_2$Cl$_2$), the desired nosyl-protected substrate (3.92 g, 56%).

A solution of the above material (3.92 g, 8.2 mmol) in 1:1 TFA/CH$_2$Cl$_2$ (26 mL) was stirred for 0.5 h and then concentrated under reduced pressure. CH$_2$Cl$_2$ (50 mL), saturated aqueous NaHCO$_3$ solution (50 mL), and 15% aqueous NaOH (10 mL) was added until pH=14. The organic phase was separated, and the aqueous was extracted with CH$_2$Cl$_2$ (30 mL). The combined organic phases were then dried (MgSO$_4$), filtered, and concentrated under reduced pressure. This afforded the desired unprotected cyclic amine (2.74 g, 89%).

To a solution of the cyclic amine (2.74 g, 7.3 mmol) in anhydrous acetonitrile (73 mL) was added 2-bromoethanol (0.52 mL, 7.3 mmol), and triethylamine (1.25 mL, 8.7 mmol). The reaction was stirred at 50° C. for 16 hours, and saturated aqueous NaHCO$_3$ solution (50 mL) and ethyl acetate (50 mL) was added. After separating the organic phase and washing with brine (35 mL), the extracts were dried (MgSO$_4$), filtered and concentrated under reduced pressure. This gave, after column chromatography (2:98 MeOH/CH$_2$Cl$_2$), N-benzyl-N-[1-(2-hydroxy-ethyl)-piperidin-4-yl]-2-nitro-benzenesulfonamide as a colorless solid (1.62 g, 53%). ¹H NMR (CDCl₃) δ 1.62-1.71 (m, 4H), 2.14 (dt, 2H, J=12.0, 3.0 Hz), 2.47 (t, 2H, J=6.0 Hz), 2.88 (br d, 2H, J=12.0 Hz), 3.53 (t, 2H, J=4.5 Hz), 3.92 (m, 1H), 4.54 (s, 2H), 7.21 (m, 3H), 7.30 (m, 2H), 7.47 (m, 1H), 7.61 (d, 2H, J=4.5 Hz), 7.77 (d, 1H, J=9.0 Hz).

Methanesulfonyl chloride (100 µL, 1.2 mmol) and triethylamine (0.20 mL, 1.4 mmol) was added to a solution of the above alcohol (0.40 g, 0.95 mmol) in CH₂Cl₂ (3 mL) at 0° C. and then allowed to warm to room temperature over 20 minutes. This gave, after aqueous work up, the desired crude methanesulfonate (0.53 g, quant) as a white solid which was used immediately in the next reaction.

Using the general procedure for N-alkylation, the crude methanesulfonate (0.47 g, 0.94 mmol) and (N-tert-butoxycarbonylbenzimidazol-2-ylmethyl)-(5,6,7,8-tetrahydroquinolin-8-yl)-amine (0.36 g, 0.94 mmol) was stirred at room temperature in acetonitrile (10 mL) and diisopropylethylamine (0.25 mL, 1.4 mmol) for 16 hours. This yielded, after work-up and column chromatography (5:95 MeOH/CH₂Cl₂), 2-{[{2-[4-(benzyl-2-nitrobenzenesulfonyl-amino)-piperidin-1-yl]-ethyl}-(5,6,7,8-tertahydroquinolin-8-yl)-amino]-methyl}-benzimidazole-1-carboxylic acid tert-butyl ester as a colorless flaky solid (0.25 g, 34%).

To a solution of the above material (0.25 g, 0.32 mmol) and thiophenol (0.17 mL, 1.6 mmol) in anhydrous acetonitrile (2.0 mL) was added potassium carbonate (0.27 g, 1.9 mmol). The reaction was stirred for 5 h. CH₂Cl₂ (10 mL) was then added and the mixture was filtered through a celite pad and concentrated under reduced pressure. This afforded, after column chromatography (5:95 MeOH/CH₂Cl₂), the desired nosyl-deprotected product (0.75 g, 60%).

To a solution of the above material (75 mg, 0.15 mmol) in anhydrous THF (1.5 mL) was added di-tert-butyldicarbonate (100 mg, 0.45 mmol). The solution was allowed to stir for 16 h and then concentrated under reduced pressure. This gave, after radial chromatography (1.5:1.5:97 MeOH/NH₄OHCH₂Cl₂), the desired di-boc-protected product (42 mg, 40%). ¹H NMR (CDCl₃) δ 1.32 (br s, 9H), 1.47 (br s, 5H), 1.67 (s, 9H), 1.77 (br s, 4H), 1.97 (m, 1H), 2.15 (m, 2H), 2.29 (m, 1H), 2.73 (m, 6H), 4.22 (m, 1H), 4.26 (br s, 2H), 4.53 (d, 1H, J=15.0 Hz), 4.73 (d, 1H, J=15.0 Hz), 6.97 (m, 1H), 7.16 (m, 3H), 7.23 (m, 5H), 7.68 (m, 1H), 7.81 (m, 1H), 8.36 (d, 1H, J=3.0 Hz).

Using general procedure D: The above material (24 mg, 0.0345 mmol) was converted to the hydrobromide salt to provide COMPOUND 85 (26 mg) as a white solid. ¹H NMR (D₂O) δ 1.82 (br m, 1H), 1.97 (m, 3H), 2.17 (br m, 1H), 2.45 (m, 3H), 3.00-123 (br m, 5H), 3.38-3.75 (br m, 6H), 4.29 (s, 2H), 4.39 (d, 1H, J=16.8 Hz), 4.50 (m, 1H), 4.56 (d, 1H, J=16.8 Hz), 7.47 (br s, 5H), 7.60 (m, 2H), 7.79 (m, 2H), 7.83 (t, 1H, J=6.0 Hz), 8.32 (d, 1H, J=7.8 Hz), 8.61 (d, 1H, J=5.7 Hz), ¹³C NMR (D₂O) δ 20.29, 20.64, 26.15 (2C), 27.65, 46.41, 47.13, 49.13, 51.39 (2C), 51.91, 54.39, 60.07, 114.41 (2C), 126.16, 127.06 (2C), 129.82 (2C), 130.16 (2C), 130.26, 130.71, 131.30, 139.85 (2C), 140.96, 148.27, 149.95, 150.18. ES-MS m/z 495 (M+H). Anal. Calcd. for C₃₁H₃₈N₆.4.2HBr.3.0H₂O: C, 42.05; H, 5.49; N, 9.49; Br, 37.51. Found: C, 42.13; H, 5.64; N, 9.16; Br, 37.53.

Example 86

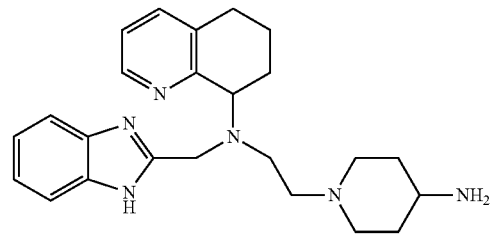 [SMILES: NC1CCN(CCN(Cc2nc3ccccc3[nH]2)C2CCCc3cccnc32)CC1]

Compound 86: Preparation of [2-(4-amino-piperidin-1-yl)-ethyl]-[(1H-benzimidazol-2-ylmethyl)-(5,6,7,8-tetrahydroquinolin-8-yl)-amine (hydrobromide salt)

To a solution of N-benzyl-N-[1-(2-hydroxy-ethyl)-piperidin-4-yl]-2-nitro-benzenesulfonamide (0.62 g, 1.5 mmol) and thiophenol (0.76 mL, 7.4 mmol) in anhydrous acetonitrile (9 mL) was added potassium carbonate (1.22 g, 8.8 mmol). The reaction was stirred for 16 h. The mixture was then filtered through a celite to give, after column chromatography (10:90 MeOH/CH₂Cl₂), the desired nosyl-deprotected intermediate (0.30 g, 86%).

The above material (0.30 g, 1.3 mmol) was dissolved in anhydrous ethanol (15 mL) and the solution purged with nitrogen gas. 10% palladium on carbon (130 mg) was added and the reaction mixture was allowed to stir under a new atmosphere of hydrogen (1 atm) for 16 h. The mixture was then filtered through celite to afford a crude yellow residue of 2-(4-amino-piperidin-1-yl)-ethanol (0.20 g, quant.).

To a solution of the above material (0.20 g, 1.5 mmol) in anhydrous THF (7.5 mL) was added di-tert-butyldicarbonate (0.37 g, 1.7 mmol). The solution was allowed to stir for 16 h and then concentrated under reduced pressure. This afforded, after column chromatography (5:95 MeOH/CH₂Cl₂), the desired boc-protected amine (0.14 g, 37%). ¹H NMR (CDCl₃) δ 1.42 (m, 2H), 1.44 (s, 9H), 1.92 (br d, 2H), 2.14 (br t, 2H), 2.50 (t, 2H, J=6.0 Hz), 2.82 (br d, 2H), 3.45 (br, 1H), 3.57 (t, 2H, J=6.0 Hz), 4.48 (br, NH).

Methanesulfonyl chloride (60 µL, 0.7 mmol) and triethylamine (0.12 mL, 0.9 mmol) was added to a solution of the above material (0.14 g, 0.6 mmol) in CH₂Cl₂ (3 mL) at 0° C. and then allowed to warm to room temperature over 20 minutes. This gave, after aqueous work up, the desired methanesulfonate (0.16 g) that was used immediately in the next reaction without further purification.

Using the general procedure for N-alkylation, the crude methanesulfonate (0.16 g, 0.5 mmol) and (5,6,7,8-tetrahydroquinolin-8-yl)-[1-(2-trimethylsilanyl-ethoxymethyl)-1H-benzimidazol-2-ylmethyl]-amine (0.18 g, 0.44 mmol) was stirred at room temperature in acetonitrile (5 mL) and diisopropylethylamine (0.13 mL, 0.75 mmol) for 16 hours. This yielded, after work-up and column chromatography (5:95 MeOH/CH₂Cl₂), the desired alkylated product (27 mg, 12%).

The material from above (27 mg, 0.042 mmol) was dissolved in 6N HCl (1 mL) and stirred at 50° C. for 3 h. 15% aqueous NaOH (2 mL) was added until pH=12, and the aqueous phase was concentrated under reduced pressure. This gave, after filtering from methanol and radial chromatography (5:1:94 MeOH/NH₄OH/CH₂Cl₂) the desired SEM-deprotected free base (12 mg, 69%). ¹H NMR (CDCl₃) δ 1.48

(m, 2H), 1.70 (m, 1H), 1.82 (m, 3H), 1.98 (m, 2H), 2.23 (m, 2H), 2.66-2.95 (m, 8H), 3.74 (s, 1H), 3.98 (d, 2H, J=15.0 Hz), 4.13 (m, 1H), 7.13 (m, 1H), 7.19 (m, 2H), 7.40 (d, 1H, J=9.0 Hz), 7.58 (m, 2H), 8.49 (d, 1H, J=3.0 Hz).

Using general procedure D: The material from above (12 mg, 0.030 mmol) was converted to the hydrobromide salt to provide COMPOUND 86 (14 mg) as a white solid. $^1$H NMR (D$_2$O) δ 1.85-2.05 (br m, 3H), 2.20-2.30 (br m, 3H), 2.47 (m, 1H), 3.00 (br m, 2H), 3.15 (br m, 2H), 3.34 (m, 1H), 3.44-3.63 (br m, 4H), 4.35 (d, 1H, J=16.5 Hz), 4.47 (m, 1H), 4.53 (d, 1H, J=16.5 Hz), 4.80-4.93 (br, 4H), 7.58 (m, 2H), 7.80 (m, 3H), 8.30 (d, 1H, J=7.5 Hz), 8.58 (d, 1H, J=5.7 Hz), $^{13}$C NMR (D$_2$O) δ 20.30, 20.64, 27.29 (2C), 27.65, 45.53, 46.43, 47.14, 51.41 (2C), 54.36, 60.08, 114.44 (2C), 126.08, 126.90 (2C), 131.59, 139.88, 140.86 (2C), 148.10, 150.06, 150.30. ES-MS m/z 405 (M+H). Anal. Calcd. for C$_{24}$H$_{32}$N$_6$.4.1HBr.3.3H$_2$O: C, 36.41; H, 5.42; N, 10.62; Br, 40.93. Found: C, 36.52; H, 5.49; N, 10.26; Br, 40.94.

Example 87

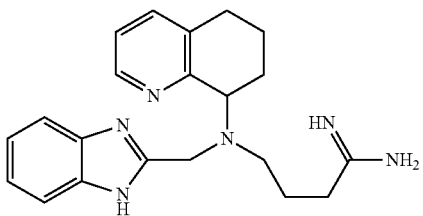 [SMILES: N=C(N)CCCN(Cc1nc2ccccc2[nH]1)C1CCCc2cccnc21]

Compound 87: Preparation of 4-[(1H-benzimidazol-2-ylmethyl)-(5,6,7,8-tetrahydroquinolin-8-yl)-amino]-butyramidine (hydrobromide salt)

[N-(tert-butoxycarbonyl)-benzimidazol-2-ylmethyl)]-(5,6,7,8-tetrahydroquinolin-8-yl)-(3-cyano-prop-1-yl)-amine (0.14 g, 0.30 mmol) was dissolved in anhydrous methanol (3 mL) and anhydrous diethyl ether (5 mL) was added. The solution was cooled to 0° C. and hydrogen chloride gas was bubbled through the solution over 0.5 hour to saturation. The reaction was then allowed to stir at room temperature for 16 hours, after which the solvent was removed under reduced pressure. The residue was then washed with diethyl ether (3×20 mL) and dried in vacuo. This afforded the required 4-[(1H-benzimidazol-2-ylmethyl)-(5,6,7,8-tetrahydroquinolin-8-yl)-amino]-butyrimidic acid methyl ester (hydrochloride salt), which was used immediately in the next reaction.

The salt from above (0.30 mmol) was dissolved in a solution of ammonia in methanol (2 M, 3 mL, 1.5 mmol), and stirred for 16 hours. The solution was then concentrated under reduced pressure and purified by column chromatography (10:1:89 MeOH/NH$_4$OH/CH$_2$Cl$_2$) to give the desired 4-[(1H-benzimidazol-2-ylmethyl)-(5,6,7,8-tetrahydroquinolin-8-yl)-amino]-butyramidine free base as a crystalline solid (42 mg, 38%, 2 steps). $^1$H NMR (CDCl$_3$) δ 1.50 (m, 1H), 1.73-1.95 (br m, 4H), 2.14 (m, 1H), 2.40-2.80 (br m, 6H), 3.91 (m, 1H), 3.95 (br d, 1H, J=15.0 Hz), 4.10 (br d, 1H, J=15.0 Hz), 7.10 (br, 3H), 7.37 (d, 1H, J=6.0 Hz), 7.55 (br, 2H), 8.44 (br, 1H), 8.87 (br, NH), 9.51 (br, NH).

Using general procedure D: The material from above (42 mg, 0.11 mmol) was converted to the hydrobromide salt to provide COMPOUND 87 (28 mg). $^1$H NMR (D$_2$O) δ 1.85 (br m, 3H), 1.95 (m, 1H), 2.17 (br m, 1H), 2.37 (t, 3H, J=7.8 Hz), 2.56 (m, 1H), 2.86 (m, 1H), 3.00 (br, 2H), 4.37 (d, 1H, J=16.8 Hz), 4.48 (m, 1H), 4.53 (d, 1H, J=16.8 Hz), 7.60 (m, 2H), 7.79 (m, 2H), 7.86 (t, 1H, J=6.9 Hz), 8.34 (d, 1H, J=7.8 Hz), 8.62 (d, 1H, J=5.4 Hz); $^{13}$C NMR (D$_2$O) δ 20.37, 20.50, 25, 60, 27.63, 30.11, 47.89, 50.91, 60.41, 114.27 (2C), 126.01, 127.02 (2C), 130.99, 139.43, 140.74 (2C), 148.20, 151.41, 152.06. ES-MS m/z 363 (M+H). Anal. Calcd. for C$_{21}$H$_{26}$N$_6$.3.1HBr.1.3H$_2$O.0.3C$_4$H$_{10}$O: C, 40.17; H, 5.27; N, 12.66; Br, 37.32. Found: C, 40.09; H, 5.27; N, 12.62; Br, 37.31.

Example 88

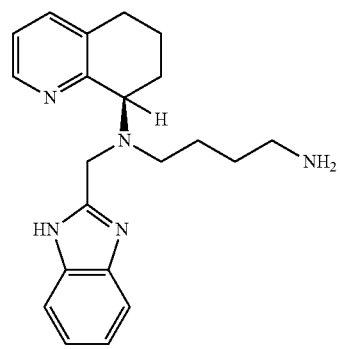 [SMILES: NCCCCN(Cc1nc2ccccc2[nH]1)[C@@H]1CCCc2cccnc21]

Compound 88: Preparation of N$^1$-(1H-Benzimidazol-2-ylmethyl)-N$^1$-(R)-5,6,7,8-tetrahydro-quinolin-8-yl-butane-1,4-diamine (crystal)

Solution A: To a solution of anhydrous zinc (II) chloride (70.80 g, 0.52 mol) in tetrahydrofuran (320 mL) at room temperature was added sodium borohydride (17.86 g, 0.47 mol) and the mixture stirred for 1 hour. The solution was then chilled to −20° C.

Solution B: To a solution of (R)-(5,6,7,8-tetrahydro-quinolin-8-yl)amine (70.0 g, 0.47 mol) and 4-(1,3-dioxo-1,3-dihydro-isoindol-2-yl)-butyraldehyde (102.59 g, 0.47 mol) in tetrahydrofuran (160 mL) at room temperature was added potassium carbonate (65.28 g, 0.47 mol) and the mixture stirred for 1 hour. The suspension was then filtered and chilled to −20° C. The cold filtrate was slowly added to Solution A via canula over 35 minutes. The resulting mixture was stirred at −20° C. for 1 hour, until reaction was complete by NMR aliquot. The reaction was then neutralized by the careful addition of 6N HCl until pH=2-3, keeping the temperature below −7° C. The solution was then warmed to 22° C. and basified with 13 w/v % Na$_2$CO$_{3(aq)}$ until pH=4. The tetrahydrofuran was removed under reduced pressure and the concentrate diluted with water (700 mL) and CH$_2$Cl$_2$ (530 mL). The phases were separated and the organic phase washed with concentrated ammonium hydroxide (1×230 mL) and water (1×315 mL). The organic phase was then concentrated to 200-250 mL and filtered through a conditioned silica gel pad (14 g). The silica gel was rinsed with CH$_2$Cl$_2$ (2×20 mL). The combined filtrate was concentrated to 100-150 mL and diluted with diisopropyl ether (1000 mL). The solution was concentrated to 300-350 mL and chilled to −10° C., at which temperature the product began to precipitate. Mechanical stirring was continued for 45 minutes at −10° C., after which time the product was collected by filtration. The product was washed with diisopropyl ether (100 mL) and dried under reduced pressure to give pure 2-{4-[(R)-(5,6,7,8-tetrahydroquinolin-8-yl)amino]-butyl}-isoindole-1,3-dione (135.3 g, 82%). ¹H NMR (300 MHz, CDCl₃, δ ppm) 1.55-1.85 (m, 6H), 1.95-2.05 (m, 1H), 2.05-2.20 (m, 1H), 2.50 (b, 1H), 2.65-2.85 (m, 4H), 3.65-3.80 (m, 3H), 7.04 (dd, 1H, J=4.5 & 7.5 Hz), 7.35 (d, 1H, J=7.5 Hz), 7.65-7.75 (m, 2H), 7.75-7.85 (m, 2H), 8.36 (d, 1H, J=4.5 Hz).

To a solution of 2-{4-[(R)-(5,6,7,8-tetrahydro-quinolin-8-yl)amino]-butyl}-isoindole-1,3-dione (135.3 g, 0.39 mol) and 2-chloromethyl-benzimidazole-1-carboxylic acid tert-butyl ester (103 g, 0.39 mol) in acetonitrile (780 mL) at room temperature was added diisopropylethylamine (101 mL, 0.58 mol) and potassium iodide (6.4 g, 0.04 mol) and the mixture heated to 50° C. for 3 hours. The mixture was then concentrated under reduced pressure and redissolved in methyl t-butyl ether (500 mL) and water (500 mL). The pH was adjusted to 2 with 6N HCl then the phases were separated. The aqueous layer was washed with methyl t-butyl ether (500 mL). The aqueous phase was stirred for 22 hours, adding 6N HCl as needed to maintain pH=2. The solution was basified to pH 10-11 with 10N NaOH and extracted with toluene (2×1.5 L). The organic phase was washed with 1N NaOH (1×200 mL) and brine (1×200 mL). The organic phase was dried (Na₂SO₄), filtered and concentrated under reduced pressure to give 2-{4-[(R)-(1H-benzimidazol-2-ylmethyl)-5,6,7,8-tetrahydro-quinolin-8-yl-amino]-butyl}-isoindole-1,3-dione (209 g). ¹H NMR (300 MHz, CDCl₃, δ ppm) 0.75-1.75 (series of m, 5H), 1.80-2.10 (2m, 2H), 2.15-2.25 (m, 1H), 2.55-2.90 (m, 4H), 3.52 (t, 2H, J=7.0 Hz), 3.95-4.10 (m, 1H), 4.01 (d, 1H, J=17.0 Hz), 4.11 (d, 1H, J=17.0 Hz), 7.10-7.30 (m, 4H), 7.39 (d, 1H, J=7.5 Hz), 7.50-7.55 (m, 1H), 7.60-7.70 (m, 2H), 7.70-7.80 (m, 2H), 8.60 (d, 1H, J=3.5 Hz).

To a solution of 2-{4-[(R)-(1H-benzimidazol-2-ylmethyl)-5,6,7,8-tetrahydro-quinolin-8-yl-amino]-butyl}-isoindole-1,3-dione (209 g, max 0.39 mol) in methanol (2 L) at room temperature was added hydrazine hydrate (179 mL, 3.12 mol) and the mixture stirred for 16 hours. The solution was filtered and the filtrate concentrated. The residue was taken up in 1N HCl until pH=2-3. The resulting suspension was filtered. The filtrate was basified to pH=6 with 10 N NaOH and washed with CH₂Cl₂ (2×400 mL). The aqueous phase was further basified to pH=12 with 10N NaOH and extracted with CH₂Cl₂ (3×1000 mL). The combined organic phase was concentrated under reduced pressure to about 1.4 L. Charcoal (48 g) was added and the suspension stirred for 1 hour. The charcoal was removed by filtration and the filtrate was filtered through a dry silica gel pad (140 g). The silica was eluted with 20:1 CH₂Cl₂: MeOH until no more product could be seen by UV (1.0 L). The filtrate was washed with 0.1N NaOH (1×800 mL), dried (Na₂SO₄), filtered and concentrated under reduced pressure to give amorphous N¹-(1H-benzimidazol-2-ylmethyl)-N¹-(R)-5,6,7,8-tetrahydro-quinolin-8-yl-butane-1,4-diamine (99 g, 73% over two steps). ¹H NMR (300 MHz, CDCl₃, δ ppm) 1.05-1.35 (m, 4H), 1.30-1.50 (m, 1H), 1.60-1.85 (2m, 2H), 1.90-2.05 (m, 1H), 2.25-2.70 (m, 6H), 3.75-4.00 (m, 3H), 6.90 (dd, 1H, J=4.5 & 7.5 Hz), 6.95-7.05 (m, 2H), 7.15 (d, 1H, J=7.5 Hz), 7.35-7.45 (m, 2H), 8.37 (d, 1H, J=4.5 Hz).

Amorphous N¹-(1H-Benzimidazol-2-ylmethyl)-N¹-(R)-5,6,7,8-tetrahydro-quinolin-8-yl-butane-1,4-diamine (90.98 g, 0.260 mol) was diluted with ethyl acetate (730 ml, 0.125 g/mL) and heated with stirring until all solids had dissolved (T$_{max}$=62° C.). The solution was allowed to slowly cool to room temperature while stirring. Stirring at room temperature was continued for 20 hours. The crystals were then collected on a buchner funnel under N₂ atmosphere. The crystals were dried under reduced pressure, then ground with a mortar and pestle. The crystals were then dried in a vacuum oven (40° C., greater then 30" Hg) for two nights to give dry N¹-(1H-benzimidazol-2-ylmethyl)-N¹-(R)-5,6,7,8-tetrahydro-quinolin-8-yl-butane-1,4-diamine crystals (69.52 g, 77%). ¹H NMR (CDCl₃) δ 1.21-1.47 (m, 4H), 1.58-1.73 (m, 1H), 1.82-2.06 (m, 2H), 2.12-2.23 (m, 2H), 2.45-2.59 (m, 3H), 2.64-2.89 (m, 3H), 3.97-4.12 (m, 3H), 7.08-7.20 (m, 3H), 7.49 (d, 1H, J=7.4 Hz), 7.53-7.60 (m, 2H), 8.57 (d, 1H, J=4.2 Hz). ¹³C NMR (CDCl₃) δ 21.15, 23.50, 25.78, 28.96, 30.96, 41.61, 49.23, 50.26, 61.62, 114.83, 121.22, 121.88, 134.28, 137.01, 146.42, 156.49, 157.39. Purity (HPLC)=99.40%. Enantiomeric Excess (HPLC)=99.66%. Hydrazine (HPLC)=4.7 ppm. ES-MS m/z 350 (M+H). Anal Calc. for C₂₁H₂₇N₅: C, 72.17; H, 7.79; N, 20.04. Found: C, 71.82; H, 7.74; N, 19.74.

Example 89

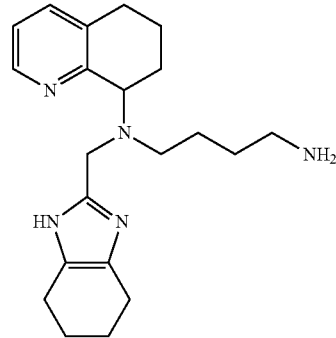 [SMILES: NCCCCN(Cc1nc2c([nH]1)CCCC2)C1CCCc2cccnc21]

Compound 89: Preparation of N¹-(4,5,6,7-tetrahydro-1H-benzoimidazol-2-ylmethyl)-N¹-(5,6,7,8-tetrahydro-quinolin-8-yl)-butane-1,4-diamine To solution of 4,5,6,7-tetrahydro-1H-benzoimidazole (1.9992 g, 16.4 mmol) and triethylamine (4.60 mL, 32.8 mmol) in CH₂Cl₂ (20 mL) at 0° C. was added dropwise a solution of dimethyl sulfamoyl chloride (1.76 mL, 16.4 mmol) in CH₂Cl₂ (10 mL). The reaction was warmed to room temperature and stirred for 3.5 hours. CH₂Cl₂ (80 mL) was added and the organic phase was washed with distilled water (1×80 mL). The aqueous washing was extracted with CH₂Cl₂ (2×40 mL), and the combined organic extracts were washed with brine (1×80 mL), dried (Na₂SO₄), and concentrated. Purification of the crude material by column chromatography on silica gel (2:1 hexanes-EtOAc) provided 2.89 g (77%) of 4,5,6,7-tetrahydro-benzoimidazole-1-sulfonic acid dimethylamide as a white solid. ¹H NMR (CDCl₃) δ 1.77-1.86 (m, 4H), 2.58-2.61 (m, 2H), 2.72 (t, 2H, J=6 Hz), 2.87 (s, 6H), 7.77 (s, 1H).

2-Formyl-4,5,6,7-tetrahydro-benzoimidazole-1-sulfonic acid dimethylamide was prepared following a modification of the procedure found in the Journal of Medicinal Chemistry, 40; 14, 1997, 2205. To a solution of 4,5,6,7-tetrahydro-benzoimidazole-1-sulfonic acid dimethylamide (2.67 g, 11.6 mmol) in dry THF (100 mL) under argon at −78° C. was added dropwise 2.5 M n-butyllithium in hexanes (7.0 mL, 17.5 mmol). The reaction was stirred at −78° C. for 1 hour, then DMF (1.1 mL, 13.9 mmol) was added dropwise, and the reaction was warmed to room temperature and stirred for 2 hours. Saturated NH₄Cl (25 mL) was added, and the reaction mixture was concentrated, and then diluted with CH₂Cl₂ (500 mL) and distilled water (25 mL). The layers were separated and the aqueous phase was extracted with CH$_2$Cl$_2$ (2×100 mL). The combined organic extracts were washed with brine (1×100 mL), dried (Na$_2$SO$_4$), and concentrated. Purification of the crude material by column chromatography on silica gel (1:1 hexanes-EtOAc) provided 1.53 g (51%) of 2-formyl-4,5,6,7-tetrahydro-benzoimidazole-1-sulfonic acid dimethylamide as a yellow solid. $^1$H NMR (CDCl$_3$) δ 1.82-1.86 (m, 4H), 2.66-2.68 (m, 2H), 2.86-2.88 (m, 2H), 2.96 (s, 6H), 9.99 (s, 1H).

To a solution of 2-formyl-4,5,6,7-tetrahydro-benzoimidazole-1-sulfonic acid dimethylamide (0.3991 g, 1.5 mmol) and 2-[4-(5,6,7,8-tetrahydro-quinolin-8-ylamino)-butyl]-isoindole-1,3-dione (0.4424 g, 1.3 mmol) in CH$_2$Cl$_2$ (13 mL) was added sodium triacetoxyborohydride (0.5539 g, 2.6 mmol), and the reaction stirred at room temperature for 22 hours. Saturated NaHCO$_3$ (20 mL) was added and the aqueous phase was extracted with CH$_2$Cl$_2$ (2×100 mL), and the combined organic extracts were washed with brine (1×75 mL), dried (NaSO$_4$), and concentrated. Purification of the crude material by column chromatography on silica gel (33:1:1 CH$_2$Cl$_2$—MeOH—NH$_4$OH) provided 0.4564 g (52%) of 2-{[[4-(1,3-dioxo-1,3-dihydro-isoindol-2-yl)-butyl]-(5,6,7,8-tetrahydro-quinolin-8-yl)-amino]-methyl}-4,5,6,7-tetrahydro-benzoimidazole-1-sulfonic acid dimethylamide as a yellow foam. $^1$H NMR (CDCl$_3$) δ 1.28 (t, 2H, J=9 Hz), 1.49-1.52 (m, 2H), 1.74-1.81 (m, 6H), 1.91-2.00 (m, 1H), 2.11-2.20 (m, 1H), 2.50-2.73 (m, 7H), 2.92 (s, 2H), 2.95 (s, 4H), 3.52-3.57 (m, 2H), 4.17-4.22 (m, 2H), 4.32-4.37 (m, 1H), 4.81 (s, 1H), 6.95-6.98 (m, 1H), 7.27-7.28 (m, 1H), 7.68-7.70 (m, 2H), 7.79-7.82 (m, 2H), 8.32 (d, 1H, J=3 Hz).

2-{[[4-(1,3-Dioxo-1,3-dihydro-isoindol-2-yl)-butyl]-(5,6,7,8-tetrahydro-quinolin-8-yl)-amino]-methyl}-4,5,6,7-tetrahydro-benzoimidazole-1-sulfonic acid (0.4564 g, 0.77 mmol) and 2 N HCl (7.5 mL) were stirred at reflux for 23 hours. The reaction mixture was cooled to room temperature and 15% (w/v) aqueous NaOH (5 mL) was added. The aqueous layer was extracted with CH$_2$Cl$_2$ (3×150 mL), and the combined organic extracts were washed with brine (1×100 mL), dried (Na$_2$SO$_4$), and concentrated. 0.2466 g (64%) of the crude 2-{4-[(4,5,6,7-tetrahydro-1H-benzoimidazol-2-ylmethyl)-(5,6,7,8-tetrahydro-quinolin-8-yl)-amino]-butyl}-isoindole-1,3-dione was isolated as a pale yellow foam. $^1$H NMR (CDCl$_3$) δ 1.37-1.39 (m, 2H), 1.79-1.88 (m, 10H), 1.98-2.11 (m, 2H), 2.51-2.63 (m, 8H), 3.50-3.52 (m, 1H), 3.66-3.86 (m, 2H), 3.97-3.99 (m, 1H), 7.02-7.11 (m, 2H), 7.37-7.40 (m, 2H), 7.68-7.71 (m, 1H), 7.80-7.82 (m, 1H), 8.44-8.46 (m, 1H).

To a solution of 2-{4-[(4,5,6,7-tetrahydro-1H-benzoimidazol-2-ylmethyl)-(5,6,7,8-tetrahydro-quinolin-8-yl)-amino]-butyl}-isoindole-1,3-dione (0.2466 g, 0.51 mmol) in ethanol (5 mL) was added hydrazine hydrate (0.3 mL, 2.5 mmol), and stirred at room temperature for 18 hours. The reaction mixture was concentrated, and purification of the crude material by column chromatography on silica gel (20:1:1 CH$_2$Cl$_2$—MeOH—NH$_4$OH) provided 0.1031 g (58%) of COMPOUND 89 as a pale yellow solid. $^1$H NMR (CDCl$_3$) δ 1.32-1.43 (m, 5H), 1.60-1.68 (m, 1H), 1.72-1.81 (m, 5H), 1.96-2.02 (m, 1H), 2.08-2.17 (m, 1H), 2.45-2.60 (m, 9H), 2.69-2.71 (m, 1H), 2.76-2.86 (m, 1H), 3.70-3.84 (m, 2H), 3.95-4.01 (m, 1H), 7.05-7.10 (m, 1H), 7.36 (d, 1H, J=7.5 Hz), 8.44 (d, 1H, J=3 Hz). $^{13}$C NMR (CDCL$_3$) δ 20.80, 22.38, 22.71, 23.07, 25.37, 28.77, 30.54, 41.23, 48.53, 49.81, 60.54, 121.36, 133.94, 136.52, 146.20, 146.32, 157.37. ES-MS m/z 354.5 (M+H). Anal. Calcd. for (C$_{21}$H$_{31}$N$_5$)0.7(H$_2$O)0.1 (CH$_2$Cl$_2$): C, 67.65; H, 8.77; N, 18.69. Found: C, 67.46; H, 8.80; N, 18.43.

Example 90

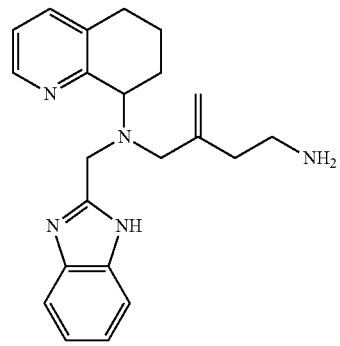 [SMILES: C=C(CCN)CN(Cc1nc2ccccc2[nH]1)C1CCCc2cccnc21]

Compound 90: Preparation of N$^1$-(1H-Benzimidazol-2-ylmethyl)-2-methylene-N$^1$-(5,6,7,8-tetrahydro-quinolin-8-yl)-butane-1,4-diamine (hydrobromide salt)

To a cold (0° C.), stirred solution of AlCl$_3$ (9.43 g, 70.7 mmol) in Et$_2$O (250 mL) was added powdered LiAlH$_4$ (8.10 g, 213 mmol). After the resultant grey suspension was stirred for 40 minutes, a solution of dimethyl itaconate (8.49 g, 53.7 mmol) in Et$_2$O (130 mL) was added dropwise, by cannula, over 30 minutes. The mixture was stirred for an additional 60 minutes, and then treated with saturated aqueous NH$_4$Cl (110 mL). The mixture was diluted with Et$_2$O (500 mL) and filtered through filter paper. The filtrate was concentrated and provided 4.52 g of 2-methylene-butane-1,4-diol as a pale yellow oil. To a stirred solution of 2-methylene-butane-1,4-diol (4.52 g, 44.3 mmol) in CH$_2$Cl$_2$ (330 mL), at room temperature, was added triethylamine (10.0 mL, 71.7 mmol) followed by benzoic anhydride (7.53 g, 33.3 mmol). After 16 hours, the mixture was washed sequentially with 1.0 M HCl (2×35 mL), saturated aqueous NH$_4$Cl (2×50 mL), and brine (2×50 mL), dried (Na$_2$SO$_4$), and concentrated. Purification of the crude material by column chromatography on silica gel (2:1 hexanes-ethyl acetate) provided 3.57 g (32% from dimethyl itaconate) of an ~5.5:1 mixture of benzoic acid 4-hydroxy-2-methylene-butyl ester and benzoic acid 3-hydroxymethyl-but-3-enyl ester.

To an ~5.5:1 mixture of benzoic acid 4-hydroxy-2-methylene-butyl ester and benzoic acid 3-hydroxymethyl-but-3-enyl ester (3.57 g, 17.3 mmol) in CH$_2$Cl$_2$ (175 mL) was added Et$_3$N (6.00 mL, 43.0 mmol) followed by methanesulfonyl chloride (2.40 mL, 31.0 mmol). The resultant mixture was stirred at room temperature for 15 hours. The mixture was washed with brine (3×50 mL), dried (Na$_2$SO$_4$), and concentrated. The resultant oil was dissolved in DMF (90 mL), treated with potassium phthalimide (6.38 g, 34.4 mmol), and the resultant mixture was heated at 80° C. for 24 hours then cooled to room temperature. The mixture was diluted with ethyl acetate (200 mL), brine (90 mL), and water (45 mL) and the phases were separated. The organic phase was washed with brine (5×25 mL), dried (MgSO$_4$), and concentrated. The crude material was purified by column chromatography on silica gel (4:1 hexanes-ethyl acetate) and provided 4.11 g (71%) of an ~3:1 mixture of benzoic acid 4-(1,3-dioxo-1,3-dihydro-isoindol-2-yl)-2-methylene-butyl ester and benzoic acid 3-(1,3-dioxo-1,3-dihydro-isoindol-2-ylmethyl)-but-3-enyl ester.

To an ~3:1 mixture of benzoic acid 4-(1,3-dioxo-1,3-dihydro-isoindol-2-yl)-2-methylene-butyl ester and benzoic acid 3-(1,3-dioxo-1,3-dihydro-isoindol-2-ylmethyl)-but-3-enyl ester (4.11 g, 12.3 mmol) in methanol (123 mL) was added NaOH (1.21 g, 30.3 mmol) and the mixture was stirred at room temperature for 30 minutes. The mixture was diluted with ethyl acetate (250 mL) and saturated aqueous NaHCO$_3$ (125 mL). The phases were separated and the aqueous phase was extracted with ethyl acetate (3×100 mL). The combined organic extracts were washed with brine (3×30 mL), dried (MgSO$_4$), and concentrated. Purification of the crude material by column chromatography on silica gel (2:1 hexanes-ethyl acetate) provided 0.83 g (29%) of 2-(3-Hydroxymethyl-but-3-enyl)-isoindole-1,3-dione as a white solid and 0.19 g (7%) of 2-(4-Hydroxy-2-methylene-butyl)-isoindole-1,3-dione as a white solid.

2-(3-Hydroxymethyl-but-3-enyl)-isoindole-1,3-dione: $^1$H NMR (CDCl$_3$) δ 2.07 (br s, 1H), 2.49 (t, 2H, J=6.0 Hz), 3.91 (t, 2H, J=6.0 Hz), 4.18 (m, 2H), 4.79 (s, 1H), 5.01 (s, 1H), 7.70-7.73 (m, 2H), 7.81-7.85 (m, 2H); $^{13}$C NMR (CDCl$_3$) δ 32.67, 37.04, 66.30, 113.60, 123.30, 132.00, 134.02, 145.30, 168.60; ES-MS m/z 231 (M+H).

2-(4-Hydroxy-2-methylene-butyl)-isoindole-1,3-dione: $^1$H NMR (CDCl$_3$) δ 1.88 (br s, 1H), 2.36 (t, 2H, J=6.0 Hz); 3.83 (m, 2H), 4.29 (s, 2H), 4.99 (s, 1H), 5.02 (s, 1H), 7.72-7.77 (m, 2H), 7.84-7.88 (m, 2H); $^{13}$C NMR (CDCl$_3$) δ 37.64, 42.24, 61.21, 114.23, 123.84, 132.37, 134.53, 140.73, 168.57; ES-MS m/z 231 (M+H).

To a solution of 2-(3-Hydroxymethyl-hut-3-enyl)-isoindole-1,3-dione (0.229 g, 0.99 mmol) in CH$_2$Cl$_2$ (10 mL) was added Et$_3$N (0.28 mL, 2.01 mmol) followed by methanesulfonyl chloride (0.12 mL, 1.55 mmol). The resultant mixture was stirred at room temperature for 1 hour. The mixture was diluted with CH$_2$Cl$_2$ (40 mL), washed with brine (3×10 mL), dried (Na$_2$SO$_4$), and concentrated to provide 0.31 g (100%) of a yellow oil.

Using General N-alkylation Procedure: A solution of the oil from above (0.31 g), (1-tert-butoxycarbonyl-1H-Benzimidazol-2-ylmethyl)-(5,6,7,8-tetrahydro-quinolin-8-yl)-amine (0.252 g, 0.67 mmol), KI (33 mg, 0.20 mmol), and N,N-diisopropylethylamine (0.35 mL, 2.00 mmol) in CH$_3$CN (13 mL) was heated at 60° C. for 21 hours. Purification of the crude material by column chromatography on silica gel (50:1:1 CH$_2$Cl$_2$—CH$_3$OH—NH$_4$OH) provided 239 mg (60%) of 2-{[[4-(1,3-Dioxo-1,3-dihydro-isoindol-2-yl)-2-methylene-butyl]-(5,6,7,8-tetrahydro-quinolin-8-yl)-amino]-methyl}-benzimidazole-1-carboxylic acid tert-butyl ester as a beige foam.

To a solution of 2-{[[4-(1,3-Dioxo-1,3-dihydro-isoindol-2-yl)-2-methylene-butyl]-(5,6,7,8-tetrahydro-quinolin-8-yl)-amino]-methyl}-benzimidazole-1-carboxylic acid tert-butyl ester (0.239 g, 0.40 mmol) in ethanol (8 mL) was added hydrazine monohydrate (0.40 mL, 8.26 mmol) and the resultant mixture was stirred at room temperature overnight. The mixture was filtered through filter paper and concentrated. Purification of the crude material by column chromatography on silica gel (20:1:1 CH$_2$Cl$_2$—CH$_3$OH—NH$_4$OH) provided 86 mg (55%) of the free base of the title compound as a yellow oil.

Using General Procedure D: Conversion of the free base to the hydrobromide salt followed by reprecipitation of the intermediate solid from methanol/ether gave COMPOUND 90 (97 mg, 69%) as a beige solid. $^1$H NMR (D$_2$O) δ 1.75-1.84 (m, 1H), 2.03-2.15 (m, 2H), 2.24-2.40 (m, 3H), 2.79-2.88 (m, 1H), 2.94-3.01 (m, 3H), 3.18 (d, 1H, J=13.8 Hz), 3.41 (d, 1H, J=13.8 Hz), 4.37 (d, 1H, J=16.5 Hz), 4.48 (d, 1H, J=16.5 Hz), 4.59-4.62 (m, 1H), 4.89 (s, 1H), 5.25 (s, 1H), 7.60-7.62 (m, 2H), 7.78-7.81 (m, 2H), 7.87-7.91 (m, 1H), 8.37 (br d, 1H, J=7.8 Hz), 8.69 (br d, 1H, J=5.4 Hz); $^{13}$C NMR (D$_2$O) δ 20.06, 20.30, 27.82, 31.03, 37.47, 48.28, 57.13, 60.45, 114.26, 118.52, 126.12, 127.05, 130.93, 139.65, 139.79, 141.16, 148.31, 150.83, 151.36; ES-MS m/z 362 (M+H). Anal. Calcd. for C$_{22}$H$_{27}$N$_5$.3.0HBr.2.2H$_2$O: C, 41.04; H, 5.39; N, 10.88; Br, 37.23. Found: C, 40.99; H, 5.25; N, 10.78; Br, 37.21.

Example 91

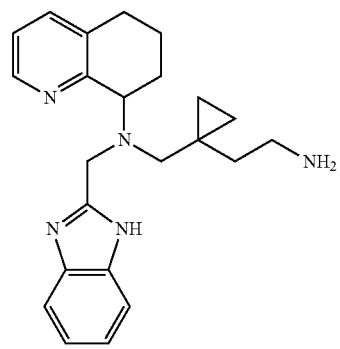 [SMILES: NCCC1(CN(Cc2nc3ccccc3[nH]2)C2CCCc3cccnc32)CC1]

Compound 91: Preparation of [1-(2-Amino-ethyl)-cyclopropylmethyl]-(1H-benzimidazol-2-ylmethyl)-(5,6,7,8-tetrahydro-quinolin-8-yl)-amine (hydrobromide salt)

To a cold (0° C.), stirred solution of diethyl zinc (1.0 M in hexanes, 4.0 mL, 4.0 mmol) in CH$_2$Cl$_2$ (10 mL) was added neat ClCH$_2$I (0.59 mL, 8.10 mmol) drop wise by syringe. After 30 minutes, a solution of 2-(3-Hydroxymethyl-but-3-enyl)-isoindole-1,3-dione (0.456 g, 1.97 mmol) in CH$_2$Cl$_2$ (6 mL) was added by cannula. After 60 minutes, the reaction mixture was treated with saturated aqueous NH$_4$Cl (20 mL), diluted with CH$_2$Cl$_2$ (20 mL), and warmed to room temperature. The phases were separated and the aqueous phase was extracted with CH$_2$Cl$_2$ (3×20 mL). The combined organic extracts were dried (Na$_2$SO$_4$) and concentrated. The crude material was purified by column chromatography on silica gel (1:1 hexanes-ethyl acetate) and provided 0.31 g (64%) of 1-[2-(1,3-Dioxo-1,3-dihydro-isoindol-2-yl)-ethyl]-cyclopropane-methanol as a white solid. $^1$H NMR (CDCl$_3$) δ 0.31-0.34 (m, 2H), 0.38-0.43 (m, 2H), 1.75 (t, 2H, J=6.9 Hz), 3.54 (s, 2H), 3.90 (t, 2H, J=6.6 Hz), 7.70-7.73 (m, 2H), 7.81-7.85 (m, 2H);

To a solution of 1-[2-(1,3-Dioxo-1,3-dihydro-isoindol-2-yl)-ethyl]-cyclopropane-methanol (0.31 g, 1.26 mmol) in CH$_2$Cl$_2$ (6 mL) was added sequentially 3 Å molecular sieves (0.644 g), N-methylmorpholine N-oxide (0.223 g, 1.90 mmol), and tetrapropylammonium perruthenate (88 mg, 0.25 mmol). After 30 minutes, the mixture was filtered through silica gel and the cake was washed with ether. The solvent was removed from the filtrate under reduced pressure and provided 0.25 g (82%) of 1-[2-(1,3-Dioxo-1,3-dihydro-isoindol-2-yl)-ethyl]-cyclopropanecarboxaldehyde as a colorless oil.

Using General Procedure B: Reaction of (1-tert-butoxycarbonyl-1H-Benzimidazol-2-ylmethyl)-(5,6,7,8-tetrahydroquinolin-8-yl)-amine (0.269 g, 0.70 mmol) and 1-[2-(1,3-Dioxo-1,3-dihydro-isoindol-2-yl)-ethyl]-cyclopropanecarboxaldehyde (0.25, 1.03 mmol) with NaBH(OAc)$_3$ (0.433 g, 2.04 mmol) in CH$_2$Cl$_2$ (7 mL) for 6 hours followed by purification of the crude material by column chromatography on silica gel (50:1:1 CH$_2$Cl$_2$—CH$_3$OH—NH$_4$OH) followed by radial chromatography on silica gel (1 mm plate, 100:1:1 CH$_2$Cl$_2$—CH$_3$OH—NH$_4$OH) provided 0.125 g (29%) of 2-{[{1-[2-(1,3-Dioxo-1,3-dihydro-isoindol-2-yl)-ethyl]-cyclopropylmethyl}-(5,6,7,8-tetrahydroquinolin-8-yl)-amino]-methyl}-benzimidazole-1-carboxylic acid tert-butyl ester as a white foam.

To a solution of 2-{[{1-[2-(1,3-Dioxo-1,3-dihydro-isoindol-2-yl)-ethyl]-cyclopropylmethyl}-(5,6,7,8-tetrahydroquinolin-8-yl)-amino]-methyl}-benzimidazole-1-carboxylic acid tert-butyl ester (0.121 g, 0.20 mmol) in ethanol (4 mL) was added hydrazine monohydrate (0.20 mL, 4.12 mmol) and the resultant mixture was stirred at room temperature overnight. The mixture was filtered through filter paper and concentrated. Purification of the cnide material by column chromatography on silica gel (20:1:1 CH$_2$Cl$_2$—CH$_3$OH—NH$_4$OH) provided 39 mg (50%) of the free base of the title compound as a yellow oil.

Using General Procedure D: Conversion of the free base to the hydrobromide salt followed by reprecipitation of the intermediate solid from methanol/ether gave COMPOUND 91 (50 mg, 76%) as a white solid. $^1$H NMR (D$_2$O) δ 0.31-0.41 (m, 3H), 0.52-0.58 (m, 1H), 1.34-1.45 (m, 1H), 1.75-1.98 (m, 1H), 2.02-2.20 (m, 3H), 2.27-2.33 (m, 1H), 2.44 (d, 1H, J=13.5 Hz), 2.81-2.91 (m, 3H), 2.98-3.01 (m, 2H), 4.39 (s, 2H), 4.69 (dd, 1H, J=6.3, 9.3 Hz), 7.60-7.63 (m, 2H), 7.79-7.90 (m, 3H), 8.36 (br d, 1H, J=7.8 Hz), 8.71 (br d, 1H, J=5.7 Hz); $^{13}$C NMR (D$_2$O) δ 9.00, 12.17, 15.30, 19.79, 20.30, 27.87, 31.06, 37.62, 48.20, 57.47, 59.82, 114.31, 126.04, 127.00, 131.20, 139.66, 141.14, 148.20, 151.16, 151.31; ES-MS m/z 376 (M+H). Anal. Calcd. for C$_{23}$H$_{29}$N$_5$·3.0HBr·2.2H$_2$O: C, 41.99; H, 5.58; N, 10.65; Br, 37.44. Found: C, 42.03; H, 5.41; N, 10.62; Br, 36.42.

Example 92

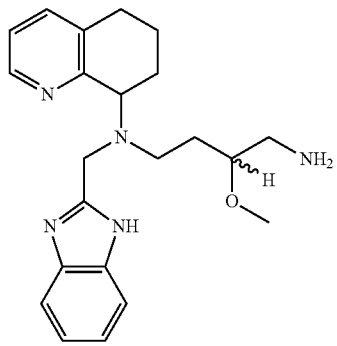 [SMILES: COC(CN)CCN(Cc1nc2ccccc2[nH]1)C1CCCc2cccnc21]

Compound 92 Preparation of N$^1$-(1H-Benzimidazol-2-ylmethyl)-3-methoxy-N$^1$-(5,6,7,8-tetrahydroquinolin-8-yl)-butane-1,4-diamine (hydrobromide salt)

Preparation of 4-(1,3-Dioxo-1,3-dihydro-isoindol-2-yl)-3-methoxy-butyraldehyde

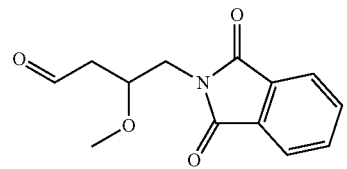 [SMILES: COC(CC=O)CN1C(=O)c2ccccc2C1=O]

To a solution of 2-[4-(tert-Butyl-dimethyl-silanyloxy)-2-hydroxy-butyl]-isoindole-1,3-dione (see N$^1$-(1H-benzimidazol-2-ylmethyl)-3,3-difluoro-N$^1$-(5,6,7,8-tetrahydroquinolin-8-yl)-butane-1,4-diamine example for preparation) (455 mg, 1.30 mmol) in neat MeI (2 mL) was added Ag$_2$O (224 mg, 0.97 mmol) and the reaction stirred at 60° C. for 2 days. The mixture was cooled, concentrated, diluted with CH$_2$Cl$_2$ (10 mL), and filtered through Celite, washing with Et$_2$O (75 mL). The filtrate was concentrated and purified by column chromatography (3:1 hexanes/EtOAc) to afford the methylated product (291 mg, 62%) as a clear oil.

A solution of the TBS-protected alcohol from above (291 mg, 0.80 mmol) in THF/1 N HCl (1:1, 7 mL) was stirred for 3 h. The mixture was diluted with EtOAc (35 mL) and water (10 mL) and saturated aqueous ammonium chloride (10 mL). The phases were separated and the organic phase was washed with brine (1×25 mL), dried (Na$_2$SO$_4$) and concentrated to give the crude product (242 mg) as a clear oil which was used without further purification in the next reaction.

To a solution of the alcohol from above (242 mg) in CH$_2$Cl$_2$ (10 mL) was added 3 Å molecular seives (265 mg), NMO (137 mg, 1.17 mmol) and TPAP (25 mg, 0.071 mmol) and the reaction stirred 1.5 h. The mixture was concentrated and purified by flash chromatography (EtOAc/hexanes, 1:2) to afford the title compound (95 mg, 48% over 2 steps) as a clear solid. $^1$H NMR (CDCl$_3$) δ 2.65-2.69 (m, 2H), 3.46 (s, 3H), 3.82 (t, 2H, J=6 Hz), 4.02-4.08 (m, 1H), 7.74 (dd, 2H, J=6, 3 Hz), 7.86 (dd, 2H, J=6, 3 Hz), 9.78 (s, 1H).

Following General Procedure B: To a stirred solution (1H-benzimidazol-2-ylmethyl)-(5,6,7,8-tetrahydro-quinolin-8-yl)-amine (108 mg, 0.39 mmol) and 4-(1,3-dioxo-1,3-dihydro-isoindol-2-yl)-3-methoxy-butyraldehyde (95 mg, 0.385 mmol) in dry CH$_2$Cl$_2$ (10 mL) was added NaBH(OAc)$_3$ (125 mg, 0.59 mmol) and the mixture stirred for 2.5 h at room temperature. The resultant crude yellow foam (230 mg) was used without further purification in the next step.

To a solution of the phthalimide from above (0.38 mmol) in EtOH (3.5 mL) was added anhydrous hydrazine (0.06 mL, 1.89 mmol) and the mixture stirred overnight. The resultant white solid was filtered through filter paper, washing thoroughly with CH$_2$Cl$_2$ and the filtrate concentrated in vacuo. The crude product was purified by radial chromatography on silica gel (1 mm plate, CH$_2$Cl$_2$/MeOH/NH$_4$OH, 50:1:1 then 25:1:1) to give the desired free amine (85 mg, 58% 2 steps) as a pale yellow oil.

Using General Procedure D: Conversion of the material from above (78 mg, 0.21 mmol) to the hydrobromide salt gave COMPOUND 92 (124 mg, 89%) as a yellow solid. $^1$H NMR (D$_2$O) mixture of diastereomers δ 1.81-1.86 (br m, 3H), 2.01-

2.07 (m, 1H), 2.18-2.24 (m, 1H), 2.37-2.42 (m, 1H), 2.54-2.63 (m, 1H), 2.88-3.10 (m, 5H), 3.24 (s, 3H), 3.51-3.56 (m, 1H), 4.40 (d, 1H, J=16.8 Hz), 4.50-4.58 (m, 2H), 7.60 (dd, 2H, J=6.3, 3.3 Hz), 7.81 (dd, 2H, J=6.3, 3.3 Hz), 7.88 (br t, 1H, J=6.8 Hz), 8.36 (d, 1H, J=8.1 Hz), 8.63-8.66 (m, 1H); $^{13}$C NMR (D$_2$O) mixture of diastereomers δ 20.43, 27.65, 29.90, 30.52, 42.10, 47.48, 48.01, 48.20, 57.04, 57.28, 60.47, 75.71, 75.92, 114.30, 126.02, 127.00, 131.01, 139.45, 140.69, 140.78, 148.21, 151.06, 151.51. ES-MS m/z 380 (M+H). Anal. Calcd. for C$_{22}$H$_{29}$N$_5$O.3.1HBr.1.5H$_2$O.0.3C$_4$H$_{10}$O: C, 41.00; H, 5.65; N, 10.31; Br, 36.45. Found: C, 41.01; H, 5.62; N, 10.34; Br, 36.39.

Example 93

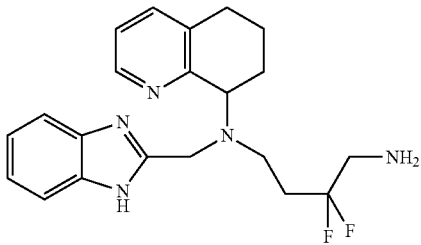 [SMILES: NCC(F)(F)CCN(Cc1nc2ccccc2[nH]1)C1CCCc2cccnc21]

Compound 93: Preparation of N$^1$-(1H-benzimidazol-2-ylmethyl)-3,3-difluoro-N$^1$-(5,6,7,8-tetrahydro-quinolin-8-yl)-butane-1,4-diamine To a mixture of potassium phthalimide (310.39 g, 1.68 mol) in DMF (1.0 L) at 0° C. was added allyl bromide (290.4 mL, 3.36 mol) from a dropping funnel over 30 minutes. The reaction was then warmed to room temperature and allowed to stir for 5 days. The mixture was filtered to remove salts while washing the residue with ethyl acetate (1 L), and the filtrate concentrated under reduced pressure. The residue was then partitioned between saturated aqueous NaHCO$_3$ (0.5 L) and CH$_2$Cl$_2$ (0.8 L) and the organic phase separated. The aqueous phase was extracted with CH$_2$Cl$_2$ (2×0.8 L), and the combined organic phases were dried (Na$_2$SO$_4$), filtered and concentrated under reduced pressure to give N-allylphthalimide as a white powder (294 g, 94%). $^1$H NMR (CDCl$_3$) δ 4.30 (d, 2H, J=6.0 Hz), 5.22 (m, 2H), 5.88 (m, 1H), 7.73 (m, 2H), 7.85 (m, 2H).

A solution of paraformaldehyde (245 g) was heated to 70° C. in a solution of H$_2$SO$_4$ (360 mL) and H$_2$O (90 mL) using a hot water bath until the mixture became homogenous. Solid N-allylphthalimide (133 g, 0.71 mol) was then added over 10 minutes, keeping the exotherm generated under control. The solution was then stirred at this temperature for an additional 0.5 hour and poured into ice water (1.5 L). The mixture was extracted with ethyl acetate (3×1 L), dried (MgSO$_4$), filtered and concentrated under reduced pressure. The crude solid was then purified through a silica gel plug (1 kg SiO$_2$) from CH$_2$Cl$_2$ as the eluent. This afforded the desired 1,3-dioxane-4-ylmethylphthalimide as a white solid (95 g, 54%).

1,3-dioxane-4-ylmethylphthalimide (95 g, 390 mmol) was dissolved in a saturated solution of hydrochloric acid in methanol (600 mL) and stirred for 2 days at 80° C. The reaction was then cooled to room temperature, and the acid neutralised to pH 7 with solid NaHCO$_3$. Ethyl acetate (1 L) was added and the mixture was filtered to remove salts. The filtrate was then concentrated under reduced pressure and dried overnight in vacuo. The crude was purified through a silica gel plug (1 kg silica) using 2:98 CH$_3$OH:CH$_2$Cl$_2$ eluent to give the desired N-(2,4-dihydroxybutyl)phthalimide as a white solid (45 g, 50%). $^1$H NMR (MeOD) δ 1.62 (m, 1H), 1.75 (m, 1H), 3.31 (s, 1H), 3.64 (m, 2H), 3.69 (d, 2H, J=5.1 Hz), 4.06 (sept, 1H), 7.79 (m, 2H), 7.85 (m, 2H).

To a solution of N-(2,4-dihydroxybutyl)phthalimide (51 g, 217 mmol) in pyridine (725 mL) at 0° C. was added acetic anhydride (20.5 mL, 217 mmol). The solution was stirred at 0° C. for 4 hours and then concentrated on the rotary evaporator using a water bath temperature of 35° C. The crude residue was then purified through a silica gel plug (1 kg silica) with 0.5:99.5 CH$_3$OH:CH$_2$Cl$_2$ eluent to give the desired product which was unfortunately contaminated with pyridine. CH$_2$Cl$_2$ (100 mL) was then added and the organic was washed with 1N HCl (3×50 mL), saturated aqueous NH$_4$Cl (50 mL), and brine (50 mL). The organic phase was then separated, dried (Na$_2$SO$_4$), filtered, and concentrated under reduced pressure to afford clean N-(4-acetoxy-2-hydroxybutyl)phthalimide as a white solid (10.2 g, 17%).

A solution of N-(4-acetoxy-2-hydroxybutyl)phthalimide (10.2 g, 36.8 mmol) in CH$_2$Cl$_2$ (185 mL) at 0° C. was treated with molecular seives (18.4 g), N-methylmorpholine oxide (6.46 g, 55.2 mmol), and tetrapropylammonium perruthenate (1.29 g, 3.7 mmol). The mixture was allowed to warm to room temperature over 20 minutes and immediately filtered through silica (using 500 g SiO$_2$ in a coarse glass flitted funnel). The silica was washed with excess diethyl ether (2 L) and concentrated under reduced pressure to afford the desired N-(4-acetoxy-2-oxobutyl)phthalimide (9.22 g, 92%).

The above ketone (8.0 g, 29 mmol) was added as dry solid to neat DAST (20 mL) at 0° C. and then heated to 50° C. for 40 hours. The homogenous solution was then cooled to 0° C., diluted with CH$_2$Cl$_2$ (75 mL), and quenched with excess brine (50 ml). The organic phase was separated and the aqueous phase extracted with CH$_2$Cl$_2$ (3×75 mL). The combined organic phases were then dried (Na$_2$SO$_4$), filtered and concentrated under reduced pressure. The crude red solid was then purified by column chromatography on silica gel (1:4 ethyl acetate/hexane) to give the desired N-(4-acetoxy-2,2-difluorobutyl)phthalimide as a peach colored solid (3.84 g, 44%). $^1$H NMR (CDCl$_3$) δ 2.07 (s, 3H), 2.32 (tt, 2H, J=16.5, 6.0 Hz), 4.11 (t, 2H, J=13.5 Hz), 4.35 (t, 2H, J=7.5 Hz), 7.75 (m, 2H), 7.90 (m, 2H).

The above N-(4-acetoxy-2,2-difluorobutyl)phthalimide (3.84 g, 12.9 mmol) was dissolved in THF (65 mL) and cooled to −78° C. A solution of DIBAL-H (32.3 mL, 1.0 M in hexanes, 32.3 mmol) was added slowly and the solution allowed to stir 0.5 h. Saturated aqueous NH$_4$Cl solution (15 mL) was then added and the solution was warmed to room temperature. MgSO$_4$ (15 g) and diethyl ether (200 mL) were added, and the mixture was filtered through celite, washing with excess 1:1 Et$_2$O/THF (1 L). The filtrate was then concentrated under reduced pressure and the crude material was purified by column chromatography on silica gel (1:2 EtOAc/hexanes) to give the desired N-(2,2-difluoro-4-hydroxybutyl) phthalimide as a pale yellow solid (1.47 g, 45%). $^1$H NMR (CDCl$_3$) δ 1.97 (t, OH, J=6.0 Hz), 2.22 (tt, 2H, J=16.5, 6.0 Hz), 3.95 (q, 2H, J=6.0 Hz), 4.19 (t, 2H, J=15 Hz), 7.75 (m, 2H), 7.90 (m, 2H).

Methanesulfonyl chloride (0.50 mL, 6.3 mmol) and triethylamine (1.20 mL, 8.6 mmol) was added to a solution of the above alcohol (1.47 g, 5.76 mmol) in CH$_2$Cl$_2$ (29 mL) at 0° C. and allowed to warm to room temperature over 30 minutes. This gave, after aqueous work up, the desired crude methanesulfonate (1.84 g, 96%) as a fine, pale yellow powder that was used immediately in the next reaction.

A solution of the above crude methanesulfonate (1.84 g) in DMF (19 mL) was treated with sodium azide (1.87 g, 28.8 mmol) and heated to 80° C. for 2 h. The reaction mixture was then concentrated and the residue partitioned between ethyl acetate (20 mL) and brine (15 mL). The organic phase was separated, washed with brine (3×15 mL), and dried over MgSO$_4$. The mixture was then filtered and concentrated under reduced pressure to give the desired N-(4-azido-2,2-difluorobutyl)phthalimide (1.37 g, 85% 2 steps).

The material from above (1.37 g) was dissolved in anhydrous methanol (50 mL) and the reaction vessel purged with nitrogen. 10% palladium on carbon (275 mg) was added and the mixture stirred under an atmosphere of hydrogen (30 psi) for 16 hours. The reaction mixture was then filtered through celite and purified by column chromatography with silica gel (2:98 methanol:dichloromethane) to afford N-(4-amino-2,2-difluorobutyl)phthalimide (0.71 g, 57%). $^1$H NMR (CDCl$_3$) δ 2.32 (tt, 2H, J=16.5, 6.0 Hz), 3.02 (t, 2H, J=15.0 Hz), 3.94 (t, 2H, J=7.5 Hz), 7.73 (m, 2H), 7.85 (m, 2H).

Using general procedure B from above, N-(4-amino-2,2-difluorobutyl)phthalimide (0.28 g, 1.1 mmol), 6,7-dihydro-5H-quinolin-8-one (0.21 g, 1.4 mmol) and sodium triacetoxyborohydride (0.45 g, 2.2 mmol) were stirred at room temperature in dichloromethane (5.5 mL) for 16 hours to yield, after work-up and column chromatography (2:98 MeOH:CH$_2$Cl$_2$), 2-[2,2-difluoro-4-(5,6,7,8-tetrahydro-quinolin-8-ylamino)-butyl]-isoindole-1,3-dione as a sticky oil (0.36 g, 85%).

To a solution of the above secondary amine (0.36 g, 0.93 mmol), N-(tert-butoxycarbonyl)-2-chloromethylbenzimidazole (0.25 g, 0.93 mmol), and potassium iodide (8 mg, 0.05 mmol) in anhydrous acetonitrile (9.3 mL) was added diisopropylethylamine (0.24 mL, 1.4 mmol) and stirred at 60° C. for 16 hours. The mixture was then concentrated under reduced pressure and the residue partitioned between dichloromethane (20 mL) and brine (15 mL). The organic phase was separated and the aqueous phase was extracted with dichloromethane (2×15 mL). The combined organic phases were then dried (Na$_2$SO$_4$), filtered, and concentrated under reduced pressure to give a crude residue that was purified by column chromatography with silica gel (2:98 MeOH/CH$_2$Cl$_2$). This afforded 2-{[[4-(1,3-dioxo-1,3-dihydroisoindol-2-yl)-3,3-difluorobutyl]-(5,6,7,8-tertahydroquinolin-8-yl)-amino]-methyl}-benzimidazole-1-carboxylic acid tert-butyl ester (0.24 g, 41%).

A solution of the above substrate (0.24 g, 0.39 mmol) in anhydrous ethanol (3.7 mL) was treated with hydrazine monohydrate (0.20 mL, 3.9 mmol) and stirred for 16 h. The white mixture was then filtered, concentrated under reduced pressure, and purified by column chromatography with silica gel (5:0.5:94.5 methanol:ammonium hydroxide:dichloromethane) to afford N-(1H-benzimidazol-2-ylmethyl)-3,3-difluoro-N-(5,6,7,8-tetrahydroquinolin-8-yl)-butane-1,4-diamine as a light beige solid (87 mg, 66%). $^1$H NMR (CDCl$_3$) δ 1.67 (m, 1H), 1.70-2.20 (m, 4H), 2.28 (m, 1H), 2.55-3.00 (m, 5H), 3.10 (m, 1H), 4.12 (m, 1H), 4.26 (s, 2H), 7.20 (m, 3H), 7.45 (d, 1H, J=7.5 Hz), 7.59 (br, 2H), 8.61 (d, 1H, J=3.9 Hz). $^{13}$C NMR (CDCl$_3$) δ 21.88, 24.85, 29.49, 35.88 (t, 1C, J=20 Hz), 38.24 (t, 1C, J=92 Hz), 51.74, 55.25 (t, 1C, J=116 Hz), 62.99, 115.41 (br, 3C), 122.14 (2C), 122.92, 125.40, 128.61, 135.29, 137.93, 147.10, 155.75, 156.98. ES-MS m/z 385 (M+H). Anal. Calcd. for C$_{21}$H$_{25}$N$_5$F$_2$.0.2CH$_2$Cl$_2$: C, 63.27; H, 6.36; N, 17.40. Found: C, 63.27; H, 6.60; N, 17.26.

Example 94

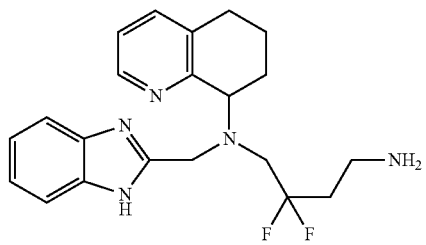 [SMILES: NCCC(F)(F)CN(Cc1nc2ccccc2[nH]1)C1CCCc2cccnc21]

Compound 94: Preparation of N$^1$-(1H-benzimidazol-2-ylmethyl)-2,2-difluoro-N$^1$-(5,6,7,8-tetrahydro-quinolin-8-yl)-butane-1,4-diamine To a solution of N-(4-amino-2,2-difluorobutyl)phthalimide (0.33 g, 1.3 mmol) in anhydrous THF (7 mL) was added di-tert-butyldicarbonate (0.31 g, 1.4 mmol) and a drop of water. The solution was stirred 30 minutes and saturated aqueous ammonium chloride solution (25 mL) was added and the solution was extracted with ethyl acetate (2×30 mL). The combined organic phases were then dried (MgSO$_4$), filtered, and concentrated under reduced pressure. This afforded the crude boc-protected primary amine as yellow solid (0.42 g, 91%).

A solution of the above amine (0.42 g, 1.2 mmol) in anhydrous ethanol (12 mL) was treated with hydrazine monohydrate (0.57 mL, 12 mmol) and stirred for 16 h. The turbid white mixture was then filtered, concentrated under reduced pressure, and purified by column chromatography with silica gel (1:1:10 methanol:ammonium hydroxide:dichloromethane) to give (4-amino-3,3-difluorobutyl)-carbamic acid tert-butyl ester (0.21 g, 77%). $^1$H NMR (CDCl$_3$) δ 1.30 (br, NH$_2$), 1.45 (s, 9H), 2.01 (tt, 2H, J=16.5, 6.0 Hz), 2.95 (t, 2H, J=6.0 Hz), 3.52 (td, 2H, J=15.0, 7.0 Hz), 5.00 (br, NH).

Using general procedure B from above, N-(4-amino-2,2-difluorobutyl)phthalimide (0.26 g, 1.2 mmol), 6,7-dihydro-5H-quinolin-8-one (0.22 g, 1.5 mmol) and sodium triacetoxyborohydride (0.49 g, 2.3 mmol) were stirred at room temperature in dichloromethane (5.5 mL) for 16 hours to yield, after work-up and column chromatography (1:99 MeOH:CH$_2$Cl$_2$), [3,3-difluoro-4-(5,6,7,8-tetrahydroquinolin-8-ylamino)-butyl]-carbamic acid tert-butyl ester as a sticky oil (0.37 g, 90%).

To a solution of the above secondary amine (0.37 g, 1.0 mmol), N-(tert-butoxycarbonyl)-2-chloromethylbenzimidazole (0.44 g, 1.7 mmol), and potassium iodide (9 mg, 0.05 mmol) in anhydrous acetonitrile (10.0 mL) was added diisopropylethylamine (0.36 mL, 2.1 mmol) and stirred at 60° C. for 16 hours. The mixture was then concentrated under reduced pressure and the residue partitioned between dichloromethane (20 mL) and brine (15 mL). The organic phase was separated and the aqueous phase was extracted with dichloromethane (2×15 mL). The combined organic phases were then dried (Na$_2$SO$_4$), filtered, and concentrated under reduced pressure to give a crude residue that was purified by column chromatography with silica gel (2:98 MeOH/CH$_2$Cl$_2$). This afforded 2-{[(4-tert-butoxycarbonylamino-2,2-difluorobutyl)-(5,6,7,8-tertahydroquinolin-8-yl)-amino]-methyl}-benzimidazole-1-carboxylic acid tert-butyl ester as a pale yellow solid (0.23 g, 41%).

A solution of the above material (0.23 g, 0.4 mmol) in neat TFA (4 mL) was stirred for 0.5 h. The solution was diluted with CH$_2$Cl$_2$ (20 mL), and 15% aqueous NaOH was added until pH>10. The organic phase was separated, and the aqueous was extracted with CH$_2$Cl$_2$ (2×20 mL). The combined organic phases were then dried (Na$_2$SO$_4$), filtered, and concentrated under reduced pressure. This afforded, after radial chromatography (2:1:97 MeOH:NH$_4$OH:CH$_2$Cl$_2$), N-(1H-benzimidazol-2-ylmethyl)-2,2-difluoro-N-(5,6,7,8-tetrahydroquinolin-8-yl)-butane-1,4-diamine as a pale yellow flaky solid (0.11 g, 72%). $^1$H NMR (CDCl$_3$) δ 1.69 (m, 1H), 1.85-2.10 (m, 4H), 2.23 (m, 1H), 2.70-2.97 (m, 6H), 4.03 (d, 1H, J=17.1 Hz), 4.07 (m, 1H), 4.15 (d, 1H, J=16.8 Hz), 7.15-7.24 (m, 3H), 7.45 (d, 1H, J=7.8 Hz), 7.58 (br, 2H), 8.57 (d, 1H, J=3.9 Hz). $^{13}$C NMR (CDCl$_3$) δ 21.62, 24.35, 29.47, 34.03 (t, 1C, J=93 Hz), 44.55 (t, 1C, J=20 Hz), 47.26 (t, 1C, J=112 Hz), 50.12, 62.87, 118 (br, 3C), 122.09 (2C), 122.80, 123.86, 127.06, 135.10, 137.99, 147.06, 156.27, 157.41. ES-MS m/z 385 (M+H). Anal. Calcd. for C$_{21}$H$_{25}$N$_5$F$_2$.0.2CH$_2$Cl$_2$: C, 63.27; H, 6.36; N, 17.40. Found: C, 63.34; H, 6.68; N, 17.29.

Example 95

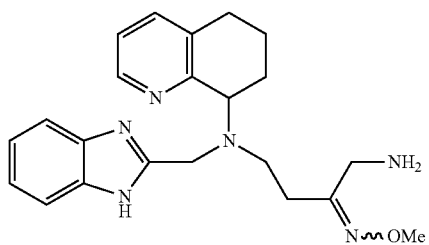 [SMILES: CON=C(CN)CCN(Cc1nc2ccccc2[nH]1)C1CCCc2cccnc21]

Compound 95: Preparation of (1H-benzimidazol-2-ylmethyl)-(5,6,7,8-tetrahydro-quinolin-8-yl)-(1-amino-2-(O-methyloxime)-butan-4-yl)-amine To a solution of 3-buten-1-ol (10 g, 138 mmol) in dichloromethane (150 mL) was added acetic anhydride (13 mL, 138 mmol) and 4-dimethylaminopyridine (244 mg, 2 mmol). The mixture was then stirred at room temperature for 8 hours. The reaction mixture was then poured into a saturated aqueous sodium bicarbonate solution (100 mL). After separation of the aqueous and organic layers, the aqueous layer was extracted twice with 100 mL portions of dichloromethane. The combined organic fractions were then dried over anhydrous sodium sulfate, filtered, and concentrated in vacuo to afford 3-buten-1-yl acetate as a colourless oil in a yield of 12.9 g (82%). $^1$H NMR (CDCl$_3$) δ 2.04 (s, 3H), 2.38 (m, 2H), 4.11 (t, 3H, J=7.1 Hz), 5.04 (d, 1H, J=9.1 Hz), 5.08 (d, 1H, J=15.3 Hz), 5.77 (m, 1H).

To a solution of 3-buten-1-yl acetate (5.7 g, 50 mmol) in dichloromethane (200 mL) was added m-chloroperoxybenzoic acid (12.9 g, 75 mmol). The reaction was then stirred at room temperature for 3 hours. The reaction mixture was then filtered through celite and concentrated in vacuo. The residue was purified by silica gel flash chromatography (4:1 hexanes:ethyl acetate) to yield 3,4-epoxybutan-1-yl acetate as a colourless oil in a yield of 3.8 g (58%). $^1$H NMR (CDCl$_3$) δ 1.78-1.88 (m, 2H), 2.03 (s, 3H), 2.47 (m, 1H), 2.75 (m, 1H), 2.99 (m, 1H), 4.18 (t, 1H, J=6.6 Hz).

To a solution of 3,4-epoxybutan-1-yl acetate (3.9 g, 29 mmol) in DMF (50 mL) was added potassium phthalimide (6.47 g, 35 mmol). The stirred mixture was then heated to 90° C. for 16 hours. After cooling, the mixture was diluted with ethyl acetate (200 mL) and extracted repeatedly with water. The organic fraction was then dried over anhydrous sodium sulfate, filtered and concentrated in vacuo. The residue was purified by silica gel flash chromatography (1:1 hexanes:ethyl acetate) to afford N-(3-hydroxybutan-4-yl-1-acetate)-phthalimide as a pale yellow oil in a yield of 1.65 g (20%). $^1$H NMR (CDCl$_3$) δ 1.69-1.88 (m, 2H), 2.04 (s, 3H), 2.90 (m, 1H(OH)), 3.79 (d, 2H, J=5.7 Hz), 4.03 (m, 1H), 4.21-4.31 (m, 2H), 7.70 (m, 2H), 7.83 (m, 2H). MS m/z 300 (M+Na).

To a solution of afford N-(3-hydroxybutan-4-yl-1-acetate)-phthalimide (554 mg, 2.0 mmol) in acetonitrile (15 mL) was added imidazole (150 mg, 2.2 mmol) and t-butyldimethylsilyl chloride (310 mg, 2.05 mmol). The mixture was then stirred overnight at room temperature. Dichloromethane (50 mL) was then added to the reaction, and the mixture was extracted with a saturated ammonium chloride solution. The organic layer was then dried over anhydrous sodium sulfate, filtered and concentrated to leave a yellow oily residue which was purified by silica gel flash chromatography (3:1 hexanes:ethyl acetate) to afford N-(3-t-butyldimethylsiloxybutan-4-yl-1-acetate)-phthalimide in a yield of 570 mg (73%). $^1$H NMR (CDCl$_3$) δ −0.04 (s, 3H), −0.01 (s, 3H), 0.84 (s, 9H), 1.78 (m, 2H), 3.68 (dd, 1H, J=8.1, 6.5 Hz), 3.73 (dd, 1H, J=8.1, 6.2 Hz), 4.15 (m, 3H), 7.71 (m, 2H), 7.85 (m, 2H).

To a stirred −78° C. solution of afford N-(3-t-butyldimethylsiloxybutan-4-yl-1-acetate)-phthalimide (670 mg, 1.71 mmol) in THF (20 mL) was added DIBAL-H (5.1 mL of a 1.0M solution in hexanes, 5.1 mmol). The reaction was stirred at −78° C. for 45 minutes, then a saturated solution of ammonium chloride (5 mL) was added. The mixture was allowed to warm to room temperature, then ethyl acetate (20 mL) and 1N HCl (2 mL) were added. The mixture was then shaken in a separatory funnel to speed the clarification of the layers, then the organic and aqueous layers were separated. The aqueous layer was extracted twice with ethyl acetate, then the combined organic fractions were separated and the aqueous layer was extracted twice with ethyl acetate. The combined organic fractions were then dried over anhydrous sodium sulfate, filtered and concentrated in vacuo. The residue was purified by silica gel flash chromatography (1:1 hexanes:ethyl acetate) to afford N-(3-t-butyldimethylsiloxybutan-1-ol-4-yl)-phthalimide as a colourless oil in a yield of 465 mg (78%). $^1$H NMR (CDCl$_3$) δ −0.02 (s, 3H), 0.09 (s, 3H), 0.86 (s, 9H), 1.71-1.82 (m, 2H), 2.11 (m, 1H(OH)), 3.76 (m, 4H), 4.28 (m, 1H), 7.73 (m, 2H), 7.85 (m, 2H).

To a solution of N-(3-t-butyldimethylsiloxybutan-1-ol-4-yl)-phthalimide (160 mg, 0.4 mmol) in dichloromethane (10 mL) was added Dess-Martin Periodinane (212 mg, 0.5 mmol). The mixture was then stirred at room temperature for 30 minutes. A 5% solution of sodium thiosulfate (10 mL) and a saturated sodium bicarbonate solution (10 mL) was added along with another 20 mL of dichloromethane. The mixture was then stirred rapidly for 20 minutes, and the aqueous and organic layers were separated. The aqueous layer was extracted twice with dichloromethane, and the combined organic fractions were dried over anhydrous sodium sulfate, filtered and concentrated in vacuo to afford N-(3-t-butyldimethylsiloxybutan-1-a1-4-yl)-phthalimide as a yellow oil, which was used immediately in the next reaction without further purification. $^1$H NMR (CDCl$_3$) δ −0.02 (s, 3H), 0.05 (s, 3H), 0.81 (s, 9H), 2.61 (m, 2H), 3.74 (m, 2H), 4.51 (m, 1H), 7.71 (m, 2H), 7.85 (m, 2H), 9.81 (m, 1H).

To a solution of N-(3-t-butyldimethylsiloxybutan-1-al-4-yl)-phthalimide (0.4 mmol) in dichloromethane (15 mL) was added (5,6,7,8-tetrahydroquinolin-8-yl)-[(N-t-butoxycarbonyl)-benzimidazol-2-yl)methyl]-amine (151 mg, 0.4 mmol). The mixture was stirred at room temperature for 30 minutes, then sodium triacetoxyborohydride (170 mg, 0.8 mmol) was added, and the reaction was allowed to stir for 16 hours. A saturated sodium bicarbonate solution (10 mL) was added, and the aqueous and organic layers were separated. The aqueous layer was then extracted twice with dichloromethane, and the combined organic fractions were dried over anhydrous sodium sulfate, filtered and concentrated in vacuo. The residue was then purified by silica gel flash chromatography (3%, methanol in dichloromethane) to afford [(N-t-butoxycarbonyl)-benzimidazol-2-ylmethyl]-(5,6,7,8-tetrahydro-quinolin-8-yl)-(1-(N-phthalimidyl)-butan-2-(t-butyldimethylsiloxy)-4-yl)-amine as a pale yellow foam in a yield of 224 mg (79%). $^1$H NMR (CDCl$_3$) δ −0.25 (s, 3H), −0.23 (s, 3H), 0.69 (s, 9H), 1.44-1.63 (m, 4H), 1.68 (s, 9H), 2.00 (m, 2H), 2.16 (m, 1H), 2.65-2.74 (m, 3H), 3.48-3.62 (m, 2H), 3.94 (m, 1H), 4.23 (m, 1H), 4.44 (d, 1H, J=15.3 Hz), 4.72 (m, 1H, J=15.3 Hz), 6.95 (m, 1H), 7.20 (m, 3H), 7.67 (m, 3H), 7.77 (m, 3H), 8.44 (m, 1H).

To a solution of [(N-t-butoxycarbonyl)-benzimidazol-2-ylmethyl]-(5,6,7,8-tetrahydro-quinolin-8-yl)-(1-(N-phthalimidyl)-butan-2-(t-butyldimethylsiloxy)-4-yl)-amine (170 mg, 0.24 mmol) in THF (8 mL) was added 1N HCl (2 mL). The mixture was then heated to 50° C. for 2 hours. After cooling, dichloromethane (50 mL) was added, and the mixture was shaken with a saturated sodium bicarbonate solution (20 mL). After separation of the aqueous and organic layers, the aqueous layer was extracted twice with dichloromethane. The combined organic fractions were then dried over anhydrous sodium sulfate, filtered and concentrated in vacuo to afford a foamy residue, which was purified by silica gel flash chromatography (5% methanol in dichloromethane) to afford (1-H-benzimidazol-2-ylmethyl)-(5,6,7,8-tetrahydro-quinolin-8-yl)-(1-(N-phthalimidyl)-butan-2-ol-4-yl)-amine as a white foam in a yield of 73 mg (49%). $^1$H NMR (CDCl$_3$) δ 1.50-1.59 (m, 2H), 1.70-2.07 (m, 5H), 2.21 (m, 1H), 2.75-3.00 (m, 4H), 3.78-3.94 (m, 2H), 4.00-4.22 (m, 2H), 7.04 (m, 1H), 7.16 (m, 2H), 7.24 (d, 1H, J=5.8 Hz), 7.68 (br s, 1H(NH)), 7.71 (m, 3H), 7.81 (m, 3H), 8.21 and 8.42 (d, total of 1H, J=4.9, 5.1 Hz respectively).

To a solution of (1-H-benzimidazol-2-ylmethyl)-(5,6,7,8-tetrahydro-quinolin-8-yl)-(1-(N-phthalimidyl)-butan-2-ol-4-yl)-amine (132 mg, 0.246 mmol) in dichloromethane (10 mL) was added Dess Martin Periodinane (145 mg, 0.344 mmol). The reaction mixture was then stirred for 60 minutes. A 5% Na$_2$S$_2$O$_3$/5% NaHCO$_3$ aqueous solution (10 mL) was then added, and the resulting mixture was stirred vigorously at room temperature for 20 minutes (until the aqueous and organic layers had clarified). The layers were then separated, and the aqueous layer was extracted twice with dichloromethane. The combined organic fractions were then dried over anhydrous sodium sulfate, filtered and concentrated, and the residue was purified by silica gel flash chromatography (5% methanol in dichloromethane) to give the desired product, (1-H-benzimidazol-2-ylmethyl)-(5,6,7,8-tetrahydro-quinolin-8-yl)-(1-(N-phthalimidyl)-butan-2-one-4-yl)-amine as a pale yellow foam in a yield of 109 mg (84%). $^1$H NMR (CDCl$_3$) δ 1.73 (m, 1H), 1.85 (m, 1H), 2.03 (m, 1H), 2.26 (m, 1H), 2.57-2.81 (m, 4H), 3.10 (m, 1H), 4.08 (s, 2H), 4.08 (m, 1H), 4.35 (d, 1H, J=16.5 Hz), 4.63 (d, 1H, J=16.5 Hz), 7.00 (m, 1H), 7.19 (m, 2H), 7.18 (m, 1H), 7.38 (br s, 1H (NH)), 7.75 (m, 4H), 7.88 (m, 2H), 8.56 (m, 1H).

To a solution of (1-H-benzimidazol-2-ylmethyl)-(5,6,7,8-tetrahydro-quinolin-8-yl)-(1-(N-phthalimidyl)-butan-2-one-4-yl)-amine (58 mg, 0.117 mmol) in methanol (5 mL) was added hydroxylamine hydrochloride (83.5 mg, 1.0 mmol). The resulting solution was stirred at room temperature overnight. Aqueous sodium bicarbonate (5 mL of a saturated solution) was then added, dichloromethane (10 mL) was also added the aqueous and organic layers were separated and the aqueous layer was extracted twice with dichloromethane. The combined organic fractions were then dried over anhydrous sodium sulfate, filtered and concentrated. The residue was purified by silica gel flash chromatography using a 5% methanol in dichloromethane mixture as an eluent to afford (1-H-benzimidazol-2-ylmethyl)-(5,6,7,8-tetrahydro-quinolin-8-yl)-(1-(N-phthalimidyl)-butan-2-(O-methyloxime)-4-yl)-amine as a pale yellow foam in a yield of 29 mg (49%). $^1$H NMR (CDCl$_3$) δ 1.73-2.05 (series of m, 5H), 2.45 (t, 2H, J=6.9 Hz), 2.87-2.98 (m, 4H), 3.16 and 3.79 (s, total of 3H), 4.01-4-12 (m, 3H), 4.26 and 4.30 (d, J=16.7 and 16.9 Hz respectively, total of 1H), 4.47 and 4.85 (d, J=16.7 and 16.9 Hz respectively, total of 1H), 7.13-7.17 (m, 2H), 7.25 (m, 2H), 7.22 (m, 1H), 7.60 (br s, 1H(NH)), 7.75 (m, 4H), 7.87 (m, 2H), 8.38 and 8.44 (m, total of 1H).

To a solution of (1-H-benzimidazol-2-ylmethyl)-(5,6,7,8-tetrahydro-quinolin-8-yl)-(1-(N-phthalimidyl)-butan-2-(O-methyloxime)-4-yl)-amine (29 mg, 0.055 mmol) in denatured ethanol (5 mL) was added hydrazine hydrate (0.07 mL, 1.5 mmol). The mixture was then heated to 60° C. for 60 minutes. After cooling, the reaction was concentrated in vacuo, taken up in dichloromethane (20 mL) and washed with an aqueous sodium carbonate solution (5 mL). The aqueous layer was then extracted twice with dichloromethane, and the combined organic fractions were dried over anhydrous sodium sulfate, filtered and concentrated to afford a foamy residue which was purified by silica gel flash chromatography (10% methanol, 0.5% ammonium hydroxide in dichloromethane) to afford (1H-benzimidazol-2-ylmethyl)-(5,6,7,8-tetrahydro-quinolin-8-yl)-(1-amino-2-(O-methyloxime)-butan-4-yl)-amine (COMPOUND 95—diastereomeric mixture) as a white foam in a yield of 10 mg. $^1$H NMR (CDCl$_3$) δ 1.65 (m, 1H), 1.98 (m, 1H), 2.02 (m, 1H) 2.19 (m, 1H), 2.42 (m, 2H), 2.78-2.87 (m, 4H), 3.31 (m, 2H), 3.55 and 3.73 (s, 3H), 4.03 (m, 3H), 7.13 (m, 3H), 7.40 (t, 1H, J=8.1 Hz), 7.56 (m, 2H), 8.51 and 8.51 (d, J=5.4 Hz, 5.3 Hz respectively, total of 1H); $^{13}$C NMR (both isomers —CDCl$_3$) δ 21.77, 23.51, 27.85, 29.58, 32.47, 43.34, 47.55, 49.09, 49.62, 49.94, 53.81, 61.60, 62.02, 122.07, 122.61, 132.33, 134.41, 137.79, 142.65, 147.04, 154.98.

Example 96

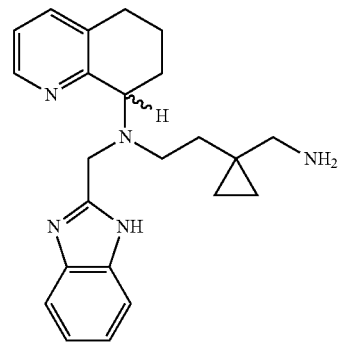 [SMILES: NCC1(CCN(Cc2nc3ccccc3[nH]2)C2CCCc3cccnc32)CC1]

Compound 96: Preparation of (1H-benzimidazol-2-ylmethyl)-(5,6,7,8-tetrahydro-quinolin-8-yl)-(1-amino-2-(cyclopropanyl)-butan-4-yl)-amine To an ~7:1 mixture of benzoic acid 4-hydroxy-2-methylene-butyl ester and benzoic acid 3-hydroxymethyl-but-3- enyl ester (0.705 g, 3.42 mmol) in $CH_2Cl_2$ (17 mL) was added $Et_3N$ (1.00 mL, 7.17 mmol) followed by tert-butyldimethylsilyl chloride (0.792 g, 5.25 mmol) and 4-(dimethylamino)pyridine (84 mg, 0.69 mmol). The mixture was stirred at room temperature for 2 hours, diluted with $CH_2Cl_2$ (50 mL), washed with brine (3×20 mL), dried ($Na_2SO_4$), and concentrated. Purification of the crude material by column chromatography on silica gel (25:1 hexanes-ethyl acetate) provided 1.00 g (92%) of an ~7:1 mixture of benzoic acid 4-(tert-butyldimethylsilyloxy)-2-methylene-butyl ester and benzoic acid 3-(tert-butyldimethylsilyloxymethyl)-but-3-enyl ester as a colorless oil.

To an ~7:1 mixture of benzoic acid 4-(tert-butyldimethylsilyloxy)-2-methylene-butyl ester and benzoic acid 3-(tert-butyldimethylsilyloxymethyl)-but-3-enyl ester (1.00 g, 3.13 mmol) in methanol (31 mL) was added NaOH (0.306 g, 7.64 mmol) and the mixture was stirred at room temperature for 2 hours. The mixture was diluted with ethyl acetate (75 mL) and saturated aqueous $NaHCO_3$ (20 mL). The phases were separated and the organic phase was washed with brine (2×10 mL), dried ($MgSO_4$), and concentrated. Purification of the crude material by column chromatography on silica gel (9:1 hexanes-ethyl acetate) provided 0.58 g (58%) of 4-(tert-butyldimethylsilyloxy)-2-methylene-butan-1-ol as a colorless oil. $^1H$ NMR ($CDCl_3$) δ 0.06 (s, 6H), 0.90 (s, 9H), 2.34 (t, 2H, J=6.0 Hz); 2.78 (br s, 1H), 3.75 (t, 2H, J=6.0 Hz), 4.07-4.11 (m, 2H), 4.90 (s,1H), 5.04 (s, 1H);

To a cold (0° C.), stirred solution of diethyl zinc (1.0 M in hexanes, 4.0 mL, 4.0 mmol) in $CH_2Cl_2$ (8 mL) was added neat $ClCH_2I$ (0.58 mL, 7.96 mmol) drop wise by syringe. After 1 hour, a solution of 4-(tert-butyldimethylsilyloxy)-2-methylene-butan-1-ol (0.395 g, 1.83 mmol) in $CH_2Cl_2$ (4 mL) was added by cannula. After 30 minutes, the reaction mixture was treated with saturated aqueous $NH_4Cl$ (10 mL), diluted with $CH_2Cl_2$ (12 mL), and warmed to room temperature. The phases were separated and the aqueous phase was extracted with $CH_2Cl_2$ (3×10 mL). The combined organic extracts were dried ($Na_2SO_4$) and concentrated. The crude material was purified by column chromatography on silica gel (9:1 hexanes-ethyl acetate) and provided 0.41 g (97%) of {1-[2-(tert-butyldimethylsilyloxy)-ethyl]-cyclopropyl}-methanol as a colorless oil.

To solution of {1-[2-(tert-butyldimethylsilyloxy)-ethyl]-cyclopropyl}-methanol (0.41 g, 1.78 mmol) in $CH_2Cl_2$ (18 mL) was added $Et_3N$ (0.50 mL, 3.59 mmol) followed by methanesulfonyl chloride (0.21 mL, 231 mmol). The resultant mixture was stirred at room temperature for 17 hours. The mixture was diluted $CH_2Cl_2$ (50 mL), washed with brine (3×20 mL), dried ($Na_2SO_4$), and concentrated. The resultant oil was dissolved in DMF (16 mL), treated with potassium phthalimide (0.606 g, 3.27 mmol), and the mixture was heated at 80° C. for 6 hours then cooled to room temperature. The mixture was diluted with ethyl acetate (40 mL), brine (20 mL), and water (10 mL) and the phases were separated. The organic phase was washed with brine (3×10 mL), dried ($MgSO_4$), and concentrated. The crude material was purified by column chromatography on silica gel (20:1 hexanes-ethyl acetate) and provided 0.24 g (38%) of 2-{1-[2-(tert-butyldimethylsilyloxy)-ethyl]-cyclopropylmethyl}-isoindole-1,3-dione as a colorless oil.

To a solution of 2-{1-[2-(tert-butyldimethylsilyloxy)-ethyl]-cyclopropylmethyl}-isoindole-1,3-dione (0.24 g, 0.68 mmol) in THF (3 mL) was added 1.0 M HCl (3 mL). The resultant solution was stirred, at room temperature, for 3 hours. The mixture was diluted with saturated aqueous $NH_4Cl$ (10 mL) and extracted with $CH_2Cl_2$ (3×20 mL). The combined organic extracts were dried ($Na_2SO_4$) and concentrated. The crude material was purified by column chromatography on silica gel (2:1 hexanes-ethyl acetate) and provided 0.146 g (88%) of 2-[1-(2-hydroxy-ethyl)-cyclopropylmethyl]-isoindole-1,3-dione as a white solid. $^1H$ NMR ($CDCl_3$) δ 0.29-0.35 (m, 2H), 0.59-0.62 (m, 2H), 1.41 (t, 2H, J=6.6 Hz), 2.80 (br s, 1H), 3.53 (s, 2H), 3.76 (t, 2H, J=6.6 Hz), 7.59-7.63 (m, 2H), 7.69-7.74 (m, 2H);

To a solution of the alcohol from above (146 mg, 0.595 mmol) in dichloromethane (15 mL) was added Dess-Martin Periodinane (303 mg, 0.715 mmol). The mixture was then stirred at room temperature for 45 minutes. A 5% solution of sodium thiosulfate (10 mL) and a saturated sodium bicarbonate solution (10 mL) was added along with another 20 mL of dichloromethane. The mixture was then stirred rapidly for 20 minutes, and the aqueous and organic layers were separated. The aqueous layer was extracted twice with dichloromethane, and the combined organic fractions were dried over anhydrous sodium sulfate, filtered and concentrated in vacuo to afford N-(3-cyclopropanyl-butan-1-al-4-yl)-phthalimide as a yellow foam, which was used immediately in the next reaction without further purification. $^1H$ NMR ($CDCl_3$) δ 0.43 (m, 2H), 0.86 (m, 2H), 2.40 (s, 2H), 3.65 (s, 2H), 7.68 (m, 2H), 7.83 (m, 2H), 9.79 (s, 1H).

To a solution of N-(3-cyclopropanyl-butan-1-al-4-yl)-phthalimide (0.595 mmol) in dichloromethane (15 mL) was added (5,6,7,8-tetrahydroquinolin-8-yl)-[(N-t-butoxycarbonyl)-benzimidazol-2-yl)methyl]-amine (227 mg, 0.6 mmol). The mixture was stirred at room temperature for 30 minutes, then sodium triacetoxyborohydride (254 mg, 1.2 mmol) was added, and the reaction was allowed to stir for 16 hours. A saturated sodium bicarbonate solution (10 mL) was added, and the aqueous and organic layers were separated. The aqueous layer was then extracted twice with dichloromethane, and the combined organic fractions were dried over anhydrous sodium sulfate, filtered and concentrated in vacuo. The residue was then purified by silica gel flash chromatography (3% methanol in dichloromethane) to afford [(N-t-butoxycarbonyl)-benzimidazol-2-ylmethyl]-(5,6,7,8-tetrahydro-quinolin-8-yl)-[1-(N-phthalimidyl)-butan-2-(cyclopropanyl)-4-yl]-amine as a pale yellow foam in a yield of 130 mg (36%). $^1H$ NMR ($CDCl_3$) δ 0.23 (m, 2H), 0.55 (m, 2H), 1.15 (m, 1H), 1.35 (m, 1H), 1.66 (s, 9H), 1.70 (m, 2H), 2.00 (m, 2H), 2.16 (m, 1H), 2.69 (m, 2H), 2.97 (m, 2H), 3.31 (d, 1H, J=15.3 Hz), 3.51 (d, 1H, J=15.3 Hz), 4.23 (m, 1H), 4.43 (d, 1H, J=17.1 Hz), 4.62 (d, 1H, J=17.1 Hz), 7.00 (m, 1H), 7.23 (m, 4H), 7.65 (m, 2H), 7.74 (m, 2H), 7.74 (m, 1H), 8.38 (m, 1H).

To a solution of [(N-t-butoxycarbonyl)-benzimidazol-2-ylmethyl]-(5,6,7,8-tetrahydro-quinolin-8-yl)-(1-(N-phthalimidyl)-butan-2-(cyclopropanyl)-4-yl)-amine (187 mg, 0.31 mmol) in ethanol (8 mL) was added hydrazine hydrate (0.1 mL). The mixture was then heated to 60° C. for 60 minutes. After cooling, the reaction was concentrated in vacuo, taken up in dichloromethane (20 mL) and washed with an aqueous sodium carbonate solution (5 mL). The aqueous layer was then extracted twice with dichloromethane, and the combined organic fractions were dried over anhydrous sodium sulfate, filtered and concentrated to afford a foamy residue which was purified by silica gel flash chromatography (10% methanol, 0.5% ammonium hydroxide in dichloromethane) to afford (1H-benzimidazol-2-ylmethyl)-(5,6,7,8-tetrahydroquinolin-8-yl)-(1-amino-2-(cyclopropanyl)-butan-4-yl)-amine as a white foam in a yield of 100 mg (86%). $^1H$ NMR ($CDCl_3$) δ 0.17 (s, 2H), 0.25 (s, 2H), 1.32 (m, 1H), 1.61 (m, 2H), 1.85 (m, 1H), 1.93 (m, 1H), 2.19 (m, 1H), 2.39 (s, 1H), 2.86 (m, 4H), 3.99 (m, 4H), 5.40 (br s, 2H($NH_2$)), 7.03 (dd, 1H, J=4.8, 8.1 Hz), 7.15 (m, 2H), 7.32 (d, 1H, J=8.1 Hz), 7.54 (m, 2H), 8.48 (d, 1H, J=4.8 Hz).

Following General Procedure D: To a solution of (1H-benzimidazol-2-ylmethyl)-(5,6,7,8-tetrahydroquinolin-8-yl)-(1-amino-2-(cyclopropanyl)-butan-4-yl)-amine (100 mg, 0.267 mmol) in glacial acetic acid (2 mL) was added a saturated solution of HBr in acetic acid (0.5 mL) to yield, after precipitation and drying, (1H-benzimidazol-2-ylmethyl)-(5,6,7,8-tetrahydroquinolin-8-yl)-(1-amino-2-(cyclopropanyl)-butan-4-yl)-amine (HBr salt—COMPOUND 96) as a cream-coloured powder (126 mg, 69%). $^1$H NMR (D$_2$O) δ 0.36 (m, 1H), 0.52 (m, 2H), 1.31 (m, 1H), 1.75 (m, 2H), 2.01 (m, 1H), 2.06 (m, 1H), 2.63 (m, 1H), 2.64 (d, 1H, J=13.5 Hz), 2.87 (d, 1H, J=13.5 Hz), 2.99 (m, 3H), 4.36 (d, 1H, J=16.8 Hz), 4.55 (m, 1H), 4.49 (d, 1H, J=16.8 Hz), 7.60 (m, 2H), 7.79 (m, 2H), 7.85 (dd, 1H, J=7.8, 5.4 Hz), 8.32 (d, 1H, J=7.8 Hz), 8.60 (d, 1H, J=5.4 Hz); $^{13}$C NMR (D$_2$O) δ 11.39, 11.52, 17.02, 20.44, 27.64, 32.22, 45.79, 47.91, 49.32, 49.82, 60.58, 114.26, 125.98, 126.97, 130.98, 139.32, 140.69, 148.15, 151.17, 151.72. ES-MS m/z 376 (M+H). Anal. Calcd. for C$_{23}$H$_{29}$N$_5$×1.4H$_2$O×3.1HBr×0.4Et$_2$O: C, 43.37; H, 5.76; N, 10.28; Br, 36.36. Found: C, 43.41; H, 5.73; N, 10.27; Br, 36.37.

Example 97

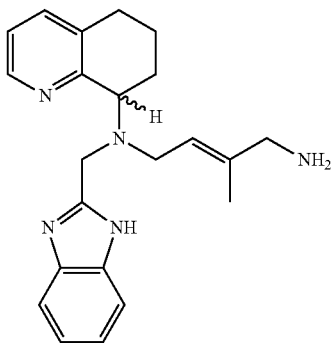 [SMILES: C/C(=C\CN(Cc1nc2ccccc2[nH]1)C1CCCc2cccnc21)CN]

Compound 97: Preparation of (1H-benzimidazol-2-ylmethyl)-(5,6,7,8-tetrahydro-quinolin-8-yl)-(1-amino-2-methyl-but-2-en-4-yl)-amine To a solution of N-(3-methylenyl-butan-1-ol-4-yl)-phthalimide (180 mg, 0.83 mmol—(See preparation of N$^1$-(1H-Benzimidazol-2-ylmethyl)-2-methylene-N$^1$-(5,6,7,8-tetrahydro-quinolin-8-yl)-butane-1,4-diamine, hydrobromide salt for details)) in dichloromethane (15 mL) was added Dess-Martin Periodinane (424 mg, 1.0 mmol). A 5% solution of sodium thiosulfate (10 mL) and a saturated sodium bicarbonate solution (10 mL) was added along with another 20 mL of dichloromethane. The mixture was then stirred rapidly for 20 minutes, and the aqueous and organic layers were separated. The aqueous layer was extracted twice with dichloromethane, and the combined organic fractions were dried over anhydrous sodium sulfate, filtered and concentrated in vacuo to afford N-(3-methylenyl-butan-1-al-4-yl)-phthalimide as a yellow foam, which was used immediately in the next reaction without further purification. $^1$H NMR (CDCl$_3$) δ 3.19 (s, 2H), 4.32 (s, 2H), 5.07 (s, 1H), 5.24 (s, 1H), 7.70 (m, 2H), 7.84 (s, 2H), 9.66 (s, 1H).

To a solution of N-(3-methylenyl-butan-1-al-4-yl)-phthalimide (0.83 mmol) in dichloromethane (15 mL) was added (5,6,7,8-tetrahydroquinolin-8-yl)-[(N-t-butoxycarbonyl)-benzimidazol-2-ylmethyl]-amine (227 mg, 0.6 mmol). The mixture was stirred at room temperature for 30 minutes, then sodium triacetoxyborohydride (254 mg, 1.2 mmol) was added, and the reaction was allowed to stir for 16 hours. A saturated sodium bicarbonate solution (10 mL) was added, and the aqueous and organic layers were separated. The aqueous layer was then extracted twice with dichloromethane, and the combined organic fractions were dried over anhydrous sodium sulfate, filtered and concentrated in vacuo. The residue was then purified by silica gel flash chromatography (3% methanol in dichloromethane) to afford [(N-t-butoxycarbonyl)-benzimidazol-2-ylmethyl]-(5,6,7,8-tetrahydro-quinolin-8-yl)-[1-(N-phthalimidyl)-2-methyl-but-2-en-4-yl]-amine as a pale yellow foam in a yield of 88 mg (26%). $^1$H NMR (CDCl$_3$) δ 1.26 (s, 3H) 1.48 (m, 3H), 1.68 (s, 9H), 2.04 (m, 1H), 2.74 (m, 2H), 3.47 (dd, 1H, J=13.1, 5.9 Hz), 3.61 (dd, 1H, J=13.1, 5.9 Hz), 4.19 (m, 1H), 4.33 (d, 1H, J=16.1 Hz), 4.49 (d, 1H, J=16.1 Hz), 5.43 (t, 1H, J=5.9 Hz), 6.95 (m, 1H), 7.13 (m, 2H), 7.64 (m, 2H), 7.73 (m, 2H), 7.81 (m, 2H), 8.22 (m, 1H), 8.61 (m, 1H).

To a solution of [(N-t-butoxycarbonyl)-benzimidazol-2-ylmethyl]-(5,6,7,8-tetrahydro-quinolin-8-yl)-[1-(N-phthalimidyl)-2-methyl-but-2-en-4-yl]-amine 88 mg, 0.15 mmol) in ethanol (8 mL) was added hydrazine hydrate (0.1 mL). The mixture was then heated to 60° C. for 60 minutes. After cooling, the reaction was concentrated in vacuo, taken up in dichloromethane (20 mL) and washed with an aqueous sodium carbonate solution (5 mL). The aqueous layer was then extracted twice with dichloromethane, and the combined organic fractions were dried over anhydrous sodium sulfate, filtered and concentrated to afford a foamy residue which was purified by silica gel flash chromatography (10% methanol, 0.5% ammonium hydroxide in dichloromethane) to afford [(N-t-butoxycarbonyl)-benzimidazol-2-ylmethyl]-(5,6,7,8-tetrahydro-quinolin-8-yl)-[1-amino-2-methyl-but-2-en-4-yl]-amine as a white foam in a yield of 33 mg (61%). $^1$H NMR(CDCl$_3$) δ 1.57 (s, 9H), 1.71 (m, 1H), 1.89 (m, 1H), 2.01 (m, 2H), 2.27 (m, 1H), 2.74 (m, 3H), 3.01 (s, 3H), 3.16 (dd, 1H, J=7.1, 4.3 Hz), 3.31 (dd, 1H, J=7.1, 4.3 Hz), 4.02 (m, 3H), 5.30 (m, 1H), 7.13 (m, 4H), 7.40 (d, 1H, J=7.8 Hz), 7.54 (m, 1H), 8.54 (d, 1H, J=4.8 Hz).

To a solution of [(N-t-butoxycarbonyl)-benzimidazol-2-ylmethyl]-(5,6,7,8-tetrahydro-quinolin-8-yl)-[1-amino-2-methyl-but-2-en-4-yl]-amine (33 mg, 0.091 mmol) in glacial acetic acid (2 mL) was added a saturated solution of HBr in acetic acid (0.5 mL). The resulting mixture was stirred and treated as per standard procedure D to yield, after precipitation and drying, [(1H-benzimidazol-2-yl)methyl]-(5,6,7,8-tetrahydro-quinolin-8-yl)-[1-amino-2-methyl-but-2-en-4-yl]-amine (HBr salt—COMPOUND 97) as a cream-coloured powder (28 mg, 46%). $^1$H NMR (D$_2$O) δ 1.63 (s, 3H), 1.83 (m, 1H), 2.06 (m, 1H), 2.17 (m, 1H), 2.40 (m, 1H), 3.01 (m, 5H), 3.21 (m, 1H), 4.30 (d, 1H, J=16.8 Hz), 4.48 (d, 1H, J=16.8 Hz), 4.49 (m, 1H), 5.47 (t, 1H, J=5.8 Hz), 7.60 (m, 2H), 7.79 (m, 2H), 7.80 (m, 1H), 8.33 (d, 1H, J=7.8 Hz), 8.63 (d, 1H, J=5.1 Hz); $^{13}$C NMR (D$_2$O) δ 14.12, 20.41, 20.69, 27.63, 46.26, 48.25, 49.15, 60.97, 114.24, 125.95, 127.10, 127.52, 130.87, 132.88, 139.45, 140.69, 148.08, 151.08, 151.73. ES-MS m/z 362 (M+H). Anal. Calcd. for C$_{22}$H$_{25}$N$_5$×1.5H$_2$O×3.1HBr×0.5Et$_2$O: C, 42.62; H, 5.68; N, 10.35; Br, 36.62. Found: C, 42.37; H, 5.31; N, 10.18; Br, 36.31.

Example 98

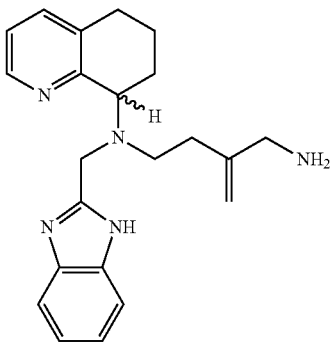 [SMILES: C=C(CN)CCN(Cc1nc2ccccc2[nH]1)C1CCCc2cccnc21]

Compound 98: Preparation of (1H-benzimidazol-2-ylmethyl)-(5,6,7,8-tetrahydro-quinolin-8-yl)-(1-amino-2-methylenyl-butan-4-yl)-amine To a solution of N-(3-methylenyl-butan-1-ol-4-yl)-phthalimide (209 mg, 0.90 mmol (See preparation of N$^1$-(1H-Benzimidazol-2-ylmethyl)-2-methylene-N$^1$-(5,6,7,8-tetrahydroquinolin-8-yl)-butane-1,4-diamine, hydrobromide salt, for details) in dichloromethane (5 mL) was methanesulfonyl chloride (0.092 mL, 1.2 mmol). The mixture was then stirred for 30 minutes at room temperature before being treated with aqueous ammonium chloride (5 mL). The layers were then separated, and the aqueous layer was washed twice with 10 mL fractions of dichloromethane. The combined organic fractions were then dried over anhydrous sodium sulfate and concentrated. The residue was taken up in DMF (5 mL) to which sodium azide (25 mg, 0.38 mmol) was added. The mixture was then heated to 80° C. and was stirred overnight. The reaction was then cooled and poured into ethyl acetate (100 mL). The solution was then extracted repeatedly (5×) with distilled water. The organic layer was then dried over anhydrous sodium sulfate and concentrated. The residue was purified by silica gel flash chromatography using a 1:1 mixture of ethyl acetate:hexancs as an eluent. The product 1-N-phthalimidyl-(2-methylenyl-butan-4-yl)-azide was collected as a white solid. $^1$H NMR (CDCl$_3$) δ 2.36 (t, 2H, J=6.9 Hz), 3.49 (t, 2H, J=6.9 Hz), 4.13 (s, 2H), 5.03 (s, 1H), 5.08 (s, 1H), 7.72 (m, 2H), 7.88 (m, 2H).

To a solution of [1-N-phthalimidyl-(2-methylenyl-butan-4-yl)]-azide (199 mg, 0.78 mmol) in methanol (20 mL) was added palladium on calcium carbonate (Lindlar's Catalyst, 40 mg). The mixture was then placed under 1 atm hydrogen gas and was stirred rapidly for 3 hours. The mixture was then filtered and concentrated to afford the product [1-(N-phthalimidyl)-2-methylenyl-butan-4-yl]-amine as a yellow gum (160 mg, 84%). $^1$H NMR (CDCl$_3$) δ 3.32 (t, 2H, J=7.1 Hz), 3.76 (t, 2H, J=7.1 Hz), 4.28 (s, 2H), 5.14 (s, 1H), 5.30 (s, 1H), 7.70 (m, 2H), 7.82 (m, 2H).

To a solution of [1-(N-phthalimidyl)-2-methylenyl-butan-4-yl]-amine (160 mg, 0.658 mmol) in dichloromethane (8 mL) was added 5,6,7,8-tetrahydroquinoline-8-one (58 mg, 0.4 mmol). The mixture was stirred at room temperature for 30 minutes, then sodium triacetoxyborohydride (348 mg, 1.65 mmol) was added, and the reaction was allowed to stir for 16 hours. A saturated sodium bicarbonate solution (10 mL) was added, and the aqueous and organic layers were separated. The aqueous layer was then extracted twice with dichloromethane, and the combined organic fractions were dried over anhydrous sodium sulfate, filtered and concentrated in vacuo. The residue was then purified by silica gel flash chromatography (3% methanol in dichloromethane) to afford (5,6,7,8-tetrahydro-quinolin-8-yl)-[1-(N-phthalimidyl)-2-methylenyl-butan-4-yl]-amine as a pale yellow foam in a yield of 75 mg (52%). $^1$H NMR (CDCl$_3$) δ 1.74 (m, 1H), 2.02 (m, 1H), 2.52 (m, 2H), 2.77 (m, 4H), 3.41 (d, 1H, J=7.7 Hz), 3.55 (d, 1H, J=7.7 Hz), 3.78 (m, 3H), 4.86 (m, 1H), 5.05 (1H), 7.04 (m, 1H), 7.37 (m, 1H), 7.68 (m, 2H), 7.80 (m, 2H), 8.36 (m, 1H).

To a solution of (5,6,7,8-tetrahydro-quinolin-8-yl)-[1-(N-phthalimidyl)-2-methylenyl-butan-4-yl]amine (75 mg, 0.21 mmol) in acetonitrile (5 mL) was added N-t-butoxycarbonyl-2-chloromethylbenzimidazole (80 mg, 0.3 mmol). Di-isopropylethylamine (0.052 mL, 0.3 mmol) was then added, and the resulting solution was warmed to 70° C. and was stirred overnight. After cooling, a saturated ammonium solution (10 mL), and dichloromethane (30 mL) was added, and the aqueous and organic layers were separated. The aqueous layer was then extracted twice with dichloromethane, and the combined organic fractions were dried over anhydrous sodium sulfate, filtered and concentrated in vacuo. The residue was then purified by silica gel flash chromatography (3% methanol in dichloromethane) to afford [(N-t-butoxycarbonyl)-benzimidazol-2-ylmethyl]-(5,6,7,8-tetrahydro-quinolin-8-yl)-[1-(N-phthalimidyl)-2-methylen-4-yl]-amine as a pale yellow foam in a yield of 62 mg (50%). $^1$H NMR (CDCl$_3$) δ 1.68 (s, 9H), 1.89 (m, 1H), 2.03 (m, 2H), 2.11 (m, 1H), 2.40 (t, 2H, J=6.9 Hz), 2.75 (m, 2H), 3.27 (d, 1H, J=13.1 Hz), 3.46 (d, 1H, J=13.1 Hz), 3.61 (m, 2H), 4.11 (m, 1H), 4.48 (d, 1H, J=16.1 Hz), 4.63 (d, 1H, J=16.1 Hz), 6.95 (m, 1H), 7.23 (m, 2H), 7.64 (m, 2H), 7.76 (m, 3H), 8.61 (m, 2H).

To a solution of [(N-t-butoxycarbonyl)-benzimidazol-2-ylmethyl]-(5,6,7,8-tetrahydro-quinolin-8-yl)-[1-(N-phthalimidyl)-2-methylen-4-yl]-amine (62 mg, 0.10 mmol) in ethanol (8 mL) was added hydrazine hydrate (0.1 mL). The mixture was then heated to 80° C. for 60 minutes. After cooling, the reaction was concentrated in vacuo, taken up in dichloromethane (20 mL) and washed with an aqueous sodium carbonate solution (5 mL). The aqueous layer was then extracted twice with dichloromethane, and the combined organic fractions were dried over anhydrous sodium sulfate, filtered and concentrated to afford a foamy residue which was purified by silica gel flash chromatography (10% methanol, 0.5% ammonium hydroxide in dichloromethane) to afford [(N-t-butoxycarbonyl)-benzimidazol-2-ylmethyl]-(5,6,7,8-tetrahydro-quinolin-8-yl)-[1-(amino)-2-methylen-4-yl]-amine as a white foam in a yield of 29 mg (74%). $^1$H NMR (CDCl$_3$) δ 1.64 (m, 1H), 1.89-2.02 (m, 3H), 2.08 (m, 1H), 2.35 (m, 2H), 2.77 (m, 1H), 2.81 (m, 1H), 2.94 (m, 1H), 3.04 (d, 1H, J=13.1 Hz), 3.16 (d, 1H, J=13.1 Hz), 4.03 (m, 3H), 4.87 (s, 1H), 5.06 (s, 1H), 7.12 (m, 3H), 7.40 (d, 1H, J=8.1 Hz), 7.57 (m, 2H), 8.58 (m, 1H).

To a solution of [(N-t-butoxycarbonyl)-benzimidazol-2-ylmethyl]-(5,6,7,8-tetrahydro-quinolin-8-yl)-[1-(amino)-2-methylen-4-yl]-amine (29 mg, 0.080 mmol) in glacial acetic acid (2 mL) was added a saturated solution of HBr in acetic acid (0.5 mL). The resulting mixture was stirred and treated as per standard procedure D to yield, after precipitation and drying, [(1H-benzimidazol-2-yl)methyl]-(5,6,7,8-tetrahydro-quinolin-8-yl)-[1-(amino)-2-methylen-4-yl]-amine (HBr salt—COMPOUND 98) as a cream-coloured powder (28 mg, 55%). $^1$H NMR (D$_2$O) δ 1.81 (m, 1H), 2.05 (m, 2H), 2.23 (m, 3H), 2.79 (m, 1H), 2.94 (m, 3H), 3.18 (d, 1H, J=14.1 Hz), 3.41 (d, 1H, J=14.1 Hz), 4.34 (d, 1H, J=16.1 Hz), 4.48 (d, 1H, J=16.1 Hz), 4.60 (m, 1H), 5.26 (m, 2H), 7.53 (m, 2H), 7.79 (m, 2H), 7.89 (dd, 1H, J=5.1, 7.8 Hz), 8.54 (d, 1H, J=7.8 Hz), 8.68 (d, 1H, J=5.1 Hz); $^{13}$C NMR (D$_2$O) δ 20.05, 20.29, 27.81, 31.02, 37.45, 48.26, 57.09, 60.44, 114.26, 118.49, 126.09, 127.01, 131.00, 139.67, 139.79, 141.13, 148.25, 150.85, 151.38. ES-MS m/z 362 (M+H). Anal. Calcd. for C$_{22}$H$_{25}$N$_5$×1.8H$_2$O×3.0 HBr: C, 41.50; H, 5.32; N, 11.00; Br, 37.65. Found: C, 41.54; H, 5.17; N, 10.85; Br, 37.55.

Example 99

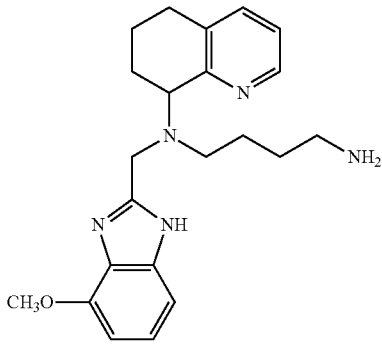

Compound 99: Preparation of (1H-benzimidazol-4-methoxy-2-ylmethyl)-(5,6,7,8-tetrahydroquinolin-8-yl)-(1-aminobutan-4-yl)-amine

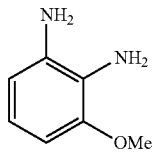

To a 0° C. solution of potassium t-butoxide (5.87 g, 52.3 mmol) in DMF (40 mL) under an inert atmosphere of argon was added copper (I) chloride (0.2 g, 2.0 mmol). The resulting suspension was stirred for 10 minutes, then a solution of 3-nitroanisole (1.55 g, 10.1 mmol) and methoxylamine hydrochloride (1.08 g, 12.9 mmol) in DMF (15 mL) was added in a dropwise manner over 15 minutes. The mixture was then allowed to slowly warm to room temperature and was stirred for 48 hours. Water (20 mL) was then added to the reaction, and the mixture was poured into a separatory funnel containing 100 mL ethyl acetate. The aqueous and organic layers were then separated, and the organic layer was extracted 5 times with 20 mL portions of water. The organic layer was then dried over anhydrous sodium sulfate, filtered and concentrated. The residue was purified by silica gel flash chromatography using a 3:1 hexanes:ethyl acetate mixture as an eluent. Three isomeric products were isolated consecutively from the column, the first being the desired 2-amino-3-nitroanisole, which was isolated as an orange powder in a yield of 465 mg (29%). $^1$H NMR (CDCl$_3$) δ 3.95 (s, 3H), 6.44 (br s, 2H (NH)), 6.61 (dd, 1H, J=7.8, 7.1 Hz), 6.87 (d, 1H, J=7.1 Hz), 7.73 (d, 1H, J=7.8 Hz)

To a solution of 2-amino-3-nitroanisole (465 mg, 2.94 mmol) in methanol (50 mL) was added palladium on carbon (10% Pd, 100 mg). The mixture was then placed under an atmosphere of hydrogen gas (1 atm) and was stirred for one hour. The mixture was then filtered through celite and concentrated to give 2,3-diaminoanisole as a yellow foam in a yield of 400 mg (98%). $^1$H NMR (CDCl$_3$) δ 3.45 (br s, 4H (NH)), 3.84 (s, 3H), 6.40 (m, 2H), 6.67 (t, 1H, J=7.8 Hz)

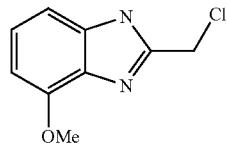 [SMILES: COc1cccc2[nH]c(CCl)nc12]

A solution of 2,3-diaminoanisole (400 mg, 2.89 mmol) and chloroacetic acid (557 mg, 6 mmol) in 4 N HCl was heated to 105° C. for 16 hours. The mixture was then cooled, neutralized (to a pH of 8) with aqueous sodium bicarbonate, and extracted twice with dichloromethane. The organic fractions were then dried over anhydrous sodium sulfate, filtered and concentrated. The residue was purified by silica gel flash chromatography using a 1:1 mixture of hexanes:ethyl acetate as an eluent to give 1H-2-chloromethyl-4-methoxybenzimidazole as a yellow foam in a yield of 386 mg (68%). $^1$H NMR (CDCl$_3$) δ 3.96 (s, 3H), 4.85 (s, 2H), 6.71 (m, 1H), 7.19 (m, 2H).

To a solution of 1H-2-chloromethyl-4-methoxybenzimidazole (138 mg, 0.7 mmol) and (5,6,7,8-tetrahydroquinolin-8-yl)-(1-(N-phthalimidyl)-butan-4-yl)-amine (180 mg, 0.515 mmol) in acetonitrile (8 mL) was added di-isopropylethylamine (0.13 mL, 0.75 mmol). The resulting solution was heated to 70° C. for 6 hours. The reaction was then cooled, and partitioned between aqueous ammonium chloride and dichloromethane. After separation of the layers, the aqueous layer was extraced twice with dichloromethane. The combined organic fractions were then dried over anhydrous sodium sulfate, filtered and concentrated. The residue was purified by silica gel flash chromatography using a 5% methanol in dichloromethane solution as an eluent. The product (1H-benzimidazol-4-methoxy-2-ylmethyl)-(5,6,7,8-tetrahydroquinolin-8-yl)-[1-(N-phthalimidyl)-aminobutan-4-yl]-amine was isolated as a pale yellow foam in a yield of 212 mg (8268 (m, 4H), 1.90-2.05 (m, 2H), 2.03 (m, 2H), 2.61-2.83 (m, 4H), 3.80-4.10 (m, 8H), 6.60 (m, 1H), 7.06 (m, 3H), 7.63 (m 1H), 7.63-7.77 (m, 4H), 8.40 (m, 1H).

To a solution of product (1H-benzimidazol-4-methoxy-2-ylmethyl)-(5,6,7,8-tetrahydroquinolin-8-yl)-[1-(N-phthalimidyl)-aminobutan-4-yl]-amine (212 mg, 0.417 mmol) in denatured ethanol (10 mL) was added hydrazine hydrate (0.25 mL). The resulting mixture was heated to 80° C. for 60 minutes, then cooled and concentrated. The residue was filtered through a silica gel plug (5 g silica) using a 10:1 dichloromethane:methanol mixture as an eluent. The collected eluent (200 mL) was then concentrated, re-dissolved in THF (10 mL) and di-t-butyl carbonate (212 mg, 1.0 mmol) was added. The mixture was then stirred at room temperature overnight. The reaction was then concentrated, and the residue was purified by silica gel flash chromatography using a 5% methanol in dichloromethane mixture as an eluent to afford the desired (1-t-butoxycarbonyl-benzimidazol-4-methoxy-2-ylmethyl)-(5,6,7,8-tetrahydroquinolin-8-yl)-[1-(N-t-butoxycarbonyl)-aminobutan-4-yl]-amine as a pale foam in a yield of 68 mg (28%). $^1$H NMR (CDCl$_3$) δ 1.18-1.23 (m, 4H), 1.39 (s, 9H), 1.70 (s, 9H), 1.97-2.07 (m, 4H), 2.58-2.95 (m, 6H), 4.01 (s, 3H), 4.18 (m, 1H), 4.58 (m, 2H), 4.92 (br s, 1H(NH)), 6.72 (d, 1H, J=8.1 Hz), 6.91 (m, 1H), 7.16 (m, 2H), 7.35 (d, 1H, J=8.1 Hz), 8.33 (m, 1H).

(1-t-butoxycarbonyl-benzimidazol-4-methoxy-2-ylmethyl)-(5,6,7,8-tetrahydroquinolin-8-yl)-[1-(N-t-butoxycarbonyl)-aminobutan-4-yl]-amine (68 mg, 0.117 mmol) was taken up in acetic acid (1 mL), to which a saturated solution of HBr in acetic acid (0.1 mL) was added. The mixture was then stirred, precipitated and isolated as per procedure D to yield COMPOUND 99 as a white crystalline solid in a yield of 49 mg (65%). $^1$H NMR (D$_2$O). δ 1.52 (m, 4H), 1.79 (m, 1H), 1.98 (m, 1H), 2.14 (m, 1H), 2.35 (m, 1H), 2.53 (m, 1H), 2.79 (m, 3H), 2.99 (m, 2H), 4.03 (s, 3H), 4.36 (d, 1H, J=16.8 Hz), 4.49 (m, 1H), 4.50 (d, 1H, J=16.8 Hz), 7.10 (d, 1H, J=8.1 Hz), 7.34 (d, 1H, J=8.4 Hz), 7.51 (t, 1H, J=8.4 Hz), 7.85 (dd, 1H, J=8.1, 5.4 Hz), 8.34 (d, 1H, J=8.1 Hz), 8.60 (d, 1H, J=5.4 Hz). $^{13}$C NMR (D$_2$O) δ 20.44, 20.84, 25.05, 25.41, 27.66, 39.54, 48.10, 51.76, 56.70, 60.54, 106.20, 107.45, 121.85, 125.90, 128.14, 132.39, 139.30, 140.56, 147.45, 148.05, 150.89, 151.30. ES-MS m/z 380 (M+H); Anal. Calcd. for (C$_{22}$H$_{29}$N$_5$O×3.0 HBr×1.0 H$_2$O): C, 41.27; H, 5.35; N, 10.94; Br 37.44. Found: C, 41.28; H, 5.33; N, 10.67; Br, 37.24.

Example 100

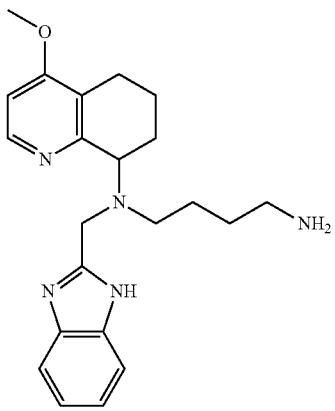 [SMILES: COc1ccnc2c1CCCC2N(CCCCN)Cc1nc2ccccc2[nH]1]

Compound 100: Preparation of N$^1$-(1H-Benzimidazol-2-ylmethyl)-N$^1$-(4-methoxy-5,6,7,8-tetrahydroquinolin-8-yl)-butane-1,4-diamine (hydrobromide salt)

8-amino-4-methoxy-5,6,7,8-tetrahydroquinoline was prepared in 68% yield from 8-hydroxy-4-methoxy-5,6,7,8-tetrahydroquinoline (preparation and characterization described by: Uchida, M.; Morita, S.; Chihiro, M.; Kanbe, T.; Yamasaki, K.; Yabuuchi, Y.; Nakagawa, K. Chem. Pharm. Bull. 1989, 37, 1517-1523.) using the same procedure employed to prepare 8-amino-5,6,7,8-tetrahydroquinoline (according to the procedures described in Bridger et al. U.S. patent application U.S. Ser. No. 09/535,314). $^1$H NMR (CDCl$_3$) δ 1.59-2.15 (m, 6H), 2.60-2.65 (m, 2H), 3.84 (s, 3H), 3.95 (dd, 1H, J=6.0, 9.0 Hz), 6.61 (d, 1H, J=6.0 Hz). 8.32 (d, 1H, J=6.0 Hz); $^{13}$C NMR (CDCl$_3$) δ 19.53, 22.89, 31.94, 51.57, 55.62, 104.04, 120.94, 148.52, 160.42, 163.71; ES-MS m/z 179 (M+H).

Using General Procedure B: Reaction of 8-amino-4-methoxy-5,6,7,8-tetrahydroquinoline (0.297 g, 1.67 mmol) and 4-(1,3-Dioxo-1,3-dihydro-isoindol-2-yl)-butyraldehyde (0.371, 1.71 mmol) with NaBH(OAc)$_3$ (0.493 g, 2.33 mmol) in CH$_2$Cl$_2$ (8 mL) for 60 minutes followed by purification of the crude material by column chromatography on silica gel (20:1 CH$_2$Cl$_2$—CH$_3$OH) provided 0.345 g (54%) of 2-[4-(4-Methoxy-5,6,7,8-tetrahydro-quinolin-8-ylamino)-butyl]-isoindole-1,3-dione as an off-white solid.

Using the General Procedure for N-alkylation: A solution of 2-[4-(4-Methoxy-5,6,7,8-tetrahydro-quinolin-8-ylamino)-butyl]-isoindole-1,3-dione (0.340 g, 0.90 mmol), 1-tert-(butoxycarbonyl)-2-(chloromethyl)-benzimidazole (0.492 g, 1.84 mmol), and N,N-diisopropylethylamine (0.48 mL, 2.76 mmol) in CH$_3$CN (9 mL) was heated at 80° C. for 22 hours. Purification of the crude material by column chromatography on silica gel (20:1:1 CH$_2$Cl$_2$—CH$_3$OH—NH$_4$OH) followed by radial chromatography on silica gel (2 mm plate, 100:1:1 CH$_2$Cl$_2$—CH$_3$OH—NH$_4$OH) provided 133 mg (24%) of 2-{[[4-(1,3-Dioxo-1,3-dihydro-isoindol-2-yl)-butyl]-(4-methoxy-5,6,7,8-tetrahydro-quinolin-8-yl)-amino]-methyl}-benzimidazole-1-carboxylic acid tert-butyl ester a yellow solid.

To a solution of 2-{[[4-(1,3-Dioxo-1,3-dihydro-isoindol-2-yl)-butyl]-(4-methoxy-5,6,7,8-tetrahydro-quinolin-8-yl)-amino]-methyl}-benzimidazole-1-carboxylic acid tert-butyl ester (0.133 g, 0.22 mmol) in ethanol (4 mL) was added hydrazine monohydrate (0.20 mL, 4.12 mmol) and the resultant mixture was stirred at room temperature overnight. The mixture was filtered through filter paper and concentrated. Purification of the crude material by column chromatography on silica gel (10:1:1 CH$_2$Cl$_2$—CH$_3$OH—NH$_4$OH) provided 56 mg (68%) of the free base of the title compound as a yellow oil.

Using General Procedure D: Conversion of the free base to the hydrobromide salt followed by reprecipitation of the intermediate solid from methanol/ether gave COMPOUND 100 (72 mg, 71%) as a tan solid. $^1$H NMR (D$_2$O) δ 1.53 (br s, 4H), 1.64-1.74 (m, 1H), 1.86-1.98 (m, 1H), 2.14-2.19 (m, 1H), 2.28-2.32 (m, 1H), 2.50-2.63 (m, 2H), 2.71-2.87 (m, 4H), 4.09 (s, 3H), 4.31-4.40 (m, 2H), 4.48 (d, 1H, J=16.8 Hz), 7.34 (d, 1H, J=7.2 Hz), 7.56-7.61 (m, 2H), 7.76-7.80 (m, 2H), 8.49 (d, 1H, J=7.2 Hz); $^{13}$C NMR (D$_2$O) δ 19.74, 20.00, 21.76, 25.03, 25.37, 39.51, 47.98, 51.69, 58.09, 60.11, 107.55, 114.22, 126.91, 128.05, 130.98, 141.05, 150.21, 151.88, 170.91; ES-MS m/z 380 (M+H). Anal. Calcd. for C$_{22}$H$_{29}$N$_5$O.3.2HBr.2.2H$_2$O: C, 38.97; H, 5.44; N, 10.335; Br, 37.71. Found: C, 39.08; H, 5.13; N, 10.46; Br, 37.57.

Example 101

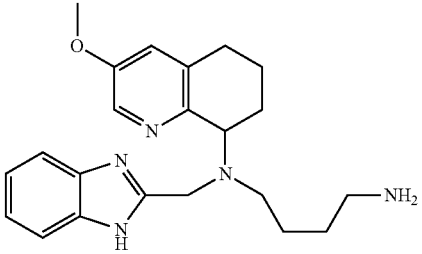 [SMILES: COc1cnc2c(c1)CCCC2N(CCCCN)Cc1nc2ccccc2[nH]1]

Compound 101: Preparation of N$^1$-(1H-benzimidazol-2-ylmethyl)-N$^1$-(3-methoxy-5,6,7,8-tetrahydroquinolin-8-yl)-butane-1,4-diamine (hydrobromide salt)

A solution of 3-bromoquinoline (24.4 g, 117 mmol) in anhydrous DMF (250 mL) was treated with sodium methoxide (12.7 g, 235 mmol) and stirred at 140° C. for 40 hours. The reaction mixture was then concentrated under reduced pressure and diluted with ethyl acetate (300 mL) and water (60 mL). The organic phase was separated, washed with brine (2×60 mL) and dried (MgSO$_4$), filtered, and concentrated under reduced pressure. This gave, after purification by column chromatography on silica gel (ethyl acetate/hexane; 1:4), 3-methoxyquinoline as a pale yellow liquid (1.15 g, 6%). $^1$H NMR (CDCl$_3$) δ 3.95 (s, 3H), 7.38 (d, 1H, J=1.5 Hz), 7.54 (m, 2H), 7.72 (d, 1H, J=7.5 Hz), 8.04 (d, 1H, J=7.5 Hz), 8.67 (d, 1H, J=1.5 Hz).

A solution of 3-methoxyquinoline (1.15 g, 7.2 mmol) in TFA (24 mL) was prepared and the reaction flask was purged with argon. Platinum oxide (82 mg, 0.36 mmol) was then added, and hydrogen gas was bubbled through the solution for 16 h at room temperature. The mixture was then cooled to 0° C., basisified to pH 12 with 15% aqueous sodium hydroxide solution, and extracted with ethyl acetate (3×100 mL). The organic phase was then dried (MgSO$_4$), filtered, and concentrated to yield 3-methoxy-5,6,7,8-tetrahydroquinoline (0.88 g, 74%). $^1$H NMR (CDCl$_3$) δ 1.77 (m, 2H), 1.85 (m, 2H), 2.75 (t, 2H, J=6.0 Hz), 2.85 (t, 2H, J=6.0 Hz), 3.81 (s, 3H), 6.88 (d, 1H, J=1.5 Hz), 8.07 (d, 1H, J=1.5 Hz).

50% Hydrogen peroxide (0.30 mL, 5.4 mmol, 1 equivalent) was added to a solution of 3-methoxy-5,6,7,8-tetrahydroquinoline (0.87 g, 5.3 mmol) in acetic acid (12 mL) and heated to 70° C. for 7 h. A second equivalent of 50% hydrogen peroxide (0.30 mL, 5.4 mmol) was then added and the solution stirred another 16 h at 70° C. The solution was then concentrated under reduced pressure and chloroform (20 mL) and sodium carbonate (5 g) was added. The mixture was stirred for a short period and the supernatant was decanted and the solids washed with chloroform (50 mL). The organic was then dried (Na$_2$SO$_4$), filtered, and concentrated under reduced pressure to provide the N-oxide as a yellow crystalline solid (0.67 g, 70%). $^1$H NMR (CDCl$_3$) δ 1.76 (m, 2H), 1.86 (m, 2H), 2.74 (t, 2H, J=6.0 Hz), 2.88 (t, 2H, J=6.0 Hz), 3.81 (s, 3H), 6.67 (d, 1H, J=1.5 Hz), 7.98 (d, 1H, J=1.5 Hz).

A solution of 3-methoxy-5,6,7,8-tetrahydroquinolinium oxide (0.67 g, 3.7 mmol) in acetic anhydride (9 mL, 95 mmol) was heated to 90° C. for 18 h followed by concentration under reduced pressure. This provided the rearranged 8-acetyl-3-methoxy-5,6,7,8-tetrahydroquinoline as a crude brown oil (0.83 g, 100%) that was again used immediately in the next reaction. $^1$H NMR (CDCl$_3$) δ 1.83 (m, 2H), 2.09 (s, 3H), 2.11 (m, 2H), 2.80 (m, 2H), 3.84 (s, 3H), 5.94 (t, 1H, J=4.5 Hz), 6.94 (d, 1H, J=1.5 Hz), 8.22 (d, 1H, J=1.5 Hz).

A solution of 8-acetyl-3-methoxy-5,6,7,8-tetrahydroquinoline (0.83 g, 3.7 mmol) in anhydrous methanol (18 mL) was treated with potassium carbonate (1.03 g, 7.5 mmol) and stirred at room temperature for 16 h. The mixture was concentrated under reduced pressure and CH$_2$Cl$_2$ (30 mL) and water (15 ml) was added. The aqueous phase was then extracted with CH$_2$Cl$_2$ (2×30 mL) and the combined organic phases were dried (MgSO$_4$), filtered, and concentrated to yield, after column chromatography (1:3 ethyl acetate/hexane), (3-methoxy-5,6,7,8-tetrahydroquinolin-8-yl)-alcohol as a pale yellow solid (0.35 g, 51%), $^1$H NMR (CDCl$_3$) δ 1.81 (m, 2H), 1.99 (m, 1H), 2.22 (m, 1H), 2.77 (m, 2H), 3.83 (s, 3H), 4.69 (t, 1H, J=7.5 Hz), 6.92 (d, 1H, J=3.0 Hz), 8.12 (d, 1H, J=3.0 Hz).

The alcohol from above (0.35 g, 1.9 mmol) was then dissolved in anhydrous CH$_2$Cl$_2$ (19 mL) and treated with manganese dioxide (1.67 g, 19 mmol) for 18 h at room temperature. The black mixture was filtered through a celite pad and the filtrate concentrated under reduced pressure. This gave the desired 3-methoxy-5,6,7,8-tetrahydroquinolin-8-one (0.23 g, 68%) which was used in the next reaction unpurified. $^1$H NMR (CDCl$_3$) δ 2.18 (m, 2H), 2.74 (t, 2H, J=6.0 Hz), 2.99 (t, 2H, J=6.0 Hz), 3.90 (s, 3H), 7.00 (d, 1H, J=3.0 Hz), 8.35 (d, 1H, J=4.0 Hz).

Using general procedure B from above, 3-methoxy-5,6,7,8-tetrahydroquinolin-8-one (0.23 g, 1.3 mmol), (4-aminobutyl)-carbamic acid tert-butyl ester (0.27 g, 1.4 mmol) and sodium triacetoxyborohydride (0.55 g, 2.6 mmol) were stirred at room temperature in CH$_2$Cl$_2$ (7 mL) for 18 hours. This yielded, after work-up and column chromatography (3:97 MeOH/CH$_2$Cl$_2$ to 15:1:84 MeOH/NH$_4$OH/CH$_2$Cl$_2$), [4-(3-methoxy-5,6,7,8-tetrahydroquinolin-8-ylamino)-butyl]-carbamic acid tert-butyl ester (0.38 g, 84%).

To a solution of the above secondary amine (0.15 g, 0.43 mmol), N-(t-butoxycarbonyl)-2-chloromethylbenzimidazole (0.18 g, 0.69 mmol), and potassium iodide (5 mg, 0.02 mmol) in anhydrous acetonitrile (4.3 mL) was added diisopropylethylamine (0.15 mL, 0.9 mmol) and stirred at 60° C. for 16 hours. The mixture was then concentrated under reduced pressure and the residue partitioned between CH$_2$Cl$_2$ (10 mL) and brine (5 mL). The organic phase was separated and the aqueous phase was extracted with CH$_2$Cl$_2$ (2×10 mL). The combined organic phases were then dried (Na$_2$SO$_4$), filtered, and concentrated under reduced pressure to give a crude residue that was purified by column chromatography with silica gel (1:99 MeOH/CH$_2$Cl$_2$) followed by a second column with silica gel (saturated NH$_3$/Et$_2$O). This gave 2-{[(4-tert-butoxycarbonylaminobutyl)-(3-methoxy-5,6,7,8-tetrahydroquinolin-8-yl)-amino]-methyl}-benzimidazole-1-carboxylic acid tert-butyl ester (98 mg, 39%). $^1$H NMR (CDCl$_3$) δ 1.40 (s, 9H), 1.43 (br m, 4H), 1.62 (m, 1H), 1.69 (s, 9H), 1.87-2.05 (m, 3H), 2.62-2.80 (m, 4H), 3.01 (br, 2H), 3.75 (s, 3H), 4.16 (m, 1H), 4.44 (d, 1H, J=15.0 Hz), 4.55 (d, 1H, J=15.0 Hz), 4.90 (br, 1H), 6.71 (d, 1H, J=3.0 Hz), 7.27 (m, 2H), 7.70 (m, 1H), 7.79 (m, 1H), 8.08 (d, 1H, J=3.0 Hz).

Using general procedure D: The above material (97 mg, 0.17 mmol) was converted to the hydrobromide salt to provide COMPOUND 101 (85 mg) as a white solid. $^1$H NMR (D$_2$O) δ 1.54 (br, 4H), 1.75 (m, 1H), 1.93 (m, 1H), 2.15 (m, 1H), 2.33 (m, 1H), 2.56 (br, 1H), 2.80 (br m, 1H), 2.87 (br, 2H), 2.96 (br d, 2H), 3.96 (s, 3H), 4.37 (d, 1H, J=17.1 Hz), 4.43 (m, 1H), 4.50 (d, 1H, J=16.8 Hz), 7.60 (m, 2H), 7.79 (m, 2H), 7.93 (br, 1H), 8.28 (d, 1H, J=2.1 Hz). $^{13}$C NMR (D$_2$O) δ 20.54 (2C), 25.08, 25.43, 28.01, 39.54, 47.95, 51.73, 57.43, 60.13, 114.25 (2C), 126.95 (2C), 127.25, 131.00, 131.96, 141.38, 143.54, 151.85, 157.19. ES-MS m/z 380 (M+H). Anal. Calcd. for C$_{22}$H$_{29}$N$_5$O.3.2HBr.1.7H$_2$O: C, 39.50; H, 5.36; N, 10.47; Br, 38.22. Found: C, 39.77; H, 5.27; N, 10.34; Br, 37.96.

Example 102

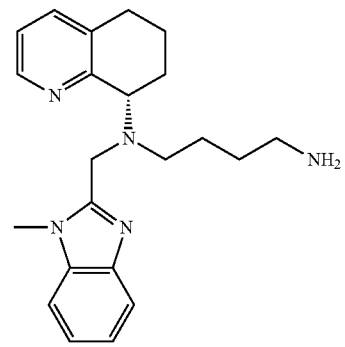 [SMILES: Cn1c(CN(CCCCN)[C@H]2CCCc3cccnc32)nc2ccccc21]

Compound 102: Preparation of N$^1$-(1-Methyl-1H-benzoimidazol-2-ylmethyl)-N$^1$-(S)-(5,6,7,8-tetrahydro-quinolin-8-yl)-butane-1,4-diamine hydrochloride salt

Preparation of 2-{4-[(1-methyl-1H-benzoimidazol-2-ylmethyl)-(5,6,7,8-tetrahydro-quinolin-8-yl)-amino]-butyl}-isoindole-1,3-dione To a solution of (S)-2-[4-(5,6,7,8-tetrahydro-quinolin-8-ylamino)-butyl]-isoindole-1,3-dione (3.89 g, 11.1 mmol) in acetonitrile (111 ml) was added 2-chloromethyl-1-methyl-1H-benzoimidazole (prepared by reaction of N-methyl-ortho-phenylenediamine with chloroacetic acid according to literature procedure Phillips, M. A. *J. Chem. Soc.* 1928, 2393; Goker, H.; Kus, C. *Arch. Pharm.* (*Weinheim*) 1995, 328, 425-430) (2.42 g, 13.4 mmol), diisopropylethylamine (1.93 ml, 11.1 ml), and potassium iodide (0.18 g, 1.11 ml). The mixture was stirred for 16 hours at 50° C. The mixture was concentrated, redissolved in methylene chloride (200 ml) and diluted with saturated NaCl (400 ml). The reaction was extracted with methylene chloride (3×300 ml) and the combined organic extracts were dried (Na$_2$SO$_4$), filtered, and concentrated in vacuo to afford a dark red oil. Purification via column chromatography on silica gel (CH$_2$Cl$_2$:MeOH:NH$_4$OH, 95:4:1, v/v/v) afforded the product as a light red foam (5.12 g, 77%). $^1$H NMR (CDCl$_3$) δ 1.63 (m, 8H), 2.65 (m, 4H), 3.54 (m, 2H), 4.10 (m, 6H), 6.98 (dd, 1H, J=7.89, 4.38 Hz), 7.21 (m, 4H), 7.71 (m, 5H), 8.49 (d, 1H, J=3.95 Hz).

Preparation of N-(1-Methyl-1H-benzoimidazol-2-ylmethyl)-N-(5,6,7,8-tetrahydro-quinolin-8-yl)-butane-1,4-diamine To a solution of the material from above (5.12 g, 10.37 mmol) in ethanol (75 ml) was added hydrazine hydrate (1.94 ml, 62.2 mmol). The solution was stirred for 16 hours at room temperature under a N$_2$ atmosphere. A white precipitate formed. Diethyl ether (75 ml) was added to the mixture and the reaction was stirred for 10 min. The mixture was filtered and concentrated. Purification via column chromatography on silica gel (CH$_2$Cl$_2$:MeOH:NH$_4$OH, 94:5:1, v/v/v) followed by a second purification by column chromatography on silica gel (CH$_2$Cl$_2$:MeOH:NH$_4$OH, 94:5:1, v/v/v) afforded the product as a light yellow oil (2.63 g, 55%). $^1$H NMR (CDCl$_3$) δ 1.39 (m, 5H), 1.99 (m, 3H), 2.63 (m, 6H), 3.48 (s, 2H), 3.97 (s, 3H), 4.11 (m, 3H), 7.00 (dd, 1H, J=7.45, 4.38 Hz), 7.25 (m, 4H), 7.71 (d, 1H, J=7.45 Hz), 8.46 (d, 1H, J=4.38 Hz).

Preparation of Compound 102

To a solution of N-(1-Methyl-1H-benzoimidazol-2-ylmethyl)-N-(5,6,7,8-tetrahydro-quinolin-8-yl)-butane-1,4-diamine (2.63 g, 5.62 mmol) was added HCl-saturated methanol (11 ml) and the mixture was stirred for 1 hour at room temperature under a N$_2$ atmosphere. The solution was added dropwise to diethyl ether (1 L) to yield a chunky white precipitate. The white solid was isolated via suction filtration under a steady stream of nitrogen, washed with diethyl ether and dried at 40° C. in vacuo overnight (2.75 g, 91%). $^1$H NMR (D$_2$O) δ 1.67 (m, 3H), 1.99 (m, 4H), 2.55 (m, 2H), 2.89 (m, 3H), 3.07 (m, 2H), 3.31 (s, 1H), 4.07 (s, 3H), 4.43 (d, 1H, J=17.9 Hz), 4.69 (m, 2H), 7.62 (m, 2H), 7.92 (m, 3H), 8.42 (d, 1H, J=7.89 Hz), 8.85 (d, 1H, J=5.7 Hz). $^{13}$C NMR δ (D$_2$O) 21.92, 26.65, 29.17, 32.42, 40.78, 53.61, 61.82, 113.89, 115.76, 127.15, 127.89, 128.11, 131.79, 135.1, 141.38, 141.91, 149.14, 152.75, 153.72. ES-MS m/z 364 (M+H). Anal. Calcd. For C$_{22}$H$_{29}$N$_5$3.05HCl 0.06C$_2$H$_4$O$_2$3.07H$_2$O: C, 49.80; H, 7.26; N, 13.13; Cl, 20.24. Found. C, 49.80; 7.25; N, 13.13; Cl, 20.24.

Example 103

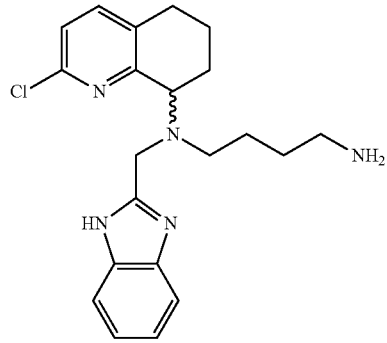 [SMILES: NCCCCN(Cc1nc2ccccc2[nH]1)C1CCCc2ccc(Cl)nc21]

Compound 103: Preparation of N$^1$-(1H-benzimidazol-2-ylmethyl)-N$^1$-(2-chloro-5,6,7,8-tetrahydro-quinolin-8-yl)-butane-1,4-diamine (hydrobromide salt)

Preparation of methanesulfonic acid 2-chloro-5,6,7,8-tetrahydro-quinolin-8-yl ester To a solution of 2-chloro-8-hydroxy-5,6,7,8-tetrahydro-quinoline (prepared as described by Zimmerman, S. C.; Zeng, Z.; Wu, W.; Reichert, D. E. *J. Am. Chem. Soc.* 1991, 113, 183-196) (700 mg, 3.81 mmol) in CH$_2$Cl$_2$ (19 mL), cooled to 0° C. under nitrogen, was added NEt$_3$ (0.80 mL, 5.7 mmol) followed by MsCl (0.35 mL, 4.5 mmol). The solution was stirred at 0° C. for 40 minutes, then was diluted with saturated aqueous NaHCO$_3$ (20 mL). The layers were separated and the aqueous solution was extracted with CH$_2$Cl$_2$ (20 mL×2). The combined organic solution was dried (MgSO$_4$), filtered and concentrated under reduced pressure. Purification by flash column chromatography on silica (hexane/EtOAc, 2:1) gave the mesylate as a white solid (904 mg, 3.45 mmol, 91%). $^1$H NMR (CDCl$_3$) δ 1.82-2.17 (m, 3H), 2.35-2.47 (m, 1H), 2.63-2.77 (m, 1H), 2.79-2.91 (m, 1H), 3.29 (s, 3H), 5.62 (t, 1H, J=3.9 Hz), 7.23 (d, 1H, J=8.1 Hz), 7.45 (d, 1H, J=8.1 Hz).

Preparation of 8-azido-2-chloro-5,6,7,8-tetrahydro-quinoline

A solution of the mesylate (886 mg, 3.39 mmol) and NaN$_3$ (285 mg, 4.38 mmol) in DMF (10 mL) was stirred at 80° C. under nitrogen for 35 minutes. Once cooled, the mixture was diluted with brine (20 mL) and was extracted with EtOAc (20 mL×3). The combined organic solution was dried (MgSO$_4$), filtered and concentrated under reduced pressure. Purification by flash column chromatography on silica (hexane/EtOAc, 2:1) gave the azide as a pale yellow oil (679 mg, 3.25 mmol, 96%). $^1$H NMR (CDCl$_3$) δ 1.75-2.11 (m, 4H), 2.63-2.86 (m, 2H), 4.66 (t, 1H, J=4.2 Hz), 7.20 (d, 1H, J=8.1 Hz), 7.42 (d, 1H, J=8.1 Hz).

Preparation of 8-amino-2-chloro-5,6,7,8-tetrahydro-quinoline

To a solution of the azide (351 mg, 1.68 mmol) in 10% H$_2$O in THF (10 mL) was added PPh$_3$ (867 mg, 3.31 mmol) and the reaction was stirred at room temperature for 18 hours. The solution was concentrated under reduced pressure and the residue was purified by flash column chromatography on silica (CH$_2$Cl$_2$/MeOH, 9:1) giving the amine as a pale yellow oil (276 mg, 1.51 mmol, 90%). $^1$H NMR (CDCl$_3$) δ 1.62-1.83 (m, 2H), 1.86-2.03 (m, 3H), 2.13-2.22 (m, 1H), 2.66-2.84 (m, 2H), 3.97 (dd, 1H, J=7.5, 5.4 Hz), 7.09 (d, 1H, J=8.1 Hz), 7.33 (d, 1H, J=8.1 Hz).

Preparation of 2-[4-(2-chloro-5,6,7,8-tetrahydro-quinolin-8-ylamino)-butyl]-isoindole-1,3-dione A solution of the amine (269 mg, 1.47 mmol) and 4-(1,3-dioxo-1,3-dihydro-isoindol-2-yl)-butyraldehyde (266 mg, 1.22 mmol) in CH$_2$Cl$_2$ (8 mL) was stirred at room temperature under nitrogen for 30 minutes. NaBH(OAc)$_3$ (398 mg, 1.88 mmol) was then added in one portion as a solid and the reaction was stirred for a further 15 hours. The mixture was washed with 1M NaOH (10 mL×2) and brine (10 mL), dried (Na$_2$SO$_4$), filtered and concentrated under reduced pressure. Purification by flash column chromatography on silica (CH$_2$Cl$_2$/MeOH/NH$_4$OH, 49:1:0.25) gave the secondary amine as a colourless oil (289 mg, 0.75 mmol, 62%). $^1$H NMR (CDCl$_3$) δ 1.55-1.81 (m, 6H), 1.93-2.03 (m, 1H), 2.06-2.14 (m, 1H), 2.26 (br. s, 1H), 2.73 (t, 4H, J=7.1 Hz), 3.72 (t, 3H, J=6.9 Hz), 7.07 (d, 1H, J=8.1 Hz), 7.32 (d, 1H, J=8.1 Hz), 7.69 (dd, 2H, J=5.4, 3.0 Hz), 7.83 (dd, 2H, J=5.3, 3.0 Hz).

Preparation of 2-({(2-chloro-5,6,7,8-tetrahydro-quinolin-8-yl)-[4-(1,3-dioxo-1,3-dihydro-isoindol-2-yl)-butyl]-amino}-methyl)-benzimidazole-1-carboxylic acid tert-butyl ester A solution of the amine (274 mg, 0.72 mmol), 2-chloromethyl-benzimidazole-1-carboxylic acid tert-butyl ester (227 mg, 0.85 mmol), DIPEA (0.18 mL, 1.0 mmol) and KI (24 mg, 0.14 mmol) in CH$_3$CN (5 mL) was stirred at 60° C. under nitrogen for 17 hours. Once cooled to room temperature, the solution was diluted with saturated aqueous NaHCO$_3$ (10 mL) and extracted with CH$_2$Cl$_2$ (20 mL×3). The combined organic solution was dried (MgSO$_4$), filtered and concentrated under reduced pressure. Purification by flash column chromatography on silica (CH$_2$Cl$_2$/MeOH, 19:1) gave the tertiary amine as an off-white foam (435 mg, 0.71 mmol, 99%). $^1$H NMR (CDCl$_3$) δ 1.28-1.41 (m, 2H), 1.50-1.61 (m, 2H), 1.64-1.76 (m, 10H), 1.80-1.91 (m, 1H), 1.93-2.05 (m, 1H), 2.09-2.22 (m, 1H), 2.54-2.89 (m, 4H), 3.53 (t, 2H, J=7.2 Hz), 4.18 (dd, 1H, J=9.8, 6.2 Hz), 4.49 (d, 1H, J=15.6 Hz), 4.74 (d, 1H, J=15.6 Hz), 6.93 (d, 1H, J=8.1 Hz), 7.19 (d, 1H, J=8.1 Hz), 7.22-7.26 (m, 2H), 7.63-7.71 (m, 3H), 7.74-7.85 (m, 3H).

Preparation of N$^1$-(1H-benzimidazol-2-ylmethyl)-N$^1$-(2-chloro-5,6,7,8-tetrahydro-quinolin-8-yl)-butane-1,4-diamine A solution of the amine (212 mg, 0.345:mmol) and hydrazine monohydrate (0.20 mL, 4.1 mmol) in EtOH was stirred at reflux under nitrogen for 75 minutes. The excess solvent was removed under reduced pressure, the residue was taken up into saturated aqueous NaHCO$_3$ (10 mL) and was extracted with CH$_2$Cl$_2$ (20 mL×3). The combined organic solution was dried (MgSO$_4$), filtered and concentrated under reduced pressure. Purification by flash column chromatography on silica (CH$_2$Cl$_2$/MeOH/NH$_4$OH, 9:1:0.05) gave the primary amine as a white foam (99.9 mg, 0.260 mmol, 75%). $^1$H NMR (CDCl$_3$) δ 1.29-1.52 (m, 4H), 1.61-1.77 (m, 1H), 1.79-1.94 (m, 1H), 1.99-2.11 (m, 1H), 2.18-2.30 (m, 1H), 2.47-2.62 (m, 3H), 2.65-2.88 (m, 3H), 3.94-4.09 (m, 3H), 7.15 (d, 1H, J=8.1 Hz), 7.19-7.23 (m, 2H), 7.38 (d, 1H, J=8.1 Hz), 7.60-7.64 (m, 2H).

Preparation of Compound 103

To a solution of the amine (99.9 mg, 0.260 mmol) in glacial HOAc (1.5 mL) was added a saturated solution of HBr in HOAc (0.5 mL). The solution was stirred at room temperature for 30 minutes, then Et$_2$O (5 mL) was added. The solvent was removed by pipette, the precipitate was washed with Et$_2$O (2 mL×2) and was then dissolved into MeOH (2 mL). The mixture was stirred for about 5 minutes and the product was re-precipitated by the addition of Et$_2$O (5 mL). The solvent was again removed by pipette and the precipitate was washed with Et$_2$O (2 mL×3). The product was dried under reduced pressure, giving COMPOUND 103 as a fine, off-white powder (156 mg, 0.240 mmol, 92%). $^1$H NMR (D$_2$O) δ 1.67-2.00 (m, 5H), 2.12-2.32 (m, 2H), 2.39-2.52 (m, 1H), 2.67-2.82 (m, 2H), 3.03 (t, 2H, J=7.4 Hz), 3.40-3.56 (m, 2H), 4.80-4.89 (m, 3H), 6.96 (d, 1H, J=8.1 Hz), 7.35 (d, 1H, J=8.1 Hz), 7.51-7.55 (m, 2H), 7.68-7.71 (m, 2H). $^{13}$C NMR (D$_2$O) δ 20.3, 21.1, 23.2, 24.6, 27.0, 39.3, 46.6, 54.1, 63.2, 114.9, 124.2, 126.9, 132.6, 134.5, 141.7, 144.4, 147.9, 150.2. ES-MS m/z 384 (M+H), 386 (M+2+H).
Anal. Calcd. for C$_{21}$H$_{26}$ClN$_5$.3.1HBr.0.2C$_4$H$_{10}$O: C, 40.31; H, 4.83; N, 10.78; Br 38.13. Found: C, 40.20; H, 4.91; N, 10.73; Br 38.44.

Example 105

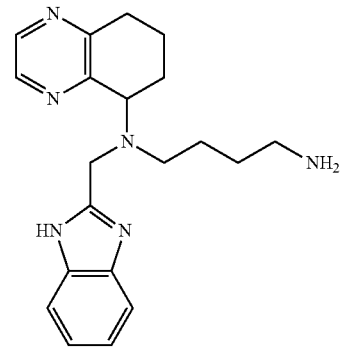 [SMILES: NCCCCN(Cc1nc2ccccc2[nH]1)C1CCCc2nccnc21]

Compound 105: N$^1$-(1H-Benzoimidazol-2-ylmethyl)-N$^1$-(5,6,7,8-tetrahydroquinoxalin-5-yl)-butane-1,4-diamine Preparation of 5-bromo-5,6,7,8-tetrahydroquinoxaline To a solution of commercially available 5,6,7,8-tetrahydroquinoxaline (3.08 g, 23.0 mmol) in CCl$_4$ (200 mL) was added N-bromosuccinamide (4.09 g, 23.0 mmol) and a catalytic amount (56 mg) of benzoyl peroxide. The reaction mixture was heated at reflux for 17 hours. Saturated sodium bicarbonate solution was added (100 mL), the layers were separated and the aqueous phase was extracted with CH$_2$Cl$_2$ (2×200 mL). The organic extracts were dried and concentrated. The crude material contained 1:3:1 ratio (GC) of starting material, mono- and dibromo products which were separated by column chromatography on silica gel using a mixture of 1:1 EtOAc:hexanes to give 5-bromo-5,6,7,8-tetrahydroquinoxaline (3.03 g, 54%) as a brown liquid: $^1$H NMR (CDCl$_3$): δ 1.99-2.03 (m, 1H), 2.20-2.49 (m, 3H), 2.97-3.10 (m, 1H), 3.11-3.20 (m, 1H), 5.48 (t, 1H, J=1.5 Hz), 8.40 (s, 2H). It should be noted that this material is unstable when exposed to air over 2-3 days and was used immediately in the next reaction.

Preparation of 5-azido-5,6,7,8-tetrahydroquinoxaline 5-bromo-5,6,7,8-tetrahydroquinoxaline (2.75 g, 12.9 mmol) and sodium azide (1.68 g, 25.8 mmol) were dissolved in DMF (50 mL) under nitrogen atmosphere and the reaction mixture was warmed to 60° C. for 2 days. The mixture was cooled to room temperature and poured over water (500 mL), and was extracted with CH$_2$Cl$_2$ (3×300 mL). The organic extracts were washed with brine (2×200 mL), dried and concentrated in vacuo. The crude material was purified by flash column chromatography on silica gel using 1:1 EtOAc/hexanes to afford 2.19 g (97%) of 5-azido-5,6,7,8-tetrahydroquinoxaline as a yellow liquid: $^1$H NMR (CDCl$_3$): δ 1.80-1.96 (m, 1H), 2.00-2.10 (m, 3H), 2.75-3.06 (m, 2H), 4.74 (t, 1H, J=6.5 Hz), 8.44 (d, 1H, J=3 Hz), 8.45 (d, 1H, J=3 Hz); $^{13}$C NMR (CDCl$_3$): δ 18.6, 28.9, 31.7, 60.2, 142.6, 144.3, 150.3, 153.6.

Preparation of 5,6,7,8-tetrahydroquinoxalin-5-ylamine

A Parr shaker flask was charged with 5-azido-5,6,7,8-tetrahydroquinoxaline (1.81 g, 10.33 mmol) and 10% palladium on carbon (10 wt % of Pd/C, 0.18 g). The reaction vessel was evacuated and filled with nitrogen. Methanol (30 mL) was added and the reaction was hydrogenated at 30 psi for 40 minutes. The reaction mixture was flushed with nitrogen and filtered through a plug of Celite® to provide 5,6,7,8-tetrahydroquinoxalin-5-ylamine as an orange liquid (1.54 g, 99%), which would rapidly turn dark brown. It was stored under an argon atmosphere at −20° C. $^1$H NMR (CDCl$_3$): δ 1.62-1.79 (m, 1H), 1.80-2.18 (m, 4H), 2.18-2.30 (m, 1H), 2.91-3.01 (m, 2H), 4.07 (dd, 1H, J=8.4, 5.4 Hz), 8.32-8.38 (m, 2H); $^{13}$C NMR (CDCl$_3$): δ 19.7, 31.7, 32.2, 51.5, 142.0, 142.5, 152.6, 155.4; MS m/z: 150 (M+H$^+$), 133.

Preparation of 2-[4-(5,6,7,8-tetrahydro-quinoxalin-5-ylamino)-butyl]-isoindole-1,3-dione To a solution of 5,6,7,8-tetrahydroquinoxalin-5-ylamine (313 mg, 2.09 mmol) in CH$_2$Cl$_2$ (20 mL) at room temperature under inert atmosphere was added 4-(1,3-dioxo-1,3-dihydro-isoindol-2-yl)-butyraldehyde (227.8 mg, 1.05 mmol) followed by sodium triacetoxyborohydride (444 mg, 2.10 mmol). The reaction mixture was stirred at room temperature for 2 hours. Saturated sodium bicarbonate solution (10 mL) was added and the mixture was extracted with dichloromethane (3×20 mL). The combined organic extracts were washed with brine, dried (MgSO$_4$), filtered and concentrated. The resultant material was purified by column chromatography on silica gel (10:1:0.5 CH$_2$Cl$_2$: MeOH: NH$_4$OH) to provide the product as a clear oil (298 mg, 81%): $^1$H NMR (CDCl$_3$): δ 1.56-1.66 (m, 2H), 1.70-1.95 (m, 4H), 2.04-2.22 (m, 4H), 2.71-2.85 (m, 2H), 2.87-3.05 (m, 2H), 7.69-7.73 (m, 2H), 7.80-7.85 (m, 2H), 8.34 (br s, 2H).

Preparation of 2-{[[4-(1,3-dioxo-1,3-dihydro-isoindol-2-yl)-butyl]-(5,6,7,8-tetrahydroquinoxalin-5-yl)-amino]-methyl}-benzoimidazole-1-carboxylic acid tert-butyl ester To a solution of 2-[4-(5,6,7,8-tetrahydro-quinoxalin-5-ylamino)-butyl]-isoindole-1,3-dione (298 mg, 0.850 mmol) in CH$_3$CN (12 mL) was added 2-chloromethyl-benzoimidazole-1-carboxylic acid tert-butyl ester (295 mg, 1.11 mmol), potassium iodide (14 mg), and diisopropylethylamine (0.296 ml, 1.70 mmol). The reaction mixture was stirred at 60° C. for 17 hours. Saturated sodium bicarbonate (15 mL) was added and the mixture was extracted with CH$_2$Cl$_2$ (3×30 mL). The combined organic extracts were dried (MgSO$_4$), filtered and concentrated. Purification of the crude material by column chromatography on silica gel (1:10 EtOAc:hexanes then EtOAc then 1:10 McOH:EtOAc) provided the product as a clear oil (422 mg, 85%): $^1$H NMR (CDCl$_3$): δ 1.34-1.43 (m, 2H), 1.48-1.60 (m, 2H), 1.68 (s, 9H), 1.71-1.81 (m, 1H), 1.88-1.97 (m, 1H), 2.00-2.21 (m, 2H), 2.60-2.69 (m, 1H), 2.76-2.93 (m, 3H), 3.55 (t, 2H, J=6.9 Hz), 4.29 (dd, 1H, J=9.6, 5.4 Hz), 4.46 (d, 1H, J=15.3 Hz), 4.61 (d, 1H, J=15.3 Hz), 7.19-7.24 (m, 2H), 7.63-7.69 (m, 3H), 7.74-7.81 (m, 3H), 8.18 (d, 1H, J=2.1 Hz), 8.27 (d, 1H, J=2.1 Hz).

Preparation of N$^1$-(1H-Benzoimidazol-2-ylmethyl)-N$^1$-(5,6,7,8-tetrahydroquinoxalin-5-yl)-butane-1,4-diamine (Compound 105)

To a solution of 2-{[[4-(1,3-dioxo-1,3-dihydro-isoindol-2-yl)-butyl]-(5,6,7,8-tetrahydroquinoxalin-5-yl)-amino]-methyl}-benzoimidazole-1-carboxylic acid tert-butyl ester (420 mg, 0.723 mmol) in ethanol (20 mL) at room temperature was added hydrazine hydrate (0.20 mL). The mixture was stirred for 17 hours. The mixture was concentrated in vaccuo and the resultant material was purified by column chromatography on silica gel (1:1:10 MeOH: NH$_4$OH: CH$_2$Cl$_2$) to provide COMPOUND 105 as a colourless foam (161 mg, 64%): $^1$H NMR (CDCl$_3$) δ 1.37-1.48 (m, 5H), 1.70-1.79 (m, 1H), 1.81-1.97 (m, 1H), 2.07-2.16 (m, 1H), 2.18-2.31 (m, 1H), 2.49-2.59 (m, 4H), 2.71-2.78 (m, 1H), 2.90-3.08 (m, 2H), 3.98 (d, 1H, J=16.5 Hz), 4.07 (d, 1H, J=16.5 Hz), 4.06-4.12 (m, 1H), 7.18-7.21 (m, 2H), 7.57-7.59 (m, 2H), 8.41 (s, 1H), 8.54 (s, 1H); $^{13}$C NMR (CDCl$_3$) δ 21.2, 22.9, 26.3, 30.5, 32.6, 41.7, 49.8, 51.4, 62.0, 122.3, 142.1, 143.3, 153.8, 155.4, 155.5; ES-MS m/z 351 (M+H). Anal. Calcd. for C$_{20}$H$_{26}$N$_6$.0.3CH$_2$Cl$_2$.0.2H$_2$O: C, 64.24; H, 7.17; N, 22.14. Found: C, 64.16; H, 7.41; N, 22.15.

Example 106

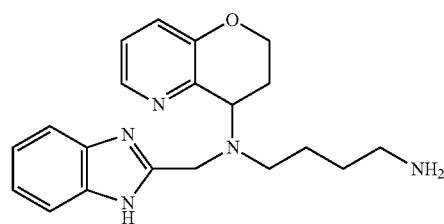 [SMILES: NCCCCN(Cc1nc2ccccc2[nH]1)C1CCOc2cccnc21]

Compound 106: Preparation of N$^1$-(1H-Benzimidazol-2-ylmethyl)-N$^1$-(3,4-dihydro-2H-pyrano[3,2-b]pyridin-4-yl)-butane-1,4-diamine (hydrobromide)

To a solution of triphenylphosphine (10.9 g, 41.5 mmol), 3-buten-ol (2.49 g, 34.6 mmol) and 2-bromo-3-pyridinol (6.01 g, 34.6 mmol) in THF (200 mL) at 0° C. was added diisopropyl azodicarboxylate (7.49 mL, 38.0 mmol) very slowly. Ice bath was removed after addition of diisopropyl azodicarboxylate and the mixture was allowed to stir at 50° C. for 20 hours under argon. The reaction mixture was diluted with EtOAc (300 mL), and washed with sat. NaHCO$_3$ (2×150 mL), brine (2×150 mL) and dried over Na$_2$SO$_4$. Evaporation of the solvent and purification of the residue by flash chromatography on silica gel (Hexanes/EtOAc, 90:10 followed by 85:15) afforded 2-bromo-3-but-3-enyloxy-pyridine (7.04 g, 89%) as a colourless oil. $^1$H NMR (CDCl$_3$) δ 2.58-2.66 (m, 2H), 4.08 (t, 2H, J=6.9 Hz), 5.13-5.24 (m, 2H), 5.87-5.98 (m, 1H), 7.10-7.14 (m, 1H), 7.18-7.22 (m, 1H), 7.97 (dd, 1H, J=6.0, 1.5 Hz).

An anhydrous DMF solution (120 mL) of 2-bromo-3-but-3-enyloxy-pyridine (6.43 g, 28.2 mmol) in a round bottom schlenk flask was degassed with argon using the freeze/pump/thaw method. To this freshly degassed solution was added triphenylphosphine (2.66 g, 10.2 mmol), palladium acetate (696 mg, 3.10 mmol), potassium acetate (13.84 g, 141 mmol), and tetraethylammoniumchloride hydrate (9.35 g, 56.4 mmol). The resultant mixture was heated at 110° C. under argon for 18 hours. The reaction mixture was cooled to room temperature and diluted with EtOAc (300 mL), brine (120 mL) and H$_2$O (60 mL). The organic phase was separated and washed with brine (3×120 mL) and dried over Na$_2$SO$_4$. Evaporation of the solvent and purification of the residue by flash chromatograph on silica gel (Hexanes/EtOAc, 95:5) afforded 4-methylene-3,4-dihydro-2H-pyrano[3,2-b]pyridine (2.8 g, 67%) as a white solid. $^1$H NMR (CDCl$_3$) δ 2.79-2.86 (m, 2H), 4.25 (t, 2H, J=5.7 Hz), 5.08 (d, 1H, J=1.6 Hz), 6.19 (d, 1H, J=1.6 Hz), 7.08-7.17 (m, 2H), 8.20 (dd, 1H, J=4.7, 1.6 Hz).

To a solution of 4-methylene-3,4-dihydro-2H-pyrano[3,2-b]pyridine (2.77 g, 18.8 mmol) and 4-methylmorpholine N-oxide (6.61 g, 56.5 mmol) in CH$_2$Cl$_2$ (45 mL) was added osmium tetroxide (2.5 wt. % solution in 2-methyl-2-propanol, 6.8 mL, 0.68 mmol). The resultant mixture was stirred at room temperature under N$_2$ for 80 hours, diluted with EtOAc (300 mL), and then filtered through a pad of celite. Evaporation of the solvent and purification of the residue by flash chromatograph on silica gel (CH$_2$Cl$_2$/MeOH/NH$_4$OH, 95:4:1) afforded the 4-hydroxymethyl-3,4-dihydro-2H-pyrano[3,2-b]pyridinyl-4-ol (2.13 g, 62%) as a yellow solid.

To a solution of 4-hydroxymethyl-3,4-dihydro-2H-pyrano[3,2-b]pyridinyl-4-ol (2.13 g, 11.8 mmol) in H$_2$O (15 mL) was added sodium periodate (5.03 g, 23.5 mmol) and the mixture was allowed to stir at room temperature for 2 hours. The mixture was diluted with EtOAc (100 mL) and H$_2$O (20 mL) and stirred vigorously for 10 minutes. The aqueous phase was separated and extracted with CH$_2$Cl$_2$ (2×50 mL). The combined organic extracts were dried (Na$_2$SO$_4$), filtered and concentrated. Purification of the residue by flash chromatograph on silica gel (Hexanes/EtOAc, 60:40 followed by 0:100) gave 2,3-Dihydro-pyrano[3,2-b]pyridin-4-one (1.28 g, 73%) as a white solid. $^1$H NMR (CDCl$_3$) δ 2.98 (t, 2H, J=6.6 Hz), 4.62 (t, 2H, J=6.6 Hz), 7.36-7.44 (m, 2H), 8.44 (dd, 1H, J=12.6, 2.1 Hz).

Reaction of 2,3-Dihydro-pyrano[3,2-b]pyridin-4-one (277 mg, 1.85 mmol) with (4-Amino-butyl)-carbamic acid tert-butyl ester (269 mg, 1.43 mmol) using general procedure B for reductive amination with NaBH(OAc)$_3$ (605 mg, 2.86 mmol), followed by flash chromatography on silica gel (CH$_2$Cl$_2$/MeOH/NH$_4$OH, 97:2:1 followed by 95:4:1) afforded [4-(3,4-Dihydro-2H-pyrano[3,2-b]pyridin-4-ylamino)-butyl]-carbamic acid tert-butyl ester (330 mg, 72%) as a pale yellow oil.

To a solution of [4-(3,4-Dihydro-2H-pyrano[3,2-b]pyridin-4-ylamino)-butyl]-carbamic acid tert-butyl ester (329 mg, 1.02 mmol) in CH$_3$CN (5 mL) was added N,N-diisopropylethylamine (0.28 mL, 1.63 mmol) followed by 2-chloromethyl-benzimidazole-1-carboxylic acid tert-butyl ester (328 mg, 1.23 mmol) and potassium iodide (20 mg, 0.1 mmol). The resultant mixture was heated to 60° C. for 16 hours then cooled to room temperature. The mixture was concentrated and the residue was partitioned between CH$_2$Cl$_2$ (25 mL) and saturated aqueous NaHCO$_3$ (20 mL). The phases were separated and the aqueous phase was extracted with CH$_2$Cl$_2$ (2×15 mL). The combined organic extracts were dried (Na$_2$SO$_4$), filtered, and concentrated. Purification of the crude material by flash column chromatography on silica gel (CH$_2$Cl$_2$/MeOH/NH$_4$OH, 95:4:1) provided 2-{[(4-tert-Butoxycarbonylamino-butyl)-(3,4-dihydro-2H-pyrano[3,2-b]pyridin-4-yl)-amino]-methyl}-benzimidazole-1-carboxylic acid tert-butyl ester (380 mg, 67%) as a white foam.

Using General Procedure D: Conversion of the white foam from above (107 mg, 0.19 mmol) to the hydrobromide salt followed by re-precipitation of the intermediate solid from methanol/ether gave COMPOUND 106 (110 mg, 90%) as a cream solid. $^1$H NMR (D$_2$O) δ 1.43-1.66 (m, 4H), 2.38-2.50 (m, 2H), 2.53-2.63 (m, 1H), 2.78-2.92 (m, 3H), 4.33-4.43 (m, 1H), 4.43 (d, 1H, J=17.4 Hz), 4.55 (d, 1H, J=17.1 Hz), 4.64-4.78 (m, 2H), 7.57-7.63 (m, 2H), 7.76-7.87 (m, 3H), 7.98 (dd, 1H, J=8.7, 0.9 Hz), 8.40 (dd, 1H, J=5.4, 0.9 Hz); $^{13}$C NMR (CDCl$_3$) δ 19.72, 24.98, 25.32, 39.52, 47.95, 51.48, 56.53, 67.48, 114.28, 126.93, 127.55, 131.03, 134.75, 134.84, 138.80, 151.75, 155.80; ES-MS m/z 352 (M+H). Anal. Calcd. for C$_{20}$H$_{25}$N$_5$O.3.1HBr.1.0H$_2$O.0.2C$_4$H$_{10}$O: C, 39.34; H, 5.09; N, 11.03; Br, 39.00. Found: C, 39.29; H, 4.92; N, 10.96; Br, 39.02.

Example 107

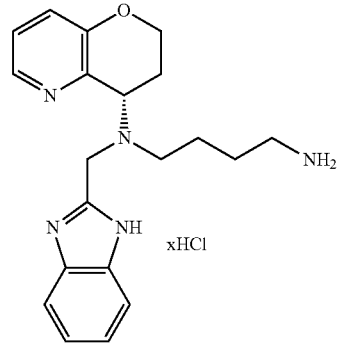 [SMILES: NCCCCN(Cc1nc2ccccc2[nH]1)[C@H]1CCOc2cccnc21]

Compound 107: Preparation of N$^1$-(1H-Benzimidazol-2-ylmethyl)-N$^1$-(S)-3,4-dihydro-2H-pyrano[3,2-b]pyridin-4-yl-butane-1,4-diamine (hydrochloride salt)

Preparation of 4-methylene-3,4-dihydro-2H-pyrano[3,2-b]pyridine

To a stirred 0° C. solution of 2-bromo-3-pyridinol (14.7 g, 84 mmol), 3-buten-1-ol (7.25 mL, 84 mmol), and triphenylphosphine (26.5 g, 100 mmol) in THF (420 mL) was added DIAD (18.3 mL, 93 mmol) over 5 min. The mixture was heated to 50° C. under a nitrogen atmosphere for 21 h, cooled to room temperature, and concentrated. The resultant brown oil was dissolved in ethyl acetate (1 L), washed with saturated sodium bicarbonate solution (2×500 mL), washed with brine (2×500 mL), dried over $Na_2SO_4$, and concentrated. Purification of the crude material by column chromatography over silica gel (5:1 hexanes/EtOAc) provided the desired bromide (20.2 g, 100%) as a yellow oil.

A solution of the bromide (19.2 g, 84 mmol) from above in anhydrous DMF (170 mL) was frozen under an argon atmosphere, and thawed while under high vacuum to degas the solution. This freeze-thaw cycle was repeated four times. A pressure-flask was purged with argon and charged with triphenylphosphine 7.96 g, 30 mmol), potassium acetate (41.4 g, 420 mmol), tetraethylammonium chloride hydrate (27.9 g, 170 mmol), palladium (II) acetate (2.08 g, 9.3 mmol), and the degassed solution from above. The flask was evacuated and back-filled with argon four times, sealed, and heated to 110° C. with stirring for 39 h. The mixture was cooled to room temperature, diluted with ethyl acetate (1 L) and stirred with a mixture of brine (500 mL) and water (200 mL) for 30 min. The layers were separated and the organic layer was washed with saturated sodium bicarbonate solution (500 mL) and brine (3×500 mL). The organic layer was dried over $Na_2SO_4$, concentrated, and dried under high vacuum for 1 h. Purification of the crude material (25 g) by column chromatography on silica gel (200:1 $CH_2Cl_2$/MeOH) provided the title compound (5.9 g, 47%) as a yellow oil. $^1H$ NMR ($CDCl_3$) δ 2.80-2.85 (m, 2H), 4.25 (t, 2H, J=5.7 Hz), 5.08 (s, 1H), 6.20 (s, 1H), 7.08-7.17 (m, 2H), 8.20 (dd, 1H, J=4.0, 1.8 Hz).

Preparation of (S)-(3,4-Dihydro-2H-pyrano[3,2-b] pyridin-4-yl)amine

A solution of 4-methylene-3,4-dihydro-2H-pyrano[3,2-b] pyridine (5.9 g, 40 mmol), 4-methylmorpholine-N-oxide (14.0 g, 120 mmol), and osmium tetroxide (15.4 mL, 2.5 wt % in tert-butanol, 1.2 mmol) in dichloromethane (100 mL) was stirred at room temperature under a nitrogen atmosphere for 7 days. The mixture was diluted with diethyl ether (100 mL), filtered through diatomaceous earth, and concentrated. Purification of the crude material by column chromatography over silica gel (25:1 $CH_2Cl_2$/MeOH) provided the diol (4.5 g, 62%) as a brown oil.

To a stirred solution of the diol (4.5 g, 25 mmol) from above in deionized water (100 mL) was carefully added sodium periodate (10.7 g, 50 mmol)—exothermic—and stirring was continued for 1.5 h. The mixture was diluted with ethyl acetate (200 mL), stirred for 2 h, and the layers were separated. The aqueous layer was extracted with dichloromethane (2×50 mL). The organic layers were combined, dried over $Na_2SO_4$, and concentrated to give the desired ketone (2.9 g, 78%) as an off-white solid.

A solution of the ketone (2.9 g, 19 mmol) from above and hydroxylamine hydrochloride (1.6 g, 23 mmol) in methanol (100 mL) was stirred at room temperature for 1 h. Saturated sodium bicarbonate solution (80 mL) was added and the mixture was concentrated on a rotary evaporator to remove the methanol. The resultant mixture was extracted with dichloromethane (1×200 mL, 3×75 mL) and 9:1 $CHCl_3$/MeOH (5×200 mL). The organic layers were combined, dried over $Na_2SO_4$, and concentrated to give the oxime (3.0 g, 94%) as a brown solid.

Zinc dust was added slowly to a stirred 0° C. suspension of oxime (3.0 g, 18 mmol) from above, ammonium acetate (1.6 g, 20 mmol), ammonium hydroxide (85 mL), and ethanol (16 mL). The cooling bath was removed and stirring was continued for 2.5 h. The slurry was filtered through celite and the filtrate was extracted with dichloromethane (3×150 mL). The organic extracts were combined, dried over $MgSO_4$, concentrated, and dried under high vacuum to provide the racemic amine (2.6 g, 94%).

A stirred slurry of the amine (2.6 g, 17 mmol) and CAL (0.80 g) in ethyl acetate (65 mL) was heated to 40° C. for 3 h. The mixture was cooled to room temperature, filtered, and concentrated. Purification of the crude material by column chromatography on silica (20:1 $CH_2Cl_2$/MeOH, then 20:1:1 $CH_2Cl_2$/MeOH/$NH_4OH$) afforded the title compound (1.14 g, 88%) as a red-brown oil. $^1H$ NMR ($CDCl_3$) δ 1.90-2.02 (m, 1H), 2.24-2.35 (m, 1H), 4.13 (t, 1H, J=6.4 Hz), 4.18-4.36 (m, 2H), 7.06-7.13 (m, 2H), 8.17 (dd, 1H, J=3.9, 2.2 Hz).

Preparation of $N^1$-(1H-Benzimidazol-2-ylmethyl)-$N^1$—(S)-3,4-dihydro-2H-pyrano[3,2-b]pyridin-4-yl-butane-1,4-diamine hydrochloride salt (Compound 107)

A slurry of (S)-(3,4-Dihydro-2H-pyrano[3,2-b]pyridin-4-yl)amine (1.14 g, 7.6 mmol) from above, 4-(1,3-dioxo-1,3-dihydro-isoindol-2-yl)-butyraldehyde (1.57 g, 7.2 mmol), and potassium carbonate (1.00 g, 7.2 mmol) in THF (15 mL) was stirred at room temperature for 1 h. The mixture was filtered through a glass-fritted funnel and the filter cake was washed with THF (15 mL). The combined filtrate was treated with sodium triacetoxyborohydride (4.7 g, 22 mmol) and the mixture was stirred for 1 h. The reaction was quenched with saturated sodium bicarbonate solution (150 mL) and stirred for 15 min. The layers were separated and the aqueous layer was extracted with dichloromethane (3×75 mL). The combined organic layers were dried over $Na_2SO_4$ and concentrated. Purification of the crude brown oil by column chromatography on silica gel (EtOAc) gave the desired secondary amine (2.25 g, 89%) as a white solid.

A slurry of the amine (2.25 g, 6.4 mmol) from above, N-boc-2-chloromethyl-benzimidazole (1.87 g, 7.0 mmol), diisopropylethylamine (1.8 mL, 10 mmol), potassium iodide (50 mg, 0.3 mmol), and acetonitrile (65 mL) was stirred at 50° C. under a nitrogen atmosphere for 40 h. The mixture was cooled to room temperature and concentrated. The resultant residue was dissolved in dichloromethane (75 mL), washed with saturated sodium bicarbonate solution (3×50 mL), and washed with brine (50 mL). The organic layer was dried over $Na_2SO_4$ and concentrated. Purification of the crude material by repetitive column chromatography on silica (first column: EtOAc, second column: 30:1 $CH_2Cl_2$/MeOH) provided the desired protected amine (2.97 g, 80%) as a pale yellow foamy solid.

To a stirred solution of the protected amine (2.97 g, 5.1 mmol) from above in ethanol (50 mL) was added hydrazine hydrate (2.5 mL, 50 mmol) and stirring was continued at room temperature for 66 h. The mixture was diluted with diethyl ether (50 mL). The resultant white slurry was filtered and concentrated. Purification of the crude material by column chromatography on silica gel (20:1:1 $CH_2Cl_2$/MeOH/$NH_4OH$) gave the desired amine (1.80 g, 100%) as a white foamy solid.

Following General Procedure D: Conversion of the free base (1.80 g, 5.1 mmol) from above to the hydrochloride salt gave COMPOUND 107 (2.14 g, 82%) as a white solid. $^1H$ NMR ($D_2O$) δ 1.49-1.60 (m, 4H), 2.39-2.49 (m, 2H), 2.52-2.63 (m, 1H), 2.78-2.91 (m, 3H), 4.32-4.42 (m, 1H), 4.48 (q, 2H, J=17.2 Hz), 4.65-4.72 (m, 2H), 7.56-7.7.63 (m, 2H), 7.76-7.85 (m, 3H), 7.97 (dd, 1H, J=8.7, 1.2 Hz), 8.39 (dd, 1H, J=5.7, 1.2 Hz); $^{13}C$ NMR ($D_2O$) δ 19.74, 24.95, 25.27, 39.48, 47.87, 51.46, 56.51, 67.41, 114.25(2), 126.92 (2), 127.50, 131.04, 134.66, 134.82, 138.84, 151.77, 155.74; ES-MS m/z 352 (M+H). Anal. Calcd. for C$_{20}$H$_{25}$N$_5$O.3.0HCl.2.5H$_2$O.0.1 (C$_2$H$_5$)$_2$O: C, 47.74; H, 6.68; N, 13.64; Cl, 20.72. Found: C, 47.74; H, 6.94; N, 13.33; Cl, 20.75.

The enantiomeric purity of COMPOUND 107 was determined to be 100% ee by chiral HPLC using the following conditions: Instrument: Hewlett Packard 1100 HPLC (VWD1); Column: ChiralCel OD, 0.46 cm×25 cm; Mobile Phases: A: 90:5:5 hexanes/reagent alcohol/methanol with 0.1% DEA, B: hexanes; Isocratic: 80% A, 20% B; Total Run Time: 25 min; Flow Rate: 1.0 mL/min; Temperature: 40° C.; Detector: UV @ 270 nm; Injection volume: 10 μL.

Retention time of the S enantiomer=12.0 min.
Retention time of the R enantiomer=15.2 min.

Example 108

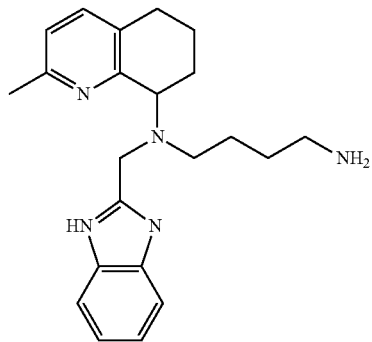 [SMILES: Cc1ccc2c(n1)C(N(CCCCN)Cc1nc3ccccc3[nH]1)CCC2]

Compound 108: N$^1$-(1H-Benzoimidazol-2-ylmethyl)-N$^1$-(2-methyl-5,6,7,8-tetrahydroquinolin-8-yl)-butane-1,4-diamine (hydrobromide salt)

Preparation of N-(2-methyl-5,6,7,8-tetrahydroquinolin-8-yl)acetamide

To a 3-neck, 500 mL round bottom flask containing a stir bar was added 2-methyl-8-acetamidoquinoline (5.69 g, 28.4 mmol) and platinum(IV) oxide (322 mg, 5 mol %). The flask was equipped with two Teflon cannulae: one for purging of the reaction flask with nitrogen gas and introduction of hydrogen, and the other leading to a flask connected to a bubbler. Trifluoroacetic acid (100 mL) was added to the reaction flask under an atmosphere of nitrogen. The stirred reaction mixture was flushed with nitrogen gas and warmed to 60° C. Hydrogen gas was bubbled through the stirred reaction for 3 h. The progress of the reaction was monitored by GC and/or TLC. The reaction mixture was cooled to room temperature, purged with nitrogen gas and the catalyst was filtered through a pad of Celite and washed with CH$_2$Cl$_2$ (100 mL). The solvent was removed in vacuo and the residue was basified with saturated NaOH (pH>14). The mixture was then extracted with CHCl$_3$ (3×250 mL). The organic extracts were dried (MgSO$_4$), filtered and concentrated. The crude material was purified by flash chromatography using 10% MeOH in EtOAc to provide the product (3.83 g, 66%) as a white solid. $^1$H NMR δ 1.57-1.66 (m, 1H), 1.77-1.86 (m, 2H), 2.02 (s, 3H), 2.44 (s, 3H), 2.43-2.57 (m, 1H), 2.68-2.73 (m, 2H), 4.67-4.74 (m, 1H), 6.79 (br s, 1H), 6.92 (d, 1H, J=8 Hz), 7.24 (d, 1H, J=8 Hz); $^{13}$C NMR δ 21.6, 25.4, 25.8, 29.6, 31.0, 53.0, 123.4, 131.4, 139.2, 155.9, 157.2, 172.2; ES-MS m/z: 227 (M+Na$^+$).

Preparation of 2-methyl-5,6,7,8-tetrahydroquinolin-8-ylamine

N-(2-Methyl-5,6,7,8-tetrahydroquinolin-8-yl)acetamide (4.51 g, 22.1 mmol) was dissolved in 6 N HCl (40 mL). The mixture was heated at reflux for 17 h. The reaction mixture was cooled to room temperature, basified with saturated NaOH (pH>14) and extracted with chloroform (5×100 mL). The organic extracts were dried (MgSO$_4$) and concentrated. The crude material was purified by distillation (bp 102-104° C. at 0.20 mm Hg) to yield the product as a clear liquid (3.25 g, 99%). $^1$H NMR (CDCl$_3$, 300 MHz) δ 1.62-1.82 (m, 2H), 1.84-2.00 (m, 3H), 2.11-2.20 (m, 1H), 2.49 (s, 3H), 2.61-2.82 (m, 2H), 3.93-4.00 (m, 1H), 6.91 (d, 1H, J=7.8 Hz), 7.25 (d, 1H, J=7.8 Hz); $^{13}$C NMR (CDCl$_3$) δ 20.4, 24.6, 29.1, 32.6, 51.8, 121.7, 128.6, 137.6, 155.9, 159.0; ES-MS m/z: 163 (M+H$^+$), 146 (M−NH$_2$).

Preparation of 2-[4-(2-methyl-5,6,7,8-tetrahydroquinolin-8-ylamino)-butyl]-isoindole-1,3-dione To a solution of 2-methyl-5,6,7,8-tetrahydroquinolin-8-ylamine (237 mg, 1.46 mmol) in CH$_2$Cl$_2$ (20 mL) at room temperature under inert atmosphere was added 4-(1,3-dioxo-1,3-dihydro-isoindol-2-yl)-butyraldehyde (159 mg, 0.731 mmol) followed by sodium triacetoxyborohydride (309 mg, 2.92 mmol). The reaction mixture was stirred at room temperature for 2 hours. Saturated sodium bicarbonate solution (10 mL) was added and the mixture was extracted with dichloromethane (3×20 mL). The combined organic extracts were washed with brine, dried (MgSO$_4$), filtered and concentrated. The resultant material was purified by column chromatography on silica gel (10:1:0.5 CH$_2$Cl$_2$: MeOH: NH$_4$OH) to provide the product as a yellow oil (210 mg, 79%): $^1$H NMR (CDCl$_3$): δ 1.56-1.83 (m, 6H), 1.90-2.04 (m, 2H), 2.04-2.18 (m, 2H), 2.47 (s, 3H), 2.64-2.80 (m, 4H), 3.70-3.76 (m, 3H), 6.90 (d, 1H, J=7.8 Hz), 7.24 (d, 1H, J=7.8 Hz), 7.69-7.73 (m, 2H), 7.81-7.85 (m, 2H).

Preparation of 2-{[[4-(1,3-dioxo-1,3-dihydro-isoindol-2-yl)-butyl]-(2-methyl-5,6,7,8-tetrahydroquinolin-8-yl)-amino]-methyl}-benzoimidazole-1-carboxylic acid tert-butyl ester To a solution of 2-[4-(2-methyl-5,6,7,8-tetrahydroquinolin-8-ylamino)-butyl]-isoindole-1,3-dione (210 mg, 0.578 mmol) in CH$_3$CN (12 mL) was added 2-chloromethyl-benzoimidazole-1-carboxylic acid tert-butyl ester (200 mg, 0.751 mmol), potassium iodide (14 mg), and diisopropylethylamine (0.201 ml, 1.16 mmol). The reaction mixture was stirred at 60° C. for 17 hours. Saturated sodium bicarbonate (15 mL) was added and the mixture was extracted with CH$_2$Cl$_2$ (3×30 mL). The combined organic extracts were dried (MgSO$_4$), filtered and concentrated. Purification of the crude material by column chromatography on silica gel (1:10 EtOAc:hexanes then EtOAc then 1:10 MeOH:EtOAc) provided the product as a clear oil (228 mg, 66%): $^1$H NMR (CDCl$_3$): δ 1.23-1.31 (m, 2H), 1.46-1.58 (m, 2H), 1.63-1.73 (m, 1H), 1.68 (s, 9H), 1.73-1.85 (m, 1H), 1.89-1.98 (m, 1H), 2.10-2.18 (m, 1H), 2.40 (s, 3H), 2.60-2.83 (m, 5H), 3.50 (t, 2H, J=7.2 Hz), 4.20 (dd, 1H, J=9.6, 6.0 Hz), 4.50 (d, 1H, J=15.6 Hz), 4.72 (d, 1H, J=15.6 Hz), 6.79 (d, 1H, J=7.5 Hz), 7.14 (d, 1H, J=7.5 Hz), 7.19-7.24 (m, 2H), 7.63-7.69 (m, 3H), 7.74-7.81 (m, 3H).

Preparation of N$^1$-(1H-Benzoimidazol-2-ylmethyl)-N$^1$-(2-methyl-5,6,7,8-tetrahydroquinolin-8-yl)-butane-1,4-diamine To a solution of 2-{[[4-(1,3-dioxo-1,3-dihydro-isoindol-2-yl)-butyl]-(2-methyl-5,6,7,8-tetrahydroquinolin-8-yl)-amino]-methyl}-benzoimidazole-1-carboxylic acid tert-butyl ester (228 mg, 0.384 mmol) in ethanol (10 mL) at room temperature was added hydrazine hydrate (0.10 mL). The mixture was stirred for 4 days. The mixture was concentrated in vaccuo and the resultant material was purified by column chromatography on silica gel (1:1:10 MeOH: NH$_4$OH: CH$_2$Cl$_2$) to provide the product as a colourless oil (82 mg, 59%): $^1$H NMR (CDCl$_3$) δ 1.25-1.45 (m, 4H), 1.60-1.70 (m, 1H), 1.81-1.93 (m, 1H), 1.97-2.04 (m, 1H), 2.10-2.18 (m, 1H), 2.46-2.56 (m, 3H), 2.62-2.82 (m, 6H), 3.95-3.99 (m, 1H), 4.00 (d, 1H, J=17.1 Hz), 4.09 (d, 1H, J=17.1 Hz), 6.98 (d, 1H, J=7.8 Hz), 7.15-7.21 (m, 2H), 7.30 (d, 1H, J=7.8 Hz), 7.57-7.60 (m, 2H).

Preparation of N$^1$-(1H-benzoimidazol-2-ylmethyl)-N$^1$-(2-methyl-5,6,7,8-tetrahydroquinolin-8-yl)-butane-1,4-diamine (hydrobromide salt) (Compound 108)

To a solution of N$^1$-(1H-benzoimidazol-2-ylmethyl)-N$^1$-(2-methyl-5,6,7,8-tetrahydroquinolin-8-yl)-butane-1,4-diamine (82 mg, 0.23 mmol) in glacial acetic acid (0.5 mL) was added HBr saturated acetic acid (1 mL). The reaction mixture was stirred for 10 minutes, then diethyl ether was added (50 mL). The white precipitate was allowed to settle and the solvent was removed with a pipette. Et$_2$O (50 mL) was again added then decanted. The resulting precipitate was dissolved in methanol (1.5 mL), ether was added (3×50 mL) then it was removed with a pipette. The resultant yellow powder was dried under reduced pressure to give 113 mg (76%) of the product: $^1$H NMR (D$_2$O) δ 1.48-1.63 (m, 4H), 1.65-1.78 (m, 1H), 1.82-2.01 (m, 1H), 2.02-2.15 (m, 1H), 2.25-2.31 (m, 1H), 2.50-2.63 (m, 1H), 2.67-2.78 (m, 4H), 2.78-3.00 (m, 4H), 4.39 (d, 1H, J=16.8 Hz), 4.49 (d, 1H, J=16.8 Hz), 7.52-7.64 (m, 3H), 7.70-7.79 (m, 2H), 8.13 (d, 1H, J=7.8 Hz); $^{13}$C NMR (D$_2$O) δ 19.7, 20.3, 20.5, 25.1, 27.4, 39.6, 47.7, 51.8, 60.1, 114.3, 126.9, 130.9, 137.6, 147.8, 150.0, 151.7, 152.8; ES-MS m/z 365 (M+H). Anal. Calcd. for C$_{17}$H$_{22}$N$_4$.3.0HBr.2.3H$_2$O: C, 40.80; H, 5.70; N, 10.81; Br 37.01. Found: C 40.78, H 5.82, N 10.54, Br 37.09.

Example 110

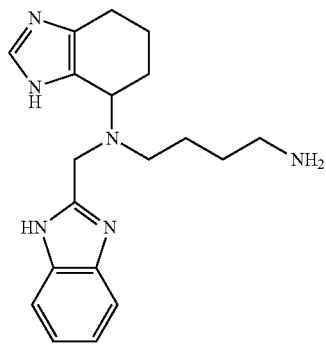 [SMILES: NCCCCN(Cc1nc2ccccc2[nH]1)C1CCCc2nc[nH]c21]

Compound 110: N1-(1H-Benzoimidazol-2-ylmethyl)-N1-(4,5,6,7-tetrahydro-3H-benzoimidazol-4-yl)-butane-1,4-diamine (hydrobromide salt)

Preparation of 4,5,6,7-tetrahydrorbenzoimidazol-4-one

Following a modified literature procedure (Helv. Chim. Acta 1979, 62, 497), N$_2$O$_4$ was bubbled into a heterogeneous mixture of 1,3-cyclohexanedione (6.98 g, 62.3 mmol) (recrystallized from benzene) in dry diethyl ether (500 mL) at 0° C. for about 10 minutes. The mixture was warmed to room temperature and N$_2$O$_4$ was further bubbled until the reaction mixture became homogenous and orange in colour. The mixture was stirred for 0.5 hr. Excess N$_2$O$_4$ was removed by bubbling argon gas and the solvent was removed on rotorvap to provide a dark orange oil which rapidly turned black.

Approximately half of this material was dissolved in glacial acetic acid (50 mL) in a Parr shaker flask. Freshly prepared formic acetic anhydride (50 mL) (prepared by mixing 50 mL of formic acid with 25 mL of acetic anhydride and stirring for 2 hours—J. Med. Chem. 2001, 44, 36-46) and ~2 g of palladium on carbon (10%) were added and the mixture was hydrogenated at 50 psi for 2 hrs. The volatiles were removed on high vacuum rotorvap and the $^1$H NMR of the crude material (5.2 g, black tar) contained a signal at δ 7.99 ppm (formylated amine product).

To the crude black oil was added 15 mL of formic acid and 60 mL formamide and the mixture was heated at 150° C. for 30 minutes. The volatiles were rotorvaped on high vacuum rotorvap (heated bath to 80° C.). Freshly prepared formic acetic anhydride (40 mL) and glacial acetic acid (20 mL) were added and the black mixture was heated at 100° C. for 1 hr. The volatiles were again removed using hagh vacuum. Repeated purification of the material by flash column chromatography (4:1:0.2 CH$_2$Cl$_2$:MeOH:NH$_4$OH) on silica gel provided 4,5,6,7-tetrahydrorbenzoimidazol-4-one (893 mg) contaminated with formamide and other impurities. $^1$H NMR (CDCl$_3$): δ 2.02 (p, 2H, J=6.3 Hz), 2.39 (t, 2H, J=6.3 Hz), 2.75 (t, 2H, J=6.3 Hz), 7.82 (s, 1H).

Preparation of 7-oxo-4,5,6,7-tetrahydrorbenzoimidazole-1-carboxylic acid tert-butyl ester This material (893 mg, 6.56 mmol) was treated with tert-butylanhydride (2.15 g, 9.84 mmol) in DMF (15 mL) and diisopropylethylamine (2.29 mL, 13.0 mL) at room temperature for 17 hours. The residue was dissolved in MeOH and EtOAc and was left in the fridge for 3 days. The solid which precipitated (2 recrystallizations) was clean 7-oxo-4,5,6,7-tetrahydrorbenzoimidazole-1-carboxylic acid tert-butyl ester (759 mg, 5.5% from 1,3-cyclohexanedione). $^1$H NMR (CDCl$_3$): δ 1.64 (s, 9H), 2.21 (m, 2H), 2.56 (dd, 2H, J=6.6, 6.3 Hz), 3.14 (dd, 2H, J=6.3, 6.0 Hz), 8.05 (s, 1H).

Preparation of 7-(4-tert-butoxycarbonylamino-butylamino)-4,5,6,7-tetrahydrobenzoimidazole-1-carboxylic acid tert-butyl ester To a solution of 7-oxo-4,5,6,7-tetrahydrorbenzoimidazole-1-carboxylic acid tert-butyl ester (632 mg, 2.82 mmol) in CH$_2$Cl$_2$ (50 mL) at room temperature under inert atmosphere was added (4-amino-butyl)carbamic acid tert-butyl ester (745 mg, 4.23 mmol) followed by sodium triacetoxyborohydride (896 mg, 4.23 mmol). The reaction mixture was stirred at room temperature for 17 hours. Saturated sodium bicarbonate solution (20 mL) was added and the mixture was extracted with dichloromethane (3×30 mL). The combined organic extracts were washed with brine, dried (MgSO$_4$), filtered and concentrated. The resultant material was purified by column chromatography on silica gel (20:1:1 CH$_2$Cl$_2$:MeOH:NH$_4$OH) to provide the product (558 mg, 48%); $^1$H NMR (CDCl$_3$): δ 1.42 (s, 9H), 1.59 (s, 9H), 1.50-1.62 (m, 4H), 1.71-1.77 (2H), 1.82-2.00 (m, 2H), 2.06 (s, 1H), 2.73-2.87 (m, 4H), 3.09-3.13 (m, 2H), 3.33 (br s, 1H), 3.75-3.80 (m, 1H), 5.01 (br s, 1H), 7.96 (s, 1H).

Preparation of 2-{[[4-tert-butoxycarbonylamino-butyl)-(3-tert-butoxylcarbonyl-4,5,6,7-tetrahydro-3H-benzamidazol-4-yl)-amino]-methyl}-benzoimidazole-1-carboxylic acid tert-butyl ester To a solution of 7-(4-tert-butoxycarbonylamino-butylamino)-4,5,6,7-tetrahydrobenzoimidazole-1-carboxylic acid tert-butyl ester (365 mg, 0.893 mmol) in CH$_3$CN (12 mL) was added 2-chloromethyl-benzoimidazole-1-carboxylic acid tert-butyl ester (357 mg, 1.33 mmol), potassium iodide (14 mg), and diisopropylethylamine (0.311 ml, 1.78 mmol). The reaction mixture was stirred at 40° C. for 17 hours. Saturated sodium bicarbonate (15 mL) was added and the mixture was extracted with CH$_2$Cl$_2$ (3×30 mL). The combined organic extracts were dried (MgSO$_4$), filtered and concentrated. Purification of the crude material by column chromatography on silica gel (diethyl ether saturated with ammonia) provided the product as a white foam (269 mg, 47%): $^1$H NMR (CDCl$_3$): δ 1.41 (s, 9H), 1.34-1.50 (m, 6H), 1.59 (s, 9H), 1.68 (s, 9H), 1.60-1.75 (m, 2H), 1.88 (s, 2H), 1.93-2.03 (m, 2H), 2.63-2.76 (m, 4H), 2.79-3.01 (m, 2H), 4.04-4.80 (m, 1H), 4.35 (d, 1H, J=16.2 Hz), 4.45 (d, 1H, J=16.2 Hz), 4.94-4.99 (m, 1H), 7.26-7.31 (m, 2H), 7.71-7.76 (m, 2H), 7.80-7.86 (m, 1H), 7.94 (s, 1H).

Preparation of N$^1$-(1H-benzoimidazol-2-ylmethyl)-N$^1$-(4,5,6,7-tetrahydro-3H-benzoimidazol-4-yl)-butane-1,4-diamine (hydrobromide salt) (Compound 110)

To a solution of 2-{[[4-tert-butoxycarbonylamino-butyl)-(3-tert-butoxycarbonyl-4,5,6,7-tetrahydro-3H-benzamidazol-4-yl)-amino]-methyl}-benzoimidazole-1-carboxylic acid tert-butyl ester (204 mg, 0.319 mmol) in glacial acetic acid (1.0 mL) was added HBr saturated acetic acid (1.5 mL). The reaction mixture was stirred for 30 minutes, then diethyl ether was added (50 mL). The white precipitate was allowed to settle and the solvent was removed with a pipette. Et$_2$O (50 mL) was again added then decanted. The resulting precipitate was dissolved in methanol (1 mL), ether was added (3×50 mL) then it was removed with a pipette. The resultant white powder was dried under reduced pressure to give 170 mg (78%) of COMPOUND 110: $^1$H NMR (D$_2$O) δ 1.45-1.67 (m, 4H), 1.67-1.86 (m, 2H), 2.06-2.21 (m, 2H), 2.50-2.66 (m, 3H), 2.74-2.78 (m, 1H), 2.79-2.89 (m, 2H), 4.26-4.40 (m, 3H), 7.55-7.60 (m, 2H), 7.75-7.80 (m, 2H), 8.54 (s, 1H); $^{13}$C NMR (D$_2$O) δ 20.3, 21.3, 22.0, 25.0, 25.6, 39.7, 47.3, 51.2, 55.4, 114.2, 126.9, 127.9, 130.9, 131.7, 132.8, 153.5; ES-MS m/z 339 (M+H). Anal. Calcd. for C$_{17}$H$_{22}$N$_4$.3.5HBr.2.1H$_2$O.0.3C$_4$H$_{10}$O: C, 35.59; H, 5.43; N, 12.33, Br 41.02. Found: C, 35.44; H, 5.35; N, 12.25, Br 41.26.

Example 111

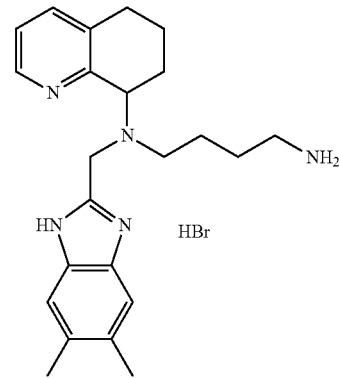 [SMILES: Cc1cc2nc(CN(CCCCN)C3CCCc4cccnc43)[nH]c2cc1C ; Br]

Compound 111: Preparation of N$^1$-(5,6-dimethyl-1H-benzimidazol-2-ylmethyl)-N$^1$-(5,6,7,8-tetrahydro-quinolin-8-yl)-butane-1,4-diamine (HBr salt)

To a stirred solution of 2-[4-(5,6,7,8-tetrahydro-quinolin-8-ylamino)-butyl]-isoindole-1,3-dione (154 mg, 0.441 mmol), diisopropylethylamine (0.15 mL, 0.861 mmol) and potassium iodide (15 mg, 0.090 mmol) in acetonitrile (2.5 mL) was added 2-chloromethyl-5,6-dimethyl-1H-benzimidazole (prepared according to the procedures described in Bridger et al. U.S. patent application U.S. Ser. No. 09/535,314) (77 mg, 0.426 mmol) and the mixture heated at 60° C. for 18 hours. The mixture was then concentrated and the residue diluted with CH$_2$Cl$_2$ (30 mL). The solution was washed with saturated aqueous NaHCO$_3$ (1×20 mL) and brine (2×15 mL). The combined aqueous phase was extracted with CH$_2$Cl$_2$ (1×15 mL). The combined organic phase was dried (Na$_2$SO$_4$), filtered and concentrated under reduced pressure to give a crude brown foam. The foam was purified by flash chromatography (1.75 cm ID, 12 g silica, 50:1:1 CH$_2$Cl$_2$:MeOH: NH$_4$OH) to give pure 2-{4-[(5,6-dimethyl-1H-benzimidazol-2-ylmethyl)-(5,6,7,8-tetrahydro-quinolin-8-yl)-amino]-butyl}-isoindole-1,3-dione (60 mg, 28%). $^1$H NMR (CDCl$_3$) δ 1.34-1.51 (m, 2H), 1.53-1.73 (m, 3H), 1.81-2.06 (m, 2H), 2.12-2.22 (m, 1H), 2.34 (s, 6H), 2.55-2.89 (m, 4H), 3.51 (t, 2H, J=7.3 Hz), 3.93-4.08 (m, 3H), 7.1 (dd, 1H, J=7.5, 4.8 Hz), 7.31-7.39 (m, 3H), 7.63-7.67 (m, 2H), 7.72-7.77 (m, 2H), 8.58 (d, 1H, J=4.0 Hz).

To a stirred solution of 2-{4-[(5,6-dimethyl-1H-benzimidazol-2-ylmethyl)-(5,6,7,8-tetrahydro-quinolin-8-yl)-amino]-butyl}-isoindole-1,3-dione (60 mg, 0.118 mmol) in ethanol (2.5 mL) was added hydrazine hydrate (0.05 mL, 1.03 mmol) and the mixture stirred at room temperature for 16 hours. The mixture was then diluted with diethyl ether, dried (MgSO$_4$), filtered and concentrated under reduced pressure to give a crude yellow oil. The oil was purified by flash chromatography (1.75 cm ID, 12 g silica, 10:1:1 CH$_2$Cl$_2$:MeOH: NH$_4$OH) to give pure N$^1$-(5,6-dimethyl-1H-benzimidazol-2-ylmethyl)-N$^1$-(5,6,7,8-tetrahydro-quinolin-8-yl)-butane-1,4-diamine (18 mg, 38%). $^1$H NMR (CDCl$_3$) δ 1.30-1.46 (m, 4H), 1.60-1.75 (m, 1H), 1.82-1.96 (m, 1H), 1.98-2.08 (m, 11$^{-1}$), 2.14-2.24 (m, 1H), 2.35 (s, 6H), 2.47-2.59 (m, 3H), 2.65-2.90 (m, 3H), 3.92-4.06 (m, 3H), 7.13 (dd, 1H, J=7.9, 4.8 Hz), 7.34 (s, 2H), 7.40 (d, 1H, J=7.1 Hz), 8.58 (s, 1H, J=3.5 Hz).

Following the standard HBr salting procedure D: N¹-(5,6-dimethyl-1H-benzimidazol-2-ylmethyl)-N¹-(5,6,7,8-tetrahydro-quinolin-8-yl)-butane-1,4-diamine (17 mg, 0.045 mmol) was converted to the HBr salt (28 mg, 97%). ¹H NMR (D₂O) δ 1.46-1.59 (m, 4H), 1.76-1.89 (m, 1H), 1.94-2.08 (m, 1H), 2.13-2.24 (m, 1H), 2.29-2.63 (m, 8H) containing 2.41 (s, 6H), 2.77-2.92 (m, 3H), 2.95-3.05 (m, 2H), 4.33 (d, 1H, J=16.2 Hz), 4.43-4.52 (m, 2H), 7.56 (s, 2H), 7.81-7.88 (m, 1H), 8.30-8.35 (m, 1H), 8.58-8.63 (m, 1H). ¹³C NMR (D₂O) δ 19.96, 20.38, 25.03, 25.38, 27.62, 39.50, 47.99, 51.72, 60.53, 113.72, 125.86, 129.54, 137.22, 139.31, 140.54, 147.98, 150.29, 151.36. ES-MS m/z 378 (M+H). Anal Calc. for $C_{23}H_{31}N_5 \cdot 3.0HBr \cdot 1.5H_2O$: C, 42.68; H, 5.76; N, 10.82; Br, 37.03. Found: C, 42.53; 14, 5.64; N, 10.59; Br, 37.32.

Example 112

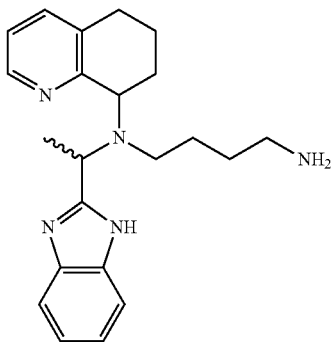 [SMILES: CC(c1nc2ccccc2[nH]1)N(CCCCN)C1CCCc2cccnc21]

Compound 112: Preparation of N¹-[1-(1H-Benzimidazol-2-yl)-ethyl]-N¹-(5,6,7,8-tetrahydro-quinolin-8-yl)-butane-1,4-diamine (hydrobromide salt)

Preparation of 1-(1H-Benzimidazol-2-yl)-ethanone

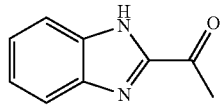

A solution of 1,2-phenylene diamine (3.25 g, 0.030 mol) and L-lactic acid (2.3 mL, 0.026 mol) in 3 M HCl (15 mL) was refluxed overnight. The reaction was cooled to room temperature, diluted with EtOAc (50 mL) and saturated aqueous Na₂CO₃ and solid Na₂CO₃ to pH 10. The aqueous phase was washed with EtOAc (1×50 mL) and the combined organic extracts dried (Na₂SO₄) and concentrated to afford a brown-orange solid which was used in the next reaction without further purification.

To a stirred solution of the crude alcohol from above (0.026 mol) in dry CH₂Cl₂/MeOH (6:1, 35 mL) was added activated manganese dioxide (85% purity, <5 micron, 23.28 g, 0.228 mol) and the suspension stirred overnight, at which point the black slurry was filtered through a cake of celite and washed with MeOH (3×50 mL). The combined washings were concentrated to afford a dark brown solid. Purification of the crude product by column chromatography on silica gel (CH₂Cl₂/MeOH, 98:2 to 95:5) afforded the title compound as a red-brown solid (1.65 g, 39%). ¹H NMR (CD₃OD) δ 2.72 (s, 3H), 7.37 (dd, 2H, J=6, 3 Hz), 7.66-7.73 (br m, 2H).

Using General Procedure B: To a solution of 8-amino-5,6,7,8-tetrahydroquinoline (266 mg, 1.80 mmol) in MeOH (5 mL) was added 1-(1H-benzimidazol-2-yl)-ethanone (285 mg, 1.78 mmol) and the resultant solution was stirred at room temperature for 4.5 h. Solid NaBH₄ (125 mg, 3.30 mmol) was added to the solution and the mixture was stirred at room temperature for 30 min. The resultant crude brown oil was purified by column chromatography on silica gel (CH₂Cl₂/MeOH, 98:2 then 96:4) to give the desired amine (125 mg, 24%) as a brown foam and mixture of diastereomers (6:1).

Following General Procedure B: To a stirred solution of the amine from above (mixture of diastereomers, 125 mg, 0.43 mmol) and 4-(1,3-Dioxo-1,3-dihydro-isoindol-2-yl)-butyraldehyde (97 mg, 0.45 mmol) in dry CH₂Cl₂ (5 mL) was added NaBH(OAc)₃ (127 mg, 0.59 mmol) and the mixture stirred at room temperature overnight. The resultant crude brown oil (215 mg) was purified by column chromatography on silica gel (CH₂Cl₂/MeOH, 98:2 then 96:4) to afford the desired amine (175 mg, 83%) as a brown foam.

To a solution of the phthalimide from above (175 mg, 0.355 mmol) in EtOH (3 mL) was added anhydrous hydrazine (0.06 mL, 1.89 mmol) and the mixture stirred overnight. The resultant white solid was filtered through filter paper, washing thoroughly with CH₂Cl₂ and the filtrate concentrated in vacuo. The crude product was purified by radial chromatography on silica gel (1 mm plate, CH₂Cl₂/MeOH/NH₄OH, 50:1:1 then 25:1:1) to give the desired free amine (67 mg, 52% 2 steps) as a pale yellow oil.

Using General Procedure D: Conversion of the material from above (67 mg, 0.18 mmol) to the hydrobromide salt gave COMPOUND 112 (95 mg, 78%) as a pale green solid. ¹H NMR (D₂O) mixture of diastereomers δ 1.37-1.55 (m, 4H), 1.81-1.85 (m, 1H), 1.83 (d, 3H, J=6.9 Hz), 2.05-2.16 (m, 3H), 2.69-2.74 (m, 1H), 2.85 (t, 2H, J=7.8 Hz), 2.86-3.00 (m, 3H), 4.52-4.57 (m, 1H), 4.79-4.85 (m, 1H, overlap with HOD), 7.61 (dd, 2H, J=6.3, 3.3 Hz), 7.79 (dd, 2H, J=6.3, 3.3 Hz), 7.84 (dd, 1H, J=7.5, 6 Hz), 8.31 (d, 1H, J=8.1 Hz), 8.60 (d, 1H, J=5.4 Hz); ¹³C NMR (D₂O) mixture of diastereomers δ 16.56, 20.64, 23.25, 25.19, 25.77, 27.47, 39.46, 48.19, 53.93, 58.37, 114.33, 125.82, 127.06, 130.91, 139.02, 140.22, 148.02, 152.36, 154.55. ES-MS m/z 364 (M+H). Anal. Calcd. for $C_{22}H_{29}N_5 \cdot 3.1HBr \cdot 0.9H_2O \cdot 0.4C_4H_{10}O$: C, 42.94; H, 5.79; N, 10.61; Br, 37.52. Found: C, 42.99; H, 5.58; N, 10.64; Br, 37.42.

Example 113

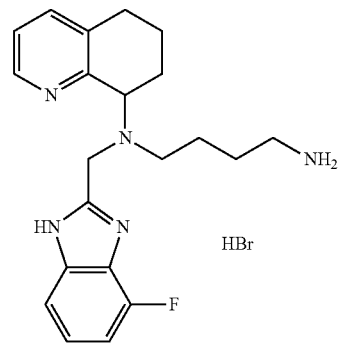 [SMILES: NCCCCN(Cc1nc2c(F)cccc2[nH]1)C1CCCc2cccnc21 ; Br]

Compound 113: Preparation of $N^1$-(4-fluoro-1H-benzimidazol-2-ylmethyl)-$N^1$-(5,6,7,8-tetrahydro-quinolin-8-yl)-butane-1,4-diamine (HBr salt)

To a stirred solution of 2-[4-(5,6,7,8-tetrahydro-quinolin-8-ylamino)-butyl]-isoindole-1,3-dione (146 mg, 0.418 mmol), diisopropylethylamine (0.15 mL, 0.861 mmol) and potassium iodide (14 mg, 0.084 mmol) in acetonitrile (2.5 mL) was added 2-chloromethyl-7-fluoro-1H-benzimidazole (prepared according to the procedures described in Bridger et al. U.S. Provisional Application 60/232,891 filed 15 Sep. 2000 and from Application 60/234,510 filed 22 Sep. 2000) (80 mg, 0.433 mmol) and the mixture heated at 60° C. for 18 hours. The mixture was then concentrated and the residue diluted with $CH_2Cl_2$ (30 mL). The solution was washed with brine (3×15 mL). The combined aqueous phase was extracted with $CH_2Cl_2$ (1×15 mL). The combined organic phase was dried ($Na_2SO_4$), filtered and concentrated under reduced pressure to give a crude brown foam. The foam was purified by flash chromatography (1.75 cm ID, 12 g silica, 50:1:1 $CH_2Cl_2$: MeOH: $NH_4OH$) to give pure 2-{4-[(4-fluoro-1H-benzimidazol-2-ylmethyl)-(5,6,7,8-tetrahydro-quinolin-8-yl)-amino]-butyl}-isoindole-1,3-dione (86 mg, 41%). $^1H$ NMR ($CDCl_3$) δ 1.33-1.76 (m, 5H), 1.85-2.10 (m, 3H), 2.14-2.25 (m, 1H), 2.54-2919 (m, 4H), 3.45-3.55 (m, 2H), 3.98-4.24 (m, 3H), 7.29-7.45 (m, 2H), 7.63-7.69 (m, 2H), 7.72-7.77 (m, 2H), 8.56-8.63 (m, 1H).

To a stirred solution of 2-{4-[(4-fluoro-1H-benzimidazol-2-ylmethyl)-(5,6,7,8-tetrahydro-quinolin-8-yl)-amino]-butyl}-isoindole-1,3-dione (86 mg, 0.173 mmol) in ethanol (2.0 mL) was added hydrazine hydrate (0.05 mL, 1.03 mmol) and the mixture stirred at room temperature for 20 hours. The mixture was then diluted with diethyl ether, dried ($MgSO_4$), filtered and concentrated under reduced pressure to give a crude yellow oil. The oil was purified by flash chromatography (1.75 cm ID, 12 g silica, 25:1:1 $CH_2Cl_2$: MeOH: $NH_4OH$) to give pure $N^1$-(4-fluoro-1H-benzimidazol-2-ylmethyl)-$N^1$-(5,6,7,8-tetrahydro-quinolin-8-yl)-butane-1,4-diamine (29 mg, 46%). $^1H$ NMR ($CDCl_3$) δ 1.28-1.47 (m, 4H), 1.63-1.77 (m, 1H), 1.85-2.09 (m, 2H), 2.15-2.25 (m, 1H), 2.46-2.60 (m, 3H), 2.65-2.76 (m, 2H), 2.79-2.91 (m, 1H), 4.01-4.18 (m, 3H), 6.89 (dd, 1H, J=10.3, 8.0 Hz), 7.05-7.11 (m, 1H), 7.12-7.18 (m, 1H), 7.35 (d, 1H, J=7.8 Hz), 7.43 (d, 1H, J=7.9 Hz), 8.59 (d, 1H, J=4.4 Hz).

Following the standard HBr salting procedure D: $N^1$-(4-fluoro-1H-benzimidazol-2-ylmethyl)-$N^1$-(5,6,7,8-tetrahydro-quinolin-8-yl)-butane-1,4-diamine (29 mg, 0.079 mmol) was converted to the HBr salt (40 mg, 79%). $^1H$ NMR ($D_2O$) δ 1.50-1.62 (m, 4H), 1.77-1.91 (m, 1H), 1.98-2.12 (m, 1H), 2.15-2.25 (m, 1H), 2.33-2.43 (m, 1H), 2.54-2.64 (m, 1H), 2.81-2.93 (m, 3H), 2.97-3.04 (m, 2H), 4.38 (d, 1H, J=16.7 Hz), 4.46-4.55 (m, 2H), 7.30-7.37 (m, 1H), 7.49-7.60 (m, 2H), 7.84 (dd, 1H, J=7.9, 6.1 Hz), 8.32 (d, 1H, J=8.0 Hz), 8.60 (d, 1H, J=5.6 Hz). $^{13}C$ NMR ($D_2O$) δ 20.37, 20.44, 25.01, 25.33, 27.61, 39.49, 48.39, 51.76, 60.64, 110.31, 111.57, 111.78, 125.81, 127.28, 127.38, 139.35, 140.44, 147.80, 149.83 (d, 1C, $J_{C-F}$=227.9 Hz), 151.35, 152.82. ES-MS m/z 368 (M+H). Anal Calc. for $C_{21}H_{26}N_5F$·3.0HBr·1.9$H_2O$: C, 39.14; H, 5.13; N, 10.87; F, 2.95; Br, 37.20. Found: C, 39.43; H, 4.99; N, 10.53; F, 2.86; Br, 37.02.

Example 114

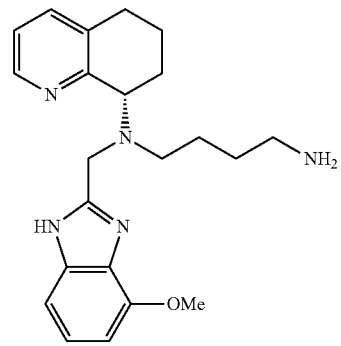 [SMILES: COc1cccc2[nH]c(CN(CCCCN)[C@H]3CCCc4cccnc43)nc12]

Compound 114: Preparation of $N^1$-(4-Methoxy-1H-benzoindiazol-2-ylmethyl)-$N^1$-(S)-(5,6,7,8-tetrahydro-quinolin-8-yl)-butane-1,4-diamine)hydrochloride salt)

Preparation of (S)-2-{[(4-Amino-butyl)-(5,6,7,8-tetrahydro-quinolin-8-yl)-amino]-methyl}-4-methoxy-benzoimidazole-1-carboxylic acid tert-butyl ester To a solution of (S)-2-[4-(5,6,7,8-tetrahydro-quinolin-8-ylamino)-butyl]-isoindole-1,3-dione (3.65 g, 10.46 mmol) in acetonitrile (52 ml) was added 2-chloromethyl-4-methoxy-benzoimidazole-1-carboxylic acid tert-butyl ester (3.10 g, 10.46 mmol), potassium iodide (87 mg, 0.52 mmol), and diisopropylethylamine (1.82 ml, 10.46 mmol). The mixture was stirred for 16 hours at 50° C. under a $N_2$ atmosphere. The mixture was concentrated, redissolved in methylene chloride (100 ml) and diluted with $H_2O$ (300 ml). The aqueous layer was extracted with methylene chloride (2×75 ml) and the combined organic extracts were dried ($Na_2SO_4$), filtered, and concentrated in vacuo to afford a dark orange oil. Purification via column chromatography on silica gel ($CH_2Cl_2$:MeOH: $NH_4OH$, 94:5:1, v/v/v) followed by a second purification by column chromatography on silica gel (ethyl acetate:$NH_4OH$, 98:2, v/v) afforded the product as a yellow oil (4.22 g, 66%). $^1H$ NMR ($CDCl_3$) δ 1.23 (m, 2H), 1.45 (m, 2H), 1.69 (s, 9H), 1.93 (m, 2H), 2.62 (m, 2H), 2.75 (m, 2H), 3.50 (t, 2H), 3.98 (s, 3H), 4.10 (m, 2H), 4.60 (m, 2H), 6.68 (dd, 1H, J=7.89, 2.19 Hz), 6.92 (m, 1H), 7.13 (m, 2H), 7.36 (dd, 1H, J=8.77, 2.63 Hz), 7.68 (m, 2H), 7.78 (m, 2H), 8.31 (m, 1H).

Preparation of N-(4-Methoxy-1H-benzoindiazol-2-ylmethyl)-N(5,6,7,8-tetrahydro-quinolin-8-yl)-butane-1,4-diamine To a solution of 2-{[(4-Amino-butyl)-(5,6,7,8-tetrahydro-quinolin-8-yl)-amino]-methyl}-4methoxy-benzoimidazole-1-carboxylic acid tert-butyl ester (4.22 g, 6.93 mmol) in ethanol (69 ml) was added hydrazine hydrate (1.09 ml, 34.65 mmol). The solution was stirred for 16 hours at room temperature under a $N_2$ atmosphere. A white precipitate formed. Diethyl ether (69 ml) was added to the mixture and the mixture stirred for 10 min. The mixture was filtered and concentrated. Purification via column chromatography on silica gel ($CH_2Cl_2$:MeOH:$NH_4OH$, 94:5:1, v/v/v) afforded the product as a yellow oil (2.60 g, 98%). $^1H$ NMR ($CDCl_3$) δ 1.35 (m, 4H), 1.93 (m, 6H), 2.68 (m, 5H), 4.06 (m, 5H), 6.63 (d, 1H, J=8.33 Hz), 7.15 (m, 3H), 7.43 (d, 1H, J=7.02 Hz), 8.60 (d, 1H, J=4.38 Hz)

Preparation of Compound 114

To a solution of N-(4-Methoxy-1H-benzoindiazol-2-ylmethyl)-N(5,6,7,8-tetrahydro-quinolin-8-yl)-butane-1,4-diamine dissolved in methanol (20 ml) was added HCl-saturated methanol (50 ml) and the mixture was stirred for 1 hour at room temperature under a $N_2$ atmosphere. The solution was added dropwise to diethyl ether (1.5 l) to yield a chunky white precipitate. The white solid was isolated via suction filtration under a steady stream of nitrogen, washed with diethyl ether and dried at 40° C. in vacuo overnight (4.32 g, 76%). $^1$H NMR ($D_2O$) δ 1.52 (m, 4H), 1.78 (m, 1H), 2.00 (m, 1H), 2.13 (m, 1H), 2.36 (m, 1H), 2.53 (m, 1H), 2.74 (m, 1H), 2.79 (m, 2H), 2.88 (m, 2H), 4.20 (s, 2H), 4.42 (t, 1H), 7.75 (d, 1H, J=7.89 Hz), 7.83 (dd, 1H, J=7.89, 5.70 Hz), 7.80 (d, 1H, J=8.33 Hz), 8.38 (m, 2H), 8.57 (d, 1H, J=5.70 Hz); $^{13}$C NMR δ ($D_2O$) 19.53, 20.12, 20.44, 25.11, 25.23, 27.64, 39.57, 51.18, 53.04, 59.60, 124.72, 125.79, 127.50, 139.29, 140.53, 147.21, 147.87, 151.71, 152.96, 155.00. ES-MS m/z 326 (M+H). Anal. Calcd. For $C_{20}H_{28}N_4$·3.91HCl·2.47$H_2O$: C, 46.95; H, 7.26; N, 10.95; Cl, 27.10. Found: C, 46.93; H, 7.32; N, 11.05; Cl, 27.11.

Example 115

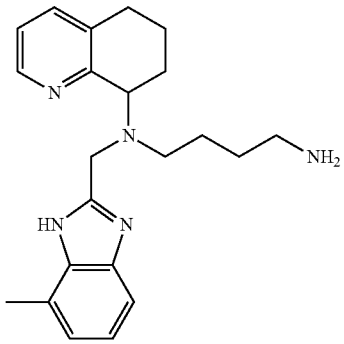 [SMILES: Cc1cccc2nc(CN(CCCCN)C3CCCc4cccnc43)[nH]c12]

Compound 115: $N^1$-(4-methyl-1H-benzoimidazol-2-ylmethyl)-$N^1$-(5,6,7,8-tetrahydro-quinolin-8-yl)-butane-1,4-diamine Preparation of 2-{-(4-methyl-1H-indol-2-ylmethyl)-(5,6,7,8-tetrahydro-quinolin-8-yl)-amino]-butyl}-isoindole-1,3-dione 2-[4-(5,6,7,8-Tetrahydro-quinolin-8-ylamino)-butyl]-isoindol-1,3-dione (95 mg, 0.27 mmol), 2-chloromethyl-4-methyl-1H-benzoimidazole (59 mg, 0.33 mmol), N,N-diisopropylethylamine (62 μL, 0.35 mmol), and potassium iodide (4 mg, 0.03 mmol) in acetonitril (5 mL) were heated at 60° C. overnight. The reaction mixture was cooled and the solvent was removed under reduced pressure to afford a brown oil. Purification by flash column chromatography on silica gel using $NH_4OH/CH_3OH/CH_2Cl_2$ (1:2:100) afforded the desired product as an orange foam (109 mg, 81%). $^1$H NMR (CDCl$_3$) δ 1.41-1.71 (m, 5H), 1.89-2.04 (m, 2H), 2.15-2.19 (m, 1H), 2.58-2.88 (m, 7H), 3.43-3.51 (m, 2H), 4.01-4.15 (m, 3H), 6.97 (d, 1H, J=7.2 Hz), 7.06-7.14 (m, 2H), 7.39 (d, 1H, J=7.5 Hz), 7.64 (br m, 2H), 7.71 (br m, 2H), 8.59 (d, 1H, J=4.2 Hz).

Preparation of $N^1$-(4-methyl-1H-benzoimidazol-2-ylmethyl)-$N^1$-(5,6,7,8-tetrahydro-quinolin-8-yl)-butane-1,4-diamine To a solution of the above amine (109 mg, 0.22 mmol) in ethanol (8 mL) was added hydrazine hydrate (54 μL, 1.10 mmol). The reaction mixture was stirred for 2 days at room temperature. Then the mixture was concentrated to dryness. Purification by radial chromatography on silica gel (1 mm plate, using $NH_4OH/CH_3OH/CH_2Cl_2$; 1:1:100→1:5:100, gradient elution) afforded the desired product as a yellow oil (45 mg, 56%). $^1$H NMR (CDCl$_3$) δ 1.29-1.45 (m, 4H), 1.66-1.71 (m, 1H), 1.91-2.05 (m, 2H), 2.17-2.21 (m, 1H), 2.47-2.55 (m, 3H), 2.64 (s, 3H), 2.67-2.74 (m, 2H), 2.80-2.90 (m, 1H), 4.02-4.18 (m, 3H), 6.98 (d, 1H, J=7.2 Hz), 7.07-7.16 (m, 2H), 7.40-7.51 (m, 2H), 8.58 (d, 1H, J=3.9 Hz).

Preparation of $N^1$-(4-methyl-1H-benzolimidazol-2-ylmethyl)-$N^1$-(5,6,7,8-tetrahydro-quinolin-8-yl)-butane-1,4-diamine (hydrobromide salt)

To a solution of the above amine (45 mg, 0.12 mmol) in acetic acid (3 mL) was added hydrobromic acid saturated acetic acid (2 mL) and the reaction mixture was stirred for 30 minutes. Then it was triturated with diethyl ether three times to afford a white solid. The solid was dissolved in methanol (1 mL) and was triturated with diethyl ether three times to afford COMPOUND 115 as a white solid (62 mg, 76%). $^1$H NMR ($D_2O$) δ 1.54 (m, 4H), 1.76-1.90 (m, 1H), 1.97-2.09 (m, 1H), 2.17-2.22 (m, 1H), 2.36-2.40 (m, 1H), 2.55-2.62 (m, 4H), 2.81-2.88 (m, 3H), 3.00-3.02 (m, 2H), 4.35-4.79 (m, 3H), 7.51 (ABq, 2H, J=62.7, 7.8 Hz), 7.79 (t, 1H, J=7.5 Hz), 7.86 (dd, 1H, J=7.5, 6.3 Hz), 8.34 (d, 1H, J=7.8 Hz), 8.61 (d, 1H, J=5.7 Hz). $^{13}$C NMR ($D_2O$) δ 16.44, 20.33, 20.45, 25.06, 25.39, 27.64, 39.52, 48.12, 51.75, 60.50, 111.46, 125.29, 125.89, 126.99, 127.30, 130.83, 139.26, 140.56, 148.02, 151.29, 151.38. ES-MS m/z 364 [M+H]$^+$. Anal. Calcd. for $C_{22}H_{29}N_5$·3.1HBr·2.3$H_2O$: C, 40.30; H, 5.64; N, 10.68; Br, 37.77. Found: C, 40.50; H, 5.56; N, 10.67; Br, 37.48.

Example 116

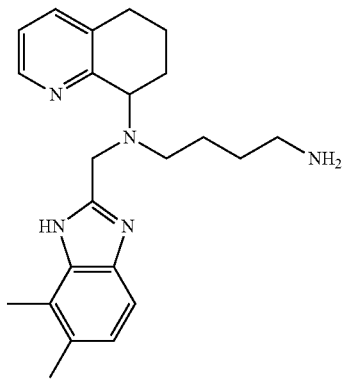 [SMILES: Cc1ccc2nc(CN(CCCCN)C3CCCc4cccnc43)[nH]c2c1C]

Compound 116: N¹-(4,5-dimethyl-1H-benzoimidazol-2-ylmethyl)-N¹-(5,6,7,8-tetrahydro-quionlin-8-yl)-butane-1,4-diamine (hydrobromide salt)

Preparation of {4-[(4,5-dimethyl-1H-benzoimidazol-2-ylmethyl)-(5,6,7,8-tetrahydro-quinolin-8-yl)-amino]-butyl}-carbamic acid tert-butyl ester 2-[4-(5,6,7,8-Tetrahydro-quinolin-8-ylamino)-butyl]-isoindol-1,3-dione (490 mg, 1.40 mmol), 2-chloromethyl-4,5-dimethyl-1H-benzoimidazole (328 mg, 1.68 mmol), N,N-diisopropylethylamine (0.32 mL, 1.82 mmol), and potassium iodide (23 mg, 0.14 mmol) in acetonitrile (5 mL) were stirred at 60° C. overnight. Then the reaction mixture was cooled and the solvent was removed under reduced pressure. Purification by flash column chromatography on silica gel using $NH_4OH$/$CH_3OH$/$CH_2Cl_2$ (2:1:97) afforded the product impurely as a brown oil (440 mg).

To a solution of the above amine (440 mg, 0.87 mmol) in ethanol (10 mL) was added hydrazine hydrate (0.21 mL, 4.33 mmol). The reaction mixture was stirred at room temperature overnight. Then the solvent was removed under reduced pressure and the orange solid was dried in vacuo. Purification by radial chromatography on silica gel (2 mm plate, using $NH_4OH.CH_3$—$OH$/$CH_2Cl_2$; 1:1:100→1:5:100, gradient elution) afforded partially pure product (183 mg) as a yellow oil.

To a solution of the above amine (183 mg, 0.49 mmol) in THF (10 mL) was added di-tert-butyl dicarbonate. The reaction mixture was stirred at room temperature for 1 hours. The solvent was removed under reduced pressure to afford a yellow oil. Purification by flash column chromatography on silica gel using $NH_4OH$/$CH_3OH$/$CH_2Cl_2$ (1:2:97) afforded the desired product as a yellow oil (67 mg, 29%). ¹H NMR ($CDCl_3$) δ 1.35-1.41 (m, 11H), 1.63-1.67 (m, 2H), 1.91-2.02 (m, 2H), 2.09-2.14 (m, 1H), 2.35 (s, 3H), 2.53 (s, 3H), 2.59-2.68 (m, 2H), 2.71-2.81 (m, 2H), 2.97-2.99 (m, 2H), 4.24 (dd, 1H, J=9.0, 6.0 Hz), 4.54 (q, 2H, J=14.7 Hz), 4.97 (br s, 1H), 6.93 (dd, 1H, J=7.7, 4.8 Hz), 7.05 (d, 1H, J=8.4 Hz), 7.22 (d, 1H, J=7.5 Hz), 7.18 (d, 1H, J=8.1 Hz), 8.36 (d, 1H, J=3.6 Hz).

Preparation of N¹-(4,5-dimethyl-1H-benzoimidazol-2-ylmethyl)-N¹-(5,6,7,8-tetrahydro-quinolin-8-yl)-butane-1,4-diamine (hydrobromide salt)

To a solution of the above amine (67 mg, 0.14 mmol) in acetic acid (3 mL) was added hydrobromic acid saturated acetic acid (2 mL) and the reaction mixture was stirred for 30 minutes. Then it was triturated with diethyl ether three times to afford a white solid. The solid was dissolved in methanol (1 mL) and was triturated with diethyl ether three times to afford COMPOUND 116 as a white solid (66 mg, 62%). ¹H NMR ($D_2O$) δ 1.54 (br m, 4H), 1.79-1.86 (m, 1H), 2.03 (q, 1H, J=12.9 Hz), 2.20 (br d, 1H, J=13.2 Hz), 2.36-2.43 (m, 4H), 2.47 (s, 3H), 2.52-2.60 (m, 1H), 2.81-2.88 (m, 3H), 3.00-3.03 (m, 2H), 4.33-4.79 (m, 3H), 7.46 (ABq, 2H, J=24.9, 8.4 Hz), 7.85 (dd, 1H, J=7.8, 6.0 Hz), 8.33 (d, 1H, J=7.8 Hz), 8.60 (d, 1H, J=5.1 Hz). ¹³C NMR ($D_2O$) δ 13.37, 18.87, 20.28, 20.43, 25.04, 25.36, 27.62, 39.50, 47.98, 51.75, 60.42, 110.75, 122.89, 125.85, 129.03, 131.47, 135.59, 139.22, 140.53, 147.97, 150.84, 151.38. ES-MS m/z 378 [M+H]⁺. Anal. Calcd. for $C_{23}H_{31}N_5$.3.0HBP.2.1$H_2O$: C, 41.98; H, 5.85; N, 10.64; Br, 36.42. Found: C, 41.95; H, 5.47; N, 10.39; Br, 36.17.

Example 117

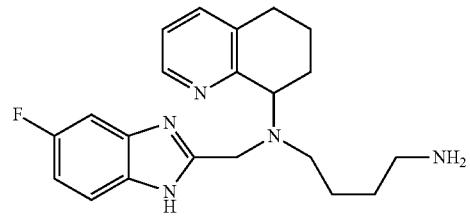 [SMILES: NCCCCN(Cc1nc2cc(F)ccc2[nH]1)C1CCCc2cccnc21]

Compound 117: Preparation of N¹-(6-Fluoro-1H-benzimidazol-2-ylmethyl)-N¹-(5,6,7,8-tetrahydro-quinolin-8-yl)-butane-1,4-diamine To a solution of 2-[4-(5,6,7,8-Tetrahydroquinolin-8-ylamino)-butyl]-isoindole-1,3-dione (0.17 g, 0.5 mmol), 2-Chloromethyl-5-fluoro-1H-benzimidazole (0.44 g, 1.7 mmol), and potassium iodide (5 mg, 0.02 mmol) in anhydrous acetonitrile (5.0 mL) was added diisopropylethylamine (0.13 mL, 0.73 mmol) and stirred at 60° C. for 16 hours. The mixture was then concentrated under reduced pressure and the residue partitioned between dichloromethane (20 mL) and brine (15 mL). The organic phase was separated and the aqueous phase was extracted with dichloromethane (2×15 mL). The combined organic phases were then dried ($Na_2SO_4$), filtered, and concentrated under reduced pressure to give a crude residue that was purified by column chromatography with silica gel (2:98 MeOH/$CH_2Cl_2$). This afforded 2-{4-[(6-Fluoro-1H-benzimidazol-2-ylmethyl)-(5,6,7,8-tetrahydroquinolin-8-yl)-amino]-butyl}-isoindole-1,3-dione as an orange solid (0.17 g, 71%).

A solution of the above compound (0.15 g, 0.3 mmol) in anhydrous ethanol (3 mL) was treated with hydrazine monohydrate (0.15 mL, 3.0 mmol) and stirred for 16 h. The white mixture was then filtered, concentrated under reduced pressure, and purified by column chromatography with silica gel (4:1:95 methanol:ammonium hydroxide:dichloromethane) to give COMPOUND 117 as a pale yellow solid (0.070 g, 58%). ¹H NMR ($CDCl_3$) δ 1.41 (br, 4H), 1.68 (m, 1H), 1.89 (q, 1H, J=7.2 Hz), 2.02 (m, 1H), 2.21 (m, 1H), 2.53 (br, 3H), 2.71 (m, 2H), 2.82 (m, 1H), 4.03 (m, 3H), 6.93 (t, 1H, J=8.4 Hz), 7.13 (t, 1H, J=6.0 Hz), 7.25 (br, 1H), 7.41 (d, 1H, J=7.8 Hz), 7.49 (m, 1H), 8.57 (d, 4.5 Hz). ¹³C NMR ($CDCl_3$) δ 21.75, 23.00, 26.30, 29.51 (2C), 41.12, 49.69, 51.00, 62.10, 101.63 (br, 1C), 110.24 (d, 1C, J=25.52 Hz), 115.72 (br, 1C), 122.62, 135.11 (2C), 137.91, 146.73, 147.02, 156.83, 157.93, 159.20 (d, 1C, J=281.69 Hz). ES-MS m/z 368 (M+H). Anal. Calcd. for $C_{21}H_{26}N_5F.0.5CH_2Cl_2$: C, 62.99; H, 6.64; N, 17.08. Found: C, 63.39; H, 6.88; N, 16.77.

Example 118

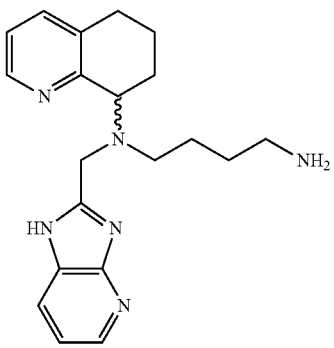 [SMILES: NCCCCN(Cc1nc2ncccc2[nH]1)C1CCCc2cccnc21]

Compound 118: Preparation of N¹-(1H-imidazo[4,5-b]pyridin-2-ylmethyl)-N¹-(5,6,7,8-tetrahydro-quinolin-8-yl)-butane-1,4-diamine (hydrobromide salt)

Preparation of 1-(2-trimethylsilanyl-ethoxymethyl)-1H-imidazo[4,5-b]pyridine-2-carbox-aldehyde (prepared as described by Whitten, J. P.; Matthews, D. P.; McCarthy, J. R. *J. Org. Chem.* 1986, 51, 1891-1894)

To a solution of 4-azabenzimidazole (605 mg, 5.08 mmol) in DMF (10 mL) under nitrogen was added DIPEA (1.3 mL, 7.5 mmol) followed by SEMCl (1.1 mL, 6.2 mmol). The reaction was stirred at 80° C. for 2 hours and, once cooled to room temperature, was poured into brine (20 mL) and diluted with EtOAc (30 mL). The layers were separated and the aqueous solution was extracted with EtOAc (15 mL×2). The combined organic solution was dried (MgSO₄), filtered and concentrated under reduced pressure. Purification through a short silica plug (CH₂Cl₂/MeOH, 9:1) gave the SEM-protected benzimidazole as an orange oil (984 mg, 77%).

A solution of this material (132 mg, 0.527 mmol) in THF (1.5 mL) was cooled to −78° C. under nitrogen and t-BuLi (1.7 M in pentane, 0.33 mL, 0.56 mmol) was added slowly. The resulting dark red solution was warmed to 0° C. and stirred for 10 minutes, before the addition of DMF (0.10 mL, 1.3 mmol). The reaction was stirred at room temperature for an additional 17 hours, then was quenched by the addition of saturated aqueous NH₄Cl (10 mL). The mixture was extracted with EtOAc (15 mL×2), and the organic solution was dried (MgSO₄), filtered and concentrated under reduced pressure. Purification by flash column chromatography on silica (hexane/EtOAc, 4:1, then 1:1) gave the aldehyde as a yellow oil (43.2 mg, 0.156 mmol, 30%). $^1$H NMR (CDCl₃) δ −0.09 (s, 9H), 0.91 (t, 2H, J=8.3 Hz), 3.63 (t, 2H, J=8.3 Hz), 6.08 (s, 2H), 7.39 (dd, 1H, J=8.4, 4.8 Hz), 8.24 (dd, 1H, J=8.4, 1.2 Hz), 8.62 (dd, 1H, J=4.8, 1.2 Hz), 10.11 (s, 1H).

Preparation of 2-(4-{(5,6,7,8-tetrahydro-quinolin-8-yl)-[1-(2-trimethylsilanyl-ethoxy-methyl)-1H-imidazo[4,5-b]pyridin-2-ylmethyl]-amino}-butyl)-isoindole-1,3-dione A solution of the aldehyde (43.2 mg, 0.156 mmol) and 2-[4-(5,6,7,8-tetrahydro-quinolin-8-ylamino)-butyl]-isoindole-1,3-dione (63 mg, 0.18 mmol) in CH₂Cl₂ (1 mL) was stirred at room temperature under nitrogen for 35 minutes, then NaBH(OAc)₃ (53 mg, 0.25 mmol) was added. The reaction was stirred for an additional 17.5 hours, then was diluted with CH₂Cl₂ (5 mL) and washed with 1M NaOH (2 mL×2) and brine (2 mL). The organic solution was dried (MgSO₄), filtered and concentrated under reduced pressure. Purification by flash column chromatography on silica (CH₂Cl₂/MeOH/NH₄OH, 33:1:0.2) gave the tertiary amine as a light yellow foam (74.2 mg, 0.121 mmol, 78%). $^1$H NMR (CDCl₃) δ −0.13 (s, 9H), 0.81 (dd, 2H, J=9.3, 7.2 Hz), 1.35-1.48 (m, 2H), 1.53-1.72 (m, 3H), 1.87-2.03 (m, 2H), 2.05-2.16 (m, 1H), 2.55-2.64 (m, 2H), 2.72-2.82 (m, 2H), 146-3.56 (m, 4H), 4.03 (dd, 1H, J=9.3, 6.6 Hz), 4.18 (d, 1H, J=13.8 Hz), 4.41 (d, 1H, J=13.5 Hz), 6.03 (d, 1H, J=10.8 Hz), 6.11 (d, 1H, J=10.8 Hz), 6.94 (dd, 1H, J=7.7, 4.7 Hz), 7.15 (dd, 1H, J=7.8, 4.8 Hz), 7.23 (d, 1H, J=7.5 Hz), 7.66-7.71 (m, 2H), 7.76-7.80 (m, 2H), 7.92 (dd, 1H, J=8.1, 1.2 Hz), 8.30 (dd, 1H, J=4.7, 1.4 Hz), 8.40 (d, 1H, J=3.3 Hz).

Preparation of N¹-(1H-imidazo[4,5-b]pyridin-2-ylmethyl)-N¹-(5,6,7,8-tetrahydro-quinolin-8-yl)-butane-1,4-diamine A solution of the phthalimide (74.2 mg, 0.121 mmol) and hydrazine monohydrate (0.06 mL, 1.2 mmol) in EtOH (1.5 mL) was heated at reflux under nitrogen for 1 hour. The excess solvent was then removed under reduced pressure. The residue was taken up into saturated aqueous NaHCO₃ (5 mL) and extracted with CH₂Cl₂ (10 mL×3). The combined organic solution was dried (Na₂SO₄), filtered and concentrated under reduced pressure, giving the crude primary amine as a colourless oil (55 mg, 95%).

To a solution of this material in CH₂Cl₂ (1.5 mL) was added TFA (0.5 mL) and the reaction was stirred at room temperature under nitrogen for 3 hours. The excess solvent was removed under reduced pressure, the residue was taken up into saturated aqueous NaHCO₃ (10 mL) and the mixture was extracted with CH₂Cl₂ (10 mL×3). The combined organic solution was dried (Na₂SO₄), filtered and concentrated under reduced pressure. Purification by flash column chromatography on silica (CH₂Cl₂/MeOH/NH₄OH, 9:1:0.1) gave the free base as an off-white foam (23 mg, 0.066 mmol, 58%). $^1$H NMR (CDCl₃) δ 1.27-1.50 (m, 4H), 1.61-1.78 (m, 1H), 1.84-1.96 (m, 1H), 1.98-2.10 (m, 1H), 2.14-2.26 (m, 1H), 2.44-2.61 (m, 3H), 2.65-2.91 (m, 3H), 4.03-4.15 (m, 3H), 5.09 (br. s, 2H), 7.11-7.15 (m, 2H), 7.41 (d, 1H, J=7.8 Hz), 7.88 (d, 1H, J=8.1 Hz), 8.32 (d, 1H, J=4.8 Hz), 8.65 (d, 1H, J=4.2 Hz).

Preparation of Compound 118

A solution of the amine (22.5 mg, 0.064 mmol) and saturated HBr in HOAc (0.5 mL) in glacial HOAc (1.0 mL) was stirred at room temperature for 30 minutes. Et₂O (5 mL) was added and the suspension was stirred for 5 minutes before the excess solvent was removed by pipette. The precipitate was washed with Et₂O (~2 mL×5), then dried under reduced pressure giving COMPOUND 118 as an off-white powder (35.4 mg, 0.053 mmol, 83%). $^1$H NMR (D₂O) δ 1.45-1.65 (m, 4H), 1.72-1.89 (m, 1H), 1.94-2.08 (m, 1H), 2.12-2.23 (m, 1H), 2.27-2.42 (m, 1H), 2.52-2.64 (m, 1H), 2.77-2.92 (m, 3H), 2.94-3.04 (m, 2H), 4.32 (d, 1H, J=16.8 Hz), 4.42 (d, 1H, J=16.8 Hz), 4.46 (dd, 1H, J=9.9, 6.0 Hz), 7.73-7.84 (m, 2H), 8.30 (d, 1H, J=7.8 Hz), 8.55-8.63 (m, 3H). $^{13}$C NMR (D₂O) δ 20.4, 20.5, 25.1, 25.3, 27.6, 39.6, 49.7, 51.5, 60.4, 119.9, 125.7, 129.4, 137.3, 139.2, 140.4, 146.9, 147.6, 151.9, 161.3. ES-MS m/z 351 (M+H). Anal. Calcd. for C₂₀H₂₆N₆·3.2HBr·1.5H₂O·0.7C₂H₄O₂: C, 38.52; H, 5.29; N, 12.60; Br 38.32. Found: C, 38.54; H, 5.00; N, 12.63; Br 38.25.

Example 119

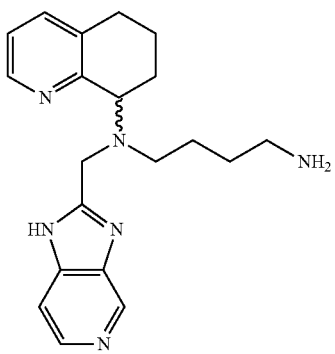 [SMILES: NCCCCN(Cc1nc2cnccc2[nH]1)C1CCCc2cccnc21]

Compound 119: Preparation of $N^1$-(1H-imidazo[4,5-c]pyridin-2-ylmethyl)-$N^1$-(5,6,7,8-tetrahydro-quinolin-8-yl)-butane-1,4-diamine (hydrobromide salt)

To a solution of 5-azabenzimidazole (460 mg, 3.86 mmol) in DMF (8 mL) under nitrogen was added DIPEA (1.0 mL, 5.7 mmol), followed by SEMCl (0.82 mL, 4.6 mmol). The reaction was stirred at 80° C. for 2 hours, then was cooled to room temperature, poured into brine (20 mL) and diluted with EtOAc (30 mL). The layers were separated and the aqueous solution was extracted with EtAOc (15 mL×2). The organic solution was washed with brine (5 mL×3), dried (MgSO$_4$), filtered and concentrated under reduced pressure. Purification by flash column chromatography on silica (CH$_2$Cl$_2$/MeOH, 9:1) gave the SEM-protected benzimidazole as an approximately 1:1 mixture of the two regioisomers (811 mg, 84%).

A solution of this material (802 mg, 3.22 mmol) in THF (10 mL) was cooled to −78° C. under nitrogen and t-BuLi (1.7M in pentane, 2.0 mL, 3.4 mmol) was slowly added. The solution was warmed to 0° C. and stirred for 20 minutes, before the addition of DMF (0.60 mL, 7.7 mmol). The reaction was stirred for an additional 15 hours, while slowly warming to room temperature. Saturated aqueous NH$_4$Cl (25 mL) was added and the mixture was extracted with EtOAc (25 mL×2). The combined organic solution was dried (MgSO$_4$), filtered and concentrated under reduced pressure. Attempted purification by flash column chromatography on silica (CH$_2$Cl$_2$/MeOH, 19:1) gave the aldehyde as a mixture containing starting material, DMF and some other unidentified species. This material was used as is in the reductive amination.

This material and 2-[4-(5,6,7,8-tetrahydro-quinolin-8-ylamino)-butyl]-isolindole-1,3-dione (74 mg, 0.21 mmol) were stirred in CH$_2$Cl$_2$ (1.5 mL) for 25 minutes, then NaBH(OAc)$_3$ (61 mg, 0.29 mmol) was added. The reaction was stirred for 16 hours, then was diluted with CH$_2$Cl$_2$ (5 mL) and washed with 1M NaOH (2 mL×2) and brine (5 mL). The organic solution was dried (MgSO$_4$), filtered and concentrated under reduced pressure. Purification by flash column chromatography on silica (CH$_2$Cl$_2$/MeOH/NH$_4$OH, 49:1:0.25) gave the tertiary amine as an approximately 55% by weight mixture with the SEM-protected azabenzimidazole (140 mg, 0.126 mmol, 4% from the SEM-protected 5-azabenzimidazole).

A solution of this material and hydrazine monohydrate (0.06 mL, 1.2 mmol) in EtOH (1.5 mL) was heated at reflux under nitrogen for 1 hour. The excess solvent was evaporated under reduced pressure and the residue was taken up into saturated aqueous NaHCO$_3$ (5 mL) and extracted with CH$_2$Cl$_2$ (10 mL×3). The combined organic solution was dried (Na$_2$SO$_4$), filtered and concentrated under reduced pressure. Purification by flash column chromatography on silica (CH$_2$Cl$_2$/MeOH/NH$_4$OH, 9:1:0.05, then MeOH) gave the primary amine as a light yellow foam (2:1 mixture of regioisomers, δ0.1 mg, 0.083 mmol, 66%).

To a solution of this material in CH$_2$Cl$_2$ (1 mL) was added TFA (0.1 mL, 1.3 mmol) and the reaction was stirred at room temperature under nitrogen for 3.5 hours. The solution was diluted with saturated aqueous NaHCO$_3$ (10 mL) and was extracted with CH$_2$Cl$_2$ (10 mL×3). The combined organic solution was dried (Na$_2$SO$_4$), filtered and concentrated under reduced pressure. Purification by flash column chromatography on silica (CH$_2$Cl$_2$/MeOH/NH$_4$OH, 9:1:0.1) gave the free base as a white foam (10.1 mg, 0.029 mmol, 35%).

To a solution of the free base in HOAc (0.5 mL) was added a solution of saturated HBr in HOAc (0.25 mL) and the reaction was stirred at room temperature for 20 minutes. The solution was diluted with Et$_2$O (4 mL) and the solvent was removed by pipette. The precipitate was washed with Et$_2$O (~2 mL×5), then dried under reduced pressure, giving COMPOUND 119 as a white powder (14.9 mg, 0.022 mmol, 75%). $^1$H NMR (D$_2$O) δ 1.48-1.67 (m, 4H), 1.72-1.88 (m, 1H), 1.96-2.08 (m, 1H), 2.12-2.22 (m, 1H), 2.28-2.40 (m, 1H), 2.53-2.65 (m, 1H), 2.79-3.02 (m, 5H), 4.29 (d, 1H, J=16.4 Hz), 4.39 (d, 1H, J=16.4 Hz), 4.44 (dd, 1H, J=11.1, 6.0 Hz), 7.81 (dd, 1H, J=8.1, 6.0 Hz), 8.11 (d, 1H, J=6.6 Hz), 8.29 (d, 1H, J=7.8 Hz), 8.50 (d, 1H, J=6.9 Hz), 8.59 (d, 1H, J=5.4 Hz), 9.16 (s, 1H). $^{13}$C NMR (D$_2$O) δ 20.4, 20.5, 25.0, 25.2, 27.6, 39.6, 49.6, 51.4, 60.2, 111.6, 125.6, 132.7, 133.9, 138.3, 139.2, 140.3, 147.5, 152.1, 162.5. ES-MS m/z 351 (M+H). Anal. Calcd. for C$_{20}$H$_{26}$N$_6$·3.3HBr·1.2C$_2$H$_4$O$_2$: C, 39.02; H, 4.98; N, 12.19; Br 38.24. Found: C, 38.90; H, 5.03; N, 12.50; Br 38.10.

Example 120

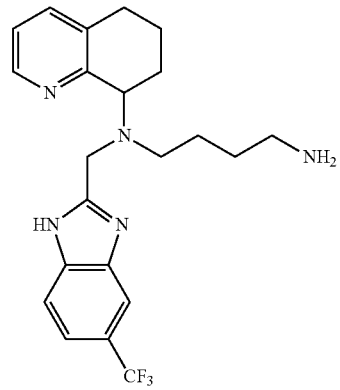 [SMILES: NCCCCN(Cc1nc2cc(C(F)(F)F)ccc2[nH]1)C1CCCc2cccnc21]

Compound 120: $N^1$-(5-trifluoromethyl-1H-benzoimidazol-2-ylmethyl)-$N^1$-(5,6,7,8-tetrahydro-quinolin-8-yl)-butane-1,4-diamine (hydrobromide salt)

Preparation of 2-{4-[(5,6,7,8-tetrahydro-quinolin-8-yl)-(5-trifluoromethyl-1H-benzoimidazol-2-ylmethyl)-amino]-butyl}-isoindole-1,3-dione 2-[4-(5,6,7,8-tetrahydro-quinolin-8-ylamino)-butyl]-isoindol-1,3-dione (160 mg, 0.46 mmol) and 2-chloromethyl- 6-trifluoromethyl-1H-benzoimidazole (129 mg, 0.55 mmol), N,N-diisopropylethylamine (100 μL, 0.60 mmol), and potassium iodide (8 mg, 0.05 mmol) in acetonitrile were stirred at 40° C. for 3 days. Then the reaction mixture was cooled and the solvent was removed under reduced pressure to afford a red oil. Purification by flash column chromatography on silica gel using NH$_4$OH/CH$_3$OH/CH$_2$Cl$_2$ (1:2:97) afforded the product as an orange foam (190 mg, 76%). $^1$H NMR (CDCl$_3$) δ 1.37-1.45 (m, 5H), 1.56-1.70 (m, 2H), 2.18-2.20 (m, 1H), 2.57-2.61 (m, 1H), 2.72-2.80 (m, 3H), 3.49-3.54 (m, 2H), 3.98-4.16 (m, 3H), 7.13-7.15 (m, 1H), 7.40-7.45 (m, 2H), 7.62-7.74 (m, 5H), 7.86 (br m, 1H), 8.62 (br m, 1H).

Preparation of 2-{[(4-amino-butyl)-(5,6,7,8-tetrahydro-quinolin-8-yl)-amino]-methyl}-5-trifluoromethyl-benzoimidazole-1-carboxylic acid tert-butyl ester To a solution of the above amine (190 mg, 0.35 mmol) in ethanol (10 mL) was added hydrazine hydrate (80 μL, 1.74 mmol). The reaction mixture was stirred overnight at room temperature and then the solvent was removed under reduced pressure. Purification by radial chromatography on silica gel (1 mm plate, using NH$_4$OH/CH$_3$OH/CH$_2$Cl$_2$; 1:1:100→1:4:100, gradient elution) afforded the product partially clean as a yellow oil (140 mg).

To a solution of the above amine (140 mg, 0.34 mmol) in THF (10 mL) was added di-tert-butyl dicarbonate (146 mg, 0.67 mmol). The reaction mixture was stirred for 1 hour and the solvent was removed under reduced pressure to yield a yellow oil. Purification by radial chromatography on silica gel (1 mm plate, using NH$_4$OH/CH$_3$OH/CH$_2$Cl$_2$; 1:1:100) afforded the desired product as a yellow oil (34 mg, 19% over two steps). $^1$H NMR (CDCl$_3$) δ 1.45-1.48 (m, 9H), 1.68-1.76 (m, 1H), 1.92 (q, 1H, J=12.3 Hz), 2.02-2.07 (m, 1H), 2.18-2.22 (m, 1H), 2.31 (br s, 1H), 2.51-2.60 (m, 1H), 2.60-2.72 (m, 2H), 2.75-2.91 (m, 3H), 4.03 (t, 1H, J=6.3 Hz), 4.10 (d, 1H, J=11.4 Hz), 4.48 (br t, 1H), 7.17 (dd, 1H, J=7.2, 4.8 Hz), 7.44 (d, 2H, J=8.1 Hz), 7.56 and 7.73 (d, total 1H, J=7.2 Hz), 7.79 and 7.94 (s, total 1H), 8.59 (s, 1H).

Preparation of N$^1$-(5-trifluoromethyl-1H-benzoimidazol-2-ylmethyl)-N$^1$-(5,6,7,8-tetrahydro-quinolin-8-yl)-butane-1,4-diamine (hydrobromide salt)

To a solution of the above amine (34 mg, 0.07 mmol) in acetic acid (2 mL) was added hydrobromic acid saturated acetic acid (2 mL) and the reaction mixture was stirred for 30 minutes. Then it was triturated with diethyl ether five times to afford COMPOUND 120 as a white solid (29 mg, 60%). $^1$H NMR (D$_2$O) δ 1.55 (br s, 4H), 1.83-1.86 (m, 1H), 2.05 (q, 1H, J=11.6 Hz), 2.17-2.21 (m, 1H), 2.37 (br s, 1H), 2.57-2.59 (m, 1H), 2.88 (br s, 3H), 3.00-3.01 (m, 2H), 4.37-4.59 (m, 3H), 7.82-7.93 (m, 3H), 8.17 (s, 1H), 8.32 (d, 1H, J=7.5 Hz), 8.62 (d, 1H, J=5.4 Hz). $^{13}$C NMR (D$_2$O) δ ES-MS m/z 418 [M+H]$^+$. Anal. Calcd. for C$_{22}$H$_{26}$N$_5$F$_3$.3.0HBr.2.0H$_2$O: C, 37.95; H, 4.78; N, 10.06; Br, 34.43. Found: C, 37.86; H, 4.61; N, 9.89; Br, 34.71.

Example 121

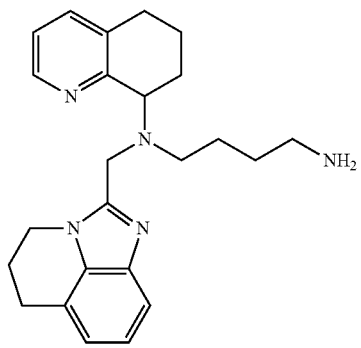 [SMILES: NCCCCN(Cc1nc2cccc3c2n1CCC3)C1CCCc2cccnc21]

Compound 121: N$^1$-(5,6-dihydro-4H-imidazo[4,5,1-ij]quinolin-2-ylmethyl)-N$^1$-(5,6,7,8-tetrahydro-quinolin-8-yl)-butane-1,4-diamine (hydrobromide salt)

Preparation of 2-{4-[(5,6-dihydro-4H-imidazo[4,5,1-ij]quinolin-2-ylmethyl)-(5,6,7,8-tetrahydro-quinolin-8-yl)-amino]-butyl}-isoindole-1,3-dione To a solution of 2-methyl-5,6-dihydro-4H-imidazol[4,5,1-ij]quinoline (497 mg, 2.67 mmol) in dioxane/water (10 mL:1 mL) was added selenium (IV) oxide (326 mg, 2.94 mmol). The reaction mixture was heated to 110° C. overnight. Then the mixture was cooled and the solvent was removed in vacuo to afford a dark brown solid. Purification by flash column chromatography on silica gel using 2% CH$_3$OH/CH$_2$Cl$_2$ afforded the product as a yellow oil (180 mg), which was used without further purification.

To a solution of the above crude aldehyde (180 mg, 0.97 mmol) and 2-[4-(5,6,7,8-tetrahydro-quinolin-8-ylamino)-butyl]-isoindol-1,3-dione (372 mg, 1.06 mmol) in CH$_2$Cl$_2$ (10 mL) was added sodium triacetoxyborohydride (410 mg, 1.93 mmol). The reaction mixture was stirred at room temperature for 3 days. Then the solvent was removed under reduced pressure to afford a yellow oil. Purification by flash column chromatography on silica gel using 2% CH$_3$OH/CH$_2$Cl$_2$ afforded the product as a yellow oil (135 mg, 27%). $^1$H NMR (CDCl$_3$) 1.42-1.47 (m, 2H), 1.56-1.63 (m, 2H), 1.93-1.96 (m, 2H), 2.06-2.07 (m, 2H), 2.22 (t, 2H, J=6.0 Hz), 2.60-2.67 (m, 3H), 2.70 (m, 1H), 2.95 (t, 2H, J=6.0 Hz), 3.56 (t, 2H, J=6.0 Hz), 4.01 (t, 1H, J=6.0 Hz), 4.16 (ABq, 2H, J=42.0, 15.0 Hz), 4.29-4.35 (m, 1H), 4.51 (br s, 1H), 4.58-4.66 (m, 1H), 6.94 (d, 1H, J=7.2 Hz), 7.01-7.06 (m, 1H), 7.09 (t, 1H, J=8.1 Hz), 7.29 (d, 1H, J=7.5 Hz), 7.47 (d, 1H, J=8.1 Hz), 7.68-7.70 (m, 2H), 7.78-7.81 (m, 2H), 8.41 (d, 1H, J=3.9 Hz).

Preparation of 2-{4-[(5,6-dihydro-4H-imidazo[4,5,1-ij]quinolin-2-ylmethyl)-(5,6,7,8-tetrahydro-quinolin-8-yl)-amino]-butyl}-isoindole-1,3-dione To a solution of the above amine (135 mg, 0.26 mmol) in ethanol (10 mL) was added hydrazine hydrate (63 μL, 1.30 mmol). The reaction mixture was stirred overnight. Then the solvent was removed under reduced pressure to afford a yellow oil. Purification by radial chromatography on silica gel (1 mm plate, using NH$_4$OH/CH$_3$OH/CH$_2$Cl$_2$; 1:1:100→1:6:100, gradient elution) afforded the product as a yellow oil (47 mg, 46%). ¹H NMR (CDCl₃) δ 1.30-1.47 (m, 4H), 1.67-1.69 (m, 2H), 1.86-2.00 (m, 4H), 2.08-2.10 (m, 1H), 2.21 (t, 2H, J=6.0 Hz), 2.54-2.69 (m, 4H), 2.74-2.79 (m, 1H), 2.95 (t, 2H, J=6.0 Hz), 4.08 (ABq, 2H, J=38.1, 9.6 Hz), 4.04-4.10 (m, 1H), 4.27-4.31 (m, 1H), 4.54-4.60 (m, 1H), 6.95 (d, 1H, J=7.2 Hz), 7.02 (dd, 1H, J=7.7, 4.5 Hz), 7.10 (t, 1H, J=7.2 Hz), 7.32 (d, 1H, J=7.5 Hz), 7.48 (d, 1H, J=8.1 Hz), 8.46 (d, 1H, J=4.5 Hz).

Preparation of N¹-(5,6-dihydro-4H-imidazo[4,5,1-ij]quinolin-2-ylmethyl)-N¹-(5,6,7,8-tetrahydro-quinolin-8-yl)-butane-1,4-diamine To a solution of the above amine (47 mg, 0.12 mmol) in acetic acid (3 mL) was added a hydrobromide saturated acetic acid (2 mL). The reaction mixture was stirred for 30 minutes. Then it was triturated with diethyl ether three times. The pale yellow solid was dried in vacuo, re-dissolved in methanol (1 mL), and triturated with diethyl ether three times. The resulting solid was dried in vacuo overnight (54.7 mg, 68%). ¹H NMR (D₂O) δ 1.55 (br s, 4H), 1.76-1.90 (m, 1H), 2.15 (q, 1H, J=17.4 Hz), 2.30-2.32 (m, 1H), 2.33-2.42 (m, 3H), 2.52-2.59 (m, 1H), 2.80-2.88 (m, 3H), 3.01-3.09 (m, 4H), 4.34-4.58 (m, 5H), 7.38 (d, 1H, J=7.2 Hz), 7.50-7.61 (m, 2H), 7.85 (dd, 1H, J=7.5, 6.0 Hz), 8.34 (d, 1H, J=7.8 Hz), 8.61 (d, 1H, J=6.0 Hz). ¹³C NMR (D₂O) δ 20.43, 22.12, 23.04, 25.05, 25.45, 27.68, 39.50, 43.86, 46.85, 51.94, 60.59, 111.29, 123.82, 125.92, 126.19, 127.36, 129.06, 139.36, 140.64, 148.09, 149.50, 151.30. ES-MS m/z 390 [M+H]⁺. Anal. Calcd. for C₂₄H₃₁N₅.3.0HBr.2.1H₂O: C, 43.02, H, 5.75; N, 10.45; Br, 35.77. Found: C, 42.86; H, 5.75; N, 10.49; Br, 35.88.

Example 122

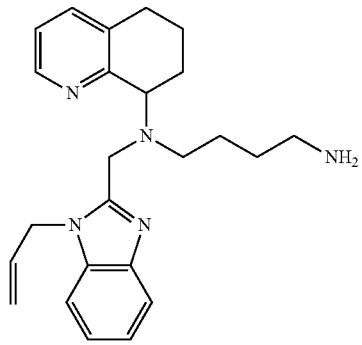 [SMILES: C=CCn1c(CN(CCCCN)C2CCCc3cccnc32)nc2ccccc21]

Compound 122: N¹-(1-allyl-1H-benzoimidazol-2-ylmethyl)-N¹-(5,6,7,8-tetrahydro-quinolin-8-yl)-butane-1,4-diamine (hydrobromide salt)

Preparation of (1-allyl-1H-benzoimidazol-2-yl)-methanol

To a solution of (1H-benzoimidazol-2-yl)-methanol (501 mg, 3.38 mmol) and allyl bromide (0.29 mL, 3.38 mmol) in DMF (15 mL) was added N,N-diisopropylethylamine (0.71 mL, 4.06 mmol). The reaction mixture was stirred at 60° C. overnight. Then the mixture was cooled to room temperature and quenched with saturated NaHCO₃ (25 mL). Then it was extracted with CH₂Cl₂ (3×25 mL). The combined organic layer was washed with brine (2×25 mL), dried (MgSO₄), filtered, concentrated, and dried in vacuo to afford a brown oil. Purification by flash column chromatography on silica gel using 2% CH₃OH/CH₂Cl₂ afforded the product as a yellow oil (180 mg, 28%). ¹H NMR (CDCl₃) δ 4.85 (br s, 5H), 4.98 (d, 1H, J=17.1 Hz), 5.17 (d, 1H, J=10.5 Hz), 5.88-6.01 (m, 1H), 7.20-7.26 (m, 3H), 7.66 (t, 1H, J=3.9 Hz).

Preparation of 1-allyl-1H-benzoimidazole-2-carbaldehyde

To a solution of the above alcohol (180 mg, 0.96 mmol) in CH₂Cl₂ (10 mL) was added manganese (IV) oxide (831 mg, 9.56 mmol). The reaction mixture was stirred for 4 hours. Then the mixture was filtered through a layer of celite and the filtrate was concentrated to dryness to afford a yellow oil (158 mg, 88%). ¹H NMR (CDCl₃) δ 5.02 (d, 2H, J=15.0 Hz), 5.16-5.27 (m, 2H), 5.96 (br s, 1H), 7.39-7.44 (m, 3H), 7.92 (d, 1H, J=6.0 Hz), 10.09 (s, 1H).

Preparation of 2-{4-[(1-allyl-1H-benzoimidazol-2-ylmethyl)-(5,6,7,8-tetrahydro-quinolin-8-yl)-amino]-butyl}-isoindole-1,3-dione To a solution of the above aldehyde (158 mg, 0.85 mmol) and 2-[4-(5,6,7,8-tetrahydro-quinolin-8-ylamino)-butyl]-isoindol-1,3-dione (326 mg, 0.93 mmol) in CH₂Cl₂ (10 mL) was added sodium triacetoxyborohydride (360 mg, 1.70 mmol). The reaction mixture was stirred overnight. Then the solvent was removed under reduced pressure to afford a yellow foam. Purification by flash column chromatography on silica gel using NH₄OH/CH₃OH/CHCl₂ (0:2:98→1:2:98) to afford the product as a yellow oil (165 mg, 37%), which was used without further purification.

The above amine (165 mg, 0.32 mmol) in concentrated H₂SO₄ (2 mL)/water (20 mL) was refluxed overnight. Then the reaction was cooled and basified to pH=11 with 10 N NaOH. Then it was extracted with CHCl₃ (5×25 mL). The organic layer was dried (Na₂SO₄), filtered, concentrated, and dried in vacuo to afford a yellow oil. Purification by radial chromatography on silica gel (1 mm plate, using NH₄OH/CH₃OH/CH₂Cl₂; 1:1:100→1:6:100) to afford the product as a yellow oil (23 mg, 19%). ¹H NMR (CDCl₃) δ 1.23-1.46 (m, 4H), 1.65-1.70 (m, 1H), 1.93-2.10 (m, 3H), 2.53 (t, 2H, J=6.9 Hz), 2.62 (t, 2H, J=7.8 Hz), 2.68-2.70 (m, 1H), 2.75-2.80 (m, 1H), 4.03-4.13 (m, 3H), 4.81 (d, 1H, J=18.0 Hz), 5.02-5.09 (m, 2H), 5.47 (dm, 1H, J=16.2 Hz), 5.84-5.96 (m, 1H), 7.02 (dd, 1H, J=7.5, 4.8 Hz), 7.18-7.24 (m, 2H), 7.29-7.33 (m, 3H), 7.67-7.72 (m, 1H), 8.46 (d, 1H, J=4.2 Hz).

Preparation of N¹-(1-allyl-1H-benzoimidazol-2-ylmethyl)-N¹-(5,6,7,8-tetrhaydro-quinolin-8-yl)-butane-1,4-diamine (hydrobromide salt)

To a solution of the above amine (23 mg, 0.06 mmol) in acetic acid (3 mL) was added hydrobromide saturated acetic acid (2 mL). The reaction mixture was stirred for 30 minutes. Then it was triturated with diethyl ether five times to afford COMPOUND 122 as a cream-coloured solid, which was dried in vacuo for three days. ¹H NMR (D₂O) δ 1.54 (s, 4H), 1.74-1.88 (m, 1H), 2.05 (q, 1H, J=10.5 Hz), 2.17-2.22 (m, 1H), 2.39-2.43 (m, 1H), 2.54-2.59 (m, 1H), 238-2.88 (m, 3H), 3.01 (br d, 2H, J=4.8 Hz), 4.49 (dd, 1H, J=10.8, 5.7 Hz), 4.50 (ABq, 2H, J=57.5, 17.7 Hz), 5.09-5.14 (m, 3H), 5.35 (d, 1H, J=10.2 Hz), 6.01-6.14 (m, 1H) 7.61-7.67 (m, 2H), 7.80-7.89 (m, 3H), 8.35 (d, 1H, J=7.8 Hz), 8.63 (d, 1H, J=5.7 Hz). ¹³C NMR (D₂O) δ 20.42, 25.03, 25.47, 27.69, 39.50, 47.43, 47.62, 52.00, 60.90, 113.16, 114.52, 119.04, 125.95, 126.94, 127.31, 130.34, 130.57, 132.81, 139.37, 140.65, 148.13, 151.09, 151.68. ES-MS m/z 390 [M+H]⁺. Anal. Calcd. for C$_{24}$H$_{31}$N$_5$.3.0HBr.2.0H$_2$O: C, 43.13; H, 5.73; N, 10.48; Br, 35.87. Found: C, 43.09; H, 5.60; N, 10.28; Br, 36.08.

Example 123

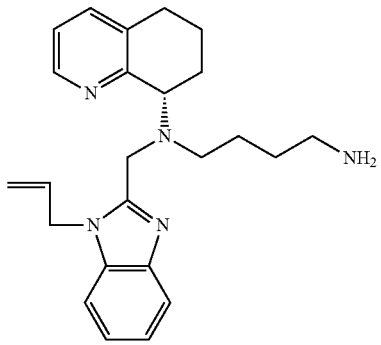 [SMILES: C=CCn1c(CN(CCCCN)[C@H]2CCCc3cccnc32)nc2ccccc21]

Compound 123: Preparation of N$^1$-(1-Allyl-1H-benzimidazol-2-ylmethyl)-N$^1$-(S)-5,6,7,8-tetrahydroquinolin-8-yl-butane-1,4-diamine (hydrochloride salt)

Preparation of N-(5,6,7,8-Tetrahydro-quinolin-8-yl)-butane-1,4-diamine

To a solution of 2-[4-(5,6,7,8-tetrahydro-quinolin-8-ylamino)-butyl]-isoindole-1,3-dione (15.0 g, 42.98 mmol) dissolved in ethanol (215 ml) was added hydrazine hydrate (13.4 ml). The solution was stirred for 16 hours at room temperature under a N$_2$ atmosphere. A white precipitate formed. Diethyl ether (215 ml) was added and the mixture was stirred for 10 min then filtered and concentrated. Purification via column chromatography on silica gel (CH$_2$Cl$_2$:MeOH:NH$_4$OH, 96:3:1, v/v/v) afforded the product as a brown oil (6.77 g, 74%). $^1$H NMR (CDCl$_3$) δ 1.57 (m, 9H), 2.05 (m, 2H), 2.75 (m, 6H), 3.78 (t, 1H), 7.06 (dd, 1H, J=7.89, 4.82 Hz), 7.37 (d, 1H, J=7.89 Hz), 8.39 (d, 1H, J=4.82 Hz).

Preparation of [4-(5,6,7,8-Tetrahydro-quinolin-8-ylamino)-butyl]-carbamic acid tert-butyl ester To a solution of N-(5,6,7,8-tetrahydro-quinolin-8-yl)-butane-1,4-diamine (6.77 g, 30.9 mmol) in tetrahydrofuran (155 ml) was added slowly triethylamine (4.30 ml, 30.9 mmol) and Boc-ON (7.60 g, 30.9 mmol). The mixture was stirred for 72 hours at room temperature under a N$_2$ atmosphere. The mixture was concentrated and purified by column chromatography on silica gel (CH$_2$Cl$_2$:MeOH:NH$_4$OH, 96:3:1, v/v/v). A second purification by column chromatography on silica gel (ethyl acetate) afforded the product as a brown oil (8.03 g, 80%). $^1$H NMR (CDCl$_3$) δ 1.43 (s, 9H), 1.60 (s, 4H), 1.78 (m, 2H), 1.99 (m, 2H), 2.78 (m, 5H), 3.15 (m, 2H), 3.77 (t, 1H), 4.87 (s, 1H), 7.07 (dd, 1H, J=7.45, 4.82 Hz), 7.83 (d, 1H, J=7.89 Hz), 8.38 (d, 1H, J=4.38 Hz).

Preparation of {4-[1-Allyl-1H-benzoimidazol-2-ylmethyl)-(5,6,7,8-tetrahydro-quinolin-8-yl)-amino]-butyl}-carbamic acid tert-butyl ester To a solution of [4-(5,6,7,8-tetrahydro-quinolin-8-ylamino)-butyl]-carbamic acid tert-butyl ester (5.12 g, 16.04 mmol) in tetrahydrofuran (80 ml) was added 1-allyl-1H-benzoimidazole-2-carbaldehyde (3.0 g, 16.04 mmol) and potassium carbonate (2.22 g, 16.04 mmol). The mixture was stirred for 1 hour then filtered, concentrated and diluted with methylene chloride (80 ml). Sodium triacetoxyborohydride (6.80 g, 32.08 mmol) was added and the mixture was stirred for 16 hours at room temperature under a N$_2$ atmosphere. The reaction mixture was quenched with a solution of saturated aqueous NaHCO$_3$ (100 ml). Extract with methylene chloride (2×100 ml). The combined organic extracts were dried (Na$_2$SO$_4$), filtered, and concentrated in vacuo to afford a brown oil. Purification via column chromatography on silica gel (CH$_2$Cl$_2$:MeOH:NH$_4$OH, 96:3:1, v/v/v) afforded the product as a white foam (4.64 g, 74%). $^1$H NMR (CDCl$_3$) δ 1.41 (s, 1H), 1.63 (s, 3H), 1.99 (m, 3H), 2.36 (m, 3H), 2.99 (m, 2H), 4.01 (s, 2H), 4.13 (m, 1H), 4.80 (m, 2H), 5.07 (m, 2H), 5.40 (d, 1H, J=18 Hz), 5.91 (m, 1H), 7.02 (dd, 1H, J=7.45, 4.82 Hz), 7.31 (m, 4H), 7.71 (m, 1H), 8.47 (d, 1H, J=3.95 Hz).

Preparation of Compound 123

To a solution of {4-[1-Allyl-1H-benzoimidazol-2-ylmethyl)-(5,6,7,8-tetrahydro-quinolin-8-yl)-amino]-butyl}-carbamic acid tert-butyl ester (5.84 g, 15.01 mmol) in methanol (20 ml) was added HCl-saturated methanol (40 ml) and the mixture stirred for 1.5 hours at room temperature under a N$_2$ atmosphere. The solution was added dropwise to diethyl ether (1.5 l) to yield a chunky white precipitate. The white solid was isolated via suction filtration under a steady stream of nitrogen, washed with diethyl ether and dried at 40° C. in vacuo overnight (4.92 g, 73%). $^1$H NMR (D$_2$O) δ 1.56 (s, 4H), 1.81 (m, 1H), 2.07 (m, 2H), 2.41 (m, 2H), 2.89 (m, 2H), 3.54 (m, 2H), 4.49 (m, 3H), 5.10 (m, 3H), 5.37 (d, 1H, J=10.52 Hz), 6.08 (m, 1H), 7.63 (m, 1H), 7.88 (m, 3H), 8.37 (d, 1H, J=8.33 Hz), 8.67 (d, 1H, J=5.26 Hz); $^{13}$C NMR (D$_2$O) δ 13.47, 19.30, 23.92, 24.36, 26.58, 38.41, 46.36, 46.52, 50.85, 59.76, 65.34, 112.09, 113.34, 118.0, 124.88, 125.87, 126.29, 129.19, 131.60, 138.27, 139.55, 147.09, 149.90, 150.56. ES-MS m/z 390 (M+H). Anal. Calcd. For (C$_{24}$H$_{31}$N$_5$)2.87(HCl)1.51(H$_2$O)0.47(C$_4$H$_{10}$O): C, 55.91; H, 7.54; N, 12.60; Cl, 18.27. Found: C, 55.91; H, 7.55; N, 12.60; Cl, 18.27.

Example 124

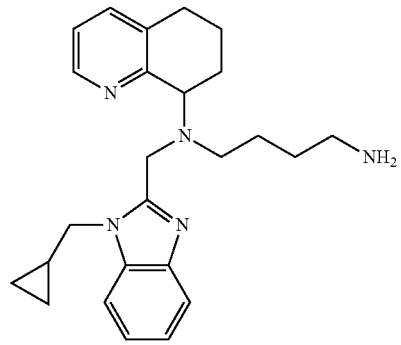 [SMILES: NCCCCN(Cc1nc2ccccc2n1CC1CC1)C1CCCc2cccnc21]

Compound 124: N$^1$-(1-cyclopropylmethyl-1H-benzoimidazol-2-ylmethyl)-N$^1$-(5,6,7,8-tetrahydroquinolin-8-yl)-butane-1,4-diamine (hydrobromide salt)

Preparation of (1-cyclopropylmethyl-1H-benzoimidazol-2-yl)-methanol

To a solution of (bromomethyl)cyclopropane (0.39 mL, 4.02 mmol) and (1H-benzoimidazol-2-yl)-methanol (596 mg, 4.02 mmol) in DMF (10 mL) was added N,N-diisopropylethylamine (0.84 mL, 4.82 mmol). The reaction mixture was stirred at 60° C. for 3 days. Then it was cooled to room temperature and quenched with saturated NaHCO$_3$ (15 mL) and the phases were separated. The aqueous phase was washed with CH$_2$Cl$_2$ (3×20 mL). Then the combined organic layers were washed with brine (2×30 mL), dried (MgSO$_4$), filtered, concentrated, and dried in vacuo to afford a dark brown oil. Purification by flash column chromatography on silica gel using 2% CH$_3$OH/CH$_2$Cl$_2$ afforded the product as a yellow solid (210 mg, 26%). $^1$H NMR (CDCl$_3$) δ 0.40-0.45 (m, 2H), 0.52-0.61 (m, 2H), 1.22-1.33 (m, 1H), 4.13 (d, 2H, J=6.6 Hz), 4.88 (s, 2H), 7.22-7.24 (m, 2H), 7.36-7.38 (m, 1H), 7.66-7.69 (m, 1H).

Preparation of 1-cyclopropylmethyl-1H-benzoimidazole-2-carbaldehyde

To a solution of the above alcohol (210 mg, 1.05 mmol) in CH$_2$Cl$_2$ (15 mL) was added manganese (IV) oxide (910 mg, 10.50 mmol). The reaction mixture was stirred overnight. Then it was filtered through a layer of celite and the filtrate was concentrated to dryness to afford a brown oil (160 mg, 76%), which was used without further purification. $^1$H NMR (CDCl$_3$) δ 0.43-0.48 (m, 2H), 0.50-0.58 (m, 2H), 1.33-1.38 (m, 1H), 4.54 (d, 2H, J=9.0 Hz), 7.38-7.53 (m, 3H), 7.95 (d, 1H, J=9.0 Hz), 10.12 (s, 1H).

Preparation of 2-{4-[(1-cyclopropylmethyl-1H-benzoimidazol-2-ylmethyl)-(5,6,7,8-tetrahydro-quinolin-8-yl)-amino]butyl}-isoindole-1,3-dione To a solution of the above aldehyde (160 mg, 0.80 mmol) and 2-[4,5,6,7,8-tetrahydro-quinolin-8-ylamino)-butyl]-isoindol-1,3-dione (307 mg, 0.88 mmol) in CH$_2$Cl$_2$ (10 mL) was added sodium triacetoxyborohydride (339 mg, 1.60 mmol). The reaction mixture was stirred overnight. Then the solvent was removed under reduced pressure to afford a yellow oil. Purification by flash column chromatography on silica gel using 2% CH$_3$OH/CH$_2$Cl$_2$ afforded the product as a yellow oil (332 mg, 79%). $^1$H NMR (CDCl$_3$) δ 0.17-0.22 (m, 1H), 0.28-0.33 (m, 1H), 1.04-1.06 (m, 1H), 1.38-1.45 (m, 2H), 1.51-1.65 (m, 3h), 1.96-2.06 (m, 3H), 2.58-2.64 (m, 3H), 2.77-2.81 (m, 1H), 3.52 (t, 2H, J=7.5 Hz), 4.04-4.09 (m, 3H), 4.18-4.25 (m, 1H), 4.48-4.55 (m, 1H), 6.96 (dd, 1H, J=7.5, 4.8 Hz), 7.14-7.20 (m, 2H), 7.25-7.34 (m, 2H), 7.63-7.69 (m, 3H), 7.70-7.80 (m, 2H), 8.44 (d, 1H, J=3.3 Hz).

Preparation of N$^1$-(1-cyclopropylmethyl-1H-benzoimidazol-2-ylmethyl)-N$^1$-(5,6,7,8-tetrahydro-quinolin-8-yl)-butane-1,4-diamine To a solution of the above amine (332 mg, 0.62 mmol) in ethanol (15 mL) was added hydrazine hydrate (0.15 mL, 3.11 mmol). The reaction mixture was stirred overnight. Then the solvent was removed under reduced pressure to afford a pale yellow oil. Purification by radial chromatography on silica gel (2 mm plate; using NH$_4$OH/CH$_3$OH/CH$_2$Cl$_2$; 1:3:100→1:7:100; gradient elution) afforded the desired product as a yellow oil (168 mg, 67%). $^1$H NMR (CDCl$_3$) δ 0.21-0.23 (m, 1H), 0.28-0.31 (m, 1H), 0.42-0.47 (m, 2H), 1.09-1.12 (m, 1H), 1.32-1.41 (m, 3H), 1.65-1.73 (m, 1H), 1.95-2.05 (m, 3H), 2.52-2.61 (m, 3H), 2.70-2.73 (m, 1H), 2.75-2.81 (m, 3H), 3.66 (s, 2H), 4.03-4.07 (m, 1H), 4.19-4.21 (m, 1H), 4.49-4.52 (m, 1H), 7.03 (dd, 1H, J=7.7, 4.5 Hz), 7.15-7.23 (m, 2H), 7.31-7.36 (m, 2H), 7.65-7.71 (m, 1H), 8.47 (d, 1H, J=3.9 Hz).

Preparation of N$^1$-(1-cyclopropylmethyl-1H-benzoimidazol-2-ylmethyl)-N$^1$-(5,6,7,8-tetrahydro-quinolin-8-yl)-butane-1,4-diamine (hydrobromide salt)

To a solution of the above amine (142 mg, 0.35 mmol) in acetic acid (3 mL) was added hydrobromide saturated acetic acid (2 mL). The reaction mixture was stirred for 30 minutes. Then it was triturated with diethyl ether three times and the solid was dried in vacuo. The solid was then re-dissolved in anhydrous methanol (1 mL) and was triturated with diethyl ether three times. The pale yellow solid (198 mg, 80%) was dried in vacuo overnight. $^1$H NMR (D$_2$O) δ 0.51 (d, 2H, J=4.8 Hz), 0.65 (d, 2H, J=7.5 Hz), 1.31-1.32 (m, 1H), 1.53 (br s, 4H), 1.77-1.91 (m, 1H), 2.02-2.23 (m, 2H), 2.42-2.46 (m, 1H), 2.55-2.60 (m, 1H), 2.86 (s, 3H), 3.02 (d, 2H, J=4.5 Hz), 4.39 (d, 2H, J=7.2 Hz), 4.47 (s, 1H), 4.45-4.50 (m, 1H), 4.65 (d, 1H, J=17.4 Hz), 7.62-7.65 (m, 2H), 7.83-7.89 (m, 3H), 8.35 (d, 1H, J=7.8 Hz), 8.64 (d, 1H, J=5.7 Hz). $^{13}$C NMR (D$_2$O) δ 4.11, 4.15, 14.55, 20.45, 25.06, 25.55, 27.73, 39.50, 48.03, 49.95, 52.08, 60.97, 113.35, 114.33, 125.98, 126.80, 127.22, 130.45, 132.94, 139.40, 140.67, 148.18, 151.08, 151.32. ES-MS m/z 404 [M+H]$^+$. Anal. Calcd. for C$_{25}$H$_{33}$N$_5$.3.1HBr.1.5H$_2$O.0.3C$_4$H$_{10}$O: C, 44.72; H, 6.03; N, 9.95; Br, 35.20. Found: C, 44.82; H, 6.07; N, 9.98; Br, 35.00.

Example 125

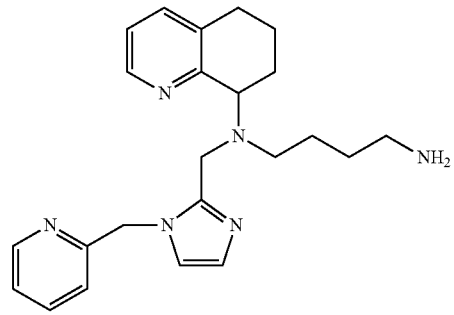 [SMILES: NCCCCN(Cc1nccn1Cc1ccccn1)C1CCCc2cccnc21]

Compound 125: N$^1$-(1-pyridin-2-ylmethyl-1H-imidazol-2-ylmethyl)-N$^1$-(5,6,7,8-tetrahydro-quinolin-8-yl)-butane-1,4-diamine (hydrobromide salt)

Preparation of 1-pyridine-2-ylmethyl-1H-imidazole-2-carbaldehyde

To a solution of the 2-imidazolecarboxaldehyde (545 mg, 5.67 mmol) and 2-(bromomethyl)pyridine hydrobromide (1.58 g, 6.24 mmol) in DMF (20 mL) was added N,N-diisopropylethylamine (3.0 mL, 17.01 mmol). The reaction mixture was heated to 80° C. overnight. Then it was cooled and quenched with saturated NaHCO$_3$ (20 mL). It was extracted with CH$_2$Cl$_2$ (c×20 mL). The combined organic layers were washed with brine (20 mL), dried (MgSO$_4$), filtered, concentrated, and dried in vacuo to afford a dark brown oil. Purification by flash column chromatography on silica gel using 1%→2% CH$_3$OH/CH$_2$Cl$_2$ afforded the product as a yellow solid (397 mg, 37%). $^1$H NMR (CDCl$_3$) δ 5.71 (s, 2H), 7.18-7.24 (m, 2H), 7.32 (s, 1H), 7.36 (s, 1H), 7.65 (td, 1H, J=10.4, 1.5 Hz), 8.56 (d, 1H, J=4.5 Hz), 9.82 (s, 1H).

Preparation of 2-{4-[(1-pyridin-2-ylmethyl-1H-imidazol-2-ylmethyl)-(5,6,7,8-tetrahydro-quinolin-8-yl)-amino]-butyl}-isoindole-1,3-dione To a solution of the above aldehyde (543 mg, 2.90 mmol) and 2-[4-(5,6,7,8-tetrahydro-quinolin-8-ylamino)-butyl]-isoindol-1,3-dione (1.11 g, 3.19 mmol) in $CH_2Cl_2$ (20 mL) was added sodium triacetoxyborohydride (1.23 g, 5.80 mmol). The reaction mixture was stirred overnight. Then it was extracted with saturated $NaHCO_3$ (3×25 mL). The combined aqueous washings were washed once with $CH_2Cl_2$ (30 mL). The organic layer was dried ($MgSO_4$), filtered, concentrated, and dried in vacuo to afford a yellow foam. Purification by radial chromatography on silica gel using $NH_4OH/CH_3OH/CH_2Cl_2$ (1:1:100) afforded the desired product as a yellow oil (135 mg, 9%). $^1H$ NMR ($CDCl_3$) d 1.18-1.28 (m, 2H), 1.49-1.67 (m, 3H), 1.75-1.95 (m, 2H), 2.01-2.06 (m, 1H), 2.51-2.777 (m, 4H), 3.51 (t, 2H, J=7.2 Hz), 3.87 (s, 2H), 4.00 (dd, 1H, J=6.3, 2.7 Hz), 5.70 (ABq, 2H, J=94.8, 16.5 Hz), 6.79 (d, 1H, J=7.6 Hz), 6.86 (d, 2H, J=7.5, 4.5 Hz), 7.12 (dd, 1H, J=7.2, 5.1 Hz), 7.24 (d, 1H, J=7.8 Hz), 7.55 (td, 1H, J=6.9, 1.8 Hz), 7.66-7.69 (m, 2H), 7.78-7.81 (m, 2H), 8.24 (d, 1H, J=3.6 Hz), 8.53 (d, 1H, J=4.8 Hz).

Preparation of $N^1$-(1-pyridin-2-ylmethyl-1H-imidazol-2-ylmethyl)-$N^1$-(5,6,7,8-tetrahydro-quinolin-8-yl)-butane-1,4-diamine To a solution of the above amine (135 mg, 0.26 mmol) in ethanol (5 mL) was added hydrazine hydrate (60 µL, 1.30 mmol). The reaction mixture was stirred overnight. Then the solvent was removed under reduced pressure to afford a white solid. Purification by radial chromatography on silica gel (1 mm plate; using $NH_4OH/CH_3OH/CH_2Cl_2$; 1:3:100→1:8:100) afforded the desired product as a yellow oil (42 mg, 41%). $^1H$ NMR ($CDCl_3$) δ 1.30-1.33 (m, 4H), 1.57-1.66 (m, 1H), 1.82-1.97 (m, 2H), 2.02-2.06 (m, 2H), 2.51-2.60 (m, 5H), 2.64-2.73 (m, 2H), 3.87 (d, 2H, J=3.0 Hz), 4.02 (dd, 1H, J=9.0, 6.0 Hz), 5.69 (ABq, 2H, J=108.0, 18.0 Hz), 6.77 (d, 1H, J=7.8 Hz), 6.89 (s, 1H), 6.91-6.94 (m, 1H), 6.96 (d, 1H, J=0.9 Hz), 7.16 (dd, 1H, J=7.2, 5.1 Hz), 7.29 (s, 1H), 7.56 (td, 1H, J=7.7, 1.5 Hz), 8.29 (d, 1H, J=4.2 Hz), 8.55 (d, 1H, J=4.5 Hz).

Preparation of $N^1$-(1-pyridine-2-ylmethyl-1H-imidazol-2-ylmethyl)-$N^1$-(5,6,7,8-tetrahydro-quinolin-8-yl)-butane-1,4-diamine (hydrobromide salt)

To a solution of the above amine (42 mg, 0.11 mmol) in acetic acid (3 mL) was added hydrobromic acid saturated acetic acid (2 mL). The reaction mixture was stirred for 30 minutes and then it was triturated with diethyl ether three times. The resulting precipitate was dried in vacuo. The precipitate was dissolved in methanol (1 mL) and triturated with diethyl ether three times. The isolated cream solid (66 mg, 83%) was dried in vacuo. $^1H$ NMR ($D_2O$) δ 1.44 (br s, 4H), 1.69-1.72 (m, 1H), 1.87 (q, 1H, J=12.0 Hz), 2.09 (br d, 2H, J=8.7 Hz), 2.40 (br s, 1H), 2.60 (br d, 1H, J=8.1 Hz), 2.84 (br s, 2H), 2.95 (br d, 2H, J=4.8 Hz), 4.23 (q, 2H, J=18.9 Hz), 4.32 (m, 1H), 5.71 (d, 2H, J=8.7 Hz), 7.55 (s, 2H), 7.64-7.71 (m, 2H), 7.83 (t, 1H, J=6.6 Hz), 8.16-8.21 (m, 1H), 8.31 (d, 1H, J=7.8 Hz), 8.55 (d, 1H, J=5.4 Hz), 8.61 (m, 1H). $^{13}C$ NMR ($D_2O$) δ 20.02, 20.42, 25.00, 25.30, 27.63, 46.66, 50.83, 51.63, 60.15, 119.89, 124.23, 124.84, 125.92, 126.11, 139.36, 140.58, 142.86, 146.09, 147.42, 148.11, 151.05. ES-MS m/z 391 [M+H]$^+$. Anal. Calcd. for $C_{23}H_{30}N_6$·3.9HBr·1.7$H_2O$: C, 37.35; H, 4.95; N, 11.28; Br, 42.59. Found: C, 37.50; H, 5.10; N, 11.41; Br, 42.30.

Example 126

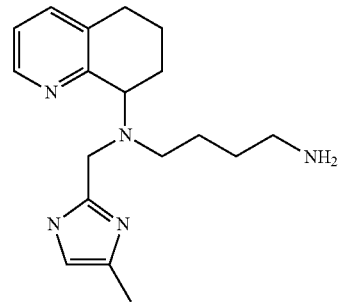 [SMILES: Cc1c[nH]c(CN(CCCCN)C2CCCc3cccnc32)n1]

Compound 126: $N^1$-(4-methyl-1H-imidazol-2-ylmethyl)-$N^1$-(5,6,7,8-tetrahydro-quinolin-8-yl)-butane-1,4-diamine (hydrobromide salt)

Preparation of 2-{[[4-(1,3-dioxo-1,3-dihydro-isoindol-2-yl)-butyl]-(5,6,7,8-tetrahydro-quinolin-8-yl)-amino]-methyl}-4-methyl-imidazole-1-sulfonic acid dimethylamide To a solution of 4-methylimidazole (1.0 g, 12.18 mmol) and triethylamine (1.3 mL, 12.18 mmol) in $CH_2Cl_2$ (25 mL) at 0° C. was added dimethyl sulfamoyl chloride (3.4 mL, 24.36 mmol). The reaction mixture was warmed to room temperature and was stirred overnight. Then the mixture was extracted with water (25 mL) and saturated NaCl (2×25 mL). The organic layer was dried ($MgSO_4$), filtered, concentrated, and dried in vacuo to afford a pale yellow solid. Purification by flash column chromatography on silica gel using 5% $CH_3OH/CH_2Cl_2$ afforded a mixture of product and starting material as a pale yellow solid, which was used without further purification.

To a solution of the above amine (505 mg, 2.67 mmol) in dry THF (27 mL) at −78° C. and under $Ar_2(g)$ was added n-butyl lithium (1.18 mL, 2.94 mmol, 2.5 M in hexanes). After 45 minutes, N,N-dimethylformamide (0.25 mL, 3.20 mmol) was added dropwise and the reaction mixture was warmed to room temperature. After 1.5 hours, the reaction was quenched with saturated $NH_4Cl$ (6 mL). The solvent was removed under reduced pressure. Then it was dissolved in $CH_2Cl_2$ (25 mL) and water (10 mL) and the phases were separated. The aqueous layer was washed with $CH_2Cl_2$ (2×25 mL). The combined organic washings was washed with brine (50 mL), dried ($Na_2SO_4$), filtered, concentrated, and dried in vacuo to afford a yellow oil. Purification by flash column chromatography on silica gel using 2% $CH_3OH/CH_2Cl_2$ afforded an impure yellow oil, which was used without further purification.

To a solution of the above aldehyde (190 mg, 0.88 mmol) and 2-[4-(5,6,7,8-tetrahydro-quinolin-8-ylamino)-butyl]-isoindol-1,3-dione (338 mg, 0.97 mmol) in $CH_2Cl_2$ (10 mL) was added sodium triacetoxyborohydride (373 mg, 1.76 mmol). The reaction mixture was stirred for 3 days. Then it was extracted with saturated $NaHCO_3$ (3×25 mL). The organic layer was dried ($MgSO_4$), filtered, concentrated, and dried in vacuo to afford a yellow foam. Purification by flash column chromatography on silica gel using 2% $CH_3OH/CH_2Cl_2$ afforded the product as a pale yellow solid (307 mg, 67%). $^1H$ NMR ($CDCl_3$) δ 1.19-1.27 (m, 2H), 1.43-1.51 (m, 2H), 1.64-1.78 (m, 2H), 1.91-1.96 (m, 1H), 2.07 (s 1H), 2.10-2.14 (m, 1H), 2.53-2.75 (m, 4H), 2.92 (s, 6H), 3.53 (t, 2H, J=7.2 Hz), 4.17 (t, 1H, J=8.4 Hz), 4.25 (q, 2H, J=14.4 Hz), 6.81 (s, 1H), 6.94 (dd, 1H, J=7.5, 4.8 Hz), 7.26 (d, 1H, J=6.9 Hz), 7.65-7.70 (m, 2H), 7.75-7.81 (m, 2H), 8.31 (d, 1H, J=3.6 Hz).

Preparation of $N^1$-(4-methyl-1H-imidazol-2-ylmethyl)-$N^1$-(5,6,7,8-tetrahydro-quinolin-8-yl)-butane-1,4-diamine The above amine (300 mg, 0.58 mmol) in 2N HCl (6 mL) was stirred at reflux overnight. The reaction mixture was cooled and basified with 15% aqueous NaOH. Then it was extracted with $CH_2Cl_2$ (3×15 mL). The combined organic washings was washed with saturated NaCl (25 mL), dried ($Na_2SO_4$), filtered, concentrated, and dried in vacuo to afford a yellow oil. Purification by radial chromatography on silica gel (1 mm plate; using $NH_4OH/CH_3OH/CH_2Cl_2$; 1:3:100→1:10:100; gradient elution) afforded the product as a yellow oil (72.5 mg, 40%). $^1H$ NMR ($CDCl_3$) δ 1.24-1.38 (m, 4H), 1.63-1.68 (m, 1H), 1.82-1.86 (m, 1H), 1.96-2.00 (m, 1H), 2.10-2.15 (m, 1H), 2.21 (s, 3H), 2.42-2.81 (m, 6H), 3.77 (q, 2H, J=15.9 Hz), 3.96 (dd, 1H, J=9.2, 6.0 Hz), 6.63 (s, 1H), 7.08 (dd, 1H, J=7.5, 4.8 Hz), 7.37 (d, 1H, J=7.5 Hz), 8.45 (d, 1H, J=4.2 Hz).

Preparation of $N^1$-(4-methyl-1H-imidazol-2-ylmethyl)-$N^1$-(5,6,7,8-tetrahydro-quinolin-8-yl)-butane-1,4-diamine (hydrobromide salt)

To a solution of the above amine (72.5 mg, 0.23 mmol) in acetic acid (3 mL) was added hydrobromic acid saturated acetic acid (2 mL). The reaction mixture was stirred for 30 minutes. Then it was triturated with diethyl ether three times and the precipitate was dried in vacuo. The solid was re-dissolved in methanol (1 mL) and triturated an additional three times with diethyl ether. The resulting yellow solid (82 mg, 58%) was dried in vacuo. $^1H$ NMR ($D_2O$) δ 1.45-1.61 (m, 4H), 1.78-2.01 (m, 2H), 2.15-2.19 (m, 1H), 2.25-2.31 (m, 4H), 2.48-2.53 (m, 1H), 2.71-2.78 (m, 1H), 2.89-2.91 (m, 2H), 2.98-3.00 (m, 2H), 4.16 (q, 2H, J=18.0 Hz), 4.39 (dd, 1H, J=10.7, 5.4 Hz), 7.11 (s, 1H), 7.85 (dd, 1H, J=10.7, 6.3 Hz), 8.34 (d, 1H, J=7.8 Hz), 8.59 (d, 1H, J=5.7 Hz). $^{13}C$ NMR ($D_2O$) δ 9.43, 20.24, 20.45, 25.07, 25.32, 27.61, 39.59, 47.07, 51.25, 60.06, 66.48, 115.91, 125.84, 125.84, 130.37, 139.25, 140.47, 144.17, 147.98, 151.58. ES-MS m/z 314 [M+H]$^+$. Anal. Calcd. for $C_{18}H_{27}N_5 \cdot 3.0HBr \cdot 1.8H_2O \cdot 0.2C_4H_{10}O$: C, 37.42; H, 5.95; N, 11.61; Br, 39.72. Found: C, 37.17; H, 5.65; N, 11.37; Br, 40.10.

Example 127

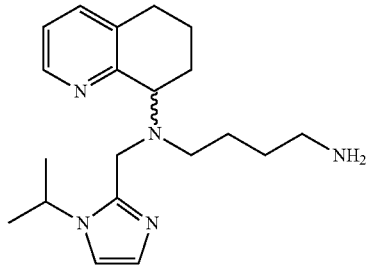 [SMILES: CC(C)n1ccnc1CN(CCCCN)C1CCCc2cccnc21]

Compound 127: Preparation of $N^1$-(1-isopropyl-1H-imidazol-2-ylmethyl)-$N^1$-(5,6,7,8-tetrahydro-quinolin-8-yl)-butane-1,4-diamine (hydrobromide salt)

Preparation of 1-isopropyl-1H-imidazole (prepared as described by Gridnev, A. A.; Mihaltseva, I. M. Synth. Commun. 1994, 24, 1547-1555)

A solution of isopropylamine (4.25 mL, 50 mmol) in $H_2O$ (5 mL) was acidified to approximately pH 2 with concentrated $H_3PO_4$. Glyoxal (40% in $H_2O$, 7.5 mL, 52 mmol) and formaldehyde (37% in $H_2O$, 4.0 mL, 49 mmol) were added and the reaction flask was fitted with a reflux condenser and a dropping funnel. The solution was warmed to 90-95° C. and a saturated aqueous solution of $NR_4Cl$ (10 mL) was added dropwise over 20 minutes. The reaction was stirred at 100° C. for 30 minutes then, once cooled, was made basic (pH~10) by the addition of solid NaOH. The solution was extracted with EtOAc (25 mL×3) and the combined organic solution was dried ($Na_2SO_4$), filtered and concentrated under reduced pressure. Purification by vacuum distillation (b.p. 57-70° C./0.25 mmHg) gave the imidazole as a colourless liquid (899 mg, 8.16 mmol, 17%). $^1H$ NMR ($CDCl_3$) δ 1.47 (d, 6H, J=6.9 Hz), 4.33 (septet, 1H, J=6.8 Hz), 6.95 (s, 1H), 7.04 (s, 1H), 7.52 (s, 1H).

Preparation of 1-isopropyl-1H-imidazole-2-carboxaldehyde

A solution of the imidazole (890 mg, 8.08 mmol) in THF (10 mL) under nitrogen was cooled to −78° C. and n-BuLi (2.5M in hexanes, 4.5 mL, 11.3 mmol) was added. The bright yellow solution was stirred at 0° C. for 25 minutes, then DMF (1.5 mL, 19 mmol) was added. The reaction was stirred at room temperature for one hour, then was quenched by the addition of saturated aqueous $NH_4Cl$ (10 mL). The layers were separated and the aqueous solution was extracted with EtAOc (10 mL×2). The combined organic solution was dried ($Na_2SO_4$), filtered and concentrated under reduced pressure. Purification by flash column chromatography on silica (hexane/EtOAc, 1:1) gave the aldehyde as a pale yellow solid (731 mg, 5.29 mmol, 65%). $^1H$ NMR ($CDCl_3$) δ 1.46 (d, 6H, J=6.6 Hz), 5.46 (septet, 1H, J=6.8 Hz), 7.29 (s, 1H), 7.31 (s, 1H), 9.81 (s, 1H).

Preparation of 2-{4-[(1-isopropyl-1H-imidazol-2-ylmethyl)-(5,6,7,8-tetrahydro-quinolin-8-yl)-amino]-butyl}-isoindole-1,3-dione A solution of the aldehyde (222 mg, 1.61 mmol), 2-[4-(5,6,7,8-tetrahydro-quinolin-8-ylamino)-butyl]-isoindole-1,3- dione (354 mg, 1.01 mmol) and NaBH(OAc)$_3$ (319 mg, 1.51 mmol) in CH$_2$Cl$_2$ (7 mL) was stirred at room temperature under nitrogen for 15 hours. The reaction was diluted with CH$_2$Cl$_2$ (10 mL) and washed with 1M NaOH (10 mL) and brine (10 mL). The organic solution was dried (Na$_2$SO$_4$), filtered and concentrated under reduced pressure. Purification by flash column chromatography on silica (CH$_2$Cl$_2$/MeOH, 19:1) gave the tertiary amine as a white foam (210 mg, 0.45 mmol, 44%). $^1$H NMR (CDCl$_3$) δ 1.27 (d, 3H, J=6.9 Hz), 1.41 (d, 3H, J=6.6 Hz), 1.49-1.72 (m, 3H), 1.78-2.10 (m, 5H), 2.46-2.84 (m, 4H), 3.58 (t, 2H, J=7.1 Hz), 3.85 (d, 1H, J=13.5 Hz), 3.92-4.02 (m, 2H), 5.07 (septet, 1H, J=6.6 Hz), 6.83 (s, 1H), 6.87 (s, 1H), 7.01 (dd, 1H, J=7.5, 4.8 Hz), 7.31 (d, 1H, J=7.5 Hz), 7.69-7.73 (m, 2H), 7.79-7.83 (m, 2H), 8.41 (d, 1H, J=3.6 Hz).

Preparation of N$^1$-(1-isopropyl-1H-imidazol-2-ylmethyl)-N$^1$-(5,6,7,8-tetrahydro-quinolin-8-yl)-butane-1,4-diamine A solution of the phthalimide (206 mg, 0.44 mmol) and hydrazine monohydrate (0.20 mL, 4.1 mmol) in EtOH (4.5 mL) was heated at reflux for 1.5 hours. The solvent was removed under reduced pressure, and the residue was taken up into saturated aqueous NaHCO$_3$ (10 mL) and extracted with CH$_2$Cl$_2$ (10 mL×3). The organic solution was dried (Na$_2$SO$_4$), filtered and concentrated under reduced pressure. Purification by flash column chromatography on silica (CH$_2$Cl$_2$/MeOH/NH$_4$OH, 9:1:0.1) gave the primary amine as a pale yellow oil (128 mg, 0.37 mmol, 85%). $^1$H NMR (CDCl$_3$) δ 1.26 (d, 3H, J=6.6 Hz), 1.31-1.37 (m, 4H), 1.41 (d, 3H, J=6.6 Hz), 1.54-1.77 (m, 3H), 1.86-2.10 (m, 3H), 2.51-2.60 (m, 4H), 2.62-2.86 (m, 2H), 3.84 (s, 2H), 4.04 (dd, 1H, J=8.1, 5.7 Hz), 5.07 (septet, 1H, J=6.6 Hz), 6.91 (s, 1H), 6.92 (s, 1H), 7.05 (dd, 1H, J=7.7, 4.7 Hz), 7.35 (d, 1H, J=7.5 Hz), 8.46 (d, 1H, J=3.3 Hz).

Preparation of Compound 127

To a solution of the free base (121 mg, 0.35 mmol) in glacial HOAc (1.0 mL) was added saturated HBr in HOAc (0.5 mL). The reaction was stirred at room temperature for 20 minutes, then was diluted with Et$_2$O (5 mL). The salt formed an oil and the solvent was removed by pipette. The residue was dissolved into anhydrous MeOH (0.5 mL), stirred for approximately five minutes, then was diluted with Et$_2$O (5 mL). The solvent was again removed by pipette, the insoluble material was washed with Et$_2$O (2 mL×2) and dried under reduced pressure, giving the hydrobromide salt as a fine, white powder (136 mg, 0.25 mmol, 71%). $^1$H NMR (D$_2$O) δ 1.45 (d, 6H, J=6.6 Hz), 1.46-1.62 (m, 4H), 1.67-1.84 (m, 1H), 1.92-2.16 (m, 2H), 2.20-2.32 (m, 1H), 2.49-2.62 (m, 1H), 2.75-2.94 (m, 5H), 4.08 (d, 1H, J=16.5 Hz), 4.23-4.33 (m, 2H), 4.65 (septet, 1H, J=6.6 Hz), 7.37 (d, 1H, J=1.8 Hz), 7.49 (d, 1H, J=1.5 Hz), 7.54 (dd, 1H, J=7.7, 5.6 Hz), 7.95 (d, 1H, J=8.1 Hz), 8.48 (d, 1H, J=4.8 Hz). $^{13}$C NMR (D$_2$O) δ 23.0, 24.0, 24.7, 27.4, 30.6, 42.0, 49.0, 52.8, 53.9, 63.4, 121.7, 122.6, 127.1, 140.8, 145.4, 145.9, 147.0, 155.7. ES-MS m/z 342 (M+H). Anal. Calcd. for C$_{20}$H$_{31}$N$_5$.2.0HBr.1.2CH$_4$O: C, 47.00; H, 7.03; N, 12.93; Br 29.50. Found: C, 47.20; H, 6.92; N, 12.91; Br 29.13.

Example 128

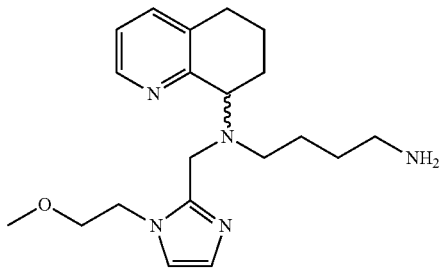 [SMILES: COCCn1ccnc1CN(CCCCN)C1CCCc2cccnc21]

Compound 128: Preparation of N$^1$-[1-(2-methoxy-ethyl)-1H-imidazol-2-ylmethyl]-N$^1$-(5,6,7,8-tetrahydro-quinolin-8-yl)-butane-1,4-diamine (hydrobromide salt)

Preparation of imidazol-1-yl-acetic acid ethyl ester

To a 0° C. suspension of NaH (60% in mineral oil, 658 mg, 16.5 mmol) in THF (20 mL) under nitrogen was slowly added a solution of imidazole (1.03 g, 15.1 mmol) in THF (20 mL). The resulting suspension was stirred at 0° C. for 15 minutes, then ethyl bromoacetate (2.2 mL, 20 mmol) was added. The reaction was stirred at room temperature for 4.5 hours, then was diluted with H$_2$O (25 mL). The THF was evaporated under reduced pressure and the remaining aqueous solution was extracted with CH$_2$Cl$_2$ (25 mL×3). The combined organic solution was dried (Na$_2$SO$_4$), filtered and concentrated under reduced pressure. Purification by flash column chromatography on silica (CH$_2$Cl$_2$/MeOH, 19:1) gave the ester as a yellow liquid (1.52 g, 9.87 mmol, 65%). $^1$H NMR (CDCl$_3$) δ 1.28 (t, 3H, J=7.1 Hz), 4.24 (q, 2H, J=7.1 Hz), 4.68 (s, 2H), 6.95 (s, 1H), 7.09 (s, 1H), 7.50 (s, 1H).

Preparation of 1-(2-methoxy-ethyl)-1H-imidazole

A solution of the ester (1.51 g, 9.81 mmol) in THF (25 mL) under nitrogen was cooled to 0° C. and LiAlH$_4$ (1.0M in THF, 5.0 mL, 5.0 mmol) was slowly added. The reaction was stirred at room temperature for 20 minutes, then was quenched by the addition of H$_2$O (0.2 mL), 15% aqueous NaOH (0.2 mL) and H$_2$O (0.6 mL). The mixture was filtered with suction through Celite, washing with EtOAc. The filtrate was dried (Na$_2$SO$_4$), filtered and concentrated under reduced pressure, giving the elude alcohol as a yellow oil (896 mg, 81%).

To a 0° C. suspension of NaH (60% in mineral oil, 410 mg, 10.3 mmol) in THF (10 mL) under nitrogen was slowly added a solution of the alcohol (890 mg, 7.94 mmol) in THF (10 mL). The mixture was stirred at 0° C. for 10 minutes, then dimethyl sulfate (0.95 mL, 10.0 mmol) was added. The reaction was stirred at room temperature for an additional 30 minutes, and then THF was removed under reduced pressure. The residue was taken up into H$_2$O (25 mL) and was extracted with CH$_2$Cl$_2$ (25 mL×3). The combined organic solution was dried (Na$_2$SO$_4$), filtered and concentrated under reduced pressure. Purification by flash column chromatography on silica (CH$_2$Cl$_2$/MeOH, 19:1) gave the methyl ether as a colourless oil (347 mg, 2.75 mmol, 35%). $^1$H NMR (CDCl$_3$) δ 3.34 (s, 3H), 3.63 (t, 2H, J=5.1 Hz), 4.09 (t, 2H, J=5.1 Hz), 6.97 (s, 1H), 7.05 (s, 1H), 7.52 (s, 1H).

Preparation of 1-(2-methoxy-ethyl)-1H-imidazole-2-carboxaldehyde

A solution of the imidazole (342 mg, 2.71 mmol) in THF (3.5 mL) was cooled to −78° C. under nitrogen and n-BuLi (2.5M in hexanes, 1.4 mL, 3.5 mmol) was added. The resulting bright yellow solution was stirred at 0° C. for 10 minutes, then DMF (0.5 mL, 6.5 mmol) was added. The reaction was stirred at room temperature for 45 minutes, then was quenched by the addition of saturated aqueous $NH_4Cl$ (5 mL). The layers were separated and the aqueous solution was extracted with $CH_2Cl_2$ (10 mL×2). The organic solution was dried ($Na_2SO_4$), filtered and concentrated under reduced pressure. Purification by flash column chromatography on silica ($CH_2Cl_2$/MeOH, 32:1) gave the aldehyde as a yellow liquid (1:1 with DMF, 254 mg, 1.12 mmol, 41%). $^1H$ NMR ($CDCl_3$) δ 3.30 (s, 3H), 3.66 (t, 2H, J=5.1 Hz), 4.58 (t, 2H, J=5.0 Hz), 7.26 (s, 1H), 7.27 (s, 1H), 9.80 (s, 1H).

Preparation of 2-{4-[[1-(2-methoxy-ethyl)-1H-imidazol-2-ylmethyl]-(5,6,7,8-tetrahydro-quinolin-8-yl)-amino]-butyl}-isoindole-1,3-dione A solution of the aldehyde (170 mg, 1.10 mmol), 2-[4-(5,6,7,8-tetrahydro-quinolin-8-ylamino)-butyl]-isoindole-1,3-dione (422 mg, 1.21 mmol) and $NaBH(OAc)_3$ (324 mg, 1.53 mmol) in $CH_2Cl_2$ (8 mL) was stirred at room temperature under nitrogen for 16 hours. The reaction was diluted with $CH_2Cl_2$ (10 mL) and was washed with 1M NaOH (10 mL) and brine (10 mL). The organic solution was dried ($Na_2SO_4$), filtered and concentrated under reduced pressure. Purification by flash column chromatography on silica ($CH_2Cl_2$/MeOH/$NH_4OH$, 49:1:0.25) gave the tertiary amine as a white foam (244 mg, 0.50 mmol, 45%). $^1H$ NMR ($CDCl_3$) δ 1.20-1.35 (m, 2H), 1.47-1.70 (m, 3H), 1.80-2.16 (m, 3H), 2.55 (t, 2H, J=7.2 Hz), 2.60-2.85 (m, 2H), 3.27 (s, 3H), 3.48-3.67 (m, 4H), 3.87 (s, 2H), 3.98 (dd, 1H, J=9.3, 6.0 Hz), 4.24-4.35 (m, 1H), 4.54-4.66 (m, 1H), 6.80 (d, 1H, J=1.2 Hz), 6.89 (d, 1H, J=1.2 Hz), 7.00 (dd, 1H, J=7.7, 4.7 Hz), 7.31 (d, 1H, J=7.5 Hz), 7.67-7.73 (m, 2H), 7.79-7.84 (m, 2H), 8.40 (d, 1H, J=3.9 Hz).

Preparation of $N^1$-[1-(2-methoxy-ethyl)-1H-imidazol-2-ylmethyl]-$N^1$-(5,6,7,8-tetrahydro-quinolin-8-yl)-butane-1,4-diamine A solution of the phthalimide (238 mg, 0.49 mmol) and hydrazine monohydrate (0.25 mL) in EtOH (5 mL) was stirred at reflux for 1.5 hours. The solvent was removed under reduced pressure, the residue was taken up into saturated aqueous $NaHCO_3$ (10 mL) and was extracted with $CH_2Cl_2$ (15 mL×3). The combined organic solution was dried ($Na_2SO_4$), filtered and concentrated under reduced pressure. Purification by flash column chromatography on silica ($CH_2Cl_2$/MeOH/$NH_4OH$, 9:1:0.1) gave the primary amine as a colourless oil (130 mg, 0.36 mmol, 74%). $^1H$ NMR ($CDCl_3$) δ 1.23-1.42 (m, 4l), 1.60-1.75 (m, 1H), 1.84-2.14 (m, 3H), 2.48-2.60 (m, 4H), 2.63-2.86 (m, 2H), 3.28 (s, 3H), 3.49-3.56 (m, 1H), 3.58-3.66 (m, 1H), 3.83 (s, 2H), 4.03 (dd, 1H, J=8.4, 6.0 Hz), 4.22-4.31 (m, 1H), 4.56-4.64 (m, 1H), 6.88 (d, 1H, J=1.5 Hz), 6.93 (d, 1H, J=1.5 Hz), 7.04 (dd, 1H, J=7.5, 4.5 Hz), 7.34 (dd, 1H, J=7.5, 1.5 Hz), 8.45 (dd, 1H, J=4.5, 1.5 Hz).

Preparation of Compound 128

To a solution of the free base (48 mg, 0.13 mmol) in glacial AcOH (1.0 mL) was added saturated HBr in AcOH (0.5 mL). The reaction was stirred at room temperature for 20 minutes, then was diluted with $Et_2O$ (5 mL). The salt formed a yellow oil and the solvent was removed by pipette. The residue was dissolved into anhydrous MeOH (0.5 mL), stirred for approximately five minutes, then was diluted with $Et_2O$ (5 mL). The solvent was again removed by pipette, the insoluble material was washed with $Et_2O$ (2 mL×2) and dried under reduced pressure, giving the hydrobromide salt as a fine, off-white powder (76 mg, 0.12 mmol, 87%). $^1H$ NMR ($D_2O$) δ 1.41-1.60 (m, 4H), 1.74-1.88 (m, 1H), 1.92-2.08 (m, 1H), 2.12-2.24 (m, 1H), 2.31-2.42 (m, 1H), 2.43-2.55 (m, 1H), 2.68-2.81 (m, 1H), 2.84-2.94 (m, 2H), 2.96-3.06 (m, 2H), 3.33 (s, 3H), 3.83 (t, 2H, J=4.8 Hz), 4.16 (d, 1H, J=16.5 Hz), 4.35 (d, 1H, J=16.5 Hz), 4.40-4.44 (m, 3H), 7.49 (d, 1H, J=1.8 Hz), 7.51 (d, 1H, J=1.8 Hz), 7.86 (dd, 1H, J=7.8, 6.0 Hz), 8.34 (d, 1H, J=7.8 Hz), 8.60 (d, 1H, J=5.7 Hz). $^{13}C$ NMR ($D_2O$) δ 20.2, 20.5, 25.1, 25.4, 27.7, 39.6, 46.8, 47.9, 51.7, 59.0, 60.3, 70.5, 119.3, 123.3, 125.9, 139.4, 140.6, 145.6, 148.1, 151.3. ES-MS m/z 358 (M+H). Anal. Calcd. for $C_{20}H_{31}N_5O$·3.1HBr·1.4$H_2O$·0.2$C_4H_{10}O$: C, 38.34; H, 6.02; N, 10.75; Br 38.02. Found: C, 38.59; H, 5.93; N, 10.77; Br 37.63.

Example 129

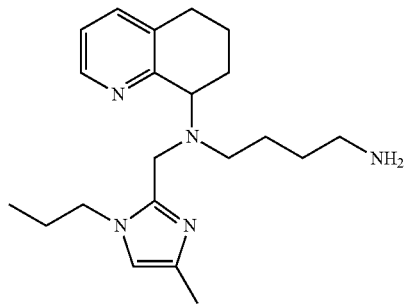 [SMILES: CCCn1cc(C)nc1CN(CCCCN)C1CCCc2cccnc21]

Compound 129: $N^1$-(4-methyl-1-propyl-1H-imidazol-2-ylmethyl)-$N^1$-(5,6,7,8-tetrahydro-quinolin-8-yl)-butane-1,4-diamine (hydrobromide salt)

Preparation of 1-allyl-4-methyl-1H-imidazole

4-Methylimidazole (2.0 g, 24.36 mmol), allyl bromide (2.2 mL, 24.36 mmol), N,N-diisopropylethylamine (5.0 mL, 29.24 mmol) in DMF (50 mL) were stirred at 80° C. overnight. Then the reaction mixture was cooled, quenched with saturated $NaHCO_3$ (30 mL), and extracted with $CH_2Cl_2$ (4×40 mL). The combined organic layers were dried ($MgSO_4$), filtered, concentrated, and dried in vacuo to afford a brown oil. Purification by flash column chromatography on silica using 2% $CH_3OH$/$CH_2Cl_2$ afforded the product as a yellow oil (1.13 g, 40%). $^1H$ NMR ($CDCl_3$) (as a mixture of regio-isomers) δ 2.17 and 2.22 (s, total 3H), 4.44-4.48 (m, total 2H), 5.19-5.24 (m, total 2H), 5.89-6.00 (m, total 1H), 6.61 and 6.79 (s, total 1H), 7.35 and 7.39 (s, total 1H).

Preparation of 1-allyl-4-methyl-1H-imidzaole-2-carbaldehyde

To a solution of the above imidazole (1.23 g, 10.07 mmol) in THF (40 mL) at −78° C. and under Ar(g), was added n-butyllithium (2.5 M in hexanes). After 45 minutes, DMF was added dropwise the reaction mixture was stirred at room temperature for 1 hour. Then it was quenched with saturated NH$_4$Cl (20 mL) and the solvent was removed under reduced pressure. The residue was dissolved in CH$_2$Cl$_2$ (20 mL) and water (10 mL) and the phases were separated. The aqueous layer was washed twice with CH$_2$Cl$_2$ (25 mL). The organic layer was dried (Na$_2$-SO$_4$), filtered, concentrated, and dried in vacuo to afford a yellow oil. Purification by flash column chromatography on silica gel using 2% CH$_3$OH/CH$_2$Cl$_2$ afforded the product as a yellow oil (575 mg, 38%). $^1$H NMR (CDCl$_3$) (as a mixture of regio-isomers) δ 2.26 and 2.30 (s, total 3H), 4.96-5.25 (m, total 4H), 5.91-5.97 (m, total 1H), 6.74 and 6.92 (m, total 1H), 9.70 and 9.73 (s, total 1H).

Preparation of 2-{4-[(1-allyl-4-methyl-1H-imidazol-2-ylmethyl)-(5,6,7,8-tetrahydro-quinolin-8-yl)-amino]-butyl}-isoindole-1,3-dione To a solution of the above aldehyde (268 mg, 1.773 mmol) and 2-[4-(5,6,7,8-tetrahydro-quinolin-8-ylamino)-butyl]-isoindol-1,3-dione (743 mg, 2.13 mmol) in CH$_2$Cl$_2$ (17 mL) was added sodium triacetoxyborohydride (752 mg, 3.55 mmol). The reaction mixture was stirred at room temperature overnight. Then it was extracted with saturated NaHCO$_3$ (3×20 mL). The organic layer was dried (MgSO$_4$), filtered, concentrated, and dried in vacuo to afford a yellow foam. Purification by flash column chromatography on silica gel using 10% CH$_3$OH/ethyl acetate afforded the product as a pale yellow foam (263 mg, 31%). $^1$H NMR (CDCl$_3$) (as a mixture of regio-isomers) δ 1.52-1.60 (m, total 4H), 1.89-2.11 (m, total 8H), 2.56-2.66 (m, total 4H), 2.55 (t, 2H, J=7.5 Hz), 3.76 (d, 2H, J=6.0 Hz), 3.99 (t, 1H, J=–6.0 Hz), 4.84-4.90 (m, total 1H) 4.93 and 4.96 (s, total 1H), 5.03-5.06 (m, total 2H), 5.83-5.87 (m, 1H), 6.43 (s, 1H), 6.99 (dd, 1H, J=3.0 Hz), 7.27 (d, 114, J=6.0 Hz), 7.68-7.70 (m, 2H), 7.80-7.82 (m, 2H), 8.39 (d, 1H, J=3.0 Hz).

Preparation of N$^1$-(4-methyl-1-propyl-1H-imidazol-2-ylmethyl)-N$^1$-(5,6,7,8-tetrahydro-quinolin-8-yl)-butane-1,4-diamine To a solution of the above amine (263 mg, 0.54 mmol) in ethanol (10 mL) was added hydrazine hydrate (0.13 mL, 2.72 mmol). The reaction mixture was stirred at room temperature for 3 days. Then the solvent was removed under reduced pressure. Purification by radial chromatography on silica gel (2 mm plate; using NH$_4$OH/CH$_3$OH/CH$_2$Cl$_2$; 1:4:100→1:6:100) afforded a yellow oil, which the $^1$H NMR indicated as a mixture of the allyl product and the n-propyl product.

The above amine (150 mg, 0.31 mmol) in methanol (15 mL) was hydrogenated at 40 psi in the presence of palladium/carbon (15 mg) overnight. Then the reaction mixture was filtered through a layer of celite and the filtrated was concentrated down to dryness to afford a yellow oil. Purification by radial chromatography (1 mm plate; using NH$_4$OH/CH$_3$OH/CH$_2$Cl$_2$; 1:4:100→1:7:100) afforded the product as a yellow oil (67 mg, 61%). $^1$H NMR (CDCl$_3$) δ 0.83 (t, 3H, J=7.5 Hz), 1.59-1.69 (m, 3H), 1.97-2.02 (m, 4H), 2.13 (s, 3H), 2.53-2.70 (m, 8H), 3.72 (d, 2H), 3.87-3.92 (m, 1H), 4.03-4.07 (m, 2H), 6.50 (s, 1H), 7.04 (d, 1H, J=3.0 Hz), 7.34 (d, 1H, J=9.0 Hz), 8.50 (d, 1H, J=6.0 Hz).

Preparation of N$^1$-(4-methyl-1-propyl-1H-imidazol-2-ylmethyl)-N$^1$-(5,6,7,8-tetrahydro-quinolin-8-yl)-butane-1,4-diamine (hydrobromide salt)

To a solution of the above amine (67 mg, 0.19 mmol) in acetic acid (2 mL) was added hydrobromide saturated acetic acid (2 mL). The reaction mixture was stirred for 30 minutes. Then it was triturated with diethyl ether three times and the precipitate was dried in vacuo. The solid was re-dissolved in anhydrous methanol (0.5 mL) and was triturated with diethyl ether three times to afford a yellow solid (40 mg, 32%). $^1$H NMR (D$_2$O) δ 0.89 (t, 3H, J=7.5 Hz), 1.51 (br s, 4H), 1.80 (q, 3H, J=7.5 Hz0, 1.97-2.01 (m, 1H), 2.16-2.20 (m, 1H), 2.31-2.35 (m, 4H), 2.49 (br m, 1H), 2.71-2.76 (m, 1H), 2.88-2.90 (m, 2H), 2.99-3.01 (m, 2H), 4.06 (t, 3H, J=6.9 Hz), 4.27 (d, 1H, J=16.8 Hz), 4.38-4.43 (m, 1H), 7.14 (s, 1H), 7.87 (t, 1H, J=6.3 Hz), 8.35 (d, 1H, J=7.8 Hz), 8.59 (d, 1H, J=5.4 Hz). $^{13}$C NMR (D$_2$O) δ 9.40, 10.39, 20.24, 20.42, 23.27, 25.08, 25.42, 27.66, 39.55, 46.43, 49.39, 51.59, 60.27, 119.71, 125.90, 129.96, 139.27, 140.56, 143.47, 148.08, 151.38. ES-MS m/z 356 [M+H]$^+$. Anal. Calcd. for C$_{21}$H$_{33}$N$_5$.3.0HBr.2.0H$_2$O.0.3C$_4$H$_{10}$O: C, 40.61; H, 6.60; N, 10.67; Br, 36.51. Found: C, 4.35; H, 635; N, 10.43; Br, 36.39.

Example 130

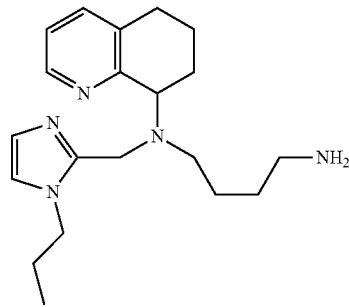 [SMILES: CCCn1ccnc1CN(CCCCN)C1CCCc2cccnc21]

Compound 130: Preparation of N$^1$-(1-propyl-1H-imidazol-2-ylmethyl)-N$^1$-(5,6,7,8-tetrahydroquinolin-8-yl)-butane-1,4-diamine (hydrobromide salt)

To a solution of 2-Imidazolecarboxaldehyde (0.81 g, 8.4 mmol) and diisopropylethylamine (2.2 mL, 12.6 mmol) in anhydrous DMF (28 mL) was added allyl bromide (0.88 mL, 10.1 mmol) and the solution was stirred at 60° C. for 16 hours. The mixture was then concentrated under reduced pressure and the residue partitioned between dichloromethane (20 mL) and sodium bicarbonate (15 mL). The organic phase was separated and the aqueous phase was extracted with dichloromethane (2×15 mL). The combined organic phases were then dried (Na$_2$SO$_4$), filtered, and concentrated under reduced pressure to give a crude residue that was purified by column chromatography with silica gel (1:99 MeOH/CH$_2$Cl$_2$). This afforded 2-(N-allylimidazole)-carboxaldehyde (0.62 g, 54%). $^1$H NMR (CDCl$_3$) δ 5.02 (d, 2H, J=6.0 Hz), 5.10 (d, 1H, J=18.0 Hz), 5.25 (d, 1H, J=9.0 Hz), 5.96 (m, 1H), 7.16 (s, 1H), 7.30 (s, 1H), 9.81 (s, 1H).

Using general procedure B, 2-[4-(5,6,7,8-Tetrahydro-quinolin-8-ylamino)-butyl]-isoindole-1,3-dione (0.80 g, 2.3 mmol), 2-(N-allylimidazole)-carboxaldehyde (0.62 g, 4.5 mmol) and sodium triacetoxyborohydride (1.16 g, 5.5 mmol) were stirred at room temperature in dichloromethane (22 mL) for 16 hours to yield, after work-up and column chromatography (1:4 ethyl acetate:hexane), 2-{4-[(1-Allyl-1H-imidazol-2-ylmethyl)-(5,6,7,8-tetrahydroquinolin-8-yl)-amino]-butyl}-isoindole-1,3-dione as a yellow oil (0.45 g, 40%). $^1$H NMR (CDCl$_3$) δ 1.26 (m, 2H), 1.50-1.70 (m, 3H), 1.75-2.00 (m, 1H), 2.03 (m, 2H), 2.54 (m, 2H), 2.57-2.80 (m, 2H), 3.55

(t, 2H, J=6.0 Hz), 3.83 (s, 2H), 3.97 (m, 1H), 4.84 (d, 1H, J=15.0 Hz), 4.92 (d, 1H, J=15.0 Hz), 5.07 (br d, 2H, J=7.5 Hz), 5.93 (m, 1H), 6.77 (s, 1H), 6.82 (s, 1H), 7.01 (m, 1H), 7.30 (d, 1H, J=7.0 Hz), 7.70 (m, 2H), 7.82 (m, 2H), 8.40 (d, 1H, J=3.0 Hz).

A solution of the above compound (0.45 g, 0.96 mmol) in anhydrous ethanol (10 mL) was treated with hydrazine monohydrate (0.50 mL, 9.6 mmol) and stirred for 16 h. The white mixture was then filtered, concentrated under reduced pressure, and purified by column chromatography with silica gel (10:1:84 methanol:ammonium hydroxide:dichloromethane) to give a mixture of N-propyl and N-allylimidazole products. (0.19 g, 58%).

The material from above (0.19 g) was dissolved in anhydrous methanol (5.6 mL) and the reaction vessel purged with nitrogen. 10% palladium on carbon (40 mg) was added and the mixture stirred under an atmosphere of hydrogen (30 psi) for 16 hours. The reaction mixture was then filtered through celite and the solvent removed under reduced pressure. The crude material was then diluted with ethyl acetate (20 mL) and washed with brine (4×15 mL) to remove DMF. The organic phase was then dried ($Na_2SO_4$), filtered, and concentrated under reduced pressure to give a residue that was purified by column chromatography with silica gel (5:1:94 methanol:ammonium hydroxide:dichloromethane). This afforded N-(1-propyl-1H-imidazol-2-ylmethyl)-N-(5,6,7,8-tetrahydroquinolin-8-yl)-butane-1,4-diamine (67 mg, 35%). $^1$H NMR ($CDCl_3$) δ 0.84 (t, 3H, J=7.5 Hz), 1.40 (br, 4H), 1.67 (m, 3H), 1.80-2.05 (m, 3H), 2.50-2.85 (m, 6H), 3.31 (br, 2H, NH), 3.78 (s, 2H), 3.96 (m, 1H), 4.07 (m, 1H), 4.14 (m, 1H), 6.81 (s, 1H), 6.89 (s, 1H), 7.06 (m, 1H), 7.35 (d, 1H, J=6.0 Hz), 8.51 (d, 1H, J=6.0 Hz).

Using general procedure D: The above material (67 mg, 0.19 mmol) was converted to the hydrobromide salt to provide COMPOUND 130 (108 mg) as a white solid. $^1$H NMR ($D_2O$) δ 0.90 (t, 3H, J=7.4 Hz), 1.50 (br, 4H), 1.81 (m, 3H), 2.04 (m, 1H), 2.17 (br m, 1H), 2.36 (br m, 1H), 2.48 (br m, 1H), 2.75 (br m, 1H), 2.89 (br, 2H), 3.00 (br, 2H), 4.10-4.18 (m, 3H), 4.34 (d, 1H, J=16.8 Hz), 4.40 (m, 1H), 7.47 (s, 2H), 7.86 (t, 2H, J=7.0 Hz), 8.34 (d, 1H, J=8.1 Hz), 8.59 (d, 1H, J=5.7 Hz). $^{13}$C NMR ($D_2O$) δ 10.43, 20.30, 20.42, 23.28, 25.08, 25.42, 27.68, 39.56, 46.60, 49.72, 51.63, 60.36, 119.11, 123.29, 125.93, 139.35, 140.59, 144.68, 148.12, 151.28. ES-MS m/z 342 (M+H). Anal. Calcd. for $C_{20}H_{31}N_5 \cdot 3.5HBr \cdot 1.9H_2O \cdot 0.3C_4H_{10}O$: C, 37.38; H, 6.11; N, 10.28; Br, 41.06. Found: C, 37.43; H, 5.86; N, 10.28; Br, 40.90.

Example 131

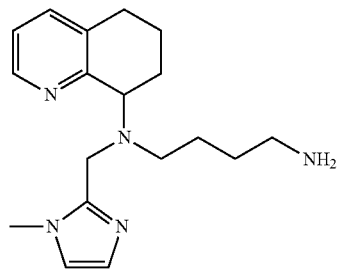 [SMILES: Cn1ccnc1CN(CCCCN)C1CCCc2cccnc21]

Compound 131: $N^1$-(1-methyl-1H-imidazol-2-ylmethyl)-$N^1$-(5,6,7,8-tetrahydro-quinolin-8-yl)butane-1,4-diamine (hydrobromide salt)

Preparation of 2-{4-[(1-methyl-1H-imidazol-2-ylmethyl)-(5,6,7,8-tetrahydro-quinolin-8-yl)-amino]-butyl}-isoindole-1,3-dione To a solution of 2-[4-(5,6,7,8-tetrahydro-quinolin-8-ylamino)-butyl]-isoindol-1,3-dione (190 mg, 0.544 mmol) and 1-methyl-2-imidazolecarboxaldehyde (54 mg, 0.49 mmol) in $CH_2Cl_2$ (2.5 mL) was added sodium triacetoxyborohydride (209 mg, 0.99 mmol). It was then diluted with $CH_2Cl_2$ (15 mL) and extracted with saturated $NaHCO_3$ (2×15 mL). The organic layer was dried ($MgSO_4$), filtered, concentrated, and dried in vacuo to afford a yellow oil. Purification by radial chromatography on silica gel (2 mm plate, using $NH_4OH/CH_3OH/CH_2Cl_2$; 1:1:100→1:3:100, gradient elution) afforded the desired product as a yellow oil (160 mg, 73%). $^1$H NMR ($CDCl_3$) δ 1.24-1.31 (m, 2H), 1.51-1.66 (m, 2H), 1.84-2.07 (m, 3H), 2.53-2.76 (m, 5H), 3.54 (t, 2H, J=7.2 Hz), 3.77 (2, 3H), 3.74 (d, 2H, J=15.9 Hz), 3.97 (t, 1H, J=9.0 Hz), 6.73 (s, 1H), 6.77 (s, 1H), 6.99 (dd, 1H, J=7.5, 4.8 Hz), 7.30 (d, 1H, J=7.5 Hz), 7.68-7.72 (m, 2H), 7.78-7.84 (m, 2H), 8.40 (d, 1H, J=3.9 Hz).

Preparation of $N^1$-(1-methyl-1H-imidazol-2-ylmethyl)-$N^1$-(5,6,7,8-tetrahydro-quionlin-8-yl)-butane-1,4-diamine To a solution of the above amine (152 mg, 0.34 mmol) in ethanol (8 mL) was added hydrazine hydrate (83 µL, 1.71 mmol). The reaction mixture was stirred overnight. Then the solvent was removed under reduced pressure to afford a yellow solid. Purification by radial chromatography on silica gel (1 mm plate, using $NH_4OH/CH_3OH/CH_2Cl_2$; 1:3:100→1:6:100, gradient elution) afforded the desired product as a yellow oil (48 mg, 47%). $^1$H NMR ($CDCl_3$) δ 1.33-1.35 (br s, 2H), 1.64-1.67 (m, 1H), 1.87-2.05 (m, 3H), 2.52-2.77 (m, 6H), 3.43 (s, 2H), 3.71 (s, 3H), 3.81 (s, 2H), 4.00 (t, 1H, J=7.4 Hz), 6.76 (s, 1H), 6.84 (s, 1H), 7.03 (dd, 1H, J=7.7, 4.8 Hz), 7.33 (d, 1H, J=7.5 Hz), 8.44 (d, 1H, J=4.5 Hz), Preparation of $N^1$-(1-methyl-1H-imidazol-2-ylmethyl)-$N^1$-(5,6,7,8-tetrahydro-quionlin-8-yl)-butane-1,4-diamine (hydrobromide salt)

To a solution of the above amine (48 mg, 0.015 mmol) in acetic acid (3 mL) was added hydrobromic acid saturated acetic acid (2 mL) and the reaction mixture was stirred for 30 minutes. Then it was triturated with diethyl ether three times to afford a white solid. The solid was dissolved in methanol (1 mL) and was triturated with diethyl ether three times to afford COMPOUND 131 as a white solid (72 mg, 79%). $^1$H NMR ($D_2O$) δ 1.52-1.55 (m, 4H), 1.75-1.89 (m, 1H), 2.01 (q, 1H, J=13.2 Hz), 2.15-2.21 (m, 1H), 2.36-2.39 (m, 1H), 2.49-2.55 (m, 1H), 2.74-2.82 (m, 1H), 2.89-2.91 (m, 2H), 3.00-3.03 (m, 2H), 3.83 (s, 3H), 4.22 (ABq, 2H, J=53.9, 16.8 Hz), 4.42 (dd, 1H, J=9.0, 5.4 Hz), 7.42 (ABq, 2H, J=12.9, 2.1 Hz), 7.86 (dd, 1H, J=8.1, 6.0 Hz), 8.35 (d, 1H, J=8.1 Hz), 8.59 (d, 1H, J=5.1 Hz). $^{13}$C NMR ($D_2O$) δ 20.29, 20.43, 25.08, 25.36, 27.67, 34.73, 39.56, 46.37, 51.71, 60.28, 118.73, 124.50, 125.90, 139.35, 140.60, 144.98, 148.10, 151.33. ES-MS m/z 314 [M+H]$^+$. Anal. Calcd. for $C_{18}H_{27}N_5 \cdot 3.0HBr \cdot 2.1H_2O$: C, 36.40; H, 5.80; N, 11.79; Br, 40.35. Found: C, 36.28; H, 5.78; N, 11.48; Br, 40.66.

Example 132

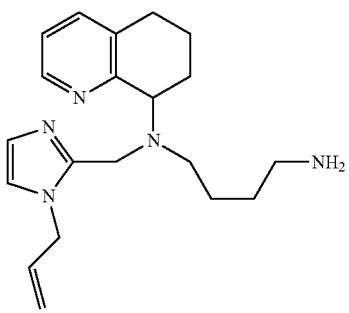 [SMILES: C=CCn1ccnc1CN(CCCCN)C1CCCc2cccnc21]

Compound 132: Preparation of $N^1$-(1-allyl-1H-imidazol-2-ylmethyl)-$N^1$-(5,6,7,8-tetrahydroquinolin-8-yl)-butane-1,4-diamine (hydrobromide salt)

To a solution of 2-Imidazolecarboxaldehyde (0.81 g, 8.4 mmol) and diisopropylethylamine (2.2 mL, 12.6 mmol) in anhydrous DMF (28 mL) was added allyl bromide (0.88 mL, 10.1 mmol) and the solution was stirred at 60° C. for 16 hours. The mixture was then concentrated under reduced pressure and the residue partitioned between dichloromethane (20 mL) and sodium bicarbonate (15 mL). The organic phase was separated and the aqueous phase was extracted with dichloromethane (2×15 mL). The combined organic phases were then dried ($Na_2SO_4$), filtered, and concentrated under reduced pressure to give a crude residue that was purified by column chromatography with silica gel (1:99 MeOH/$CH_2Cl_2$). This afforded 2-(N-allylimidazole)-carboxaldehyde (0.62 g, 54%). $^1$H NMR ($CDCl_3$) δ 5.02 (d, 2H, J=6.0 Hz), 5.10 (d, 1H, J=18.0 Hz), 5.25 (d, 1H, J=9.0 Hz), 5.96 (m, 1H), 7.16 (s, 1H), 7.30 (s, 1H), 9.81 (s, 1H).

Using general procedure B, 2-[4-(5,6,7,8-Tetrahydro-quinolin-8-ylamino)-butyl]-isoindole-1,3-dione (0.80 g, 2.3 mmol), 2-(N-allylimidazole)-carboxaldehyde (0.62 g, 4.5 mmol) and sodium triacetoxyborohydride (1.16 g, 5.5 mmol) were stirred at room temperature in dichloromethane (22 mL) for 16 hours to yield, after work-up and column chromatography (1:4 ethyl acetate:hexane), 2-{4-[(1-Allyl-1H-imidazol-2-ylmethyl)-(5,6,7,8-tetrahydroquinolin-8-yl)-amino]-butyl}-isoindole-1,3-dione as a yellow oil (0.45 g, 40%). $^1$H NMR ($CDCl_3$) δ 1.26 (m, 2H), 1.50-1.70 (m, 3H), 1.75-2.00 (m, 1H), 2.03 (m, 2H), 2.54 (m, 2H), 2.57-2.80 (m, 2H), 3.55 (t, 2H, J=6.0 Hz), 3.83 (s, 2H), 3.97 (m, 1H), 4.84 (d, 1H, J=15.0 Hz), 4.92 (d, 1H, J=15.0 Hz), 5.07 (br d, 2H, J=7.5 Hz), 5.93 (m, 1H), 6.77 (s, 1H), 6.82 (s, 1H), 7.01 (m, 1H), 7.30 (d, 1H, J=7.0 Hz), 7.70 (m, 2H), 7.82 (m, 2H), 8.40 (d, 1H, J=3.0 Hz).

A solution of the above compound (0.40 g, 0.85 mmol) in anhydrous ethanol (8.4 mL) was treated with n-butylamine (0.85 mL, 8.5 mmol) and stirred for 16 h at 80° C. The solution was then concentrated under reduced pressure and purified by column chromatography with silica gel (2:1:97 methanol:ammonium hydroxide:dichloromethane) to give N-(1-allyl-1H-imidazol-2-ylmethyl)-N-(5,6,7,8-tetrahydroquinolin-8-yl)-butane-1,4-diamine. (0.19 g, 66%). $^1$H NMR ($CDCl_3$) δ 1.35 (br, 4H), 1.67 (m, 1H), 1.80-2.10 (m, 3H), 2.55 (br, 4H), 2.62-2.80 (m, 2H), 3.80 (s, 2H), 4.02 (m, 1H), 4.75 (dd, 1H, J=4.5, 18.0 Hz), 4.89 (d, 1H, J=18.0 Hz), 5.05 (dd, 1H, J=4.5, 18.0 Hz), 5.09 (d, 1H, J=18.0 Hz), 5.88 (m, 1H), 6.81 (s, 1H), 6.90 (s, 1H), 7.04 (m, 1H), 7.33 (d, 1H, J=6.0 Hz), 8.45 (d, 1H, J=6.0 Hz).

Using general procedure D: The above material (180 mg, 0.53 mmol) was converted to the hydrobromide salt to provide COMPOUND 132 (312 mg) as a white solid. $^1$H NMR ($D_2O$) δ 1.53 (br, 5H), 1.81 (br m, 1H), 1.96 (m, 1H), 2.18 (br m, 1H), 2.34 (br m, 1H), 2.48 (br m, 1H), 2.74 (br m, 1H), 2.89 (br, 2H), 3.00 (br, 2H), 4.14 (d, 1H, J=16.8 Hz), 4.32 (d, 1H, J=16.5 Hz), 4.38 (m, 1H), 4.85 (br d, 2H, J=5.1 Hz), 5.18 (d, 1H, J=17.1 Hz), 5.40 (d, 1H, J=10.5 Hz), 6.02 (m, 1H), 7.48 (d, 1H, J=1.8 Hz), 7.51 (d, 1H, J=1.8 Hz), 7.87 (t, 2H, J=6.8 Hz), 8.35 (d, 1H, J=7.8 Hz), 8.60 (d, 1H, J=5.7 Hz). $^{13}$C NMR ($D_2O$) δ 20.23, 20.39, 25.08, 25.39, 27.66, 39.57, 46.51, 50.32, 51.57, 60.32, 119.20, 119.92, 123.65, 125.95, 131.00, 139.35, 140.60, 145.01, 148.14, 151.27. ES-MS m/z 340 (M+H). Anal. Calcd. for $C_{20}H_{29}N_5$.3.0HBr.1.6$H_2O$: C, 39.31; H, 5.81; N, 11.46; Br, 39.23. Found: C, 39.54; H, 5.80; N, 11.07; Br, 39.13.

Example 133

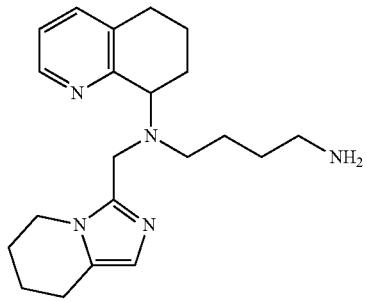 [SMILES: NCCCCN(Cc1ncc2n1CCCC2)C1CCCc2cccnc21]

Compound 133: Preparation of $N^1$-(5,6,7,8-Tetrahydro-imidazo[1,5-a]pyridin-3-ylmethyl)-$N^1$-(5,6,7,8-tetrahydro-quinolin-8-yl)-butane-1,4-diamine (hydrobromide salt)

Preparation of 5,6,7,8-Tetrahydro-imidazo[1,5-a]pyridine-3-carbaldehyde

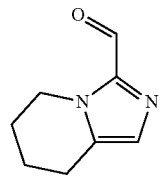 [SMILES: O=Cc1ncc2n1CCCC2]

To a solution of 5,6,7,8-tetrahydro-imidazo[1,5-a]pyridine (prepared as described by Lattrell, R. et al. *The J. of Antibiotics* 1988, 41, 1395-1408) in THF (7 mL) at −78° C. was added a solution of n-BuLi (2.5 M in hexanes, 0.70 mL, 1.75 mmol) and the reaction stirred at −78° C. for 10 min. DMF (1.0 mL) was added to the mixture at −78° C. and the reaction warmed to room temperature and stirred for 2 h before quenching with saturated aqueous NH₄Cl (5 mL). The mixture was diluted with EtOAc (30 mL) and brine and the organic phase washed with brine (1×30 mL), dried (Na₂SO₄) and concentrated in vacuo. The resultant brown oil (191 mg) was purified by column chromatography on silica gel (CH₂Cl₂/MeOH, 96:4) to afford the desired aldehyde (105 mg, 40%) as an orange oil. $^1$H NMR (CDCl₃) δ 1.83-1.89 (m, 2H), 1.94-2.02 (m, 2H), 2.85 (t, 2H, J=6 Hz), 4.39 (t, 2H, J=6 Hz), 7.05 (s, 1H), 9.71 (s, 1H).

Following General Procedure B: To a stirred solution of 2-[4-(5,6,7,8-tetrahydro-quinolin-8-ylamino)-butyl]-isoindole-1,3-dione (174 mg, 0.50 mmol) and 5,6,7,8-tetrahydro-imidazo[1,5-a]pyridine-3-carbaldehyde (82 mg, 0.48 mmol) in dry CH₂Cl₂ (7 mL) was added NaBH(OAc)₃ (152 mg, 0.72 mmol) and the mixture stirred at room temperature for 5.5 h. The resultant yellow foam (271 mg) was purified by column chromatography on silica gel (CH₂Cl₂/MeOH/NH₄OH, 96:4:0 then 92:8:0 then 94:4:2) to afford the desired amine (153 mg, 66%) as a white foam.

To a solution of the phthalimide from above (153 mg, 0.32 mmol) in EtOH (4 mL) was added anhydrous hydrazine (0.055 mL, 1.73 mmol) and the mixture stirred overnight. The resultant white solid was filtered through filter paper, washing thoroughly with CH₂Cl₂ and the filtrate concentrated in vacuo. The crude product was purified by radial chromatography on silica gel (1 mm plate, CH₂Cl₂/MeOH/NH₄OH, 50:1:1 then 20:1:1 then 10:1:1 to give the desired free amine (72 mg, 64%) as a pale yellow oil.

Using General Procedure D: Conversion of the material from above (72 mg, 0.20 mmol) to the hydrobromide salt gave COMPOUND 133 (106 mg, 78%) as a yellow solid. $^1$H NMR (D₂O) δ 1.48-1.60 (m, 4H), 1.75-1.87 (m, 3H), 1.96-2.07 (m, 3H), 2.16-2.20 (m, 1H), 2.34-2.38 (m, 1H), 2.49-2.55 (m, 1H), 2.74-2.83 (m, 3H), 2.89-2.95 (m, 2H), 2.99-3.02 (m, 2H), 4.06-4.13 (m, 3H), 4.24 (d, 1H, J=16.8 Hz), 4.42 (dd, 1H, J=10.5, 5.4 Hz), 7.14 (s, 1H), 7.85 (dd, 1H, J=7.8, 6 Hz), 8.33 (d, 1H, J=7.8 Hz), 8.58 (d, 1H, J=5.7 Hz); $^{13}$C NMR (D₂O) δ 18.77, 20.19, 20.42, 21.77, 25.10, 25.39, 27.68, 39.59, 44.44, 46.04, 51.84, 60.13, 114.38, 125.85, 132.38, 139.32, 140.57, 142.58, 148.04, 151.44. ES-MS m/z 354 (M+H). Anal Calcd. for C₂₁H₃₁N₅·3.3HBr·0.9H₂O·0.4C₄H₁₀O: C, 40.73; H, 6.07; N, 10.51; Br, 39.57. Found: C, 40.48; H, 5.71; N, 10.34; Br, 39.83.

Example 134

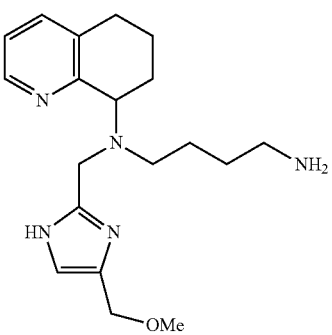 [SMILES: COCc1c[nH]c(CN(CCCCN)C2CCCc3cccnc32)n1]

Compound 134: Preparation of N¹-(4-Methoxymethyl-1H-imidazol-2-ylmethyl)-N¹-(5,6,7,8-tetrahydro-quinolin-8-yl)-butane-1,4-diamine (hydrobromide salt)

Preparation of 4(and 3)-Methoxymethyl-1-(2-trimethylsilanyl-ethoxymethyl)-1H-imidazole-2-carbaldehyde

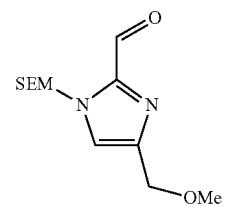 [SMILES: COCc1cn(COCC[Si](C)(C)C)c(C=O)n1]

To a solution of 4-(hydroxymethyl)imidazole hydrochloride (578 mg, 4.30 mmol) in DMF (3.5 mL) was added DIPEA (1.9 mL, 10.9 mmol) and 2-(trimethylsilyl)ethoxymethyl chloride (0.83 mL, 4.69 mmol) and the mixture stirred overnight. The reaction was diluted with EtOAc (60 mL) and brine (40 mL) and the organic layer washed with brine (2×40 mL), dried (Na₂SO₄) and concentrated. The resultant yellow oil (1.04 g) was purified by column chromatography on silica gel (CH₂Cl₂/MeOH/NH₄OH, 96:4:0 then 94:4:2 then 88:10:2) to afford the desired SEM-protected imidazole (416 mg, 42%) as a mixture of regioisomers.

To a solution of the alcohol from above (416 mg, 1.82 mmol) in THF (10 mL) at 0° C. was added NaH and the mixture stirred for 30 min. To the resultant suspension was added MeI and the reaction stirred from 0° C. to room temperature over 2.5 h before diluting with H2O (20 mL) and EtOAc (25 mL). The organic phase was washed with brine (1×25 mL), dried (Na₂SO₄) and concentrated to afford the desired methyl ether (430 mg) as a yellow oil.

To a solution of the imidazole from above (430 mg, 1.78 mmol) in THF (10 mL) at 78° C. was added a solution of n-BuLi (2.5 M in hexanes, 0.71 mL, 1.78 mmol) and the reaction stirred at −78° C. for 10 min. DMF (1.0 mL) was added to the mixture at −78° C. and the reaction warmed to room temperature and stirred for 2 h before quenching with saturated aqueous NH₄Cl (10 mL). The mixture was diluted with EtOAc (30 mL) and brine (20 mL) and the organic phase washed with brine (1×30 mL), dried (Na₂SO₄) and concentrated in vacuo. The resultant yellow oil was purified by column chromatography on silica gel (Hexanes/EtOAc, 2:1) to afford a mixture of the desired two regioisomeric aldehydes (194 mg, 40%) as a yellow oil. $^1$H NMR (CDCl₃) δ 1.83-1.89 (m, 2H), 1.94-2.02 (m, 2H), 2.85 (t, 2H, J=6 Hz), 4.39 (t, 2H, J=6 Hz), 7.05 (s, 1H), 9.71 (s, 1H).

Following General Procedure B: To a stirred solution of 2-[4-(5,6,7,8-tetrahydro-quinolin-8-ylamino)-butyl]-isoindole-1,3-dione (269 mg, 0.77 mmol) and 4(and 3)-methoxymethyl-1-(2-trimethylsilanyl-ethoxymethyl)-1H-imidazole-2-carbaldehyde (194 mg, 0.72 mmol) in dry CH₂Cl₂ (8 mL) was added NaBH(OAc)₃ (236 mg, 1.11 mmol) and the mixture stirred at room temperature for 4 h. The resultant crude brown oil (459 mg) was purified by column chromatography on silica gel (CH₂Cl₂/MeOH, 96:4) to afford the desired amine (329 mg, 76%) as a pale yellow oil.

A solution of the SEM-protected imidazole (329 mg, 0.55 mmol) in 4 N HCl (8 mL) was stirred at 60° C. for 4.5 h then cooled to room temperature and neutralized with solid $K_2CO_3$ (8.1 g). The slurry was diluted with $H_2O$ (15 mL) and $CH_2Cl_2$ (30 mL) and the aqueous phase extracted with $CH_2Cl_2$ (3×30 mL). The combined organic layers were dried ($Na_2SO_4$), concentrated and purified by column chromatography on silica gel ($CH_2Cl_2$/MeOH, 96:4 then 92:8) to afford the desired product (248 mg, 96%) as a clear oil.

To a solution of the phthalimide from above (248 mg, 0.52 mmol) in EtOH (4 mL) was added anhydrous hydrazine (0.10 mL, 3.15 mmol) and the mixture stirred overnight. The resultant white solid was filtered through filter paper, washing thoroughly with $CH_2Cl_2$ and the filtrate concentrated in vacuo. The crude product was purified by radial chromatography on silica gel (1 mm plate, $CH_2Cl_2$/MeOH/$NH_4OH$, 50:1:1 then 25:1:1 then 10:1:1) to give the desired free amine (83 mg, 46%) as a clear oil.

Using General Procedure D: Conversion of the material from above (83 mg, 0.18 mmol) to the hydrobromide salt gave COMPOUND 134 (137 mg, 88%) as a white solid. $^1$H NMR ($D_2O$) δ 1.44-1.55 (m, 4H), 1.79-2.01 (m, 2H), 2.14-2.18 (m, 1H), 2.26-2.31 (m, 1H), 2.43-2.53 (m, 1H), 2.72-2.79 (m, 1H), 2.88-2.92 (m, 2H), 2.98-3.01 (m, 2H), 3.40 (s, 3H), 4.16 (d, 1H, J=16.2 Hz), 4.29 (d, 1H, J=16.2 Hz), 4.42 (dd, 1H, J=10.5, 5.4 Hz), 4.58 (s, 2H), 7.47 (s, 1H), 7.86 (dd, 1H, J=7.8, 6 Hz), 8.34 (d, 1H, J=7.8 Hz), 8.59 (d, 1H, J=5.7 Hz); $^{13}$C NMR ($D_2O$) δ 20.33, 20.46, 25.08, 25.37, 27.63, 39.59, 47.43, 51.36, 58.23, 60.30, 63.39, 118.68, 125.90, 129.93, 139.28, 140.51, 146.34, 148.04, 151.45. ES-MS m/z 344 (M+H). Anal. Calcd. for $C_{19}H_{29}N_5O \cdot 3.2HBr \cdot 0.7H_2O \cdot 0.4C_4H_{10}O$: C, 38.38; H, 5.88; N, 10.86; Br, 39.66. Found: C, 38.42; H, 5.75; N, 10.92; Br, 39.56.

Example 135

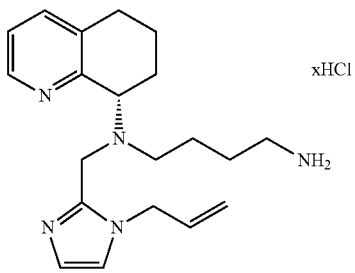 [SMILES: C=CCn1ccnc1CN(CCCCN)[C@H]1CCCc2cccnc21]

Compound 135: Preparation of $N^1$-(1-Allyl-1H-imidazol-2-ylmethyl)-$N^1$-(S)-5,6,7,8-tetrahydro-quinolin-8-yl-butane-1,4-diamine (Hydrochloride salt)

Preparation of 1-Allyl-1H-imidazole-2-carbaldehyde

A solution of 2-imidazole carboxaldehyde (15.0 g, 156 mmol), allyl bromide (22.6 g, 187 mmol) and diisopropylethylamine (40.7 mL, 234 mmol) was stirred in N,N-dimethylformamide (500 mL) for 23 hours. The solvent was removed under reduced pressure and the residue was dissolved in dichloromethane (370 mL). The solution was washed once with a saturated solution of sodium carbonate (185 mL). The layers were separated and the aqueous layer was extracted with dichloromethane (2×280 mL). The combined organic portions were dried with sodium sulfate, filtered and concentrated under reduced pressure to afford a yellow oil. The crude material was then purified by flash chromatography (99:1 $CH_2Cl_2$/methanol) to provide the desired compound (12.8 g, 60%) as yellow oil. $^1$H NMR (300 MHz, CDCl$_3$, δ ppm) 5.04 (d, 2H, J=5.5 Hz), 5.11 (d, 1H, J=17.5 Hz), 5.25 (d, 1H, J=10.0 Hz), 5.90-6.05 (m, 1H), 7.16 (s, 1H), 7.30 (s, 1H), 9.81 (s, 1H); $^{13}$C NMR (75 MHz, CDCl$_3$, ppm) 49.77, 118.61, 126.00, 131.74, 132.39, 143.17, 182.05.

Preparation of $N^1$-(1-Allyl-1H-imidazol-2-ylmethyl)-$N^1$—(S)-5,6,7,8-tetrahydro-quinolin-8-yl-butane-1,4-diamine (Compound 135)

Using general procedure B: Reaction of N'-(S)-5,6,7,8-tetrahydro-quinolin-8-yl-butane-1,4-diamine (29.86 g, 85 mmol) and 1-Allyl-1H-imidazole-2-carbaldehyde (12.8 g, 94 mmol) with NaBH(OAc)$_3$ (18.0 g, 85 mmol) in $CH_2Cl_2$ (470 mL) for 39 hours followed by purification of the crude material by flash chromatography (4:1 AcOEt/hexane) provided 21 g of a yellow oil. $^1$H NMR (300 MHz, CDCl$_3$, δ ppm) 3.55 (t, 2H, J=7.0 Hz), 1.20-2.80 (series of m, 12H), 3.84 (s, 2H), 3.98 (m, 1H), 4.87 (dd, 1H, J=1.0 & 17.0 Hz), 4.70-5.15 (m, 2H), 5.08 (dd, 1H, J=1.0 & 10.0 Hz), 5.80-6.00 (m, 1H), 6.76 (d, 1H, J=1.0 Hz), 6.82 (d, 1H, J=1.0 Hz), 7.00 (dd, 1H, J=4.5 & 7.5 Hz), 7.31 (d, 1H, J=7.5 Hz), 7.65-7.75 (m, 2H), 7.75-7.85 (m, 2H), 8.41 (d, 1H, J=4.5 Hz).

The 2-{4-[(S)-(1-Allyl-1H-imidazol-2-ylmethyl)-5,6,7,8-tetrahydro-quinolin-8-yl-amino]-butyl}-isoindole-1,3-dione (21 g, 45 mmol) was dissolved in ethanol (450 mL) and was treated with n-butylamine (44.6 mL, 450 mmol). The solution was stirred at 60° C. for 21 hours. The mixture was concentrated under reduced pressure and was purified by flash chromatography (97:2:1 $CH_2Cl_2$/methanol/$NH_4OH$ and slowly raised the amount of methanol from 2% to 10%). The cleanest fractions (7.37 g, 77%) were carried through the salting procedure.

Following general procedure D, conversion of the material to his hydrochloride salt and re-precipitation from methanol/diethylether gave COMPOUND 135 (7.97 g, 82%) as beige solid. $^1$H NMR (300 MHz, $D_2O$, δ ppm) 1.45-1.60 (m, 4H), 1.65-1.85 (m, 1H), 1.85-2.05 (m, 1H), 2.05-2.20 (m, 1H), 2.25-2.40 (m, 1H), 2.40-2.55 (m, 1H), 2.65-2.80 (m, 1H), 2.85-2.95 (m, 2H), 2.95-3.05 (m, 2H), 4.10 (d, 1H, J=17.0 Hz), 4.28 (d, 1H, 17.0 Hz), 4.30-4.40 (m, 1H), 4.80-4.85 (m, 2H), 5.14 (d, 1H, J=17.0 Hz), 5.36 (d, 1H, J=10.5 Hz), 5.90-6.10 (m, 1H), 7.46 (d, 1H, J=2.0 Hz), 7.81 (dd, 1H, J=5.5 & 8.0 Hz), 8.28 (d, 1H, J=8.0 Hz), 8.57 (d, 1H, J=5.5 Hz); $^{13}$C NMR ((75 MHz, $D_2O$, δ ppm) 20.20, 20.40, 25.06, 25.37, 27.66, 39.58, 46.50, 50.30, 51.56, 60.29, 119.17, 119.91, 123.62, 125.93, 131.02, 139.34, 140.55, 145.01, 148.11, 151.23. ES-MS m/z 340 (M+H). Anal. Calcd. for $C_{20}H_{29}N_5 \cdot 3.2HCl \cdot 3H_2O \cdot 0.3C_4H_{10}O$: C, 47.82; H, 7.80; N, 13.15; Cl, 21.31. Found: C, 47.98; H, 7.60; N, 13.11; Cl, 21.17.

Example 136

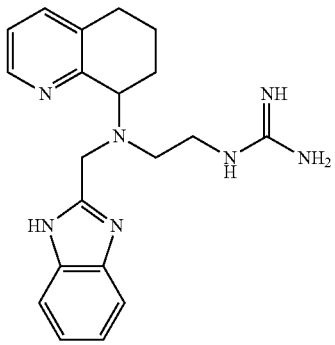 [SMILES: N=C(N)NCCN(Cc1nc2ccccc2[nH]1)C1CCCc2cccnc21]

Compound 136: Preparation of N¹-{2-[(1H-Benz-imidazol-2-ylmethyl)-N¹-(5,6,7,8-tetrahydro-quinolin-8-yl)-amino]-ethyl}-guanidine (hydrobromide salt)

Using General Procedure B: Reaction of N-(tert-butoxycarbonyl)-2-amino-acetaldehyde (0.204 g, 1.28 mmol) and (1H-Benzimidazol-2-ylmethyl)-(5,6,7,8-tetrahydro-quinolin-8-yl)-amine (0.284 g, 1.02 mmol) with NaBH(OAc)$_3$ (0.430 g, 2.03 mmol) in CH$_2$Cl$_2$ (10 mL) provided 0.71 g of a yellow foam. The foam was dissolved in THF (10 mL) and treated with 6N hydrochloric acid (10 mL). The resultant solution was stirred at room temperature overnight. The solution was neutralized with solid K$_2$CO$_3$ (5 g), diluted with water (5 mL) and extracted with CH$_2$Cl$_2$ (3×20 mL). The combined organic extracts were dried (Na$_2$SO$_4$) and concentrated. Purification of the crude material by column chromatography on silica gel (20:1:1 CH$_2$Cl$_2$—CH$_3$OH—NH$_4$OH) provided 0.205 g (64%) of N¹-(1H-Benzimidazol-2-ylmethyl)-1-(5,6,7,8-tetrahydro-quinolin-8-yl)-ethane-1,2-diamine as a yellow solid. To a solution of N¹-(1H-Benzimidazol-2-ylmethyl)-N¹-(5,6,7,8-tetrahydro-quinolin-8-yl)-ethane-1,2-diamine (0.205 g, 0.64 mmol) in dry THF (6 mL) was added N,N'-bis(tert-butoxycarbonyl)-1H-pyrazole-1-carboxamidine (*Tetrahedron Lett.* 1993, 34, 3389.) (0.201 g, 0.64 mmol) and the resultant mixture was stirred at room temperature for 18 hours. The mixture was concentrated and the resultant oil was purified by column chromatography on silica gel (40:1:1 CH$_2$Cl$_2$—CH$_3$OH—NH$_4$OH) and provided 0.267 g (74%) of N,N'-bis(tert-butoxycarbonyl)-N'''-{2-[(1H-Benzimidazol-2-ylmethyl)-(5,6,7,8-tetrahydro-quinolin-8-yl)-amino]-ethyl}-guanidine as a white foam.

Using General Procedure D: Conversion of the white foam (257 mg) to the hydrobromide salt with simultaneous removal of the BOC-protecting groups, followed by reprecipitation of the intermediate solid from methanol/ether gave COMPOUND 136 (253 mg, 86%) as a white solid. ¹H NMR (D$_2$O) δ 1.77-1.87 (m, 1H), 1.97-2.18 (m, 2H), 2.32-2.37 (m, 1H), 2.75-2.84 (m, 1H), 2.96-3.10 (m, 3H), 3.19-3.33 (m, 2H), 4.39 (d, 1H, J=16.5 Hz), 4.51-4.57 (m, 2H), 7.58-7.61 (m, 2H), 7.77-7.88 (m, 3H), 8.34 (d, 1H, J=8.1 Hz), 8.65 (d, 1H, J=5.7 Hz); ¹³C NMR (D$_2$O) δ 20.33, 20.57, 27.71, 39.96, 48.11, 50.17, 60.70, 114.33, 126.03, 126.99, 131.28, 139.68, 140.87, 148.18, 150.46, 150.84; ES-MS m/z 364 (M+H). Anal. Calcd. for C$_{20}$H$_{25}$N$_7$·3.0HBr·1.5H$_2$O·0.2C$_4$H$_{10}$O: C, 38.55; H, 5.13; N, 15.13; Br, 36.99. Found: C, 38.54; H, 5.07; N, 15.05; Br, 36.95.

Example 137

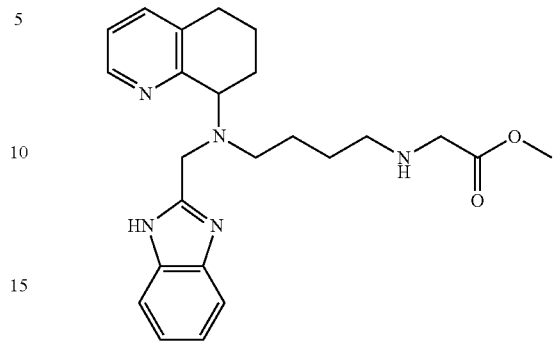

Compound 137: Preparation of {4-[(1H-Benzimidazol-2-ylmethyl)-(5,6,7,8-tetrahydro-quinolin-8-yl)-amino]-butylamino}-acetic acid methyl ester (hydrobromide salt)

Preparation of [(2-Nitro-benzenesulfonyl)-(4-oxobutyl)-amino]-acetic acid methyl ester

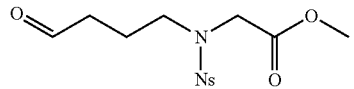

To a solution of 4-amino-1-butanol (555 mg, 6.23 mmol) in THF/saturated aqueous NaHCO$_3$ (2:1, 15 mL) at 0° C. was added 2-nitrobenzenesulfonyl chloride (1.4492 g, 6.54 mmol) and the reaction stirred overnight. The mixture was diluted with CH$_2$Cl$_2$ (40 mL) and saturated aqueous NaHCO$_3$ (30 mL) and the aqueous layer extracted with CH$_2$Cl$_2$ (1×30 mL). The combined organic extracts were dried (Na$_2$SO$_4$) and concentrated in vacuo. The resultant yellow solid (1.74 g) was washed with Et$_2$O (3×15 mL) and dried in vacuo to afford the nosyl-protected alcohol (1.34 g, 78%) as a white solid.

To a suspension of the alcohol from above (1.34 g, 4.89 mmol) and K$_2$CO$_3$ (1.346 g, 9.74 mmol) in CH$_3$CN (20 mL) was added methyl bromoacetate (0.55 mL, 5.81 mmol) and the reaction stirred overnight then at 50° C. for 4 h. The mixture was cooled to room temperature, concentrated, diluted with CH$_2$Cl$_2$ (50 mL) and washed with H$_2$O (40 mL). The aqueous layer was extracted with CH$_2$Cl$_2$ (1×15 mL) and the combined organic layers dried (Na$_2$SO$_4$) and concentrated to afford the alkylated amine (1.59 g) as a pale yellow oil.

A solution of the above alcohol (881 mg, 2.55 mmol) in CH$_2$Cl$_2$ (10 mL) was treated with molecular sieves (837 mg), N-methylmorpholine oxide (673 mg, 5.75 mmol), and TPAP (64 mg, 0.18 mmol). The mixture was stirred for 1.5 hours and then filtered through silica, washing with 1:1 EtOAc/hexanes. The filtrate was then concentrated under reduced pressure to afford the title compound (414 mg, 47%) as a pale yellow oil. ¹H NMR (CDCl$_3$) δ 1.86 (q, 2H, J=6 Hz), 2.57 (t, 2H, J=6 Hz), 3.43 (t, 2H, J=6 Hz), 3.65 (s, 3H), 4.17 (s, 2H), 7:59-7.62 (m, 1H), 7.68-7.71 (m, 2H), 8.02-8.05 (m, 1H), 9.75 (s, 1H).

Following General Procedure B: To a stirred solution of (1H-benzimidazol-2-ylmethyl)-(5,6,7,8-tetrahydro-quinolin-8-yl)-amine (155 mg, 0.56 mmol) and [(2-nitro-benzene-sulfonyl)-(4-oxo-butyl)-amino]-acetic acid methyl ester (189 mg, 0.55 mmol) in dry CH$_2$Cl$_2$ (10 mL) was added NaBH(OAc)$_3$ (159 mg, 0.75 mmol) and the mixture stirred at room temperature overnight. The resultant crude brown oil (0.81 g) was purified by column chromatography on silica gel (CH$_2$Cl$_2$/MeOH/NH$_4$OH, 95:4:1) to afford the desired amine (166 mg, 48%) as a yellow foam.

To a stirred solution of the nosyl-protected amine from above (125 mg, 0.21 mmol) in anhydrous CH$_3$CN (5 mL) at room temperature, was added thiophenol (0.12 mL, 1.17 mmol) followed by powdered K$_2$CO$_3$ (177 mg, 1.28 mmol). The resulting bright yellow solution was stirred at room temperature overnight. The solvent was removed under reduced pressure and CH$_2$Cl$_2$ (30 mL) and water (30 mL) were added to the residue. The phases were separated and the aqueous phase was extracted with CH$_2$Cl$_2$ (2×10 mL). The combined organic phases were dried (Na$_2$SO$_4$) and concentrated. Purification of the crude material by column chromatography on silica gel (CH$_2$Cl$_2$/1V1e0H/NH$_4$OH, 94:4:2) followed by radial chromatography on silica gel (1 mm plate, CH$_2$Cl$_2$/MeOH/NH$_4$OH, 100:1:1 the 50:1:1 then 25:1:1) provided the free base (33 mg, 37%) as a clear oil.

Using General Procedure D: Conversion of the material from above (33 mg, 0.078 mmol) to the hydrobromide salt gave COMPOUND 137 (43 mg, 78%) as a white solid. $^1$H NMR (D$_2$O) δ 1.54-1.59 (m, 4H), 1.76-1.90 (m, 1H), 1.97-2.09 (m, 1H), 2.16-2.21 (m, 1H), 2.36-2.39 (m, 1H), 2.55-2.61 (m, 1H), 2.81-2.88 (m, 1H), 2.99-3.02 (br m, 4H), 3.78 (s, 3H), 3.93 (s, 2H), 4.40 (d, 1H, J=16.8 Hz), 4.49-4.57 (m, 1H), 4.54 (d, 1H, J=16.8 Hz), 7.60 (dd, 2H, J=6, 3 Hz), 7.80 (dd, 2H, J=6, 3 Hz), 7.87 (dd, 1H, J=7.8, 6 Hz), 8.34 (d, 1H, J=7.8 Hz), 8.64 (d, 1H, J=5.7 Hz); $^{13}$C NMR (D$_2$O) δ 20.44, 23.66, 25.38, 27.65, 47.57, 47.62, 48.26, 51.64, 53.85, 60.67, 114.27, 125.94, 126.93, 131.00, 139.35, 140.61, 148.11, 151.24, 151.77, 168.15. ES-MS m/z 422 (M+H). Anal. Calcd. for C$_{24}$H$_{31}$N$_5$O$_2$.3.0HBr.2.2H$_2$O: C, 40.95; H, 5.50; N, 9.95; Br, 34.05. Found: C, 40.91; H, 5.57; N, 9.67; Br, 34.32.

Example 138

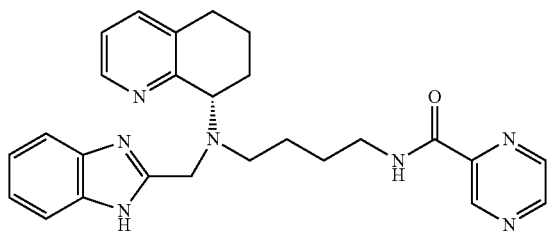 [SMILES: O=C(NCCCCN(Cc1nc2ccccc2[nH]1)[C@H]1CCCc2cccnc21)c1cnccn1]

Compound 138: Preparation of pyrazine-2-carboxylic acid {4-[(1H-benzimidazol-2-ylmethyl)-(S)-5,6,7,8-tetrahydro-quinolin-8-yl-amino]-butyl}-amide To a solution of N'-(1H-benzimidazol-2-ylmethyl)-N'-(S)-5,6,7,8-tetrahydro-quinolin-8-yl-butane-1,4-diamine (211 mg, 0.60 mmol) in CH$_2$Cl$_2$ (5 mL) was added 2-pyrazinecarboxylic acid (74.8 mg, 0.60 mmol), N,N-diisopropylethylamine (0.21 mL, 1.2 mmol), HOBT (97.7 mg, 0.72 mmol) and EDC (139 mg, 0.72 mmol). The resultant solution was stirred at room temperature for 16 h. The reaction mixture was diluted with CH$_2$Cl$_2$ (15 mL) and brine (25 mL) and the phases mixed and separated. The aqueous layer was extracted with CH$_2$Cl$_2$ (2×15 mL) and the combined organic extracts dried (Na$_2$SO$_4$), filtered, and concentrated in vacuo. Purification of the crude white foam by flash chromatography on silica gel (CH$_2$Cl$_2$/MeOH/NH$_4$OH, 100:3:1) gave the title compound (166 mg, 60%) as a white foam. $^1$H NMR (CDCl$_3$) δ 1.42-1.80 (m, 7H), 1.86-2.09 (m, 2H), 2.16-2.26 (m, 1H), 2.58-2.90 (m, 4H), 3.23-3.37 (m, 2H), 4.13 (d, 1H, J=16.8 Hz), 4.04 (d, 1H, J=16.8 Hz), 4.02-4.11 (m, 1H), 7.11-7.22 (m, 3H), 7.42 (d, 1H, J=7.5 Hz), 7.46-7.52 (m, 1H), 7.60-7.76 (m, 2H), 8.43 (t, 1H, J=1.5 Hz), 8.58 (d, 1H, J=3.9 Hz), 8.71 (d, 1H, J=2.4 Hz), 9.34 (d, 1H, J=1.2 Hz); $^{13}$C NMR (CDCl$_3$) δ 21.76, 24.03, 26.20, 27.35, 29.56, 39.38, 49.92, 50.39, 62.15, 111.37, 119.11, 121.91, 122.59, 134.98, 137.73, 142.83, 144.64, 144.83, 147.01, 147.47, 156.91, 157.84, 163.25; ES-MS m/z 456 (M+H). Anal. Calcd. for C$_{24}$H$_{25}$N$_7$O$_2$.0.6H$_2$O: C, 66.96; H, 6.53; N, 21.02. Found: C, 66.94; H, 6.54; N, 21.05.

Example 139

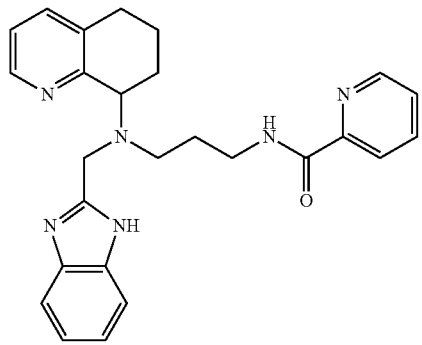 [SMILES: O=C(NCCCN(Cc1nc2ccccc2[nH]1)C1CCCc2cccnc21)c1ccccn1]

Compound 139: Preparation of Pyridine-2-carboxylic acid {3-[(1H-benzimidazol-2-ylmethyl)-(5,6,7,8-tetrahydro-quinolin-8-yl)-amino]-propyl}-amide (hydrobromide)

To a stirred solution of picolinic acid (36.7 mg, 0.30 mmol) in anhydrous DMF (3 mL) was added N,N-diisopropylethylamine (0.10 mL, 0.6 mmol), HOBT (48.3 mg, 0.36 mmol), EDC (68.6 mg, 0.36 mmol) and N$^1$-(1H-Benzimidazol-2-ylmethyl)-N$^1$-(5,6,7,8-tetrahydro-quinolin-8-yl)-propane-1,3-diamine (100 mg, 0.30 mmol). The resultant solution was stirred at room temperature for 16 h. The reaction mixture was diluted with EtOAc (40 mL), brine (15 mL) and H$_2$O (5 mL) and the two layers mixed vigorously for 15 minutes. The layers were separated and the organic layer washed with brine (5×15 mL), dried (Na$_2$SO$_4$), filtered and concentrated in vacuo. Purification of the beige foam by radial chromatography on a 1 mm TLC grade silica gel plate (CH$_2$Cl$_2$/MeOH/NH$_4$OH, 50:1:1) gave the free base of the title compound (63.0 mg, 48%) as a white foam.

Using General Procedure D: Conversion of the white foam from above (63.0 mg, 0.14 mmol) to the hydrobromide salt followed by re-precipitation of the intermediate solid from methanol/ether gave COMPOUND 139 (81.3 mg, 79%) as a cream solid. $^1$H NMR (D$_2$O) δ 1.72-1.92 (m, 3H), 1.93-2.10 (m, 1H), 2.11-2.23 (m, 1H), 2.33-2.44 (m, 1H), 2.52-2.64 (m, 1H), 2.83-3.05 (m, 3H), 3.24-3.50 (m, 2H), 4.29 (d, 1H, 16.2 Hz), 4.44 (d, 1H, J=16.5 Hz), 4.55 (dd, 1H, J=10.4, 5.7 Hz), 7.42-7.49 (m, 2H), 7.59-7.66 (m, 2H), 7.80 (t, 1H, J=6.8 Hz), 7.89 (t, 1H, J=6.5 Hz), 7.95 (d, 1H, J=8.1 Hz), 8.24-8.34 (m, 2H), 8.62 (d, 2H J=5.1 Hz); $^{13}$C NMR (D$_2$O) δ 20.43, 27.63, 37.76, 48.05, 48.93, 59.91, 114.12, 123.82, 125.87, 126.99, 129.16, 130.71, 139.39, 140.66, 144.19, 144.86, 145.77, 148.03, 151.25, 163.22; ES-MS m/z 441 (M+H). Anal. Calcd. for C$_{26}$H$_{28}$N$_6$O.2.9 HBr.2.7H$_2$O: C, 43.14; H, 5.05; N, 11.61; Br, 32.01. Found: C, 43.26; H, 5.07; N, 11.24; Br, 32.37.

Example 140

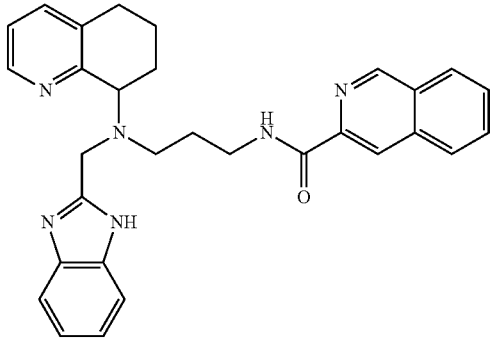 [SMILES: O=C(NCCCN(Cc1nc2ccccc2[nH]1)C1CCCc2cccnc21)c1cc2ccccc2cn1]

Compound 140: Preparation of Isoquinoline-3-carboxylic acid {3-[(1H-benzimidazol-2-ylmethyl)-(5,6,7,8-tetrahydro-quinolin-8-yl)-amino]-propyl}-amide (hydrobromide)

To a stirred solution of 1-isoquinolinecarboxylic acid (51.6 mg, 0.30 mmol) in anhydrous DMF (3 mL) was added N,N-diisopropylethylamine (0.10 mL, 0.6 mmol), HOBT (48.3 mg, 0.36 mmol), EDC (68.6 mg, 0.36 mmol) and N$^1$-(1H-Benzimidazol-2-ylmethyl)-N$^1$-(5,6,7,8-tetrahydro-quinolin-8-yl)-propane-1,3-diamine (100 mg, 0.30 mmol). The resultant solution was stirred at room temperature for 16 h. The reaction mixture was diluted with EtOAc (40 mL), brine (15 mL) and H$_2$O (5 mL) and the two layers mixed vigorously for 15 minutes. The layers were separated and the organic layer washed with brine (5×15 mL), dried (Na$_2$SO$_4$), filtered and concentrated in vacuo. Purification of the crude material by radial chromatography on a 1 mm TLC grade silica gel plate (CH$_2$Cl$_2$/MeOH/NH$_4$OH, 50:1:1) gave the free base of the title compound (79.2 mg, 54%) as a white foam.

Using General Procedure D: Conversion of the white foam from above (79.2 mg, 0.16 mmol) to the hydrobromide salt followed by re-precipitation of the intermediate solid from methanol/ether gave COMPOUND 140 (106 mg, 86%) as a yellow solid. $^1$H NMR (D$_2$O) δ 1.76-1.97 (m, 3H), 1.95-2.12 (m, 1H), 2.12-2.23 (m, 1H), 2.33-2.45 (m, 1H), 2.57-2.70 (m, 1H), 2.88-3.04 (m, 3H), 3.39-3.54 (m, 2H), 4.33 (d, 1H, J=16.5 Hz), 4.48 (d, 1H, J=16.5 Hz), 4.57 (dd, 1H, J=10.8, 5.7 Hz), 7.32-7.40 (m, 2H), 7.51-7.60 (m, 2H), 7.73-7.83 (m, 2H), 8.02 (t, 1H, J=7.2 Hz), 8.12 (d, 1H, J=6.3 Hz), 8.14 (d, 1H, J=7.8 Hz), 8.22 (d, 1H, J=6.3 Hz), 8.27 (d, 1H, J=7.8 Hz), 8.36 (d, 1H, J=6.0 Hz), 8.61 (d, 1H J=5.4 Hz); $^{13}$C NMR (D$_2$O) δ 620.40, 27.66, 38.12, 48.23, 49.24, 60.06, 114.00, 124.73, 125.86, 126.61, 126.74, 126.83, 128.43, 130.67, 131.35, 134.81, 135.30, 139.41, 140.61, 148.07, 149.02, 151.26, 164.46; ES-MS m/z 491 (M+H). Anal. Calcd. for C$_{30}$H$_{30}$N$_6$O.2.9 HBr.2.3H$_2$O: C, 47.00; H, 4.93; N, 10.96; Br, 30.22. Found: C, 47.21; H, 5.01; N, 10.65; Br, 30.06.

Example 141

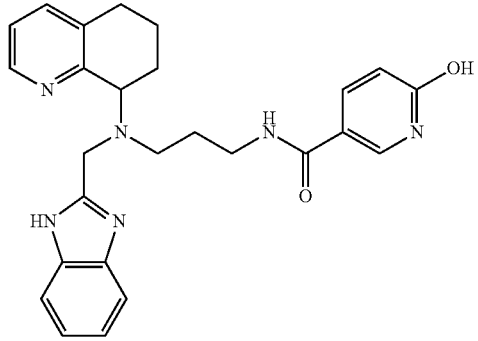 [SMILES: O=C(NCCCN(Cc1nc2ccccc2[nH]1)C1CCCc2cccnc21)c1ccc(O)nc1]

Compound 141: N-{3-[(1H-benzoimidazol-2-ylmethyl)-(5,6,7,8-tetrahydro-quinolin-8-yl)-amino]-propyl}-6-hydroxy-nicotinamide (hydrobromide salt)

Preparation of (4-oxo-propyl)-carbamic acid tert-butyl ester

To a solution of oxalyl chloride in CH$_2$Cl$_2$ (2.0 M, 12.3 mL, 24.63 mmol) at 78° C. was added DMSO dropwise. The reaction mixture was stirred for 20 minutes at −78° C. Then a solution of (4-hydroxy-propyl)-carbamic acid tert-butyl ester (3.32 g, 18.95 mmol) in CH$_2$Cl$_2$ (58 mL) was added, followed by triethylamine (13.2 mL, 94.75 mmol), and the reaction mixture was warmed to room temperature. After 1.5 hours, the mixture was diluted with brine (50 mL) and the phases were separated. The organic layer was washed with brine (2×50 mL) and saturated NaHCO$_3$ (2×50 mL). The combined organic layer was dried (MgSO$_4$), filtered, concentrated, and dried in vacuo to afford an orange oil (2.76 g, 84%). $^1$H NMR (CDCl$_3$) δ 1.42 (s, 9H), 2.710 (t, 2H, J=6.0 Hz), 3.42 (q, 2H, J=7.5 Hz), 4.90 (br s, 1H), 9.80 (s, 1H).

Preparation of 2-{[(3-tert-butoxycarbonylamino-propyl)-(5,6,7,8-tetrahydro-quinolin-8-yl)-amino]-methyl}-benzoimidazole-1-carboxylic acid tert-butyl ester To a solution of the above aldehyde (1.70 g, 9.82 mmol) and 2-[(5,6,7,8-tetrahydro-quinolin-8-ylamino)-methyl]-benzimidazole-1-carboxylic acid tert-butyl ester (3.38 g, 8.92 mmol) in CH$_2$Cl$_2$ (20 mL) was added sodium triacetoxyborohydride (3.78 g, 17.84 mmol). The reaction mixture was stirred at room temperature for 4 days. Then it was extracted with saturated NaHCO$_3$ (3×50 mL). The organic layer was dried (MgSO$_4$), filtered, concentrated, and dried in vacuo to afford a yellow foam. Purification by flash column chromatography on silica gel using 2% CH$_3$OH/CH$_2$Cl$_2$ afforded the product as a yellow foam (4.23 g, 91%). $^1$H NMR (CDCl$_3$) δ 1.41 (s, 9H), 1.60 (s, 9H), 1.64-1.75 (m, 2H), 1.89-2.04 (m, 3H), 2.21-2.25 (m, 1H), 2.66-2.89 (m, 3H), 3.20-3.24 (m, 2H), 3.40-3.44 (m, 1H), 4.17-4.43 (m, 3H), 6.90 (d, 1H, J=3.0 Hz), 7.19-7.25 (m, 2H), 7.40 (m, 1H), 7.74-7.76 (m, 1h), 7.82-7.84 (m, 1H), 8.35 (d, 1H, J=6.0 Hz).

Preparation of N¹-(1H-benzoimidazol-2-ylmethyl)-
N¹-(5,6,7,8-tetrahydro-quinolin-8-yl)-propane-1,3-
diamine The above amine (4.23 g, 8.11 mmol) in 3N HCl/THF (2:1) (30 mL) was stirred at room temperature overnight. Then it was basified to pH=9 using potassium carbonate and it was extracted with CHCl₃ (3×50 mL). The combined organic layer was dried (Na₂SO₄), filtered, concentrated, and dried in vacuo to afford a yellow foam (2.88 g, 100%). ¹H NMR (CDCl₃) δ 1.62-1.79 (m, 3H), 2.09 (m, 1H), 2.42-2.68 (m, 3H), 2.76-2.84 (m, 4H), 3.35 (d, 1H, J=12.0 Hz), 4.00 (d, 1H, J=12.0 Hz), 4.10-4.15 (m, 1H), 4.34 (d, 1H, J=15.0 Hz), 7.05-7.09 (m, 1H), 7.13-7.16 (m, 2H), 7.39 (d, 1H, J=9.0 Hz), 7.60-7.61 (br m, 2H), 8.59 (d, 1H, J=3.0 Hz).

Preparation of N-[3-[(1H-benzoimidazol-2-ylm-
ethyl)-(5,6,7,8-tetrahydro-quinolin-8-yl)-amino]-
propyl}-6-hydroxy-nicotinamide To a solution of the above amine (173 mg, 0.52 mmol) in DMF (3 mL) was added 1-hydroxybenzotriazole hydrate (104 mg, 0.77 mmol), 1-(3-dimethylaminopropyl)-3-ethyl-carbodiimide hydrochloride (148 mg, 0.77 mmol), and 6-hydroxynicotinic acid (86 mg, 0.62 mmol). The reaction was stirred overnight at room temperature. Then it was diluted with ethyl acetate (40 mL) and water (25 mL). The organic layer was washed with saturated NaHCO₃ (30 mL) and brine (30 mL), dried (Na₂SO₄), filtered, concentrated, and dried in vacuo to afford a yellow oil. Purification by radial chromatography on silica gel (1 mm plate; using NH₄—OH/CH₃OH/CH₂Cl₂; 1:2:100→1:10:100) afforded the product as a yellow foam (63 mg, 27%). ¹H NMR (CDCl₃) δ 1.61-1.88 (m, 4H), 2.01-2.06 (m, 1H), 2.20-2.24 (m, 1H), 2.61-2.70 (m, 1H), 2.76-2.85 (m, 3H), 3.26-3.30 (m, 1H), 3.45-3.51 (m, 1H), 4.00 (s, 2H), 4.13 (dd, 1H, J=9.0, 6.0 Hz). 6.37 (d, 1H, J=9.6 Hz), 7.13-7.18 (m, 3H), 7.43-7.46 (m, 3H), 7.52 (br s, 1H), 7.66 (dd, 1H, J=9.6, 2.4 Hz), 7.91 (d, 1H, J=2.1 Hz), 8.48 (d, 1H, J=3.6 Hz).

Preparation of N-{3-[(1H-benzoimidazol-2-ylm-
ethyl)-(5,6,7,8-tetrahydro-quinolin-8-yl)-amino]-
propyl}-6-hydroxy-nicotinamide (hydrobromide
salt)

To a solution of the above amine (63 mg, 0.14 mmol) in acetic acid (2 mL) was added hydrobromide saturated acetic acid (2 mL). The reaction mixture was stirred for 30 minutes. Then it was triturated with diethyl ether four times to afford the title compound as a white solid (80 mg), which was dried in vacuo. ¹H NMR (D₂O) δ 1.81-2.01 (m, 4H), 2.16-2.20 (m, 1H), 2.37-2.41 (m, 1H), 2.50-2.59 (m, 1H), 2.87-2.92 (m, 1H), 3.00 (br s, 2H), 3.11-3.16 (m, 1H), 3.37-3.42 (m, 1H), 3.53 (q, 1H, J=6.0 Hz), 4.25 (ABq, 2H, J=43.8, 15.3 Hz), 4.57-4.79 (m, 1H), 6.36 (d, 1H, J=9.6 Hz), 7.46-7.48 (m, 2H), 7.53 (s, 1H), 7.57-7.63 (m, 3H), 7.85 (t, 1H, J=6.3 Hz), 8.34 (d, 1H, J=7.8 Hz), 8.65 (d, 1H, J=5.4 Hz). ¹³C NMR (D₂O) δ 20.33, 20.45, 36.87, 47.77, 48.22, 59.04, 114.10, 119.38, 125.90, 126.99, 130.69, 137.16, 139.46, 139.85, 140.66, 148.01, 150.87, 151.39. ES-MS m/z 457 [M+H]⁺. Anal. Calcd. for C₂₆H₂₈N₆O₂·3.0HBr·3.4H₂O·0.2C₄H₁₀O: C, 41.52; H, 5.17; N, 10.84; Br, 30.92. Found: C, 41.70; H, 4.90; N, 10.71; Br, 30.63.

Example 142

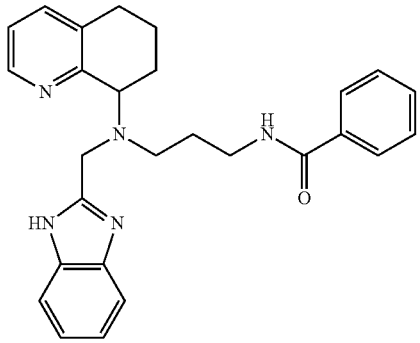 [SMILES: O=C(NCCCN(Cc1nc2ccccc2[nH]1)C1CCCc2cccnc21)c1ccccc1]

Compound 142: N-3-[(1H-benzoimidazol-2-ylm-
ethyl)-(5,6,7,8-tetrahydro-quinolin-8-yl)-amino]-
propyl}-benzamide (hydrobromide salt)

Preparation of N-{3-[(1H-benzoimidazol-2-ylm-
ethyl)-(5,6,7,8-tetrahydro-quinolin-8-yl)-amino]-
propyl}-benzamide To a solution of N¹-(1H-benzoimidazol-2-ylmethyl)-N¹-(5,6,7,8-tetrahydro-quinolin-8-yl)-propane-1,3-diamine (166 mg, 0.50 mmol) in DMF (3 mL) was added 1-hydroxybenzotriazole hydrate (100 mg, 0.74 mmol), 1-(3-dimethylaminopropyl)-3-ethylcarbodiimide hydrochloride (142 mg, 0.74 mmol), and benzoic acid (73 mg, 0.59 mmol). The reaction mixture was stirred overnight at room temperature. Then it was diluted with ethyl acetate (40 mL) and water (25 mL). The organic layer was washed with saturated NaHCO₃ (30 mL) and brine (30 mL), dried (Na₂SO₄), filtered, concentrated, and dried in vacuo to afford a yellow oil. Purification by radial chromatography on silica gel (1 mm plate; using NH₄OH/CH₃OH/CH₂Cl₂; 1:1:100→1:3:100) afforded the product as a yellow foam (80 mg, 37%). ¹H NMR (CDCl₃) δ 1.68-1.74 (m, 4H), 2.02-2.04 (m, 1H), 2.22 (m, 1H), 2.62-2.69 (m, 2H), 2.81 (t, 1H, J=4.8 Hz), 2.84-2.90 (m, 2H), 3.34-3.38 (m, 1H), 3.55-3.59 (m, 1H), 4.01-4.05 (m, 2H), 7.10-7.18 (m, 4H), 7.32 (t, 2H, J=7.8 Hz), 7.42-7.48 (m, 2H), 7.59 (dd, 2H, J=8.0, 1.5 Hz), 7.65 (br s, 1H), 8.43 (dd, 1H, J=3.9, 1.2 Hz).

Preparation of N-{3-[(1H-benzoimidazol-2-ylm-
ethyl)-(5,6,7,8-tetrahydro-quinolin-8-yl)-amino]-
propyl}-benzamide (hydrobromide salt)

To a solution of the amine (80 mg, 0.18 mmol) in acetic acid (2 mL) was added hydrobromide saturated acetic acid (2 mL). The reaction mixture was stirred for 30 minutes. Then it was triturated with diethyl ether four times to afford the title compound as a yellow solid (99 mg), which was dried in vacuo. ¹H NMR (D₂O) δ 1.73-1.86 (m, 2H), 1.93-2.01 (m, 1H), 2.13-2.17 (m, 1H), 2.34-2.38 (m, 1H), 2.43-2.53 (m, 1H), 2.80-2.87 (m, 1H), 2.95-2.97 (br m, 2H), 3.17-3.23 (m, 1H), 3.28-3.35 (m, 1H), 3.53 (q, 1H, J=6.9 Hz), 4.28-4.54 (m, 3H), 7.31-7.38 (m, 4H), 7.49-7.51 (m, 3H), 7.63-7.72 (m, 3H), 8.24 (d, 1H, J=7.8 Hz), 8.55 (d, 1H, J=5.7 Hz). ¹³C NMR (D₂O) δ 20.36, 20.49, 27.63, 28.08, 37.37, 48.27, 49.01, 60.18, 114.12, 125.86, 126.98, 129.20, 130.75, 132.67, 132.99, 139.30, 140.59, 147.99, 151.17, 172.84. ES-MS m/z

Example 143

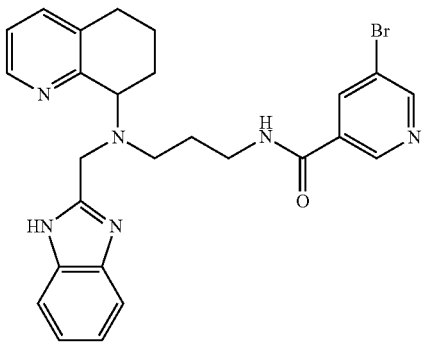 [SMILES: O=C(NCCCN(Cc1nc2ccccc2[nH]1)C1CCCc2cccnc21)c1cncc(Br)c1]

Compound 143: N-{3-[(1H-benzoimidazol-2-ylmethyl)-(5,6,7,8-tetrahydro-quinolin-8-yl)-amino]-propyl}-5-bromo-nicotinamide Preparation of N-[3-[(1H-benzoimidazol-2-ylmethyl)-(5,6,7,8-tetrahydro-quinolin-8-yl)-amino]-propyl}-5-bromo-nicotinamide To a solution of 5-bromonicotinic acid (120 mg, 0.60 mmol) in DMF (3 mL) was added 1-hydroxybenzotriazole hydrate (96 mg, 0.72 mmol), 1-(3-dimethylaminopropyl)-3-ethylcarbodiimide hydrochloride (137 mg, 0.72 mmol), N,N-diisopropylethylamine (0.21 mL, 1.19 mmol), and $N^1$-(1H-benzoimidazol-2-ylmethyl)-$N^1$-(5,6,7,8-tetrahydro-quinolin-8-yl)-propane-1,3-diamine (200 mg, 0.60 mmol). The reaction mixture was stirred at room temperature overnight. Then it was diluted with ethyl acetate (40 mL) and water (25 mL). The aqueous layer was concentrated and dried in vacuo to afford a brown oil. Purification by radial chromatography (1 mm plate, using $NH_4OH/CH_3OH/CH_2Cl_2$; 1:1:100→1:4:100) afforded the product as pale yellow foam (220 mg, 71%). $^1$H NMR (CDCl$_3$) δ 1.59-1.85 (m, 4H), 1.99-2.03 (m, 1H), 2.16-2.20 (m, 1H), 2.58-2.62 (m, 1H), 2.73-2.85 (m, 3H), 3.27-3.34 (m, 1H), 3.50-3.54 (m, 1H), 3.95 (d, 2H, J=2.4 Hz), 4.03-4.08 (m, 1H), 7.09-7.16 (m, 3H), 7.31 (br s, 1H), 7.42 (d, 1H, J=7.5 Hz), 7.58 (br s, 1H), 7.91 (t, 1H, J=5.7 Hz), 8.07 (t, 1H, J=2.1 Hz), 8.40 (d, 1H, J=3.6 Hz), 8.64 (d, 1H, J=2.4 Hz), 8.74 (d, 1H, J=1.8 Hz).

Preparation of N-{3-[(1H-benzoimidazol-2-ylmethyl)-(5,6,7,8-tetrahydro-quinolin-8-yl)-amino]-propyl}-5-bromo-nicotinamide To a solution of the above amine (220 mg, 0.42 mmol) in acetic acid (2 mL) was added hydrobromide saturated acetic acid (2 mL). The reaction mixture was stirred for 30 minutes. Then it was triturated with diethyl ether four times to precipitate out the product. The solid was re-dissolved in anhydrous methanol (0.5 mL) and was triturated twice with diethyl ether. The pale yellow solid (225 mg) was dried in vacuo. $^1$H NMR (D$_2$O) δ 1.82-1.99 (m, 4H), 2.17-2.21 (m, 1H), 2.38-2.42 (m, 1H), 2.50-2.59 (m, 1H), 2.86-2.95 (m, 1H), 3.00-3.02 (m, 2H), 3.19-3.25 (m, 1H), 3.36-3.43 (m, 1H), 4.32 (ABq, 2H, J=45.2, 16.2 Hz), 4.57 (dd, 1H, J=10.7, 5.4 Hz), 7.43-7.46 (m, 2H), 7.59-7.62 (m, 2H), 7.83 (dd, 1H, J=7.5, 6.0 Hz), 8.08 (t, 1H, J=1.8 Hz), 8.34 (d, 1H, J=7.8 Hz), 8.51 (d, 1H, J=1.5 Hz), 8.65 (d, 1H, J=5.1 Hz), 8.74 (d, 1H, J=1.8 Hz). $^{13}$C NMR (D$_2$O) δ 20.47, 27.48, 27.68, 37.82, 48.12, 48.88, 59.78, 114.04, 121.93, 125.94, 126.96, 130.59, 132.11, 139.48, 140.66, 142.49, 142.93, 148.09, 149.65, 149.81, 151.20. ES-MS m/z 521 [M+H]$^+$. Anal. Calcd. for $C_{26}H_{27}N_6OBr.2.9HBr.2.1H_2O$: C, 39.52; H, 4.32; N, 10.64; Br, 39.44. Found: C, 39.47; H, 4.33; N, 10.26; Br, 39.55.

Example 144

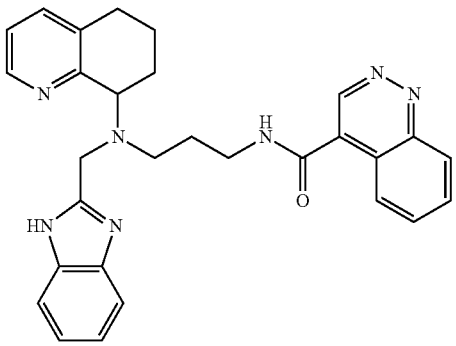 [SMILES: O=C(NCCCN(Cc1nc2ccccc2[nH]1)C1CCCc2cccnc21)c1cnnc2ccccc12]

Compound 144: Cinnoline-4-carboxylic acid-{3-[(1H-benzoimidazol-2-ylmethyl)-(5,6,7,8-tetrahydro-quinolin-8-yl)-amino]-propyl}-amide (hydrobromide salt)

Preparation of cinnoline-4-carboxylic acid-{3-[(1H-benzoimidazol-2-ylmethyl-(5,6,7,8-tetrahydro-quinolin-8-yl)-amino]-propyl}-amide To a solution of cinnoline-4-carboxylic acid (80 mg, 0.46 mmol) in DMF (3 mL) was added 1-hydroxybenzotriazole hydrate (74 mg, 0.55 mmol), 1-(3-dimethylaminopropyl)-3-ethylcarbodiimide hydrochloride (106 mg, 0.55 mmol), N,N-diisopropylethylamine (0.16 mL, 0.92 mmol), and $N^1$-(1H-benzoimidazol-2-ylmethyl)-$N^1$-(5,6,7,8-tetrahydro-quinolin-8-yl)-propane-1,3-diamine (154 mg, 0.46 mmol). The reaction mixture was stirred for 3 days. Then it was diluted with ethyl acetate (40 mL) and water (25 mL) and the phases were separated. The organic layer was washed with saturated NaHCO$_3$ (30 mL) and saturated NaCl (30 mL). The combined aqueous layer was washed with ethyl acetate (2×30 mL). The combined organic layer was dried (MgSO$_4$), filtered, concentrated, and dried in vacuo to afford a yellow oil. Purification by radial chromatography on silica gel (1 mm plate; using $NH_4OH/CH_3OH/CH_2Cl_2$; 1:1:100→1:2:100) afforded the product as a yellow foam (85 mg, 38%). $^1$H NMR (CDCl$_3$) δ 1.61-1.67 (m, 1H), 1.80-1.90 (m, 3H), 2.00-2.06 (m, 1H), 2.20-2.24 (m, 2H), 2.64-2.75 (m, 3H), 3.00-3.06 (m, 1H), 3.27-3.29 (m, 1H), 3.80-3.83 (m, 1H), 3.86 (d, 2H, J=3.6 Hz), 4.02 (dd, 1H, J=10.1, 6.0 Hz), 6.78 (dd, 1H, J=7.5 Hz), 7.12-7.17 (m, 2H), 7.21 (d, 1H, J=6.9 Hz), 7.59 (br s, 1H), 7.67-7.73 (m, 2H), 7.78-7.83 (m, 1H), 8.06 (d, 1H, J=8.4 Hz), 8.14 (br s, 1H), 8.48 (d, 1H, J=8.4 Hz), 9.11 (s, 1H).

Preparation of cinnoline-4-carboxylic acid-{3-[(1H-benzoimidazol-2-ylmethyl)-(5,6,7,8-tetrahydro-quinolin-8-yl)-amino]-propyl}-amide (hydrobromide salt)

To a solution of the above amine (85 mg, 0.17 mmol) in acetic acid (2 mL) was added hydrobromide saturated acetic acid (2 mL) and the reaction mixture was stirred for 30 minutes. Then it was triturated with diethyl ether three times and the precipitate was dried in vacuo. Then the solid was re-dissolved in methanol (0.5 mL) and it was triturated with diethyl ether an additional three times. The yellow solid (61 mg) was dried in vacuo. $^1$H NMR (D$_2$O) δ 1.65-1.89 (m, 3H), 2.04 (q, 1H, J=12.9 Hz), 2.18-2.23 (m, 1H), 2.41-2.44 (m, 1H), 2.59-2.68 (m, 1H), 2.89-3.01 (m, 3H), 3.32-3.57 (m, 2H), 4.38 (ABq, 2H, J=48.3, 15.9 Hz), 4.58-4.61 (m, 1H), 7.32-7.37 (m, 2H), 7.49-7.57 (m, 2H), 7.82 (t, 1H, J=6.6 Hz), 7.89-8.08 (m, 3H), 8.33 (d, 1H, J=7.8 Hz), 8.46 (d, 1H, J=8.4 Hz), 8.65 (d, 1H, J=5.7 Hz), 8.92 (s, 1H). ES-MS m/z 492 [M+H]$^+$. Anal. Calcd. for C$_{29}$H$_{29}$N$_7$O.2.8HBr.2.0H$_2$O: C, 46.19; H, 4.78; N, 13.00; Br, 29.67. Found: C, 46.35; H, 4.92; N, 12.68; Br, 29.50.

25.93, 26.48, 27.68, 39.05, 49.88, 52.68, 62.22, 114.01, 115.18, 119.26, 125.89, 126.76, 130.65, 137.11, 139.27, 140.41, 140.53, 148.05, 151.29, 152.59, 165.27, 166.17. ES-MS m/z 471.4 (M+H). Anal. Calcd for C$_{27}$H$_{30}$N$_6$O$_2$.3.1HBr.1.8H$_2$O.0.8C$_4$H$_{10}$O: C, 44.61; H, 5.54; N, 10.34; Br, 30.46. Found: C, 44.42; H, 5.30; N, 10.26; Br, 30.77.

Example 146

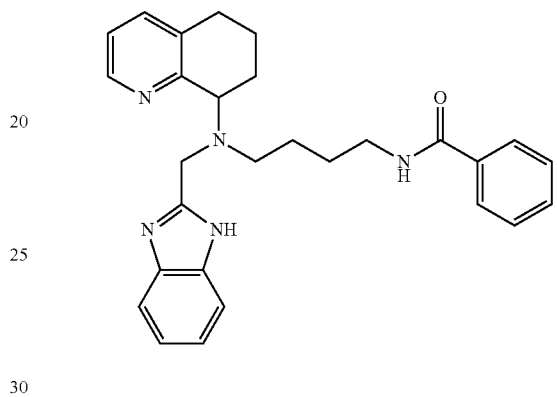

Compound 146: Preparation of N-{4-[(1H-benzolimidazol-2-ylmethyl)-(5,6,7,8-tetrahydroquinolin-8-yl)-amino]-butyl}-benzamide hydrobromide Example 145

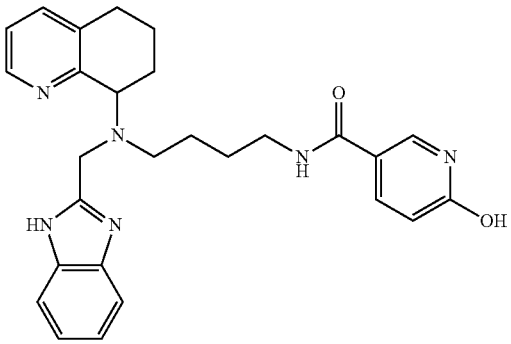 [SMILES: O=C(NCCCCN(Cc1nc2ccccc2[nH]1)C1CCCc2cccnc21)c1ccc(O)nc1]

Compound 145: Preparation of N-{4-[1H-benzolimidazol-2-ylmethyl)-(5,6,7,8-tetrahydroquinolin-8-yl)-amino]-butyl}-6-hydroxynicotinamide hydrobromide To a solution of 6-hydroxynicotinic acid (0.049 g, 0.35 mmoles) in DMF (2.7 mL) was added EDC (0.083 g, 0.43 mmoles), HOBT (0.056 g, 0.41 mmoles) and N$^1$-(1H-Benzimidazol-2-ylmethyl)-N$^1$-(5,6,7,8-tetrahydro-quinolin-8-yl)-butane-1,4-diamine (0.1 g, 0.29 mmoles) and the reaction stirred overnight at room temperature. Ethyl acetate (40 mL) and water (25 mL) were added and the organic layer was washed with brine (30 mL) and saturated aqueous NaHCO$_3$ (30 mL). The aqueous layers were extracted with ethyl acetate (3×30 mL) and the combined organic extracts dried with Na$_2$SO$_4$ and concentrated. The crude product was purified by radial chromatography on silica gel (1 mm plate, 2% MeOH/1% NH$_4$OH/CH$_2$Cl$_2$, then 10% MeOH/1% NH$_4$OH/CH$_2$Cl$_2$) to give N-{4-[1H-benzolimidazol-2-ylmethyl)-(5,6,7,8-tetrahydroquinolin-8-yl)-amino]-butyl}-6-hydroxynicotinamide as an offwhite foam (30 mg, 16%).

Using General Procedure D, the free base was converted to the HBr salt to form COMPOUND 145 (42 mg. 81%). $^1$H NMR (D$_2$O): δ 1.1-1.24 (m, 2H), 1.27-1.4 (m, 2H), 1.75-1.85 (m,1H), 1.85-2.01 (m, 1H), 2.04-2.15 (m, 1H), 2.15-2.31 (m, 1H), 2.50-2.53 (m, 1H), 2.71-2.8 (m, 1H), 2.80-3.05 (m, 2H) 3.09-3.2 (m, 1 H), 3.22-3.30 (m, 1H), 4.31-4.60 (m, 3H), 6.48-6.51 (d, 1H, J=9.3 Hz), 7.45-7.47 (m, 2H), 7.61-7.62 (m, 4H), 7.82-7.86 (t, 1H, J=7.2 Hz), 8.3-8.33 (d, 1H, J=7.8 Hz), 8.60-8.62 (d, 1H, J=5.4 Hz). $^{13}$C NMR (D$_2$O): δ 20.44, 20.65, To a solution of benzoic acid in DMF (3 mL) was added EDC (0.097 g, 0.51 mmol), HOBT (0.064 g, 0.47 mmol), N$^1$-(1H-Benzimidazol-2-ylmethyl)-N$^1$-(5,6,7,8-tetrahydroquinolin-8-yl)-butane-1,4-diamine (0.12 g, 0.34 mmol) and DIPEA. The orange solution was stirred at room temperature overnight then diluted with dichloromethane (20 mL) and water (20 mL). The organic layer was washed with brine (20 mL) and saturated NaHCO$_3$ solution (20 mL), dried with Na$_2$SO$_4$ and concentrated to give an orange oil. The crude product was purified by radial chromatography on silica gel (1 mm plate, 2% MeOH/1% NH$_4$OH/CH$_2$Cl$_2$, then 4% MeOH/1% NH$_4$OH/CH$_2$Cl$_2$) to give N-{4-[(1H-benzolimidazol-2-ylmethyl)-(5,6,7,8-tetrahydroquinolin-8-yl)-amino]-butyl}-benzamide as an offwhite foam (80 mg, 51%).

Using general procedure D, conversion of the foam to the HBr salt and its reprecipitation in methanol/ether formed COMPOUND 146 (93 mg. 77%). $^1$H NMR (D$_2$O): 1.25-1.37 (m, 2 H), 1.37-1.54 (m, 2H), 1.75-1.85 (m, 1H), 1.90-2.02 (m, 1H), 2.02-2.23 (m, 1H), 2.25-2.35 (m, 1H), 2.50-2.60 (m, 1H), 2.70-2.82 (m, 1H), 2.82-3.0 (m, 2H), 3.13-3.26 (m, 2H), 4.33-4.57 (m, 3H), 7.44 (s, 4H), 7.49-7.50 (m, 2H), 7.50-7.60 (m, 1H), 7.60-7.75 (m, 2H), 7.75-7.80 (m, 1H), 8.21 (d, 1H, J=7.8 Hz), 8.54 (d, 1H, J=5.1 Hz). $^{13}$C NMR (D$_2$O): δ 20.44 (2 carbons), 25.83, 26.48, 27.61, 39.29, 49.50, 52.22, 61.57, 114.08 (2 carbons), 125.85, 126.87 (2 carbons), 127.15 (2 carbons), 129.21 (2 carbons), 130.73, 132.57, 132.59, 139.13, 140.26 (2 carbons), 147.97, 151.32, 152.10. ES-MS m/z 454.4 (M+H). Anal. Calcd. for C$_{28}$H$_{31}$N$_5$O.2.2HBr.1.9H$_2$O.0.3C$_4$H$_{10}$O: C, 50.97; H, 5.86; N, 10.18; Br 25.55. Found: C, 51.23; H, 5.70; N, 10.17; Br, 25.28.

Example 147

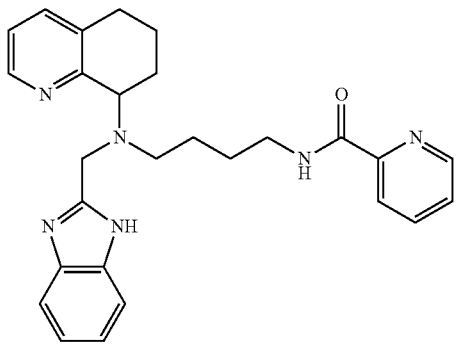 [SMILES: O=C(NCCCCN(Cc1nc2ccccc2[nH]1)C1CCCc2cccnc21)c1ccccn1]

Compound 147: Preparation of pyridine-2-carboxylic acid {4-[1H-benzoimidazol-2-ylmethyl)-(5,6,7,8-tetrahydroquinolin-8-yl)-amino]-butyl}-amide hydrobromide To a solution of picolinic acid (0.042 g, 0.34 mmol) in DMF (2.5 mL) was added EDC (0.077 g, 0.40 mmol), HOBT (0.051 g, 0.38 mmol), $N^1$-(1H-Benzimidazol-2-ylmethyl)-$N^1$-(5,6,7,8-tetrahydro-quinolin-8-yl)-butane-1,4-diamine (0.096 g, 0.28 mmol) and DIPEA (0.10 ml, 0.56 mmol) and the orange solution stirred at room temperature overnight. The mixture was diluted with dichloromethane (20 mL) and water (20 mL) and the organic layer washed with brine (3×20 mL) and saturated aqueous $NaHCO_3$ solution (20 mL). The organic layer was dried with $Na_2SO_4$ and concentrated to an orange oil. The crude product was purified by radial chromatography on silica gel (1 mm plate, 2% MeOH/1% $NH_4OH$/$CH_2Cl_2$ and then 4% MeOH/1% $NH_4OH$/$CH_2Cl_2$) to give pyridine-2-carboxylic acid {4-[1H-benzoimidazol-2-ylmethyl)-(5,6,7,8-tetrahydroquinolin-8-yl)-amino]-butyl}-amide as a offwhite foam (55 mg, 44%)

Using General Procedure D, the free base was converted to the hydrobromide with HBr/acetic acid to yield COMPOUND 147 (67.4 mg, 73%) as an offwhite solid. $^1H$ NMR ($D_2O$): δ 1.25-1.40 (m, 2H), 1.40-1.68 (m, 2H), 1.75-1.95 (m, 1H), 2.00-2.12 (q, 1H, J=13.2 Hz), 2.12-2.25 (m, 1H), 2.26-2.48 (m, 1H), 2.51-2.57 (m, 1H), 2.75-2.88 (m, 1H), 2.90-3.05 (m, 2H), 3.25-3.48 (m, 2H), 4.44-4.58 (q, 2H, J=17.1 Hz), 4.48-4.55 (m, 1H), 7.44-7.47 (m, 2H), 7.61-7.64 (m, 2H), 7.77-7.98 (m, 3H), 8.23-8.30 (m, 2H), 8.58-8.73 (m, 2H). $^{13}C$ NMR ($D_2O$): δ 20.43, 20.54, 25.92, 26.43, 27.65, 39.61, 49.47, 52.34, 61.77, 114.05 (2 carbons), 123.99, 125.87, 126.79 (2 carbons), 129.10, 130.69, 139.24, 140.49 (2 carbons), 144.32, 145.18, 145.69, 148.02, 151.33, 152.38, 162.96. ES-MS m/z 455.4 (M+H). Anal. Calcd. for $C_{27}H_{30}N_6O$.3.2 HBr.2.1$H_2O$.0.2 $C_4H_{10}O$: C, 43.58; H, 5.18; N, 10.97; Br, 33.37. Found: C, 43.44; H, 5.05; N, 10.91; Br, 33.64.

Example 148

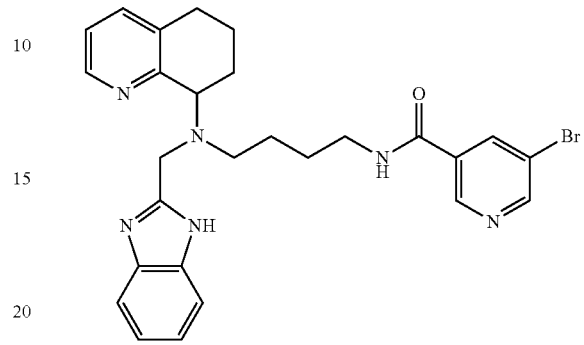

Compound 148: Preparation of N-{4-[(1H-Benzoimidazol-2-ylmethyl)-(5,6,7,8-tetrahydroquinolin-8-yl)-amino]-butyl}-5-bromo-nicotinamide hydrobromide To a solution of 5-Bromonicotinic acid (0.061 g, 0.30 mmol) in DMF (2.2 mL) was added EDC (0.086 g, 0.45 mmol), HOBT (0.57 g, 0.42 mmol), COMPOUND 18 free base (0.105 g, 0.30 mmol) and DIPEA (0.10 ml, 0.57 mmol) and the orange solution stirred at room temperature overnight. The mixture was diluted with dichloromethane (20 mL) and water (20 mL) and the organic layer washed with brine (20 mL) and aqueous saturated $NaHCO_3$ solution (20 mL). The organic layer was dried with $Na_2SO_4$ and concentrated to an orange oil. The crude product was purified by radial chromatography on silica gel (1 mm plate, 2% MeOH/1% $NH_4OH$/$CH_2Cl_2$) to give the final product as an offwhite foam (110 mg, 69%).

Using General Procedure D, the foam was converted to the hydrobromide salt by dissolving it in acetic acid/HBr and precipitating the HBr salt in methanol/ether to yield COMPOUND 148 (133 mg. 78%) as an offwhite solid. $^1H$ NMR ($D_2O$): δ 1.23-1.37 (m, 4H), 1.37-1.5 (m, 4H), 1.75-1.90 (m, 2H), 1.90 (q, 2H, J=11.7 Hz), 2.12-2.25 (m, 2H), 2.26-2.45 (m, 2H), 2.48-2.55 (m, 2H), 2.75-2.88 (m, 2H), 2.90-3.01 (m, 4H), 3.12-3.25 (m, 2H), 3.25-3.37 (m, 2H), 4.33 (d, 1H, J=17.1 Hz) 4.51-4.60 (m, 1H), 4.60 (d, 1H, J=17.1 Hz), 7.4-7.42 (m, 2H), 7.58-7.61 (m, 2H), 7.76-7.93 (m, 1H), 8.09 (s, 1H) 8.30 (d, 1H, J=7.5 Hz), 8.50 (s, 1H), 8.60 (d, 1H, J=5.4 Hz), 8.82 (d, 1H, J=3 Hz). $^{13}C$ NMR ($D_2O$): δ 20.45, 20.63, 26.01, 26.56, 27.69, 39.55, 49.66, 52.53, 62.02, 113.96 (2 carbons), 121.79, 125.90, 126.74 (2 carbons), 130.62 (2 carbons), 132.32, 138.30, 140.54, 141.84, 143.51, 148.06, 150.30, 151.28, 152.49, 165.0. ES-MS m/z 534.8 (M+H). Anal. Calcd for $C_{27}H_{29}N_6BrO$.3.1 HBr.2.1$H_2O$.0.1$C_4H_{10}O$: C, 39.67; H, 4.52; N, 10.13; Br, 39.49. Found: C, 39.63; H, 4.40; N, 10.09; Br, 39.45.

Example 149

Example 150

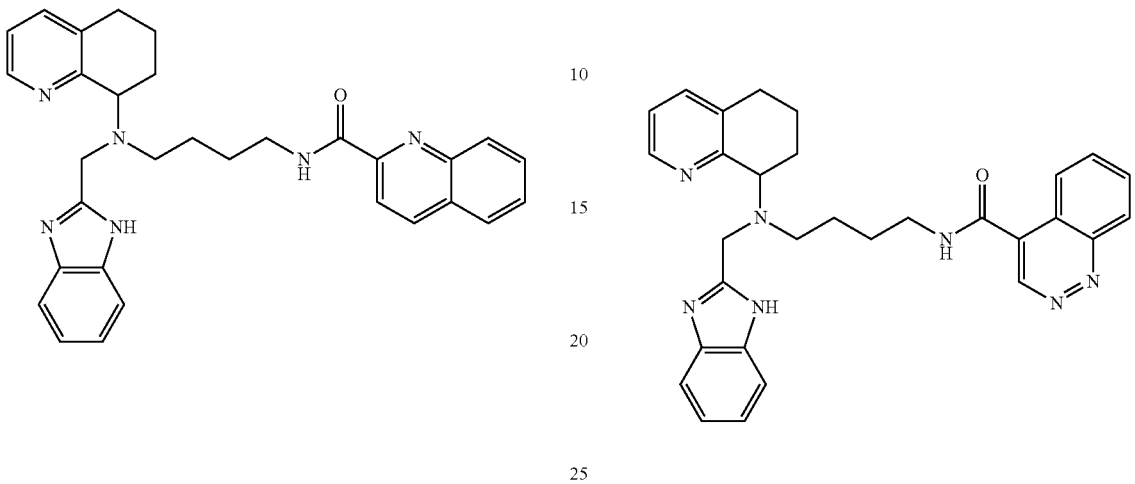

Compound 149: Preparation of quinoline-2-carboxylic acid {2-[(1H-benzoimidazol-2-ylmethyl)-(5,6,7,8-tetrahydroquinolin-8-yl)-amino]-butyl}-amide hydrobromide To a solution of isoquinolinecarboxylic acid (0.061 g, 0.55 mmol) and $N^1$-(1H-Benzimidazol-2-ylmethyl)-$N^1$-(5,6,7,8-tetrahydro-quinolin-8-yl)-butane-1,4-diamine (0.12, 0.35 mmoles) in DMF (2.5 mL) was added EDC (0.10 g, 0.52 mmol), HOBT (0.066 g, 0.49 mmol) and DIPEA (0.12 ml, 0.69 mmol) and the orange solution stirred at room temperature for 2 days. The mixture was diluted with dichloromethane (20 mL) and water (20 mL) and the organic layer washed with brine (3×20 mL) and saturated NaHCO$_3$ solution (20 mL). The organic layer was dried with Na$_2$SO$_4$ and concentrated to an orange oil. The crude product was purified by radial chromatography on silica gel (1 mm plate, 2% MeOH/1% NH$_4$OH/CH$_2$Cl$_2$) to give final product as an off-white foam (95 mg, 53%)

Using General Procedure D: the freebase was converted to the hydrobromide salt by dissolving the foam in acetic acid and adding acetic acid saturated with hydrobromic acid. The HBr salt was precipitated out of methanol/ether to yield COMPOUND 149 (115 mg. 72%) as an offwhite solid. $^1$H NMR (D$_2$O): δ 1.37-1.65 (m, 4H), 1.75-1.95 (m, 1H), 2.12-2.25 (m, 1H), 2.27-2.48 (m, 1H), 2.57-2.75 (m, 1H), 2.75-3.02 (m, 2H), 3.28-3.51 (m 2H), 4.35 (d, 2H, J=17.1 Hz), 4.56 (d, 2H, J=16.8 Hz), 4.5-4.65 (m, 1H), 7.18-7.21 (dd, 2H, J=6.3, 3.0 Hz), 7.40-7.43 (dd, 2H, J=6.3, 3.3 Hz), 7.78-7.84 (m, 2H), 8.05-8.07 (t, 1H, J=9 Hz), 8.15-8.18 (m, 2H), 8.25-8.29 (m, 2H), 8.41 (d, 1H, J=7.8 Hz), 8.68 (d, 1H, J=5.4 Hz). $^{13}$C NMR (D$_2$O): δ 20.45, 20.69. 26.35, 26.78, 27.67, 39.93, 49.42, 52.52, 61.85, 113.78 (2 carbons), 124.56, 125.89, 126.41 (2 carbons), 126.94, 127.08, 128.56, 130.51 (2 carbons), 131.70, 133.75, 135.99, 139.29, 139.67, 140.56 (2 carbons), 148.07, 148.96, 151.24, 152.29. ES-MS m/z 505.4 (M+H). Anal. Calcd. for C$_{31}$H$_{32}$N$_6$O.3.1 HBr.1.9H$_2$O.0.8C$_4$H$_{10}$O: C, 48.38; H, 5.57; N, 9.90; Br, 29.18. Found: C, 48.47; H, 5.52; N, 9.93; Br, 29.04.

Compound 150: Preparation of cinnoline-4-carboxylic acid {4-[(1H-benzoimidazol-2-ylmethyl)-5,6,7,8-tetrahydroquinolin-8-yl)-amino]-butyl}-amide To a solution of cinnoline-4-carboxylic acid (0.061 g, 0.34 mmol) and $N^1$-(1H-Benzimidazol-2-ylmethyl)-$N^1$-(5,6,7,8-tetrahydro-quinolin-8-yl)-butane-1,4-diamine (0.12, 0.34 mmoles) in DMF (2.5 mL) was added EDC (0.10 g, 0.52 mmol), HOBT (0.065 g, 0.48 mmol), and DIPEA (0.12 ml, 0.69 mmol) and the orange solution stirred at room temperature overnight. The mixture was diluted with dichloromethane (20 mL) and water (20 mL) and the organic layer washed with brine (3×20 mL) and saturated NaHCO$_3$ solution (20 mL). The organic layer was dried with Na$_2$SO$_4$ and concentrated to an orange oil. The crude product was purified by radial chromatography on silica gel (1 mm plate, 2% MeOH/1% NH$_4$OH/CH$_2$Cl$_2$) to give final product as an off-white foam (656 mg, 37%).

Using General procedure D: the foam was converted to its HBr salt in HBr/AcOH and COMPOUND 150 (79.3 mg. 76%) was precipitated as an offwhite solid. $^1$H NMR (D$_2$O): δ 1.25-1.62 (m, 8H), 1.74-1.97 (m, 2H), 1.97-2.25 (m, 4H), 2.25-2.50 (m, 2H), 2.50-2.75 (m, 2H), 2.75-3.13 (m, 6H) 3.23-3.55 (m, 4H), 7.0-7.13 (m, 2H), 7.27-7.37 (m, 2H), 7.76-7.87 (m, 1H), 7.95 (s, 2H), 7.99-8.07 (m, 1H), 8.31 (d, 1H, J=7.5 Hz), 8.48 (d, 1H, J=9.0 Hz), 8.61 (d, 1H, J=5.1 Hz), 9.00 (s, 1H). $^{13}$C NMR (D$_2$O): δ 20.47, 20.69, 26.25, 26.85, 27.68, 39.42, 49.64, 52.69, 62.04, 113.62 (2 carbons), 123.94, 124.21, 125.89, 126.28 (2 carbons), 128.95, 130.45 (2 carbons), 130.79, 133.55, 134.73, 139.28, 140.60 (2 carbons), 141.07, 148.08, 150.42, 151.29, 152.44, 166.11. ES-MS m/z 506.4 (M+H) Anal. Calcd. for C$_{30}$H$_{31}$N$_7$.3.1HBr.2.3H$_2$O.0.2C$_4$H$_{10}$O: C, 45.52; H, 5.05; N, 12.06; Br, 30.48. Found: C, 45.59; H, 4.91; N, 12.03; Br, 30.31.

Example 152

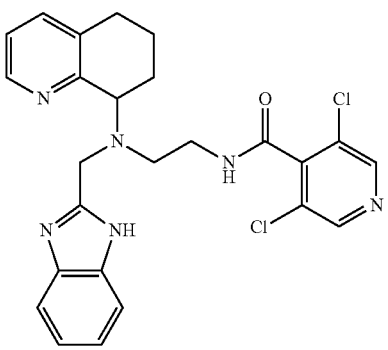 [SMILES: O=C(NCCN(Cc1nc2ccccc2[nH]1)C1CCCc2cccnc21)c1c(Cl)cncc1Cl]

Compound 152: Preparation of N-{2-[(1H-benzoimidazol-2-ylmethyl)-(5,6,7,8-tetrahydro-quinolin-8-yl)-amino]-ethyl}-3,5-dichloro-isonicotinamide To a stirred solution of (2,3-dihydroxy-propyl)-carbamic acid tert-butyl ester (0.955 g, 5.00 mmol) in water (12 mL) was added sodium periodate (2.35 g, 11.0 mmol). The mixture was stirred at room temperature for 1 h and then extracted with dichloromethane (3×10 mL). The extracts were dried over $Na_2SO_4$ and concentrated to give (2-oxo-ethyl)-carbamic acid tert-butyl ester as a colorless liquid (778 mg, 98%). $^1$H NMR ($CDCl_3$) δ 1.45 (s, 9H), 4.07 (d, J=4.5 Hz, 2H), 5.20 (brs, 1H), 9.65 (s, 1H).

To a solution of 2-[(5,6,7,8-tetrahydro-quinolin-8-ylamino)-methyl]-benzoimidazole-1-carboxylic acid tert-butyl ester (0.378 g, 1.00 mmol) and (2-oxo-ethyl)-carbamic acid tert-butyl ester (0.159 g, 1.00 mmol) in dichloromethane (5 mL) was added sodium triacetoxyborohydride (0.223 g, 1.05 mmol). The mixture was stirred at room temperature for 15 h and then poured into saturated aqueous $NaHCO_3$ (30 mL). The mixture was extracted with chloroform (3×20 mL). The extracts were dried over $Na_2SO_4$ and concentrated. Purification of the crude material by column chromatography on silica gel (98:1:1 $CH_2Cl_2$—$CH_3OH$—$NH_4OH$) provided 499 mg (96%) of 2-{[(2-tert-butoxycarbonylamino-ethyl)-(5,6,7,8-tetrahydro-quinolin-8-yl)-amino]-methyl}-benzoimidazole-1-carboxylic acid tert-butyl ester as a yellow foam. $^1$H NMR ($CDCl_3$) δ 1.48 (s, 9 H), 1.64 (s, 9 H), 1.69-1.85 (m, 2 H), 1.94-1.99 (m, 1 H), 2.24 (m, 1 H), 2.61-2.87 (m, 3 H), 3.09-3.19 (m, 3 H), 4.07 (dd, J=9.9 Hz, 5.7 Hz, 1 H), 4.26 (d, J=16.2 Hz, 1 H), 4.52 (d, J=16.2 Hz, 1 H), 6.98 (dd, 1H, J=7.7 Hz, 4.7 Hz, 1 H), 7.26-7.32 (m, 3 H), 7.57 (brs, 1 H), 7.74 (m, 1 H), 7.86 (m, 1 H), 8.41 (d, J=3.9 Hz, 1 H).

To a solution of 2-{[(2-tert-butoxycarbonylamino-ethyl)-(5,6,7,8-tetrahydro-quinolin-8-yl)-amino]-methyl}-benzoimidazole-1-carboxylic acid tert-butyl ester (0.490 g, 0.94 mmol) in dichloromethane (4 mL) was added trifluoroacetic acid (4 mL). The mixture was stirred at room temperature for 1 h. Sodium hydroxide (2 M, 30 mL) was added and the mixture was extracted with chloroform (3×20 mL). The extracts were dried over $Na_2SO_4$ and concentrated. Purification of the crude material by column chromatography on silica gel (90:5:5 $CH_2Cl_2$—$CH_3OH$—$NH_4OH$) provided 294 mg (97%) of $N^1$-(1H-benzoimidazol-2-ylmethyl)-N1-(5,6,7,8-tetrahydro-quinolin-8-yl)-ethane-1,2-diamine as a colorless oil. $^1$H NMR ($CDCl_3$) δ 1.60-1.75 (m, 1 H), 1.87-1.98 (m, 1 H), 2.01 (m, 1 H), 2.22 (m, 1 H), 2.56-2.85 (m, 6 H), 4.03 (m, 1 H), 4.04 (d, J=16.8 Hz, 1 H), 4.17 (d, J=16.8 Hz, 1 H), 7.11-7.21 (m, 3 H), 7.40 (d, J=7.8 Hz, 1 H), 7.56 (brs, 2 H), 8.55 (d, J=4.2 Hz, 1 H).

To a suspension of 3,5-dichloro-isonicotinoyl chloride (0.34 mmol) in THF (3 mL) at 0° C. was added a solution of $N^1$-(1H-benzoimidazol-2-ylmethyl)-$N^1$-(5,6,7,8-tetrahydroquinolin-8-yl)-ethane-1,2-diamine (0.100 g, 0.312 mmol) in dichloromethane (3 mL), THF (1 mL) and $Et_3N$ (0.087 mL). After stirring at 0° C. for 5 min., the mixture was warmed to room temperature and stirred for 2.5 h. The solvents were evaporated and the residue was taken into saturated aqueous $NaHCO_3$ (30 mL). The mixture was extracted with chloroform (3×20 mL). The extracts were dried over $Na_2SO_4$ and concentrated. Purification of the crude material by column chromatography on silica gel (200:1:1 $CH_2Cl_2$—$CH_3OH$—$NH_4OH$) provided 55 mg (44%) of COMPOUND 152 as a pale yellow solid $^1$H NMR ($CDCl_3$) δ 1.55-1.70 (m, 1 H), 1.78-1.85 (m, 1 H), 2.03 (m, 1 H), 2.29 (m, 1 H), 2.66-2.82 (m, 3 H), 3.20 (d, J=13.5 Hz, 1 H), 3.39 (m, 1 H), 3.55 (m, 1 H), 3.90 (dd, J=10.8 Hz, 5.7 Hz, 1 H), 4.12 (d, J=16.7 Hz, 1 H), 4.30 (d, J=16.7 Hz, 1 H), 6.99 (dd, 1H, J=7.8 Hz, 4.8 Hz, 1 H), 7.15-7.21 (m, 2 H), 7.27 (m, 1 H), 7.41 (d, J=7.8 Hz, 1 H), 7.54 (d, J=4.2 Hz, 1 H), 7.63 (d, J=4.2 Hz, 1 H), 8.40 (m, 1 H), 8.56 (s, 2 H); $^{13}$C NMR ($CDCl_3$) δ 21.79, 23.08, 29.32, 38.68, 48.54, 49.25, 61.63, 119.35, 122.24, 122.69, 123.19, 129.64, 133.76, 135.76, 138.70, 143.50, 144.39, 146.46, 148.03, 154.85, 157.38, 162.22; ES-MS m/z 496 (M+H). Anal. Calcd. for $C_{25}H_{24}N_6Cl_2O \cdot 0.9CH_2Cl_2$: C, 54.40; H, 4.55; N, 14.70; Cl, 23.56. Found: C, 54.64; H, 4.53; N, 14.62 Cl, 23.41.

Example 153

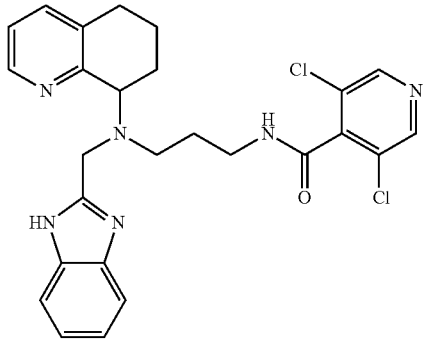 [SMILES: O=C(NCCCN(Cc1nc2ccccc2[nH]1)C1CCCc2cccnc21)c1c(Cl)cncc1Cl]

Compound 153: Preparation of N-{3-[(1H-benzoimidazol-2-ylmethyl)-(5,6,7,8-tetrahydro-quinolin-8-yl)-amino]-propyl}-3,5-dichloro-isonicotinamide To a solution of (3-hydroxy-propyl)-carbamic acid tert-butyl ester (200 mg, 1.15 mmol) in $CH_2Cl_2$ (11.5 mL) cooled to 0° C. was added Dess-Martin periodinane (489 mg, 1.15 mmol) and the resulting mixture was stirred at room temperature for 1 hour. The mixture was diluted with $CH_2Cl_2$ (40 mL) and washed with 1 N NaOH (2×10 mL). The organic phase was dried ($MgSO_4$), filtered and concentrated under reduced pressure. The colourless syrup (180 mg) was used in the next reaction without further purification.

To a stirred solution of 2-[(5,6,7,8-tetrahydro-quinolin-8-ylamino)-methyl]-benzoimidazole-1-carboxylic acid tert-butyl ester (390 mg, 0.98 mmol), (3-oxo-propyl)-carbamic acid tert-butyl ester (170 mg, 0.98 mmol) from above and THF (9.8 mL) was added $NaBH(OAc)_3$ (623 mg, 2.94 mmol) and the resulting mixture was stirred at room temperature for 1 hour. AcOH (56 μL, 0.98 mmol) was added and the mixture stirred at room temperature overnight. The mixture was concentrated under reduced pressure, diluted with CH₂Cl₂ (40 mL) and washed with 1N NaOH (10 mL). The aqueous was extracted with (2×20 mL) and the combined organic extracts were dried (MgSO₄), filtered and concentrated under reduced pressure. A solution of the resulting orange foam in CH₂Cl₂ (4 mL) and TFA (4 mL) was stirred at room temperature for 2.5 hours. The mixture was concentrated under reduced pressure, partially dissolved in H₂O (2 mL), basified with 1N NaOH and extracted with CH₂Cl₂ (3×25 mL). The combined organic extracts were dried (MgSO₄), filtered and concentrated under reduced pressure. Purification by column chromatography on silica gel (CH₂Cl₂/MeOH/NH₄OH, 100:7:1) afforded N¹-(1H-benzoimidazol-2-ylmethyl)-N¹-(5,6,7,8-tetrahydro-quinolin-8-yl)-propane-1,3-diamine (290 mg, 75% over 3 steps) as a white foam.

To a mixture of 3,5-dichloro-isonicotinic acid (52 mg, 0.27 mmol) in CH₂Cl₂ (1.1 mL) cooled to 0° C. was added oxalyl chloride (70 µL, 0.81 mmoL) and DMF (1 drop) and the resulting mixture was stirred at 0° C. for 5 minutes and at room temperature for 1.5 hours. The mixture was concentrated under reduced pressure and dried in vacuo for 5 minutes. To the resulting beige solid in THF (3 mL) was added N¹-(1H-benzoimidazol-2-ylmethyl)-N¹-(5,6,7,8-tetrahydro-quinolin-8-yl)-propane-1,3-diamine from above (100 mg, 0.30 mmol) and Et₃N (76 µL, 0.54 mmol) and the resulting mixture was stirred at room temperature for 3 hours. The mixture was concentrated under reduced pressure, diluted with EtOAc (40 mL) and washed consecutively with saturated aqueous NaHCO₃ (5 mL) and saturated aqueous NaCl (5 mL). The organic phase was dried (MgSO₄), filtered, and concentrated under reduced pressure. Purification by column chromatography on silica gel (CH₂Cl₂/MeOH/NH₄OH, 100:1:1) afforded COMPOUND 153 (55 mg, 40%) as a white foam. ¹H NMR (CDCl₃) δ 1.70-1.94 (m, 4 H), 2.04-2.15 (m, 1H), 2.26-2.33 (m, 1H), 2.64-2.96 (m, 4H), 3.10-3.15 (m, 1H), 3.68 (d, 1H, J=15.6 Hz), 3.80 (d, 1H, J=15.6 Hz), 3.98-4.07 (m, 1H), 4.19-4.25 (m, 1H), 6.83 (dd, 1H, J=7.8, 4.8 Hz), 7.20-7.23 (m, 2H), 7.35-7.40 (m, 2H), 7.66-7.68 (m, 2H), 8.34 (s, 2H), 8.78 (br s, 1H); ¹³C NMR (CDCl₃) δ 21.69, 21.92, 26.70, 29.38, 39.04, 49.41, 49.87, 59.45, 111.10, 119.37, 122.63, 122.95, 129.27, 135.68, 138.29, 143.68, 146.10, 147.70, 154.94, 157.51. 162.27. ES-MS m/z 510 (M+H). Anal. Calcd. for C₂₆H₂₆N₆Cl₂O.0.3CH₂Cl₂.0.1H₂O: C, 58.86; H, 5.03; N, 15.66; Cl, 17.17. Found: C, 59.22; H, 5.21; N, 15.74; Cl, 16.80.

Compound 154: Preparation of N-{4-[(1-allyl-1H-benzimidazol-2-ylmethyl)-(S)-5,6,7,8-tetrahydro-quinolin-8-ylamino]-butyl}-3,5-dichloro-isonicotinamide 4-[(1-Allyl-1H-benzoimidazol-2-ylmethyl)-(5,6,7,8-tetrahydro-quinolin-8-yl)-amino]-butyl hydrochloride salt (120 mg, 0.215 mmol) was neutralized with 1M NaOH (25 mL) and the free base was extracted with CHCl₃ (25 mL×3). The combined organic solution was dried (Na₂SO₄), filtered and concentrated under reduced pressure, giving the free base as a cloudy, yellow oil.

To a suspension of 3,5-dichloropyridine-4-carboxylic acid (82 mg, 0.43 mmol) and DMF (1 drop) in CH₂Cl₂ (4 mL) was added oxalyl chloride (0.11 mL, 1.3 mmol). The resulting white suspension was stirred at room temperature under nitrogen for 35 minutes, and then the solvent was evaporated under reduced pressure. The crude acid chloride was dried under reduced pressure, and then a solution of the free base in THF (4 mL) and NEt₃ (0.05 mL, 0.4 mmol) were added. The resulting suspension was stirred at room temperature under nitrogen for 1 hour and 10 minutes. The mixture was diluted with CH₂Cl₂ (25 mL) and washed with H₂O (10 mL). The aqueous solution was extracted with CH₂Cl₂ (10 mL) and the organic solution was washed with saturated aqueous NaHCO₃ (20 mL). The aqueous solution was again extracted with CH₂Cl₂ (10 mL) and the combined organic solution was dried (Na₂SO₄), filtered and concentrated under reduced pressure. Purification by flash column chromatography on silica (CH₂Cl₂/MeOH/NH₄OH, 19:1:0.2) gave the amide as a white foam (92.3 mg, 0.164 mmol, 76%). ¹H NMR (CDCl₃) δ 1.40-1.60 (m, 2H), 1.63-1.89 (m, 3H), 1.95-2.19 (m, 3H), 2.60-3.03 (m, 5H), 3.55-3.67 (m, 1H), 3.70 (d, 1H, J=13.2 Hz), 3.86 (d, 1H, J=13.2 Hz), 4.26 (dd, 1H, J=8.1, 6.3 Hz), 4.61 (d, 1H, J=17.1 Hz), 4.67 (dd, 1H, J=16.4, 5.1 Hz), 4.96 (d, 1H, J=10.5 Hz), 5.57-5.71 (m, 1H), 6.85 (dd, 1H, J=7.5, 4.8 Hz), 7.17-7.25 (m, 4H), 7.61-7.65 (m, 1H), 7.89 (d, 1H, J=3.6 Hz), 8.32 (s, 2H), 8.97 (br. t, 1H). ¹³C NMR (CDCl₃) δ 23.1, 23.8, 24.0, 28.2, 30.9, 40.3, 47.2, 49.8, 51.3, 61.0, 111.6, 118.1, 120.5, 123.5, 123.7, 124.4, 130.6, 134.1, 136.6, 137.1, 138.7, 143.7, 145.1, 147.6, 149.0, 153.7, 158.7, 164.2. ES-MS m/z 564 (M+H). Anal. Calcd. for C₃₀H₃₂Cl₂N₆O.0.2C₄H₁₀O.0.1 CH₂Cl₂: C, 63.24; H, 5.87; N, 14.32; Cl, 13.29. Found: C, 63.02; H, 5.74; N, 14.31; Cl, 13.04.

Example 154

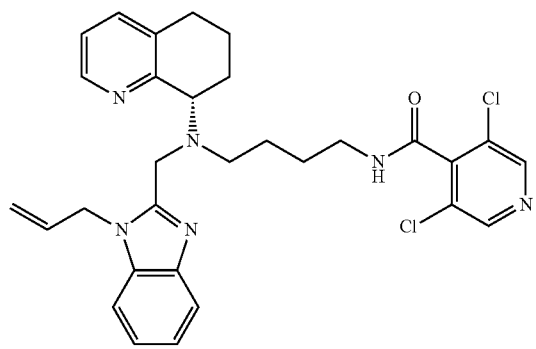 [SMILES: C=CCn1c(CN(CCCCNC(=O)c2c(Cl)cncc2Cl)[C@H]2CCCc3cccnc32)nc2ccccc21]

Example 155

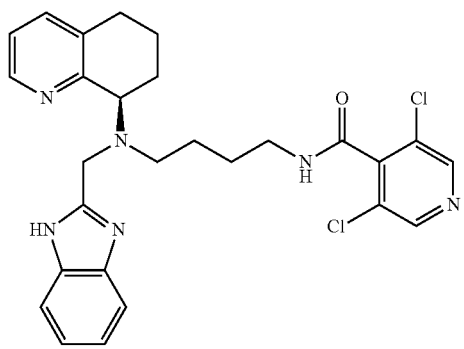 [SMILES: O=C(NCCCCN(Cc1nc2ccccc2[nH]1)[C@@H]1CCCc2cccnc21)c1c(Cl)cncc1Cl]

Compound 155: Preparation of N-{4-[(1H-benzimidazol-2-ylmethyl)-(R)-5,6,7,8-tetrahydro-quinolin-8-yl-amino]-butyl}-3,5-dichloro-isonicotinamide To a suspension of 3,5-dichloropyridine-4-carboxylic acid (135 mg, 0.70 mmol) and DMF (2 drops) in CH$_2$Cl$_2$ (7 mL) was added oxalyl chloride (0.18 mL, 2.1 mmol). The resulting suspension was stirred at room temperature under nitrogen for 35 minutes and then the solvent was evaporated under reduced pressure. The crude acid chloride was dried under reduced pressure, and then a solution of N$^1$-(1H-Benzimidazol-2-ylmethyl)-N$^1$-(R)-5,6,7,8-tetrahydro-quinolin-8-yl-butane-1,4-diamine (120 mg, 0.344 mmol) in THF (4 mL) and NEt$_3$ (0.06 mL, 0.4 mmol) were added. The resulting suspension was stirred at room temperature under nitrogen for 1 hour. The reaction was diluted with saturated aqueous NaHCO$_3$ (25 mL) and was extracted with CH$_2$Cl$_2$ (25 mL×3). The combined organic solution was dried (MgSO$_4$), filtered and concentrated under reduced pressure. Purification by flash column chromatography on silica (CH$_2$Cl$_2$/MeOH/NH$_4$OH, 32:1:0.2) gave the amide as a white foam (134 mg, 0.256 mmol, 74%). $^1$H NMR (CDCl$_3$) δ 1.47-1.61 (m, 4H), 1.63-1.78 (m, 1H), 1.81-195 (m, 1H), 2.02-2.13 (m, 111), 2.15-2.25 (m, 1H), 2.60-2.85 (m, 4H), 3.10-3.23 (m, 1H), 3.31-3.43 (m, 1H), 3.87 (d, 1H, J=16.2 Hz), 3.98 (d, 1H, J=16.2 Hz), 4.05 (dd, 1H, J=9.6, 5.7 Hz), 6.94 (br. t, 1H), 7.12 (dd, 1H, J=7.8, 4.8 Hz), 7.15-7.20 (m, 2H), 7.42 (d, 1H, J=7.8 Hz), 7.44-7.62 (m, 2H), 8.39 (s, 2H), 8.47 (d, 1H, J=4.8 Hz). $^{13}$C NMR (CDCl$_3$) δ 21.6, 23.9, 25.8, 26.9, 29.4, 39.6, 49.6, 50.5, 62.1, 122.1, 122.7, 129.2, 135.1, 138.0, 143.2, 146.8, 147.7, 156.4, 157.7, 162.6. ES-MS m/z 523 (M+H), 525 (M+2+H). Anal. Calcd. for C$_{27}$H$_{28}$Cl$_2$N$_6$O.0.3H$_2$O.0.2CH$_2$Cl$_2$: C, 59.85; H, 5.35; N, 15.40; Cl, 15.59. Found: C, 59.62; H, 5.38; N, 15.22; Cl, 15.98.

Example 156

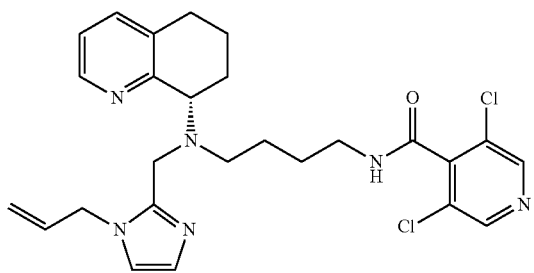 [SMILES: C=CCn1ccnc1CN(CCCCNC(=O)c1c(Cl)cncc1Cl)[C@H]1CCCc2cccnc21]

Compound 156: Preparation of N-{4-[(1-allyl-1H-imidazol-2-ylmethyl)-(S)-5,6,7,8-tetrahydro-quinolin-8-ylamino]-butyl}-3,5-dichloro-isonicotinamide N$^1$-(1-Allyl-1H-imidazol-2-ylmethyl)-N$^1$-(S)-5,6,7,8-tetrahydro-quinolin-8-yl-butane-1,4-diamine, Hydrochloride salt (115.1 mg, 0.216 mmol) was neutralized with 1M NaOH (25 mL) and the free base was extracted with CHCl$_3$ (25 mL×3). The combined organic solution was dried (Na$_2$SO$_4$), filtered and concentrated under reduced pressure, giving the free base as a cloudy, yellow oil.

To a suspension of 3,5-dichloropyridine-4-carboxylic acid (83 mg, 0.43 mmol) and DMF (1 drop) in CH$_2$Cl$_2$ (4 mL) was added oxalyl chloride (0.11 mL, 1.3 mmol). The resulting white suspension was stirred at room temperature under nitrogen for 30 minutes, and then the solvent was evaporated under reduced pressure. The crude acid chloride was dried under reduced pressure, and then a solution of the free base in THF (4 mL), and NEt$_3$ (0.04 mL, 0.3 mmol) were added. The resulting suspension was stirred at room temperature under nitrogen for 1 hour. The reaction was taken up into saturated aqueous NaHCO$_3$ (25 mL) and extracted with CH$_2$Cl$_2$ (25 mL×3). The combined organic solution was dried (Na$_2$SO$_4$), filtered and concentrated under reduced pressure. Purification by flash column chromatography on silica (CH$_2$Cl$_2$/MeOH/NH$_4$OH, 19:1:0.1) gave the amide as an off-white foam (77.4 mg, 0.151 mmol, 70%). $^1$H NMR (CDCl$_3$) δ 1.38-1.57 (m, 2H), 1.60-2.16 (m, 7H), 2.61-2.86 (m, 5H), 3.37 (d, 1H, J=13.5 Hz), 3.57 (d, 1H, J=13.5 Hz), 3.63-3.72 (m, 1H), 4.20 (dd, 1H, J=8.4, 6.3 Hz), 4.35 (dd, 1H, J=13.7, 5.1 Hz), 4.52 (dd, 1H, J=13.7, 5.7 Hz), 4.71 (dd, 1H, J=17.1, 0.9 Hz), 5.02 (dd, 1H, J=10.2, 0.9 Hz), 5.56-5.69 (m, 1H), 6.74 (d, 1H, J=1.2 Hz), 6.81 (d, 1H, J=1.2 Hz), 6.86 (dd, 1H, J=7.5, 4.8 Hz), 7.30 (d, 1H, J=6.9 Hz), 7.74 (d, 1H, J=3.9 Hz), 8.34 (s, 2H), 9.44 (br. s, 1H). $^{13}$C NMR (CDCl$_3$) δ 21.8, 22.1, 22.3, 27.3, 29.7, 38.5, 47.1, 48.1, 49.3, 59.5, 117.4, 120.5, 122.2, 127.5, 129.4, 133.5, 135.3, 137.5, 145.7, 146.1, 147.6, 157.6, 162.9. ES-MS m/z 513 (M+H). Anal. Calcd. for C$_{26}$H$_{30}$Cl$_2$N$_6$O.0.2H$_2$O.0.05CH$_2$Cl$_2$: C, 60.02; H, 5.90; N, 16.12; Cl, 14.28. Found: C, 60.20; H, 5.90; N, 15.80; Cl, 14.28.

Example 157

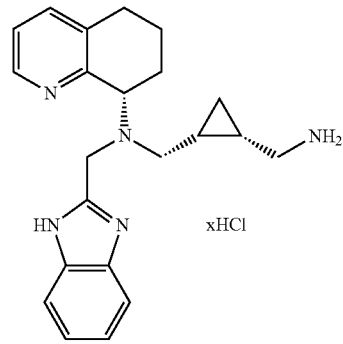

Compound 157: Preparation of (Cis-2-Aminomethyl-cylcopropylmethyl)-(1H-benzimidazol-2-ylmethyl)-(S)-5,6,7,8-tetrahydro-quinolin-8-yl-amine (hydrochloride salt)

Preparation of tert-Butyl-(Cis-2-chloromethyl-cyclopropylmethyoxy)-dimethyl-silane To a stirred 0° C. solution of dimethyl cis-1,2-cyclopropanedicarboxylate (22.0 g, 140 mmol) in anhydrous THF (185 mL) was added 1 M lithium aluminum hydride solution in THF (180 mL, 180 mmol) over 20 min under a nitrogen atmosphere. The cooling bath was removed and stirring was continued for 1.5 h. The mixture was carefully quenched with deionized water (7 mL), followed by 15% NaOH solution (7 mL), followed by deionized water (20 mL). The resultant precipitate was removed by filtration, the filter cake was washed with ethyl acetate (50 mL), and the filtrate was concentrated. The resultant orange oil was purified by column chromatography on silica gel (50:1 CH$_2$Cl$_2$/MeOH) to afford the diol (10.2 g, 72%) as a pale yellow oil.

To a stirred 0° C. suspension of sodium hydride (3.8 g, 95 mmol) in anhydrous THF (130 mL) under a nitrogen atmosphere was added a solution of the diol from above (9.22 g, 90 mmol) in anhydrous THF (50 mL) and stirring was continued for 10 min. To the above stirred solution was added tert-butyldimethylsilyl chloride (14.3 g, 95 mmol) in three parts, over 1 min. The cooling bath was removed, and stirring was continued for 30 min. The mixture was poured into saturated sodium bicarbonate solution (200 mL) and extracted with dichloromethane (3×150 mL). The organic extracts were combined, dried over Na$_2$SO$_4$, and concentrated. The resultant yellow oil (22 g) was purified by column chromatography on silica gel (5:1 hexanes/EtOAc) to provide the desired mono-protected diol (18.9 g, 97%) as a pale yellow oil.

To a stirred solution of the alcohol (18.9 g, 87 mmol) from above and triethylamine (36 mL, 260 mmol) in dichloromethane (300 mL) was added neat methanesulfonyl chloride (15 mL, 190 mmol) over 5 min. The stirred mixture was heated to reflux for 16 h; then it was cooled to room temperature, washed with water (2×200 mL), washed with brine (200 mL), dried over MgSO$_4$, and concentrated. Purification of the resultant brown oil (21 g) by column chromatography on silica gel (20:1 hexanes/EtOAc) afforded the title compound (13.5 g, 66%) as a yellow oil. $^1$N NMR (CDCl$_3$) δ 0.06 (s, 3H), 0.07 (s, 3H), 0.38 (q, 1H, J=6.0 Hz), 0.85-0.89 (m, 1H), 0.90 (s, 9H), 1.23-1.36 (m, 2H), 3.57-3.68 (m, 3H), 3.78-3.84 (m, 1H).

Preparation of Methanesulfonic acid Cis-2-(1,3-di-oxo-1,3-dihydro-isoindol-2-ylmethyl)-cyclopropylm-ethyl ester A stirred slurry of tert-butyl-(cis-2-chloromethyl-cyclopropylmethyoxy)-dimethyl-silane (115 g, 57 mmol) from above and potassium phthalimide (16.0 g, 86 mmol) in DMF (380 mL) was heated to 100° C. under a nitrogen atmosphere for 3 h. the mixture was cooled to room temperature and concentrated. The resultant residue was dissolved in ethyl acetate (500 mL), washed with brine (3×200 mL), dried over MgSO$_4$, and concentrated. Purification of the crude material by column chromatography on silica gel (9:1 hexanes/EtOAc) gave the desired phthalimide (8:55 g, 43%) as a white crystalline solid.

The phthalimide (8.5 g, 25 mmol) from above was stirred vigorously in a mixture THF (100 mL) and 1 N HCl (100 mL) for 20 min. The mixture was concentrated to remove THF then extracted with dichloromethane (3×100 mL). The combined organic extracts were dried over MgSO$_4$ and concentrated. The resultant material was filtered through a plug of silica gel. First the plug was eluted with 9:1 hexanes/EtOAc to wash away the non-polar impurities; then it was eluted with EtOAc to provide the desired alcohol (5.6 g, 97%) as a white solid.

To a stirred 0° C. solution of the alcohol (5.6 g, 24 mmol) from above and triethylamine (5.0 mL, 36 mmol) in dichloromethane (80 mL) was added methanesulfonyl chloride (2.3 mL, 29 mmol) and stirring was continued for 40 minutes at room temperature. The reaction was quenched by addition of saturated sodium bicarbonate solution (100 mL). The layers were separated and the aqueous layer was extracted with dichloromethane (50 mL). The organic layers were combined, dried over MgSO$_4$, and concentrated to give the title compound (7.9 g, 100%) as a white solid. $^1$H NMR (CDCl$_3$) δ 0.53 (q, 1H, J=6.0 Hz), 0.91-0.99 (m, 1H), 1.28-1.41 (m, 1H), 1.55-1.62 (m, 1H), 3.01 (s, 3H), 3.67-3.83 (m, 2H), 4.24 (dd, 1H, J=12.0, 9.0 Hz), 4.58 (dd, 1H, J=10.5, 7.5 Hz), 7.72-7.76 (m, 2H), 7.83-7.87 (m, 2H).

Preparation of (Cis-2-Aminomethyl-cylcopropylm-ethyl)-(1H-benzimidazol-2-ylmethyl)-(S)-5,6,7,8-tetrahydro-quinolin-8-yl-amine (hydrochloride salt) (Compound 157)

A stirred slurry of methanesulfonic acid (1R,2S)-2-(1,3-dioxo-1,3-dihydro-isoindol-2-ylmethyl)-cyclopropylmethyl ester (7.4 g, 24 mmol) from above, (1H-benzimidazol-2-ylmethyl)-(S)-5,6,7,8-tetrahydro-quinolin-8-yl-amine (7.6 g, 20 mmol, prepared according to the procedures in Bridger et al. U.S. patent application Ser. No. 09/535,314), diisopropylamine (5.2 mL, 30 mmol), and potassium iodide (170 mg, 1.0 mmol) in anhydrous acetonitrile (200 mL) was heated to 60° C. for 16 h. The mixture was cooled to room temperature and concentrated. The resultant residue was partitioned between ethyl acetate (200 mL) and saturated sodium bicarbonate solution (100 mL). The layers were separated and the organic layer was washed with water (2×100 mL) and brine (2×100 mL), dried over MgSO$_4$ and concentrated. Purification of the resultant crude brown oil by repetitive column chromatography on silica gel (first column: 2% MeOH/CH$_2$Cl$_2$, second column: 5% NH$_4$OH/EtOAc) provided the desired protected amine (2.3 g, 19%) as a white foamy solid.

To a stirred solution of the protected amine (6.3 g, 11 mmol) from above in ethanol (50 mL) was added hydrazine hydrate (3.1 mL, 64 mmol). The mixture was heated to 50° C. for 1 h with stirring. The resultant white slurry was cooled to room temperature, diluted with diethyl ether (50 mL), filtered through a glass-fritted funnel to remove the precipitate, and concentrated. Purification of the crude material by repetitive column chromatography on silica gel (first column: 20:1:1 CH$_2$Cl$_2$/MeOH/NH$_4$OH, second column: 50:1:1 CH$_2$Cl$_2$/MeOH/NH$_4$OH) afforded the desired primary amine (2.80 g, 74%) as a white foamy solid.

Following General Procedure D: Conversion of the free base (2.80 g, 7.7 mmol) from above to the hydrochloride salt provided COMPOUND 157 (3.30 g, 87%) as a white solid. $^1$H NMR (D$_2$O) δ 0.08 (q, 1H, J=5.0 Hz), 0.22 (q, 1H, J=5.0 Hz), 0.46-0.52 (m, 1H), 0.62 (q, 1H, J=6.0 Hz), 1.01-1.09 (m, 2H), 1.80-1.92 (m, 1H), 2.02-2.10 (m, 1H), 2.16-2.21 (m, 114), 2.32-2.38 (m, 1H), 2.51-2.63 (m, 1H), 2.64-2.71 (m, 1H), 2.99-3.16 (m, 4H), 4.43-4.69 (m, 3H), 7.55-7.59 (m, 2H), 7.75-7.85 (m, 3H), 8.32 (t, 1H, J=7.5 Hz), 8.62 (dd, 1H, J=7.5, 6.2 Hz); $^{13}$C NMR (D$_2$O) δ 9.99, 10.85, 12.41, 13.59, 15.40, 20.46, 20.69, 27.65, 39.84, 48.54, 49.49, 51.76, 61.21, 61.81, 114.31, 114.35, 125.80, 126.56, 126.61, 131.41, 131.69, 139.41, 139.53, 140.33, 140.46, 147.74, 147.86, 151.31, 151.97, 152.61; ES-MS m/z 362 (M+H). Anal. Calcd. for C$_{22}$H$_{27}$N$_5$.3.0HCl.1.3H$_2$O: C, 53.46; H, 6.65; N, 14.17; Cl, 21.52. Found: C, 53.67; H, 6.87; N, 13.85; Cl, 21.53.

The enantiomeric purity of COMPOUND 157 at the 5,6,7,8-tetrahydroquinolin-8-yl center) was determined to be 100% ee by chiral HPLC using the following conditions: Instrument: Hewlett Packard 1100 HPLC (VWD2); Column: ChiralPak AD-H, 0.46 cm×25 cm; Mobile Phases: A: 90:10 hexanes/reagent alcohol with 0.1% DEA, B: reagent alcohol; Isocratic: 90% A, 10% B; Total Run Time: 40 min; Flow Rate: 0.5 mL/min; Temperature: 40° C.; Detector: UV @ 270 nm; Injection volume: 10 μL.

Retention time of the R enantiomer=17.0 min.
Retention time of the S enantiomer=20.4 min.

Example 158

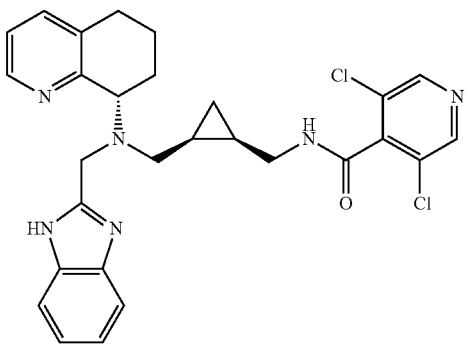 [SMILES: O=C(NC[C@@H]1C[C@@H]1CN(Cc1nc2ccccc2[nH]1)[C@H]1CCCc2cccnc21)c1c(Cl)cncc1Cl]

Compound 158: Preparation of N-(2-{[(1H-benzimidazol-2-ylmethyl)-(S)-(5,6,7,8-tetrahydro-quinolin-8-yl)-amino]-methyl}-cis-cyclopropylmethyl)-3,5-dichloro-isonicotinamide ((1R,2S)-2-Aminomethyl-cylcopropylmethyl)-(1H-benzimidazol-2-ylmethyl)-(S)-5,6,7,8-tetrahydro-quinolin-8-yl-amine, hydrochloride salt (107.2 mg, 0.217 mmol) was neutralized with 1M NaOH (25 mL) and the free base was extracted with CHCl$_3$ (25 mL×3). The combined organic solution was dried (Na$_2$SO$_4$), filtered and concentrated under reduced pressure, giving the free base as a white foam.

To a suspension of 3,5-dichloropyridine-4-carboxylic acid (85 mg, 0.44 mmol) and DMF (1 drop) in CH$_2$Cl$_2$ (4 mL) was added oxalyl chloride (0.11 mL, 1.3 mmol). The resulting white suspension was stirred at room temperature under nitrogen for 30 minutes, and then the solvent was evaporated under reduced pressure. The crude acid chloride was dried under reduced pressure, then NEt$_3$ (0.06 mL, 0.4 mmol) and a solution of the free base in THF (4 mL) were added. The solution was stirred at room temperature under nitrogen for 1 hour and 15 minutes. The reaction was taken up into CH$_2$Cl$_2$ (25 mL) and washed with H$_2$O (10 mL). The aqueous solution was extracted with CH$_2$Cl$_2$ (10 mL×2) and the combined organic solution was washed with saturated aqueous NaHCO$_3$ (15 mL). This aqueous solution was extracted with CH$_2$Cl$_2$ (10 mL) and the combined organic solution was dried (Na$_2$SO$_4$), filtered and concentrated under reduced pressure. Purification by flash column chromatography on silica (CH$_2$Cl$_2$/MeOH, 99:1, increased to 49:1) gave diastereomer A as a white foam (44.9 mg, 0.084 mmol, 39%) along with diastereomer B as a white foam (48.0 mg, 0.090 mmol, 41%).

Characterization data for diastereomer A: $^1$H NMR (CDCl$_3$) δ 0.07 (q, 1H, J=5.2 Hz), 0.72-0.84 (m, 1H), 1.09-1.35 (m, 2H), 1.61-1.96 (m, 2H), 2.03-2.18 (m, 2H), 2.24-2.40 (m, 2H), 2.77-2.88 (m, 2H), 3.32 (dd, 1H, J=13.2, 5.1 Hz), 4.41 (ddd, 1H, J=13.8, 9.6, 3.0 Hz), 4.68 (dd, 1H, J=10.5, 5.4 Hz), 6.81 (dd, 1H, J=7.8, 4.8 Hz), 7.16-7.28 (m, 2H), 7.33-7.45 (m, 2H), 7.64 (d, 1H, J=6.6 Hz), 8.36 (s, 2H), 9.48 (d, 1H, J=8.1 Hz), 10.37 (br. s, 1H). $^{13}$C NMR (CDCl$_3$) δ 9.5, 12.4, 16.2, 20.9, 21.4, 28.9, 38.5, 49.1, 51.9, 58.9, 110.5, 119.1, 121.7, 122.3, 122.7, 129.0, 133.4, 135.2, 137.8, 142.9, 143.4, 145.4, 147.2, 154.1, 157.3, 162.3. ES-MS m/z 535 (M+H), 537 (M+2+H). Anal. Calcd. for C$_{28}$H$_{28}$Cl$_2$N$_6$O.0.5CH$_3$OH.0.4CH$_2$Cl$_2$: C, 59.29; H, 5.30; N, 14.35; Cl, 16.96. Found: C, 59.46; H, 5.24; N, 14.31; Cl, 16.60.

Characterization data for diastereomer B: $^1$H NMR (CDCl$_3$) δ −0.01 (dd, 1H, J=9.0, 6.0 Hz), 0.54-0.92 (m, 3H), 1.65-1.92 (m, 2H), 2.03-2.15 (m, 1H), 2.18-2.30 (m, 1H), 2.47 (dd, 1H, J=13.5, 10.8 Hz), 2.67 (ddd, 1H, J=14.6, 10.7, 2.1 Hz), 2.74-2.86 (m, 2H), 3.29 (dd, 1H, J=13.5, 3.3 Hz), 3.77 (d, 1H, J=15.9 Hz), 3.92 (d, 1H, J=15.9 Hz), 4.08 (dd, 1H, J=9.6, 5.4 Hz), 4.41 (ddd, 1H, J=14.6, 8.4, 4.8 Hz), 6.97 (dd, 1H, J=7.8, 4.8 Hz), 7.20 (d, 2H, J=5.7 Hz), 7.39 (d, 1H, J=7.2 Hz), 7.59 (br. s, 1H), 7.70 (d, 1H, J=3.9 Hz), 8.38 (s, 2H), 8.60 (d, 1H, J=7.5 Hz).

Example 159

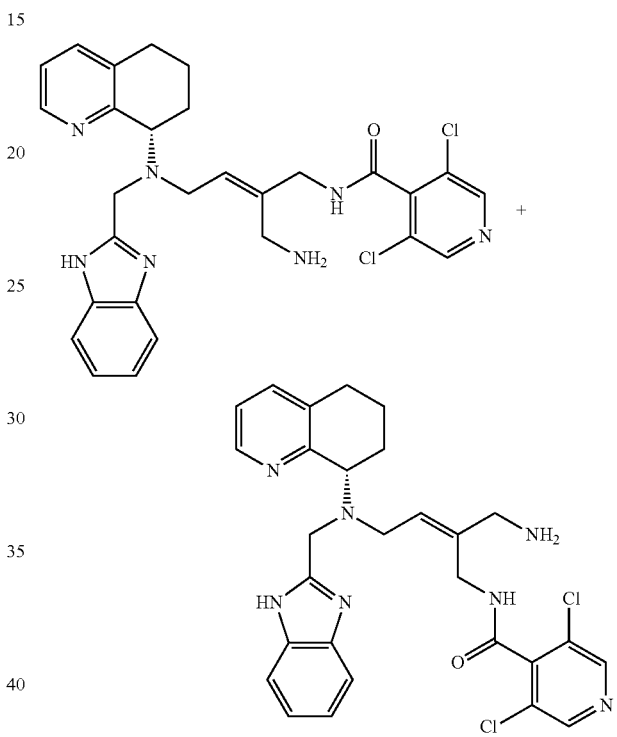

Compound 159: Preparation of N-{(E)-2-aminomethyl-4-[(1H-benzimidazol-2-ylmethyl)-(S)-(5,6,7,8-tetrahydro-quinolin-8-yl)-amino]-but-2-enyl}-3,5-dichloro-isonicotinamide and N-{(Z)-2-aminomethyl-4-[(1H-benzimidazol-2-ylmethyl)-(S)-(5,6,7,8-tetrahydro-quinolin-8-yl)-amino]-but-2-enyl}-3,5-dichloro-isonicotinamide 3-Aminomethyl-N-(1H-benzoimidazol-2-ylmethyl)-N-(5,6,7,8-tetrahydro-quinolin-8-yl)-but-2-ene-1,4-diamine, hydrochloride salt (213.8 mg, 0.365 mmol) was neutralized with 1M NaOH (25 mL) and the free base was extracted with CHCl$_3$ (25 mL×3). The combined organic solution was dried (Na$_2$SO$_4$), filtered and concentrated under reduced pressure, giving the free base as a yellow foam.

To a suspension of 3,5-dichloropyridine-4-carboxylic acid (86 mg, 0.45 mmol) and DMF (1 drop) in CH$_2$Cl$_2$ (4 mL) was added oxalyl chloride (0.12 mL, 1.4 mmol). The resulting white suspension was stirred at room temperature under nitrogen for 30 minutes, and then the solvent was evaporated under reduced pressure. The crude acid chloride was dried under reduced pressure, and then a solution of the free base in THF (7 mL), and NEt$_3$ (0.08 mL, 0.6 mmol) were added. The resulting suspension was stirred at room temperature under nitrogen for 1.5 hours. The reaction was taken up into H$_2$O (25 mL) and extracted with CH$_2$Cl$_2$ (25 mL×3). The combined organic solution was dried (Na$_2$SO$_4$), filtered and concentrated under reduced pressure. Purification by flash column chromatography on silica (CH$_2$Cl$_2$/MeOH/NH$_4$OH, 19:1:0.1) gave both regioisomeric amides as an approximately 1:1 mixture (26.1 mg, 0.047 mmol, 13%) (the regioisomeric ratio was estimated based on differentiation of the two components in the $^1$H NMR spectrum. Separation of the two isomers was not observed during chromatography or during analysis by HPLC.) along with the bis-amide as a yellow foam (39.9 mg, 0.055 mmol, 15%).

Data for the mono-amide mixture: $^1$H NMR (CDCl$_3$) δ 1.67-1.96 (m, 6H), 2.02-2.30 (m, 4H), 2.71-2.95 (m, 4H), 3.24 (s, 2H), 3.27-3.39 (m, 5H), 3.44-3.51 (m, 1H), 3.61 (d, 1H, J=15.3 Hz), 3.76 (d, 1H, J=15.3 Hz), 3.83-3.98 (m, 5H), 4.08-4.22 (m, 3H), 5.47 (t, 1H, J=6.9 Hz), 5.55 (t, 1H, J=6.9 Hz), 6.52 (br. s, 1H), 6.97-7.08 (m, 3H), 7.12-7.23 (m, 3H), 7.36-7.49 (m, 6H), 8.06 (d, 1H, J=4.2 Hz), 8.47 (s, 2H), 8.51 (s, 2H), 8.56 (d, 1H, J=3.9 Hz), 9.79 (br. t, 1H). ES-MS m/z 551 (M+H). Anal. Calcd. for C$_{28}$H$_{29}$Cl$_2$N$_7$O.2.0H$_2$O.0.2CH$_2$Cl$_2$.0.4C$_4$H$_8$O$_2$: C, 56.04; H, 5.78; N, 15.35; Cl, 13.32. Found: C, 56.19; H, 5.38; N, 15.36; Cl, 13.02.

Example 160

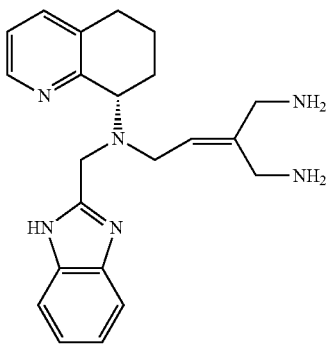 [SMILES: NCC(=CCN(Cc1nc2ccccc2[nH]1)[C@H]1CCCc2cccnc21)CN]

Compound 160: 3-Aminomethyl-N$^1$-(1H-benzoimidazol-2-ylmethyl)-N$^1$-(S)-(5,6,7,8-tetrahydro-quinolin-8-yl)-but-2-ene-1,4-diamine hydrochloride salt Preparation of (3-tert-Butoxycarbonylamino-2-hydroxy-propyl)-carbamic acid tert-butyl ester To a solution of 1,3 diamino-2-hydroxypropane (10 g, 0.11 mol) in methanol (500 ml) was added di-tert-butyl dicarbonate (48 g, 0.22 mol) and the reaction stirred for 2 hours at room temperature under a N$_2$ atmosphere. The mixture was concentrated to afford the product as a light yellow oil (31.9 g, 100%). $^1$HNMR (CD$_3$OD) δ 1.44 (s, 18H), 3.10 (m, 4H), 3.63 (m, 1H).

Preparation of (3-tert-Butoxycarbonylamino-2-oxo-propyl)-carbamic acid tert-butyl ester To a solution of dimethyl sulfoxide (25.2 ml, 0.36 mol) in methylene chloride (357 ml) at −78° C. (dry ice/acetone) was added a solution of oxalyl chloride (20 ml, 0.23 mol) in methylene chloride (115 ml). The reaction mixture was stirred at −78° C. for 30 min under an atmosphere of N$_2$ then a solution of (3-tert-Butoxycarbonylamino-2-hydroxy-propyl)-carbamic acid tert-butyl ester (31.9 g, 0.11 mol) in methylene chloride (300 ml) and triethylamine (75 ml, 0.54 mol) were added. The reaction was stirred for 16 hours, allowing the reaction to warm up to room temperature. The mixture was diluted with water (800 ml) and extracted with methylene chloride (2×300 ml). The combined organic extracts were dried (Na$_2$SO$_4$), filtered, and concentrated in vacuo to afford a yellowish oil. Purification via column chromatography on silica gel (ethyl acetate:hexane, 3:7, v/v) afforded the product as a white solid (28 g, 88%). $^1$H NMR (CDCl$_3$) δ 1.44 (s, 18H), 4.04 (m, 4H), 5.19 (s, 1H).

Preparation of 4-tert-butoxycarbonylamino-3-(tert-butoxycarbonylamino-methyl)-but-2-enoic acid ethyl ester To a solution of (3-tert-Butoxycarbonylamino-2-oxo-propyl)-carbamic acid tert-butyl ester (28 g, 97.0 mmol) dissolved in benzene (350 ml) was added (carbethoxymethylene)-triphenyl phosphorane (89 g, 0.26 mol) and the reaction mixture stirred for 16 hours at 45° C., under a N$_2$ atmosphere. The mixture was concentrated and purified by column chromatography on silica gel (ethyl acetate:hexane, 1:3, v/v) to afford the product as a yellowish solid (26 g, 75%). $^1$H NMR (CDCl$_3$) δ 1.43 (s, 18H), 1.59 (s, 3H), 3.90 (d, 2H, J=4.75 Hz), 4.11 (m, 4H), 5.35 (m, 2H), 5.87 (s, 1H).

Preparation of [2-(tert-butoxycarbonylamino-methyl)-4-hydroxy-but-2-enyl]-carbamic acid tert-butyl ester To a solution of 4-tert-butoxycarbonylamino-3-(tert-butoxycarbonylamino-methyl)-but-2-enoic acid ethyl ester (7.0 g, 19.5 mmol) in tetrahydrofuran (195 ml), at a reaction temperature of −78° C. (dry ice/acetone) was added a solution of diisobutylaluminum hydride (1 M in CH$_2$Cl$_2$, 59 ml, 59 mmol) and the reaction mixture stirred at −78° C. for 2 hours under a N$_2$ atmosphere. The reaction was quenched with a saturated solution of sodium tartrate tetrahydrate (300 ml), stirred vigorously until the layers clarified then extracted with methylene chloride (2×100 ml). The combined organic extracts were dried (Na$_2$SO$_4$), filtered, and concentrated in vacuo to afford a yellow oil. Purification via column chromatography on silica gel (ethyl acetate:hexane, 1:1, v/v) afforded the product as a yellow oil (5.90 g, 96%). $^1$HNMR (CDCl$_3$) δ 1.43 (s, 18H), 3.72 (s, 4H), 4.18 (t, 2H), 4.76 (s, 1H), 5.54 (s, 1H), 5.96 (t, 1H).

Preparation of methane sulfonic acid 4-tert-butoxycarbonyl amino-3-(tert-butoxycarbonyl amino-methyl)-but-2-enyl ester To a solution of [2-(tert-butoxycarbonylamino-methyl)-4-hydroxy-but-2-enyl]-carbamic acid tert-butyl ester (9.13 g, 29 mmol) in dichloromethane (290 ml), at a reaction temperature of 0° C. was added triethylamine (8.1 ml, 58 mmol) and methanesulfonyl chloride (2.24 ml, 29 mmol). The reaction mixture was stirred at 0° C. for 30 min under a $N_2$ atmosphere then diluted with a saturated solution of ammonium chloride (250 ml). The aqueous layer was extracted with methylene chloride (3×150 ml). The combined organic extracts were dried ($Na_2SO_4$), filtered, and concentrated in vacuo to afford a yellow oil (11.0 g, 93%). $^1$HNMR ($CDCl_3$) δ 1.43 (s, 18H), 3.03 (s, 3H), 3.78 (m, 4H), 4.92 (d, 1H, J=4.75 Hz), 5.01 (s, 1H), 5.17 (s, 1H), 5.66 (t, 1H).

Preparation of 2-{[[4-tert-butoxycarbonylamino-3-(tert-butoxycarbonylamino-methyl)—but-2-enyl]-N-(S)-(5,6,7,8-tetrahydro-quinolin-8-yl)-amino]-methyl}-benzoimidazole-1-carboxylic acid tert-butyl ester To a solution methane sulfonic acid 4-tert-butoxycarbonyl amino-3-(tert-butoxycarbonyl amino-methyl)-but-2-enyl ester (5.2 g, 13.2 mmol) in acetonitrile (60 ml) was added potassium iodide (1.1 g, 6.6 mmol), diisopropylethylamine (2.3 ml, 13.2 mmol), and a solution of 2-[(5,6,7,8-tetrahydro-quinolin-8-yl amino)-methyl]-benzoimidazole-1-carboxylic acid tert-butyl ester (5.0 g, 13.2 mmol) in acetonitrile (60 ml) and the reaction stirred at room temperature for 2 hours under a $N_2$ atmosphere. A solution of methane sulfonic acid 4-tert-butoxycarbonyl amino-3-(tert-butoxycarbonyl amino-methyl)-but-2-enyl ester (5.2 g, 13.2 mmol) in acetonitrile (60 ml) was added and the reaction mixture stirred at room temperature for 16 hours under a $N_2$ atmosphere. The reaction mixture was concentrated, redissolved in methylene chloride (200 ml), and diluted with saturated NaCl (200 ml). The aqueous layer was extracted with methylene chloride (3×150 ml) and the combined organic extracts were dried ($Na_2SO_4$), filtered, and concentrated in vacuo to afford a yellow oil (6.3 g, 70%). $^1$HNMR ($CDCl_3$) δ 1.43 (s, 18H), 2.10 (m, 3H), 2.53 (m, 1H), 2.77 (m, 1H), 3.19 (m, 1H), 3.52 (m, 3H), 3.77 (m, 1H), 3.94 (m, 1H), 4.29 (m, 3H), 5.21 (s, 1H), 5.47 (s, 1H), 6.73 (s, 1H), 7.05 (s, 1H), 7.25 (s, 1H), 7.69 (m, 3H), 8.25 (s, 1H).

Preparation of 3-Aminomethyl-N-(1H-benzoimidazol-2-ylmethyl)-N-(S)-(5,6,7,8-tetrahydro-quinolin-8-yl)-but-2-ene-1,4-diamine A solution of 2-{[[4-tert-butoxycarbonylamino-3-(tert-butoxycarbonylamino-methyl)-but-2-enyl]-N-(S)-(5,6,7,8-tetrahydro-quinolin-8-yl)-amino]-methyl}-benzoimidazole-1-carboxylic acid tert-butyl ester dissolved in HCl saturated acetic acid (35 ml) was stirred for 5 hours at room temperature under a $N_2$ atmosphere. The solution was added dropwise to diethyl ether (550 ml) to yield a chunky white precipitate. The white solid was isolated via suction filtration under a steady stream of nitrogen, washed with diethyl ether and dried at 40° C. in vacuo overnight (3.8 g, 71%). $^1$HNMR ($D_2O$) δ 1.79 (m, 1H), 1.83 (m, 1H), 2.01 (m, 1H), 2.43 (m, 1H), 3.00 (s, 2H), 3.31 (m, 2H), 3.76 (m, 5H), 4.49 (m, 3H), 6.66 (dd, 1H, J=8.77, 3.95 Hz), 7.62 (m, 2H), 7.88 (m, 3H), 8.41 (d, 1H, J=7.45 Hz), 8.83 (d, 1H, J=5.7 Hz); $^{13}$CNMR δ ($D_2O$) 20.32, 27.61, 37.09, 42.34, 46.68, 48.93, 59.29, 114.32, 126.01, 126.98, 128.73, 131.22, 136.30, 139.63, 140.36, 148.08, 150.73. ES-MS m/z 377 (M+H). Anal. Calcd. For $C_{22}H_{28}N_6$·3.93HCl·2.16$H_2O$·0.46($C_2H_4O_2$): C, 46.96; H, 6.55; N, 14.44; Cl, 23.74. Found: C, 46.97; H, 6.67; N, 14.31; Cl, 23.75.

Example 161

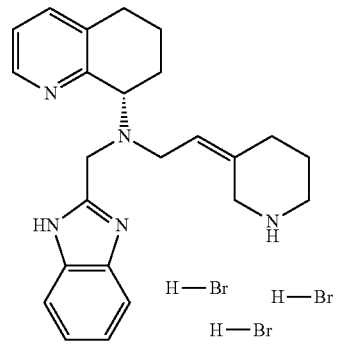

Compound 161: Preparation of (1H-Benzoimidazol-2-ylmethyl)-(2-piperidin-3-ylidene-ethyl)-(5,6,7,8-tetrahydro-quinolin-8-yl)-amine (hydrobromide salt)

To a solution of 3-hydroxy-piperidine-1-carboxylic acid tert-butyl ester (1.9169 g, 9.5 mmol) in $CH_2Cl_2$ (50 mL) was added Dess-Martin Periodinane (4.8470 g, 11.4 mmol), and the mixture was stirred at room temperature for 5 hours. $CH_2Cl_2$ (75 mL), saturated $NaHCO_3$ (100 mL), and 20% aqueous sodium thiosulfate (100 mL) were added, and the mixture was stirred for 30 minutes. The layers were separated, and the aqueous layer was extracted with $CH_2Cl_2$ (1×75 mL). The organic extracts were washed with brine (1×100 mL), dried ($Na_2SO_4$), and concentrated. Purification of the crude material by column chromatography on silica gel (4:1 hexanes-EtOAc) provided 1.80 g (95%) of 3-oxo-piperidine-1-carboxylic acid tert-butyl ester as a colorless oil. $^1$H NMR ($CDCl_3$) δ 1.49 (s, 9H), 1.93-2.02 (m, 2H), 2.46 (t, 2H, J=6 Hz), 3.58 (t, 2H, J=6 Hz), 4.00 (s, 2H).

To a solution of 3-oxo-piperidine-1-carboxylic acid tert-butyl ester (1.80 g, 9.0 mmol) in benzene (20 mL) was added (carbethoxymethylene)-triphenylphosphorane (4.72 g, 13.6 mmol) and stirred at 65° C. for 3.5 hours. The reaction was brought to reflux (80° C.) and stirred for 23 hours before it as cooled to room temperature and concentrated. Purification of the crude material by column chromatography on silica gel (6:1 hexanes-EtOAc) provided 0.4874 g (20%) of cis-3-ethoxycarbonylmethylene-piperidine-1-carboxylic acid tert-butyl ester as white crystals. A NOESY experiment was run to determine which product was the desired cis isomer. $^1$H NMR ($CDCl_3$) δ 1.23-1.30 (m, 3H), 1.45 (s, 9H), 1.70-1.76 (m, 2H), 2.34 (t, 2H, J=6 Hz), 3.48 (t, 2H, J=6 Hz), 4.13-4.21 (m, 2H), 4.61 (s, 2H), 5.66 (s, 1H).

A solution of cis-3-ethoxycarbonylmethylene-piperidine-1-carboxylic acid tert-butyl ester (0.4701 g, 1.7 mmol) in $CH_2Cl_2$ (17 mL) was cooled to −78° C. and was flushed with argon. 1.0 M Diisobutylaluminum hydride in hexanes (5.1 mL, 5.1 mmol) was added dropwise to this solution, and the reaction was stirred at −78° C. for 50 minutes. The reaction was brought to room temperature and stirred for 3.5 hours before it was cooled to 0° C. Saturated aqueous KNa Tartrate (Rochelle's salt, 6 mL) was added dropwise, and then water (10 mL) and $CH_2Cl_2$ (75 mL) were added. The phases were separated and the aqueous phase was extracted with $CH_2Cl_2$ (2×50 mL). The combined organic extracts were dried ($Na_2SO_4$) and concentrated. Purification of the crude material by column chromatography on silica gel (3:1 hexanes- EtOAc) provided 0.1652 g (43%) of cis-3-(2-hydroxy-ethylidene)-piperidine-1-carboxylic acid tert-butyl ester. ¹H NMR (CDCl₃) δ 1.45 (s, 9H), 1.60-1.68 (m, 2H), 2.27 (t, 2H, J=6.1 Hz), 2.87 (s, 1H), 3.47 (t, 2H, J=6 Hz), 3.96 (s, 2H), 4.06-4.13 (m, 2H), 5.59 (s, 1H).

To a solution of cis-3-(2-hydroxy-ethylidene)-piperidine-1-carboxylic acid tert-butyl ester (0.1652 g, 0.7 mmol) in CH₂Cl₂ (10 mL) at −78° C. was slowly added triethylamine (0.2 mL, 1.4 mmol) and methane sulfonyl chloride (0.1 mL, 0.9 mmol). The reaction was stirred at −78° C. for 40 minutes and then stirred at room temperature for 40 minutes. Water (10 mL) and CH₂Cl₂ (40 mL) were added and the layers were separated. The aqueous phase was extracted with CH₂Cl₂ (3×50 mL), and the combined organic extracts were dried (Na₂SO₄) and concentrated to yield 0.1985 g (93%) of cis-3-(2-methanesulfonyloxy-ethylidene)-piperidine-1-carboxylic acid tert-butyl ester as a pale pink oil. ¹H NMR (CDCl₃) δ 1.46 (s, 9H), 1.78 (s, 2H), 2.31 (t, 2H, J=6 Hz), 3.01 (s, 3H), 3.48 (t, 2H, J=6 Hz), 4.01 (s, 2H), 4.82 (d, 2H, J=7.4 Hz), 5.46 (t, 1H, J=7.4 Hz).

To a solution of cis-3-(2-methanesulfonyloxy-ethylidene)-piperidine-1-carboxylic acid tert-butyl ester (0.1985 g, 0.6 mmol) in CH₃CN (6 mL) was added 2-[(5,6,7,8-tetrahydro-quinolin-8-ylamino)-methyl]-benzoimidazole-1-carboxylic acid tert-butyl ester (0.2531 g, 0.6 mmol), potassium iodide (0.0110 g, 0.06 mmol), and DIPEA (0.2 mL, 0.9 mmol) and was stirred at 60° C. for 17 hours. Saturated NaHCO₃ (15 mL) and CH₂Cl₂ (50 mL) were added and separated. The aqueous phase was extracted with CH₂Cl₂ (2×30 mL), and the combined organic extracts were dried (Na₂SO₄) and concentrated. Purification of the crude material by column chromatography on silica gel (70:1:1 CH₂Cl₂—CH₃OH—NH₄OH) followed by another column on silica gel (ether saturated with NH₄OH) provided 0.1282 g (36%) of cis-2-{[[2-(1-tert-butoxycarbonyl-piperidin-3-ylidene)-ethyl]-(5,6,7,8-tetrahydro-quinolin-8-yl)-amino]-methyl}-benzoimidazole-1-carboxylic acid tert-butyl ester as a white solid. ¹H NMR (CDCl₃) δ 1.41-1.47 (m, 1H), 1.68 (s, 9H), 1.73 (s, 9H), 1.85-1.96 (m, 5H), 2.17 (s, 2H), 2.59-2.79 (m, 2H), 3.21-3.31 (m, 1H), 3.37-3.60 (m, 3H), 3.72 (s, 1H), 3.94-4.01 (m, 1H), 4.21-4.29 (m, 1H), 4.38-4.62 (m, 2H), 5.21-5.30 (m, 1H), 6.94-6.98 (m, 1H), 7.27-7.28 (m, 3H), 7.68-7.71 (m, 1H), 7.79-7.82 (m, 1H), 8.39-8.40 (m, 1H).

Following the general procedure D, cis-2-{[[2-(1-tert-butoxycarbonyl-piperidin-3-ylidene)-ethyl]-(S)-(5,6,7,8-tetrahydro-quinolin-8-yl)-amino]-methyl}-benzoimidazole-1-carboxylic acid tert-butyl ester (0.1282 g, 0.2 mmol) was converted to the hydrobromide salt followed by reprecipitation of the intermediate solid from methanol/ether gave COMPOUND 161 (0.1168 g, 87%) as a white solid. ¹H NMR (D₂O) 1.12-1.21 (m, 2H), 1.58-1.67 (m, 3H), 1.79-1.94 (m, 2H), 1.98-2.24 (m, 2H), 2.33-2.43 (m, 1H), 2.97-3.04 (m, 2H), 3.07-3.24 (m, 2H), 3.46-3.65 (m, 2H), 3.78-3.84 (m, 1H), 4.29-4.38 (m, 1H), 4.49-4.61 (m, 3H), 5.44 (s, 1H), 7.61-7.62 (m, 2H), 7.77-7.80 (m, 2H), 7.86 (t, 1H, J=6.9 Hz), 8.34 (d, 1H, J=7.5 Hz), 8.64 (d, 1H, J=4.8 Hz). ¹³C NMR (D₂O) δ 20.36, 20.63, 23.60, 27.63, 30.03, 31.84, 43.82, 44.67, 48.82, 61.29, 114.22, 125.97, 126.29, 127.06, 130.93, 132.83, 139.48, 140.66, 148.09, 150.93, 151.83. ES-MS m/z 388 (M+H). Anal. Calcd. for C₂₄H₂₉N₅.3.0HBr.2.3H₂O: C, 42.92; H, 5.49; N, 10.43; Br, 35.69. Found: C, 43.20; H, 5.38; N, 10.03; Br, 35.92.

Example 162

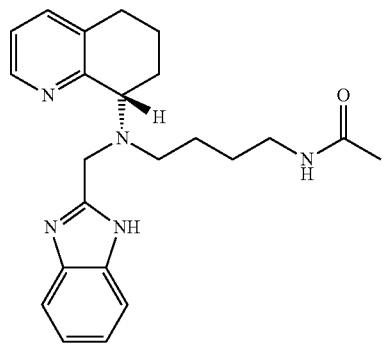

Compound 162: Preparation of N-{4-[(1H-Benzimidazol-2-ylmethyl)-(S)-5,6,7,8-tetrahydro-quinolin-8-yl-amino]-butyl}-acctamide (free base)

Preparation of Compound 162

N'-(1H-benzimidazol-2-ylmethyl)-N'-(S)-5,6,7,8-tetrahydro-quinolin-8-yl-butane-1,4-diamine (500 mg, 1.43 mmol) was dissolved in ethyl acetate (10 mL) to give a yellow solution. The reaction mixture was stirred at reflux for 48 hours. The resulting yellow/orange solution was concentrated under reduced pressure to afford an orange oil. Purification via column chromatography on silica gel (CH₂Cl₂:MeOH:NH₄OH, 90:5:5, v/v/v) afforded the product as a pale yellow foam (56 mg, 10%). ¹H NMR (CDCl₃) δ 1.37-1.45 (m, 4H), 1.65-1.73 (m, 1H), 1.85 (s, 3H), 1.87-1.90 (m, 1H), 2.04-2.10 (m, 1H), 2.14-2.22 (m, 1H), 2.60-2.65 (m, 1H), 2.69-2.77 (m, 2H), 2.77-2.83 (m, 1H), 3.02-3.06 (m, 2H), 3.97 (d, 1H, J=15.0 Hz), 4.02 (m, 1H), 4.08 (d, 1H, J=15.0 Hz), 5.48 (br t, 1H), 7.16-7.22 (m, 3H), 7.44 (d, 1H, J=6.0), 7.53 (br s, 2H), 8.58 (d, 1H, J=3.0 Hz). ¹³C NMR (CDCl₃) δ 21.61, 23.60, 24.24, 26.10, 27.26, 29.51, 39.47, 49.82, 50.69, 62.46, 115.26, 122.08, 122.69, 135.10, 137.92, 146.92, 156.89, 157.84, 170.47. ES-MS m/z 392 [M+H]⁺. Anal. Calcd. for C₂₃H₂₉N₅O.0.7H₂O: C, 68.36; H, 7.58; N, 17.33. Found: C, 68.45; H, 7.47; N, 17.25.

Example 163

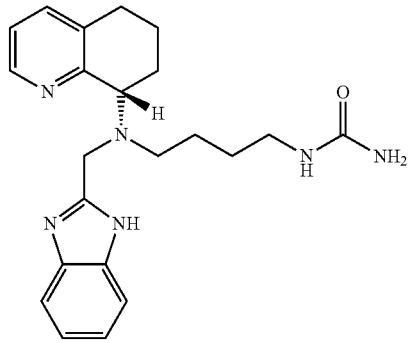

Compound 163: Preparation of {4-[(1H-Benzimidazol-2-ylmethyl)-(S)-5,6,7,8-tetrahydro-quinolin-8-yl-amino]-butyl}-urea (free base)

Preparation of Compound 163

In a flask purged with nitrogen, N'-(1H-benzimidazol-2-ylmethyl)-N'-(S)-5,6,7,8-tetrahydro-quinolin-8-yl-butane-1,4-diamine (208 mg, 0.60 mmol) was dissolved in iso-propanol (4 mL) to give a yellow solution. Trimethylsilyl isocyanate (113 μL, 0.83 mmol) was added via syringe and the reaction mixture was stirred at room temperature for 18 hours. The resulting yellow solution was concentrated under reduced pressure to afford a yellow oil. Purification via column chromatography on silica gel ($CH_2Cl_2$:MeOH:$NH_4OH$, 90:5:5, v/v/v) afforded the product as a white solid (167 mg, 71%). $^1$H NMR ($CDCl_3$) δ 1.37-1.45 (m, 4H), 1.65-1.75 (m, 1H), 1.88-1.92 (m, 1H), 2.00-2.07 (m, 1H), 2.17-2.24 (m, 2H), 2.51-2.59 (m, 1H), 2.66-2.77 (m, 2H), 2.80-2.83 (m, 1H), 2.96-3.00 (m, 2H), 3.95 (d, 1H, J=15.0 Hz), 4.03 (m, 1H), 4.04 (d, 1H, J=15.0 Hz), 4.47 (s, 2H), 5.20 (br t, 1H), 7.16-7.22 (m, 3H), 7.43 (d, 1H, J=7.5), 7.53 (br s, 2H), 8.55 (d, 1H, J=3.0 Hz). $^{13}$C NMR ($CDCl_3$) δ 21.51, 24.18, 25.88, 27.64, 29.50, 40.34, 49.67, 50.99, 62.64, 111.64, 119.13, 122.19, 122.74, 135.23, 137.99, 146.95, 156.64, 157.78, 159.33. ES-MS m/z 393 [M+H]$^+$. Anal. Calcd. for $C_{22}H_{28}N_6O \cdot 0.15 CH_2Cl_2$: C, 65.65; H, 7.04; N, 20.74. Found: C, 65.56; H, 7.26; N, 20.90.

Example 164

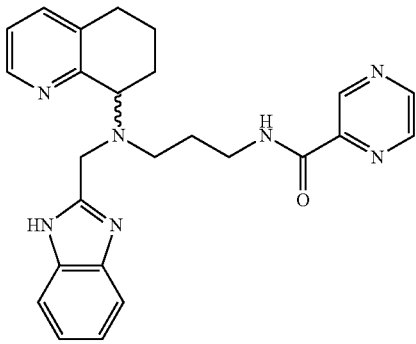 [SMILES: O=C(NCCCN(Cc1nc2ccccc2[nH]1)C1CCCc2cccnc21)c1cnccn1]

Compound 164: Preparation of pyrazine-2-carboxylic acid {3-[(1H-benzimidazol-2-ylmethyl)-(5,6,7,8-tetrahydro-quinolin-8-yl)-amino]-propyl}-amide Preparation of pyrazine-2-carboxylic acid (3-hydroxy-propyl)-amide To a solution of 3-amino-1-propanol (1.20 mL, 15.7 mmol) in $CH_2Cl_2$ (80 mL) was added 2-pyrazinecarboxylic acid (1.99 g, 16.0 mmol), DIPEA (5.6 mL, 32.1 mmol), HOBT (2.61 g, 19.3 mmol) and EDC.HCl (3.70 g, 19.3 mmol). The solution was stirred at room temperature under nitrogen for 14.5 hours, then was diluted with brine (25 mL). The layers were separated and the aqueous solution was extracted with EtOAc (50 mL×3) and $CHCl_3$ (50 mL×3). The combined organic solution was dried ($Na_2SO_4$), filtered and concentrated under reduced pressure. Purification by flash column chromatography on silica ($CH_2Cl_2$/MeOH/$NH_4OH$, 19:1:0.1) gave the amide as a white solid (1.94 g, 10.7 mmol, 68%). $^1$H NMR ($CDCl_3$) δ 1.83 (quint, 2H, J=5.9 Hz), 3.03 (br. s, 1H), 3.61-3.74 (m, 4H), 8.12 (br. s, 1H), 8.53 (dd, 1H, J=2.4, 1.5 Hz), 8.75 (d, 1H, J=2.4 Hz), 9.40 (d, 1H, J=1.5 Hz).

Preparation of pyrazine-2-carboxylic acid (3-oxo propyl)-amide

To a solution of the amide (184 mg, 1.02 mmol) in $CH_2Cl_2$ (5 mL) was added Dess-Martin periodinane (468 mg, 1.10 mmol) and the reaction was stirred at room temperature for 20 minutes. The mixture was diluted with 10% aqueous $Na_2S_2O_3$ (20 mL) and saturated aqueous $NaHCO_3$ (20 mL), stirred vigorously for 15 minutes and extracted with $CH_2Cl_2$ (25 mL×3). The combined organic solution was dried ($MgSO_4$), filtered and concentrated under reduced pressure giving the crude aldehyde as an orange solid (143 mg, 0.80 mmol, 78%). $^1$H NMR ($CDCl_3$) δ 2.85 (quint, 2H, J=6.0 Hz), 3.77 (q, 2H, J=6.0 Hz), 8.16 (br. s, 1H), 8.50 (dd, 1H, J=2.4, 1.5 Hz), 8.72 (d, 1H, J=2.4 Hz), 9.35 (d, 1H, J=1.5 Hz), 9.83 (s, 1H).

Preparation of Compound 164

A solution of the aldehyde (140 mg, 0.78 mmol) and (1H-benzimidazol-2-ylmethyl)-(5,6,7,8-tetrahydro-quinolin-8-yl)-amine (201 mg, 0.72 mmol) in $CH_2Cl_2$ (4.5 mL) was stirred at room temperature for 10 minutes, then NaBH(OAc)$_3$ (180 mg, 0.85 mmol) was added. The reaction mixture was stirred for another 6.5 hours, then was washed with 1M NaOH (10 mL×2) and brine (10 mL). The organic solution was dried ($MgSO_4$), filtered and concentrated under reduced pressure. Purification by flash column chromatography on silica ($CH_2Cl_2$/MeOH/$NH_4OH$, 19:1:0.1) gave the tertiary amine as a yellow foam (271 mg, 0.63 mmol, 85%). $^1$H NMR ($CDCl_3$) δ 1.60-2.10 (m, 5H), 2.18-2.29 (m, 1H), 2.65-2.74 (m, 2H), 2.79-2.90 (m, 2H), 3.41-3.59 (m, 21), 4.03-4.15 (m, 3H), 7.11-7.20 (m, 3H), 7.41 (d, 1H, J=7.5 Hz), 7.45-7.63 (m, 2H), 8.06 (m, 1H), 8.31 (dd, 1H, J=2.1, 1.8 Hz), 8.51 (d, 1H, J=3.6 Hz), 8.67 (d, 1H, J=2.4 Hz), 9.32 (d, 1H, J=1.2 Hz). $^{13}$C NMR ($CDCl_3$) δ 21.8, 23.5, 28.2, 29.6, 37.9, 48.5, 49.7, 62.0, 122.1, 122.6, 135.1, 137.8, 142.6, 144.8, 147.2, 147.4, 156.3, 157.7, 163.4. ES-MS m/z 442 (M+H). Anal. Calcd. for $C_{25}H_{27}N_7O \cdot 0.3 CH_2Cl_2$: C, 65.07; H, 5.96; N, 20.99. Found: C, 64.74; H, 6.10; N, 20.90.

Example: 165

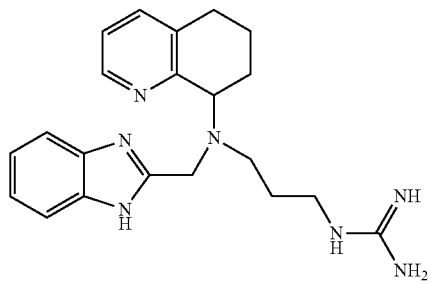 [SMILES: N=C(N)NCCCN(Cc1nc2ccccc2[nH]1)C1CCCc2cccnc21]

Compound 165: Preparation of N-{3-[(1H-benzimidazol-2-ylmethyl)-(5,6,7,8-tetrahydro-quinolin-8-yl)-amino]-propyl}-guanidine (hydrobromide salt)

A solution of (3-hydroxypropyl)-carbamic acid tert-butyl ester (0.60 g, 3.4 mmol) in anhydrous $CH_2Cl_2$ (17 mL) was treated with Dess-Martin reagent (1.74 g, 4.1 mmol) for 3 hours at room temperature. The reaction mixture was diluted with Et$_2$O (30 mL) and washed with a 20% aqueous solution of sodium thiosulfate (15 mL) followed by a saturated aqueous solution of sodium bicarbonate (15 mL). The combined aqueous phase was then extracted with Et$_2$O (2×35 mL) and re-washed with 20% sodium thiosulfate solution (30 mL), saturated NaHCO$_3$ solution (25 mL), and brine (25 mL). The organic component was then dried (MgSO$_4$), filtered, and concentrated under reduced pressure to provide (3-oxopropyl)-carbamic acid tert-butyl ester as a colorless oil (0.54 g, 91%).

Using general procedure B, (1H-benzimidazol-2-ylmethyl)-(5,6,7,8-tetrahydro-quinolin-8-yl)-amine (0.69 g, 2.5 mmol), (3-oxopropyl)-carbamic acid tert-butyl ester (0.54 g, 3.1 mmol) and sodium triacetoxyborohydride (0.95 g, 4.5 mmol) were stirred at room temperature in CH$_2$Cl$_2$ (13 mL) for 18 hours. This yielded, after work-up and column chromatography (5:0.5:94.5 MeOH:NH$_4$OH:CH$_2$Cl$_2$), a mixture of desired alkylated product plus product containing a boronic acetyl ester group coordinated to the benzimidazole (1.31 g, excess). This was taken forward to the next reaction.

A solution of the above compounds (1.31 g) was dissolved in CH$_2$Cl$_2$ (2 mL) and treated with trifluoroacetic acid (20 mL) for 2 hours. The solution was cooled to 0° C. and diluted with CH$_2$Cl$_2$ (50 mL). 10N aqueous NaOH solution (5 mL) was then added slowly until the acid content was neutralized and the solution was basic (pH>9). The phases were then separated and the aqueous extracted with CH$_2$Cl$_2$ (2×50 mL). The combined organics were then dried (Na$_2$SO$_4$) and concentrated under reduced pressure to give, after column chromatography (10:1:89 MeOH:NH$_4$OH:CH$_2$Cl$_2$), N-(1H-benzimidazol-2-ylmethyl)-N-(5,6,7,8-tetrahydroquinolin-8-yl)-propane-1,3-diamine as a pale yellow crystalline solid (0.57 g, 68%, 2 steps). $^1$H NMR (CDCl$_3$): δ 1.55-1.85 (m, 3H), 2.10 (br, 1H), 2.25 (q, 1H, J=13.5 Hz), 2.54 (t, 1H, J=12.0 Hz), 2.65 (br, 1H), 2.79 (br, 4H), 3.31 (d, 1H, J=12.0 Hz), 3.98 (d, 1H, J=15.0 Hz), 4.00-4.25 (m, 2H), 7.08 (m, 1H), 7.16 (m, 2H), 7.40 (d, 1H), J=7.5 Hz), 7.57 (br, 2H), 8.42 (d, 1H, J=4.5 Hz), 9.35 (br, 2H).

The above amine (0.14 g, 0.43 mmol) and (tert-butoxycarbonylimino-pyrazol-1-yl-methyl)-carbamic acid tert-butyl ester (0.13 g, 0.39 mmol) were dissolved in THF (0.4 mL) and stirred for 5 hours. The solvent was removed under reduced pressure and CH$_2$Cl$_2$ (10 mL) was added. The organic phase was washed with a 15% aqueous solution of NaOH (5×5 mL), dried (Na$_2$SO$_4$), and concentrated under reduced pressure. This afforded, after column chromatography (2:0.5:97.5 MeOH:NH$_4$OH:CH$_2$Cl$_2$), the di-BOC-protected guanidine adduct as a pale yellow oil (0.18 g, 73%). $^1$H NMR (CDCl$_3$): δ 1.45 (s, 9H), 1.49 (s, 9H), 1.66 (m, 3H), 1.85-2.10 (m, 2H), 2.18 (br, 1H), 2.50-2.85 (m, 4H), 3.38 (m, 2H), 4.05 (m, 2H), 4.17 (d, 1H, J=15.0 Hz), 7.13 (m, 1H), 7.17 (m, 2H), 7.40 (d, 1H, J=7.0 Hz), 7.47 (m, 1H), 7.67 (m, 1H), 8.06 (br, 1H), 8.58 (d, 1H, J=4.5 Hz).

Using general procedure D: The above material (176 mg, 0.29 mmol) was converted to the hydrobromide salt to provide COMPOUND 165 (152 mg) as a white solid. $^1$H NMR (D$_2$O) δ 1.69 (m, 2H), 1.80 (m, 1H), 1.98 (q, 1H, J=12.0 Hz), 2.15 (br, 1H), 2.34 (br, 1H), 2.52 (m, 1H), 2.80 (m, 1H), 2.97 (br d, 2H, J=4.5 Hz), 3.01 (m, 2H), 4.32 (d, 1H, J=16.5 Hz), 4.48 (m, 1H), 4.48 (d, 1H, J=16.8 Hz), 7.56 (m, 2H), 7.76 (m, 2H), 7.83 (m, 1H), 8.31 (d, 1H, J=7.8 Hz), 8.59 (d, 1H, J=4.8 Hz). $^{13}$C NMR (D$_2$O) δ 20.40, 20.49, 27.49, 27.67, 39.10, 48.31, 49.21, 60.60, 114.30 (2C), 126.00, 126.96 (2C), 131.05, 139.41, 140.69 (2C), 148.14, 151.13, 151.51, 156.93. ES-MS m/z 378 (M+H). Anal. Calcd. for C$_{21}$H$_{27}$N$_7$.3.1HBr.1.5H$_2$O.0.2C$_4$H$_{10}$O: C, 39.07; H, 5.28; N, 14.63; Br, 36.96. Found: C, 39.20; H, 5.41; N, 14.69; Br, 36.85.

Example 166

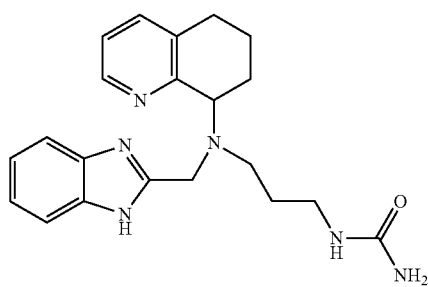 [SMILES: NC(=O)NCCCN(Cc1nc2ccccc2[nH]1)C1CCCc2cccnc21]

Compound 166: Preparation of {3-[(1H-benzimidazol-2-ylmethyl)-(5,6,7,8-tetrahydroquinolin-8-yl)-amino]-propyl}-urea (hydrobromide salt)

A solution of N-(1H-benzimidazol-2-ylmethyl)-N-(5,6,7,8-tetrahydroquinolin-8-yl)-propane-1,3-diamine (0.14 g, 0.42 mmol—see preparation of N-{3-[(1H-benzimidazol-2-ylmethyl)-(S)-(5,6,7,8-tetrahydroquinolin-8-yl)-amino]-propyl}-guanidine) in isopropanol (2.8 mL) was treated with trimethylsilylisocyanate (80 µL, 0.58 mmol) at room temperature. The reaction was stirred 20 hours and concentrated under reduced pressure. This afforded, after column chromatography with silica gel (5:1:94 MeOH:NH$_4$OH:CH$_2$Cl$_2$), the desired urea (37 mg, 23%). $^1$H NMR (CDCl$_3$) δ 1.57 (m, 1H), 1.70-1.85 (m, 3H), 2.06 (br, 1H), 2.26 (br, 1H), 2.62 (m, 1H), 2.70-3.00 (m, 4H), 3.38 (br, 1H), 3.87 (m, 2H), 4.18 (m, 1H), 4.50 (br, 2H, NH$_2$), 6.95 (br, 1H, NH), 7.18 (m, 3H), 7.46 (d, 1H, J=7.0 Hz), 7.45-7.70 (br, 2H), 8.55 (d, 1H, J=4.0 Hz).

Using general procedure D: The above material (37 mg, 0.10 mmol) was converted to the hydrobromide salt to provide COMPOUND 166 (45 mg) as a white solid. $^1$H NMR (D$_2$O) δ 1.61 (m, 2H), 1.83 (m, 1H), 2.04 (q, 1H, J=10.8 Hz), 2.18 (m, 1H), 2.36 (br, 1H), 2.50 (m, 1H), 2.79 (m, 1H), 2.98 (m, 4H), 4.34 (d, 1H, J=16.5 Hz), 4.50 (m, 1H), 4.50 (d, 1H, J=16.5 Hz), 7.60 (m, 2H), 7.79 (m, 2H), 7.86 (m, 1H), 8.34 (d, 1H, J=7.2 Hz), 8.62 (d, 1H, J=5.1 Hz). $^{13}$C NMR (D$_2$O) δ 20.28, 20.37, 27.62, 28.54, 37.60, 48.22, 49.16, 60.38, 114.22 (2C), 125.88, 126.90 (2C), 130.95, 139.32, 140.58 (2C), 148.02, 151.28, 151.56, 161.67. ES-MS m/z 379 (M+H). Anal. Calcd. for C$_{21}$H$_{26}$N$_6$O.2.8HBr.1.6H$_2$O: C, 39.79; H, 5.09; N, 13.26; Br, 35.30. Found: C, 40.13; H, 5.12; N, 12.91; Br, 35.09.

Example 167

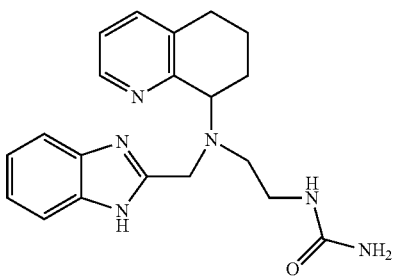 [SMILES: NC(=O)NCCN(Cc1nc2ccccc2[nH]1)C1CCCc2cccnc21]

Compound 167: Preparation of {2-[(1H-benzimidazol-2-ylmethyl)-(5,6,7,8-tetrahydroquinolin-8-yl)-amino]-ethyl}-urea (hydrobromide salt)

To a solution of 3-aminopropane-1,2-diol (9.92 g, 109 mmol) in THF (350 mL) and H$_2$O (15 mL) was added di-tert-butyldicarbonate (25.0 g, 114 mmol). The solution was allowed to stir for 16 h and then concentrated under reduced pressure. EtOAc (200 mL) was added, and the solution was washed with saturated aqueous NaHCO$_3$ solution (100 mL). The aqueous phase was then extracted with EtOAc (2×100 mL), and the organic phase dried (MgSO$_4$), filtered and concentrated under reduced pressure. This gave, after a purification through a plug of silica gel (1:99 MeOH/CH$_2$Cl$_2$ ramping to 4:96 MeOH/CH$_2$Cl$_2$), (2,3-dihydroxy-propyl)-carbamic acid tert-butyl ester (20.2 g, 97%). $^1$H NMR (CDCl$_3$) δ 1.44 (s, 9H), 3.11 (br, 1H, OH), 3.25 (m, 2H), 3.58 (m, 2H), 3.74 (m, 1H), 5.03 (br, 1H, NH).

A solution of the above compound (0.28 g, 1.5 mmol) in water (5 mL) was treated with sodium periodate (0.29 g, 1.4 mmol), stirring for 16 hours at room temperature. The solution was extracted with CH$_2$Cl$_2$ (2×20 mL) and the combined organic phases dried (Na$_2$SO$_4$) and concentrated under reduced pressure to afford (2-oxo-ethyl)-carbamic acid tert-butyl ester (0.17 g, 73%).

Using general procedure B, (1H-benzimidazol-2-ylmethyl)-(S)-(5,6,7,8-tetrahydro-quinolin-8-yl)-amine (0.11 g, 0.41 mmol), (2-oxo-ethyl)-carbamic acid tert-butyl ester (0.17 g, 1.1 mmol) and sodium triacetoxyborohydride (0.17 g, 0.82 mmol) were stirred at room temperature in CH$_2$Cl$_2$ (3 mL) for 18 hours. This yielded, after work-up and column chromatography (2:0.5:97.5 MeOH:NH$_4$OH:CH$_2$Cl$_2$), {2-[(1H-benzimidazol-2-ylmethyl)-(5,6,7,8-tetrahydroquinolin-8-yl)-amino]-ethyl}-carbamic acid tert-butyl ester (0.17 g, 100%) which was used in the next reaction.

A solution of the above compound (0.17 g) was dissolved in CH$_2$Cl$_2$ (0.5 mL) and treated with trifluoroacetic acid (0.5 mL) for 2 hours. CH$_2$Cl$_2$ (10 mL) was added and the solution was basisified to pH>9 with 15% aqueous NaOH solution (3 mL). The phases were then separated and the aqueous extracted with CH$_2$Cl$_2$ (2×5 mL). The combined organics were then dried (Na$_2$SO$_4$) and concentrated under reduced pressure to give N-(1H-benzimidazol-2-ylmethyl)-N-(5,6,7,8-tetrahydroquinolin-8-yl)-ethane-1,2-diamine (0.10 g, 76%, 2 steps). $^1$H NMR (CDCl$_3$): δ 1.65-1.95 (m, 3H), 2.02 (br, 1H), 2.25 (br, 1H), 2.60-2.90 (m, 5H), 4.05 (m, 2H), 4.17 (d, 1H, J=15.0 Hz), 7.14 (m, 3H), 7.42 (d, 1H, J=7.5 Hz), 7.58 (br, 2H), 8.57 (d, 1H, J=4.5 Hz).

A solution of N-(1H-benzimidazol-2-ylmethyl)-N-(5,6,7,8-tetrahydroquinolin-8-yl)-ethane-1,2-diamine (0.10 g, 0.31 mmol) in isopropanol (2 mL) was treated with trimethylsilyl-isocyanate (60 μL, 0.44 mmol) at room temperature. The reaction was stirred 20 hours and concentrated under reduced pressure. This afforded, after column chromatography with silica gel (2:0.5:97.5 MeOH:NH$_4$OH:CH$_2$Cl$_2$), {2-[(1H-benzimidazol-2-ylmethyl)-(5,6,7,8-tetrahydroquinolin-8-yl)-amino]-ethyl}-urea (67 mg, 59%). $^1$H NMR (CDCl$_3$) δ 1.68 (m, 1H), 1.86 (m, 1H), 2.02 (br, 1H), 2.23 (br, 1H), 2.65 (m, 1H), 2.82 (m, 3H), 3.17 (m, 2H), 4.00 (m, 1H), 4.07 (d, 1H, J=15.0 Hz), 4.18 (d, 1H, J=15.0 Hz), 4.43 (br, 2H, NH$_2$), 6.00 (br, 1H, NH), 7.18 (m, 3H), 7.46 (d, 1H, J=7.0 Hz), 7.45-7.70 (br, 2H), 8.55 (d, 1H, J=4.0 Hz).

Using general procedure D: The above material (67 mg, 0.18 mmol) was converted to the hydrobromide salt to provide COMPOUND 167 (88 mg) as a white solid. $^1$H NMR (D$_2$O) δ 1.83 (m, 1H), 2.02 (q, 1H, J=12.8 Hz), 2.15 (m, 1H), 2.36 (br, 1H), 2.59 (m, 1H), 2.90-3.10 (m, 4H), 3.26 (m, 1H), 4.29 (d, 1H, J=16.2 Hz), 4.46 (d, 1H, J=16.5 Hz), 4.47 (m, 1H), 7.60 (m, 2H), 7.79 (m, 2H), 7.86 (m, 1H), 8.33 (d, 1H, J=7.8 Hz), 8.64 (d, 1H, J=5.1 Hz). $^{13}$C NMR (D$_2$O) δ 20.41, 20.47, 27.72, 38.81, 47.77, 52.14, 60.29, 114.33 (2C), 125.89, 126.99 (3C), 131.03, 139.61, 140.71, 147.92, 150.93 (2C), 161.79. ES-MS m/z 365 (M+H). Anal. Calcd. for C$_{20}$H$_{24}$N$_6$O.2.8HBr.1.8H$_2$O.0.3C$_4$H$_{10}$O: C, 39.44; H, 5.21; N, 13.02; Br, 34.65. Found: C, 39.33; H, 5.09; N, 12.93; Br, 34.72.

Example 168

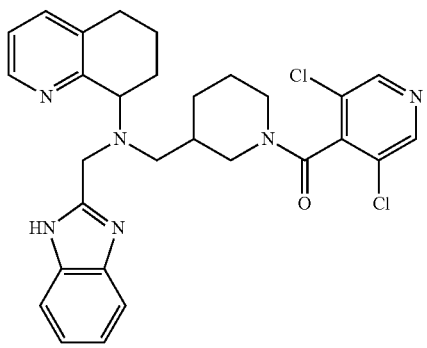 [SMILES: O=C(c1c(Cl)cncc1Cl)N1CCCC(CN(Cc2nc3ccccc3[nH]2)C2CCCc3cccnc32)C1]

Compound 168: Preparation of (3-{[(1H-Benzimidazol-2-ylmethyl)-(5,6,7,8-tetrahydro-quinolin-8-yl)-amino]-methyl}-piperidin-1-yl)-(3,5-dichloro-pyridin-4-yl)-methanone Preparation of (3,5-dichloro-pyridin-4-yl)-(3-hydroxymethyl-piperidin-1-yl)-methanone

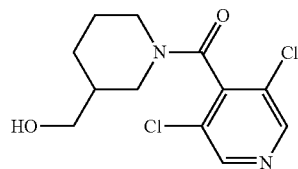 [SMILES: O=C(c1c(Cl)cncc1Cl)N1CCCC(CO)C1]

To a suspension of 3,5-dichloroisonicotinic acid (250 mg, 1.30 mmol) in CH$_2$Cl$_2$ (6.5 mL) was added DMF (cat.) and oxalyl chloride (0.45 mL, 5.2 mmol), and the mixture was stirred at room temperature for 2 h then concentrated in vacuo. To the residue was added THF (2 mL), Et₃N (0.27 mL, 1.9 mmol), and a solution of 3-piperidinemethanol (150 mg, 1.30 mmol) in THF (4.5 mL), and the mixture was stirred at room temperature for 21 h. The mixture was diluted with CH₂Cl₂ (50 mL) and brine (30 mL) and the phases were separated. The organic layer was washed with brine (2×50 mL) and saturated NaHCO₃ (2×50 mL). The organic layer was dried (MgSO₄), filtered, concentrated, and dried in vacuo to afford a crude oil. Purification of the crude material by column chromatography on silica gel (100:5:1 CH₂Cl₂/MeOH/NH₄OH) gave a yellow oil (mixture of isomers) (147 mg, 39%). ¹H NMR (CDCl₃) δ 1.28-1.96 (m, 4H), 2.89-3.26 (m, 3H), 3.35-3.45 (m, 1H), 3.50-3.72 (m, 2H), 4.29-4.56 (m, 1H), 8.54 (m, 2H).

Preparation of (3,5-dichloro-pyridin-4-yl)-{3-[(5,6,7, 8-tetrahydro-quinolin-8-ylamino)-methyl]-piperidin-1-yl}-methanone

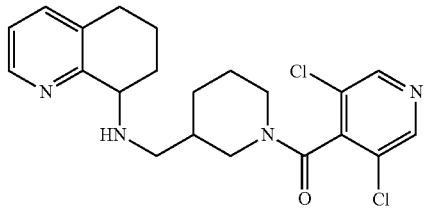 [SMILES: O=C(c1c(Cl)cncc1Cl)N1CCCC(CNC2CCCc3cccnc32)C1]

To a solution of (3,5-dichloro-pyridin-4-yl)-(3-hydroxymethyl-piperidin-1-yl)-methanone (147 mg, 0.508 mmol) in CH₂Cl₂ (5 mL) was added Dess-Martin periodinane (226 mg, 0.533 mmol) at room temperature. After stirring at room temperature for 45 minutes, the mixture was washed with 1 N NaOH(aq) (2×10 mL) then dried (MgSO₄) and concentrated in vacuo to give a colourless oil (121 mg, 83%).

Using General Procedure A: To a stirred solution of the aldehyde from above (121 mg, 0.421 mmol) and 5,6,7,8-tetrahydro-quinolin-8-ylamine (75 mg, 0.51 mmol) in 4:1 MeOH/trimethyl orthoformate (4.2 mL) was added NaBH₃CN (106 mg, 1.69 mmol), and the mixture was heated to 60° C. for 21 h. Purification of the crude material by column chromatography on silica gel (150:5:1 CH₂Cl₂/MeOH/NH₄OH) gave a colourless oil (mixture of isomers) (66 mg, 37%). ¹H NMR (CDCl₃) δ 1.24-3.79 (m, 17H), 4.48-4.67 (m, 1H), 7.05 (m, 1H), 7.36 (m, 1H), 8.24-8.52 (m, 3H).

A mixture of (3,5-dichloro-pyridin-4-yl)-{3-[(5,6,7,8-tetrahydro-quinolin-8-ylamino)-methyl]-piperidin-1-yl}-methanone (63 mg, 0.15 mmol), 2-chloromethyl-benzimidazole-1-carboxylic acid tert-butyl ester (60 mg, 0.22 mmol), potassium iodide (1 mg, 0.006 mmol), and N,N-diisopropylethylamine (0.052 mL, 0.30 mmol) in acetonitrile (3.0 mL) was heated at 60° C. for 16 h. Saturated NaHCO₃(aq) (10 mL) was added, and the mixture was extracted with CH₂Cl₂ (3×12 mL). The combined organic extracts were dried (MgSO₄) and concentrated in vacuo. Purification of the crude material by column chromatography on silica gel (300:5:1 CH₂Cl₂/MeOH/NH₄OH) gave a yellow foam (79 mg).

A solution of the amine from above (79 mg) in 1:1 TFA/CH₂Cl₂ (4 mL) was stirred at room temperature for 1 h then concentrated in vacuo. The residue was dissolved in CH₂Cl₂ (15 mL) and washed with 1 N NaOH(aq) (10 mL). The aqueous phase was extracted with CH₂Cl₂ (2×10 mL), and the combined organic extracts were dried (MgSO₄) and concentrated in vacuo to afford COMPOUND 168 as a yellow foam (mixture of isomers) (72 mg, 87%). ¹H NMR (CDCl₃) δ 1.25-4.76 (m, 20H), 7.12-8.64 (m, 9H); ¹³C NMR (CDCl₃) δ 21.37, 21.47, 21.75, 22.83, 23.51, 23.87, 24.06, 24.20, 24.87, 25.26, 26.90, 27.18, 27.61, 27.94, 29.03, 29.24, 29.45, 29.68, 34.12, 34.54, 34.85, 35.53, 38.16, 38.69, 39.37, 42.30, 42.38, 44.48, 45.57, 46.22, 47.05, 47.23, 48.61, 49.61, 49.83, 49.97, 51.06, 51.39, 52.89, 53.11, 55.30, 59.44, 61.61, 61.85, 62.03, 64.04, 64.26, 111.28, 118.80, 121.66, 121.74, 122.29, 128.10, 128.18, 128.35, 128.52, 128.60, 128.68, 134.61, 137.35, 137.48, 142.26, 142.43, 146.49, 146.74, 146.99, 147.39, 147.59, 147.63, 155.48, 155.70, 156.11, 156.74, 156.90, 157.23, 161.08, 161.20. ES-MS m/z 550 (M+H). Anal. Calcd. for C₂₉H₃₀N₆Cl₂O.0.5CH₂Cl₂.0.6H₂O.0.2C₆H₁₄: C, 59.47; H, 5.69; N, 13.55; Cl, 17.15. Found: C, 59.62; H, 5.39; N, 13.51; Cl, 16.92.

Example 169

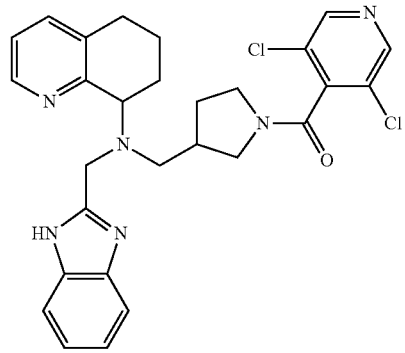 [SMILES: O=C(c1c(Cl)cncc1Cl)N1CCC(CN(Cc2nc3ccccc3[nH]2)C2CCCc3cccnc32)C1]

Compound 169: Preparation of (3-{[(1H-Benzimidazol-2-ylmethyl)-(5,6,7,8-tetrahydro-quinolin-8-yl)-amino]-methyl}-pyrrolidin-1-yl)-(3,5-dichloro-pyridin-4-yl)-methanone Preparation of carbonic acid 1-benzyl-pyrrolidin-3-ylmethyl ester vinyl ester

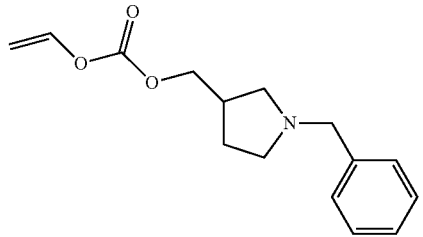 [SMILES: C=COC(=O)OCC1CCN(Cc2ccccc2)C1]

A solution of (1-benzyl-pyrrolidin-3-yl)-methanol (prepared as described by Y.-H. Wu and R. F. Feldkamp, *Pyrrolidines I*, 1961, 26, 1519-1524) (455 mg, 2.38 mmol) and vinyl chloroformate (0.40 mL, 4.7 mmol) in 1,2-dichloroethane (10 mL) was heated to reflux for 2 h then concentrated in vacuo. Purification of the crude material by column chromatography on silica gel (5% MeOH/CH₂Cl₂) gave a yellow oil (440 mg, 71%). ¹H NMR (CDCl₃) δ 1.84 (m, 1H), 2.26 (m, 1H), 3.03 (m, 5H), 4.01 (br s, 2H), 4.23 (m, 2H), 4.61 (dd, 1H, J=6.2, 2.3 Hz), 4.93 (dd, 1H, J=14, 2.1 Hz), 7.06 (dd, 1H, J=14, 6.3 Hz), 7.41 (m, 3H), 7.53 (m, 2H).

Preparation of 3-vinyloxycarbonyloxymethyl-pyrrolidine-1-carboxylic acid vinyl ester

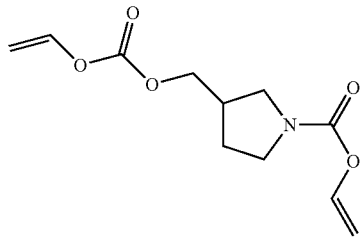 [SMILES: C=COC(=O)OCC1CCN(C(=O)OC=C)C1]

A solution of carbonic acid 1-benzyl-pyrrolidin-3-ylmethyl ester vinyl ester (440 mg, 1.68 mmol) and vinyl chloroformate (0.30 mL, 3.5 mmol) in 1,2-dichloroethane (10 mL) was heated to reflux for 6 h then concentrated in vacuo. Purification of the crude material by column chromatography on silica gel (20% EtOAc/hexanes) gave a yellow oil (335 mg, 83%). $^1$H NMR (CDCl$_3$) δ 1.68-1.85 (m, 1H), 2.03-2.16 (m, 1H), 2.59-2.71 (m, 1H), 3.26 (m, 1H), 3.41-3.52 (m, 1H), 3.55-3.72 (m, 2H), 4.11-4.28 (m, 2H), 4.45 (dd, 1H, J=6.3, 1.5 Hz), 4.61 (m, 1H), 4.78 (dd, 1H, J=14, 1.5 Hz), 4.94 (m, 1H), 7.08 (m, 1H), 7.22 (dd, 1H, J=14, 6.3 Hz).

Preparation of carbonic acid pyrrolidin-3-ylmethyl ester vinyl ester hydrochloride

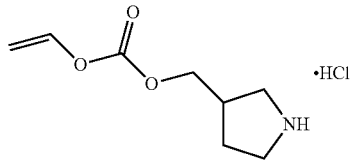

3-Vinyloxycarbonyloxymethyl-pyrrolidine-1-carboxylic acid vinyl ester (335 mg, 1.39 mmol) was dissolved in CH$_2$Cl$_2$ (10 mL), and HCl(g) was passed through the solution for 2 minutes then the solution was concentrated in vacuo. The residue was dissolved in MeOH (10 mL) and heated to reflux for 15 minutes then concentrated in vacuo to give a colourless oil (284 mg, 99%). $^1$H NMR (CD$_3$OD) δ 1.78-1.91 (m, 1H), 2.17-2.28 (m, 1H), 2.79 (m, 1H), 3.09 (dd, 1H, J=12, 7.8 Hz), 3.25-3.51 (m, 3H), 4.19-4.33 (m, 2H), 4.62 (dd, 1H, J=6.2, 2.0 Hz), 4.89 (m, 1H), 7.11 (dd, 1H, J=14, 6.0 Hz).

Preparation of (3,5-dichloro-pyridin-4-yl)-(3-hydroxymethyl-pyrrolidin-1-yl)-methanone

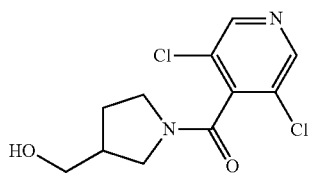 [SMILES: O=C(c1c(Cl)cncc1Cl)N1CCC(CO)C1]

To a suspension of 3,5-dichloroisonicotinic acid (267 mg, 1.39 mmol) in CH$_2$Cl$_2$ (7.0 mL) was added DMF (cat.) and oxalyl chloride (0.49 mL, 5.6 mmol), and the mixture was stirred at room temperature for 2.5 h then concentrated in vacuo. To the residue was added THF (4 mL), Et$_3$N (0.58 mL, 4.2 mmol), and a solution of carbonic acid pyrrolidin-3-ylmethyl ester vinyl ester hydrochloride (284 mg, 1.37 mmol) in THF (3 mL), and the mixture was stirred at room temperature for 21 h. The mixture was diluted with CH$_2$Cl$_2$ (50 mL) and brine (30 mL) and the phases were separated. The organic layer was washed with brine (2×50 mL) and saturated NaHCO$_3$ (2×50 mL). The organic layer was dried (MgSO$_4$), filtered, concentrated, and dried in vacuo to afford a yellow oil (315 mg).

To a solution of the crude amide from above (315 mg) in MeOH (10 mL) was added 10 N NaOH(aq) (1.0 mL, 10 mmol), and the solution was stirred at room temperature for 30 minutes. Water (15 mL) was added, the mixture was extracted with CH$_2$Cl$_2$ (4×15 mL), and the combined organic extracts were dried (MgSO$_4$) and concentrated in vacuo. Purification of the crude material by column chromatography on silica gel (100:5:1 CH$_2$Cl$_2$/MeOH/NH$_4$OH) gave a yellow oil (mixture of isomers) (172 mg, 46%). $^1$H NMR (CDCl$_3$) δ 1.44-4.24 (m, 10H), 8.54 (s, 2H).

Preparation of (3,5-dichloro-pyridin-4-yl)-{3-[(S)-(5,6,7,8-tetrahydro-quinolin-8-ylamino)-methyl]-pyrrolidin-1-yl}-methanone

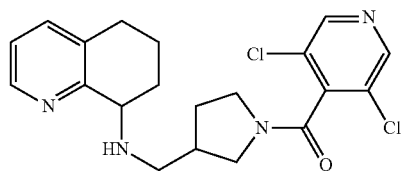 [SMILES: O=C(c1c(Cl)cncc1Cl)N1CCC(CNC2CCCc3cccnc32)C1]

To a solution of (3,5-dichloro-pyridin-4-yl)-(3-hydroxymethyl-pyrrolidin-1-yl)-methanone (172 mg, 0.625 mmol) in CH$_2$Cl$_2$ (6.3 mL) was added Dess-Martin periodinane (278 mg, 0.655 mmol) at room temperature. After stirring at room temperature for 40 minutes, the mixture was washed with 1 N NaOH(aq) (2×10 mL) then dried (MgSO$_4$) and concentrated in vacuo to give a yellow oil (163 mg, 95%).

Using General Procedure A: To a stirred solution of the aldehyde from above (163 mg, 0.597 mmol) and 5,6,7,8-tetrahydro-quinolin-8-ylamine (106 mg, 0.715 mmol) in 4:1 MeOH/trimethyl orthoformate (6.0 mL) was added NaBH$_3$CN (150 mg, 2.39 mmol), and the mixture was heated to 60° C. for 15 h. Purification of the crude material by column chromatography on silica gel (150:5:1 CH$_2$Cl$_2$/MeOH/NH$_4$OH) gave a yellow oil (mixture of isomers) (86 mg, 36%). $^1$H NMR (CDCl$_3$) δ 1.57-3.96 (m, 16H), 7.06 (m, 1H), 7.37 (m, 1H), 8.36 (m, 1H), 8.51 (m, 2H).

A mixture of (3,5-dichloro-pyridin-4-yl)-{3-[(5,6,7,8-tetrahydro-quinolin-8-ylamino)-methyl]-pyrrolidin-1-yl}-methanone (85 mg, 0.21 mmol), 2-chloromethyl-benzimidazole-1-carboxylic acid tert-butyl ester (84 mg, 0.31 mmol), potassium iodide (2 mg, 0.01 mmol), and N,N-diisopropylethylamine (0.073 mL, 0.42 mmol) in acetonitrile (4.2 mL) was heated at 60° C. for 24 h. Saturated NaHCO$_3$(aq) (10 mL) was added, and the mixture was extracted with CH$_2$Cl$_2$ (3×12 mL). The combined organic extracts were dried (MgSO$_4$) and concentrated in vacuo. Purification of the crude material by column chromatography on silica gel (300:5:1 CH$_2$Cl$_2$/MeOH/NH$_4$OH) gave a yellow oil (124 mg).

A solution of the amine from above (124 mg) in 1:1 TFA/CH$_2$Cl$_2$ (4 mL) was stirred at room temperature for 1 h then concentrated in vacuo. The residue was dissolved in CH₂Cl₂ (15 mL) and washed with 1 N NaOH(aq) (10 mL). The aqueous phase was extracted with CH₂Cl₂ (2×10 mL), and the combined organic extracts were dried (MgSO₄) and concentrated in vacuo to afford COMPOUND 169 as a yellow foam (mixture of isomers) (94 mg, 84%). $^1$H NMR (CDCl₃) δ 1.09-4.27 (m, 18H), 7.12-7.25 (m, 3H), 7.43-7.61 (m, 3H), 8.11-8.73 (m, 3H); $^{13}$C NMR (CDCl₃) δ 21.37, 23.37, 23.73, 27.80, 28.27, 28.71, 29.16, 36.35, 37.82, 38.65, 44.13, 45.13, 45.41, 45.77, 49.18, 49.44, 49.62, 50.06, 50.50, 52.37, 52.89, 53.12, 53.45, 61.92, 62.01, 62.38, 62.55, 121.80, 122.37, 122.55, 122.65, 128.04, 128.41, 134.35, 134.67, 134.90, 137.41, 137.59, 137.70, 142.99, 146.05, 146.59, 147.44, 147.68, 147.77, 155.73, 155.86, 156.56, 157.01, 161.03, 161.31. ES-MS m/z 536 (M+H). Anal. Calcd. for C₂₈H₂₈N₆Cl₂O.0.1CH₂Cl₂.1.1H₂O.0.1C₆H₁₄: C, 60.22; H, 5.60; N, 14.68; Cl, 13.63. Found: C, 60.11; H, 5.39; N, 14.42; Cl, 13.85.

3H), 1.66 (s, 9H), 1.77 (m, 3H), 2.03 (m, 4H), 2.56 (m, 1H), 2.72 (m, 1H), 2.90 (br t, 2H, J=12.0 Hz), 3.15 (br t, 1H), 4.22 (m, 1H), 4.34 (d, 1H, J=15.0 Hz), 4.48 (d, 1H, J=15.0 Hz), 6.85 (m, 1H), 7.10 (d, 1H, J=7.8 Hz), 7.24 (m, 2H), 7.64 (m, 1H), 7.75 (m, 1H), 8.31 (d, 1H, J=5.4 Hz), 10.09 (s, 1H, NH).

Using general procedure D: A portion of the above material (75 mg, 0.11 mmol) was converted to the hydrobromide salt to provide COMPOUND 170 (58 mg) as a white solid. $^1$H NMR (D₂O) δ 1.60-2.00 (m, 4H), 2.05-2.25 (m, 3H), 2.42 (m, 1H), 2.90-3.15 (m, 5H), 3.86 (m, 2H), 4.42 (d, 1H, J=16.8 Hz), 4.53 (m, 1H), 4.56 (d, 1H, J=16.8 Hz), 7.58 (m, 2H), 7.70-7.85 (m, 3H), 8.26 (d, 1H, J=7.5 Hz), 8.54 (d, 1H, J=5.4 Hz). $^{13}$C NMR (D₂O) δ 20.69, 23.95, 27.54, 29.01, 30.59, 43.81, 45.51, 45.58, 58.32, 58.71, 114.24 (2C), 125.85, 127.01 (2C), 131.02, 139.19, 140.53 (2C), 148.02, 151.32, 151.75, 156.21. ES-MS m/z 404 (M+H). Anal. Calcd. for C₂₃H₂₉N₇.3.0HBr.2.0H₂O: C, 40.49; H, 5.32; N, 14.37; Br, 35.13. Found: C, 40.57; H, 5.33; N, 14.15; Br, 35.25.

Example 170

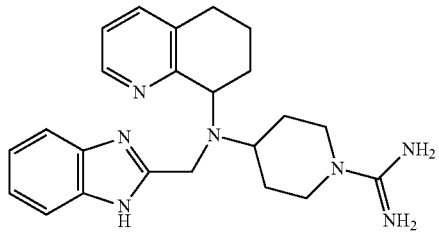 [SMILES: N=C(N)N1CCC(N(Cc2nc3ccccc3[nH]2)C2CCCc3cccnc32)CC1]

Compound 170: Preparation of 4-[(1H-Benzimidazol-2-ylmethyl)-(5,6,7,8-tetrahydroquinolin-8-yl)-amino]-piperidine-1-carboxamidine (hydrobromide salt)

Using general procedure B, [tert-butoxycarbonylimino-(4-oxo-piperidin-1-yl)-methyl]-carbamic acid tert-butyl ester (490 mg, 1.43 mmol), (5,6,7,8-tetrahydroquinolin-8-yl)-amine (210 mg, 1.43 mmol) and sodium triacetoxyborohydride (450 mg, 2.14 mmol) were stirred at room temperature in dichloromethane (4 mL) for 16 hours to yield, after work-up and column chromatography (2:0.5:97.5 MeOH:NH₄OH:CH₂Cl₂), {tert-butoxycarbonylimino-[4-(5,6,7,8-tetrahydroquinolin-8-ylamino)-piperidin-1-yl]-methyl}-carbamic acid tert-butyl ester as a white solid (560 mg, 82%).

To a solution of the above secondary amine (560 mg, 1.18 mmol), 2-chloromethyl-benzimidazole-1-carboxylic acid tert-butyl ester (470 mg, 1.77 mmol), and potassium iodide (10 mg, 0.06 mmol) in anhydrous CH₃CN (12 mL) was added diisopropylethylamine (0.41 mL, 2.35 mmol) and the reaction stirred at 40° C. for 16 hours. The mixture was then concentrated under redUced pressure and the residue partitioned between CH₂Cl₂ (30 mL) and brine (15 mL). The organic phase was separated and the aqueous phase was extracted with CH₂Cl₂ (2×15 mL). The combined organic phases were then dried (Na₂SO₄), filtered, and concentrated under reduced pressure to give a crude residue that was purified by radial chromatography with silica gel (saturated NH₃/Et₂O). This gave 2-{[[1-(tert-butoxycarbonylimino-tert-butoxycarbonyliminomethyl)-piperidin-4-yl]-(5,6,7,8-tetrahydroquinolin-8-yl)-amino]-methyl}-benzimidazole-1-carboxylic acid tert-butyl ester as a pale yellow oil (336 mg, 40%). $^1$H NMR (CDCl₃) δ 1.45 (s, 9H), 1.48 (s, 9H), 1.62 (br,

Example 171

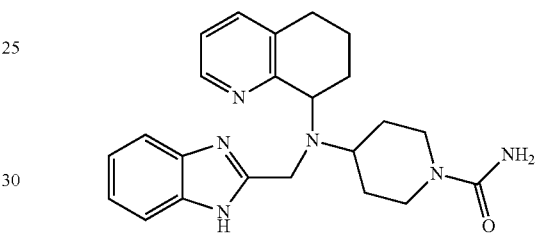

Compound 171: Preparation of 4-[(1H-benzimidazol-2-ylmethyl)-(5,6,7,8-tetrahydroquinolin-8-yl)-amino]-piperidine-1-carboxylic acid amide (hydrobromide salt)

4-Hydroxypiperidine (2.58 g, 25.5 mmol) was dissolved in THF (100 mL) and treated with di-tert-butyl dicarbonate (5.57 g, 25.5 mmol) and stirred for 40 minutes at room temperature. The solvent was removed under reduced pressure to afford 4-hydroxypiperidine-1-carboxylic acid tert-butyl ester as a light yellow oil that was used in the next reaction.

A solution of the above alcohol (0.79 g, 3.9 mmol) in CH₂Cl₂ (20 mL) was treated with molecular seives (1.95 g), N-methylmorpholine oxide (0.69 g, 5.9 mmol), and TPAP (0.14 g, 0.40 mmol). The mixture was stirred for 2 hours at room temperature and then filtered through a plug of silica gel, eluting with Et₂O. The filtrate was then concentrated under reduced pressure to afford the desired 4-oxopiperidine-1-carboxylic acid tert-butyl ester (0.69 g, 89%). $^1$H NMR (CDCl₃) δ 1.49 (s, 9H), 2.44 (t, 4H, J=7.0 Hz), 3.72 (t, 4H, J=7.0 Hz).

Using general procedure B, 4-oxopiperidine-1-carboxylic acid tert-butyl ester (0.69 g, 3.4 mmol), (5,6,7,8-tetrahydroquinolin-8-yl)-amine (0.51 g, 3.4 mmol) and sodium triacetoxyborohydride (1.10 g, 5.2 mmol) were stirred at room temperature in dichloromethane (20 mL) for 16 hours to yield, after work-up and column chromatography with silica gel (5:0.5:94.5 MeOH:NH₄OH:CH₂Cl₂), 4-(5,6,7,8-tetrahydroquinolin-8-ylamino)-piperidine-1-carboxylic acid tert-butyl ester as a white solid (1.00 g, 87%).

To a solution of 4-(5,6,7,8-tetrahydroquinolin-8-ylamino)-piperidine-1-carboxylic acid tert-butyl ester (1.00 g, 3.0 mmol), 2-chloromethyl-benzimidazole-1-carboxylic acid tert-butyl ester (1.20 g, 4.5 mmol), and potassium iodide (25 mg, 0.15 mmol) in anhydrous acetonitrile (30 mL) was added diisopropylethylamine (1.05 mL, 6.0 mmol) and stirred at 40° C. for 16 hours. The mixture was then concentrated under reduced pressure and the residue partitioned between dichloromethane (30 mL) and brine (25 mL). The organic phase was separated and the aqueous phase was extracted with dichloromethane (2×25 mL). The combined organic phases were then dried ($Na_2SO_4$), filtered, and concentrated under reduced pressure to give a crude residue that was purified by column chromatography with silica gel (2:0.5:97.5 MeOH:$NH_4OH$:$CH_2Cl_2$). This afforded 2-{[(1-tert-butoxycarbonyl-piperidin-4-yl)-(5,6,7,8-tetrahydroquinolin-8-yl)-amino]-methyl}-benzimidazole-1-carboxylic acid tert-butyl ester as an light orange solid (0.50 g, 30%).

A solution of the above compound (0.50 g, 0.9 mmol) was dissolved in $CH_2Cl_2$ (2 mL) and treated with trifluoroacetic acid (2.5 mL) for 1 hour. $CH_2Cl_2$ (20 mL) was added and the solution was basisified to pH>9 with 15% aqueous NaOH solution (10 mL). Brine (20 mL) was added to alleviate emulsification. The phases were then separated and the aqueous extracted with $CH_2Cl_2$ (2×40 mL). The combined organics were then dried ($Na_2SO_4$) and concentrated under reduced pressure to give (1H-benzimidazol-2-ylmethyl)-piperidin-4-yl-(5,6,7,8-tetrahydroquinolin-8-yl)-amine (0.32 g, 100%). $^1$H NMR ($CDCl_3$): δ 1.35 (m, 1H), 1.50-1.75 (m, 3H), 1.84 (m, 2H), 2.05 (br, 1H), 2.23 (br, 1H), 2.40-2.65 (m, 3H), 2.74 (m, 1H), 2.80-2.95 (m, 2H), 3.07 (m, 1H), 4.13 (m, 1H), 4.21 (s, 2H), 7.16 (m, 3H), 7.43 (d, 1H, J=7.5 Hz), 7.44 (br, 1H), 7.67 (br, 1H), 8.59 (d, 1H, J=4.5 Hz).

A solution of (1H-benzimidazol-2-ylmethyl)-piperidin-4-yl-(5,6,7,8-tetrahydroquinolin-8-yl)-amine (0.16 g, 0.43 mmol) in isopropanol (3 mL) was treated with trimethylsilyl-isocyanate (81 µL, 0.60 mmol) at room temperature. The reaction was stirred 20 hours and concentrated under reduced pressure. This afforded, after column chromatography with silica gel (5:0.5:94.5 MeOH:$NH_4OH$:$CH_2Cl_2$), 4-[(1H-benzimidazol-2-ylmethyl)-(5,6,7,8-tetrahydroquinolin-8-yl)-amino]-piperidine-1-carboxylic acid amide (112 mg, 66%). $^1$H NMR ($CDCl_3$) δ 1.42 (m, 1H), 1.60-1.95 (m, 5H), 2.02 (br, 1H), 2.24 (br, 1H), 2.60-2.80 (m, 4H), 2.89 (m, 1H, 3.70 (br, 1H), 4.03 (br, 1H), 4.15 (m, 3H), 4.39 (br, 2H, $NH_2$), 7.18 (m, 3H), 7.45 (d, 1H, J=7.5 Hz), 7.66 (br, 2H), 8.59 (d, 1H, J=4.0 Hz).

Using general procedure D: The above material (105 mg, 0.26 mmol) was converted to the hydrobromide salt to provide COMPOUND 171 (107 mg) as a white solid. $^1$H NMR ($D_2O$) δ 1.56 (dqt, 2H, J=2.1, 12.0 Hz), 1.82 (br, 2H), 2.14 (br, 3H), 2.42 (br, 1H), 2.77 (br t, 2H, J=12.3 Hz), 2.97 (br, 3H), 3.92 (br t, 2H, J=17.1 Hz), 4.42 (d, 1H, J=16.8 Hz), 4.54 (m, 1H), 4.57 (d, 1H, J=16.8 Hz), 7.59 (m, 2H), 7.75 (m, 2H), 7.79 (m, 1H), 8.28 (d, 1H, J=8.1 Hz), 8.55 (d, 1H, J=5.7 Hz). $^{13}$C NMR ($D_2O$) δ 20.71, 23.89, 27.55, 29.45, 31.09, 43.98 (3C), 58.88, 58.97, 114.21 (2C), 125.83, 127.03 (2C), 130.90, 139.11, 140.49 (2C), 148.02, 151.55, 151.96, 160.13. ES-MS m/z 405 (M+H). Anal. Calcd. for $C_{23}H_{28}N_6O·3.0HBr·1.3H_2O·0.3C_4H_{10}O$: C, 41.95; H, 5.32; N, 12.13; Br, 34.60. Found: C, 42.08; H, 5.30; N, 12.19; Br, 34.52.

Example 172

Assay for Inhibition of HIV-1 (NL4.3) Replication in PBMC's

Inhibition of HIV-1 NL4.3 replication assays in PBMC's (peripheral blood mononuclear cells) were performed as previously described (De Clercq et al. *Proc. Natl. Acad. Sci,* 1992, 89, 5286-5290; De Clercq et al. *Antimicrob. Agents Chemother.* 1994, 38, 668-674; Schols, D. et al. *J. Exp. Med.* 1997, 186, 1383-1388). Briefly, PBMC's from healthy donors were isolated by density gradient centrifugation and stimulated with PHA at 1 µg/ml (Sigma Chemical Co., Bornem, Belgium) for 3 days at 37° C. The activated cells (PHA-stimulated blasts) were washed three times with PBS, and viral infections were performed as described by Cocchi et al. (Science 1995, 270, 1811-1815). HIV-infected or mock-infected PHA-stimulated blasts were cultured in the presence of 25 U/mL of IL-2 and varying concentrations of test compounds. Supernatant was collected at days 6 and 10, and HIV-1 core antigen in the culture supernatant was analyzed by the p24 ELISA kit (DuPont-Merck Pharmaceutical Co, Wilmington, Del.). The 50% inhibitory concentration ($IC_{50}$) was defined as the concentration of test compound required to inhibit p24 antigen production by 50%.

When tested in the assay described above, many compounds of the invention exhibited $IC_{50}$'s in the range 5 nM-5.5 nM.

Assay for Inhibition of SDF-1α induced Ca Flux in CEM Cells

Inhibition of SDF-1 induced calcium flux was assayed using CCRF-CEM cells, a T-lymphoblastoid cell line which expresses CXCR4. CCRF-CEM cells (5×10$^6$ cells/mL in RPMI 1640 medium containing 2% foetal bovine serum) were pre-loaded with 1 µM Fluo-4 fluorescent calcium indicator dye and incubated at 37° C. for 40 minutes. The loaded cells were washed and resuspended in buffer containing 20 mM HEPES pH 7.4, 1× Hanks Balanced Salt Solution (HBSS), 0.2% bovine serum albumin, 2.5 mM probenecid and plated out in 96 well tissue culture plates at 3.5×10$^5$ cells per well. The cells were incubated with test compound, or buffer control, for 15 minutes at 37° C. Calcium flux was stimulated by addition of 25 nM SDF-1 and fluorescence measured using a FLEXstation fluorescence plate reader (Molecular Devices). Ionomycin was added 80 seconds after addition of SDF-1 in order to measure total calcium loading. Compounds were tested at a concentration range of 2000-0.128 nM. Fluorescence measurements were normalised with respect to untreated controls. The 50% inhibitory concentration ($IC_{50}$ value) was defined as the concentration of test compound required to inhibit SDF-1-induced calcium flux by 50% relative to unteated controls.

When tested in the assay described above, the compounds of the invention exhibited $IC_{50}$s in the range 5 nM-5 µM.

Example 173

Elevation of Mouse Progenitor Cell Levels

The effects of subcutaneous (s.c.) administration of 1,1'-[1,4-phenylene-bis(methylene)]-bis-1,4,8,11-tetraazacyclotetradecane (AMD3100) to C3H/H3 J mice on numbers of granulocyte macrophage (CFU-GM), erythroid (BFU-E), and multipotential (CFU-GEMM) progenitor cells per'mL of blood were measured. Progenitors were stimulated to form colonies in vitro with the combination of 1 U/ml rhu Epo, 50 ng/ml rhu SLF, 5% Vol/Vol pokeweed mitogen mouse spleen cell conditioned medium (PWMSCM), and 0.1 mM heroin. Plates were scored 7 days after incubation.

The time dependent effects on the number of progenitors mobilized with AMD3100 are for a single s.c. injection of 5 mg/Kg and are shown in Table 1.

TABLE 1

| | Absolute Progenitors Per ML Blood Methylcellulose Culture | | |
|---|---|---|---|
| | CFU-GM | BFU-E | CFU-GEMM |
| Control | 289.8 | 49.4 | 25.8 |
| AMD3100: 15" | 791.6 | 134.5 | 90.4 |
| AMD3100: 30" | 1805.5 | 209.3 | 113.5 |
| AMD3100: 120" | 828.7 | 102.3 | 47.6 |

To measure the dose-dependent effects, AMD3100 was administered at 1, 2.5, 5 and 10 mg/Kg via a single s.c. injection and the number of progenitors per mL of blood was measured at 1 hour post administration, and the results are shown in Table 2.

TABLE 2

| | Absolute Number Progenitors Per ML Blood Methylcellulose Culture | | |
|---|---|---|---|
| | CFU-GM | BFU-E | CFU-GEMM |
| Saline | 188.1 | 16 | 19 |
| AMD3100: 10 mg/kg | 825.6 | 120.5 | 79.8 |
| AMD3100: 5 mg/kg | 608.4 | 92.8 | 69.5 |
| AMD3100: 2.5 mg/kg | 687.6 | 98.9 | 70.6 |
| AMD3100: 1 mg/kg | 424 | 62 | 27.1 |

| Fold Change Compared to Time 0 | | | |
|---|---|---|---|
| | Progenitors Methylcellulose Culture | | |
| Time | GM | BFU-E | CFU-GEMM |
| 15" | 2.73 | 2.72 | 3.51 |
| 30" | 6.23 | 4.24 | 4.41 |
| 2' | 2.86 | 2.07 | 1.85 |

Maximum mobilization of mouse progenitors is achieved at a dose of 2.5 to 10 mg/kg AMD3100, approximately 0.5 to 1 hour after injection, as shown in Table 3. The compounds of the invention behave in a manner similar to AMD3100.

Example 174

Mobilization of Mouse Progenitor Cells in Combination with MIP-1α and G-CSF

The progenitor cell mobilization capacity of AMD3100 in combination with mouse (mu) macrophage inflammatory protein (MIP-1α) was tested with or without prior administration of rhu G-CSF. MIP-1α has been previously shown to mobilize progenitor cells in mice and humans (Broxmeyer, H. E., et al., Blood Cells, Molecules, and Diseases (1998) 24(2): 14-30).

Groups of mice were randomized to receive control diluent (saline) or G-CSF at a dose of 2.5 μg per mouse, twice a day, for two days via s.c. injection. Eleven hours after the final injection of saline or G-CSF, the mice were divided into groups to receive MIP-1α administered I.V. at a total dose of 5 μg, AMD3100 administered s.c. at a dose of 5 mg/Kg, or a combination of both MIP-1α and AMD3100 at the same doses. One hour later, the mice were sacrificed and the number of progenitor cells per mL of blood were measured. These data are summarized in FIG. 1.

AMD3100 acts in an additive to greater than additive manner for mobilization of progenitor cells when used in combination with mouse (mu) macrophage inflammatory protein (MIP)-1α, each given 11 hours after the addition of rhu G-CSF or control diluent (saline) and 1 hour prior to assessing the blood. The compounds of the invention behave in a manner similar to AMD3100.

Example 175

Clinical Elevation of Progenitor Cell Levels

Five healthy human volunteers having initial white blood cell counts of 4,500-7,500 cells/mm$^3$ were used in the study. Each patient was given a single subcutaneous (s.c.) injection of 80 μg/kg AMD3100 (i.e., 1,1'-[1,4-phenylene-bis(methylene)]-bis-1,4,8,11-tetraazacyclotetradecane) in 0.9% saline, from a stock solution of 10 mg/mL AMD3100 in saline, under sterile conditions. Blood samples were obtained via catheter prior to the dose, and at various times up to 24 hours after dosing.

The blood samples were evaluated for total white blood cells, CD34 positive progenitor cells (via FACS analysis) as a percentage of total white blood cells, as well as the absolute numbers per mL and cycling status of granulocyte macrophage (CFU-GM), erythroid (BFU-E), and multipotential (CFU-GEMM) progenitor cells.

As shown in Tables 3 and 4, administration of AMD3100 caused an elevation of the white blood cell count and of CD34 positive progenitor cells in human volunteers which maximized at 6 hours post-administration.

TABLE 3

AMD3100 induced mobilization of white blood cells in individual volunteers (×10$^3$ WBC's).

| | | | TREATMENT | | | | | |
|---|---|---|---|---|---|---|---|---|
| ID | Screen | Base-line | 30 Min | 1 Hr | 2 Hr | 4 Hr | 6 Hr | 9 Hr | Day 2 |
| P1 | 7.4 | 6.41 | 8.02 | 14.8 | 21.4 | 23.2 | 26.2 | 22.3 | 7.07 |
| P2 | 6.04 | 5.45 | 6.53 | 8.93 | 13.5 | 18.00 | 19.2 | 19.6 | 8.03 |
| P3 | 4.38 | 5.8 | 7.14 | 9.28 | ND | 18.10 | 17.9 | 18.4 | 4.98 |
| P4 | 5.08 | 5.31 | 4.37 | 7.38 | 12.4 | 14.6 | 15.8 | 13.9 | 4.98 |
| P5 | 4.53 | 5.02 | 6.08 | 8.43 | ND | 16.90 | 19.3 | 19.00 | 4.57 |

TABLE 4

AMD3100 induced mobilization of CD34 positive cells, expressed as the percentage of the total WBC's in individual volunteers.

| | | TREATMENT | | | |
|---|---|---|---|---|---|
| ID | Baseline | 1 Hr | 3 Hr | 6 Hr | 9 Hr | Day 2 |
| P1 | .07 | .04 | .07 | .11 | .11 | .08 |
| P2 | .08 | .06 | .08 | .13 | .11 | .12 |
| P3 | .07 | .16 | .06 | ND | .11 | .07 |
| P4 | .05 | .07 | .09 | .09 | .1 | .1 |
| P5 | .12 | .12 | .13 | .2 | .2 | .16 |

The blood was also analyzed for AMD3100 mobilized these progenitors.

Absolute numbers of unseparated and low density (Ficohypaque separated) nucleated cells per ml of blood, as well as the absolute numbers per ml and cycling status of granulocyte macrophage (CFU-GM), erythroid (BFU-E), and multipotential (CFU-GEMM) progenitor cells were measured in normal donors injected s.c. with AMD3100. The above parameters were assessed prior to injection and at 1, 3, 6, 9 and 24 hours after injection of AMD3100. All progenitor cell results are based on the scoring of 3 culture plates per assay per point.

For the progenitor cell numbers and cycling status, the numbers of CFU-GM, BFU-E and CFU-GEMM in methylcellulose cultures by stimulation of the cells with 1 Unit (U)/ml recombinant human (rhu) erythropoietin, 100 U/ml rhu granulocyte-macrophage colony stimulating factor (GM-CSF), 100 U/ml rhu interleukin-3 (IL-3) and 50 ng/ml rhu steel factor (SLF=stem cell factor (SCF)). The CFU-GM were also evaluated in agar cultures stimulated with 100 U/ml rhu GM-CSF and 50 ng/ml rhu SLF. For both types of assays, colonies were scored after 14 day incubation in a humidified atmosphere with 5% $CO_2$ and lowered (5%) $O_2$ tension. Cell cycling status of progenitors was measured using a high specific activity tritiated thymidine kill technique as previously described (Broxmeyer, H. E., et al., *Exp. Hematol.* (1989) 17:455-459).

The results are given first, as the mean fold change in absolute numbers of nucleated cells and progenitors at 1, 3, 6, 9 and 24 hours compared to the preinjection (=Time (T) 0) counts for all five donors, as seen in Tables 5-7.

In the tables below,
STD—Standard deviation
STE—Standard error
PBL-US—peripheral blood-unseparated
PBL-LD—peripheral blood-low density (Ficoll Separated)
P—Significance using a 2 tailed t test

TABLE 7

| | AGAR CULTURE CFU-GM | | | | |
|---|---|---|---|---|---|
| | MEAN | STD | STE | % CHG | P |
| T = 0 | 1.00 | 0.00 | 0.00 | 0.0% | |
| T = 1 | 2.81 | 0.00 | 0.00 | 180.8% | 0.001 |
| T = 3 | 8.54 | 0.75 | 0.34 | 754.1% | 0.000 |
| T = 6 | 17.93 | 1.62 | 0.72 | 1692.8% | 0.000 |
| T = 9 | 10.25 | 4.57 | 2.04 | 924.9% | 0.000 |
| T = 24 | 2.08 | 2.06 | 1.03 | 108.3% | 0.073 |

The results are then shown as a fold change from T=0 levels for each individual donor, as shown in Tables 8-10.

TABLE 5

| | Fold Change Compared to TIME = 0 (Average of 5 donors) | | | | | | | | | |
|---|---|---|---|---|---|---|---|---|---|---|
| | NUCLEATED CELLULARITY | | | | | | | | | |
| | PBL-US | | | | | PBL-LD | | | | |
| | MEAN | STD | STE | % CHG | P | MEAN | STD | STE | % CHG | P |
| T = 0 | 1.00 | 0.00 | 0.00 | 0.0% | | 1.00 | 0.00 | 0.00 | 0.0% | |
| T = 1 | 1.69 | 0.00 | 0.00 | 68.6% | 0.017 | 1.86 | 0.00 | 0.00 | 86.2% | 0.000 |
| T = 3 | 2.80 | 0.51 | 0.23 | 180.2% | 0.000 | 2.86 | 0.28 | 0.12 | 185.6% | 0.000 |
| T = 6 | 3.26 | 0.61 | 0.27 | 225.8% | 0.000 | 3.66 | 0.43 | 0.19 | 266.3% | 0.001 |
| T = 9 | 3.09 | 0.69 | 0.31 | 209.4% | 0.000 | 3.64 | 1.18 | 0.53 | 264.3% | 0.001 |
| T = 24 | 1.07 | 0.65 | 0.29 | 7.0% | 0.553 | 1.05 | 1.19 | 0.53 | 4.6% | 0.815 |

TABLE 6

| | METHYLCELLULOSE CULTURE | | | | | | | | | | | | | | |
|---|---|---|---|---|---|---|---|---|---|---|---|---|---|---|---|
| | CFU-GM | | | | | BFU-E | | | | | CFU-GEMM | | | | |
| | MEAN | STD | STE | % CHG | P | MEAN | STD | STE | % CHG | P | MEAN | STD | STE | % CHG | P |
| T = 0 | 1.00 | 0.00 | 0.00 | 0.0% | | 1.00 | 0.00 | 0.00 | 0.0% | | 1.00 | 0.00 | 0.00 | 0.0% | |
| T = 1 | 4.77 | 0.00 | 0.00 | 376.7% | 0.001 | 1.99 | 0.00 | 0.00 | 98.9% | 0.002 | 2.32 | 0.00 | 0.00 | 131.8% | 0.000 |
| T = 3 | 13.66 | 1.56 | 0.70 | 1266.5% | 0.001 | 3.21 | 0.50 | 0.22 | 221.3% | 0.004 | 4.33 | 0.44 | 0.20 | 332.5% | 0.000 |
| T = 6 | 21.71 | 5.78 | 2.58 | 2070.6% | 0.000 | 6.01 | 1.25 | 0.56 | 500.5% | 0.006 | 10.07 | 0.59 | 0.27 | 907.2% | 0.002 |
| T = 9 | 10.47 | 5.09 | 2.28 | 947.3% | 0.000 | 4.34 | 2.99 | 1.34 | 334.4% | 0.000 | 5.25 | 4.54 | 2.03 | 425.4% | 0.014 |
| T = 24 | 1.56 | 3.01 | 1.34 | 55.5% | 0.005 | 1.26 | 1.02 | 0.45 | 26.3% | 0.194 | 1.53 | 3.04 | 1.36 | 53.2% | 0.199 |

TABLE 8

FOLD CHANGE COMPARED TO TIME = 0 for each individual patient (P)

NUCLEATED CELLULARITY

| | PBL-US | | | | | PBL-LD | | | | |
|---|---|---|---|---|---|---|---|---|---|---|
| | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 |
| T = 1 | 2.54 | 1.38 | 1.38 | 1.36 | 1.76 | 2.07 | 1.99 | 1.48 | 1.66 | 2.10 |
| T = 3 | 3.55 | 2.74 | 2.02 | 2.46 | 3.23 | 2.83 | 3.25 | 2.17 | 2.82 | 3.20 |
| T = 6 | 3.97 | 2.94 | 2.74 | 2.60 | 4.04 | 4.07 | 3.90 | 2.27 | 2.78 | 5.30 |
| T = 9 | 3.27 | 3.30 | 2.69 | 2.24 | 3.96 | 3.65 | 4.43 | 2.47 | 2.48 | 5.17 |
| T = 24 | 1.21 | 1.43 | 0.96 | 0.77 | 0.99 | 1.01 | 1.71 | 0.79 | 0.60 | 1.12 |

TABLE 9

PROGENITORS

METHYLCELLULOSE CULTURE

| | CFU-GM | | | | | BFU-E | | | | | CFU-GEMM | | | | |
|---|---|---|---|---|---|---|---|---|---|---|---|---|---|---|---|
| | P1 | P2 | P3 | P4 | P5 | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| T = 1 | 5.09 | 5.33 | 3.70 | 6.87 | 2.84 | 2.58 | 1.48 | 2.30 | 1.46 | 2.13 | 2.07 | 2.26 | 2.22 | 1.96 | 3.07 |
| T = 3 | 7.12 | 17.02 | 15.07 | 20.72 | 8.40 | 5.13 | 1.98 | 2.61 | 2.60 | 3.75 | 4.25 | 3.47 | 4.34 | 5.14 | 4.43 |
| T = 6 | 14.66 | 23.96 | 20.99 | 28.54 | 20.39 | 9.14 | 3.67 | 4.54 | 3.34 | 9.35 | 7.47 | 9.35 | 6.52 | 9.10 | 17.92 |
| T = 9 | 6.26 | 12.51 | 9.42 | 14.08 | 10.09 | 5.43 | 4.61 | 3.71 | 2.93 | 5.05 | 2.64 | 7.09 | 2.47 | 4.52 | 9.55 |
| T = 24 | 1.10 | 1.91 | 1.43 | 1.51 | 1.83 | 1.06 | 1.88 | 1.14 | 0.79 | 1.44 | 1.12 | 2.62 | 0.69 | 0.98 | 2.25 |

TABLE 10

AGAR CULTURE CFU-GM

| | P1 | P2 | P3 | P4 | P5 |
|---|---|---|---|---|---|
| T = 0 | 1.00 | 1.00 | 1.00 | 1.00 | 1.00 |
| T = 1 | 3.05 | 3.74 | 1.67 | 2.71 | 2.87 |
| T = 3 | 8.88 | 9.49 | 7.47 | 10.46 | 6.40 |
| T = 6 | 17.77 | 24.01 | 14.04 | 13.07 | 20.75 |
| T = 9 | 10.28 | 7.72 | 10.22 | 12.78 | |
| T = 24 | 3.69 | 1.13 | 1.30 | 2.20 | |

*Note: T=9 and T=24 values shown from TABLE 10-continued; columns P1–P4.*

The actual nucleated cell and progenitor cell numbers per ml of blood and the cycling status (=% progenitors in DNA synthesis (S) phase of the cell cycle) of progenitors for each of the five donors (#'s P1, P2, P3, P4, and P5) is shown in Tables 11 and 12.

TABLE 11

| | CFU-GM P1 | | BFU-E P1 | | CFU-GEMM P1 | | CFU-GM P2 | | BFU-E P2 | | CFU-GEMM P2 | |
|---|---|---|---|---|---|---|---|---|---|---|---|---|
| | Absolute # of Pro-genitors per ML | Cycling Status of Pro-genitors | Absolute # of Pro-genitors per ML | Cycling Status of Pro-genitors | Absolute # of Pro-genitors per ML | Cycling Status of Pro-genitors | Absolute # of Pro-genitors per ML | Cycling Status of Pro-genitors | Absolute # of Pro-genitors per ML | Cycling Status of Pro-genitors | Absolute # of Pro-genitors per ML | Cycling Status of Pro-genitors |
| T = 0 | 247 | 6% | 261 | 0% | 127 | 6% | 273 | 0% | 410 | 2% | 120 | 0% |
| T = 1 | 1259 | 1% | 674 | 0% | 264 | 0% | 1455 | 0% | 608 | 3% | 272 | 6% |
| T = 3 | 1760 | 1% | 1340 | 13% | 540 | 7% | 4646 | 2% | 809 | 0% | 418 | 0% |
| T = 6 | 3624 | 0% | 2388 | 0% | 949 | 0% | 6540 | 0% | 1502 | 0% | 1126 | 0% |
| T = 9 | 1547 | 2% | 1418 | 11% | 335 | 0% | 3416 | 0% | 1886 | 0% | 854 | 4% |
| T = 24 | 271 | 0% | 278 | 0% | 142 | 0% | 521 | 3% | 768 | 2% | 316 | 0% |

| | CFU-GM P3 | | BFU-E P3 | | CFU-GEMM P3 | | CFU-GM P4 | | BFU-E P4 | | CFU-GEMM P4 | |
|---|---|---|---|---|---|---|---|---|---|---|---|---|
| | Absolute # of Pro- | Cycling Status | Absolute # of Pro- | Cycling Status | Absolute # of Pro- | Cycling Status | Absolute # of Pro- | Cycling Status | Absolute # of Pro- | Cycling Status | Absolute # of Pro- | Cycling Status |

TABLE 11-continued

| | genitors per ML | of Progenitors | genitors per ML | of Progenitors | genitors per ML | of Progenitors | genitors per ML | of Progenitors | genitors per ML | of Progenitors | genitors per ML | of Progenitors |
|---|---|---|---|---|---|---|---|---|---|---|---|---|
| T = 0 | 281 | 0% | 351 | 0% | 140 | 0% | 138 | 0% | 460 | 0% | 101 | 0% |
| T = 1 | 1040 | 0% | 808 | 0% | 312 | 0% | 947 | 0% | 672 | 0% | 199 | 0% |
| T = 3 | 4233 | 1% | 915 | 0% | 610 | 0% | 2857 | 5% | 1195 | 9% | 519 | 0% |
| T = 6 | 5895 | 0% | 1593 | 0% | 916 | 0% | 3936 | 0% | 1533 | 0% | 920 | 8% |
| T = 9 | 2647 | 0% | 1302 | 0% | 347 | 0% | 1942 | 0% | 1348 | 0% | 457 | 0% |
| T = 24 | 402 | 0% | 402 | 0% | 97 | 0% | 208 | 5% | 362 | 3% | 99 | 0% |

| | CFU-GM | | BFU-E P5 | | CFU-GEMM | |
|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 169 | 0% | 343 | 1% | 55 | 0% |
| T = 1 | 481 | 0% | 730 | 0% | 169 | 0% |
| T = 3 | 1423 | 5% | 1288 | 3% | 244 | 0% |
| T = 6 | 3454 | 0% | 3208 | 1% | 987 | 0% |
| T = 9 | 1710 | 0% | 1731 | 0% | 526 | 0% |
| T = 24 | 310 | 0% | 495 | 0% | 124 | 0% |

TABLE 12

| | AGAR Culture CFU-GM P1 | | AGAR Culture CFU-GM P2 | | AGAR Culture CFU-GM P3 | | AGAR Culture CFU-GM P4 | | AGAR Culture CFU-GM P5 | |
|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 233 | 6% | 100 | 0% | 140 | 0% | 124 | 0% | 104 | 0% |
| T = 1 | 710 | 0% | 376 | 0% | 234 | 0% | 336 | 0% | 298 | 3% |
| T = 3 | 2070 | 0% | 953 | 1% | 1049 | 0% | 1299 | 0% | 664 | 0% |
| T = 6 | 4142 | 0% | 2409 | 3% | 1972 | 3% | 1623 | 0% | 2153 | 1% |
| T = 9 | | | 1032 | 0% | 1085 | 0% | 1268 | 0% | 1326 | 0% |
| T = 24 | | | 371 | 0% | 159 | 0% | 162 | 0% | 229 | 0% |

The results for all five donors were very consistent with maximal fold increases in circulating levels of progenitor cells seen 6 hours after injection of AMD3100 into the human donor subjects. Progenitors were in a slow or non-cycling state prior to and 1, 3, 6, 9 and 24 hours after injection of AMD3100. The compounds of the invention behave in a manner similar to AMD3100.

Example 176

Mobilized Bone Marrow Stem Cells for Myocardial Repair

Adult rats are anesthetized and a thoracotomy is performed. The descending branch of the left coronary artery is ligated and not reperfused. Within 4 to 6 hours after ligation the animals are injected with limit dilution AMD-3100 or AMD-3100 plus rhG-CSF. Control rats are not treated with the reagents. The animals are monitored at one-week intervals by echocardiography and MRI. The experiment is terminated at 2, 6 to 12 weeks post-surgery. On the day of sacrifice, the hemodynamic functions are analyzed for left ventricle-end diastolic pressure, left ventricle-developed pressure and the rate of rise and fall of left ventricle pressure. The heart is then arrested in diastole and perfused via the abdominal aorta to flush residual blood from the vascular network of the myocardium. This is followed by perfusion of the heart with 10% formalin. Several slices are made through the fixed heart and these are embedded in paraffin and sections. The sections are stained and analyzed by light microscopy to determine the size of the infarct in the treated and control animals. Tissue sections from hearts taken at 2 weeks after surgery are stained with antibodies specific for immature, developing myocyte and blood vessel proteins and analyzed by confocal microscopy. The immunohistochemical analysis involves the identification of transcription factors and surface markers expressed in early stages of myocyte development. The results of this experiment will show that when the reagent AMD-3100 is administered within hours after induction of cardiac ischemia, together with or without rhG-CSF, this reagent mobilizes bone marrow stem cells rapidly, and will result in a block to cardiac remodeling and scar formation and will lead to regeneration of the dead myocardium. The compounds of the invention behave in a manner similar to AMD3100.

The invention claimed is:

1. A method to obtain isolated progenitor and/or stem cells from a subject, comprising a) administering to said subject a compound of the formula

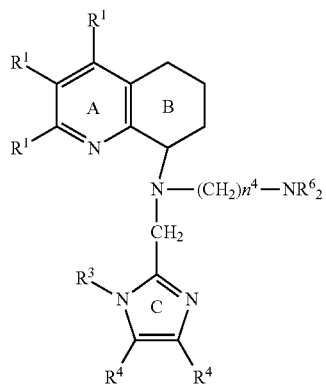

or a pharmaceutically acceptable salt or pro-drug forms thereof; and including any stereoisomeric forms thereof; wherein
$n^4$ is 2-4;
each $R^1$ is independently H, halo, alkyl, alkoxy, or $CF_3$,
$R^3$ is H, alkyl, alkyenyl, arylalkyl, or aryl;
two $R^4$ groups taken together with the ring to which they are attached form an aromatic ring; and
each $R^6$ is independently H, arylalkyl arylacyl or arylsulfonyl, wherein the aryl moieties thereof optionally contain one or more nitrogen atoms, in an amount effective to mobilize said progenitor and/or stem cells into the peripheral blood of in said subject, and
b) harvesting said progenitor and/or stem cells.

2. The method of claim 1 wherein each $R^6$ is H.

3. The method of claim 1 wherein each $R^1$ is H.

4. The method of claim 1 wherein two $R^4$ together form a phenyl group.

5. The method of claim 1, wherein the compound is (S)-$N^1$-1H-Benzimidazol-2ylmethyl)-$N^1$-(5,6,7,8-tetrahydroquinolin-8-yl)-butane-1,4-diamine or a pharmaceutically acceptable salt thereof.

6. The method of claim 1 wherein the subject is a transplantation recipient.

7. The method of claim 1 wherein the subject is a healthy stem cell donor.

8. The method of claim 1 wherein the compound is administered to said subject by an intravenous or subcutaneous route or oral route.

9. The method of claim 8 wherein the compound is administered to said subject by an oral route.

10. The method of claim 1 wherein the compound of formula IIIe is administered to said subject in the dosage range of about 0.1 µg/kg-5 mg/kg of body weight.

11. A method to enhance the population of progenitor and/or stem cells in peripheral blood or bone marrow which method comprises treating said peripheral blood or bone marrow with a compound of the formula

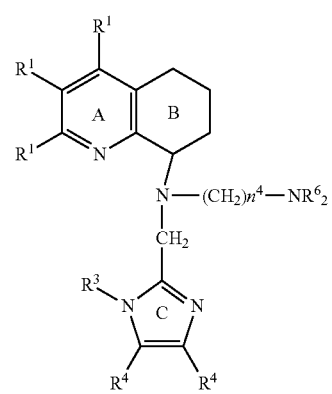

or a pharmaceutically acceptable salt or pro-drug forms thereof; and including any stereoisomeric forms thereof; wherein
$n^4$ is 2-4;
each $R^1$ is independently H, halo, alkyl, alkoxy, or $CF_3$
$R^3$ is H, alkyl, alkyenyl, arylalkyl, or aryl;
two $R^4$ groups taken together with the ring to which they are attached form an aromatic ring; and each $R^6$ is independently H, arylalkyl arylacyl or arylsulfonyl, wherein the aryl moieties thereof optionally contain one or more nitrogen atoms in an amount effective to elevate said progenitor and/or stem cell population in said peripheral blood or bone marrow.

12. The method of claim 11 which further comprises treating said peripheral blood or bone marrow with macrophage inflammatory protein.

13. The method of claim 11 wherein said treating is ex vivo.

14. The method of claim 11 wherein said peripheral blood or bone marrow is derived from a subject who has been treated with G-CSF.

15. The method of claim 1, further comprising: c) transplanting said progenitor and/or stem cells.

16. The method of claim 15, wherein the progenitor and/or stem cells are transplanted in a subject that exhibits a hematopoietic deficit from chemotherapy or radiation therapy.

17. The method of claim 15, wherein the progenitor and/or stem cells are transplanted in a subject having a condition selected from the group consisting of aplastic anemia, leukemia and drug-induced anemia.

18. The method of claim 15, wherein said progenitor and/or stem cells enhance wound healing.

19. The method of claim 15, wherein said progenitor and/or stem cells ameliorate bacterial inflammation.

20. The method of claim 15, wherein said progenitor and/or stem cells restore damaged organ tissue.

* * * * *